US009376495B2

(12) United States Patent
Bonvini et al.

(10) Patent No.: US 9,376,495 B2
(45) Date of Patent: Jun. 28, 2016

(54) DEIMMUNIZED SERUM-BINDING DOMAINS AND THEIR USE IN EXTENDING SERUM HALF-LIFE

(75) Inventors: Ezio Bonvini, Rockville, MD (US); Bhaswati Barat, Derwood, MD (US); Ling Huang, Bethesda, MD (US); Leslie S. Johnson, Darnestown, MD (US)

(73) Assignee: MacroGenics, Inc., Rockville, MD (US)

( * ) Notice: Subject to any disclaimer, the term of this patent is extended or adjusted under 35 U.S.C. 154(b) by 42 days.

(21) Appl. No.: 14/118,516

(22) PCT Filed: May 16, 2012

(86) PCT No.: PCT/US2012/038227

§ 371 (c)(1),
(2), (4) Date: Nov. 18, 2013

(87) PCT Pub. No.: WO2012/162068

PCT Pub. Date: Nov. 29, 2012

(65) Prior Publication Data

US 2015/0175697 A1 Jun. 25, 2015

Related U.S. Application Data

(60) Provisional application No. 61/488,725, filed on May 21, 2011.

(51) Int. Cl.
*A61K 39/00* (2006.01)
*C07K 16/28* (2006.01)
*C07K 16/32* (2006.01)
*C07K 16/44* (2006.01)

(52) U.S. Cl.
CPC ........... *C07K 16/2803* (2013.01); *C07K 16/283* (2013.01); *C07K 16/2809* (2013.01); *C07K 16/2851* (2013.01); *C07K 16/32* (2013.01); *C07K 16/44* (2013.01); *C07K 2317/24* (2013.01); *C07K 2317/31* (2013.01); *C07K 2317/567* (2013.01); *C07K 2317/62* (2013.01); *C07K 2317/624* (2013.01); *C07K 2317/626* (2013.01); *C07K 2317/73* (2013.01); *C07K 2317/76* (2013.01); *C07K 2317/90* (2013.01); *C07K 2317/92* (2013.01); *C07K 2319/31* (2013.01); *C07K 2319/32* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 4,752,601 | A | 6/1988 | Hahn |
| 5,116,964 | A | 5/1992 | Capon et al. |
| 5,169,933 | A | 12/1992 | Anderson et al. |
| 5,348,876 | A | 9/1994 | Michaelson et al. |
| 5,576,184 | A | 11/1996 | Better et al. |
| 5,585,089 | A | 12/1996 | Queen et al. |
| 5,624,821 | A | 4/1997 | Winter et al. |
| 5,648,260 | A | 7/1997 | Winter et al. |
| 5,698,449 | A | 12/1997 | Baumann et al. |
| 5,723,584 | A | 3/1998 | Schatz |
| 5,736,135 | A | 4/1998 | Goeddel et al. |
| 5,736,137 | A | 4/1998 | Anderson et al. |
| 5,874,239 | A | 2/1999 | Schatz |
| 5,932,433 | A | 8/1999 | Schatz |
| 5,985,599 | A | 11/1999 | Mckenzie et al. |
| 6,025,485 | A | 2/2000 | Kamb et al. |
| 6,114,147 | A | 9/2000 | Frenken et al. |
| 6,165,745 | A | 12/2000 | Ward et al. |
| 6,194,551 | B1 | 2/2001 | Idusogie et al. |
| 6,242,195 | B1 | 6/2001 | Idusogie et al. |
| 6,277,375 | B1 | 8/2001 | Ward |
| 6,300,065 | B1 | 10/2001 | Kieke et al. |
| 6,423,538 | B1 | 7/2002 | Wittrup et al. |
| 6,455,263 | B2 | 9/2002 | Payan |
| 6,492,123 | B1 | 12/2002 | Holliger et al. |
| 6,528,624 | B1 | 3/2003 | Idusogie et al. |
| 6,538,124 | B1 | 3/2003 | Idusogie et al. |
| 6,623,940 | B1 | 9/2003 | Ledbetter et al. |
| 6,737,056 | B1 | 5/2004 | Presta |
| 6,821,505 | B2 | 11/2004 | Ward |
| 7,122,646 | B2 | 10/2006 | Holliger et al. |
| 7,315,786 | B2 | 1/2008 | Dahiyat et al. |
| 7,317,091 | B2 | 1/2008 | Lazar et al. |
| 7,425,619 | B2 | 9/2008 | Koenig et al. |

(Continued)

FOREIGN PATENT DOCUMENTS

| | | |
|---|---|---|
| EP | 0 327 378 | 8/1989 |
| EP | 1354600 | 10/2003 |

(Continued)

OTHER PUBLICATIONS

Alt et al. (1999) "*Novel Tetravalent and Bispecific IgG Like Antibody Molecules Combining Single Chain Diabodies With the Immunoglobin Gamma 1 Fc or CH3 Region*," FEBS Letters 454:90-94.

(Continued)

*Primary Examiner* — Jennifer Graser

(74) *Attorney, Agent, or Firm* — AuerbachSchrot LLC; Jeffrey I. Auerbach; William C. Schrot

(57) ABSTRACT

The present invention is directed to a polypeptide (for example, an antigen-binding molecule) that comprises a polypeptide portion of a deimmunized serum-binding protein capable of binding to said serum protein. The presence of the serum-binding protein extends the serum half-life of the polypeptide, relative to the serum half-life of the polypeptide if lacking the polypeptide portion of the deimmunized serum-binding protein. The invention also pertains to methods and uses that employ such molecules.

26 Claims, 63 Drawing Sheets

(56) References Cited

U.S. PATENT DOCUMENTS

Figure 2:
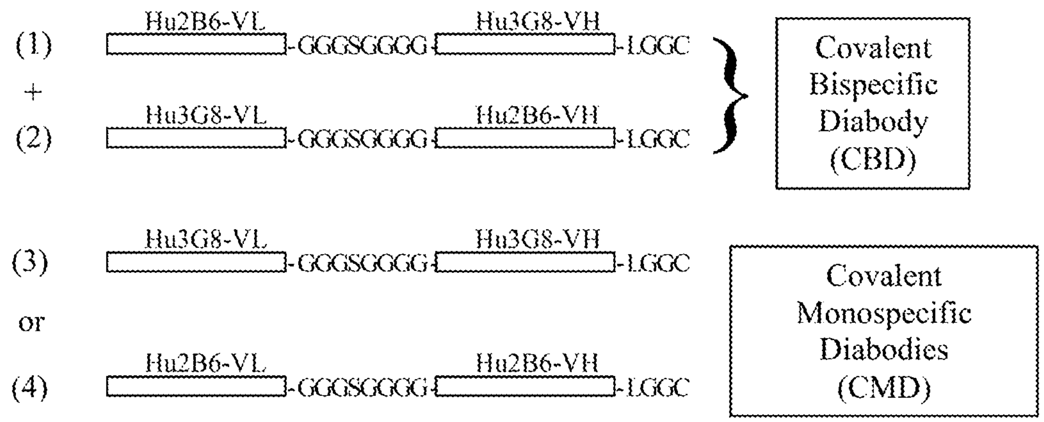

| | | | |
|---|---|---|---|
| 7,521,542 | B2 | 4/2009 | Johnson et al. |
| 7,632,497 | B2 | 12/2009 | Stavenhagen |
| 7,700,100 | B2 | 4/2010 | Johnson et al. |
| 7,960,512 | B2 | 6/2011 | Stavenhagen et al. |
| 8,003,774 | B2 | 8/2011 | Stavenhagen et al. |
| 8,044,180 | B2 | 10/2011 | Koenig et al. |
| 8,133,982 | B2 | 3/2012 | Johnson et al. |
| 8,187,593 | B2 | 5/2012 | Koenig et al. |
| 8,192,737 | B2 | 6/2012 | Stavenhagen et al. |
| 8,193,318 | B2 | 6/2012 | Koenig et al. |
| 8,216,574 | B2 | 7/2012 | Stavenhagen et al. |
| 8,216,579 | B2 | 7/2012 | Johnson et al. |
| 8,217,147 | B2 | 7/2012 | Stavenhagen et al. |
| 8,445,654 | B2 | 5/2013 | Ichikawa et al. |
| 8,530,627 | B2 | 9/2013 | Koenig et al. |
| 8,586,713 | B2 | 11/2013 | Davis et al. |
| 8,642,743 | B2 | 2/2014 | Herne |
| 2003/0077282 | A1 | 4/2003 | Bigler et al. |
| 2003/0158389 | A1 | 8/2003 | Idusogie et al. |
| 2003/0207346 | A1 | 11/2003 | Arathoon et al. |
| 2004/0002587 | A1 | 1/2004 | Watkins et al. |
| 2004/0038339 | A1 | 2/2004 | Kufer et al. |
| 2004/0058400 | A1 | 3/2004 | Holliger et al. |
| 2004/0110226 | A1 | 6/2004 | Lazar et al. |
| 2004/0132101 | A1 | 7/2004 | Lazar et al. |
| 2004/0185045 | A1 | 9/2004 | Koenig et al. |
| 2004/0220388 | A1 | 11/2004 | Mertens et al. |
| 2005/0054832 | A1 | 3/2005 | Lazar et al. |
| 2005/0100543 | A1 | 5/2005 | Hansen et al. |
| 2005/0260213 | A1 | 11/2005 | Koenig et al. |
| 2006/0193849 | A1 | 8/2006 | Krauss et al. |
| 2007/0004909 | A1 | 1/2007 | Johnson et al. |
| 2007/0036799 | A1 | 2/2007 | Stavenhagen et al. |
| 2007/0135338 | A1 | 6/2007 | O'Neil et al. |
| 2007/0140966 | A1 | 6/2007 | Chang et al. |
| 2008/0085277 | A1 | 4/2008 | Cho et al. |
| 2008/0187517 | A1 | 8/2008 | Herne |
| 2010/0174053 | A1 | 7/2010 | Johnson et al. |
| 2010/0196362 | A1 | 8/2010 | Stavenhagen et al. |
| 2010/0196372 | A1 | 8/2010 | Johnson et al. |
| 2010/0322924 | A1 | 12/2010 | Johnson et al. |
| 2011/0243941 | A1 | 10/2011 | Stavenhagen et al. |
| 2011/0305714 | A1 | 12/2011 | Stavenhagen et al. |
| 2012/0009186 | A1 | 1/2012 | Koenig et al. |
| 2012/0141476 | A1 | 6/2012 | Johnson et al. |
| 2012/0219551 | A1 | 8/2012 | Johnson et al. |
| 2012/0263711 | A1 | 10/2012 | Stavenhagen et al. |
| 2012/0269811 | A1 | 10/2012 | Johnson et al. |
| 2012/0276094 | A1 | 11/2012 | Stavenhagen et al. |
| 2013/0202606 | A1 | 8/2013 | Stavenhagen et al. |
| 2013/0295121 | A1 | 11/2013 | Johnson et al. |
| 2014/0162956 | A1 | 6/2014 | Ekblad |

FOREIGN PATENT DOCUMENTS

| | | |
|---|---|---|
| JP | 2007-531788 | 11/2007 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | WO 01/11059 | 2/2001 |
| WO | WO 02/02781 | 1/2002 |
| WO | WO 02/060919 | 8/2002 |
| WO | WO 02/086070 | 10/2002 |
| WO | WO 03/074679 | 9/2003 |
| WO | WO 03/101485 | 12/2003 |
| WO | WO 2004/016750 | 2/2004 |
| WO | WO 2004/029207 | 4/2004 |
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/097202 | 10/2005 |
| WO | WO 2006/020114 | 2/2006 |
| WO | WO 2006/113665 | 10/2006 |
| WO | WO 2008/157379 | 12/2008 |
| WO | WO 2010/080538 | 7/2010 |
| WO | WO 2012/004384 | 1/2012 |
| WO | WO 2012/018687 | 2/2012 |

OTHER PUBLICATIONS

Altman et al. (1996) "*Phenotypic Analysis of Antigen-Specific T Lymphocytes*", Science 274:94-96.

Angal et al. (1993) "*A Single Amino Acid Substitution Abolishes the Heterogeneity of Chimeric Mouse/Human (IgG4) Antibody*," Mol Immunol 30:105-108.

Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.

Anonymous, "MacroGenics Enters Global Research Collaboration and License Agreement with Pfizer;" Press Release of MacroGenics, Inc.; Oct. 26, 2010; 2 pages.

Armour et al. (1999) "*Recombinant Human Igg Molecules Lacking Fcgamma Receptor I Binding and Monocyte Triggering Activities*," Eur J Immunol 29:2613-2624.

Armour et al. (2002) "*The Contrasting IgG-Binding Interactions of Human and Herpes Simplex Virus Fc Receptors*," Biochemical Society Transactions 30:495-500.

Armour et al. (2003) "*Differential Binding to Human FcgammaRIIA and FcgammaRIIB Receptors by Human IgG Wildtype and Mutant Antibodies*," Mol Immunol 40 :585-593.

Armstrong, S. et al. (1987) "*Heterogeneity of IgG1 Monoclonal Anti-Rh(D): An Investigation Using ADCC and Macrophage Binding Assays*," Brit. J. Haematol. 66:257-262.

Asano, R. et al. (2004) "*A Diabody for Cancer Immunotherapy and its Functional Enhancement by Fusion of Human Fc Region*," Abstract 3P-683, J. Biochem. 76(8):992.

Baggiolini, M. et al. (1988) "*Cellular Models for the Detection and Evaluation of Drugs That Modulate Human Phagocyte Activity*," Experientia. Oct. 15;44(10):841-848.

Bedzyk et al. (1989) "*Comparison of Variable Region Primary Structures Within an Anti-Fluorescein Idiotype Family*," J. Biol. Chem, 264(3):1565-1569.

Boder et al. (1997) "*Yeast Surface Display for Screening Combinatorial Polypeptide Libraries*", Nature Biotechnology 15:553-557.

Boder et al. (1998) "*Optimal Screening of Surface-Displayed Polypeptide Libraries*," Biotechnol Prog 14:55-62.

Boder et al. (2000) "*Directed Evolution of Antibody Fragments With Monovalent Femtomolar Antigen-Binding Affinity*," Proc. Natl. Acad. Sci. (U.S.A.) 97:10701-10705.

Boder et al. (2000) "*Yeast Surface Display for Directed Evolution of Protein Expression, Affinity, and Stability*," Methods in Enzymology 328:430-444.

Bredius et al. (1994) "*Role of Neutrophil Fc Gamma Riia (CD32) and Fc Gamma RIIIB (CD16) Polymorphic Forms in Phagocytosis of Human IgG1- and IgG3-Opsonized Bacteria and Erythrocytes*," Immunology 83:624-630.

Brekke et al. (1994) "*Human IgG Isotype-Specific Amino Acid Residues Affecting Complement-Mediated Cell Lysis and Phagocytosis*," Eur J Immunol 24:2542-2547.

Brinkmann, U. et al. "Stabilization of a Recombinant Fv Fragment by Base-loop Interconnection and VH-VL Permutation," J. Mol. Biol. (1997) 268, 107-117.

(56) References Cited

OTHER PUBLICATIONS

Brown E.J. (1994) "*Microbes as Tools for Cell Biology*," in Methods in Cell Biology, Russell, ed. Academic Press Inc. NY 45:147-64.
Burlmeister et al. (1994) "*Crystal Structure of the Complex of Rat Neonatal Fc Receptor With Fc*," Nature 372:379-383.
Burton (1985) "*Immunoglobulin G: Functional Sites*," Mol. Immunol. 22:161-206.
Burton et al. (1988) "*Molecular Recognition of Antibody* (*IgG*) *by Cellular Fc Receptor* (*FcRI*)," Mol Immunol. 25:1175-1181.
Burton et al. (1992) "*Human Antibody Effector Function*," Advances in Immunology 51:1-84.
Canfield et al. (1991) "*The Binding Affinity of Human IgG for its High Affinity Fc Receptor is Determined by Multiple Amino Acids in the CH2 Domain and is Modulated by the Hinge Region*," J. Exp. Med. 173:1483-1491.
Caron et al. (1992) "*Engineered Humanized Dimeric Forms of IgG are More Effective Antibodies*," J. Exp. Med. 176:1191-1195.
Carter et al. (1992) "*Humanization of an Anti-P185HER2 Antibody for Human Cancer Therapy*," Proc. Natl. Acad. Sci. (U.S.A.) 89:4285-4289.
Cartron et al. (2002) "*Therapeutic Activity of Humanized Anti-CD20 Monoclonal Antibody and Polymorphism in IgG Fc Receptor FcgammaRIIIa Gene*," Blood 99:754-758.
Chappel et al. (1991) "*Identification of the Fc Gamma Receptor Class I Binding Site in Human IgG Through the Use of Recombinant IgGl/IgG2 Hybrid and Point-Mutated Antibodies*," Proc. Natl. Acad. Sci. (U.S.A.) 88:9036-9040.
Chappel et al. (1993) "*Identification of a Secondary Fc Gamma RI Binding Site Within a Genetically Engineered Human Igg Antibody*," J. Biol. Chem. 268:25124-25131.
Chu, P. G. et al. (2001) "*CD79: A Review*," Appl. Immunohistochem. Molec. Morphol. 9(2):97-106.
Ciccimarra et al. (1975) "*Localization of the IgG Effector Site for Monocyte Receptors*," Proc. Natl. Acad. Sci. (U.S.A.) 72:2081-2083.
Clynes et al. (1995) "*Cytotoxic Antibodies Trigger Inflammation Through Fc Receptors*," Immunity 3:21-26.
Clynes et al. (1998) "*Uncoupling of Immune Complex Formation and Kidney Damage in Autoimmune Glomerulonephritis*," Science 279:1052-1054.
Clynes et al. (1999) "*Modulation of Immune Complex-Induced Inflammation in Vivo by the Coordinate Expression of Activation and Inhibitory Fc Receptors*," J Exp Med 189:179-185.
Clynes et al. (2000) "*Inhibitory Fc Receptors Modulate In Vivo Cytoxicity Against Tumor Targets*," Nature Medicine 6:443-446.
Clynes et al., "*Fc Receptors are Required in Passive and Active Immunity to Melanoma*," Proc. Natl. Acad. Sci. (U.S.A.) 95:652-656.
de Haas et al. (2001) "*IgG-Fc Receptors and the Clinical Relevance of Their Polymorphisms*," Wien Klin Wochenscha 113:825-831.
Deisenhofer (1981) "*Crystallographic Refinement and Atomic Models of a Human Fc Fragment and its Complex With Fragment B of Protein A From Staphylococcus aureus at 2.9- and 2.8-A Resolution*," Biochem. 20:2361-2370.
Deo et al. (1997) "*Clinical Significance of IgG Fc Receptors and Fc Gamma R-Directed Immunotherapies*," Immunology Today 18:127-135.
Duncan et al. (1988) "*Localization of the Binding Site for the Human High-Affinity Fc Receptor on IgG*," Nature 332:563-564.
Duncan et al. (1988) "*The Binding Site for C1q on IgG*," Nature 332:738-740.
Edberg et al. (1994) "*Modulation of FcGamma and Complement Receptor Function by the Glycosyl-Phosphatidylinositol-Anchored Form of FcgammaRIII*," J. Immunol. 152:5826-5835.
European Search Report (EP 08771050) Nov. 2, 2010 (13 pages).
European Search Report(EP06750508) Nov. 2, 2010 (19 pages).
European Search Report(EP07873826) Nov. 30, 2009) (8 pages).
FitzGerald et al. (1997) "*Improved Tumour Targeting by Disulphide Stabilized Diabodies Expressed in Pichia pastoris*," Protein Engineering 10(10):1221-1225.
Flesch et al. (2000) "*Functions of the Fc Receptors for Immunoglobulin G*," J. Clin. Lab. Anal. 14:141-156.
Gergeley et al. (1984) "*Fc Receptors on Lymphocytes and K Cells*," Biochem. Soc. Trans. 12:739-743.
Gergeley et al. (1990) "*The Two Binding-Site Models of Human IgG Binding Fc Gamma Receptors*," FASEB J 4:3275-3283.
Greenwood et al (1993), "*Structural Motifs Involved in Human Igg Antibody Effector Functions*," Eur. J. Immunol 23:1098-1104.
Greenwood et al (1994) "*Engineering Multiple-Domain Forms of the Therapeutic Antibody CAMPATH-1H: Effects on Complement Lysis*," Therapeutic Immunology 1:247-255.
Greenwood et al. (1993) "*Effector Functions of Matched Sets of Recombinant Human Igg Subclass Antibodies*" (final version edited Feb. 11, 1993).
Guo, J. et al. (2003) "*New type recombinant antibody fragment scFv multimerand cancer targeting*," Sheng Wu Yi Xue Gong Cheng Xue Za Zhi 20:361-365 (Article in Chinese) Abstract only.
Hadley et al (1992), "*The Functional Activity of Fc Gamma RII and Fc Gamma RIII on Subsets of Human Lymphocytes*," Immunology 76:446-451.
Hatta et al. (1999) "*Association of Fc Gamma Receptor IIIB, But Not of Fc Gamma Receptor IIA and IIIA Polymorphisms With Systemic Lupus Erythematosus in Japanese*," Genes and Immunity 1:53-60.
Hayes (2003) "*Fc Engineering to Enhance Monoclonal Antibody Effector Functions*," (Xecor Presentation).
Herzenberg et al. (2002) "*The History and Future of the Fluorescence Activated Cell Sorter and Flow Cytometry: A View From Stanford*," Clinical Chem. 2002:48:1819-1827.
Heyman (2000) "*Regulation of Antibody Responses Via Antibodies, Complement, and Fc Receptors*," Annu Rev Immunol 18:709-737.
Hogarth et al (1994) "*Characterization of FcR Ig-Binding Sites and Epitope Mapping*," Immunomethods 4:17-24.
Holler et al (2000) "*In vitro Evolution of a T Cell Receptor With High Affinity for Peptide/MHC*," Proc. Natl. Acad. Sci. (U.S.A.) 97:5387-5392.
Holliger et al. (2005) "*Engineered Antibody Fragments and the Rise of Single Domains*," Nature Biotechnology 23(9): 1126-1135.
Hollinger et al. (1993) "*Diabodies: Small Bivalent and Bispecific Antibody Fragments*," Proc. Natl. Acad. Sci. (U.S.A.) 90:6444-6448.
Hudson et al. (1999) "*High Avidity scFv multimers; diabodies and triabodies*," Journal of Immunological Methods 231:177-189.
Hulett et al. (1991) "*Chimeric Fc Receptors Identify Functional Domains of the Murine High Affinity Receptor for IgG*," J Immunol 147 :1863-1868.
Hulett et al. (1994) "*Identification of the Igg Binding Site of the Human Low Affinity Receptor for IgG Fc Gamma RII Enhancement and Ablation of Binding by Site-Directed Mutagenesis*," J. Biol. Chem. 269:15287-15293.
Hulett et al. (1995) "*Multiple Regions of Human Fc Gamma RII* (*CD32*) *Contribute to the Binding of IgG*," J. Biol. Chem. 270:21188-21194.
Idusogie et al. (2000) "*Mapping of the C1q Binding Site on Rituxan, A Chimeric Antibody With a Human IgG1 Fc*," J. Immunol. 164:4178-4184.
Idusogie et al.(2001) "*Engineered Antibodies With Increased Activity to Recruit Complement*," J. Immunol. 166:2571-2575.
Isaacs et al. (1992) "*Therapy With Monoclonal Antibodies. An In Vivo Model for the Assessment of Therapeutic Potential*," J. Immunol. 148:3062-3071.
Isaacs et al. (1996) "*A therapeutic human IgG4 monoclonal antibody that depletes target cells in humans*," Clin. Exp. Immunol. 106:427-433.
Isaacs et al. (1998) "*Therapy With Monoclonal Antibodies. II. The Contribution of Fc Gamma Receptor Binding and the Influence of C(H)1 and C(H)3 Domains on In Vivo Effector Function*," J. Immunol. 161:3862-3869.
Jassal et al. (1998) "*Remodeling Glycans on IgG by Genetic Re-Engineering*," Biochem. Soc. Trans. 26:S113.
Jefferis et al. (1990) "*Molecular definition of interaction sites on human IgG for Fc receptors* (*huFc gamma R*)," Mol. Immunol. 27:1237-1240.
Jefferis et al. (1995) "*Recognition Sites on Human IgG for Fc Gamma Receptors: The Role of Glycosylation*," Immunol. Lett. 44:111-117.

(56) References Cited

OTHER PUBLICATIONS

Jefferis et al. (1998) "*IgG-Fc-Mediated Effector Functions: Molecular Definition of Interaction Sites for Effector Ligands and the Role of Glycosylation*," Immunol. Rev. 163:59-76.
Jefferis et al. (2002) "*Interaction Sites on Human IgG-Fc for FcgammaR: Current Models*," Immunology Letters 82:57-65.
Jendeberg et al. (1997) "*Engineering of Fc(1) and Fc(3) From Human Immunoglobulin G to Analyse Subclass Specificity for Staphylococcal Protein A*," J. Immunological Methods 201:25-34.
Johnson et al. (2010) "*Effector Cell Recruitment with Novel Fv-based Dual-affinity Re-targeting Protein Leads to Potent Tumor Cytolysis and in Vivo-B-cell Depletion*," J. Mol. Biol. 399:436-449.
Kadar et al. (1991) "*Modulatory Effect of Synthetic Human IgG Fc Peptides on the In Vitro Immune Response of Murine Spleen Cells*," Int. J. Immunpharmacol. 13:1147-1155.
Kadar et al. (1992) "*Synthetic Peptides Comprising Defined Sequences of CH-2 and CH-3 Domains of Human Igg1 Induce Prostaglandin E2 Production From Human Peripheral Blood Mononuclear Cells*," Immunol. Lett. 32:59-63.
Kato et al (2000), "*Structural Basis of the Interaction Between IgG and Fcγ Receptors*," J. Mol. Biol. 295:213-224.
Keler et al. (2000) "*Differential Effect of Cytokine Treatment on Fc Alpha Receptor I- and Fc Gamma Receptor I-Mediated Tumor Cytotoxicity by Monocyte-Derived Macrophages*," J. Immunol. 164:5746-52.
Kieke et al. (1999) "*Selection of Functional T Cell Receptor Mutants From a Yeast Surface-Display Library*," Proc. Natl. Acad. Sci. (U.S.A.) 96:5651-5656.
Kim et al. (2001) "*Analysis of FcγRIII and IgG Fc Polymorphism Reveals Functional and Evolutionary Implications of Protein-Protein Interaction*," J. Mol. Evol. 53:1-9.
Klein et al. (1981) "*Expression of Biological Effector Functions by Immunoglobulin G Molecules Lacking the Hinge Region*,"Proc. Natl. Acad. Sci. (U.S.A.) 78:524-528, 1981.
Koene et al. (1997) "*Fc gammaRIIIa-158V/F polymorphism influences the binding of IgG by natural killer cell Fc gammaRIIIa, independently of the Fc gammaRIIIa-48L/R/H phenotype*," Blood 90:1109-1114.
Kontermann et al. (1977) "*Complement recruitment using bispecific diabodies*," Nature Biotechnology 15:629-631.
Kortt et al. (2001) "*Dimeric and trimeric antibodies: high avidity scFvs for cancer targeting*" Biomolecular Engineering 18:95-108.
Kranz et al. (1982) "*Mechanisms of Ligand Binding by Monoclonal Anti-Fluorescyl Antibodies*," J. Biol. Chem. 257:6987-6995.
Kumpel (1989) "*Human Monoclonal Anti-D Antibodies*," J. Haematol. 71:415-420.
Le Gall et al. (Epub May 4, 2004)"*Effect of Linker Sequences Between the Anitbody Variable Domains on the Formation, Stability and Biological Activity of a Bispecific Tandem Diabody*." Protein Eng Des Sel. 17(4):357-366.
Lehmann et al. (2000) "*Phagocytosis: Measurement by Flow Cytometry*," J. Immunol. Methods. 243(1-2):229-242.
Lehrnbecher et al. (1999) "*Variant Genotypes of the Low-Affinity Fcgamma Receptors in Two Control Populations and a Review of Low-Affinity Fcgamma Receptor Polymorphisms in Control and Disease Populations*," Blood 94:4220-4232, 1999.
Li et al. (1996) "*Reconstitution of Human Fc Gamma RIII Cell Type Specificity in Transgenic Mice*," J Exp Med 183 :1259-1263.
Liu et al. (1987) "*Production of a Mouse-Human Chimeric Monoclonal Antibody to CD20 With Potent Fc-Dependent Biologic Activity*," J. Immunol. 139:3521-3526.
Lu, D et al. (2004) "*The Effect of Variable Domain Orientation and Arrangement on the Antigen-Binding Activity of a Recombinant Human Bispecific Diabody*," BBRC 318:507-513.
Lu, D. et al. (2003) "*Di-Diabody: A Novel Tetravalent Bispecific Antibody Molecule by Design*," J. Immunol. Meth. 279:219-232.
Lu, et al. (2005) "*A Fully Human Recombinant IgG-like Bispecific Antibody to Both the Epidermal Growth Factor Receptor and the Insulin-like-Growth Factor Receptor for Enhanced Antitumor Activity*," J. Biol. Chem. 280(20):19665-19672.
Lund et al. (1991) "*Human Fc Gamma RI and Fc Gamma RII Interact With Distinct But Overlapping Sites on Human IgG*," J. Immunol. 147:2657-2662.
Lund et al. (1992) "*Multiple Binding Sites on the CH2 Domain of Igg for Mouse Fc Gamma R11*," Molecular Immunology 29:53-59.
Lund et al. (1995) "Oligosaccharide-protein interactions in IgG can modulate recognition by Fc gamma receptors," FASEB J 9:115-119.
Lund et al. (1996) "*Multiple Interactions of IgG With its Core Oligosaccharide Can Modulate Recognition by Complement and Human Fc Gamma Receptor I and Influence the Synthesis of its Oligosaccharide Chains*," J. Immunol. 157:4963-4969.
Lund et al. (2000) "*Expression and Characterization of Truncated Forms of Humanized L243 IgG1. Architectural Features Can Influence Synthesis of its Oligosaccharide Chains and Affect Superoxide Production Triggered Through Human Fcgamma Receptor I*," Eur. J. Biochem. 267:7246-7257.
Maenaka et al. (2001) "*The Human Low Affinity Fcgamma Receptors IIA, IIB, and III Bind IgG With Fast Kinetics and Distinct Thermodynamic Properties*," J. Biol. Chem. 48:44898-44904.
Mariuzza et al. (1987) "*The Structural Basis of Antigen-Antibody Recognition*" Ann. Rev. Biophys. Biophys.Chem. 16:139-159.
Marvin et al. (2005) "*Recombinant Approaches to IgG-Like Bispeicifc Antibodies*," Acta Pharmacologica Sinica, 26(6):649-658.
Mertens, N. et al., "*New Recombinant Bi- and Trispecific Antibody DerivatIVES*," In: Novel Frontiers in the Production of Compounds for Biomedical Use, vol. 1; van Broekhoven, A. et al. (Eds.); Kluwer Academic Publishers, Dordrecht, The Netherlands; pp. 195-208.
Michaelsen et al. (1994) "*One Disulfide Bond in Front of the Second Heavy Chain Constant Region is Necessary and Sufficient for Effector Functions of Human Igg3 Without a Genetic Hinge*," Immunolgy 91:9243-9247.
Moore, P.A. et al. (2011) "*Application of Dual Affinity Retargeting Molecules to Achieve Optimal Redirected T-Cell Killing of B-Cell Lymphoma*," Blood 117:4542-4551.
Morgan et al. (1995) "*The N-terminal end of the CH2 domain of chimeric human IgG1 anti-HLA-DR is necessary for C1q, Fc gamma RI and Fc gamma RII binding*," Immunology 86:319-324.
Morrison et al. (1994) "*Structural Determinants of IgG Structure*," Immunologist 2:119-124.
Munn et al. (1990) "*Phagocytosis of Tumor Cells by Human Monocytes Cultured in Recombinant Macrophage Colony-Stimulating Factor*," J. Exp. Med. 172(1):231-237.
Nagarajan et al. (1995) "*Ligand Binding and Phagocytosis by CD16 (Fc Gamma Receptor III) Isoforms. Phagocytic Signaling by Associated Zeta and Gamma Subunits in Chinese Hamster Ovary Cells*," J. Biol. Chem. 270:25762-25770.
Nakamura, T. et al. (1992) "*Heterogeneity of Immunoglobulin-Associated Molecules on Human B Cells Identified by Monoclonal Antibodies*," Proc. Natl. Acad. Sci. (USA) 89:8522-8526).
Neuberger et al. (1984) "*Recombinant Antibodies Possessing Novel Effector Functions*," Nature 312:604-608.
Norderhaug et al. (1991) "*Chimeric Mouse Human IgG3 Antibodies With an IgG4-Like Hinge Region Induce Complement-Mediated Lysis More Efficiently Than IgG3 With Normal Hinge*," Eur. J. Immunol. 21:2379-2384.
Nose et al. (1989) "*Substitution of Asparagine324 With Aspartic Acid in the Fc Portion of Mouse Antibodies Reduces Their Capacity for C1q Binding*," Eur. J. Immunol. 19:2179-2181.
Okazaki et al. (2004) "*Fucose Depletion From Human IgG1 Oligosaccharide Enhances Binding Enthalpy and Associated Rate Between IgG1 and FcgammaRIIa*," J. Mol. Biol. 336:1239-1249.
Olafsen et al. (2004) "*Covalent Disulfide-Linked Anti-CEA Diabody Allows Site-Specific Conjugation and Radiolabeling for Tumor Targeting Applications*," Protein Engineering Design &Selection, 17(1):21-27.
Orfao et al. (1996) "*General Concepts About Cell Sorting Techniques*," Clinical Biochem. 29:5-9.
Partridge et al. (1986) "*The Use of Anti-IgG Monoclonal Antibodies in Mapping the Monocyte Receptor Site on IgG*," Mol Immunol. 23(12):1365-1372.
PCT International Search Report and Written Opinion PCT/US2009/68577 (2010) (14 pages).

(56) References Cited

OTHER PUBLICATIONS

PCT International Search Report and Written Opinion PCT/US2011/045922 (2011) (4 pages).
Perussia (2000) "*Human Natural Killer Cell Protocols*" in Methods Molecular Biology. vol. 121 (Campbell et al. eds.) Humana Press Inc., Totowa, NJ. pp. 179-192.
Radaev et al. (2001), "*Recognition of Immunoglobulins by Fcgamma Receptors*," Molecular Immunology 38:1073-1083.
Rankin et al. "CD32B, *The Human Inhibitory Fc-γ Receptor IIB, as a Target for Monoclonal Antibody Therapy of B-Cell Lymphoma*," (2006) Blood 108(7):2384-2391.
Ravetch (1994) "*Fc Receptors: Rubor Redux*," Cell 78:553-560.
Ravetch et al. (1991) "*Fc Receptors*," Ann. Rev. Immunol 9:457-492.
Ravetch et al. (1998), "*Divergent Roles for Fc Receptors and Complement In Vivo*," Ann. Rev. Immunol 16:421-432.
Ravetch et al. (2000) "*Immune Inhibitory Receptors*," Science 290:84-89.
Ravetch et al. (2001), "*IgG Fc Receptors*," Ann. Rev. Immunol 19:275-90, 2001.
Redpath et al. (1998) "*The Influence of the Hinge Region Length in Binding of Human IgG to Human Fcgamma Receptors*," Hum Immunol 59:720-727.
Reff et al. (1994) "*Depletion of B Cells In Vivo by a Chimeric Mouse Human Monoclonal Antibody to CD20*," Blood 83:435-445.
Riechmann et al. (1988) "*Reshaping Human Antibodies for Therapy*," Nature. 332(6162):323-327.
Sarmay et al. (1984) "*Ligand Inhibition Studies on the Role of Fc Receptors in Antibody-Dependent Cell-Mediated Cytotoxicity*," Mol Immunol 21:43-51.
Sarmay et al. (1988) "*The Effect of Synthetic Peptides Corresponding to Fc Sequences in Human IgG1 on Various Steps in the B Cell Activation Pathway*," Eur. J. Immunol. 18:289-294.
Sarmay et al. (1992) "*Mapping and Comparison of the Interaction Sites on the Fc Region of Igg Responsible for Triggering Antibody Dependent Cellular Cytotoxicity (ADCC) Through Different Types of Human Fc Gamma Receptor*," Mol. Immunol. 29:633-639.
Sautes-Fridman et al. (2003) "*Fc Gamma Receptors: A Magic Link With the Outside World*," ASHI Quarterley, 4th Quarter:148-151.
Schaffner et al. (1995) "*Chimeric Interleukin 2 Receptor Alpha Chain Antibody Derivatives With Fused Mu and Gamma Chains Permit Improved Recruitment of Effector Functions*," Mol Immunol 32 :9-20, 1995 (Erratum in 32 :1299, 1995).
Schatz et al. (2000) "*Use of Peptide Libraries to Map the Substrate Specificity of a Peptide-Modifying Enzyme: A 13 Residue Consensus Peptide Specifies Biotinylation in Escherichia coli*," Bio/Technology 11:1138-1143.
Sensel et al. (1997) "*Amino Acid Differences in the N-Terminus of C(H)2 Influence the Relative Abilities of Igg2 and Igg3 to Activate Complement*," Molecular Immunology 34:1019-1029.
Shields et al. (2001) "*High Resolution Mapping of the Binding Site on Human IgG1 for Fc gamma RI Fc gamma RII, Fc gamma RIII, and FcRn and Design of IgG1 Variants With Improved Binding to the Fc gamma R*," J. Biol. Chem. 276:6591-6604.
Shopes (1992) "*A Genetically Engineered Human Igg Mutant With Enhanced Cytolytic Activity*," J. Immunol. 148:2918-2922.
Shopes (1993) "*A Genetically Engineered Human Igg With Limited Flexibility Fully Initiates Cytolysis Via Complement*," Molecular Immunology 30:603-609.
Shopes et al. (1990) "*Recombinant Human IgG1-Murine IgE Chimeric Ig. Construction, Expression, and Binding to Human Fc Gamma Receptors*," J. Immunol. 145:3842-3848.
Shusta et al. (1998) "*Increasing the Secretory Capacity of Saccharomyces cerevisiae for Production of Single-Chain Antibody Fragments*," Nature Biotechnology 16:773-777.
Shusta et al. (1999) "*Yeast Polypeptide Fusion Surface Display Levels Predict Thermal Stability and Soluble Secretion Efficiency*," J. Mol. Biol. 292:949-956.
Shusta et al. (2000) "*Directed Evolution of a Stable Scaffold for T-Cell Receptor Engineering*," Nature Biotechnology 18:754-759.
Smith et al. (1994) "*Recombinant Polymeric IgG: An Approach to Engineering More Potent Antibodies*," Bio/Technology 12:683-688.
Sondermann et al. (1999) "*Crystal Structure of the Soluble Form of the Human Fcgamma-Receptor IIB: A New Member of the Immunoglobulin Superfamily at 1.7 A Resolution*," EMBO J. 18:1095-1103.
Sondermann et al. (2000) "*The 3.2-A Crystal Structure of the Human Igg1 Fc Fragment-Fc Gammariii Complex*," Nature 406:267-273.
Sondermann et al. (2001) "*Molecular Basis for Immune Complex Recognition: A Comparison of Fc-Receptor Structures*," J. Mol. Biol. 309:737-749.
Sondermann et al. (2002) "*The Structure of Fc Receptor/Ig Complexes: Considerations on Stoichiometry and Potential Inhibitors*," Immunology Letters, 82:51-56.
Steplewski et al. (1988) "*Biological Activity of Human-Mouse IgG1, IgG2, IgG3, and IgG4 chimeric Monoclonal Antibodies With Antitumor Specificity*," Proc. Natl. Acad. Sci. (U.S.A.) 85:4852-4856.
Strohmeier et al. (1995) "*Role of the Fc Gamma R Subclasses Fc gamma RII and Fc gamma RIII in the Activation of Human Neutrophils by Low and High Valency Immune Complexes*," J. Leukocyte Biol. 58:415-422.
Sylvestre et al. (1994) "*Fc Receptors Initiate the Arthus Reaction: Redefining the Inflammatory Cascade*," Science 265:1095-1098.
Sylvestre et al. (1996) "*A Dominant Role for Mast Cell Fc Receptors in the Arthus Reaction*," Immunity 5:387-390.
Takai (2002) "*Roles of Fc Receptors in Autoimmunity*," Nature Reviews 2:580-592.
Takai et al. (1994) "*Fcr Gamma Chain Deletion Results in Pleiotrophic Effector Cell Defects*," Cell 76:519-529.
Takai et al. (1996) "*Augmented Humoral and Anaphylactic Responses in Fc Gamma RIII-Deficient Mice*," Nature 379:346-349.
Takemura, S. et al. (2000) "*Construction of a Diabody (Small Recombinant Bispecific Antibody) Using a Refolding System*," Protein Eng. 13(8):583-588.
Tamm et al. (1996) "*The IgG Binding Site of Human FcγRIIIB Receptor Involves CC' and FG Loops of the Membrane-Proximal Domain*," J. Biol. Chem. 271:3659-3666.
Tao et al. (1991) "*The Differential Ability of Human IgG1 and IgG4 to Activate Complement is Determined by the COOH-Terminal Sequence of the CH2 Domain*," J. Exp. Med. 173:1025-1028.
Tao et al. (1993) "*Structural Features of Human Immunoglobulin G That Determine Isotype-Specific Differences in Complement Activation*," J. Exp. Med. 178:661-667.
Todorovska et al. (2001) "*Design and application of diabodies, triabodies and tetrabodies for cancer targeting*," Journal of Immunological and Methods 248:47-66.
Trindandapani et al. (2002) "*Regulated Expression and Inhibitory Function of FcgammaRIIB in Human Monocytic Cells*," J. Biol. Chem. 277(7):5082-5089.
Unkless et al. (1995) "*Function of human FcγRIIA and FcγRIIIB*," Immunology 7:37-44.
Van Sorge et al. (2003) "*FcgammaR Polymorphisms: Implications for Function, Disease Susceptibility and Immunotherapy*," Tissue Antigens 61:189-202.
VanAntwerp et al. (2000) "*Fine Affinity Discrimination by Yeast Surface Display and Flow Cytometry*," Biotechnol. Prog. 16:31-37.
Veri et al. (Epub Mar. 26, 2007) "*Monoclonal antibodies capable of discriminating the human inhibitory Fcgamma-receptor IIB (CD32B) from the activating Fcgamma-receptor IIA (CD32A): biochemical, biological and functional characterization*," Immunology 121(3):392-404.
Veri, et al. (Jul. 2010) "*Therapeutic Control of B Cell Activation via Recruitment of Fcγ Receptor IIb (CD32B) Inhibitory Function With a Novel Bispecific Antibody Scaffold*," Arthritis & Rheumatism, vol. 62(7): 1933-1943.
Vidarte (2001) "*Serine 132 is the C3 Covalent Attachment Point on the CH1 Domain of Human IgG1*," J. Biol. Chem. 276:38217-38233.
Ward et al. (1995) "*The Effector Functions of Immunoglobulins: Implications for Therapy*," Therapeutic Immunology 2:77-94.
Weng et al. (2003) "*Two Immunoglobulin G Fragment C Receptor Polymorphisms Independently Predict Response to Rituximab in Patients With Follicular Lymphoma*," J. Clin. Oncol. 21:3940-3947.

(56) References Cited

OTHER PUBLICATIONS

Wiener, E. et al. (1988) "*Differences Between the Activities of Human Monoclonal IgG1 and IgG3 Anti-D Antibodies of the Rh Blood Group System in Their Abilities to Mediate Effector Functions of Monocytes*," Immunol. 65:159-163.
Wing et al. (1996) "*Mechanism of First-Dose Cytokine-Release Syndrome by CAMPATH 1-H: Involvement ofCD16 (FcγRIII) and CD11a/CD18 (LFA-1) on NK cells*," J. Clin. Invest. 98:2819-2826.
Wingren et al. (1996) "*Comparison of Surface Properties of Human IgA, IgE, IgG and IgM Antibodies With Identical and Different Specificities*," Scand. J. Immunol. 44:430-436.
Wittrup (2000) "*The Single Cell As a Microplate Well*," Nat. Biotechnol. 18:1039-1040.
Wittrup (2001) "*Protein Engineering by Cell-Surface Display*," Curr. Opin. Biotechnol. 12:395-399.
Woof et al. (1986) "*Localisation of the Monocyte-Binding Region on Human Immunoglobulin G*," Mol. Immunol. 23:319-330.
Wu et al. (1997) "*A Novel Polymorphism of FcγRIIIa (CD16) Alters Receptor Function and Predisposes to Autoimmune Disease*," J. Clin. Invst. 100:1059-1070.
Wu et al. (1999) "*Designer genes: recombinant antibody fragments for biological imaging*" The Quarterly Journal of Nuclear Medicine 44:268-283.
Wu et al. (2001) "*Multiomerization of a Chimeric Anti-CD20 Single-Chain Fv-Fc Fusion Protein is Mediated Through Variable Domain Exchange*," Protein Engineering 14(2):1025-1033.
Xu et al. (1994) "*Residue at Position 331 in the IgG1 and IgG4 CH2 Domains Contributes to Their Differential Ability to Bind and Activate Complement*," J. Biol. Chem. 269:3469-3474.
Yeung et al. (2002) "*Quantitative Screening of Yeast Surface-Displayed Polypeptide Libraries by Magnetic Bead Capture*," Biotechnol. Prog. 18:212-220.
Zeidler et al. (2000) "*The Fc-Region of a New Class of Intact Bispecific Antibody Mediates Activation of Accessory Cells and NK Cells and Induces Direct Phagocytosis of Tumour Cells*," British J. Cancer 83:261-266.
Zuckier et al. (1998) "*Chimeric Human-Mouse Igg Antibodies With Shuffled Constant Region Exons Demonstrate That Multiple Domains Contribute to In Vivo Half-Life*," Cancer Res 58 :3905-3908, 1998.
Apostolovic, B. et al. (2008) "*pH-Sensitivity of the E3/K3 Heterodimeric Coiled Coil*," Biomacromolecules 9:3173-3180.
Arndt, K.M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228.
Arndt, K.M. et al. (2002) "*Comparison of In Vivo Selection and Rational Design of Heterodimeric Coiled Coils*," Structure 10:1235-1248.
Boucher, C. et al. (2010) "*Protein Detection by Western Blot Via Coiled-Coil Interactions*," Analytical Biochemistry 399:138-140.
Cachia, P.J. et al. (2004) "*Synthetic Peptide Vaccine Development: Measurement of Polyclonal Antibody Affinity and Cross-Reactivity Using a New Peptide Capture and Release System for Surface Plasmon Resonance Spectroscopy*," J. Mol. Recognit. 17:540-557.
De Crescenzo, G.D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763.
de Kruif, J. et al. (1996) "*Leucine Zipper Dimerized Bivalent and Bispecific scFv Antibodies from a Semi-synthetic Antibody Phage Display Library*," J. Biol. Cherm. 271(13):7630-7634.
Fernandez-Rodriguez, J. et al. (2012) "*Induced Heterodimerization and Purification of Two Target Proteins by a Synthetic Coiled-Coil Tag*," Protein Sci. 21:511-519.
Ghosh, T. S. et al. (2009) "*End-To-End and End-To-Middle Interhelical Interactions: New Classes of Interacting Helix Pairs in Protein Structures*," Acta Cryst. D65:1032-1041.
Grigoryan, G. et al. (2008) "*Structural Specificity in Coiled-Coil Interactions*," Curr. Opin. Struc. Biol. 18:477-483.
Litowski, J.R. et al. (2002) "Designing Heterodimeric Two-Stranded α-Helical Coiled-Coils: The Effects of Hydrophobicity and α-Helical Propensity on Protein Folding, Stability, and Specificity," J. Biol. Chem. 277:37272-37279.
Pack, P. et al. (1992) "*Miniantibodies: Use of Amphipathic Helices to Produce Functional, Flexibly Linked Dimeric Fv Fragments with High Avidity in Escherichia coli*," 31(6):1579-1584.
Rothlisberger, D. et al. (2005) "*Domain Interactions in the Fab Fragment: A Comparative Evaluation of the Single-chain Fv and Fab Format Engineered with Variable Domains of Different Stability*," J. Molec. Biol. 347:773-789.
Steinkruger, J.D. et al. (2012) "*The d'—d—d' Vertical Triad is Less Discriminating Than the a'—a—a' Vertical Triad in the Antiparallel Coiled-coil Dimer Motif*," J. Amer. Chem. Soc. 134(5):2626-2633.
Straussman, R. et al. (2007) "*Kinking the Coiled Coil—Negatively Charged Residues at the Coiled-coil Interface*," J. Molec. Biol. 366:1232-1242.
Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362.
Woolfson, D.N. (2005) "*The Design of Coiled-Coil Structures and Assemblies*," Adv. Prot. Chem. 70:79-112.
Zeng, Y. et al. (2008) "*A Ligand-Pseudoreceptor System Based on de novo Designed Peptides for the Generation of Adenoviral Vectors With Altered Tropism*," J. Gene Med. 10:355-367.
Gao, Y. et al. (2004) "*Efficient Inhibition of Multidrug-Resistant Human Tumors With a Recombinant Bispecific Anti-P-Glycoprotein x Anti-CD3 Diabody*," Leukemia 18(3):513-520.
Kontermann, R.E. (2005) "*Recombinant Bispecific Antibodies for Cancer Therapy*," Acta. Pharmacol. Sin. (2005) 26(1):1-9.
Luo et al. (1995) "*VL-Linker-VH Orientation-Dependent Expression of Single Chain Fv Containing an Engineered Disulfide-Stabilized Bond in the Framework Regions*," J. Biochem. 4(118):825-831.
Xiong, D. et al. (2002) "*Efficient Inhibition of Human B-Cell Lymphoma Xenografts With an Anti-CD20 x Anti-CD3 Bispecific Diabody*," Cancer Lett. (2002) 177(1):29-39.
Zhu, Z. et al. (1997) "*Remodeling Domain Interfaces to Enhance Heterodimer Formation*," Protein Sci. 6:781-788.
Cuesta, A.M. et al. (2010) "*Multivalent Antibodies: When Design Surpasses Evolution*," Trends in Biotechnol., 28(7):355-362.
Guo, N. et al. (2005) "*The Development of New Formats of Engineered Bispecific Antibodies," in Trends in Immunology Research*, Veskler, Ed. Nova Science Publishers. Chapter 3:33-47.
Le, P.U. et al. (2009) "*Escherichia coli Expression and Refolding of E/K-Coil-Tagged EGF Generates Fullybioactive EGF for Diverse Applications*," Protein Expression and Purification 64:108-117.
Goetsch, L. et al. (2003) "*Identification of B- and T-Cell Epitopes of BB, a Carrier Protein Derived from the G Protein of Streptococcus Strain G148*," Clin. Diag. Lab. Immun. 10(1):125-132.
Stork, R. et al. (2007) "*A Novel Tri-Functional Antibody Fusion Protein With Improved Pharmacokinetic Properties Generated by Fusing a Bispecific Single-Chain Diabody With an Albumin-Binding Domain From Streptococcal Protein G*," Prot. Eng. Des. Sel. 20(11):569-576.
EPO Communication Third Party Observations EP 12789439.2 (2015).
US 6,331,391, 12/2001, Wittrup et al. (withdrawn)

```
216                 226
E P K S C D - - K T H T C P P - - - - - - - - - - - - - - - - - - - - - - - - -  IGG1
E R K C C V - - E - - - C P P - - - - - - - - - - - - - - - - - - - - - - - - - -IGG2
E L K T P L G D T T H T C P R C P E P K S C D T P P P C P R C P E P K S C D T P  IGG3
E S K Y G P - - P - - - C P S - - - - - - - - - - - - - - - - - - - - - - - - - -IGG4

                                        230
- - - - - - - - - - - - - - - - - - - - C P
- - - - - - - - - - - - - - - - - - - - C P
P P C P R C P E P K S C D T P P P C P R C P
- - - - - - - - - - - - - - - - - - - - C P
```

FIG. 1A

```
231
A P E L L G G IgG1
A P P V A G - IgG2
A P E L L G G IgG3
A P E F L G G IgG4

240                                     260
P S V F L F P P K P K D T L M I S R T P E V T C V V V D V S H E D P E V K F N W
P S V F L F P P K P K D T L M I S R T P E V T C V V V D V S H E D P E V Q F N W
P S V F L F P P K P K D T L M I S R T P E V T C V V V D V S H E D P E V Q F K W
P S V F L F P P K P K D T L M I S R T P E V T C V V V D V S Q E D P E V Q F N W

280                                     300
Y V D G V E V H N A K T K P R E E Q Y N S T Y R V V S V L T V L H Q D W L N G K
Y V D G V E V H N A K T K P R E E Q F N S T F R V V S V L T V V H Q D W L N G K
Y V D G V Q V H N A K T K P R E Q Q F N S T F R V V S V L T V L H Q N W L D G K
Y V D G V E V H N A K T K P R E E Q F N S T Y R V V S V L T V L H Q D W L N G K

320                                     340
E Y K C K V S N K A L P A P I E K T I S K A K G Q P R E P Q V Y T L P P S R D E
E Y K C K V S N K G L P A P I E K T I S K T K G Q P R E P Q V Y T L P P S R E E
E Y K C K V S N K A L P A P I E K T I S K T K G Q P R E P Q V Y T L P P S R E E
E Y K C K V S N K G L P S S I E K T I S K A K G Q P R E P Q V Y T L P P S Q E E

360                                     380
L T K N Q V S L T C L V K G F Y P S D I A V E W E S N G Q P E N N Y K T T P P V
M T K N Q V S L T C L V K G F Y P S D I A V E W E S N G Q P E N N Y K T T P P M
M T K N Q V S L T C L V K G F Y P S D I A V E W E S S G Q P E N N Y N T T P P M
M T K N Q V S L T C L V K G F Y P S D I A V E W E S N G Q P E N N Y K T T P P V

400                                     420
L D S D G S F F L Y S K L T V D K S R W Q Q G N V F S C S V M H E A L H N H Y T
L D S D G S F F L Y S K L T V D K S R W Q Q G N V F S C S V M H E A L H N H Y T
L D S D G S F F L Y S K L T V D K S R W Q Q G N I F S C S V M H E A L H N R F T
L D S D G S F F L Y S R L T V D K S R W Q E G N V F S C S V M H E A L H N H Y T

440
Q K S L S L S P G K
Q K S L S L S P G K
Q K S L S L S P G K
Q K S L S L S L G K
```

FIG. 1B

M 1 2 3

3 2 1 M

(13) 3G8-VL -GGGSGGGG- 2.4G2-VH -LGGCGGRAKR- 2.4G2-VL -GGGSGGGG- 3G8-VH -LGGC

(14) 3G8-VL -GGGSGGGG- 2.4G2-VH -LGGCGGRAKRAPVKQTLNFDLLKLAGDVESNPGP-
2.4G2-VL -GGGSGGGG- 3G8-VH -LGGC

(15) Hu2B6-VL -GGGSGGGG- Hu3G8-VH -FNRGEC
+
(16) Hu3G8-VL -GGGSGGGG- Hu2B6-VH -VEPKSC
} Covalent Bispecific Diabody (CBD)

DART sCD32B
ka1/Ms 3.7e5 kd,1/s 7.4e-3
Kd,nM=20

ABD-DART sCD32B
ka1/Ms 2.4e5 kd,1/s 7.2e-3
Kd,nM=30

DART sCD16A
ka1/Ms5.7e5 kd,1/s0.090
Kd,nM=158

ABD-DART sCD16A
ka1/Ms 3.8e5 kd,1/s 0.052
Kd,nM=137

DART

HSA

ABD-DART

HSA
ka1/Ms 0.9e5 kd,1/s 6.4e-4
Kd,nM=7.1

MDA-MB468 (HER2 -ve)
Breast Cancer Cell Line

HT-29
Colon Cancer Cell Line

KYK2-4420 VF E coil P312-009, CHO Trans.

0.45mg/L MSA Purified pPAL7 Kcoil-ABD

SEQUENCE LISTING

<160> NUMBER OF SEQ ID NOS: 330

<210> SEQ ID NO 1
<211> LENGTH: 13
<212> TYPE: PRT
<213> ORGANISM: homo sapiens

<400> SEQUENCE: 1

```
Glu Pro Lys Ser Cys Asp Lys Thr His Thr Cys Pro Pro
1               5                   10
```

<210> SEQ ID NO 2
<211> LENGTH: 10
<212> TYPE: PRT
<213> ORGANISM: homo sapiens

<400> SEQUENCE: 2

```
Glu Arg Lys Cys Cys Val Glu Cys Pro Pro
1               5                   10
```

<210> SEQ ID NO 3
<211> LENGTH: 60
<212> TYPE: PRT
<213> ORGANISM: homo sapiens

<400> SEQUENCE: 3

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg
    50                  55                  60
```

<210> SEQ ID NO 4
<211> LENGTH: 10
<212> TYPE: PRT
<213> ORGANISM: homo sapiens

<400> SEQUENCE: 4

```
Glu Ser Lys Tyr Gly Pro Pro Cys Pro Ser
1               5                   10
```

<210> SEQ ID NO 5
<211> LENGTH: 217
<212> TYPE: PRT
<213> ORGANISM: homo sapiens

<400> SEQUENCE: 5

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 6
<211> LENGTH: 216
<212> TYPE: PRT
<213> ORGANISM: homo sapiens

<400> SEQUENCE: 6

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215


<210> SEQ ID NO 7
<211> LENGTH: 217
```

<212> TYPE: PRT
<213> ORGANISM: homo sapiens

<400> SEQUENCE: 7

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Gln Val His Asn Ala Lys Thr Lys Pro Arg Glu Gln
    50                  55                  60

Gln Phe Asn Ser Thr Phe Arg Val Val Ser Val Leu Thr Val Leu His
65                  70                  75                  80

Gln Asn Trp Leu Asp Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215
```

<210> SEQ ID NO 8
<211> LENGTH: 217
<212> TYPE: PRT
<213> ORGANISM: homo sapiens

<400> SEQUENCE: 8

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125
```

-continued

```
Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 9
<211> LENGTH: 237
<212> TYPE: PRT
<213> ORGANISM: homo sapiens

<400> SEQUENCE: 9

```
Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Val Leu Thr Met Thr Asn Met Asp Pro Val Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Leu Gly Gly Cys
225                 230                 235
```

<210> SEQ ID NO 10
<211> LENGTH: 8
<212> TYPE: PRT
<213> ORGANISM: homo sapiens

<400> SEQUENCE: 10

Gly Gly Gly Ser Gly Gly Gly Gly
1               5

<210> SEQ ID NO 11
<211> LENGTH: 244
<212> TYPE: PRT
<213> ORGANISM: homo sapiens

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Trp Ile His Trp Val Arg Gln Ala Pro
145                 150                 155                 160

Gly Gln Gly Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190

Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240

Leu Gly Gly Cys

<210> SEQ ID NO 12
<211> LENGTH: 240
<212> TYPE: PRT
<213> ORGANISM: homo sapiens

<400> SEQUENCE: 12

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala

```
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Asn Tyr Trp Ile His Trp Val Arg Gln Ala Pro Gly Gln Gly Leu
145                 150                 155                 160

Glu Trp Ile Gly Val Ile Asp Pro Ser Asp Thr Tyr Pro Asn Tyr Asn
                165                 170                 175

Lys Lys Phe Lys Gly Arg Val Thr Met Thr Val Val Val Ser Thr Ser
            180                 185                 190

Thr Ala Tyr Met Glu Leu Arg Ser Leu Arg Ser Asp Asp Thr Ala Val
        195                 200                 205

Tyr Tyr Cys Ala Arg Asn Gly Asp Ser Asp Tyr Tyr Ser Gly Met Asp
    210                 215                 220

Tyr Trp Gly Gln Gly Thr Thr Val Thr Val Ser Ser Leu Gly Gly Cys
225                 230                 235                 240


<210> SEQ ID NO 13
<211> LENGTH: 241
<212> TYPE: PRT
<213> ORGANISM: homo sapiens

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Thr Leu Arg Glu Ser Gly Pro
        115                 120                 125

Ala Leu Val Lys Pro Thr Gln Thr Leu Thr Leu Thr Cys Thr Phe Ser
    130                 135                 140

Gly Phe Ser Leu Ser Thr Ser Gly Met Gly Val Gly Trp Ile Arg Gln
145                 150                 155                 160

Pro Pro Gly Lys Ala Leu Glu Trp Leu Ala His Ile Trp Trp Asp Asp
                165                 170                 175

Asp Lys Arg Tyr Asn Pro Ala Leu Lys Ser Arg Leu Thr Ile Ser Lys
            180                 185                 190

Asp Thr Ser Lys Asn Gln Val Val Leu Thr Met Thr Asn Met Asp Pro
        195                 200                 205
```

```
Val Asp Thr Ala Thr Tyr Tyr Cys Ala Gln Ile Asn Pro Ala Trp Phe
    210                 215                 220

Ala Tyr Trp Gly Gln Gly Thr Leu Val Thr Val Ser Ser Leu Gly Gly
225                 230                 235                 240

Cys


<210> SEQ ID NO 14
<211> LENGTH: 470
<212> TYPE: PRT
<213> ORGANISM: homo sapiens

<400> SEQUENCE: 14

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Val Leu Thr Met Thr Asn Met Asp Pro Val Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Leu Gly Gly Cys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335
```

```
Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 15
<211> LENGTH: 477
<212> TYPE: PRT
<213> ORGANISM: homo sapiens

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Trp Ile His Trp Val Arg Gln Ala Pro
145                 150                 155                 160

Gly Gln Gly Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190

Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240
```

Leu Gly Gly Cys Val Glu Pro Lys Ser Cys Asp Lys Thr His Thr Cys
245 250 255

Pro Pro Cys Pro Ala Pro Glu Leu Leu Gly Gly Pro Ser Val Phe Leu
260 265 270

Phe Pro Pro Lys Pro Lys Asp Thr Leu Met Ile Ser Arg Thr Pro Glu
275 280 285

Val Thr Cys Val Val Val Asp Val Ser His Glu Asp Pro Glu Val Lys
290 295 300

Phe Asn Trp Tyr Val Asp Gly Val Glu Val His Asn Ala Lys Thr Lys
305 310 315 320

Pro Arg Glu Glu Gln Tyr Asn Ser Thr Tyr Arg Val Val Ser Val Leu
325 330 335

Thr Val Leu His Gln Asp Trp Leu Asn Gly Lys Glu Tyr Lys Cys Lys
340 345 350

Val Ser Asn Lys Ala Leu Pro Ala Pro Ile Glu Lys Thr Ile Ser Lys
355 360 365

Ala Lys Gly Gln Pro Arg Glu Pro Gln Val Tyr Thr Leu Pro Pro Ser
370 375 380

Arg Asp Glu Leu Thr Lys Asn Gln Val Ser Leu Thr Cys Leu Val Lys
385 390 395 400

Gly Phe Tyr Pro Ser Asp Ile Ala Val Glu Trp Glu Ser Asn Gly Gln
405 410 415

Pro Glu Asn Asn Tyr Lys Thr Thr Pro Pro Val Leu Asp Ser Asp Gly
420 425 430

Ser Phe Phe Leu Tyr Ser Lys Leu Thr Val Asp Lys Ser Arg Trp Gln
435 440 445

Gln Gly Asn Val Phe Ser Cys Ser Val Met His Glu Ala Leu His Asn
450 455 460

His Tyr Thr Gln Lys Ser Leu Ser Leu Ser Pro Gly Lys
465 470 475

<210> SEQ ID NO 16
<211> LENGTH: 243
<212> TYPE: PRT
<213> ORGANISM: homo sapiens

<400> SEQUENCE: 16

Glu Ile Val Leu Thr Gln Ser Pro Asp Phe Gln Ser Val Thr Pro Lys
1 5 10 15

Glu Lys Val Thr Phe Thr Cys Arg Thr Ser Gln Ser Ile Gly Thr Asn
20 25 30

Ile His Trp Tyr Gln Gln Lys Pro Asp Gln Ser Pro Lys Leu Leu Ile
35 40 45

Lys Glu Val Ser Glu Ser Ile Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys Gln Gln Ser Asn Thr Trp Pro Phe
85 90 95

Thr Phe Gly Gly Gly Thr Lys Val Glu Ile Lys Gly Gly Gly Ser Gly
100 105 110

Gly Gly Gly Gln Val Thr Leu Arg Glu Ser Gly Pro Ala Leu Val Lys
115 120 125

Pro Thr Gln Thr Leu Thr Leu Thr Cys Thr Phe Ser Gly Phe Ser Leu

```
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Val Leu Thr Met Thr Asn Met Asp Pro Val Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Leu Gly Gly Cys Phe Asn Arg
225                 230                 235                 240

Gly Glu Cys


<210> SEQ ID NO 17
<211> LENGTH: 10
<212> TYPE: PRT
<213> ORGANISM: Artificial Sequence
<220> FEATURE:
<223> OTHER INFORMATION: linker plus C-terminus of human IgG-kappa chain

<400> SEQUENCE: 17

Leu Gly Gly Cys Phe Asn Arg Gly Glu Cys
1               5                   10


<210> SEQ ID NO 18
<211> LENGTH: 477
<212> TYPE: PRT
<213> ORGANISM: homo sapiens

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Trp Ile His Trp Val Arg Gln Ala Pro
145                 150                 155                 160

Gly Gln Gly Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190
```

```
Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240

Leu Gly Gly Cys Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475


<210> SEQ ID NO 19
<211> LENGTH: 485
<212> TYPE: PRT
<213> ORGANISM: homo sapiens

<400> SEQUENCE: 19

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95
```

```
Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Gly Ser Gly Gly Gly
225                 230                 235                 240

Gly Asp Ile Val Met Thr Gln Ser Pro Asp Ser Leu Ala Val Ser Leu
                245                 250                 255

Gly Glu Arg Ala Thr Ile Asn Cys Lys Ala Ser Gln Ser Val Asp Phe
            260                 265                 270

Asp Gly Asp Ser Phe Met Asn Trp Tyr Gln Gln Lys Pro Gly Gln Pro
        275                 280                 285

Pro Lys Leu Leu Ile Tyr Thr Thr Ser Asn Leu Glu Ser Gly Val Pro
    290                 295                 300

Asp Arg Phe Ser Gly Ser Gly Ser Gly Thr Asp Phe Thr Leu Thr Ile
305                 310                 315                 320

Ser Ser Leu Gln Ala Glu Asp Val Ala Val Tyr Tyr Cys Gln Gln Ser
                325                 330                 335

Asn Glu Asp Pro Tyr Thr Phe Gly Gln Gly Thr Lys Leu Glu Ile Lys
            340                 345                 350

Gly Gly Gly Ser Gly Gly Gly Gly Gln Val Gln Leu Val Gln Ser Gly
        355                 360                 365

Ala Glu Val Lys Lys Pro Gly Ala Ser Val Lys Val Ser Cys Lys Ala
    370                 375                 380

Ser Gly Tyr Thr Phe Thr Asn Tyr Trp Ile His Trp Val Arg Gln Ala
385                 390                 395                 400

Pro Gly Gln Gly Leu Glu Trp Ile Gly Val Ile Asp Pro Ser Asp Thr
                405                 410                 415

Tyr Pro Asn Tyr Asn Lys Lys Phe Lys Gly Arg Val Thr Met Thr Val
            420                 425                 430

Val Val Ser Thr Ser Thr Ala Tyr Met Glu Leu Arg Ser Leu Arg Ser
        435                 440                 445

Asp Asp Thr Ala Val Tyr Tyr Cys Ala Arg Asn Gly Asp Ser Asp Tyr
    450                 455                 460

Tyr Ser Gly Met Asp Tyr Trp Gly Gln Gly Thr Thr Val Thr Val Ser
465                 470                 475                 480

Ser Leu Gly Gly Cys
                485

<210> SEQ ID NO 20
<211> LENGTH: 469
```

```
<212> TYPE: PRT
<213> ORGANISM: homo sapiens

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Gly Ser Gly Gly Gly
    210                 215                 220

Gly Asp Ile Val Met Thr Gln Ser Pro Asp Ser Leu Ala Val Ser Leu
225                 230                 235                 240

Gly Glu Arg Ala Thr Ile Asn Cys Lys Ala Ser Gln Ser Val Asp Phe
                245                 250                 255

Asp Gly Asp Ser Phe Met Asn Trp Tyr Gln Gln Lys Pro Gly Gln Pro
            260                 265                 270

Pro Lys Leu Leu Ile Tyr Thr Thr Ser Asn Leu Glu Ser Gly Val Pro
        275                 280                 285

Asp Arg Phe Ser Gly Ser Gly Ser Gly Thr Asp Phe Thr Leu Thr Ile
    290                 295                 300

Ser Ser Leu Gln Ala Glu Asp Val Ala Val Tyr Tyr Cys Gln Gln Ser
305                 310                 315                 320

Asn Glu Asp Pro Tyr Thr Phe Gly Gln Gly Thr Lys Leu Glu Ile Lys
                325                 330                 335

Gly Gly Gly Ser Gly Gly Gly Gly Gln Val Gln Leu Val Gln Ser Gly
            340                 345                 350

Ala Glu Val Lys Lys Pro Gly Ala Ser Val Lys Val Ser Cys Lys Ala
        355                 360                 365

Ser Gly Tyr Thr Phe Thr Asn Tyr Trp Ile His Trp Val Arg Gln Ala
    370                 375                 380

Pro Gly Gln Gly Leu Glu Trp Ile Gly Val Ile Asp Pro Ser Asp Thr
385                 390                 395                 400
```

```
Tyr Pro Asn Tyr Asn Lys Lys Phe Lys Gly Arg Val Thr Met Thr Val
                405                 410                 415

Val Val Ser Thr Ser Thr Ala Tyr Met Glu Leu Arg Ser Leu Arg Ser
            420                 425                 430

Asp Asp Thr Ala Val Tyr Tyr Cys Ala Arg Asn Gly Asp Ser Asp Tyr
        435                 440                 445

Tyr Ser Gly Met Asp Tyr Trp Gly Gln Gly Thr Thr Val Thr Val Ser
    450                 455                 460

Ser Leu Gly Gly Cys
465


<210> SEQ ID NO 21
<211> LENGTH: 466
<212> TYPE: PRT
<213> ORGANISM: homo sapiens

<400> SEQUENCE: 21

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Cys Gly Thr Lys Val Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Asp Lys Arg Tyr
                165                 170                 175

Asn Pro Ala Leu Lys Ser Arg Leu Thr Ile Ser Lys Asp Thr Ser Lys
            180                 185                 190

Asn Gln Val Val Leu Thr Met Thr Asn Met Asp Pro Val Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
```

```
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 22
<211> LENGTH: 246
<212> TYPE: PRT
<213> ORGANISM: homo sapiens

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Trp Ile His Trp Val Arg Gln Ala Pro
145                 150                 155                 160

Gly Gln Cys Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190
```

```
Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240

Phe Asn Arg Gly Glu Cys
                245


<210> SEQ ID NO 23
<211> LENGTH: 6
<212> TYPE: PRT
<213> ORGANISM: homo sapiens

<400> SEQUENCE: 23

Phe Asn Arg Gly Glu Cys
1               5


<210> SEQ ID NO 24
<211> LENGTH: 5
<212> TYPE: PRT
<213> ORGANISM: Artificial Sequence
<220> FEATURE:
<223> OTHER INFORMATION: 2B6 heavy chain variable region  CDR1

<400> SEQUENCE: 24

Asn Tyr Trp Ile His
1               5


<210> SEQ ID NO 25
<211> LENGTH: 5
<212> TYPE: PRT
<213> ORGANISM: Artificial Sequence
<220> FEATURE:
<223> OTHER INFORMATION: 3H7 Heavy chain variable region CDR1

<400> SEQUENCE: 25

Asp Ala Trp Met Asp
1               5


<210> SEQ ID NO 26
<211> LENGTH: 17
<212> TYPE: PRT
<213> ORGANISM: Artificial Sequence
<220> FEATURE:
<223> OTHER INFORMATION: 2B6 Heavy chain variable region  CDR2

<400> SEQUENCE: 26

Val Ile Asp Pro Ser Asp Thr Tyr Pro Asn Tyr Asn Lys Lys Phe Lys
1               5                   10                  15

Gly


<210> SEQ ID NO 27
<211> LENGTH: 19
<212> TYPE: PRT
<213> ORGANISM: Artificial Sequence
<220> FEATURE:
<223> OTHER INFORMATION: 3H7 Heavy chain variable region CDR2

<400> SEQUENCE: 27

Glu Ile Arg Asn Lys Ala Asn Asn Leu Ala Thr Tyr Tyr Ala Glu Ser
1               5                   10                  15

Val Lys Gly
```

-continued

<210> SEQ ID NO 28
<211> LENGTH: 12
<212> TYPE: PRT
<213> ORGANISM: Artificial Sequence
<220> FEATURE:
<223> OTHER INFORMATION: 2B6 Heavy chain variable region CDR3

<400> SEQUENCE: 28

Asn Gly Asp Ser Asp Tyr Tyr Ser Gly Met Asp Tyr
1 5 10

<210> SEQ ID NO 29
<211> LENGTH: 6
<212> TYPE: PRT
<213> ORGANISM: Artificial Sequence
<220> FEATURE:
<223> OTHER INFORMATION: 3H7 heavy chain variable region CDR3

<400> SEQUENCE: 29

Tyr Ser Pro Phe Ala Tyr
1 5

<210> SEQ ID NO 30
<211> LENGTH: 11
<212> TYPE: PRT
<213> ORGANISM: Artificial Sequence
<220> FEATURE:
<223> OTHER INFORMATION: 2B6 Light chain variable region CDR1

<400> SEQUENCE: 30

Arg Thr Ser Gln Ser Ile Gly Thr Asn Ile His
1 5 10

<210> SEQ ID NO 31
<211> LENGTH: 11
<212> TYPE: PRT
<213> ORGANISM: Artificial Sequence
<220> FEATURE:
<223> OTHER INFORMATION: 3H7 light chain variable region CDR1

<400> SEQUENCE: 31

Arg Ala Ser Gln Glu Ile Ser Gly Tyr Leu Ser
1 5 10

<210> SEQ ID NO 32
<211> LENGTH: 7
<212> TYPE: PRT
<213> ORGANISM: Artificial Sequence
<220> FEATURE:
<223> OTHER INFORMATION: 2B6 light chain variable region CDR2

<400> SEQUENCE: 32

Asn Val Ser Glu Ser Ile Ser
1 5

<210> SEQ ID NO 33
<211> LENGTH: 7
<212> TYPE: PRT
<213> ORGANISM: Artificial Sequence
<220> FEATURE:
<223> OTHER INFORMATION: 2B6 light chain variable region CDR2

<400> SEQUENCE: 33

Tyr Val Ser Glu Ser Ile Ser
1 5

<210> SEQ ID NO 34
<211> LENGTH: 7
<212> TYPE: PRT
<213> ORGANISM: Artificial Sequence
<220> FEATURE:
<223> OTHER INFORMATION: 2B6 light chain variable region CDR2

<400> SEQUENCE: 34

Tyr Ala Ser Glu Ser Ile Ser
1 5

<210> SEQ ID NO 35
<211> LENGTH: 7
<212> TYPE: PRT
<213> ORGANISM: Artificial Sequence
<220> FEATURE:
<223> OTHER INFORMATION: 3H7 light chain variable region CDR2

<400> SEQUENCE: 35

Ala Ala Ser Thr Leu Asp Ser
1 5

<210> SEQ ID NO 36
<211> LENGTH: 9
<212> TYPE: PRT
<213> ORGANISM: Artificial Sequence
<220> FEATURE:
<223> OTHER INFORMATION: 2B6 Light chain variable region CDR3

<400> SEQUENCE: 36

Gln Gln Ser Asn Thr Trp Pro Phe Thr
1 5

<210> SEQ ID NO 37
<211> LENGTH: 9
<212> TYPE: PRT
<213> ORGANISM: Artificial Sequence
<220> FEATURE:
<223> OTHER INFORMATION: 3H7 light chain variable region CDR3

<400> SEQUENCE: 37

Leu Gln Tyr Val Ser Tyr Pro Tyr Thr
1 5

<210> SEQ ID NO 38
<211> LENGTH: 121
<212> TYPE: PRT
<213> ORGANISM: Artificial Sequence
<220> FEATURE:
<223> OTHER INFORMATION: 2B6 heavy chain variable region

<400> SEQUENCE: 38

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Ile His Trp Val Arg Gln Ala Pro Gly Gln Gly Leu Glu Trp Met
35 40 45

Gly Val Ile Asp Pro Ser Asp Thr Tyr Pro Asn Tyr Asn Lys Lys Phe
50 55 60

Lys Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

```
Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120


<210> SEQ ID NO 39
<211> LENGTH: 107
<212> TYPE: PRT
<213> ORGANISM: Artificial Sequence
<220> FEATURE:
<223> OTHER INFORMATION: 2B6 light chain variable region  Hu2B6VL-1

<400> SEQUENCE: 39

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Asn Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105


<210> SEQ ID NO 40
<211> LENGTH: 107
<212> TYPE: PRT
<213> ORGANISM: Artificial Sequence
<220> FEATURE:
<223> OTHER INFORMATION: Humanized 2B6 light chain variable region
      Hu2B6VL-2

<400> SEQUENCE: 40

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105


<210> SEQ ID NO 41
<211> LENGTH: 107
<212> TYPE: PRT
<213> ORGANISM: Artificial Sequence
<220> FEATURE:
<223> OTHER INFORMATION: Humanized 2B6 light chain variable region
      Hu2B6VL-3

<400> SEQUENCE: 41
```

```
Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105


<210> SEQ ID NO 42
<211> LENGTH: 107
<212> TYPE: PRT
<213> ORGANISM: Mus musculus

<400> SEQUENCE: 42

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Arg Arg Leu Ile
        35                  40                  45

Tyr Ala Ala Ser Thr Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Tyr
                85                  90                  95

Thr Phe Gly Gly Gly Thr Lys Leu Glu Ile Lys
            100                 105


<210> SEQ ID NO 43
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 43

Lys Lys Phe Ser Arg Ser Asp Pro Asn
1               5


<210> SEQ ID NO 44
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 44

Gln Lys Phe Ser Arg Leu Asp Pro Asn
1               5


<210> SEQ ID NO 45
```

<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 45

Gln Lys Phe Ser Arg Leu Asp Pro Thr
1 5

<210> SEQ ID NO 46
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 46

Lys Lys Phe Ser Arg Leu Asp Pro Thr
1 5

<210> SEQ ID NO 47
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 47

Gln Lys Phe Ser His Leu Asp Pro Thr
1 5

<210> SEQ ID NO 48
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 48

Lys Lys Phe Ser His Leu Asp Pro Thr
1 5

<210> SEQ ID NO 49
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 49

Gln Lys Phe Ser Arg Leu Asp Pro Asn
1 5

<210> SEQ ID NO 50
<211> LENGTH: 9
<212> TYPE: PRT
<213> ORGANISM: Artificial Sequence
<220> FEATURE:
<223> OTHER INFORMATION: IgG binding site for FcgammaRIIB receptor

<400> SEQUENCE: 50

Lys Lys Phe Ser Arg Ser Asp Pro Asn
1 5

<210> SEQ ID NO 51
<211> LENGTH: 9

<212> TYPE: PRT
<213> ORGANISM: Artificial Sequence
<220> FEATURE:
<223> OTHER INFORMATION: IgG binding site of FcgammaRIIB receptor

<400> SEQUENCE: 51

Gln Lys Phe Ser Arg Leu Asp Pro Thr
1 5

<210> SEQ ID NO 52
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 52

Gln Lys Phe Ser His Leu Asp Pro Thr
1 5

<210> SEQ ID NO 53
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 53

Lys Lys Phe Ser Arg Leu Asp Pro Thr
1 5

<210> SEQ ID NO 54
<211> LENGTH: 9
<212> TYPE: PRT
<213> ORGANISM: Artificial Sequence
<220> FEATURE:
<223> OTHER INFORMATION: IgG binding site of FcgammaRIIB receptor

<400> SEQUENCE: 54

Lys Lys Phe Ser His Leu Asp Pro Thr
1 5

<210> SEQ ID NO 55
<211> LENGTH: 36
<212> TYPE: DNA
<213> ORGANISM: Artificial Sequence
<220> FEATURE:
<223> OTHER INFORMATION: Primer Lgh321F

<400> SEQUENCE: 55
cgagctagct ctagatgaga tcacagttct ctctac 36

<210> SEQ ID NO 56
<211> LENGTH: 47
<212> TYPE: DNA
<213> ORGANISM: Artificial Sequence
<220> FEATURE:
<223> OTHER INFORMATION: Primer Lgh318R

<400> SEQUENCE: 56
gcctccgcct ccggatccgc ctcctttgat ctccaccttg gtccctc 47

<210> SEQ ID NO 57
<211> LENGTH: 47
<212> TYPE: DNA
<213> ORGANISM: Artificial Sequence
<220> FEATURE:

<223> OTHER INFORMATION: Primer Lgh319F

<400> SEQUENCE: 57
ggaggcggat ccggaggcgg aggccaggtt cagctggtgc agtctgg 47

<210> SEQ ID NO 58
<211> LENGTH: 43
<212> TYPE: DNA
<213> ORGANISM: Artificial Sequence
<220> FEATURE:
<223> OTHER INFORMATION: Primer  Lgh320R

<400> SEQUENCE: 58
tttgaattct agcagcctcc cagtgaggag acggtgaccg tgg 43

<210> SEQ ID NO 59
<211> LENGTH: 46
<212> TYPE: DNA
<213> ORGANISM: Artificial Sequence
<220> FEATURE:
<223> OTHER INFORMATION: Primer Lgh315R

<400> SEQUENCE: 59
gcctccgcct ccggatccgc ctcctttgat ctcaagcttg gtcccc 46

<210> SEQ ID NO 60
<211> LENGTH: 48
<212> TYPE: DNA
<213> ORGANISM: Artificial Sequence
<220> FEATURE:
<223> OTHER INFORMATION: Primer Lgh316F

<400> SEQUENCE: 60
ggaggcggat ccggaggcgg aggccaggtt accctgagag agtctggc 48

<210> SEQ ID NO 61
<211> LENGTH: 47
<212> TYPE: DNA
<213> ORGANISM: Artificial Sequence
<220> FEATURE:
<223> OTHER INFORMATION: Primer Lgh317R

<400> SEQUENCE: 61
tttgaattcc tagcagcctc ccagtgagct cacagtgacc agagtcc 47

<210> SEQ ID NO 62
<211> LENGTH: 27
<212> TYPE: DNA
<213> ORGANISM: Artificial Sequence
<220> FEATURE:
<223> OTHER INFORMATION: Primer Lgh339R

<400> SEQUENCE: 62
ctcaacgcag cctcccagtg agctcac 27

<210> SEQ ID NO 63
<211> LENGTH: 31
<212> TYPE: DNA
<213> ORGANISM: Artificial Sequence
<220> FEATURE:
<223> OTHER INFORMATION: Primer Lgh340R

<400> SEQUENCE: 63
aacgcagcct cccagtgagg agacggtgac c 31

<210> SEQ ID NO 64
<211> LENGTH: 27
<212> TYPE: DNA
<213> ORGANISM: Artificial Sequence
<220> FEATURE:
<223> OTHER INFORMATION: Primer Lgh366R

<400> SEQUENCE: 64
tttgaattct atttacccgg agacagg 27

<210> SEQ ID NO 65
<211> LENGTH: 33
<212> TYPE: DNA
<213> ORGANISM: Artificial Sequence
<220> FEATURE:
<223> OTHER INFORMATION: Primer Lhg367F

<400> SEQUENCE: 65
ctgggaggct gcgcagagcc caaatcttgt gac 33

<210> SEQ ID NO 66
<211> LENGTH: 33
<212> TYPE: DNA
<213> ORGANISM: Artificial Sequence
<220> FEATURE:
<223> OTHER INFORMATION: Primer Lgh368R

<400> SEQUENCE: 66
gtcacaagat ttgggctctg cgcagcctcc cag 33

<210> SEQ ID NO 67
<211> LENGTH: 50
<212> TYPE: DNA
<213> ORGANISM: Artificial Sequence
<220> FEATURE:
<223> OTHER INFORMATION: Primer Lgh369R

<400> SEQUENCE: 67
tttgaattct aacactctcc cctgttgaag cagcctccca gtgaggagac 50

<210> SEQ ID NO 68
<211> LENGTH: 118
<212> TYPE: PRT
<213> ORGANISM: Artificial Sequence
<220> FEATURE:
<223> OTHER INFORMATION: humanized anti-CD16A Heavy Chain Variable
Region Hu3G8VH-1

<400> SEQUENCE: 68

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asn Pro Ala Trp Phe Ala Tyr Trp Gly Gln Gly Thr
            100                 105                 110
```

```
Leu Val Thr Val Ser Ser
        115


<210> SEQ ID NO 69
<211> LENGTH: 118
<212> TYPE: PRT
<213> ORGANISM: Artificial Sequence
<220> FEATURE:
<223> OTHER INFORMATION: Humanized anti-CD16A heavy chain variable
      region  Hu3G8VH-5

<400> SEQUENCE: 69

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115


<210> SEQ ID NO 70
<211> LENGTH: 117
<212> TYPE: PRT
<213> ORGANISM: Artificial Sequence
<220> FEATURE:
<223> OTHER INFORMATION: Humanized anti-CD16A heavy chain variable
      region Hu3G8VH-22

<400> SEQUENCE: 70

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Ser Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asn Pro Ala Tyr Phe Ala Tyr Trp Gly Gln Gly Thr
            100                 105                 110

Leu Val Thr Val Ser
        115


<210> SEQ ID NO 71
<211> LENGTH: 111
<212> TYPE: PRT
<213> ORGANISM: Artificial Sequence
<220> FEATURE:
```

<223> OTHER INFORMATION: Humanized anti-CD16A light chain variable
region Hu3G8VL-1

<400> SEQUENCE: 71

Asp Ile Val Met Thr Gln Ser Pro Asp Ser Leu Ala Val Ser Leu Gly
1 5 10 15

Glu Arg Ala Thr Ile Asn Cys Lys Ala Ser Gln Ser Val Asp Phe Asp
20 25 30

Gly Asp Ser Phe Met Asn Trp Tyr Gln Gln Lys Pro Gly Gln Pro Pro
35 40 45

Lys Leu Leu Ile Tyr Thr Thr Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Tyr Thr Phe Gly Gln Gly Thr Lys Leu Glu Ile Lys
100 105 110

<210> SEQ ID NO 72
<211> LENGTH: 111
<212> TYPE: PRT
<213> ORGANISM: Artificial Sequence
<220> FEATURE:
<223> OTHER INFORMATION: Humanized anti-CD16A light chain variable
region Hu3G8VL-43

<400> SEQUENCE: 72

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Asp Phe Asp
20 25 30

Gly Asp Ser Phe Met Asn Trp Tyr Gln Gln Lys Pro Gly Gln Pro Pro
35 40 45

Lys Leu Leu Ile Tyr Thr Thr Ser Ser Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Ser Asp Pro Tyr Thr Phe Gly Gln Gly Thr Lys Leu Glu Ile Lys
100 105 110

<210> SEQ ID NO 73
<211> LENGTH: 111
<212> TYPE: PRT
<213> ORGANISM: Artificial Sequence
<220> FEATURE:
<223> OTHER INFORMATION: Humanized anti-CD16A light chain variable
region Hu3G8VL-22

<400> SEQUENCE: 73

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Asp Phe Asp
20 25 30

Gly Asp Ser Phe Met Asn Trp Tyr Gln Gln Lys Pro Gly Gln Pro Pro
35 40 45

Lys Leu Leu Ile Tyr Thr Thr Ser Asn Leu Glu Thr Gly Val Pro Asp 50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Ser Asp Pro Tyr Thr Phe Gly Gln Gly Thr Lys Leu Glu Ile Lys
100 105 110

<210> SEQ ID NO 74
<211> LENGTH: 24
<212> TYPE: DNA
<213> ORGANISM: Homo sapiens
<220> FEATURE:
<221> NAME/KEY: misc_feature
<223> OTHER INFORMATION: DNA sequence of SEQ ID NO:10

<400> SEQUENCE: 74
ggaggcggat ccggaggcgg aggc 24

<210> SEQ ID NO 75
<211> LENGTH: 18
<212> TYPE: DNA
<213> ORGANISM: homo sapiens

<400> SEQUENCE: 75
ttcaacaggg gagagtgt 18

<210> SEQ ID NO 76
<211> LENGTH: 30
<212> TYPE: DNA
<213> ORGANISM: Artificial Sequence
<220> FEATURE:
<223> OTHER INFORMATION: Linker plus C-terminus of human IgG kappa chain

<400> SEQUENCE: 76
ctgggaggct gcttcaacag gggagagtgt 30

<210> SEQ ID NO 77
<211> LENGTH: 6
<212> TYPE: PRT
<213> ORGANISM: homo sapiens

<400> SEQUENCE: 77

Val Glu Pro Lys Ser Cys
1 5

<210> SEQ ID NO 78
<211> LENGTH: 18
<212> TYPE: DNA
<213> ORGANISM: homo sapiens

<400> SEQUENCE: 78
gttgagccca aatcttgt 18

<210> SEQ ID NO 79
<211> LENGTH: 118
<212> TYPE: PRT
<213> ORGANISM: homo sapiens

<400> SEQUENCE: 79

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Arg Thr Ser

```
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115
```

<210> SEQ ID NO 80
<211> LENGTH: 354
<212> TYPE: DNA
<213> ORGANISM: homo sapiens

<400> SEQUENCE: 80

```
caggttaccc tgaaagagtc tggccctggg atattgcagc cctcccagac cctcagtctg      60

acttgttctt tctctgggtt ttcactgagg acttctggta tgggtgtagg ctggattcgt     120

cagccttcag ggaagggtct agagtggctg gcacacattt ggtgggatga tgacaagcgc     180

tataatccag ccctgaagag ccgactgaca atctccaagg atacctccag caaccaggta     240

ttcctcaaaa tcgccagtgt ggacactgca gatactgcca catactactg tgctcaaata     300

aaccccgcct ggtttgctta ctggggccaa gggactctgg tcactgtgag ctca           354
```

<210> SEQ ID NO 81
<211> LENGTH: 354
<212> TYPE: DNA
<213> ORGANISM: homo sapiens

<400> SEQUENCE: 81

```
caggttaccc tgagagagtc tggccctgcg ctggtgaagc ccacacagac cctcacactg      60

acttgtacct tctctgggtt ttcactgagc acttctggta tgggtgtagg ctggattcgt     120

cagcctcccg ggaaggctct agagtggctg gcacacattt ggtgggatga tgacaagcgc     180

tataatccag ccctgaagag ccgactgaca atctccaagg atacctccaa aaaccaggta     240

gtcctcacaa tgaccaacat ggaccctgtg gatactgcca catactactg tgctcaaata     300

aaccccgcct ggtttgctta ctggggccaa gggactctgg tcactgtgag ctca           354
```

<210> SEQ ID NO 82
<211> LENGTH: 111
<212> TYPE: PRT
<213> ORGANISM: homo sapiens

<400> SEQUENCE: 82

```
Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60
```

Arg Phe Ser Ala Ser Gly Ser Gly Thr Asp Phe Thr Leu Asn Ile His
65 70 75 80

Pro Val Glu Glu Glu Asp Thr Ala Thr Tyr Tyr Cys Gln Gln Ser Asn
85 90 95

Glu Asp Pro Tyr Thr Phe Gly Gly Gly Thr Lys Leu Glu Ile Lys
100 105 110

<210> SEQ ID NO 83
<211> LENGTH: 333
<212> TYPE: DNA
<213> ORGANISM: homo sapiens

<400> SEQUENCE: 83
gacactgtgc tgacccaatc tccagcttct ttggctgtgt ctctagggca gagggccacc 60
atctcctgca aggccagcca aagtgttgat tttgatggtg atagttttat gaactggtac 120
caacagaaac caggacagcc acccaaactc ctcatctata ctacatccaa tctagaatct 180
gggatcccag ccaggtttag tgccagtggg tctgggacag acttcaccct caacatccat 240
cctgtggagg aggaggatac tgcaacctat tactgtcagc aaagtaatga ggatccgtac 300
acgttcggag gggggaccaa gctggaaata aaa 333

<210> SEQ ID NO 84
<211> LENGTH: 332
<212> TYPE: DNA
<213> ORGANISM: Artificial Sequence
<220> FEATURE:
<223> OTHER INFORMATION: Humanized anti-CD16A light chain variable region Hu3G8VL-1

<400> SEQUENCE: 84
gacatcgtga tgacccaatc tccagactct ttggctgtgt ctctagggga gagggccacc 60
atcaactgca aggccagcca aagtgttgat tttgatggtg atagttttat gaactggtac 120
caacagaaac caggacagcc acccaaactc ctcatctata ctacatccaa tctagaatct 180
ggggtcccag acaggtttag tggcagtggg tctgggacag acttcaccct caccatcagc 240
agcctgcagg ctgaggatgt ggcagtttat tactgtcagc aaagtaatga ggatccgtac 300
acgttcggac aggggaccaa gcttgagatc aa 332

<210> SEQ ID NO 85
<211> LENGTH: 121
<212> TYPE: PRT
<213> ORGANISM: Artificial Sequence
<220> FEATURE:
<223> OTHER INFORMATION: Humanized 2B6 heavy chain variable region

<400> SEQUENCE: 85

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Ile His Trp Val Arg Gln Ala Pro Gly Gln Gly Leu Glu Trp Ile
35 40 45

Gly Val Ile Asp Pro Ser Asp Thr Tyr Pro Asn Tyr Asn Lys Lys Phe
50 55 60

Lys Gly Arg Val Thr Met Thr Val Val Val Ser Thr Ser Thr Ala Tyr
65 70 75 80

Met Glu Leu Arg Ser Leu Arg Ser Asp Asp Thr Ala Val Tyr Tyr Cys

```
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120


<210> SEQ ID NO 86
<211> LENGTH: 363
<212> TYPE: DNA
<213> ORGANISM: Artificial Sequence
<220> FEATURE:
<223> OTHER INFORMATION: humanized 2B6 heavy chain variable region

<400> SEQUENCE: 86

caggttcagc tggtgcagtc tggagctgag gtgaagaagc ctggggcctc agtgaaggtc      60

tcctgcaagg cttctggtta cacctttacc aactactgga tacactgggt gcgacaggcc     120

cctggacaag ggcttgagtg gattggagtg attgatcctt ctgatactta tccaaattac     180

aataaaaagt tcaagggcag agtcaccatg accgtagtcg tatccacgag cacagcctac     240

atggagctga ggagcctgag atctgacgac acggccgtgt attactgtgc gagaaacggt     300

gattccgatt attactctgg tatggactac tgggggcaag ggaccacggt caccgtctcc     360

tca                                                                   363


<210> SEQ ID NO 87
<211> LENGTH: 111
<212> TYPE: PRT
<213> ORGANISM: Artificial Sequence
<220> FEATURE:
<223> OTHER INFORMATION: Humanized 2B6 light chain variable region

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110


<210> SEQ ID NO 88
<211> LENGTH: 321
<212> TYPE: DNA
<213> ORGANISM: Artificial Sequence
<220> FEATURE:
<223> OTHER INFORMATION: humanized 2B6 light chain variable region

<400> SEQUENCE: 88

gaaattgtgc tgactcagtc tccagacttt cagtctgtga ctccaaagga gaaagtcacc      60

ttcacctgca ggaccagtca gagcattggc acaaacatac actggtacca gcagaaacca     120

gatcagtctc caaagctcct catcaaggag gtttctgagt ctatctctgg agtcccatcg     180
```

-continued aggttcagtg gcagtggatc tgggacagat ttcaccctca ccatcaatag cctggaagct 240
gaagatgctg caacgtatta ctgtcaacaa agtaatacct ggccgttcac gttcggcgga 300
gggaccaagg tggagatcaa a 321

<210> SEQ ID NO 89
<211> LENGTH: 6
<212> TYPE: PRT
<213> ORGANISM: Artificial Sequence
<220> FEATURE:
<223> OTHER INFORMATION: thrombin cleavage recognition site

<400> SEQUENCE: 89

Leu Val Pro Arg Gly Ser
1 5

<210> SEQ ID NO 90
<211> LENGTH: 4
<212> TYPE: PRT
<213> ORGANISM: Artificial Sequence
<220> FEATURE:
<223> OTHER INFORMATION: Factor Xa cleavage recognition site
<220> FEATURE:
<221> NAME/KEY: VARIANT
<222> LOCATION: (2)..(2)
<223> OTHER INFORMATION: Xaa=Glu or Asp

<400> SEQUENCE: 90

Ile Xaa Gly Arg
1

<210> SEQ ID NO 91
<211> LENGTH: 5
<212> TYPE: PRT
<213> ORGANISM: Artificial Sequence
<220> FEATURE:
<223> OTHER INFORMATION: enterokinase cleavage recognition site

<400> SEQUENCE: 91

Asp Asp Asp Asp Lys
1 5

<210> SEQ ID NO 92
<211> LENGTH: 4
<212> TYPE: PRT
<213> ORGANISM: Artificial Sequence
<220> FEATURE:
<223> OTHER INFORMATION: furin cleavage recognition site
<220> FEATURE:
<221> NAME/KEY: VARIANT
<222> LOCATION: (2)..(3)
<223> OTHER INFORMATION: Xaa=any amino acid

<400> SEQUENCE: 92

Arg Xaa Xaa Arg
1

<210> SEQ ID NO 93
<211> LENGTH: 4
<212> TYPE: PRT
<213> ORGANISM: Artificial Sequence
<220> FEATURE:
<223> OTHER INFORMATION: preferred furin cleavage recognition site
<220> FEATURE:
<221> NAME/KEY: VARIANT
<222> LOCATION: (2)..(2)
<223> OTHER INFORMATION: Xaa=any amino acid
<220> FEATURE:
<221> NAME/KEY: VARIANT
<222> LOCATION: (3)..(3)
<223> OTHER INFORMATION: Xaa=Lys or Arg

<400> SEQUENCE: 93

Arg Xaa Xaa Arg
1

<210> SEQ ID NO 94
<211> LENGTH: 7
<212> TYPE: PRT
<213> ORGANISM: Artificial Sequence
<220> FEATURE:
<223> OTHER INFORMATION: AcTEV cleavage recognition site

<400> SEQUENCE: 94

Gln Asn Leu Tyr Phe Gln Gly
1 5

<210> SEQ ID NO 95
<211> LENGTH: 487
<212> TYPE: PRT
<213> ORGANISM: Artificial Sequence
<220> FEATURE:
<223> OTHER INFORMATION: covalent diabody polyprotein precursor

<400> SEQUENCE: 95

Asp Thr Val Leu Thr Gln Ser Pro Ala Ser Leu Ala Val Ser Leu Gly
1 5 10 15

Gln Arg Ala Thr Ile Ser Cys Lys Ala Ser Gln Ser Val Asp Phe Asp
20 25 30

Gly Asp Ser Phe Met Asn Trp Tyr Gln Gln Lys Pro Gly Gln Pro Pro
35 40 45

Lys Leu Leu Ile Tyr Thr Thr Ser Asn Leu Glu Ser Gly Ile Pro Ala
50 55 60

Arg Phe Ser Ala Ser Gly Ser Gly Thr Asp Phe Thr Leu Asn Ile His
65 70 75 80

Pro Val Glu Glu Glu Asp Thr Ala Thr Tyr Tyr Cys Gln Gln Ser Asn
85 90 95

Glu Asp Pro Tyr Thr Phe Gly Gly Gly Thr Lys Leu Glu Ile Lys Gly
100 105 110

Gly Gly Ser Gly Gly Gly Gly Glu Val Glu Leu Val Glu Ser Gly Gly
115 120 125

Gly Leu Val Gln Pro Gly Arg Ser Leu Lys Leu Ser Cys Ala Ala Ser
130 135 140

Gly Phe Thr Phe Ser Asp Tyr Tyr Met Ala Trp Val Arg Gln Ala Pro
145 150 155 160

Thr Thr Gly Leu Glu Trp Val Ala Ser Ile Ser Tyr Asp Gly Gly Asp
165 170 175

Thr His Tyr Arg Asp Ser Val Lys Gly Arg Phe Thr Ile Ser Arg Asp
180 185 190

Asn Ala Lys Ser Ser Leu Tyr Leu Gln Met Asp Ser Leu Arg Ser Glu
195 200 205

Asp Thr Ala Thr Tyr Tyr Cys Ala Thr Glu Thr Thr Gly Ile Pro Thr
210 215 220

Gly Val Met Asp Ala Trp Gly Gln Gly Val Ser Val Thr Val Ser Ser
225 230 235 240

Leu Gly Gly Cys Gly Gly Arg Ala Lys Arg Asp Val Gln Met Thr Gln
245 250 255

-continued

```
Ser Pro Ser Asn Leu Ala Ala Ser Pro Gly Glu Ser Val Ser Ile Asn
            260                 265                 270

Cys Lys Ala Ser Glu Ser Ile Ser Lys Tyr Leu Ala Trp Tyr Leu Gln
        275                 280                 285

Lys Pro Gly Lys Ala Asn Lys Leu Leu Met Tyr Asp Gly Ser Thr Leu
    290                 295                 300

Gln Ser Gly Ile Pro Ser Arg Phe Ser Gly Ser Gly Ser Gly Thr Asp
305                 310                 315                 320

Phe Thr Leu Thr Ile Arg Ser Leu Glu Pro Glu Asp Phe Gly Leu Tyr
                325                 330                 335

Tyr Cys Gln Gln His Tyr Glu Tyr Pro Ala Thr Phe Gly Ser Gly Thr
            340                 345                 350

Lys Leu Glu Ile Lys Gly Gly Gly Ser Gly Gly Gly Gly Gln Val Thr
        355                 360                 365

Leu Lys Glu Ser Gly Pro Gly Ile Leu Gln Pro Ser Gln Thr Leu Ser
    370                 375                 380

Leu Thr Cys Ser Phe Ser Gly Phe Ser Leu Arg Thr Ser Gly Met Gly
385                 390                 395                 400

Val Gly Trp Ile Arg Gln Pro Ser Gly Lys Gly Leu Glu Trp Leu Ala
                405                 410                 415

His Ile Trp Trp Asp Asp Asp Lys Arg Tyr Asn Pro Ala Leu Lys Ser
            420                 425                 430

Arg Leu Thr Ile Ser Lys Asp Thr Ser Ser Asn Gln Val Phe Leu Lys
        435                 440                 445

Ile Ala Ser Val Asp Thr Ala Asp Thr Ala Thr Tyr Tyr Cys Ala Gln
    450                 455                 460

Ile Asn Pro Ala Trp Phe Ala Tyr Trp Gly Gln Gly Thr Leu Val Thr
465                 470                 475                 480

Val Ser Ser Leu Gly Gly Cys
                485


<210> SEQ ID NO 96
<211> LENGTH: 1464
<212> TYPE: DNA
<213> ORGANISM: Artificial Sequence
<220> FEATURE:
<223> OTHER INFORMATION: DNA sequence of SEQ ID NO:97 (covalent diabody
      polyprotein precursor)

<400> SEQUENCE: 96

gacactgtgc tgacccaatc tccagcttct ttggctgtgt ctctagggca gagggccacc      60

atctcctgca aggccagcca aagtgttgat tttgatggtg atagttttat gaactggtac     120

caacagaaac caggacagcc acccaaactc ctcatctata ctacatccaa tctagaatct     180

gggatcccag ccaggtttag tgccagtggg tctgggacag acttcaccct caacatccat     240

cctgtggagg aggaggatac tgcaacctat tactgtcagc aaagtaatga ggatccgtac     300

acgttcggag gggggaccaa gctggaaata aaaggaggcg gatccggagg cggaggcgag     360

gtggagctag tggagtctgg gggaggctta gtgcagcctg gaaggtccct gaaactctcg     420

tgtgcagcct caggattcac tttcagtgac tattacatgg cctgggtccg gcaggctcca     480

acgacgggtc tggagtgggt cgcatccatt agttatgatg gtggtgacac tcactatcga     540

gactccgtga agggccgatt tactatttcc agagataatg caaaaagcag cctatacctg     600

caaatggaca gtctgaggtc tgaggacacg gccacttatt actgtgcaac agagactacg     660

ggaataccta caggtgttat ggatgcctgg ggtcaaggag tttcagtcac tgtctcctca     720
```

```
ctgggaggct gcggcgggag agctaagagg gatgtccaga tgacccagtc tccatctaat    780

cttgctgcct ctcctggaga aagtgtttcc atcaattgca aggcaagtga gagcattagc    840

aagtatttag cctggtatct acagaaacct gggaaagcaa ataagcttct tatgtacgat    900

gggtcaactt tgcaatctgg aattccatcg aggttcagtg gcagtggatc tggtacagat    960

ttcactctca ccatcagaag cctggagcct gaagattttg gactctatta ctgtcaacag   1020

cattatgaat atccagccac gttcggttct gggaccaagc tggagatcaa aggaggcgga   1080

tccggaggcg gaggccaggt taccctgaaa gagtctggcc ctgggatatt gcagccctcc   1140

cagaccctca gtctgacttg ttctttctct gggttttcac tgaggacttc tggtatgggt   1200

gtaggctgga ttcgtcagcc ttcagggaag ggtctagagt ggctggcaca catttggtgg   1260

gatgatgaca agcgctataa tccagccctg aagagccgac tgacaatctc caaggatacc   1320

tccagcaacc aggtattcct caaaatcgcc agtgtggaca ctgcagatac tgccacatac   1380

tactgtgctc aaataaaccc cgcctggttt gcttactggg gccaagggac tctggtcact   1440

gtgagctcac tgggaggctg ctag                                          1464
```

<210> SEQ ID NO 97
<211> LENGTH: 511
<212> TYPE: PRT
<213> ORGANISM: Artificial Sequence
<220> FEATURE:
<223> OTHER INFORMATION: covalent diabody polyprotein precursor

<400> SEQUENCE: 97

```
Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys Gly
            100                 105                 110

Gly Gly Ser Gly Gly Gly Gly Glu Val Glu Leu Val Glu Ser Gly Gly
        115                 120                 125

Gly Leu Val Gln Pro Gly Arg Ser Leu Lys Leu Ser Cys Ala Ala Ser
    130                 135                 140

Gly Phe Thr Phe Ser Asp Tyr Tyr Met Ala Trp Val Arg Gln Ala Pro
145                 150                 155                 160

Thr Thr Gly Leu Glu Trp Val Ala Ser Ile Ser Tyr Asp Gly Gly Asp
                165                 170                 175

Thr His Tyr Arg Asp Ser Val Lys Gly Arg Phe Thr Ile Ser Arg Asp
            180                 185                 190

Asn Ala Lys Ser Ser Leu Tyr Leu Gln Met Asp Ser Leu Arg Ser Glu
        195                 200                 205

Asp Thr Ala Thr Tyr Tyr Cys Ala Thr Glu Thr Thr Gly Ile Pro Thr
    210                 215                 220
```

```
Gly Val Met Asp Ala Trp Gly Gln Gly Val Ser Val Thr Val Ser Ser
225                 230                 235                 240

Leu Gly Gly Cys Gly Gly Arg Ala Lys Arg Ala Pro Val Lys Gln Thr
                245                 250                 255

Leu Asn Phe Asp Leu Leu Lys Leu Ala Gly Asp Val Glu Ser Asn Pro
            260                 265                 270

Gly Pro Asp Val Gln Met Thr Gln Ser Pro Ser Asn Leu Ala Ala Ser
        275                 280                 285

Pro Gly Glu Ser Val Ser Ile Asn Cys Lys Ala Ser Glu Ser Ile Ser
    290                 295                 300

Lys Tyr Leu Ala Trp Tyr Leu Gln Lys Pro Gly Lys Ala Asn Lys Leu
305                 310                 315                 320

Leu Met Tyr Asp Gly Ser Thr Leu Gln Ser Gly Ile Pro Ser Arg Phe
                325                 330                 335

Ser Gly Ser Gly Ser Gly Thr Asp Phe Thr Leu Thr Ile Arg Ser Leu
            340                 345                 350

Glu Pro Glu Asp Phe Gly Leu Tyr Tyr Cys Gln Gln His Tyr Glu Tyr
        355                 360                 365

Pro Ala Thr Phe Gly Ser Gly Thr Lys Leu Glu Ile Lys Gly Gly Gly
    370                 375                 380

Ser Gly Gly Gly Gly Gln Val Thr Leu Lys Glu Ser Gly Pro Gly Ile
385                 390                 395                 400

Leu Gln Pro Ser Gln Thr Leu Ser Leu Thr Cys Ser Phe Ser Gly Phe
                405                 410                 415

Ser Leu Arg Thr Ser Gly Met Gly Val Gly Trp Ile Arg Gln Pro Ser
            420                 425                 430

Gly Lys Gly Leu Glu Trp Leu Ala His Ile Trp Trp Asp Asp Asp Lys
        435                 440                 445

Arg Tyr Asn Pro Ala Leu Lys Ser Arg Leu Thr Ile Ser Lys Asp Thr
    450                 455                 460

Ser Ser Asn Gln Val Phe Leu Lys Ile Ala Ser Val Asp Thr Ala Asp
465                 470                 475                 480

Thr Ala Thr Tyr Tyr Cys Ala Gln Ile Asn Pro Ala Trp Phe Ala Tyr
                485                 490                 495

Trp Gly Gln Gly Thr Leu Val Thr Val Ser Ser Leu Gly Gly Cys
            500                 505                 510
```

<210> SEQ ID NO 98
<211> LENGTH: 1536
<212> TYPE: DNA
<213> ORGANISM: Artificial Sequence
<220> FEATURE:
<223> OTHER INFORMATION: DNA sequence of SEQ ID NO:99 (covalent diabody polyprotein precursor)

<400> SEQUENCE: 98

```
gacactgtgc tgacccaatc tccagcttct ttggctgtgt ctctagggca gagggccacc      60

atctcctgca aggccagcca aagtgttgat tttgatggtg atagttttat gaactggtac     120

caacagaaac caggacagcc acccaaactc ctcatctata ctacatccaa tctagaatct     180

gggatcccag ccaggtttag tgccagtggg tctgggacag acttcaccct caacatccat     240

cctgtggagg aggaggatac tgcaacctat tactgtcagc aaagtaatga ggatccgtac     300

acgttcggag gggggaccaa gctggaaata aaaggaggcg gatccggagg cggaggcgag     360

gtggagctag tggagtctgg gggaggctta gtgcagcctg gaaggtccct gaaactctcg     420
```

```
tgtgcagcct caggattcac tttcagtgac tattacatgg cctgggtccg gcaggctcca    480

acgacgggtc tggagtgggt cgcatccatt agttatgatg gtggtgacac tcactatcga    540

gactccgtga agggccgatt tactatttcc agagataatg caaaaagcag cctatacctg    600

caaatggaca gtctgaggtc tgaggacacg gccacttatt actgtgcaac agagactacg    660

ggaataccta caggtgttat ggatgcctgg ggtcaaggag tttcagtcac tgtctcctca    720

ctgggaggct gcggcgggag agctaagagg gcccctgtga agcagaccct gaacttcgac    780

ctgctgaagc tggccggaga cgtggagagc aaccccggcc ccgatgtcca gatgacccag    840

tctccatcta atcttgctgc ctctcctgga gaaagtgttt ccatcaattg caaggcaagt    900

gagagcatta gcaagtattt agcctggtat ctacagaaac ctgggaaagc aaataagctt    960

cttatgtacg atgggtcaac tttgcaatct ggaattccat cgaggttcag tggcagtgga   1020

tctggtacag atttcactct caccatcaga agcctggagc ctgaagattt tggactctat   1080

tactgtcaac agcattatga atatccagcc acgttcggtt ctgggaccaa gctggagatc   1140

aaaggaggcg gatccggagg cggaggccag gttaccctga aagagtctgg ccctgggata   1200

ttgcagccct cccagaccct cagtctgact tgttctttct ctgggttttc actgaggact   1260

tctggtatgg gtgtaggctg gattcgtcag ccttcaggga agggtctaga gtggctggca   1320

cacatttggt gggatgatga caagcgctat aatccagccc tgaagagccg actgacaatc   1380

tccaaggata cctccagcaa ccaggtattc ctcaaaatcg ccagtgtgga cactgcagat   1440

actgccacat actactgtgc tcaaataaac cccgcctggt ttgcttactg gggccaaggg   1500

actctggtca ctgtgagctc actgggaggc tgctag                             1536
```

<210> SEQ ID NO 99
<211> LENGTH: 239
<212> TYPE: PRT
<213> ORGANISM: homo sapiens

<400> SEQUENCE: 99

```
Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys Gly Gly Gly Ser Gly
            100                 105                 110

Gly Gly Gly Gln Val Thr Leu Arg Glu Ser Gly Pro Ala Leu Val Lys
        115                 120                 125

Pro Thr Gln Thr Leu Thr Leu Thr Cys Thr Phe Ser Gly Phe Ser Leu
    130                 135                 140

Ser Thr Ser Gly Met Gly Val Gly Trp Ile Arg Gln Pro Pro Gly Lys
145                 150                 155                 160

Ala Leu Glu Trp Leu Ala His Ile Trp Trp Asp Asp Asp Lys Arg Tyr
                165                 170                 175
```

```
Asn Pro Ala Leu Lys Ser Arg Leu Thr Ile Ser Lys Asp Thr Ser Lys
            180                 185                 190

Asn Gln Val Val Leu Thr Met Thr Asn Met Asp Pro Val Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Phe Asn Arg Gly Glu Cys
225                 230                 235


<210> SEQ ID NO 100
<211> LENGTH: 720
<212> TYPE: DNA
<213> ORGANISM: homo sapiens

<400> SEQUENCE: 100

gaaattgtgc tgactcagtc tccagacttt cagtctgtga ctccaaagga gaaagtcacc      60

ttcacctgca ggaccagtca gagcattggc acaaacatac actggtacca gcagaaacca     120

gatcagtctc caaagctcct catcaaggag gtttctgagt ctatctctgg agtcccatcg     180

aggttcagtg gcagtggatc tgggacagat ttcaccctca ccatcaatag cctggaagct     240

gaagatgctg caacgtatta ctgtcaacaa agtaatacct ggccgttcac gttcggcgga     300

gggaccaagg tggagatcaa aggaggcgga tccggaggcg gaggccaggt taccctgaga     360

gagtctggcc ctgcgctggt gaagcccaca cagaccctca cactgacttg taccttctct     420

gggttttcac tgagcacttc tggtatgggt gtaggctgga ttcgtcagcc tcccgggaag     480

gctctagagt ggctggcaca catttggtgg gatgatgaca agcgctataa tccagccctg     540

aagagccgac tgacaatctc caaggatacc tccaaaaacc aggtagtcct cacaatgacc     600

aacatggacc ctgtggatac tgccacatac tactgtgctc aaataaaccc cgcctggttt     660

gcttactggg gccaagggac tctggtcact gtgagctcat tcaacagggg agagtgttag     720


<210> SEQ ID NO 101
<211> LENGTH: 246
<212> TYPE: PRT
<213> ORGANISM: Homo sapiens

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140
```

```
Gly Tyr Thr Phe Thr Asn Tyr Trp Ile His Trp Val Arg Gln Ala Pro
145                 150                 155                 160

Gly Gln Gly Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190

Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240

Val Glu Pro Lys Ser Cys
                245


<210> SEQ ID NO 102
<211> LENGTH: 741
<212> TYPE: DNA
<213> ORGANISM: Homo sapiens

<400> SEQUENCE: 102

gacatcgtga tgacccaatc tccagactct ttggctgtgt ctctagggga gagggccacc      60

atcaactgca aggccagcca aagtgttgat tttgatggtg atagttttat gaactggtac     120

caacagaaac caggacagcc acccaaactc ctcatctata ctacatccaa tctagaatct     180

ggggtcccag acaggtttag tggcagtggg tctgggacag acttcaccct caccatcagc     240

agcctgcagg ctgaggatgt ggcagtttat tactgtcagc aaagtaatga ggatccgtac     300

acgttcggac aggggaccaa gcttgagatc aaaggaggcg gatccggagg cggaggccag     360

gttcagctgg tgcagtctgg agctgaggtg aagaagcctg gggcctcagt gaaggtctcc     420

tgcaaggctt ctggttacac ctttaccaac tactggatac actgggtgcg acaggcccct     480

ggacaagggc ttgagtggat tggagtgatt gatccttctg atacttatcc aaattacaat     540

aaaaagttca agggcagagt caccatgacc gtagtcgtat ccacgagcac agcctacatg     600

gagctgagga gcctgagatc tgacgacacg gccgtgtatt actgtgcgag aaacggtgat     660

tccgattatt actctggtat ggactactgg gggcaaggga ccacggtcac cgtctcctca     720

gttgagccca aatcttgtta g                                               741


<210> SEQ ID NO 103
<211> LENGTH: 30
<212> TYPE: PRT
<213> ORGANISM: Artificial Sequence
<220> FEATURE:
<223> OTHER INFORMATION: VH Sequences Derived from 3G8 VH FR1

<400> SEQUENCE: 103

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg
            20                  25                  30


<210> SEQ ID NO 104
<211> LENGTH: 30
<212> TYPE: PRT
<213> ORGANISM: Artificial Sequence
<220> FEATURE:
<223> OTHER INFORMATION: VH Sequences Derived from 3G8 VH FR1
```

<400> SEQUENCE: 104

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Ser
20 25 30

<210> SEQ ID NO 105
<211> LENGTH: 30
<212> TYPE: PRT
<213> ORGANISM: Artificial Sequence
<220> FEATURE:
<223> OTHER INFORMATION: VH Sequences Derived from 3G8 VH FR1

<400> SEQUENCE: 105

Gln Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser
20 25 30

<210> SEQ ID NO 106
<211> LENGTH: 30
<212> TYPE: PRT
<213> ORGANISM: Artificial Sequence
<220> FEATURE:
<223> OTHER INFORMATION: VH Sequences Derived from 3G8 VH FR1

<400> SEQUENCE: 106

Gln Val Thr Leu Arg Glu Ser Gly Pro Ala Leu Val Lys Pro Thr Gln
1 5 10 15

Thr Leu Thr Leu Thr Cys Thr Phe Ser Gly Phe Ser Leu Arg
20 25 30

<210> SEQ ID NO 107
<211> LENGTH: 30
<212> TYPE: PRT
<213> ORGANISM: Artificial Sequence
<220> FEATURE:
<223> OTHER INFORMATION: VH Sequences Derived from 3G8 VH FR1

<400> SEQUENCE: 107

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser
20 25 30

<210> SEQ ID NO 108
<211> LENGTH: 7
<212> TYPE: PRT
<213> ORGANISM: Artificial Sequence
<220> FEATURE:
<223> OTHER INFORMATION: VH Sequences Derived from 3G8 VH * CDR1

<400> SEQUENCE: 108

Thr Ser Gly Met Gly Val Gly
1 5

<210> SEQ ID NO 109
<211> LENGTH: 7
<212> TYPE: PRT
<213> ORGANISM: Artificial Sequence
<220> FEATURE:
<223> OTHER INFORMATION: VH Sequences Derived from 3G8 VH * CDR1

<400> SEQUENCE: 109

Thr Ser Gly Val Gly Val Gly
1 5

<210> SEQ ID NO 110
<211> LENGTH: 14
<212> TYPE: PRT
<213> ORGANISM: Artificial Sequence
<220> FEATURE:
<223> OTHER INFORMATION: VH Sequences Derived from 3G8 VH * FR2

<400> SEQUENCE: 110

Trp Ile Arg Gln Pro Ser Gly Lys Gly Leu Glu Trp Leu Ala
1 5 10

<210> SEQ ID NO 111
<211> LENGTH: 14
<212> TYPE: PRT
<213> ORGANISM: Artificial Sequence
<220> FEATURE:
<223> OTHER INFORMATION: VH Sequences Derived from 3G8 VH * FR2

<400> SEQUENCE: 111

Trp Ile Arg Gln Pro Pro Gly Lys Ala Leu Glu Trp Leu Ala
1 5 10

<210> SEQ ID NO 112
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 112

His Ile Trp Trp Asp Asp Asp Lys Arg Tyr Asn Pro Ala Leu Lys Ser
1 5 10 15

<210> SEQ ID NO 113
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 113

His Ile Tyr Trp Asn Asp Asp Lys Arg Tyr Asn Pro Ala Leu Lys Ser
1 5 10 15

<210> SEQ ID NO 114
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 114

His Ile Trp Trp Asp Asp Asp Lys Arg Tyr Ser Pro Ser Leu Lys Ser
1 5 10 15

<210> SEQ ID NO 115
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 115

His Ile Tyr Trp Asp Asp Asp Lys Arg Tyr Asn Pro Ala Leu Lys Ser 1 5 10 15

<210> SEQ ID NO 116
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 116

His Ile Trp Trp Asn Asp Asp Lys Arg Tyr Asn Pro Ala Leu Lys Ser
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 117

Leu Ile Asp Trp Asp Asp Asp Lys Arg Tyr Ser Pro Ser Leu Lys Ser
1 5 10 15

<210> SEQ ID NO 118
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 118

His Ile Phe Trp Asp Asp Asp Lys Arg Tyr Ser Pro Ser Leu Lys Ser
1 5 10 15

<210> SEQ ID NO 119
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 119

Leu Ile Trp Trp Asp Asp Asp Lys Arg Tyr Ser Pro Ser Leu Lys Ser
1 5 10 15

<210> SEQ ID NO 120
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 120

His Ile Asp Trp Asp Asp Asp Lys Arg Tyr Ser Pro Ser Leu Lys Ser
1 5 10 15

<210> SEQ ID NO 121
<211> LENGTH: 16
<212> TYPE: PRT
<213> ORGANISM: Artificial Sequence
<220> FEATURE:
<223> OTHER INFORMATION: VH Sequences Derived from 3G8 VH * CDR2

<400> SEQUENCE: 121

Leu Ile Trp Trp Asn Asp Asp Lys Arg Tyr Ser Pro Ser Leu Lys Ser
1 5 10 15

<210> SEQ ID NO 122
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 122

Arg Leu Thr Ile Ser Lys Asp Thr Ser Ser Asn Gln Val Phe Leu Lys
1 5 10 15

Ile Asp Thr Ala Asp Thr Ala Thr Tyr Tyr Cys Ala Gln
20 25

<210> SEQ ID NO 123
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 123

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Arg
20 25

<210> SEQ ID NO 124
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 124

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Gln
20 25

<210> SEQ ID NO 125
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 125

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Thr
20 25

<210> SEQ ID NO 126
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 126

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Lys 20 25

<210> SEQ ID NO 127
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 127

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Ala
20 25

<210> SEQ ID NO 128
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 128

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala His
20 25

<210> SEQ ID NO 129
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 129

Arg Leu Thr Ile Thr Lys Asp Thr Ser Lys Asn Gln Val Val Leu Thr
1 5 10 15

Met Asp Pro Val Asp Thr Ala Thr Tyr Tyr Cys Ala Arg
20 25

<210> SEQ ID NO 130
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 130

Arg Leu Thr Ile Thr Lys Asp Thr Ser Lys Asn Gln Val Val Leu Thr
1 5 10 15

Met Asp Pro Val Asp Thr Ala Thr Tyr Tyr Cys Ala His
20 25

<210> SEQ ID NO 131
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 131

Arg Leu Thr Ile Thr Lys Asp Thr Ser Lys Asn Gln Val Val Leu Thr
1 5 10 15

```
Met Asp Pro Val Asp Thr Ala Thr Tyr Tyr Cys Ala Gln
            20                  25


<210> SEQ ID NO 132
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 132

Arg Leu Thr Ile Ser Lys Asp Thr Ser Ser Asn Gln Val Phe Leu Lys
1               5                   10                  15

Ala Asp Thr Ala Asp Thr Ala Thr Tyr Tyr Cys Ala Gln
            20                  25


<210> SEQ ID NO 133
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 133

Arg Leu Thr Ile Ser Lys Asp Thr Ser Lys Asn Gln Val Val Leu Thr
1               5                   10                  15

Thr Asp Pro Val Asp Thr Ala Thr Tyr Tyr Cys Ala Arg
            20                  25


<210> SEQ ID NO 134
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 134

Arg Leu Thr Ile Ser Lys Asp Thr Ser Lys Asn Gln Val Val Leu Thr
1               5                   10                  15

Thr Asp Pro Val Asp Thr Ala Thr Tyr Tyr Cys Ala Gln
            20                  25


<210> SEQ ID NO 135
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 135

Arg Leu Thr Ile Ser Lys Asp Thr Ser Lys Asn Gln Val Val Leu Thr
1               5                   10                  15

Thr Asp Pro Val Asp Thr Ala Thr Tyr Tyr Cys Ala Thr
            20                  25


<210> SEQ ID NO 136
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 136

Arg Leu Thr Ile Ser Lys Asp Thr Ser Lys Asn Gln Val Val Leu Thr
1               5                   10                  15
```

Thr Asp Pro Val Asp Thr Ala Thr Tyr Tyr Cys Ala Lys
20 25

<210> SEQ ID NO 137
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 137

Arg Leu Thr Ile Ser Lys Asp Thr Ser Lys Asn Gln Val Val Leu Thr
1 5 10 15

Thr Asp Pro Val Asp Thr Ala Thr Tyr Tyr Cys Ala Ala
20 25

<210> SEQ ID NO 138
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 138

Arg Leu Thr Ile Ser Lys Asp Thr Ser Lys Asn Gln Val Val Leu Thr
1 5 10 15

Thr Asp Pro Val Asp Thr Ala Thr Tyr Tyr Cys Ala His
20 25

<210> SEQ ID NO 139
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 139

Arg Leu Thr Ile Thr Lys Asp Thr Ser Lys Asn Gln Val Val Leu Thr
1 5 10 15

Thr Asp Pro Val Asp Thr Ala Thr Tyr Tyr Cys Ala Arg
20 25

<210> SEQ ID NO 140
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 140

Arg Leu Thr Ile Thr Lys Asp Thr Ser Lys Asn Gln Val Val Leu Thr
1 5 10 15

Thr Asp Pro Val Asp Thr Ala Thr Tyr Tyr Cys Ala His
20 25

<210> SEQ ID NO 141
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 141

Arg Leu Thr Ile Thr Lys Asp Thr Ser Lys Asn Gln Val Val Leu Thr

```
1               5                   10                  15

Thr Asp Pro Val Asp Thr Ala Thr Tyr Tyr Cys Ala Gln
            20                  25


<210> SEQ ID NO 142
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 142

Arg Leu Thr Ile Ser Lys Asp Thr Ser Ser Asn Gln Val Phe Leu Lys
1               5                   10                  15

Ser Asp Thr Ala Asp Thr Ala Thr Tyr Tyr Cys Ala Gln
            20                  25


<210> SEQ ID NO 143
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 143

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala Arg
            20                  25


<210> SEQ ID NO 144
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 144

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala Gln
            20                  25


<210> SEQ ID NO 145
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 145

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala Thr
            20                  25


<210> SEQ ID NO 146
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 146
```

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala Lys
            20                  25

<210> SEQ ID NO 147
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 147

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala Ala
            20                  25

<210> SEQ ID NO 148
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 148

Arg Leu Thr Ile Ser Lys Asp Thr Ser Lys Asn Gln Val Val Leu Thr
1               5                   10                  15

Asn Asp Pro Val Asp Thr Ala Thr Tyr Tyr Cys Ala His
            20                  25

<210> SEQ ID NO 149
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 149

Arg Leu Thr Ile Thr Lys Asp Thr Ser Lys Asn Gln Val Val Leu Thr
1               5                   10                  15

Asn Asp Pro Val Asp Thr Ala Thr Tyr Tyr Cys Ala Arg
            20                  25

<210> SEQ ID NO 150
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 150

Arg Leu Thr Ile Thr Lys Asp Thr Ser Lys Asn Gln Val Val Leu Thr
1               5                   10                  15

Asn Asp Pro Val Asp Thr Ala Thr Tyr Tyr Cys Ala His
            20                  25

<210> SEQ ID NO 151
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 151

Arg Leu Thr Ile Thr Lys Asp Thr Ser Lys Asn Gln Val Val Leu Thr
1 5 10 15

Asn Asp Pro Val Asp Thr Ala Thr Tyr Tyr Cys Ala Gln
20 25

<210> SEQ ID NO 152
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 152

Arg Leu Thr Ile Ser Lys Asp Thr Ser Ser Asn Gln Val Phe Leu Lys
1 5 10 15

Val Asp Thr Ala Asp Thr Ala Thr Tyr Tyr Cys Ala Gln
20 25

<210> SEQ ID NO 153
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 153

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Arg
20 25

<210> SEQ ID NO 154
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 154

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Gln
20 25

<210> SEQ ID NO 155
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 155

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Thr
20 25

<210> SEQ ID NO 156
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 156

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Lys
20 25

<210> SEQ ID NO 157
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 157

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala Ala
20 25

<210> SEQ ID NO 158
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 158

Arg Leu Thr Ile Ser Lys Asp Thr Ser Lys Asn Gln Val Val Leu Thr
1 5 10 15

Met Asp Pro Val Asp Thr Ala Thr Tyr Tyr Cys Ala His
20 25

<210> SEQ ID NO 159
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 159

Arg Leu Thr Ile Thr Lys Asp Thr Ser Lys Asn Gln Val Val Leu Thr
1 5 10 15

Met Asp Pro Val Asp Thr Ala Thr Tyr Tyr Cys Ala Arg
20 25

<210> SEQ ID NO 160
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 160

Arg Leu Thr Ile Thr Lys Asp Thr Ser Lys Asn Gln Val Val Leu Thr
1 5 10 15

Met Asp Pro Val Asp Thr Ala Thr Tyr Tyr Cys Ala His
20 25

<210> SEQ ID NO 161
<211> LENGTH: 29
<212> TYPE: PRT
<213> ORGANISM: Artificial Sequence
<220> FEATURE:
<223> OTHER INFORMATION: VH Sequences Derived from 3G8 VH * FR3

<400> SEQUENCE: 161

Arg Leu Thr Ile Thr Lys Asp Thr Ser Lys Asn Gln Val Val Leu Thr
1 5 10 15

Met Asp Pro Val Asp Thr Ala Thr Tyr Tyr Cys Ala Gln
20 25

<210> SEQ ID NO 162
<211> LENGTH: 8
<212> TYPE: PRT
<213> ORGANISM: Artificial Sequence
<220> FEATURE:
<223> OTHER INFORMATION: VH Sequences Derived from 3G8 VH * CDR3

<400> SEQUENCE: 162

Ile Asn Pro Ala Trp Phe Ala Tyr
1 5

<210> SEQ ID NO 163
<211> LENGTH: 8
<212> TYPE: PRT
<213> ORGANISM: Artificial Sequence
<220> FEATURE:
<223> OTHER INFORMATION: VH Sequences Derived from 3G8 VH * CDR3

<400> SEQUENCE: 163

Ile Asn Pro Ala Trp Phe Asp Tyr
1 5

<210> SEQ ID NO 164
<211> LENGTH: 8
<212> TYPE: PRT
<213> ORGANISM: Artificial Sequence
<220> FEATURE:
<223> OTHER INFORMATION: VH Sequences Derived from 3G8 VH * CDR3

<400> SEQUENCE: 164

Ile Asn Pro Ala Tyr Phe Ala Tyr
1 5

<210> SEQ ID NO 165
<211> LENGTH: 8
<212> TYPE: PRT
<213> ORGANISM: Artificial Sequence
<220> FEATURE:
<223> OTHER INFORMATION: VH Sequences Derived from 3G8 VH * CDR3

<400> SEQUENCE: 165

Ile Asn Pro Ala Tyr Phe Asp Tyr
1 5

<210> SEQ ID NO 166
<211> LENGTH: 11
<212> TYPE: PRT
<213> ORGANISM: Artificial Sequence
<220> FEATURE:
<223> OTHER INFORMATION: VH Sequences Derived from 3G8 VH * FR4

<400> SEQUENCE: 166

Trp Gly Gln Gly Thr Leu Val Thr Val Ser Ala
1 5 10

<210> SEQ ID NO 167
<211> LENGTH: 11
<212> TYPE: PRT
<213> ORGANISM: Artificial Sequence -continued
<220> FEATURE:
<223> OTHER INFORMATION: VH Sequences Derived from 3G8 VH * FR4

<400> SEQUENCE: 167

Trp Gly Gln Gly Thr Leu Val Thr Val Ser Ser
1 5 10

<210> SEQ ID NO 168
<211> LENGTH: 15
<212> TYPE: PRT
<213> ORGANISM: Artificial Sequence
<220> FEATURE:
<223> OTHER INFORMATION: VL Sequences Derived from 3G8 VL* FR1

<400> SEQUENCE: 168

Asp Thr Val Leu Thr Gln Ser Pro Ala Ser Leu Ala Val Ser Leu
1 5 10 15

<210> SEQ ID NO 169
<211> LENGTH: 15
<212> TYPE: PRT
<213> ORGANISM: Artificial Sequence
<220> FEATURE:
<223> OTHER INFORMATION: VL Sequences Derived from 3G8 VL* FR1

<400> SEQUENCE: 169

Asp Ile Val Met Thr Gln Ser Pro Asp Ser Leu Ala Val Ser Leu
1 5 10 15

<210> SEQ ID NO 170
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 170

Lys Ala Ser Gln Asp Gly Asp Ser Phe Met Asn
1 5 10

<210> SEQ ID NO 171
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 171

Arg Ala Ser Gln Asp Gly Asp Ser Phe Met Asn
1 5 10

<210> SEQ ID NO 172
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 172

Lys Ser Ser Gln Asp Gly Asp Ser Phe Met Asn
1 5 10

<210> SEQ ID NO 173
<211> LENGTH: 11
<212> TYPE: PRT
<213> ORGANISM: Artificial Sequence
<220> FEATURE:

<223> OTHER INFORMATION: VL Sequences Derived from 3G8 VL* CDR1

<400> SEQUENCE: 173

Lys Ala Ser Gln Asp Gly Asp Ser Tyr Met Asn
1 5 10

<210> SEQ ID NO 174
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 174

Lys Ala Ser Gln Asp Gly Asp Ser Phe Leu Asn
1 5 10

<210> SEQ ID NO 175
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 175

Lys Ala Ser Gln Asp Gly Asp Ser Phe Met Ala
1 5 10

<210> SEQ ID NO 176
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 176

Lys Ala Ser Gln Asp Gly Asp Ser Tyr Leu Ala
1 5 10

<210> SEQ ID NO 177
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 177

Lys Ala Ser Ser Asp Gly Asp Ser Phe Met Asn
1 5 10

<210> SEQ ID NO 178
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 178

Arg Ala Ser Ser Asp Gly Asp Ser Phe Met Asn
1 5 10

<210> SEQ ID NO 179
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 179

Lys Ser Ser Ser Asp Gly Asp Ser Phe Met Asn
1               5                   10

<210> SEQ ID NO 180
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 180

Lys Ala Ser Ser Asp Gly Asp Ser Tyr Met Asn
1               5                   10

<210> SEQ ID NO 181
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 181

Lys Ala Ser Ser Asp Gly Asp Ser Phe Leu Asn
1               5                   10

<210> SEQ ID NO 182
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 182

Lys Ala Ser Ser Asp Gly Asp Ser Phe Met Ala
1               5                   10

<210> SEQ ID NO 183
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 183

Lys Ala Ser Ser Asp Gly Asp Ser Tyr Leu Ala
1               5                   10

<210> SEQ ID NO 184
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 184

Lys Ala Ser Val Asp Gly Asp Ser Phe Met Asn
1               5                   10

<210> SEQ ID NO 185
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 185

Arg Ala Ser Val Asp Gly Asp Ser Phe Met Asn
1 5 10

<210> SEQ ID NO 186
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 186

Lys Ser Ser Val Asp Gly Asp Ser Phe Met Asn
1 5 10

<210> SEQ ID NO 187
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 187

Lys Ala Ser Val Asp Gly Asp Ser Tyr Met Asn
1 5 10

<210> SEQ ID NO 188
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 188

Lys Ala Ser Val Asp Gly Asp Ser Phe Leu Asn
1 5 10

<210> SEQ ID NO 189
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 189

Lys Ala Ser Val Asp Gly Asp Ser Phe Met Ala
1 5 10

<210> SEQ ID NO 190
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 190

Lys Ala Ser Val Asp Gly Asp Ser Tyr Leu Ala
1 5 10

<210> SEQ ID NO 191
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 191

Lys Ala Ser Asp Asp Gly Asp Ser Phe Met Asn
1 5 10

<210> SEQ ID NO 192
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 192

Arg Ala Ser Asp Asp Gly Asp Ser Phe Met Asn
1 5 10

<210> SEQ ID NO 193
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 193

Lys Ser Ser Asp Asp Gly Asp Ser Phe Met Asn
1 5 10

<210> SEQ ID NO 194
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 194

Lys Ala Ser Asp Asp Gly Asp Ser Tyr Met Asn
1 5 10

<210> SEQ ID NO 195
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 195

Lys Ala Ser Asp Asp Gly Asp Ser Phe Leu Asn
1 5 10

<210> SEQ ID NO 196
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 196

Lys Ala Ser Asp Asp Gly Asp Ser Phe Met Ala
1 5 10

<210> SEQ ID NO 197
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 197

Lys Ala Ser Asp Asp Gly Asp Ser Tyr Leu Ala
1 5 10

<210> SEQ ID NO 198
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 198

Lys Ala Ser Phe Asp Gly Asp Ser Phe Met Asn
1 5 10

<210> SEQ ID NO 199
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 199

Arg Ala Ser Phe Asp Gly Asp Ser Phe Met Asn
1 5 10

<210> SEQ ID NO 200
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 200

Lys Ser Ser Phe Asp Gly Asp Ser Phe Met Asn
1 5 10

<210> SEQ ID NO 201
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 201

Lys Ala Ser Phe Asp Gly Asp Ser Tyr Met Asn
1 5 10

<210> SEQ ID NO 202
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 202

Lys Ala Ser Phe Asp Gly Asp Ser Phe Leu Asn
1 5 10

<210> SEQ ID NO 203
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 203

Lys Ala Ser Phe Asp Gly Asp Ser Phe Met Ala 1 5 10

<210> SEQ ID NO 204
<211> LENGTH: 11
<212> TYPE: PRT
<213> ORGANISM: Artificial Sequence
<220> FEATURE:
<223> OTHER INFORMATION: VL Sequences Derived from 3G8 VL* CDR1

<400> SEQUENCE: 204

Lys Ala Ser Phe Asp Gly Asp Ser Tyr Leu Ala
1 5 10

<210> SEQ ID NO 205
<211> LENGTH: 16
<212> TYPE: PRT
<213> ORGANISM: Artificial Sequence
<220> FEATURE:
<223> OTHER INFORMATION: VL Sequences Derived from 3G8 VL* FR2

<400> SEQUENCE: 205

Trp Tyr Gln Gln Lys Ala Pro Gly Gln Pro Pro Lys Leu Leu Ile Tyr
1 5 10 15

<210> SEQ ID NO 206
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 206

Thr Thr Ser Asn Leu Glu Ser
1 5

<210> SEQ ID NO 207
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 207

Asp Ala Ser Asn Leu Glu Ser
1 5

<210> SEQ ID NO 208
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 208

Trp Ala Ser Asn Leu Glu Ser
1 5

<210> SEQ ID NO 209
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 209

Thr Thr Ser Asn Leu Glu Thr
1 5

<210> SEQ ID NO 210
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 210

Asp Ala Ser Asn Leu Glu Thr
1 5

<210> SEQ ID NO 211
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 211

Asp Ala Ser Asn Leu Ala Thr
1 5

<210> SEQ ID NO 212
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 212

Ser Ala Ser Asn Leu Gln Ser
1 5

<210> SEQ ID NO 213
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 213

Ser Thr Ser Asn Leu Glu Ser
1 5

<210> SEQ ID NO 214
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 214

Ser Thr Ser Asn Leu Gln Ser
1 5

<210> SEQ ID NO 215
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 215

Thr Thr Ser Asn Leu Gln Ser
1 5

<210> SEQ ID NO 216
<211> LENGTH: 7
<212> TYPE: PRT
<213> ORGANISM: Artificial Sequence
<220> FEATURE:
<223> OTHER INFORMATION: VL Sequences Derived from 3G8 VL* CDR2

<400> SEQUENCE: 216

Thr Thr Ser Ser Leu Gln Ser
1 5

<210> SEQ ID NO 217
<211> LENGTH: 32
<212> TYPE: PRT
<213> ORGANISM: Artificial Sequence
<220> FEATURE:
<223> OTHER INFORMATION: VL Sequences Derived from 3G8 VL* FR3

<400> SEQUENCE: 217

Gly Ile Pro Ala Arg Phe Ser Ala Ser Gly Ser Gly Thr Asp Phe Thr
1 5 10 15

Leu Asn Ile His Pro Val Glu Glu Glu Asp Thr Ala Thr Tyr Tyr Cys
20 25 30

<210> SEQ ID NO 218
<211> LENGTH: 32
<212> TYPE: PRT
<213> ORGANISM: Artificial Sequence
<220> FEATURE:
<223> OTHER INFORMATION: VL Sequences Derived from 3G8 VL* FR3

<400> SEQUENCE: 218

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 219
<211> LENGTH: 9
<212> TYPE: PRT
<213> ORGANISM: Artificial Sequence
<220> FEATURE:
<223> OTHER INFORMATION: VL Sequences Derived from 3G8 VL* CDR3

<400> SEQUENCE: 219

Gln Gln Ser Asn Glu Asp Pro Tyr Thr
1 5

<210> SEQ ID NO 220
<211> LENGTH: 9
<212> TYPE: PRT
<213> ORGANISM: Artificial Sequence
<220> FEATURE:
<223> OTHER INFORMATION: VL Sequences Derived from 3G8 VL* CDR3

<400> SEQUENCE: 220

Gln Gln Ser Tyr Ser Thr Pro Tyr Thr
1 5

<210> SEQ ID NO 221
<211> LENGTH: 9
<212> TYPE: PRT
<213> ORGANISM: Artificial Sequence
<220> FEATURE:
<223> OTHER INFORMATION: VL Sequences Derived from 3G8 VL* CDR3

<400> SEQUENCE: 221

Gln Gln Ser Tyr Glu Asp Pro Tyr Thr
1 5

<210> SEQ ID NO 222
<211> LENGTH: 9
<212> TYPE: PRT
<213> ORGANISM: Artificial Sequence
<220> FEATURE:
<223> OTHER INFORMATION: VL Sequences Derived from 3G8 VL* CDR3

<400> SEQUENCE: 222

Gln Gln Ser Asn Ser Asp Pro Tyr Thr
1 5

<210> SEQ ID NO 223
<211> LENGTH: 9
<212> TYPE: PRT
<213> ORGANISM: Artificial Sequence
<220> FEATURE:
<223> OTHER INFORMATION: VL Sequences Derived from 3G8 VL* CDR3

<400> SEQUENCE: 223

Gln Gln Ser Asn Glu Thr Pro Tyr Thr
1 5

<210> SEQ ID NO 224
<211> LENGTH: 10
<212> TYPE: PRT
<213> ORGANISM: Artificial Sequence
<220> FEATURE:
<223> OTHER INFORMATION: VL Sequences Derived from 3G8 VL* FR4

<400> SEQUENCE: 224

Phe Gly Gly Gly Thr Lys Leu Glu Ile Lys
1 5 10

<210> SEQ ID NO 225
<211> LENGTH: 10
<212> TYPE: PRT
<213> ORGANISM: Artificial Sequence
<220> FEATURE:
<223> OTHER INFORMATION: VL Sequences Derived from 3G8 VL* FR4

<400> SEQUENCE: 225

Phe Gly Gln Gly Thr Lys Leu Glu Ile Lys
1 5 10

<210> SEQ ID NO 226
<211> LENGTH: 714
<212> TYPE: DNA
<213> ORGANISM: Artificial Sequence
<220> FEATURE:
<223> OTHER INFORMATION: H3G8VL-CB3.1VH

<400> SEQUENCE: 226
gacatcgtga tgacccaatc tccagactct ttggctgtgt ctctagggga gagggccacc 60
atcaactgca aggccagcca aagtgttgat tttgatggtg atagttttat gaactggtac 120
caacagaaac caggacagcc acccaaactc ctcatctata ctacatccaa tctagaatct 180
ggggtcccag acaggtttag tggcagtggg tctgggacag acttcaccct caccatcagc 240
agcctgcagg ctgaggatgt ggcagtttat tactgtcagc aaagtaatga ggatccgtac 300
acgttcggac aggggaccaa gcttgagatc aaaggaggcg gatccggagg cggaggccag 360

-continued gtccaactgc agcagcctgg ggctgagctg gtgaggcctg gggcttcagt gaagctgtcc 420
tgcaaggctt ctggctacac cttcaccagc tactggatga actgggtgaa gcagaggcct 480
ggacaaggcc ttgaatggat tggtatggtt gatccttcag acagtgaaac tcactacaat 540
caaatgttca aggacaaggc cacattgact gttgacaaat cctccagcac agcctacatg 600
cagctcagca gcctgacatc tgaggactct gcggtctatt actgtgcaag agctatgggc 660
tactggggtc aaggaacctc agtcaccgtc tcctcagttg agcccaaatc ttgt 714

<210> SEQ ID NO 227
<211> LENGTH: 238
<212> TYPE: PRT
<213> ORGANISM: Artificial Sequence
<220> FEATURE:
<223> OTHER INFORMATION: H3G8VL-CB3.1VH

<400> SEQUENCE: 227

Asp Ile Val Met Thr Gln Ser Pro Asp Ser Leu Ala Val Ser Leu Gly
1 5 10 15

Glu Arg Ala Thr Ile Asn Cys Lys Ala Ser Gln Ser Val Asp Phe Asp
20 25 30

Gly Asp Ser Phe Met Asn Trp Tyr Gln Gln Lys Pro Gly Gln Pro Pro
35 40 45

Lys Leu Leu Ile Tyr Thr Thr Ser Asn Leu Glu Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Gln Ser Asn
85 90 95

Glu Asp Pro Tyr Thr Phe Gly Gln Gly Thr Lys Leu Glu Ile Lys Gly
100 105 110

Gly Gly Ser Gly Gly Gly Gly Gln Val Gln Leu Gln Gln Pro Gly Ala
115 120 125

Glu Leu Val Arg Pro Gly Ala Ser Val Lys Leu Ser Cys Lys Ala Ser
130 135 140

Gly Tyr Thr Phe Thr Ser Tyr Trp Met Asn Trp Val Lys Gln Arg Pro
145 150 155 160

Gly Gln Gly Leu Glu Trp Ile Gly Met Val Asp Pro Ser Asp Ser Glu
165 170 175

Thr His Tyr Asn Gln Met Phe Lys Asp Lys Ala Thr Leu Thr Val Asp
180 185 190

Lys Ser Ser Ser Thr Ala Tyr Met Gln Leu Ser Ser Leu Thr Ser Glu
195 200 205

Asp Ser Ala Val Tyr Tyr Cys Ala Arg Ala Met Gly Tyr Trp Gly Gln
210 215 220

Gly Thr Ser Val Thr Val Ser Ser Val Glu Pro Lys Ser Cys
225 230 235

<210> SEQ ID NO 228
<211> LENGTH: 732
<212> TYPE: DNA
<213> ORGANISM: Artificial Sequence
<220> FEATURE:
<223> OTHER INFORMATION: CB3.1VL-h3G8VH

<400> SEQUENCE: 228
gatgttgtga tgacccagac tccactcact ttgtcggtta acattggaca accagcctcc 60

```
atctcttgta agtcaagtca gagcctctta gatactgatg gaaagacata tttgaattgg    120

ttgttacaga ggccaggcca gtctccaaac cgcctaatct atctggtgtc taaactggac    180

tctggagtcc ctgacaggtt cactggcagt ggatcaggga cagatttcac actgaaaatc    240

agcagagtgg aggctgagga tttgggaatt tattattgct ggcaaggtac acattttccg    300

ctcacgttcg gtgctgggac caagctggag ctgaaaggag gcggatccgg aggcggaggc    360

caggttaccc tgagagagtc tggccctgcg ctggtgaagc ccacacagac cctcacactg    420

acttgtacct tctctgggtt ttcactgagc acttctggta tgggtgtagg ctggattcgt    480

cagcctcccg ggaaggctct agagtggctg gcacacattt ggtgggatga tgacaagcgc    540

tataatccag ccctgaagag ccgactgaca atctccaagg atacctccaa aaaccaggta    600

gtcctcacaa tgaccaacat ggaccctgtg gatactgcca catactactg tgctcaaata    660

aaccccgcct ggtttgctta ctggggccaa gggactctgg tcactgtgag ctcattcaac    720

aggggagagt gt                                                        732
```

```
<210> SEQ ID NO 229
<211> LENGTH: 244
<212> TYPE: PRT
<213> ORGANISM: Artificial Sequence
<220> FEATURE:
<223> OTHER INFORMATION: CB3.1VL-h3G8VH

<400> SEQUENCE: 229

Asp Val Val Met Thr Gln Thr Pro Leu Thr Leu Ser Val Asn Ile Gly
1               5                   10                  15

Gln Pro Ala Ser Ile Ser Cys Lys Ser Ser Gln Ser Leu Leu Asp Thr
            20                  25                  30

Asp Gly Lys Thr Tyr Leu Asn Trp Leu Leu Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Leu Thr Phe Gly Ala Gly Thr Lys Leu Glu Leu Lys
            100                 105                 110

Gly Gly Gly Ser Gly Gly Gly Gly Gln Val Thr Leu Arg Glu Ser Gly
        115                 120                 125

Pro Ala Leu Val Lys Pro Thr Gln Thr Leu Thr Leu Thr Cys Thr Phe
    130                 135                 140

Ser Gly Phe Ser Leu Ser Thr Ser Gly Met Gly Val Gly Trp Ile Arg
145                 150                 155                 160

Gln Pro Pro Gly Lys Ala Leu Glu Trp Leu Ala His Ile Trp Trp Asp
                165                 170                 175

Asp Asp Lys Arg Tyr Asn Pro Ala Leu Lys Ser Arg Leu Thr Ile Ser
            180                 185                 190

Lys Asp Thr Ser Lys Asn Gln Val Val Leu Thr Met Thr Asn Met Asp
        195                 200                 205

Pro Val Asp Thr Ala Thr Tyr Tyr Cys Ala Gln Ile Asn Pro Ala Trp
    210                 215                 220

Phe Ala Tyr Trp Gly Gln Gly Thr Leu Val Thr Val Ser Ser Phe Asn
225                 230                 235                 240
```

-continued

```
Arg Gly Glu Cys


<210> SEQ ID NO 230
<211> LENGTH: 702
<212> TYPE: DNA
<213> ORGANISM: Artificial Sequence
<220> FEATURE:
<223> OTHER INFORMATION: 8B5-CB3.1-VEPKSC

<400> SEQUENCE: 230

gacattcaga tgacacagtc tccatcctcc ctacttgcgg cgctgggaga aagagtcagt     60

ctcacttgtc gggcaagtca ggaaattagt ggttacttaa gctggcttca gcagaaacca    120

gatggaacta ttaaacgcct gatctacgcc gcatccactt tagattctgg tgtcccaaaa    180

aggttcagtg gcagtgagtc tgggtcagat tattctctca ccatcagcag tcttgagtct    240

gaagattttg cagactatta ctgtctacaa tattttagtt atccgctcac gttcggtgct    300

gggaccaagc tggagctgaa aggaggcgga tccggaggcg gaggccaggt ccaactgcag    360

cagcctgggg ctgagctggt gaggcctggg gcttcagtga agctgtcctg caaggcttct    420

ggctacacct tcaccagcta ctggatgaac tgggtgaagc agaggcctgg acaaggcctt    480

gaatggattg gtatggttga tccttcagac agtgaaactc actacaatca aatgttcaag    540

gacaaggcca cattgactgt tgacaaatcc tccagcacag cctacatgca gctcagcagc    600

ctgacatctg aggactctgc ggtctattac tgtgcaagag ctatgggcta ctggggtcaa    660

ggaacctcag tcaccgtctc ctcagttgag cccaaatctt gt                       702


<210> SEQ ID NO 231
<211> LENGTH: 234
<212> TYPE: PRT
<213> ORGANISM: Artificial Sequence
<220> FEATURE:
<223> OTHER INFORMATION: 8B5-CB3.1-VEPKSC

<400> SEQUENCE: 231

Asp Ile Gln Met Thr Gln Ser Pro Ser Ser Leu Leu Ala Ala Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Glu Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Phe Ser Tyr Pro Leu
                85                  90                  95

Thr Phe Gly Ala Gly Thr Lys Leu Glu Leu Lys Gly Gly Gly Ser Gly
            100                 105                 110

Gly Gly Gly Gln Val Gln Leu Gln Gln Pro Gly Ala Glu Leu Val Arg
        115                 120                 125

Pro Gly Ala Ser Val Lys Leu Ser Cys Lys Ala Ser Gly Tyr Thr Phe
    130                 135                 140

Thr Ser Tyr Trp Met Asn Trp Val Lys Gln Arg Pro Gly Gln Gly Leu
145                 150                 155                 160

Glu Trp Ile Gly Met Val Asp Pro Ser Asp Ser Glu Thr His Tyr Asn
                165                 170                 175
```

```
Gln Met Phe Lys Asp Lys Ala Thr Leu Thr Val Asp Lys Ser Ser Ser
            180                 185                 190

Thr Ala Tyr Met Gln Leu Ser Ser Leu Thr Ser Glu Asp Ser Ala Val
        195                 200                 205

Tyr Tyr Cys Ala Arg Ala Met Gly Tyr Trp Gly Gln Gly Thr Ser Val
    210                 215                 220

Thr Val Ser Ser Val Glu Pro Lys Ser Cys
225                 230
```

<210> SEQ ID NO 232
<211> LENGTH: 726
<212> TYPE: DNA
<213> ORGANISM: Artificial Sequence
<220> FEATURE:
<223> OTHER INFORMATION: CB3.1-8B5-FNRGEC

<400> SEQUENCE: 232

```
gatgttgtga tgacccagac tccactcact ttgtcggtta acattggaca accagcctcc      60

atctcttgta agtcaagtca gagcctctta gatactgatg gaaagacata tttgaattgg     120

ttgttacaga ggccaggcca gtctccaaac cgcctaatct atctggtgtc taaactggac     180

tctggagtcc ctgacaggtt cactggcagt ggatcaggga cagatttcac actgaaaatc     240

agcagagtgg aggctgagga tttgggaatt tattattgct ggcaaggtac acattttccg     300

ctcacgttcg gtgctgggac caagctggag ctgaaaggag gcggatccgg aggcggaggc     360

gaagtgaagc ttgaggagtc tggaggaggc ttggtgcaac ctggaggatc catgaaactc     420

tcttgtgaag cctctggatt cacttttagt gacgcctgga tggactgggt ccgtcagtct     480

ccagagaagg ggcttgagtg ggttgctgaa attagaaaca aagctaaaaa tcatgcaaca     540

tactatgctg agtctgtgat agggaggttc accatctcaa gagatgattc caaaagtagt     600

gtctacctgc aaatgaacag cttaagagct gaagacactg gcatttatta ctgtggggct     660

ctgggccttg actactgggg ccaaggcacc actctcacag tctcctcgtt caacagggga     720

gagtgt                                                                726
```

<210> SEQ ID NO 233
<211> LENGTH: 242
<212> TYPE: PRT
<213> ORGANISM: Artificial Sequence
<220> FEATURE:
<223> OTHER INFORMATION: CB3.1-8B5-FNRGEC

<400> SEQUENCE: 233

```
Asp Val Val Met Thr Gln Thr Pro Leu Thr Leu Ser Val Asn Ile Gly
1               5                   10                  15

Gln Pro Ala Ser Ile Ser Cys Lys Ser Ser Gln Ser Leu Leu Asp Thr
            20                  25                  30

Asp Gly Lys Thr Tyr Leu Asn Trp Leu Leu Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Leu Thr Phe Gly Ala Gly Thr Lys Leu Glu Leu Lys
            100                 105                 110
```

```
Gly Gly Gly Ser Gly Gly Gly Gly Glu Val Lys Leu Glu Glu Ser Gly
        115                 120                 125

Gly Gly Leu Val Gln Pro Gly Gly Ser Met Lys Leu Ser Cys Glu Ala
    130                 135                 140

Ser Gly Phe Thr Phe Ser Asp Ala Trp Met Asp Trp Val Arg Gln Ser
145                 150                 155                 160

Pro Glu Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ser Lys Ser Ser Val Tyr Leu Gln Met Asn Ser Leu
        195                 200                 205

Arg Ala Glu Asp Thr Gly Ile Tyr Tyr Cys Gly Ala Leu Gly Leu Asp
    210                 215                 220

Tyr Trp Gly Gln Gly Thr Thr Leu Thr Val Ser Ser Phe Asn Arg Gly
225                 230                 235                 240

Glu Cys


<210> SEQ ID NO 234
<211> LENGTH: 696
<212> TYPE: DNA
<213> ORGANISM: Artificial Sequence
<220> FEATURE:
<223> OTHER INFORMATION: 8B5VL-CB3.1VH-LGGC

<400> SEQUENCE: 234

gacattcaga tgacacagtc tccatcctcc ctacttgcgg cgctgggaga aagagtcagt      60

ctcacttgtc gggcaagtca ggaaattagt ggttacttaa gctggcttca gcagaaacca     120

gatggaacta ttaaacgcct gatctacgcc gcatccactt tagattctgg tgtcccaaaa     180

aggttcagtg gcagtgagtc tgggtcagat tattctctca ccatcagcag tcttgagtct     240

gaagattttg cagactatta ctgtctacaa tattttagtt atccgctcac gttcggtgct     300

gggaccaagc tggagctgaa aggaggcgga tccggaggcg gaggccaggt ccaactgcag     360

cagcctgggg ctgagctggt gaggcctggg gcttcagtga agctgtcctg caaggcttct     420

ggctacacct tcaccagcta ctggatgaac tgggtgaagc agaggcctgg acaaggcctt     480

gaatggattg gtatggttga tccttcagac agtgaaactc actacaatca aatgttcaag     540

gacaaggcca cattgactgt tgacaaatcc tccagcacag cctacatgca gctcagcagc     600

ctgacatctg aggactctgc ggtctattac tgtgcaagag ctatgggcta ctggggtcaa     660

ggaacctcag tcaccgtctc ctcactggga ggctgc                               696


<210> SEQ ID NO 235
<211> LENGTH: 232
<212> TYPE: PRT
<213> ORGANISM: Artificial Sequence
<220> FEATURE:
<223> OTHER INFORMATION: 8B5VL-CB3.1VH-LGGC

<400> SEQUENCE: 235

Asp Ile Gln Met Thr Gln Ser Pro Ser Ser Leu Leu Ala Ala Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45
```

```
Tyr Ala Ala Ser Thr Leu Asp Ser Gly Val Pro Lys Arg Phe Ser Gly
    50                  55                  60

Ser Glu Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Phe Ser Tyr Pro Leu
                85                  90                  95

Thr Phe Gly Ala Gly Thr Lys Leu Glu Leu Lys Gly Gly Gly Ser Gly
            100                 105                 110

Gly Gly Gly Gln Val Gln Leu Gln Gln Pro Gly Ala Glu Leu Val Arg
        115                 120                 125

Pro Gly Ala Ser Val Lys Leu Ser Cys Lys Ala Ser Gly Tyr Thr Phe
    130                 135                 140

Thr Ser Tyr Trp Met Asn Trp Val Lys Gln Arg Pro Gly Gln Gly Leu
145                 150                 155                 160

Glu Trp Ile Gly Met Val Asp Pro Ser Asp Ser Glu Thr His Tyr Asn
                165                 170                 175

Gln Met Phe Lys Asp Lys Ala Thr Leu Thr Val Asp Lys Ser Ser Ser
            180                 185                 190

Thr Ala Tyr Met Gln Leu Ser Ser Leu Thr Ser Glu Asp Ser Ala Val
        195                 200                 205

Tyr Tyr Cys Ala Arg Ala Met Gly Tyr Trp Gly Gln Gly Thr Ser Val
    210                 215                 220

Thr Val Ser Ser Leu Gly Gly Cys
225                 230
```

<210> SEQ ID NO 236
<211> LENGTH: 720
<212> TYPE: DNA
<213> ORGANISM: Artificial Sequence
<220> FEATURE:
<223> OTHER INFORMATION: CB3.1-8B5-LGGC

<400> SEQUENCE: 236

```
gatgttgtga tgacccagac tccactcact ttgtcggtta acattggaca accagcctcc     60

atctcttgta agtcaagtca gagcctctta gatactgatg gaaagacata tttgaattgg    120

ttgttacaga ggccaggcca gtctccaaac cgcctaatct atctggtgtc taaactggac    180

tctggagtcc ctgacaggtt cactggcagt ggatcaggga cagatttcac actgaaaatc    240

agcagagtgg aggctgagga tttgggaatt tattattgct ggcaaggtac acattttccg    300

ctcacgttcg gtgctgggac caagctggag ctgaaaggag gcggatccgg aggcggaggc    360

gaagtgaagc ttgaggagtc tggaggaggc ttggtgcaac ctggaggatc catgaaactc    420

tcttgtgaag cctctggatt cacttttagt gacgcctgga tggactgggt ccgtcagtct    480

ccagagaagg ggcttgagtg ggttgctgaa attagaaaca aagctaaaaa tcatgcaaca    540

tactatgctg agtctgtgat agggaggttc accatctcaa gagatgattc caaaagtagt    600

gtctacctgc aaatgaacag cttaagagct gaagacactg gcatttatta ctgtggggct    660

ctgggccttg actactgggg ccaaggcacc actctcacag tctcctcgct gggaggctgc    720
```

<210> SEQ ID NO 237
<211> LENGTH: 240
<212> TYPE: PRT
<213> ORGANISM: Artificial Sequence
<220> FEATURE:
<223> OTHER INFORMATION: CB3.1-8B5-LGGC

<400> SEQUENCE: 237

```
Asp Val Val Met Thr Gln Thr Pro Leu Thr Leu Ser Val Asn Ile Gly
1               5                   10                  15

Gln Pro Ala Ser Ile Ser Cys Lys Ser Ser Gln Ser Leu Leu Asp Thr
            20                  25                  30

Asp Gly Lys Thr Tyr Leu Asn Trp Leu Leu Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Leu Thr Phe Gly Ala Gly Thr Lys Leu Glu Leu Lys
            100                 105                 110

Gly Gly Gly Ser Gly Gly Gly Gly Glu Val Lys Leu Glu Glu Ser Gly
        115                 120                 125

Gly Gly Leu Val Gln Pro Gly Gly Ser Met Lys Leu Ser Cys Glu Ala
    130                 135                 140

Ser Gly Phe Thr Phe Ser Asp Ala Trp Met Asp Trp Val Arg Gln Ser
145                 150                 155                 160

Pro Glu Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ser Lys Ser Ser Val Tyr Leu Gln Met Asn Ser Leu
        195                 200                 205

Arg Ala Glu Asp Thr Gly Ile Tyr Tyr Cys Gly Ala Leu Gly Leu Asp
    210                 215                 220

Tyr Trp Gly Gln Gly Thr Thr Leu Thr Val Ser Ser Leu Gly Gly Cys
225                 230                 235                 240
```

<210> SEQ ID NO 238
<211> LENGTH: 47
<212> TYPE: DNA
<213> ORGANISM: Artificial Sequence
<220> FEATURE:
<223> OTHER INFORMATION: Lgh628F Primer

<400> SEQUENCE: 238
ggaggcggat ccggaggcgg aggccaggtc caactgcagc agcctgg 47

<210> SEQ ID NO 239
<211> LENGTH: 49
<212> TYPE: DNA
<213> ORGANISM: Artificial Sequence
<220> FEATURE:
<223> OTHER INFORMATION: Lgh629R Primer

<400> SEQUENCE: 239
tttgaattct aacaagattt gggctcaact gaggagacgg tgactgagg 49

<210> SEQ ID NO 240
<211> LENGTH: 45
<212> TYPE: DNA
<213> ORGANISM: Artificial Sequence
<220> FEATURE:
<223> OTHER INFORMATION: Lgh630R Primer

<400> SEQUENCE: 240
gcctccgcct ccggatccgc ctcctttcag ctccagcttg gtccc 45

<210> SEQ ID NO 241
<211> LENGTH: 47
<212> TYPE: DNA
<213> ORGANISM: Artificial Sequence
<220> FEATURE:
<223> OTHER INFORMATION: Lgh631F Primer

<400> SEQUENCE: 241
ggaggcggat ccggaggcgg aggcgaagtg aagcttgagg agtctgg 47

<210> SEQ ID NO 242
<211> LENGTH: 49
<212> TYPE: DNA
<213> ORGANISM: Artificial Sequence
<220> FEATURE:
<223> OTHER INFORMATION: Lgh640R Primer

<400> SEQUENCE: 242
tttgaattct aacactctcc cctgttgaac gaggagactg tgagagtgg 49

<210> SEQ ID NO 243
<211> LENGTH: 48
<212> TYPE: DNA
<213> ORGANISM: Artificial Sequence
<220> FEATURE:
<223> OTHER INFORMATION: Lgh644R Primer

<400> SEQUENCE: 243
tttgtcgtca tcatcgtctt tgtagtcgga gtggacacct gtggagag 48

<210> SEQ ID NO 244
<211> LENGTH: 42
<212> TYPE: DNA
<213> ORGANISM: Artificial Sequence
<220> FEATURE:
<223> OTHER INFORMATION: Lgh646R Primer

<400> SEQUENCE: 244
tttgaattct agcagcctcc cagtgaggag acggtgactg ag 42

<210> SEQ ID NO 245
<211> LENGTH: 45
<212> TYPE: DNA
<213> ORGANISM: Artificial Sequence
<220> FEATURE:
<223> OTHER INFORMATION: Lgh647F Primer

<400> SEQUENCE: 245
caaagacgat gatgacgaca aagacattca gatgacacag tctcc 45

<210> SEQ ID NO 246
<211> LENGTH: 43
<212> TYPE: DNA
<213> ORGANISM: Artificial Sequence
<220> FEATURE:
<223> OTHER INFORMATION: Lgh648R Primer

<400> SEQUENCE: 246
tttgaattct agcagcctcc cagcgaggag actgtgagag tgg 43

<210> SEQ ID NO 247
<211> LENGTH: 1044
<212> TYPE: DNA

<213> ORGANISM: Artificial Sequence
<220> FEATURE:
<223> OTHER INFORMATION: 2.4G2-3G8-hKappa

<400> SEQUENCE: 247

```
gatgtccaga tgacccagtc tccatctaat cttgctgcct ctcctggaga aagtgtttcc      60

atcaattgca aggcaagtga gagcattagc aagtatttag cctggtatct acagaaacct     120

gggaaagcaa ataagcttct tatgtacgat gggtcaactt tgcaatctgg aattccatcg     180

aggttcagtg gcagtggatc tggtacagat ttcactctca ccatcagaag cctggagcct     240

gaagattttg gactctatta ctgtcaacag cattatgaat atccagccac gttcggttct     300

gggaccaagc tggagatcaa aggaggcgga tccggaggcg gaggccaggt taccctgaaa     360

gagtctggcc ctgggatatt gcagccctcc cagaccctca gtctgacttg ttctttctct     420

gggttttcac tgaggacttc tggtatgggt gtaggctgga ttcgtcagcc ttcagggaag     480

ggtctagagt ggctggcaca catttggtgg gatgatgaca agcgctataa tccagccctg     540

aagagccgac tgacaatctc caaggatacc tccagcaacc aggtattcct caaaatcgcc     600

agtgtggaca ctgcagatac tgccacatac tactgtgctc aaataaaccc cgcctggttt     660

gcttactggg gccaagggac tctggtcact gtgagctcac tgggaggctg cggcggaggg     720

agccgtacgg tggctgcacc atcggtcttc atcttcccgc catctgatga gcagttgaaa     780

tctggaactg cctctgttgt gtgcctgctg aataacttct atcccagaga ggccaaagta     840

cagtggaagg tggataacgc cctccaatcg ggtaactccc aggagagtgt cacagagcag     900

gacagcaagg acagcaccta cagcctcagc agcaccctga cgctgagcaa agcagactac     960

gagaaacaca aagtctacgc ctgcgaagtc acccatcagg gcctgagctc gcccgtcaca    1020

aagagcttca acaggggaga gtgt                                           1044
```

<210> SEQ ID NO 248
<211> LENGTH: 348
<212> TYPE: PRT
<213> ORGANISM: Artificial Sequence
<220> FEATURE:
<223> OTHER INFORMATION: 2.4G2-3G8-hKappa

<400> SEQUENCE: 248

```
Asp Val Gln Met Thr Gln Ser Pro Ser Asn Leu Ala Ala Ser Pro Gly
1               5                   10                  15

Glu Ser Val Ser Ile Asn Cys Lys Ala Ser Glu Ser Ile Ser Lys Tyr
            20                  25                  30

Leu Ala Trp Tyr Leu Gln Lys Pro Gly Lys Ala Asn Lys Leu Leu Met
        35                  40                  45

Tyr Asp Gly Ser Thr Leu Gln Ser Gly Ile Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Gly Leu Tyr Tyr Cys Gln Gln His Tyr Glu Tyr Pro Ala
                85                  90                  95

Thr Phe Gly Ser Gly Thr Lys Leu Glu Ile Lys Gly Gly Gly Ser Gly
            100                 105                 110

Gly Gly Gly Gln Val Thr Leu Lys Glu Ser Gly Pro Gly Ile Leu Gln
        115                 120                 125

Pro Ser Gln Thr Leu Ser Leu Thr Cys Ser Phe Ser Gly Phe Ser Leu
    130                 135                 140
```

-continued

```
Arg Thr Ser Gly Met Gly Val Gly Trp Ile Arg Gln Pro Ser Gly Lys
145                 150                 155                 160

Gly Leu Glu Trp Leu Ala His Ile Trp Trp Asp Asp Asp Lys Arg Tyr
                165                 170                 175

Asn Pro Ala Leu Lys Ser Arg Leu Thr Ile Ser Lys Asp Thr Ser Ser
            180                 185                 190

Asn Gln Val Phe Leu Lys Ile Ala Ser Val Asp Thr Ala Asp Thr Ala
        195                 200                 205

Thr Tyr Tyr Cys Ala Gln Ile Asn Pro Ala Trp Phe Ala Tyr Trp Gly
    210                 215                 220

Gln Gly Thr Leu Val Thr Val Ser Ser Leu Gly Gly Cys Gly Gly Gly
225                 230                 235                 240

Ser Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345
```

<210> SEQ ID NO 249
<211> LENGTH: 1734
<212> TYPE: DNA
<213> ORGANISM: Artificial Sequence
<220> FEATURE:
<223> OTHER INFORMATION: 3G8-2.4G2-hG1

<400> SEQUENCE: 249

```
gacactgtgc tgacccaatc tccagcttct ttggctgtgt ctctagggca gagggccacc     60

atctcctgca aggccagcca aagtgttgat tttgatggtg atagttttat gaactggtac    120

caacagaaac caggacagcc acccaaactc ctcatctata ctacatccaa tctagaatct    180

gggatcccag ccaggtttag tgccagtggg tctgggacag acttcaccct caacatccat    240

cctgtggagg aggaggatac tgcaacctat tactgtcagc aaagtaatga ggatccgtac    300

acgttcggag gggggaccaa gctggaaata aaaggaggcg gatccggagg cggaggcgag    360

gtggagctag tggagtctgg gggaggctta gtgcagcctg gaaggtccct gaaactctcg    420

tgtgcagcct caggattcac tttcagtgac tattacatgg cctgggtccg gcaggctcca    480

acgacgggtc tggagtgggt cgcatccatt agttatgatg gtggtgacac tcactatcga    540

gactccgtga agggccgatt tactatttcc agagataatg caaaaagcag cctatacctg    600

caaatggaca gtctgaggtc tgaggacacg gccacttatt actgtgcaac agagactacg    660

ggaataccta caggtgttat ggatgcctgg ggtcaaggag tttcagtcac tgtctcctca    720

ctgggaggct gcggcggagg gagcgcctcc accaagggcc catcggtctt ccccctggca    780

ccctcctcca agagcacctc tgggggcaca gcggccctgg gctgcctggt caaggactac    840

ttccccgaac cggtgacggt gtcgtggaac tcaggcgccc tgaccagcgg cgtgcacacc    900
```

-continued

```
ttcccggctg tcctacagtc ctcaggactc tactccctca gcagcgtggt gaccgtgccc    960

tccagcagct tgggcaccca gacctacatc tgcaacgtga atcacaagcc cagcaacacc   1020

aaggtggaca agagagttga gcccaaatct tgtgacaaaa ctcacacatg cccaccgtgc   1080

ccagcacctg aactcctggg gggaccgtca gtcttcctct tccccccaaa acccaaggac   1140

accctcatga tctcccggac ccctgaggtc acatgcgtgg tggtggacgt gagccacgaa   1200

gaccctgagg tcaagttcaa ctggtacgtg gacggcgtgg aggtgcataa tgccaagaca   1260

aagccgcggg aggagcagta caacagcacg taccgtgtgg tcagcgtcct caccgtcctg   1320

caccaggact ggctgaatgg caaggagtac aagtgcaagg tctccaacaa agccctccca   1380

gcccccatcg agaaaaccat ctccaaagcc aaagggcagc cccgagaacc acaggtgtac   1440

accctgcccc catcccggga tgagctgacc aagaaccagg tcagcctgac ctgcctggtc   1500

aaaggcttct atcccagcga catcgccgtg gagtgggaga gcaatgggca gccggagaac   1560

aactacaaga ccacgcctcc cgtgctggac tccgacggct ccttcttcct ctacagcaag   1620

ctcaccgtgg acaagagcag gtggcagcag gggaacgtct tctcatgctc cgtgatgcat   1680

gaggctctgc acaaccacta cacgcagaag agcctctccc tgtctccggg taaa         1734
```

```
<210> SEQ ID NO 250
<211> LENGTH: 578
<212> TYPE: PRT
<213> ORGANISM: Artificial Sequence
<220> FEATURE:
<223> OTHER INFORMATION: 3G8-2.4G2-hG1

<400> SEQUENCE: 250

Asp Thr Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys Gly
            100                 105                 110

Gly Gly Ser Gly Gly Gly Gly Glu Val Glu Leu Val Glu Ser Gly Gly
        115                 120                 125

Gly Leu Val Gln Pro Gly Arg Ser Leu Lys Leu Ser Cys Ala Ala Ser
    130                 135                 140

Gly Phe Thr Phe Ser Asp Tyr Tyr Met Ala Trp Val Arg Gln Ala Pro
145                 150                 155                 160

Thr Thr Gly Leu Glu Trp Val Ala Ser Ile Ser Tyr Asp Gly Gly Asp
                165                 170                 175

Thr His Tyr Arg Asp Ser Val Lys Gly Arg Phe Thr Ile Ser Arg Asp
            180                 185                 190

Asn Ala Lys Ser Ser Leu Tyr Leu Gln Met Asp Ser Leu Arg Ser Glu
        195                 200                 205

Asp Thr Ala Thr Tyr Tyr Cys Ala Thr Glu Thr Thr Gly Ile Pro Thr
    210                 215                 220
```

```
Gly Val Met Asp Ala Trp Gly Gln Gly Val Ser Val Thr Val Ser Ser
225                 230                 235                 240

Leu Gly Gly Cys Gly Gly Gly Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Leu Tyr Ser Leu Ser Ser Val Val Thr Val Pro
305                 310                 315                 320

Ser Ser Ser Leu Gly Thr Gln Thr Tyr Ile Cys Asn Val Asn His Lys
                325                 330                 335

Pro Ser Asn Thr Lys Val Asp Lys Arg Val Glu Pro Lys Ser Cys Asp
            340                 345                 350

Lys Thr His Thr Cys Pro Pro Cys Pro Ala Pro Glu Leu Leu Gly Gly
        355                 360                 365

Pro Ser Val Phe Leu Phe Pro Pro Lys Pro Lys Asp Thr Leu Met Ile
    370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
        435                 440                 445

Glu Tyr Lys Cys Lys Val Ser Asn Lys Ala Leu Pro Ala Pro Ile Glu
    450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
        515                 520                 525

Leu Asp Ser Asp Gly Ser Phe Phe Leu Tyr Ser Lys Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys
```

<210> SEQ ID NO 251
<211> LENGTH: 720
<212> TYPE: DNA
<213> ORGANISM: Artificial Sequence
<220> FEATURE:
<223> OTHER INFORMATION: CD79VL-CD32BVH

<400> SEQUENCE: 251

```
gatgttgtga tgactcagtc tccactctcc ctgcccgtca cccttggaca gccggcctcc     60

atctcctgca agtcaagtca gagcctctta gatagtgatg gaaagacata tttgaattgg    120

tttcagcaga ggccaggcca atctccaaac cgcctaattt atctggtgtc taaactggac    180

tctggggtcc cagacagatt cagcggcagt gggtcaggca ctgatttcac actgaaaatc    240

agcagggtgg aggctgagga tgttggggtt tattactgct ggcaaggtac acattttccg    300

ctcacgttcg gcggagggac caagcttgag atcaaaggag gcggatccgg aggcggaggc    360

gaagtgaagc ttgaggagtc tggaggaggc ttggtgcaac ctggaggatc catgaaactc    420

tcttgtgaag cctctggatt cacttttagt gacgcctgga tggactgggt ccgtcagtct    480

ccagagaagg ggcttgagtg ggttgctgaa attagaaaca aagctaaaaa tcatgcaaca    540

tactatgctg agtctgtgat agggaggttc accatctcaa gagatgattc caaaagtagt    600

gtctacctgc aaatgaacag cttaagagct gaagacactg gcatttatta ctgtggggct    660

ctgggccttg actactgggg ccaaggcacc actctcacag tctcctcgct gggaggctgc    720


<210> SEQ ID NO 252
<211> LENGTH: 240
<212> TYPE: PRT
<213> ORGANISM: Artificial Sequence
<220> FEATURE:
<223> OTHER INFORMATION: CD79VL-CD32BVH

<400> SEQUENCE: 252

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ala Lys Asn Ser Leu Tyr Leu Gln Met Asn Ser Leu
        195                 200                 205

Arg Ala Glu Asp Thr Ala Val Tyr Tyr Cys Gly Ala Leu Gly Leu Asp
    210                 215                 220

Tyr Trp Gly Gln Gly Thr Leu Val Thr Val Ser Ser Leu Gly Gly Cys
225                 230                 235                 240
```

```
<210> SEQ ID NO 253
<211> LENGTH: 696
<212> TYPE: DNA
<213> ORGANISM: Artificial Sequence
<220> FEATURE:
<223> OTHER INFORMATION: CD32BVL-CD79VH-1

<400> SEQUENCE: 253

gacatccaga tgacccagtc tccatcctcc ttatctgcct ctgtgggaga tagagtcacc      60

atcacttgtc gggcaagtca ggaaattagt ggttacttaa gctggctgca gcagaaacca     120

ggcaaggccc ctagacgcct gatctacgcc gcatccactt tagattctgg tgtcccatcc     180

aggttcagtg gcagtgagtc tgggaccgag ttcaccctca ccatcagcag ccttcagcct     240

gaagattttg caacctatta ctgtctacaa tattttagtt atccgctcac gttcggaggg     300

gggaccaagg tggaaataaa aggaggcgga tccggaggcg gaggccaggt tcagctggtg     360

cagtctggag ctgaggtgaa gaagcctggc gcctcagtga aggtctcctg caaggcttct     420

ggttacacct ttaccagcta ctggatgaac tgggtgcgac aggcccctgg acaagggctt     480

gagtggatcg gaatgattga tccttcagac agtgaaactc actacaatca aatgttcaag     540

gacagagtca ccatgaccac agacacatcc acgagcacag cctacatgga gctgaggagc     600

ctgagatctg acgacacggc cgtgtattac tgtgcgagag ctatgggcta ctgggggcaa     660

gggaccacgg tcaccgtctc ctcactggga ggctgc                               696


<210> SEQ ID NO 254
<211> LENGTH: 232
<212> TYPE: PRT
<213> ORGANISM: Artificial Sequence
<220> FEATURE:
<223> OTHER INFORMATION: CD32BVL-CD79VH-1

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Asn Trp Val Arg Gln Ala Pro Gly Gln Gly Leu
145                 150                 155                 160

Glu Trp Ile Gly Met Ile Asp Pro Ser Asp Ser Glu Thr His Tyr Asn
                165                 170                 175

Gln Met Phe Lys Asp Arg Val Thr Met Thr Thr Asp Thr Ser Thr Ser
            180                 185                 190
```

Thr Ala Tyr Met Glu Leu Arg Ser Leu Arg Ser Asp Asp Thr Ala Val
        195                 200                 205

Tyr Tyr Cys Ala Arg Ala Met Gly Tyr Trp Gly Gln Gly Thr Thr Val
    210                 215                 220

Thr Val Ser Ser Leu Gly Gly Cys
225                 230

<210> SEQ ID NO 255
<211> LENGTH: 696
<212> TYPE: DNA
<213> ORGANISM: Artificial Sequence
<220> FEATURE:
<223> OTHER INFORMATION: CD32BVL-CD79VH-2

<400> SEQUENCE: 255
gacatccaga tgacccagtc tccatcctcc ttatctgcct ctgtgggaga tagagtcacc 60
atcacttgtc gggcaagtca ggaaattagt ggttacttaa gctggctgca gcagaaacca 120
ggcaaggccc ctagacgcct gatctacgcc gcatccactt tagattctgg tgtcccatcc 180
aggttcagtg gcagtgagtc tgggaccgag ttcaccctca ccatcagcag ccttcagcct 240
gaagattttg caacctatta ctgtctacaa tattttagtt atccgctcac gttcggaggg 300
gggaccaagg tggaaataaa aggaggcgga tccggaggcg gaggccaggt tcagctggtg 360
cagtctggag ctgaggtgaa gaagcctggc gcctcagtga aggtctcctg caaggcttct 420
ggttacacct ttaccagcta ctggatgaac tgggtgcgac aggcccctgg acaagggctt 480
gagtggatcg gaatgattga tccttcagac agtgaaactc actacaatca aaagttcaag 540
gacagagtca ccatgaccac agacacatcc acgagcacag cctacatgga gctgaggagc 600
ctgagatctg acgacacggc cgtgtattac tgtgcgagag ctatgggcta ctgggggcaa 660
gggaccacgg tcaccgtctc ctcactggga ggctgc 696

<210> SEQ ID NO 256
<211> LENGTH: 232
<212> TYPE: PRT
<213> ORGANISM: Artificial Sequence
<220> FEATURE:
<223> OTHER INFORMATION: CD32BVL-CD79VH-2

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe

```
    130                 135                 140

Thr Ser Tyr Trp Met Asn Trp Val Arg Gln Ala Pro Gly Gln Gly Leu
145                 150                 155                 160

Glu Trp Ile Gly Met Ile Asp Pro Ser Asp Ser Glu Thr His Tyr Asn
                165                 170                 175

Gln Lys Phe Lys Asp Arg Val Thr Met Thr Thr Asp Thr Ser Thr Ser
            180                 185                 190

Thr Ala Tyr Met Glu Leu Arg Ser Leu Arg Ser Asp Asp Thr Ala Val
        195                 200                 205

Tyr Tyr Cys Ala Arg Ala Met Gly Tyr Trp Gly Gln Gly Thr Thr Val
    210                 215                 220

Thr Val Ser Ser Leu Gly Gly Cys
225                 230
```

<210> SEQ ID NO 257
<211> LENGTH: 720
<212> TYPE: DNA
<213> ORGANISM: Artificial Sequence
<220> FEATURE:
<223> OTHER INFORMATION: hHBCRCVL. R45N-h8B5VH-LGGC

<400> SEQUENCE: 257

```
gatgttgtga tgactcagtc tccactctcc ctgcccgtca cccttggaca gccggcctcc     60

atctcctgca agtcaagtca gagcctctta gatagtgatg gaaagacata tttgaattgg    120

tttcagcaga ggccaggcca atctccaaac cgcctaattt atctggtgtc taaactggac    180

tctggggtcc cagacagatt cagcggcagt gggtcaggca ctgatttcac actgaaaatc    240

agcagggtgg aggctgagga tgttggggtt tattactgct ggcaaggtac acattttccg    300

ctcacgttcg gcggagggac caagcttgag atcaaaggag gcggatccgg aggcggaggc    360

gaagtgaagc ttgaggagtc tggaggaggc ttggtgcaac ctggaggatc catgaaactc    420

tcttgtgaag cctctggatt cacttttagt gacgcctgga tggactgggt ccgtcagtct    480

ccagagaagg ggcttgagtg ggttgctgaa attagaaaca aagctaaaaa tcatgcaaca    540

tactatgctg agtctgtgat agggaggttc accatctcaa gagatgattc caaaagtagt    600

gtctacctgc aaatgaacag cttaagagct gaagacactg gcatttatta ctgtggggct    660

ctgggccttg actactgggg ccaaggcacc actctcacag tctcctcgct gggaggctgc    720
```

<210> SEQ ID NO 258
<211> LENGTH: 240
<212> TYPE: PRT
<213> ORGANISM: Artificial Sequence
<220> FEATURE:
<223> OTHER INFORMATION: hHBCRCVL. R45N-h8B5VH-LGGC

<400> SEQUENCE: 258

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ala Lys Asn Ser Leu Tyr Leu Gln Met Asn Ser Leu
        195                 200                 205

Arg Ala Glu Asp Thr Ala Val Tyr Tyr Cys Gly Ala Leu Gly Leu Asp
    210                 215                 220

Tyr Trp Gly Gln Gly Thr Leu Val Thr Val Ser Ser Leu Gly Gly Cys
225                 230                 235                 240


<210> SEQ ID NO 259
<211> LENGTH: 696
<212> TYPE: DNA
<213> ORGANISM: Artificial Sequence
<220> FEATURE:
<223> OTHER INFORMATION: H8B5VL-hHBCRCVH M48I-LGGC

<400> SEQUENCE: 259

gacatccaga tgacccagtc tccatcctcc ttatctgcct ctgtgggaga tagagtcacc     60

atcacttgtc gggcaagtca ggaaattagt ggttacttaa gctggctgca gcagaaacca    120

ggcaaggccc ctagacgcct gatctacgcc gcatccactt tagattctgg tgtcccatcc    180

aggttcagtg gcagtgagtc tgggaccgag ttcaccctca ccatcagcag ccttcagcct    240

gaagattttg caacctatta ctgtctacaa tattttagtt atccgctcac gttcggaggg    300

gggaccaagg tggaaataaa aggaggcgga tccggaggcg gaggccaggt tcagctggtg    360

cagtctggag ctgaggtgaa gaagcctggc gcctcagtga aggtctcctg caaggcttct    420

ggttacacct ttaccagcta ctggatgaac tgggtgcgac aggcccctgg acaagggctt    480

gagtggatcg gaatgattga tccttcagac agtgaaactc actacaatca aatgttcaag    540

gacagagtca ccatgaccac agacacatcc acgagcacag cctacatgga gctgaggagc    600

ctgagatctg acgacacggc cgtgtattac tgtgcgagag ctatgggcta ctgggggcaa    660

gggaccacgg tcaccgtctc ctcactggga ggctgc                              696


<210> SEQ ID NO 260
<211> LENGTH: 232
<212> TYPE: PRT
<213> ORGANISM: Artificial Sequence
<220> FEATURE:
<223> OTHER INFORMATION: H8B5VL-HBCRCVH M48I-LGGC

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30
```

```
Leu Ser Trp Leu Gln Gln Lys Pro Gly Lys Ala Pro Arg Arg Leu Ile
        35                  40                  45

Tyr Ala Ala Ser Thr Leu Asp Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Phe Ser Tyr Pro Leu
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Thr Phe
    130                 135                 140

Thr Ser Tyr Trp Met Asn Trp Val Arg Gln Ala Pro Gly Gln Gly Leu
145                 150                 155                 160

Glu Trp Ile Gly Met Ile Asp Pro Ser Asp Ser Glu Thr His Tyr Asn
                165                 170                 175

Gln Met Phe Lys Asp Arg Val Thr Met Thr Thr Asp Thr Ser Thr Ser
            180                 185                 190

Thr Ala Tyr Met Glu Leu Arg Ser Leu Arg Ser Asp Asp Thr Ala Val
        195                 200                 205

Tyr Tyr Cys Ala Arg Ala Met Gly Tyr Trp Gly Gln Gly Thr Thr Val
    210                 215                 220

Thr Val Ser Ser Leu Gly Gly Cys
225                 230
```

<210> SEQ ID NO 261
<211> LENGTH: 36
<212> TYPE: DNA
<213> ORGANISM: Artificial Sequence
<220> FEATURE:
<223> OTHER INFORMATION: Lgh321F Primer

<400> SEQUENCE: 261
cgagctagct ctagatgaga tcacagttct ctctac 36

<210> SEQ ID NO 262
<211> LENGTH: 45
<212> TYPE: DNA
<213> ORGANISM: Artificial Sequence
<220> FEATURE:
<223> OTHER INFORMATION: Lgh386R Primer

<400> SEQUENCE: 262
tttgaattct agcagcctcc cagtgaggag acggtgaccg tggtc 45

<210> SEQ ID NO 263
<211> LENGTH: 39
<212> TYPE: DNA
<213> ORGANISM: Artificial Sequence
<220> FEATURE:
<223> OTHER INFORMATION: Lgh784F Primer

<400> SEQUENCE: 263
ggcggatccg gaggcggagg ccaggttcag ctggtgcag 39

<210> SEQ ID NO 264
<211> LENGTH: 38

<212> TYPE: DNA
<213> ORGANISM: Artificial Sequence
<220> FEATURE:
<223> OTHER INFORMATION: Lgh785R Primer

<400> SEQUENCE: 264
cctccggatc cgcctccttt gatctcaagc ttggtccc 38

<210> SEQ ID NO 265
<211> LENGTH: 42
<212> TYPE: DNA
<213> ORGANISM: Artificial Sequence
<220> FEATURE:
<223> OTHER INFORMATION: Lgh786R Primer

<400> SEQUENCE: 265
tttgaattct agcagcctcc caggctggag acggtcacca gg 42

<210> SEQ ID NO 266
<211> LENGTH: 44
<212> TYPE: DNA
<213> ORGANISM: Artificial Sequence
<220> FEATURE:
<223> OTHER INFORMATION: Lgh787F Primer

<400> SEQUENCE: 266
ggaggcggat ccggaggcgg aggcgaagtg cagcttgtgg agtc 44

<210> SEQ ID NO 267
<211> LENGTH: 8
<212> TYPE: PRT
<213> ORGANISM: Artificial Sequence
<220> FEATURE:
<223> OTHER INFORMATION: Linker

<400> SEQUENCE: 267

Leu Gly Gly Cys Gly Gly Gly Ser
1 5

<210> SEQ ID NO 268
<211> LENGTH: 4
<212> TYPE: PRT
<213> ORGANISM: Artificial Sequence
<220> FEATURE:
<223> OTHER INFORMATION: Linker

<400> SEQUENCE: 268

Leu Glu Ile Lys
1

<210> SEQ ID NO 269
<211> LENGTH: 4
<212> TYPE: PRT
<213> ORGANISM: Artificial Sequence
<220> FEATURE:
<223> OTHER INFORMATION: Linker

<400> SEQUENCE: 269

Thr Val Ser Ser
1

<210> SEQ ID NO 270
<211> LENGTH: 343
<212> TYPE: PRT
<213> ORGANISM: Artificial Sequence
<220> FEATURE:
<223> OTHER INFORMATION: H8B5VL-hBCRCVH M48I, M62K_LGGCG3S_hKappa

<400> SEQUENCE: 270

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

Leu Ser Trp Leu Gln Gln Lys Pro Gly Lys Ala Pro Arg Arg Leu Ile
35 40 45

Tyr Ala Ala Ser Thr Leu Asp Ser Gly Val Pro Ser Arg Phe Ser Gly
50 55 60

Ser Glu Ser Gly Thr Glu Phe Thr Leu Thr Ile Ser Ser Leu Gln Pro
65 70 75 80

Glu Asp Phe Ala Thr Tyr Tyr Cys Leu Gln Tyr Phe Ser Tyr Pro Leu
85 90 95

Thr Phe Gly Gly Gly Thr Lys Val Glu Ile Lys Gly Gly Gly Ser Gly
100 105 110

Gly Gly Gly Gln Val Gln Leu Val Gln Ser Gly Ala Glu Val Lys Lys
115 120 125

Pro Gly Ala Ser Val Lys Val Ser Cys Lys Ala Ser Gly Tyr Thr Phe
130 135 140

Thr Ser Tyr Trp Met Asn Trp Val Arg Gln Ala Pro Gly Gln Gly Leu
145 150 155 160

Glu Trp Ile Gly Met Ile Asp Pro Ser Asp Ser Glu Thr His Tyr Asn
165 170 175

Gln Lys Phe Lys Asp Arg Val Thr Met Thr Thr Asp Thr Ser Thr Ser
180 185 190

Thr Ala Tyr Met Glu Leu Arg Ser Leu Arg Ser Asp Asp Thr Ala Val
195 200 205

Tyr Tyr Cys Ala Arg Ala Met Gly Tyr Trp Gly Gln Gly Thr Thr Val
210 215 220

Thr Val Ser Ser Leu Gly Gly Cys Gly Gly Gly Ser Arg Thr Val Ala
225 230 235 240

Ala Pro Ser Val Phe Ile Phe Pro Pro Ser Asp Glu Gln Leu Lys Ser
245 250 255

Gly Thr Ala Ser Val Val Cys Leu Leu Asn Asn Phe Tyr Pro Arg Glu
260 265 270

Ala Lys Val Gln Trp Lys Val Asp Asn Ala Leu Gln Ser Gly Asn Ser
275 280 285

Gln Glu Ser Val Thr Glu Gln Asp Ser Lys Asp Ser Thr Tyr Ser Leu
290 295 300

Ser Ser Thr Leu Thr Leu Ser Lys Ala Asp Tyr Glu Lys His Lys Val
305 310 315 320

Tyr Ala Cys Glu Val Thr His Gln Gly Leu Ser Ser Pro Val Thr Lys
325 330 335

Ser Phe Asn Arg Gly Glu Cys
340

<210> SEQ ID NO 271
<211> LENGTH: 1032
<212> TYPE: DNA
<213> ORGANISM: Artificial Sequence
<220> FEATURE:
<223> OTHER INFORMATION: H8B5VL-hBCRCVH M48I, M62K_LGGCG3S_hKappa

<400> SEQUENCE: 271

```
gacatccaga tgacccagtc tccatcctcc ttatctgcct ctgtgggaga tagagtcacc      60

atcacttgtc gggcaagtca ggaaattagt ggttacttaa gctggctgca gcagaaacca     120

ggcaaggccc ctagacgcct gatctacgcc gcatccactt tagattctgg tgtcccatcc     180

aggttcagtg gcagtgagtc tgggaccgag ttcaccctca ccatcagcag ccttcagcct     240

gaagattttg caacctatta ctgtctacaa tattttagtt atccgctcac gttcggaggg     300

gggaccaagg tggaaataaa aggaggcgga tccggaggcg gaggccaggt tcagctggtg     360

cagtctggag ctgaggtgaa gaagcctggc gcctcagtga aggtctcctg caaggcttct     420

ggttacacct ttaccagcta ctggatgaac tgggtgcgac aggcccctgg acaagggctt     480

gagtggatcg gaatgattga tccttcagac agtgaaactc actacaatca aaagttcaag     540

gacagagtca ccatgaccac agacacatcc acgagcacag cctacatgga gctgaggagc     600

ctgagatctg acgacacggc cgtgtattac tgtgcgagag ctatgggcta ctgggggcaa     660

gggaccacgg tcaccgtctc ctcactggga ggctgcggcg gagggagccg aactgtggct     720

gcaccatcgg tcttcatctt cccgccatct gatgagcagt tgaaatctgg aactgcctct     780

gttgtgtgcc tgctgaataa cttctatccc agagaggcca aagtacagtg gaaggtggat     840

aacgccctcc aatcgggtaa ctcccaggag agtgtcacag agcaggacag caaggacagc     900

acctacagcc tcagcagcac cctgacgctg agcaaagcag actacgagaa acacaaagtc     960

tacgcctgcg aagtcaccca tcagggcctg agctcgcccg tcacaaagag cttcaacagg    1020

ggagagtgtt ag                                                        1032
```

<210> SEQ ID NO 272
<211> LENGTH: 574
<212> TYPE: PRT
<213> ORGANISM: Artificial Sequence
<220> FEATURE:
<223> OTHER INFORMATION: HBCRCVL R45N-h8B5VH_LGGCGGGS-hG1

<400> SEQUENCE: 272

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175
```

Asn His Ala Thr Tyr Tyr Ala Glu Ser Val Ile Gly Arg Phe Thr Ile
180 185 190

Ser Arg Asp Asp Ala Lys Asn Ser Leu Tyr Leu Gln Met Asn Ser Leu
195 200 205

Arg Ala Glu Asp Thr Ala Val Tyr Tyr Cys Gly Ala Leu Gly Leu Asp
210 215 220

Tyr Trp Gly Gln Gly Thr Leu Val Thr Val Ser Ser Leu Gly Gly Cys
225 230 235 240

Gly Gly Gly Ser Ala Ser Thr Lys Gly Pro Ser Val Phe Pro Leu Ala
245 250 255

Pro Ser Ser Lys Ser Thr Ser Gly Gly Thr Ala Ala Leu Gly Cys Leu
260 265 270

Val Lys Asp Tyr Phe Pro Glu Pro Val Thr Val Ser Trp Asn Ser Gly
275 280 285

Ala Leu Thr Ser Gly Val His Thr Phe Pro Ala Val Leu Gln Ser Ser
290 295 300

Gly Leu Tyr Ser Leu Ser Ser Val Val Thr Val Pro Ser Ser Ser Leu
305 310 315 320

Gly Thr Gln Thr Tyr Ile Cys Asn Val Asn His Lys Pro Ser Asn Thr
325 330 335

Lys Val Asp Lys Arg Val Glu Pro Lys Ser Cys Asp Lys Thr His Thr
340 345 350

Cys Pro Pro Cys Pro Ala Pro Glu Leu Leu Gly Gly Pro Ser Val Phe
355 360 365

Leu Phe Pro Pro Lys Pro Lys Asp Thr Leu Met Ile Ser Arg Thr Pro
370 375 380

Glu Val Thr Cys Val Val Val Asp Val Ser His Glu Asp Pro Glu Val
385 390 395 400

Lys Phe Asn Trp Tyr Val Asp Gly Val Glu Val His Asn Ala Lys Thr
405 410 415

Lys Pro Arg Glu Glu Gln Tyr Asn Ser Thr Tyr Arg Val Val Ser Val
420 425 430

Leu Thr Val Leu His Gln Asp Trp Leu Asn Gly Lys Glu Tyr Lys Cys
435 440 445

Lys Val Ser Asn Lys Ala Leu Pro Ala Pro Ile Glu Lys Thr Ile Ser
450 455 460

Lys Ala Lys Gly Gln Pro Arg Glu Pro Gln Val Tyr Thr Leu Pro Pro
465 470 475 480

Ser Arg Asp Glu Leu Thr Lys Asn Gln Val Ser Leu Thr Cys Leu Val
485 490 495

Lys Gly Phe Tyr Pro Ser Asp Ile Ala Val Glu Trp Glu Ser Asn Gly
500 505 510

Gln Pro Glu Asn Asn Tyr Lys Thr Thr Pro Pro Val Leu Asp Ser Asp
515 520 525

Gly Ser Phe Phe Leu Tyr Ser Lys Leu Thr Val Asp Lys Ser Arg Trp
530 535 540

Gln Gln Gly Asn Val Phe Ser Cys Ser Val Met His Glu Ala Leu His
545 550 555 560

Asn His Tyr Thr Gln Lys Ser Leu Ser Leu Ser Pro Gly Lys
565 570

<210> SEQ ID NO 273
<211> LENGTH: 1722
<212> TYPE: DNA

<213> ORGANISM: Artificial Sequence
<220> FEATURE:
<223> OTHER INFORMATION: HBCRCVL R45N-h8B5VH_LGGCGGGS-hG1

<400> SEQUENCE: 273

```
gatgttgtga tgactcagtc tccactctcc ctgcccgtca cccttggaca gccggcctcc     60
atctcctgca agtcaagtca gagcctctta gatagtgatg gaaagacata tttgaattgg    120
tttcagcaga ggccaggcca atctccaaac cgcctaattt atctggtgtc taaactggac    180
tctggggtcc cagacagatt cagcggcagt gggtcaggca ctgatttcac actgaaaatc    240
agcagggtgg aggctgagga tgttggggtt tattactgct ggcaaggtac acattttccg    300
ctcacgttcg gcggagggac caagcttgag atcaaaggag gcggatccgg aggcggaggc    360
gaagtgcagc ttgtggagtc tggaggaggc ttggtgcaac ctggaggatc cctgagactc    420
tcttgtgccg cctctggatt cacttttagt gacgcctgga tggactgggt ccgtcaggcc    480
ccaggcaagg ggcttgagtg ggttgctgaa attagaaaca aagctaaaaa tcatgcaaca    540
tactatgctg agtctgtgat agggaggttc accatctcaa gagatgacgc caaaaacagt    600
ctgtacctgc aaatgaacag cttaagagct gaagacactg ccgtgtatta ctgtggggct    660
ctgggccttg actactgggg ccaaggcacc ctggtgaccg tctccagcct gggaggctgc    720
ggcggaggga gcgcctccac caagggccca tcggtcttcc ccctggcacc ctcctccaag    780
agcacctctg ggggcacagc ggccctgggc tgcctggtca aggactactt ccccgaaccg    840
gtgacggtgt cgtggaactc aggcgccctg accagcggcg tgcacacctt cccggctgtc    900
ctacagtcct caggactcta ctccctcagc agcgtggtga ccgtgccctc cagcagcttg    960
ggcacccaga cctacatctg caacgtgaat cacaagccca gcaacaccaa ggtggacaag   1020
agagttgagc ccaaatcttg tgacaaaact cacacatgcc caccgtgccc agcacctgaa   1080
ctcctggggg gaccgtcagt cttcctcttc cccccaaaac ccaaggacac cctcatgatc   1140
tcccggaccc ctgaggtcac atgcgtggtg gtggacgtga gccacgaaga ccctgaggtc   1200
aagttcaact ggtacgtgga cggcgtggag gtgcataatg ccaagacaaa gccgcgggag   1260
gagcagtaca acagcacgta ccgtgtggtc agcgtcctca ccgtcctgca ccaggactgg   1320
ctgaatggca aggagtacaa gtgcaaggtc tccaacaaag ccctcccagc ccccatcgag   1380
aaaaccatct ccaaagccaa agggcagccc cgagaaccac aggtgtacac cctgccccca   1440
tcccgggatg agctgaccaa gaaccaggtc agcctgacct gcctggtcaa aggcttctat   1500
cccagcgaca tcgccgtgga gtgggagagc aatgggcagc cggagaacaa ctacaagacc   1560
acgcctcccg tgctggactc cgacggctcc ttcttcctct acagcaagct caccgtggac   1620
aagagcaggt ggcagcaggg gaacgtcttc tcatgctccg tgatgcatga ggctctgcac   1680
aaccactaca cgcagaagag cctctccctg tctccgggta aa                      1722
```

<210> SEQ ID NO 274
<211> LENGTH: 335
<212> TYPE: PRT
<213> ORGANISM: Artificial Sequence
<220> FEATURE:
<223> OTHER INFORMATION: H8B5VL-HBCRCVH M48I, M62K_(-4)LEIK_hKappa

<400> SEQUENCE: 274

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30
```

-continued

Leu Ser Trp Leu Gln Gln Lys Pro Gly Lys Ala Pro Arg Arg Leu Ile
35 40 45

Tyr Ala Ala Ser Thr Leu Asp Ser Gly Val Pro Ser Arg Phe Ser Gly
50 55 60

Ser Glu Ser Gly Thr Glu Phe Thr Leu Thr Ile Ser Ser Leu Gln Pro
65 70 75 80

Glu Asp Phe Ala Thr Tyr Tyr Cys Leu Gln Tyr Phe Ser Tyr Pro Leu
85 90 95

Thr Phe Gly Gly Gly Thr Lys Val Glu Ile Lys Gly Gly Gly Ser Gly
100 105 110

Gly Gly Gly Gln Val Gln Leu Val Gln Ser Gly Ala Glu Val Lys Lys
115 120 125

Pro Gly Ala Ser Val Lys Val Ser Cys Lys Ala Ser Gly Tyr Thr Phe
130 135 140

Thr Ser Tyr Trp Met Asn Trp Val Arg Gln Ala Pro Gly Gln Gly Leu
145 150 155 160

Glu Trp Ile Gly Met Ile Asp Pro Ser Asp Ser Glu Thr His Tyr Asn
165 170 175

Gln Lys Phe Lys Asp Arg Val Thr Met Thr Thr Asp Thr Ser Thr Ser
180 185 190

Thr Ala Tyr Met Glu Leu Arg Ser Leu Arg Ser Asp Asp Thr Ala Val
195 200 205

Tyr Tyr Cys Ala Arg Ala Met Gly Tyr Trp Gly Gln Gly Thr Thr Val
210 215 220

Leu Glu Ile Lys Arg Thr Val Ala Ala Pro Ser Val Phe Ile Phe Pro
225 230 235 240

Pro Ser Asp Glu Gln Leu Lys Ser Gly Thr Ala Ser Val Val Cys Leu
245 250 255

Leu Asn Asn Phe Tyr Pro Arg Glu Ala Lys Val Gln Trp Lys Val Asp
260 265 270

Asn Ala Leu Gln Ser Gly Asn Ser Gln Glu Ser Val Thr Glu Gln Asp
275 280 285

Ser Lys Asp Ser Thr Tyr Ser Leu Ser Ser Thr Leu Thr Leu Ser Lys
290 295 300

Ala Asp Tyr Glu Lys His Lys Val Tyr Ala Cys Glu Val Thr His Gln
305 310 315 320

Gly Leu Ser Ser Pro Val Thr Lys Ser Phe Asn Arg Gly Glu Cys
325 330 335

<210> SEQ ID NO 275
<211> LENGTH: 1005
<212> TYPE: DNA
<213> ORGANISM: Artificial Sequence
<220> FEATURE:
<223> OTHER INFORMATION: H8B5VL-HBCRCVH M48I, M62K_(-4)LEIK_hKappa

<400> SEQUENCE: 275
gacatccaga tgacccagtc tccatcctcc ttatctgcct ctgtgggaga tagagtcacc 60
atcacttgtc gggcaagtca ggaaattagt ggttacttaa gctggctgca gcagaaacca 120
ggcaaggccc ctagacgcct gatctacgcc gcatccactt tagattctgg tgtcccatcc 180
aggttcagtg gcagtgagtc tgggaccgag ttcaccctca ccatcagcag ccttcagcct 240
gaagattttg caacctatta ctgtctacaa tattttagtt atccgctcac gttcggaggg 300
gggaccaagg tggaaataaa aggaggcgga tccggaggcg gaggccaggt tcagctggtg 360

```
cagtctggag ctgaggtgaa gaagcctggc gcctcagtga aggtctcctg caaggcttct    420

ggttacacct ttaccagcta ctggatgaac tgggtgcgac aggcccctgg acaagggctt    480

gagtggatcg gaatgattga tccttcagac agtgaaactc actacaatca aaagttcaag    540

gacagagtca ccatgaccac agacacatcc acgagcacag cctacatgga gctgaggagc    600

ctgagatctg acgacacggc cgtgtattac tgtgcgagag ctatgggcta ctgggggcaa    660

gggaccacgg tcctggagat caagcgaact gtggctgcac catcggtctt catcttcccg    720

ccatctgatg agcagttgaa atctggaact gcctctgttg tgtgcctgct gaataacttc    780

tatcccagag aggccaaagt acagtggaag gtggataacg ccctccaatc gggtaactcc    840

caggagagtg tcacagagca ggacagcaag gacagcacct acagcctcag cagcaccctg    900

acgctgagca aagcagacta cgagaaacac aaagtctacg cctgcgaagt cacccatcag    960

ggcctgagct cgcccgtcac aaagagcttc aacaggggag agtgt                   1005
```

<210> SEQ ID NO 276
<211> LENGTH: 566
<212> TYPE: PRT
<213> ORGANISM: Artificial Sequence
<220> FEATURE:
<223> OTHER INFORMATION: HBCRCVL R45N-h8B5VH_(-4)TVSS-hG1 = HBCRCVL R45N-h8B5VH_-hG1

<400> SEQUENCE: 276

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Asn Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Leu Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Gly Ser Leu Arg Leu Ser Cys Ala Ala
    130                 135                 140

Ser Gly Phe Thr Phe Ser Asp Ala Trp Met Asp Trp Val Arg Gln Ala
145                 150                 155                 160

Pro Gly Lys Gly Leu Glu Trp Val Ala Glu Ile Arg Asn Lys Ala Lys
                165                 170                 175

Asn His Ala Thr Tyr Tyr Ala Glu Ser Val Ile Gly Arg Phe Thr Ile
            180                 185                 190

Ser Arg Asp Asp Ala Lys Asn Ser Leu Tyr Leu Gln Met Asn Ser Leu
        195                 200                 205

Arg Ala Glu Asp Thr Ala Val Tyr Tyr Cys Gly Ala Leu Gly Leu Asp
    210                 215                 220

Tyr Trp Gly Gln Gly Thr Leu Val Thr Val Ser Ser Ala Ser Thr Lys
225                 230                 235                 240
```

```
Gly Pro Ser Val Phe Pro Leu Ala Pro Ser Ser Lys Ser Thr Ser Gly
                245                 250                 255

Gly Thr Ala Ala Leu Gly Cys Leu Val Lys Asp Tyr Phe Pro Glu Pro
            260                 265                 270

Val Thr Val Ser Trp Asn Ser Gly Ala Leu Thr Ser Gly Val His Thr
        275                 280                 285

Phe Pro Ala Val Leu Gln Ser Ser Gly Leu Tyr Ser Leu Ser Ser Val
    290                 295                 300

Val Thr Val Pro Ser Ser Ser Leu Gly Thr Gln Thr Tyr Ile Cys Asn
305                 310                 315                 320

Val Asn His Lys Pro Ser Asn Thr Lys Val Asp Lys Arg Val Glu Pro
                325                 330                 335

Lys Ser Cys Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
    370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
        435                 440                 445

Ala Pro Ile Glu Lys Thr Ile Ser Lys Ala Lys Gly Gln Pro Arg Glu
    450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
                565
```

<210> SEQ ID NO 277
<211> LENGTH: 1698
<212> TYPE: DNA
<213> ORGANISM: Artificial Sequence
<220> FEATURE:
<223> OTHER INFORMATION: HBCRCVL R45N-h8B5VH_(-4)TVSS-hG1

<400> SEQUENCE: 277

```
gatgttgtga tgactcagtc tccactctcc ctgcccgtca cccttggaca gccggcctcc      60

atctcctgca agtcaagtca gagcctctta gatagtgatg gaaagacata tttgaattgg     120

tttcagcaga ggccaggcca atctccaaac cgcctaattt atctggtgtc taaactggac     180
```

-continued tctggggtcc cagacagatt cagcggcagt gggtcaggca ctgatttcac actgaaaatc 240
agcagggtgg aggctgagga tgttggggtt tattactgct ggcaaggtac acattttccg 300
ctcacgttcg gcggagggac caagcttgag atcaaaggag gcggatccgg aggcggaggc 360
gaagtgcagc ttgtggagtc tggaggaggc ttggtgcaac ctggaggatc cctgagactc 420
tcttgtgccg cctctggatt cacttttagt gacgcctgga tggactgggt ccgtcaggcc 480
ccaggcaagg ggcttgagtg ggttgctgaa attagaaaca aagctaaaaa tcatgcaaca 540
tactatgctg agtctgtgat agggaggttc accatctcaa gagatgacgc caaaaacagt 600
ctgtacctgc aaatgaacag cttaagagct gaagacactg ccgtgtatta ctgtggggct 660
ctgggccttg actactgggg ccaaggcacc ctggtgaccg tctccagcgc ctccaccaag 720
ggcccatcgg tcttccccct ggcaccctcc tccaagagca cctctggggg cacagcggcc 780
ctgggctgcc tggtcaagga ctacttcccc gaaccggtga cggtgtcgtg gaactcaggc 840
gccctgacca gcggcgtgca caccttcccg gctgtcctac agtcctcagg actctactcc 900
ctcagcagcg tggtgaccgt gccctccagc agcttgggca cccagaccta catctgcaac 960
gtgaatcaca agcccagcaa caccaaggtg gacaagagag ttgagcccaa atcttgtgac 1020
aaaactcaca catgcccacc gtgcccagca cctgaactcc tggggggacc gtcagtcttc 1080
ctcttccccc caaaacccaa ggacaccctc atgatctccc ggacccctga ggtcacatgc 1140
gtggtggtgg acgtgagcca cgaagaccct gaggtcaagt tcaactggta cgtggacggc 1200
gtggaggtgc ataatgccaa gacaaagccg cgggaggagc agtacaacag cacgtaccgt 1260
gtggtcagcg tcctcaccgt cctgcaccag gactggctga atggcaagga gtacaagtgc 1320
aaggtctcca acaaagccct cccagccccc atcgagaaaa ccatctccaa agccaaaggg 1380
cagccccgag aaccacaggt gtacaccctg cccccatccc gggatgagct gaccaagaac 1440
caggtcagcc tgacctgcct ggtcaaaggc ttctatccca gcgacatcgc cgtggagtgg 1500
gagagcaatg ggcagccgga gaacaactac aagaccacgc ctcccgtgct ggactccgac 1560
ggctccttct tcctctacag caagctcacc gtggacaaga gcaggtggca gcaggggaac 1620
gtcttctcat gctccgtgat gcatgaggct ctgcacaacc actacacgca gaagagcctc 1680
tccctgtctc cgggtaaa 1698

<210> SEQ ID NO 278
<211> LENGTH: 10
<212> TYPE: PRT
<213> ORGANISM: Artificial Sequence
<220> FEATURE:
<223> OTHER INFORMATION: Linker

<400> SEQUENCE: 278

Phe Asn Arg Gly Glu Cys Gly Gly Gly Ser
1 5 10

<210> SEQ ID NO 279
<211> LENGTH: 13
<212> TYPE: PRT
<213> ORGANISM: Artificial Sequence
<220> FEATURE:
<223> OTHER INFORMATION: Linker

<400> SEQUENCE: 279

Phe Asn Arg Gly Glu Cys Leu Gln Val Tyr Tyr Arg Met
1 5 10

-continued

<210> SEQ ID NO 280
<211> LENGTH: 6
<212> TYPE: PRT
<213> ORGANISM: Artificial Sequence
<220> FEATURE:
<223> OTHER INFORMATION: Linker

<400> SEQUENCE: 280

Leu Glu Gly Glu Glu Gly
1               5

<210> SEQ ID NO 281
<211> LENGTH: 7
<212> TYPE: PRT
<213> ORGANISM: Artificial Sequence
<220> FEATURE:
<223> OTHER INFORMATION: Linker

<400> SEQUENCE: 281

Leu Glu Gly Glu Glu Gly Cys
1               5

<210> SEQ ID NO 282
<211> LENGTH: 4
<212> TYPE: PRT
<213> ORGANISM: Artificial Sequence
<220> FEATURE:
<223> OTHER INFORMATION: Linker

<400> SEQUENCE: 282

Leu Glu Ile Lys
1

<210> SEQ ID NO 283
<211> LENGTH: 5
<212> TYPE: PRT
<213> ORGANISM: Artificial Sequence
<220> FEATURE:
<223> OTHER INFORMATION: Linker

<400> SEQUENCE: 283

Leu Gly Glu Glu Gly
1               5

<210> SEQ ID NO 284
<211> LENGTH: 6
<212> TYPE: PRT
<213> ORGANISM: Artificial Sequence
<220> FEATURE:
<223> OTHER INFORMATION: Linker

<400> SEQUENCE: 284

Leu Gly Glu Glu Gly Cys
1               5

<210> SEQ ID NO 285
<211> LENGTH: 8
<212> TYPE: PRT
<213> ORGANISM: Artificial Sequence
<220> FEATURE:
<223> OTHER INFORMATION: Linker

<400> SEQUENCE: 285

Leu Gly Gly Cys Gly Gly Gly Ser
1               5

<210> SEQ ID NO 286

-continued

<211> LENGTH: 5
<212> TYPE: PRT
<213> ORGANISM: Artificial Sequence
<220> FEATURE:
<223> OTHER INFORMATION: Linker

<400> SEQUENCE: 286

Leu Gly Lys Lys Gly
1 5

<210> SEQ ID NO 287
<211> LENGTH: 6
<212> TYPE: PRT
<213> ORGANISM: Artificial Sequence
<220> FEATURE:
<223> OTHER INFORMATION: Linker

<400> SEQUENCE: 287

Leu Gly Lys Lys Gly Cys
1 5

<210> SEQ ID NO 288
<211> LENGTH: 6
<212> TYPE: PRT
<213> ORGANISM: Artificial Sequence
<220> FEATURE:
<223> OTHER INFORMATION: Linker

<400> SEQUENCE: 288

Leu Lys Gly Lys Lys Gly
1 5

<210> SEQ ID NO 289
<211> LENGTH: 7
<212> TYPE: PRT
<213> ORGANISM: Artificial Sequence
<220> FEATURE:
<223> OTHER INFORMATION: Linker

<400> SEQUENCE: 289

Leu Lys Gly Lys Lys Gly Cys
1 5

<210> SEQ ID NO 290
<211> LENGTH: 7
<212> TYPE: PRT
<213> ORGANISM: Artificial Sequence
<220> FEATURE:
<223> OTHER INFORMATION: Linker

<400> SEQUENCE: 290

Leu Gln Val Tyr Tyr Arg Met
1 5

<210> SEQ ID NO 291
<211> LENGTH: 8
<212> TYPE: PRT
<213> ORGANISM: Artificial Sequence
<220> FEATURE:
<223> OTHER INFORMATION: Linker

<400> SEQUENCE: 291

Leu Gln Val Tyr Tyr Arg Met Cys
1 5

<210> SEQ ID NO 292
<211> LENGTH: 4

<212> TYPE: PRT
<213> ORGANISM: Artificial Sequence
<220> FEATURE:
<223> OTHER INFORMATION: Linker

<400> SEQUENCE: 292

Thr Val Ser Ser
1

<210> SEQ ID NO 293
<211> LENGTH: 10
<212> TYPE: PRT
<213> ORGANISM: Artificial Sequence
<220> FEATURE:
<223> OTHER INFORMATION: Linker

<400> SEQUENCE: 293

Val Glu Pro Lys Ser Cys Gly Gly Gly Ser
1 5 10

<210> SEQ ID NO 294
<211> LENGTH: 14
<212> TYPE: PRT
<213> ORGANISM: Artificial Sequence
<220> FEATURE:
<223> OTHER INFORMATION: Linker

<400> SEQUENCE: 294

Val Glu Pro Lys Ser Cys Tyr Leu Tyr Leu Arg Ala Arg Val
1 5 10

<210> SEQ ID NO 295
<211> LENGTH: 7
<212> TYPE: PRT
<213> ORGANISM: Artificial Sequence
<220> FEATURE:
<223> OTHER INFORMATION: Linker

<400> SEQUENCE: 295

Val Gln Val His Tyr Arg Met
1 5

<210> SEQ ID NO 296
<211> LENGTH: 8
<212> TYPE: PRT
<213> ORGANISM: Artificial Sequence
<220> FEATURE:
<223> OTHER INFORMATION: Linker

<400> SEQUENCE: 296

Val Gln Val His Tyr Arg Met Cys
1 5

<210> SEQ ID NO 297
<211> LENGTH: 8
<212> TYPE: PRT
<213> ORGANISM: Artificial Sequence
<220> FEATURE:
<223> OTHER INFORMATION: Linker

<400> SEQUENCE: 297

Tyr Leu Tyr Leu Arg Ala Arg Val
1 5

<210> SEQ ID NO 298
<211> LENGTH: 9
<212> TYPE: PRT

<213> ORGANISM: Artificial Sequence
<220> FEATURE:
<223> OTHER INFORMATION: Linker

<400> SEQUENCE: 298

Tyr Leu Tyr Leu Arg Ala Arg Val Cys
1               5

<210> SEQ ID NO 299
<211> LENGTH: 28
<212> TYPE: PRT
<213> ORGANISM: Artificial Sequence
<220> FEATURE:
<223> OTHER INFORMATION: E-coil Linker

<400> SEQUENCE: 299

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 300
<211> LENGTH: 28
<212> TYPE: PRT
<213> ORGANISM: Artificial Sequence
<220> FEATURE:
<223> OTHER INFORMATION: K-coil Linker

<400> SEQUENCE: 300

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 301
<211> LENGTH: 5
<212> TYPE: PRT
<213> ORGANISM: Artificial Sequence
<220> FEATURE:
<223> OTHER INFORMATION: Linker

<400> SEQUENCE: 301

Gly Gly Gly Asn Ser
1               5

<210> SEQ ID NO 302
<211> LENGTH: 107
<212> TYPE: PRT
<213> ORGANISM: Artificial Sequence
<220> FEATURE:
<223> OTHER INFORMATION: YA2B6 light chain variable region

<400> SEQUENCE: 302

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

```
Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105


<210> SEQ ID NO 303
<211> LENGTH: 121
<212> TYPE: PRT
<213> ORGANISM: Artificial Sequence
<220> FEATURE:
<223> OTHER INFORMATION: YA2B6 hheavy chain variable region

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Val Ile Asp Pro Ser Asp Thr Tyr Pro Asn Tyr Asn Lys Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120


<210> SEQ ID NO 304
<211> LENGTH: 46
<212> TYPE: PRT
<213> ORGANISM: Artificial Sequence
<220> FEATURE:
<223> OTHER INFORMATION: Albumin Binding Domain

<400> SEQUENCE: 304

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45


<210> SEQ ID NO 305
<211> LENGTH: 279
<212> TYPE: PRT
<213> ORGANISM: Artificial Sequence
<220> FEATURE:
<223> OTHER INFORMATION: h3G8VL1-G3SG4-h2B6VH4-Kcoil-GGGNS

<400> SEQUENCE: 305

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
```

```
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Gly
            100                 105                 110

Gly Gly Ser Gly Gly Gly Gly Gln Val Gln Leu Val Gln Ser Gly Ala
        115                 120                 125

Glu Val Lys Lys Pro Gly Ala Ser Val Lys Val Ser Cys Lys Ala Ser
    130                 135                 140

Gly Tyr Thr Phe Thr Asn Tyr Trp Ile His Trp Val Arg Gln Ala Pro
145                 150                 155                 160

Gly Gln Gly Leu Glu Trp Ile Gly Val Ile Asp Pro Ser Asp Thr Tyr
                165                 170                 175

Pro Asn Tyr Asn Lys Lys Phe Lys Gly Arg Val Thr Met Thr Val Val
            180                 185                 190

Val Ser Thr Ser Thr Ala Tyr Met Glu Leu Arg Ser Leu Arg Ser Asp
        195                 200                 205

Asp Thr Ala Val Tyr Tyr Cys Ala Arg Asn Gly Asp Ser Asp Tyr Tyr
    210                 215                 220

Ser Gly Met Asp Tyr Trp Gly Gln Gly Thr Thr Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu Gly Gly Gly Asn Ser
        275
```

<210> SEQ ID NO 306
<211> LENGTH: 837
<212> TYPE: DNA
<213> ORGANISM: Artificial Sequence
<220> FEATURE:
<223> OTHER INFORMATION: h3G8VL1-G3SG4-h2B6VH4-Kcoil-GGGNS

<400> SEQUENCE: 306

```
gacatcgtga tgacccaatc tccagactct ttggctgtgt ctctagggga gagggccacc     60

atcaactgca aggccagcca aagtgttgat tttgatggtg atagttttat gaactggtac    120

caacagaaac caggacagcc acccaaactc ctcatctata ctacatccaa tctagaatct    180

ggggtcccag acaggtttag tggcagtggg tctgggacag acttcaccct caccatcagc    240

agcctgcagg ctgaggatgt ggcagtttat tactgtcagc aaagtaatga agatccgtac    300

acgttcggac aggggaccaa gcttgagatc aaaggaggcg gatccggcgg cggaggccag    360

gttcagctgg tgcagtctgg agctgaggtg aagaagcctg ggcctcagt gaaggtctcc    420

tgcaaggctt ctggttacac ctttaccaac tactggatac actgggtgcg acaggcccct    480

ggacaagggc ttgagtggat tggagtgatt gatccttctg atacttatcc aaattacaat    540

aaaaagttca agggcagagt caccatgacc gtagtcgtat ccacgagcac agcctacatg    600

gagctgagga gcctgagatc tgacgacacg gccgtgtatt actgtgcgag aaacggtgat    660

tccgattatt actctggtat ggactactgg gggcaaggga ccacggtcac cgtctcctcc    720

ggaggatgtg gcggtggaaa agtggccgca ctgaaggaga aagttgctgc tttgaaagag    780
```

aaggtcgccg cacttaagga aaaggtcgca gccctgaaag agggcggcgg gaattct 837

<210> SEQ ID NO 307
<211> LENGTH: 318
<212> TYPE: PRT
<213> ORGANISM: Artificial Sequence
<220> FEATURE:
<223> OTHER INFORMATION: h2B6VL5-G3SG4-h3G8VH5-Ecoil-GGGNS-ABD

<400> SEQUENCE: 307

Glu Ile Val Leu Thr Gln Ser Pro Asp Phe Gln Ser Val Thr Pro Lys
1 5 10 15

Glu Lys Val Thr Phe Thr Cys Arg Thr Ser Gln Ser Ile Gly Thr Asn
20 25 30

Ile His Trp Tyr Gln Gln Lys Pro Asp Gln Ser Pro Lys Leu Leu Ile
35 40 45

Lys Glu Val Ser Glu Ser Ile Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys Gln Gln Ser Asn Thr Trp Pro Phe
85 90 95

Thr Phe Gly Gly Gly Thr Lys Val Glu Ile Lys Gly Gly Gly Ser Gly
100 105 110

Gly Gly Gly Gln Val Thr Leu Arg Glu Ser Gly Pro Ala Leu Val Lys
115 120 125

Pro Thr Gln Thr Leu Thr Leu Thr Cys Thr Phe Ser Gly Phe Ser Leu
130 135 140

Ser Thr Ser Gly Met Gly Val Gly Trp Ile Arg Gln Pro Pro Gly Lys
145 150 155 160

Ala Leu Glu Trp Leu Ala His Ile Trp Trp Asp Asp Asp Lys Arg Tyr
165 170 175

Asn Pro Ala Leu Lys Ser Arg Leu Thr Ile Ser Lys Asp Thr Ser Lys
180 185 190

Asn Gln Val Val Leu Thr Met Thr Asn Met Asp Pro Val Asp Thr Ala
195 200 205

Thr Tyr Tyr Cys Ala Gln Ile Asn Pro Ala Trp Phe Ala Tyr Trp Gly
210 215 220

Gln Gly Thr Leu Val Thr Val Ser Ser Gly Gly Cys Gly Gly Gly Glu
225 230 235 240

Val Ala Ala Leu Glu Lys Glu Val Ala Ala Leu Glu Lys Glu Val Ala
245 250 255

Ala Leu Glu Lys Glu Val Ala Ala Leu Glu Lys Gly Gly Gly Asn Ser
260 265 270

Leu Ala Glu Ala Lys Val Leu Ala Asn Arg Glu Leu Asp Lys Tyr Gly
275 280 285

Val Ser Asp Tyr Tyr Lys Asn Leu Ile Asn Asn Ala Lys Thr Val Glu
290 295 300

Gly Val Lys Ala Leu Ile Asp Glu Ile Leu Ala Ala Leu Pro
305 310 315

<210> SEQ ID NO 308
<211> LENGTH: 954
<212> TYPE: DNA
<213> ORGANISM: Artificial Sequence
<220> FEATURE:

<223> OTHER INFORMATION: h2B6VL5-G3SG4-h3G8VH5-Ecoil-GGGNS-ABD

<400> SEQUENCE: 308
gaaattgtgc tgactcagtc tccagacttt cagtctgtga ctccaaagga gaaagtcacc 60
ttcacctgca ggaccagtca gagcattggc acaaacatac actggtacca gcagaaacca 120
gatcagtctc caaagctcct catcaaggag gtttctgagt ctatctctgg agtcccatcg 180
aggttcagtg gcagtggatc tgggacagat ttcaccctca ccatcaatag cctggaagct 240
gaagatgctg caacgtatta ctgtcaacaa agtaatacct ggccgttcac gttcggcgga 300
gggaccaagg tggagatcaa aggaggcgga tccggcggcg gaggccaggt taccctgaga 360
gagtctggcc ctgcgctggt gaagcccaca cagaccctca cactgacttg taccttctct 420
gggttttcac tgagcacttc tggtatgggt gtaggctgga ttcgtcagcc tcccgggaag 480
gctctagagt ggctggcaca catttggtgg gatgatgaca agcgctataa tccagccctg 540
aagagccgac tgacaatctc caaggatacc tccaaaaacc aggtagtcct cacaatgacc 600
aacatggacc ctgtggatac tgccacatac tactgtgctc aaataaaccc cgcctggttt 660
gcttactggg gccaagggac tctggtcact gtgagctccg gaggatgtgg cggtggagaa 720
gtggccgcac tggagaaaga ggttgctgct ttggagaagg aggtcgctgc acttgaaaag 780
gaggtcgcag ccctggagaa aggcggcggg aattctctgg ccgaagcaaa agtgctggcc 840
aaccgcgaac tggataaata tggcgtgagc gattattata agaacctgat taacaacgca 900
aagaccgtgg aaggcgtgaa agcactgatt gatgaaattc tggccgccct gcct 954

<210> SEQ ID NO 309
<211> LENGTH: 5
<212> TYPE: PRT
<213> ORGANISM: Artificial Sequence
<220> FEATURE:
<223> OTHER INFORMATION: Linker

<400> SEQUENCE: 309

Ala Pro Ser Ser Ser
1 5

<210> SEQ ID NO 310
<211> LENGTH: 8
<212> TYPE: PRT
<213> ORGANISM: Artificial Sequence
<220> FEATURE:
<223> OTHER INFORMATION: Linker

<400> SEQUENCE: 310

Val Pro Ser Met Gly Ser Ser Ser
1 5

<210> SEQ ID NO 311
<211> LENGTH: 383
<212> TYPE: PRT
<213> ORGANISM: Homo sapiens

<400> SEQUENCE: 311

Met Gly Leu Gly Pro Val Phe Leu Leu Leu Ala Gly Ile Phe Pro Phe
1 5 10 15

Ala Pro Pro Gly Ala Ala Ala Glu Pro His Ser Leu Arg Tyr Asn Leu
20 25 30

Thr Val Leu Ser Trp Asp Gly Ser Val Gln Ser Gly Phe Leu Thr Glu
35 40 45

```
Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380


<210> SEQ ID NO 312
<211> LENGTH: 305
<212> TYPE: PRT
<213> ORGANISM: Homo sapiens

<400> SEQUENCE: 312

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45
```

```
Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Leu Pro Pro Met Val Asn Val Ile
                165                 170                 175

Cys Ser Glu Val Ser Glu Gly Asn Ile Thr Val Thr Cys Arg Ala Ser
            180                 185                 190

Ser Phe Tyr Pro Arg Asn Ile Thr Leu Thr Trp Arg Gln Asp Gly Val
        195                 200                 205

Ser Leu Ser His Asn Thr Gln Gln Trp Gly Asp Val Leu Pro Asp Gly
    210                 215                 220

Asn Gly Thr Tyr Gln Thr Trp Val Ala Thr Arg Ile Arg Gln Gly Glu
225                 230                 235                 240

Glu Gln Arg Phe Thr Cys Tyr Met Glu His Ser Gly Asn His Gly Thr
                245                 250                 255

His Pro Val Pro Ser Gly Lys Ala Leu Val Leu Gln Ser Gln Arg Thr
            260                 265                 270

Asp Phe Pro Tyr Val Ser Ala Ala Met Pro Cys Phe Val Ile Ile Ile
        275                 280                 285

Ile Leu Cys Val Pro Cys Cys Lys Lys Lys Thr Ser Ala Ala Glu Gly
    290                 295                 300

Pro
305
```

<210> SEQ ID NO 313
<211> LENGTH: 7
<212> TYPE: PRT
<213> ORGANISM: Artificial Sequence
<220> FEATURE:
<223> OTHER INFORMATION: Linker

<400> SEQUENCE: 313

```
Gly Phe Asn Arg Gly Glu Cys
1               5
```

<210> SEQ ID NO 314
<211> LENGTH: 7
<212> TYPE: PRT
<213> ORGANISM: Artificial Sequence
<220> FEATURE:
<223> OTHER INFORMATION: Linker

<400> SEQUENCE: 314

```
Gly Val Glu Pro Lys Ser Cys
1               5
```

<210> SEQ ID NO 315
<211> LENGTH: 241
<212> TYPE: PRT
<213> ORGANISM: Artificial Sequence
<220> FEATURE:
<223> OTHER INFORMATION: TCRVL-HER2VH

<400> SEQUENCE: 315

Glu Ile Val Leu Thr Gln Ser Pro Ala Thr Leu Ser Leu Ser Pro Gly
1 5 10 15

Glu Arg Ala Thr Leu Ser Cys Ser Ala Thr Ser Ser Val Ser Tyr Met
20 25 30

His Trp Tyr Gln Gln Lys Pro Gly Lys Ala Pro Lys Arg Trp Ile Tyr
35 40 45

Asp Thr Ser Lys Leu Ala Ser Gly Val Pro Ser Arg Phe Ser Gly Ser
50 55 60

Gly Ser Gly Thr Glu Phe Thr Leu Thr Ile Ser Ser Leu Gln Pro Glu
65 70 75 80

Asp Phe Ala Thr Tyr Tyr Cys Gln Gln Trp Ser Ser Asn Pro Leu Thr
85 90 95

Phe Gly Gln Gly Thr Lys Leu Glu Ile Lys Gly Gly Gly Ser Gly Gly
100 105 110

Gly Gly Gln Val Gln Leu Gln Gln Ser Gly Pro Glu Leu Val Lys Pro
115 120 125

Gly Ala Ser Leu Lys Leu Ser Cys Thr Ala Ser Gly Phe Asn Ile Lys
130 135 140

Asp Thr Tyr Ile His Trp Val Lys Gln Arg Pro Glu Gln Gly Leu Glu
145 150 155 160

Trp Ile Gly Arg Ile Tyr Pro Thr Asn Gly Tyr Thr Arg Tyr Asp Pro
165 170 175

Lys Phe Gln Asp Lys Ala Thr Ile Thr Ala Asp Thr Ser Ser Asn Thr
180 185 190

Ala Tyr Leu Gln Val Ser Arg Leu Thr Ser Glu Asp Thr Ala Val Tyr
195 200 205

Tyr Cys Ser Arg Trp Gly Gly Asp Gly Phe Tyr Ala Met Asp Tyr Trp
210 215 220

Gly Gln Gly Ala Ser Val Thr Val Ser Ser Gly Phe Asn Arg Gly Glu
225 230 235 240

Cys

<210> SEQ ID NO 316
<211> LENGTH: 723
<212> TYPE: DNA
<213> ORGANISM: Artificial Sequence
<220> FEATURE:
<223> OTHER INFORMATION: TCRVL-HER2VH

<400> SEQUENCE: 316
gaaattgtgt tgacacagtc tccagccacc ctgtctttgt ctccagggga aagagccacc 60
ctctcctgca gtgccacctc aagtgtaagt tacatgcact ggtatcagca gaaaccaggg 120
aaagccccta agcgctggat ctatgacaca tccaaactgg cttctggggt cccatcaagg 180
ttcagcggca gtggatctgg gacagaattt actctcacaa tcagcagcct gcagcctgaa 240
gattttgcaa cttattactg tcagcagtgg agtagtaacc cgctcacgtt tggccagggg 300
accaagcttg agatcaaagg aggcggatcc ggcggcggag gccaggttca gctgcagcag 360
tctgggccag agcttgtgaa gccaggggcc tcactcaagt tgtcctgtac agcttctggc 420
ttcaacatta aagacaccta tatacactgg gtgaaacaga ggcctgaaca gggcctggaa 480
tggattggaa ggatttatcc tacgaatggt tatactagat atgacccgaa gttccaggac 540
aaggccacta taacagcaga cacatcctcc aacacagcct acctgcaggt cagccgcctg 600
acatctgagg acactgccgt ctattattgt tctagatggg gaggggacgg cttctatgct 660
atggactact ggggtcaagg agcctcggtc accgtgagct ccggattcaa caggggagag 720
tgt 723

<210> SEQ ID NO 317
<211> LENGTH: 242
<212> TYPE: PRT
<213> ORGANISM: Artificial Sequence
<220> FEATURE:
<223> OTHER INFORMATION: HER2VL-TCRVH

<400> SEQUENCE: 317

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Asn Thr Ala
20 25 30

Val Ala Trp Tyr Gln Gln Lys Pro Gly His Ser Pro Lys Leu Leu Ile
35 40 45

Tyr Ser Ala Ser Phe Arg Tyr Thr Gly Val Pro Asp Arg Phe Thr Gly
50 55 60

Ser Arg Ser Gly Thr Asp Phe Thr Phe Thr Ile Ser Ser Val Gln Ala
65 70 75 80

Glu Asp Leu Ala Val Tyr Tyr Cys Gln Gln His Tyr Thr Thr Pro Pro
85 90 95

Thr Phe Gly Gly Gly Thr Lys Val Glu Ile Lys Gly Gly Gly Ser Gly
100 105 110

Gly Gly Gly Gln Val Gln Leu Val Gln Ser Gly Ala Glu Val Lys Lys
115 120 125

Pro Gly Ala Ser Val Lys Val Ser Cys Lys Ala Ser Gly Tyr Lys Phe
130 135 140

Thr Ser Tyr Val Met His Trp Val Arg Gln Ala Pro Gly Gln Gly Leu
145 150 155 160

Glu Trp Ile Gly Tyr Ile Asn Pro Tyr Asn Asp Val Thr Lys Tyr Asn
165 170 175

Glu Lys Phe Lys Gly Arg Val Thr Ile Thr Ala Asp Lys Ser Thr Ser
180 185 190

Thr Ala Tyr Met Glu Leu Ser Ser Leu Arg Ser Glu Asp Thr Ala Val
195 200 205

His Tyr Cys Ala Arg Gly Ser Tyr Tyr Asp Tyr Asp Gly Phe Val Tyr
210 215 220

Trp Gly Gln Gly Thr Leu Val Thr Val Ser Ser Gly Val Glu Pro Lys
225 230 235 240

Ser Cys

<210> SEQ ID NO 318
<211> LENGTH: 726
<212> TYPE: DNA
<213> ORGANISM: Artificial Sequence
<220> FEATURE:
<223> OTHER INFORMATION: HER2VL-TCRVH

<400> SEQUENCE: 318
gacatcgtga tgacccagtc ccacaagttc atgtccacct ctgtgggcga tagggtcagc 60
atcacctgca aggccagcca ggatgtgaat actgctgtag cctggtatca gcagaaacca 120
ggacattctc ccaaactgct gatttactcc gcatccttcc ggtacactgg agtccctgat 180
cgcttcactg gcagcagatc tgggacagat ttcactttca ccatcagcag tgtgcaggct 240
gaagacctgg cagtttatta ctgtcagcaa cattatacta cacctcccac cttcggaggg 300
ggtaccaagg tggagatcaa aggaggcgga tccggcggcg gaggccaggt tcagctggtg 360
cagtctggag ctgaggtgaa gaagcctggg gcctcagtga aggtctcctg caaggccagc 420
ggttacaagt ttaccagcta cgtgatgcac tgggtgcgac aggcccctgg acaagggctt 480
gagtggatcg gatatattaa tccttacaat gatgttacta agtacaatga gaagttcaaa 540
ggcagagtca cgattaccgc ggacaaatcc acgagcacag cctacatgga gctgagcagc 600
ctgagatccg aggacacggc cgtgcactac tgtgcgagag ggagctacta tgattacgac 660
gggtttgttt actggggcca agggactctg gtcactgtga gctccggagt tgagcccaaa 720
tcttgt 726

<210> SEQ ID NO 319
<211> LENGTH: 273
<212> TYPE: PRT
<213> ORGANISM: Artificial Sequence
<220> FEATURE:
<223> OTHER INFORMATION: TCRVL-HER2VH-E coil

<400> SEQUENCE: 319

Glu Ile Val Leu Thr Gln Ser Pro Ala Thr Leu Ser Leu Ser Pro Gly
1 5 10 15

Glu Arg Ala Thr Leu Ser Cys Ser Ala Thr Ser Ser Val Ser Tyr Met
20 25 30

His Trp Tyr Gln Gln Lys Pro Gly Lys Ala Pro Lys Arg Trp Ile Tyr
35 40 45

Asp Thr Ser Lys Leu Ala Ser Gly Val Pro Ser Arg Phe Ser Gly Ser
50 55 60

Gly Ser Gly Thr Glu Phe Thr Leu Thr Ile Ser Ser Leu Gln Pro Glu
65 70 75 80

Asp Phe Ala Thr Tyr Tyr Cys Gln Gln Trp Ser Ser Asn Pro Leu Thr
85 90 95

Phe Gly Gln Gly Thr Lys Leu Glu Ile Lys Gly Gly Gly Ser Gly Gly
100 105 110

Gly Gly Gln Val Gln Leu Gln Gln Ser Gly Pro Glu Leu Val Lys Pro
115 120 125

Gly Ala Ser Leu Lys Leu Ser Cys Thr Ala Ser Gly Phe Asn Ile Lys
130 135 140

Asp Thr Tyr Ile His Trp Val Lys Gln Arg Pro Glu Gln Gly Leu Glu
145 150 155 160

Trp Ile Gly Arg Ile Tyr Pro Thr Asn Gly Tyr Thr Arg Tyr Asp Pro
165 170 175

Lys Phe Gln Asp Lys Ala Thr Ile Thr Ala Asp Thr Ser Ser Asn Thr
180 185 190

Ala Tyr Leu Gln Val Ser Arg Leu Thr Ser Glu Asp Thr Ala Val Tyr
195 200 205

Tyr Cys Ser Arg Trp Gly Gly Asp Gly Phe Tyr Ala Met Asp Tyr Trp
210 215 220

Gly Gln Gly Ala Ser Val Thr Val Ser Ser Gly Gly Cys Gly Gly Gly
225 230 235 240

Glu Val Ala Ala Leu Glu Lys Glu Val Ala Ala Leu Glu Lys Glu Val
245 250 255

Ala Ala Leu Glu Lys Glu Val Ala Ala Leu Glu Lys Gly Gly Gly Asn
260 265 270

Ser

<210> SEQ ID NO 320
<211> LENGTH: 819
<212> TYPE: PRT
<213> ORGANISM: Artificial Sequence
<220> FEATURE:
<223> OTHER INFORMATION: TCRVL-HER2VH-E coil

<400> SEQUENCE: 320

Gly Ala Ala Ala Thr Thr Gly Thr Gly Thr Thr Gly Ala Cys Ala Cys
1 5 10 15

Ala Gly Thr Cys Thr Cys Cys Ala Gly Cys Cys Ala Cys Cys Cys Thr
20 25 30

Gly Thr Cys Thr Thr Thr Gly Thr Cys Thr Cys Cys Ala Gly Gly Gly
35 40 45

Gly Ala Ala Ala Gly Ala Gly Cys Cys Ala Cys Cys Cys Thr Cys Thr
50 55 60

Cys Cys Thr Gly Cys Ala Gly Thr Gly Cys Cys Ala Cys Cys Thr Cys
65 70 75 80

Ala Ala Gly Thr Gly Thr Ala Ala Gly Thr Thr Ala Cys Ala Thr Gly
85 90 95

Cys Ala Cys Thr Gly Gly Thr Ala Thr Cys Ala Gly Cys Ala Gly Ala
100 105 110

Ala Ala Cys Cys Ala Gly Gly Gly Ala Ala Ala Gly Cys Cys Cys Cys
115 120 125

Thr Ala Ala Gly Cys Gly Cys Thr Gly Gly Ala Thr Cys Thr Ala Thr
130 135 140

Gly Ala Cys Ala Cys Ala Thr Cys Cys Ala Ala Ala Cys Thr Gly Gly
145 150 155 160

Cys Thr Thr Cys Thr Gly Gly Gly Gly Thr Cys Cys Cys Ala Thr Cys
165 170 175

Ala Ala Gly Gly Thr Thr Cys Ala Gly Cys Gly Gly Cys Ala Gly Thr
180 185 190

Gly Gly Ala Thr Cys Thr Gly Gly Gly Ala Cys Ala Gly Ala Ala Thr
195 200 205

Thr Thr Ala Cys Thr Cys Thr Cys Ala Cys Ala Ala Thr Cys Ala Gly
210 215 220

Cys Ala Gly Cys Cys Thr Gly Cys Ala Gly Cys Cys Thr Gly Ala Ala
225 230 235 240

Gly Ala Thr Thr Thr Thr Gly Cys Ala Ala Cys Thr Thr Ala Thr Thr
245 250 255

Ala Cys Thr Gly Thr Cys Ala Gly Cys Ala Gly Thr Gly Gly Ala Gly
260 265 270

Thr Ala Gly Thr Ala Ala Cys Cys Cys Gly Cys Thr Cys Ala Cys Gly
275 280 285

Thr Thr Thr Gly Gly Cys Cys Ala Gly Gly Gly Gly Ala Cys Cys Ala
290 295 300

Ala Gly Cys Thr Thr Gly Ala Gly Ala Thr Cys Ala Ala Ala Gly Gly

-continued

```
305                 310                 315                 320

Ala Gly Gly Cys Gly Gly Ala Thr Cys Cys Gly Gly Cys Gly Gly Cys
                325                 330                 335

Gly Gly Ala Gly Gly Cys Cys Ala Gly Gly Thr Thr Cys Ala Gly Cys
            340                 345                 350

Thr Gly Cys Ala Gly Cys Ala Gly Thr Cys Thr Gly Gly Gly Cys Cys
        355                 360                 365

Ala Gly Ala Gly Cys Thr Thr Gly Thr Gly Ala Ala Gly Cys Cys Ala
    370                 375                 380

Gly Gly Gly Gly Cys Cys Thr Cys Ala Cys Thr Cys Ala Ala Gly Thr
385                 390                 395                 400

Thr Gly Thr Cys Cys Thr Gly Thr Ala Cys Ala Gly Cys Thr Thr Cys
                405                 410                 415

Thr Gly Gly Cys Thr Thr Cys Ala Ala Cys Ala Thr Thr Ala Ala Ala
            420                 425                 430

Gly Ala Cys Ala Cys Cys Thr Ala Thr Ala Thr Ala Cys Ala Cys Thr
        435                 440                 445

Gly Gly Gly Thr Gly Ala Ala Ala Cys Ala Gly Ala Gly Gly Cys Cys
    450                 455                 460

Thr Gly Ala Ala Cys Ala Gly Gly Gly Cys Cys Thr Gly Gly Ala Ala
465                 470                 475                 480

Thr Gly Gly Ala Thr Thr Gly Gly Ala Ala Gly Gly Ala Thr Thr Thr
                485                 490                 495

Ala Thr Cys Cys Thr Ala Cys Gly Ala Ala Thr Gly Gly Thr Thr Ala
            500                 505                 510

Thr Ala Cys Thr Ala Gly Ala Thr Ala Thr Gly Ala Cys Cys Cys Gly
        515                 520                 525

Ala Ala Gly Thr Thr Cys Cys Ala Gly Gly Ala Cys Ala Ala Gly Gly
    530                 535                 540

Cys Cys Ala Cys Thr Ala Thr Ala Ala Cys Ala Gly Cys Ala Gly Ala
545                 550                 555                 560

Cys Ala Cys Ala Thr Cys Cys Thr Cys Cys Ala Ala Cys Ala Cys Ala
                565                 570                 575

Gly Cys Cys Thr Ala Cys Cys Thr Gly Cys Ala Gly Gly Thr Cys Ala
            580                 585                 590

Gly Cys Cys Gly Cys Cys Thr Gly Ala Cys Ala Thr Cys Thr Gly Ala
        595                 600                 605

Gly Gly Ala Cys Ala Cys Thr Gly Cys Cys Gly Thr Cys Thr Ala Thr
    610                 615                 620

Thr Ala Thr Thr Gly Thr Thr Cys Thr Ala Gly Ala Thr Gly Gly Gly
625                 630                 635                 640

Gly Ala Gly Gly Gly Gly Ala Cys Gly Gly Cys Thr Thr Cys Thr Ala
                645                 650                 655

Thr Gly Cys Thr Ala Thr Gly Gly Ala Cys Thr Ala Cys Thr Gly Gly
            660                 665                 670

Gly Gly Thr Cys Ala Ala Gly Gly Ala Gly Cys Cys Thr Cys Gly Gly
        675                 680                 685

Thr Cys Ala Cys Cys Gly Thr Gly Ala Gly Cys Thr Cys Cys Gly Gly
    690                 695                 700

Ala Gly Gly Ala Thr Gly Thr Gly Gly Cys Gly Gly Thr Gly Gly Ala
705                 710                 715                 720

Gly Ala Ala Gly Thr Gly Gly Cys Cys Gly Cys Ala Cys Thr Gly Gly
                725                 730                 735
```

```
Ala Gly Ala Ala Ala Gly Ala Gly Gly Thr Thr Gly Cys Thr Gly Cys
            740                 745                 750

Thr Thr Thr Gly Gly Ala Gly Ala Ala Gly Gly Ala Gly Gly Thr Cys
        755                 760                 765

Gly Cys Thr Gly Cys Ala Cys Thr Thr Gly Ala Ala Ala Ala Gly Gly
    770                 775                 780

Ala Gly Gly Thr Cys Gly Cys Ala Gly Cys Cys Cys Thr Gly Gly Ala
785                 790                 795                 800

Gly Ala Ala Ala Gly Gly Cys Gly Gly Cys Gly Gly Gly Ala Ala Thr
                805                 810                 815

Thr Cys Thr


<210> SEQ ID NO 321
<211> LENGTH: 274
<212> TYPE: PRT
<213> ORGANISM: Artificial Sequence
<220> FEATURE:
<223> OTHER INFORMATION: HER2VL-TCRVH-K coil

<400> SEQUENCE: 321

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Lys Phe
    130                 135                 140

Thr Ser Tyr Val Met His Trp Val Arg Gln Ala Pro Gly Gln Gly Leu
145                 150                 155                 160

Glu Trp Ile Gly Tyr Ile Asn Pro Tyr Asn Asp Val Thr Lys Tyr Asn
                165                 170                 175

Glu Lys Phe Lys Gly Arg Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

His Tyr Cys Ala Arg Gly Ser Tyr Tyr Asp Tyr Asp Gly Phe Val Tyr
    210                 215                 220

Trp Gly Gln Gly Thr Leu Val Thr Val Ser Ser Gly Gly Cys Gly Gly
225                 230                 235                 240

Gly Lys Val Ala Ala Leu Lys Glu Lys Val Ala Ala Leu Lys Glu Lys
                245                 250                 255

Val Ala Ala Leu Lys Glu Lys Val Ala Ala Leu Lys Glu Gly Gly Gly
            260                 265                 270
```

-continued

Asn Ser

<210> SEQ ID NO 322
<211> LENGTH: 822
<212> TYPE: DNA
<213> ORGANISM: Artificial Sequence
<220> FEATURE:
<223> OTHER INFORMATION: HER2VL-TCRVH-K coil

<400> SEQUENCE: 322
gacatcgtga tgacccagtc ccacaagttc atgtccacct ctgtgggcga tagggtcagc 60
atcacctgca aggccagcca ggatgtgaat actgctgtag cctggtatca gcagaaacca 120
ggacattctc ccaaactgct gatttactcc gcatccttcc ggtacactgg agtccctgat 180
cgcttcactg gcagcagatc tgggacagat ttcactttca ccatcagcag tgtgcaggct 240
gaagacctgg cagtttatta ctgtcagcaa cattatacta cacctcccac cttcggaggg 300
ggtaccaagg tggagatcaa aggaggcgga tccggcggcg gaggccaggt tcagctggtg 360
cagtctggag ctgaggtgaa gaagcctggg gcctcagtga aggtctcctg caaggccagc 420
ggttacaagt ttaccagcta cgtgatgcac tgggtgcgac aggcccctgg acaagggctt 480
gagtggatcg gatatattaa tccttacaat gatgttacta agtacaatga gaagttcaaa 540
ggcagagtca cgattaccgc ggacaaatcc acgagcacag cctacatgga gctgagcagc 600
ctgagatccg aggacacggc cgtgcactac tgtgcgagag ggagctacta tgattacgac 660
gggtttgttt actggggcca agggactctg gtcactgtga gctccggagg atgtggcggt 720
ggaaaagtgg ccgcactgaa ggagaaagtt gctgctttga aagagaaggt cgccgcactt 780
aaggaaaagg tcgcagccct gaaagagggc ggcgggaatt ct 822

<210> SEQ ID NO 323
<211> LENGTH: 46
<212> TYPE: PRT
<213> ORGANISM: Artificial Sequence
<220> FEATURE:
<223> OTHER INFORMATION: Synthetic ABD Construct

<400> SEQUENCE: 323

Leu Ala Glu Ala Lys Val Leu Ala Asn Arg Glu Leu Asp Lys Tyr Gly
1 5 10 15

Val Ser Asp Tyr Tyr Lys Asn Ala Ala Asn Asn Ala Lys Thr Val Glu
20 25 30

Gly Val Lys Ala Leu Ile Ala Glu Ile Leu Ala Ala Leu Pro
35 40 45

<210> SEQ ID NO 324
<211> LENGTH: 46
<212> TYPE: PRT
<213> ORGANISM: Artificial Sequence
<220> FEATURE:
<223> OTHER INFORMATION: Synthetic ABD Construct

<400> SEQUENCE: 324

Leu Ala Glu Ala Lys Val Leu Ala Asn Arg Glu Leu Asp Lys Tyr Gly
1 5 10 15

Val Ser Asp Tyr Tyr Lys Asn Leu Ile Ser Asn Ala Lys Ser Val Glu
20 25 30

Gly Val Lys Ala Leu Ile Ala Glu Ile Leu Ala Ala Leu Pro
35 40 45

<210> SEQ ID NO 325
<211> LENGTH: 21
<212> TYPE: PRT
<213> ORGANISM: Artificial Sequence
<220> FEATURE:
<223> OTHER INFORMATION: Artificial ABD Construct

<400> SEQUENCE: 325

```
Tyr Tyr Lys Asn Leu Ile Asn Asn Ala Lys Thr Val Glu Gly Val Lys
1               5                   10                  15

Ala Leu Ile Asp Glu
            20
```

<210> SEQ ID NO 326
<211> LENGTH: 21
<212> TYPE: PRT
<213> ORGANISM: Artificial Sequence
<220> FEATURE:
<223> OTHER INFORMATION: Synthetic ABD Construct (ABD Y60-E80 Variant N66D/T70S/V71A )

<400> SEQUENCE: 326

```
Tyr Tyr Lys Asn Leu Ile Asp Asn Ala Lys Ser Ala Glu Gly Val Lys
1               5                   10                  15

Ala Leu Ile Asp Glu
            20
```

<210> SEQ ID NO 327
<211> LENGTH: 21
<212> TYPE: PRT
<213> ORGANISM: Artificial Sequence
<220> FEATURE:
<223> OTHER INFORMATION: Synthetic ABD Construct (ABD Y60-E80 Variant L64A/I65A/V71A)

<400> SEQUENCE: 327

```
Tyr Tyr Lys Asn Ala Ala Asn Asn Ala Lys Thr Ala Glu Gly Val Lys
1               5                   10                  15

Ala Leu Ile Asp Glu
            20
```

<210> SEQ ID NO 328
<211> LENGTH: 46
<212> TYPE: PRT
<213> ORGANISM: Artificial Sequence
<220> FEATURE:
<223> OTHER INFORMATION: Synthetic ABD Construct (L64A/I65A/V71A ("ABD (AAA)"))

<400> SEQUENCE: 328

```
Leu Ala Glu Ala Lys Val Leu Ala Asn Arg Glu Leu Asp Lys Tyr Gly
1               5                   10                  15

Val Ser Asp Tyr Tyr Lys Asn Ala Ala Asn Asn Ala Lys Thr Ala Glu
            20                  25                  30

Gly Val Lys Ala Leu Ile Asp Glu Ile Leu Ala Ala Leu Pro
        35                  40                  45
```

<210> SEQ ID NO 329
<211> LENGTH: 46
<212> TYPE: PRT
<213> ORGANISM: Artificial Sequence
<220> FEATURE:
<223> OTHER INFORMATION: Synthetic ABD Construct (N66D/T70S/V71A ("ABD (DSA)"))

<400> SEQUENCE: 329

-continued

```
Leu Ala Glu Ala Lys Val Leu Ala Asn Arg Glu Leu Asp Lys Tyr Gly
1               5                   10                  15

Val Ser Asp Tyr Tyr Lys Asn Leu Ile Asp Asn Ala Lys Ser Ala Glu
            20                  25                  30

Gly Val Lys Ala Leu Ile Asp Glu Ile Leu Ala Ala Leu Pro
        35                  40                  45


<210> SEQ ID NO 330
<211> LENGTH: 4
<212> TYPE: PRT
<213> ORGANISM: Artificial Sequence
<220> FEATURE:
<223> OTHER INFORMATION: Linker

<400> SEQUENCE: 330

Leu Gly Gly Cys
1
```

DEIMMUNIZED SERUM-BINDING DOMAINS AND THEIR USE IN EXTENDING SERUM HALF-LIFE

CROSS-REFERENCE TO RELATED APPLICATIONS

This application is a §371 National Stage Application of PCT/US2012/038227 (filed May 16, 2012; pending) which application claims the benefit of U.S. Patent Application Ser. No. 61/488,725 (filed May 21, 2011) each of which applications is herein incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

1. Field of the Invention

The present invention is directed to a polypeptide (for example, an antigen-binding molecule) that comprises a polypeptide portion of a deimmunized serum-binding protein capable of binding to said serum protein. The presence of the serum-binding protein extends the serum half-life of the polypeptide, relative to the serum half-life of the polypeptide if lacking the polypeptide portion of the deimmunized serum-binding protein. The invention also pertains to methods and uses that employ such molecules.

The present invention is particularly directed to diabody molecules, otherwise referred to as "dual affinity retargeting reagents" ("DARTS"), and uses thereof in the treatment of a variety of diseases and disorders, including immunological disorders and cancers. The diabody molecules of the invention comprise at least two polypeptide chains that associate to form at least two epitope binding sites, which may recognize the same or different epitopes. Additionally, the epitopes may be from the same or different molecules or located on the same or different cells. The individual polypeptide chains of the diabody molecule may be covalently bound through non-peptide bond covalent bonds, such as, but not limited to, disulfide bonding of cysteine residues located within each polypeptide chain. In particular embodiments, the diabody molecules of the present invention further comprise an Fc region, which allows antibody-like functionality to be engineered into the molecule.

2. Description of Related Art

The design of covalent diabodies is based on the single chain Fv construct (scFv) (Holliger et al. (1993) "'*Diabodies': Small Bivalent And Bispecific Antibody Fragments*," Proc. Natl. Acad. Sci. USA 90:6444-6448; herein incorporated by reference in its entirety). In an intact, unmodified IgG, the VL and VH domains are located on separate polypeptide chains, i.e., the light chain and the heavy chain, respectively. Interaction of an antibody light chain and an antibody heavy chain and, in particular, interaction of VL and VH domains forms one of the epitope binding sites of the antibody. In contrast, the scFv construct comprises a VL and VH domain of an antibody contained in a single polypeptide chain wherein the domains are separated by a flexible linker of sufficient length to allow self-assembly of the two domains into a functional epitope binding site. Where self assembly of the is impossible due to a linker of insufficient length (less than about 12 amino acid residues), two of the scFv constructs interact with each other to form a bivalent molecule, the VL of one chain associating with the VH of the other (reviewed in Marvin et al. (2005) "*Recombinant Approaches To IgG-Like Bispecific Antibodies*," Acta Pharmacol. Sin. 26:649-658). Moreover, addition of a cysteine residue to the c-terminus of the construct has been show to allow disulfide bonding of the polypeptide chains, stabilizing the resulting dimer without interfering with the binding characteristics of the bivalent molecule (see e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27). Further, where VL and VH domains of differing specificity are selected, not only a bivalent, but also a bispecific molecule may be constructed.

Bivalent diabodies have wide ranging applications including therapy and immunodiagnosis. Bivalency allows for great flexibility in the design and engineering of diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the filed of tumor imaging (Fitzgerald et al. (1997) "*Improved Tumour Targeting By Disulphide Stabilized Diabodies Expressed In Pichia pastoris*," Protein Eng. 10:1221). Of particular importance is the cross linking of differing cells, for example the cross linking of cytotoxic T cells to tumor cells (Staerz et al. (1985) "*Hybrid Antibodies Can Target Sites For Attack By T Cells*," Nature 314:628-631, and Holliger et al. (1996) "*Specific Killing Of Lymphoma Cells By Cytotoxic T-Cells Mediated By A Bispecific Diabody*," Protein Eng. 9:299-305). Diabody epitope binding domains may also be directed to a surface determinant of any immune effector cell such as CD3, CD16, CD32, or CD64, which are expressed on T lymphocytes, natural killer (NK) cells or other mononuclear cells. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins*," Cancer Res. 59:2909-2916). Normally, effector cell activation is triggered by the binding of an antigen bound antibody to an effector cell via Fc-FcγR interaction; thus, in this regard, diabody molecules of the invention may exhibit Ig-like functionality independent of whether they comprise an Fc domain (e.g., as assayed in any efferctor function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197, hereby incorporated by reference herein in its entirety).

2.1 Effector Cell Receptors and their Roles in the Immune System

In traditional immune function the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related an antigen binding domains which presumably mediate intracellular signaling.

The Fcγ receptors, members of the immunoglobulin gene superfamily of proteins, are surface glycoproteins that can bind the Fcγ portion of immunoglobulin molecules. Each member of the family recognizes immunoglobulins of one or more isotypes through a recognition domain on the alpha chain of the Fcγ receptor. Fcγ receptors are defined by their specificity for immunoglobulin subtypes. Fcγ receptors for IgG are referred to as FcγR, for IgE as FcεR, and for IgA as FcαR. Different accessory cells bear Fcγ receptors for antibodies of different isotype, and the isotype of the antibody determines which accessory cells will be engaged in a given response (reviewed by Ravetch J. V. et al. (1991) "*Fc Receptors*," Annu Rev. Immunol. 9: 457-92; Gerber J. S. et al. (2001) "*Stimulatory And Inhibitory Signals Originating From The Macrophage Fcgamma Receptors*," Microbes and Infection, 3: 131-139; Billadeau D. D. et al. (2002), "*ITAMs Versus ITIMs: Striking A Balance During Cell Regulation*," The Journal of Clinical Investigation, 2(109): 161-1681; Ravetch J. V. et al. (2000) "*Immune Inhibitory Receptors*," Science, 290: 84-89; Ravetch J. V. et al., (2001) "*IgG Fc Receptors*," Annu. Rev. Immunol. 19:275-90; Ravetch J. V. (1994) "*Fc Receptors: Rubor Redux*," Cell, 78(4): 553-60). The different Fcγ receptors, the cells that express them, and their isotype specificity is summarized in Table 1 (adapted from *Immunobiology: The Immune System in Health and Disease*, $4^{th}$ ed. 1999, Elsevier Science Ltd/Garland Publishing, New York).

Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology between the three family members suggest they arose from a common progenitor perhaps by gene duplication.

FcγRII(CD32)

FcγRII proteins are 40 kDa integral membrane glycoproteins which bind only the complexed IgG due to a low affinity for monomeric Ig ($10^6$ $M^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRII-A and FcγRII-B create two functionally heterogenous responses to receptor ligation. The fundamental difference is that the A isoform initiates intracellular signaling leading to cell activation such as phagocytosis and respiratory burst, whereas the B isoform initiates inhibitory signals, e.g., inhibiting B-cell activation.

FcγRIII(CD16)

Due to heterogeneity within this class, the size of FcγRIII ranges between 40 and 80 kDa in mouse and man. Two human genes encode two transcripts, FcγRIIIA, an integral membrane glycoprotein, and FcγRIIIB, a glycosylphosphatidyl-inositol (GPI)-linked version. One murine gene encodes an FcγRIII homologous to the membrane spanning human FcγRIIIA. The FcγRIII shares structural characteristics with each of the other two FcγRs. Like FcγRII, FcγRIII binds IgG with low affinity and contains the corresponding two extracellular Ig-like domains. FcγRIIIA is expressed in macrophages, mast cells and is the lone FcγR in NK cells. The GPI-linked FcγRIIIB is currently known to be expressed only in human neutrophils.

Signaling Through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When co-ligated along with an activating FcγR, the ITIM in FcγRIIB becomes phosphorylated and attracts the SH2 domain of the inosital polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus crosslinking of FcγRIIB dampens the activating response to FcγR ligation and inhibits cellular responsiveness. B cell activation, B cell proliferation and antibody secretion is thus aborted.

TABLE 1

Receptors for the Fc Regions of Immunoglobulin Isotypes

| Receptor | Binding | Cell Type | Effect of Ligation |
|---|---|---|---|
| FcγRI (CD64) | IgG1<br>$10^8$ $M^{-1}$ | Macrophages<br>Neutrophils<br>Eosinophils<br>Dendritic cells | Uptake Stimulation<br>Activation of respiratory burst<br>Induction of killing |
| FcγRII-A (CD32) | IgG1<br>$2 \times 10^6$ $M^{-1}$ | Macrophages<br>Neutrophils<br>Eosinophils<br>Dendritic cells<br>Platelets<br>Langerhan cells | Uptake Granule Release |
| FcγRII-B2 (CD32) | IgG1<br>$2 \times 10^6$ $M^{-1}$ | Macrophages<br>Neutrophils<br>Eosinophils | Uptake Inhibition of Stimulation |

TABLE 1-continued

| Receptors for the Fc Regions of Immunoglobulin Isotypes | | | |
|---|---|---|---|
| Receptor | Binding | Cell Type | Effect of Ligation |
| FcγRII-B1 (CD32) | IgG1 $2 \times 10^6 M^{-1}$ | B cells Mast cells | No Uptake Inhibition of Stimulation |
| FcγRIII (CD16) | IgG1 $5 \times 10^5 M^{-1}$ | NK cells Eosinophil Macrophages Neutrophils Mast cells | Induction of Killing |
| FcεRI | IgE $10^{10} M^{-1}$ | Mast cells Eosinophil Basophils | Section of granules |
| FcαRI (CD89) | IgA1, IgA2 $10^7 M^{-1}$ | Macrophages Neutrophils Eosinophils | Uptake Induction of Killings |

3. SUMMARY OF THE INVENTION

The present invention particularly relates to covalent diabodies and/or covalent diabody molecules and to their use in the treatment of a variety of diseases and disorders including cancer, autoimmune disorders, allergy disorders and infectious diseases caused by bacteria, fungi or viruses. Preferably, the diabody of the present invention can bind to two different epitopes on two different cells wherein the first epitope is expressed on a different cell type than the second epitope, such that the diabody can bring the two cells together.

In detail, the invention provides a polypeptide (and especially an antigen-binding molecule) comprising a polypeptide chain that comprises a portion of a deimmunized serum-binding protein capable of binding to said serum protein; wherein said serum-binding protein portion extends the serum half-life of said polypeptide, relative to the serum half-life of said polypeptide if lacking said portion of said deimmunized serum-binding protein.

The invention also concerns the uses of (or methods involving the use of) such polypeptide portion of a deimmunized serum-binding protein to extend the serum half-life of a polypeptide covalently linked thereto, the extension of serum half-life being relative to the serum half-life of the antigen-binding molecule if lacking the albumin binding protein.

The invention additionally concerns the embodiment of the above-described polypeptide or uses, wherein the polypeptide chain comprises an additional portion of a deimmunized serum-binding protein, wherein the portions of the deimmunized serum-binding protein are both capable of binding to the serum protein.

The invention particularly concerns the embodiment of the above-described polypeptides or uses wherein the polypeptide portion of the deimmunized serum-binding protein is an albumin-binding domain (ABD) of a Streptococcal Protein G, or albumin-binding variant thereof, and especially wherein the albumin-binding domain (ABD) of the Streptococcal Protein G is an albumin-binding domain 3 (ABD3) of protein G of *Streptococcus* strain G148.

The invention particularly concerns the embodiment of the above-described polypeptides or uses wherein the albumin binding domain comprises:

(A) a valine to alanine variation at position 71, a valine to alanine variation at position 74, or an aspartate to alanine variation at position 79;

(B) a leucine to alanine variation at position 64, isoleucine to alanine variation at position 65, and valine to alanine variation at position 71; or (C) an asparagine to aspartic acid variation at position 66, a threonine to serine substitution at position 70, and a valine to alanine variation at position 71.

The invention further concerns the embodiment of the above-described polypeptides or uses wherein the albumin-binding domain has the sequence of SEQ ID NO: 304, SEQ ID NO: 323, SEQ ID NO: 324, SEQ ID NO: 325, SEQ ID NO: 326, SEQ ID NO: 327, SEQ ID NO: 328, or SEQ ID NO: 329.

The invention further concerns the embodiment of the above-described antigen-binding molecules or uses wherein the antigen-binding molecule is an antigen-binding molecule. The invention further concerns the embodiment in which the antigen-binding molecule is a diabody composed of at least a first and a second polypeptide chain which interact with one another to form two antigen-binding sites, wherein at least one of the polypeptide chains comprises the second polypeptide portion that comprises the portion of the deimmunized serum-binding protein that is capable of binding to the serum protein. The invention further concerns the embodiments of such diabodies wherein both the first and the second polypeptide chains comprise second polypeptide portions that comprise the portion of the deimmunized serum-binding protein capable of binding to the serum protein and/or wherein the first and the second polypeptide chains are covalently linked to one another.

The invention particularly concerns the embodiment of the above-described diabodies or uses, wherein the diabody binds to:

(A) the Natural Killer Group 2D (NKG2D) receptor or the T-cell receptor (TCR); and (B) a tumor-associated antigen The invention particularly concerns the embodiment of all of the above-described diabodies or uses, wherein the antigen is a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkins lymphoma, or an antigen associated with chronic lymphocytic leukemia.

In one embodiment, the present invention is directed to a covalent bispecific diabody, which diabody comprises a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope, and, optionally, (iii) a third domain comprising at least one cysteine residue, which first and second domains are covalently linked such that the first and second domains do not associate to form an epitope binding site; which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and, optionally, (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL1)(VH1) that binds the first epitope; wherein the second domain and the fourth domain associate to form a second binding site (VL2)(VH2) that binds the second epitope.

In another embodiment, the present invention is directed to a covalent bispecific diabody, which diabody comprises a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site; which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), which fourth and fifth domains are covalently linked such that the third and fourth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL1)(VH1) that binds the first epitope; wherein the second domain and the fourth domain associate to form a second binding site (VL2)(VH2) that binds the second epitope.

In certain aspects, the present invention is directed to diabody molecule, which molecule comprises a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site; which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL1)(VH1) that binds the first epitope; wherein the second domain and the fourth domain associate to form a second binding site (VL2)(VH2) that binds the second epitope.

In certain embodiments, the present invention is directed to a covalent bispecific diabody, which diabody is a dimer of diabody molecules, each diabody molecule comprising a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site; and which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain of each diabody molecule are covalently linked, with the proviso that the covalent link is not a peptide bond; wherein the first domain and the fifth domain of each diabody molecule associate to form a first binding site (VL1)(VH1) that binds the first epitope; wherein the second domain and the fourth domain of each diabody molecule associate to form a second binding site (VL2)(VH2) that binds the second epitope.

In yet other embodiments, the present invention is directed to a covalent tetrapecific diabody, which diabody is a dimer of diabody molecules, the first diabody molecule comprising a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site; and which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL1)(VH1) that binds the first epitope; wherein the second domain and the fourth domain associate to form a second binding site (VL2)(VH2) that binds the second epitope; and the second diabody molecule comprising a first and a second polypeptide chain, which first polypeptide chain comprises (i) a first domain comprising a binding region of a light chain variable domain of a third immunoglobulin (VL3) specific for a third epitope, (ii) a second domain comprising a binding region of a heavy chain variable domain of a fourth immunoglobulin (VH4) specific for a fourth epitope and (iii) a third domain comprising an Fc domain or portion thereof, which first and second domains are covalently linked such that the first and second domains do not associate to form an epitope binding site; and which second polypeptide chain comprises (i) a fourth domain comprising a binding region of a light chain variable domain of the fourth immunoglobulin (VL4), (ii) a fifth domain comprising a binding region of a heavy chain variable domain of the third immunoglobulin (VH3), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL3)(VH3) that binds the third epitope; wherein the second domain and the fourth domain associate to form a second binding site (VL4)(VH4) that binds the fourth epitope.

In certain aspects of the invention the first epitope, second epitope, and where applicable, third epitope and fourth epitope can be the same. In other aspects, the first epitope, second epitope, and where applicable, third epitope and fourth epitope can each different from the other. In certain aspects of the invention comprising a third epitope binding domain, the first epitope and third epitope can be the same. In certain aspects of the invention comprising a fourth epitope binding domain, the first epitope and fourth epitope can be the same. In certain aspects of the invention comprising a third epitope binding domain, the second epitope and third epitope can be the same. In certain aspects of the invention comprising a fourth epitope binding domain, the second epitope and fourth epitope can be the same. In preferred aspects of the invention, the first eptitope and second epitope are different. In yet other aspects of the invention comprising a third epitope binding domain and a fourth epitope binding domain, the third epitope and fourth epitope can be different. It is to be understood that any combination of the foregoing is encompassed in the present invention.

In particular aspects of the invention, the first domain and the fifth domain of the diabody or diabody molecule can be derived from the same immunoglobulin. In another aspect, the second domain and the fourth domain of the diabody or diabody molecule can be derived from the same immunoglobulin. In yet another aspect, the first domain and the fifth domain of the diabody or diabody molecule can be derived from a different immunoglobulin. In yet another aspect, the second domain and the fourth domain of the diabody or diabody molecule can be derived from a different immunoglobulin. It is to be understood that any combination of the foregoing is encompassed in the present invention.

In certain aspects of the invention, the covalent linkage between the first polypeptide chain and second polypeptide chain of the diabody or diabody molecule can be via a disulfide bond between at least one cysteine residue on the first polypeptide chain and at least one cysteine residue on the second polypeptide chain. The cysteine residues on the first or second polypeptide chains that are responsible for disulfide bonding can be found anywhere on the polypeptide chain including within the first, second, third, fourth, fifth and sixth domains. In a specific embodiment the cysteine residue on the first polypeptide chain is found in the first domain and the cysteine residue on the second polypeptide chain is found in the fifth domain. The first, second, fourth and fifth domains correspond to the variable regions responsible for binding. In preferred embodiments, the cysteine residues responsible for the disulfide bonding between the first and second polypeptide chains are located within the third and sixth domains, respectively. In a particular aspect of this embodiment, the third domain of the first polypeptide chain comprises the C-terminal 6 amino acids of the human kappa light chain, FNRGEC (SEQ ID NO: 23), which can be encoded by the amino acid sequence (SEQ ID NO: 17). In another aspect of this embodiment, the sixth domain of the second polypeptide chain comprises the C-terminal 6 amino acids of the human kappa light chain, FNRGEC (SEQ ID NO: 23), which can be encoded by the amino acid sequence (SEQ ID NO: 17). In still another aspect of this embodiment, the third domain of the first polypeptide chain comprises the amino acid sequence VEPKSC (SEQ ID NO: 77), derived from the hinge domain of a human IgG, and which can be encoded by the nucleotide sequence (SEQ ID NO: 78). In another aspect of this embodiment, the sixth domain of the second polypeptide chain comprises the amino acid sequence VEPKSC (SEQ ID NO: 77), derived from the hinge domain of a human IgG, and which can be encoded by the nucleotide sequence (SEQ ID NO: 78). In certain aspects of this embodiment, the third domain of the first polypeptide chain comprises the C-terminal 6 amino acids of the human kappa light chain, FNRGEC (SEQ ID NO: 23); and the sixth domain of the second polypeptide chain comprises the amino acid sequence VEPKSC (SEQ ID NO: 77). In other aspects of this embodiment, the sixth domain of the second polypeptide chain comprises the C-terminal 6 amino acids of the human kappa light chain, FNRGEC (SEQ ID NO: 23); and the third domain of the first polypeptide chain comprises the amino acid sequence VEPKSC (SEQ ID NO: 77). In yet other aspects of this embodiment, the third domain of the first polypeptide chain comprises the C-terminal 6 amino acids of the human kappa light chain, FNRGEC (SEQ ID NO: 23); and the sixth domain of the second polypeptide chain comprises a hinge domain. In other aspects of this embodiment, the sixth domain of the second polypeptide chain comprises the C-terminal 6 amino acids of the human kappa light chain, FNRGEC (SEQ ID NO: 23); and the third domain of the first polypeptide chain comprises the hinge domain. In yet other aspects of this embodiment, the third domain of the first polypeptide chain comprises the C-terminal 6 amino acids of the human kappa light chain, FNRGEC (SEQ ID NO: 23); and the sixth domain of the first polypeptide chain comprises an Fc domain, or portion thereof. In still other aspects of this embodiment, the sixth domain of the second polypeptide chain comprises the C-terminal 6 amino acids of the human kappa light chain, FNRGEC (SEQ ID NO: 23); and the third domain of the first polypeptide chain comprises an Fc domain, or portion thereof.

In other embodiments, the cysteine residues on the first or second polypeptide that are responsible for the disulfide bonding can be located outside of the first, second or third domains on the first polypeptide chain and outside of the fourth, fifth and sixth domain on the second polypeptide chain. In particular, the cysteine residue on the first polypeptide chain can be N-terminal to the first domain or can be C-terminal to the first domain. The cysteine residue on the first polypeptide chain can be N-terminal to the second domain or can be C-terminal to the second domain. The cysteine residue on the first polypeptide chain can be N-terminal to the third domain or can be C-terminal to the third domain. Further, the cysteine residue on the second polypeptide chain can be N-terminal to the fourth domain or can be C-terminal to the fourth domain. The cysteine residue on the second polypeptide chain can be N-terminal to the fifth domain or can be C-terminal to the fifth domain. Accordingly, the cysteine residue on the second polypeptide chain can be C-terminal to the sixth domain or can be N-terminal to the sixth domain. In a particular aspect, disulfide bond can between at least two cysteine residues on the first polypeptide chain and at least two cysteine residues on the second polypeptide chain. In a particular aspect, wherein the third domain and sixth domain do not comprise an Fc domain, or portion thereof, the cysteine residue can be at the C-terminus of the first polypeptide chain and at the C-terminus of the second polypeptide chain. It is to be understood that any combination of the foregoing is encompassed in the present invention.

In specific embodiments of the invention described supra, the covalent diabody of the invention encompasses dimers of diabody molecules, wherein each diabody molecule comprises a first and second polypeptide chain. In certain aspects of this embodiment the diabody molecules can be covalently linked to form the dimer, with the proviso that the covalent linkage is not a peptide bond. In preferred aspects of this embodiment, the covalent linkage is a disulfide bond between at least one cysteine residue on the first polypeptide chain of each of the diabody molecules of the dimer. In yet more preferred aspects of this invention, the covalent linkage is a disulfide bond between at least one cysteine residue on the first polypeptide chain of each of the diabody molecules forming the dimer, wherein said at least one cysteine residue is located in the third domain of each first polypeptide chain.

In certain aspects of the invention, the first domain on the first polypeptide chain can be N-terminal to the second domain or can be C-terminal to the second domain. The first domain on the first polypeptide chain can be N-terminal to the third domain or can be C-terminal to the third domain. The second domain on the first polypeptide chain can be N-terminal to the first domain or can be C-terminal to the first domain. Further, the second domain on the first polypeptide chain can be N-terminal to the third domain or can be C-terminal to the third domain. Accordingly, the third domain on the first polypeptide chain can be N-terminal to the first domain or can be C-terminal to the first domain. The third domain on the first polypeptide chain can be N-terminal to the second domain or can be C-terminal to the second domain. With respect to the second polypeptide chain, the fourth domain can be N-terminal to the fifth domain or can be C-terminal to the fifth domain. The fourth domain can be N-terminal to the sixth domain or can be C-terminal to the sixth domain. The fifth domain on the second polypeptide chain can be N-terminal to the fourth domain or can be C-terminal to the fourth domain. The fifth domain on the second polypeptide chain can be N-terminal to the sixth domain or can be C-terminal to the sixth domain. Accordingly the sixth domain on the second polypeptide chain can be N-terminal to the fourth domain or can be C-terminal to the fourth domain. The sixth domain on the second polypeptide chain can be N-terminal to the fifth domain or can be C-terminal to the fifth domain. It is to be understood that any combination of the foregoing is encompassed in the present invention.

In certain embodiments, first domain and second domain can be located C-terminal to the third domain on the first polypeptide chain; or the first domain and second domain can be located N-terminal to the third domain on the first polypeptide chain. With respect to the second polypeptide chain, the fourth domain and fifth domain can be located C-terminal to the sixth domain, or the fourth domain and fifth domain can be located N-terminal to the sixth domain. In certain aspects of this embodiment, the present invention is directed to a covalent bispecific diabody, which diabody is a dimer of diabody molecules, each diabody molecule comprising a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site and wherein the third domain is located N-terminal to both the first domain and second domain; and which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain of each diabody molecule are covalently linked, with the proviso that the covalent link is not a peptide bond; wherein the first domain and the fifth domain of each diabody molecule associate to form a first binding site (VL1)(VH1) that binds the first epitope; wherein the second domain and the fourth domain of each diabody molecule associate to form a second binding site (VL2)(VH2) that binds the second epitope.

In yet another embodiment, the present invention is directed to a covalent tetrapecific diabody, which diabody is a dimer of diabody molecules, the first diabody molecule comprising a first and a second polypeptide chain, which first polypeptide chain comprises (i) a first domain comprising a binding region of a light chain variable domain of a first immunoglobulin (VL1) specific for a first epitope, (ii) a second domain comprising a binding region of a heavy chain variable domain of a second immunoglobulin (VH2) specific for a second epitope and (iii) a third domain comprising an Fc domain or portion thereof, which first and second domains are covalently linked such that the first and second domains do not associate to form an epitope binding site and wherein the third domain is located N-terminal to both the first domain and second domain; and which second polypeptide chain comprises (i) a fourth domain comprising a binding region of a light chain variable domain of the second immunoglobulin (VL2), (ii) a fifth domain comprising a binding region of a heavy chain variable domain of the first immunoglobulin (VH1), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL1)(VH1) that binds the first epitope; wherein the second domain and the fourth domain associate to form a second binding site (VL2)(VH2) that binds the second epitope; and the second diabody molecule comprises a first and a second polypeptide chain, which first polypeptide chain comprises (i) a first domain comprising a binding region of a light chain variable domain of a third immunoglobulin (VL3) specific for a third epitope, (ii) a second domain comprising a binding region of a heavy chain variable domain of a fourth immunoglobulin (VH4) specific for a fourth epitope and (iii) a third domain comprising an Fc domain or portion thereof, which first and second domains are covalently linked such that the first and second domains do not associate to form an epitope binding site and wherein the third domain is located N-terminal to both the first domain and second domain; and which second polypeptide chain comprises (i) a fourth domain comprising a binding region of a light chain variable domain of the fourth immunoglobulin (VL4), (ii) a fifth domain comprising a binding region of a heavy chain variable domain of the third immunoglobulin (VH3), and (iii) a sixth domain comprising at least one cysteine residue, which fourth and fifth domains are covalently linked such that the fourth and fifth domains do not associate to form an epitope binding site; and wherein the first polypeptide chain and the second polypeptide chain are covalently linked, with the proviso that the covalent link is not a peptide bond; wherein the first domain and the fifth domain associate to form a first binding site (VL3)(VH3) that binds the third epitope; wherein the second domain and the fourth domain associate to form a second binding site (VL4)(VH4) that binds the fourth epitope.

As discussed above, the domains on the individual polypeptide chains are covalently linked. In specific aspects, the covalent link between the first and second domain, first and third domain, second and third domain, fourth and fifth domain, fourth and sixth domain, and/or fifth and sixth domain can be a peptide bond. In particular, the first and second domains, and the fourth and fifth domains can be separated by the third domain and sixth domain, respectively, or by additional amino acid residues, so long as the first and second, and fourth and fifth domains do not associate to form a binding site. The number of amino acid residues can be 0, 1, 2, 3, 4, 5, 6, 7, 8 or 9 amino acid residues. In one preferred aspect, the number of amino acid residues between the domains is 8.

In certain aspects of the invention, the domains of the first and second polypeptid chain comprising an Fc domain, i.e., optionally, the third and sixth domains, respectively, can further comprise a hinge domain such that the domain comprises a hinge-Fc region. In alternative embodiments, the first polypeptide chain or the second polypeptide chain can comprise a hinge domain without also comprising an Fc domain. The heavy chains, light chains, hinge regions, Fc domains, and/or hinge-Fc domains for use in the invention can be derived from any immunoglobulin type including IgA, IgD, IgE, IgG or IgM. In a preferred aspect, the immunoglobulin type is IgG, or any subtype thereof, i.e., $IgG_1$, $IgG_2$, $IgG_3$ or $IgG_4$. In other aspects, the immunoglobulin from which the light and heavy chains are derived is humanized or chimerized.

Further, the first epitope and second epitopes, and, where applicable, third epitope and fourth epitope, to which the diabody or diabody molecule binds can be different epitopes from the same antigen or can be different epitopes from different antigens. The antigens can be any molecule to which an antibody can be generated. For example, proteins, nucleic acids, bacterial toxins, cell surface markers, autoimmune markers, viral proteins, drugs, etc. In particular aspects, at least one epitope binding site of the diabody is specific for an antigen on a particular cell, such as a B-cell, a T-cell, a phagocytic cell, a natural killer (NK) cell or a dendritic cell.

In certain aspects of the present embodiment, at least one epitope binding site of the diabody or diabody molecule is specific for a Fc receptor, which Fc receptor can be an activating Fc receptor or an inhibitory Fc receptor. In particular aspects, the Fc receptor is a Fcγ receptor, and the Fcγ receptor is a FcγRI, FcγRII or FcγRIII receptor. In more preferred aspects, the FcγRIII receptor is the FcγRIIIA (CD16A) receptor or the FcγRIIIB (CD16B) receptor, and, more preferably, the FcγRIII receptor is the FcγRIIIA (CD16A) receptor. In another preferred aspect, the FcγRII receptor is the FcγRIIA (CD32A) receptor or the FcγRIIB (CD32B) receptor, and more preferably the FcγRIIB (CD32B) receptor. In a particularly preferred aspect, one binding site of the diabody is specific for CD32B and the other binding site is specific for CD16A. In a specific embodiment of the invention, at least one epitope binding site of the diabody or diabody molecule is specific for an activating Fc receptor and at least one other site is specific for an inhibitory Fc receptor. In certain aspects of this embodiment the activating Fc receptor is CD32A and the inhibitory Fc receptor is CD32B. In other aspects of this embodiment the activating Fc receptor is BCR and the inhibitory Fc receptor is CD32B. In still other aspects of this embodiment, the activating Fc receptor is IgERI and the inhibitory Fc receptor is CD32B.

In cases where one epitope binding site is specific for CD16A, the VL and VH domains can be the same as or similar to the VL and VH domains of the mouse antibody 3G8, the sequence of which has been cloned and is set forth herein. In other cases where one epitope binding site is specific for CD32A, the VL and VH domains can be the same as or similar to the VL and VH domains of the mouse antibody IV.3. In yet other cases where one epitope binding site is specific for CD32B, the VL and VH domains can be the same as or similar to the VL and VH domains of the mouse antibody 2B6, the sequence of which has been cloned and is set forth herein. It is to be understood that any of the VL or VH domains of the 3G8, 2B6 and IV.3 antibodies can be used in any combination. The present invention is also directed to a bispecific diabody or diabody molecule wherein the first epitope is specific for CD32B, and the second epitope is specific for CD16A.

In other aspects, an epitope binding site can be specific for a pathogenic antigen. As used herein, a pathogenic antigen is an antigen involved in a specific pathogenic disease, including cancer, infection and autoimmune disease. Thus, the pathogenic antigen can be a tumor antigen, a bacterial antigen, a viral antigen, or an autoimmune antigen. Exemplary pathogenic antigens include, but are not limited to lipopolysaccharide, viral antigens selected from the group consisting of viral antigens from human immunodeficiency virus, Adenovirus, Respiratory Syncitial Virus, West Nile Virus (e.g., E16 and/or E53 antigens) and hepatitis virus, nucleic acids (DNA and RNA) and collagen. Preferably, the pathogenic antigen is a neutralizing antigen. In a preferred aspect, where one epitope binding site is specific for CD16A or CD32A, the other epitope binding site is specific for a pathogenic antigen excluding autoimmune antigens. In yet another preferred aspect, where one epitope binding site is specific for CD32B, the other epitope binding site is specific for any pathogenic antigen. In specific embodiments, the diabody molecule of the invention binds two different antigens on the same cell, for example, one antigen binding site is specific for an activating Fc receptor while the other is specific for an inhibitory Fc receptor. In other embodiments, the diabody molecule binds two distinct viral neutralizing epitopes, for example, but not limited to, E16 and E53 of West Nile Virus.

In yet another embodiment of the present invention, the diabodies of the invention can be used to treat a variety of diseases and disorders. Accordingly, the present invention is directed to a method for treating a disease or disorder comprising administering to a patient in need thereof an effective amount of a covalent diabody or diabody molecule of the invention in which at least one binding site is specific for a pathogenic antigen, such as an antigen expressed on the surface of a cancer cell or on the surface of a bacterium or virion and at least one other binding site is specific for a Fc receptor, e.g., CD16A.

In yet another embodiment, the invention is directed to a method for treating a disease or disorder comprising administering to a patient in need thereof an effective amount of a diabody or diabody molecule of the invention, in which at least one binding site is specific for CD32B and at least one other binding site is specific for CD16A.

In yet another embodiment, the invention is directed to a method for inducing immune tolerance to a pathogenic antigen comprising administering to a patient in need there an effective amount of a covalent diabody or dovalent diabody molecule of the invention, in which at least one binding site is specific for CD32B and at least one other binding site is specific for said pathogenic antigen. In aspects of this embodiment, the pathogenic antigen can be an allergen or another molecule to which immune tolerance is desired, such as a protein expressed on transplanted tissue.

In yet another embodiment, the present invention is directed to a method for detoxification comprising administering to a patient in need thereof an effective amount of a covalent diabody or diabody molecule of the invention, in which at least one binding site is specific for a cell surface marker and at least one other binding site is specific for a toxin. In particular aspects, the diabody of the invention administered is one where one binding site is specific for a cell surface marker such as an Fc and the other binding site is specific for a bacterial toxin or for a drug. In one aspect, the cell surface marker is not found on red blood cells.

The present invention additionally provides a method for increasing the half life of a molecule that comprises an antigen-binding domain of an antibody, wherein the method comprises linking (e.g., directly or indirectly via conjugation, or by bonding, etc.), two or more albumin binding domains to the molecule. The invention particularly concerns the embodiment of such method wherein the linking of two or more albumin binding domains comprises linking 2, 3, 4, 5, 6, 7, 8, 9, 10 or more albumin binding domains to the molecule, and more particularly concerns the embodiment of such method wherein the linking of two or more albumin binding domains comprises linking 2 albumin binding domains to the molecule. Such two or more albumin binding domains may be the same or different and are preferably independently selected from the group consisting of the sequence of SEQ ID NO: 304, SEQ ID NO: 323, SEQ ID NO: 324, SEQ ID NO: 325, SEQ ID NO: 326, SEQ ID NO: 327, SEQ ID NO: 328, or SEQ ID NO: 329. The invention particularly concerns the embodiment of such methods wherein the two or more albumin binding domains are the same or wherein 2 of the albumin binding domains are the same. The invention particularly concerns the embodiment of such method wherein the molecule that comprises an antigen-binding domain of an antibody is a diabody.

3.1 Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, Current Protocols in Immunology (J. E. Coligan et al., eds., 1999, including supplements through 2001); Current Protocols in Molecular Biology (F. M. Ausubel et al., eds., 1987, including supplements through 2001); Molecular Cloning: A Laboratory Manual, third edition (Sambrook and Russel, 2001); PCR: The Polymerase Chain Reaction, (Mullis et al., eds., 1994); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane Using Antibodies: A Laboratory Manual Cold Spring Harbor Laboratory Press, Cold Spring Harbor, N.Y., 1999; and Beaucage et al. eds., Current Protocols in Nucleic Acid Chemistry John Wiley & Sons, Inc., New York, 2000).

As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the terms "immunospecifically binds," "immunospecifically recognizes," "specifically binds," "specifically recognizes" and analogous terms refer to molecules that specifically bind to an antigen (e.g., eptiope or immune complex) and do not specifically bind to another molecule. A molecule that specifically binds to an antigen may bind to other peptides or polypeptides with lower affinity as determined by, e.g., immunoassays, BIAcore, or other assays known in the art. Preferably, molecules that specifically bind an antigen do not cross-react with other proteins. Molecules that specifically bind an antigen can be identified, for example, by immunoassays, BIAcore, or other techniques known to those of skill in the art.

As used herein, "immune complex" refers to a structure which forms when at least one target molecule and at least one heterologous Fcγ region-containing polypeptide bind to one another forming a larger molecular weight complex. Examples of immune complexes are antigen-antibody complexes which can be either soluble or particulate (e.g., an antigen/antibody complex on a cell surface.).

As used herein, the terms "heavy chain," "light chain," "variable region," "framework region," "constant domain," and the like, have their ordinary meaning in the immunology art and refer to domains in naturally occurring immunoglobulins and the corresponding domains of synthetic (e.g., recombinant) binding proteins (e.g., humanized antibodies, single chain antibodies, chimeric antibodies, etc.). The basic structural unit of naturally occurring immunoglobulins (e.g., IgG) is a tetramer having two light chains and two heavy chains, usually expressed as a glycoprotein of about 150,000 Da. The aminoterminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of an IgG molecule is n-$V_L$-$C_L$-c and the structure of IgG heavy chains is n-$V_H$-$C_{H1}$-H—$C_{H2}$-$C_{H3}$-c (where H is the hinge region). The variable regions of an IgG molecule consist of the complementarity determining regions (CDRs), which contain the residues in contact with antigen and non-CDR segments, referred to as framework segments, which in general maintain the structure and determine the positioning of the CDR loops (although certain framework residues may also contact antigen). Thus, the $V_L$ and $V_H$ domains have the structure n-FR1, CDR1, FR2, CDR2, FR3, CDR3, FR4-c.

When referring to binding proteins or antibodies (as broadly defined herein), the assignment of amino acids to each domain is in accordance with the definitions of Kabat, Sequences of Proteins of Immunological Interest (National Institutes of Health, Bethesda, Md., 1987 and 1991). Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain.

As used herein, the term "heavy chain" is used to define the heavy chain of an IgG antibody. In an intact, native IgG, the heavy chain comprises the immunoglobulin domains VH, CH1, hinge, CH2 and CH3. Throughout the present specification, the numbering of the residues in an IgG heavy chain is that of the EU index as in Kabat et al., *Sequences of Proteins of Immunological Interest,* $5^{th}$ Ed. Public Health Service, NH1, MD (1991), expressly incorporated herein by references. The "EU index as in Kabat" refers to the numbering of the human IgG1 EU antibody. Examples of the amino acid sequences containing human IgG1 hinge, CH2 and CH3 domains are shown in FIGS. 1A and 1B as described, infra. FIGS. 1A and 1B also set forth amino acid sequences of the hinge, CH2 and CH3 domains of the heavy chains of IgG2, IgG3 and IgG4. The amino acid sequences of IgG2, IgG3 and IgG4 isotypes are aligned with the IgG1 sequence by placing the first and last cysteine residues of the respective hinge regions, which form the inter-heavy chain S—S bonds, in the same positions. For the IgG2 and IgG3 hinge region, not all residues are numbered by the EU index.

The "hinge region" or "hinge domain" is generally defined as stretching from Glu216 to Pro230 of human IgG1. An example of the amino acid sequence of the human IgG1 hinge region is shown in FIG. 1A (amino acid residues in FIG. 1A are numbered according to the Kabat system). Hinge regions of other IgG isotypes may be aligned with the IgG1 sequence by placing the first and last cysteine residues forming inter-heavy chain S—S binds in the same positions as shown in FIG. 1A.

As used herein, the term "Fc region," "Fc domain" or analogous terms are used to define a C-terminal region of an IgG heavy chain. An example of the amino acid sequence containing the human IgG1 is shown in FIG. 1B. Although boundaries may vary slightly, as numbered according to the Kabat system, the Fc domain extends from amino acid 231 to amino acid 447 (amino acid residues in FIG. 1B are numbered according to the Kabat system). FIG. 1B also provides examples of the amino acid sequences of the Fc regions of IgG isotypes IgG2, IgG3, and IgG4.

The Fc region of an IgG comprises two constant domains, CH2 and CH3. The CH2 domain of a human IgG Fc region usually extends from amino acids 231 to amino acid 341 according to the numbering system of Kabat (FIG. 1B). The CH3 domain of a human IgG Fc region usually extends from amino acids 342 to 447 according to the numbering system of Kabat (FIG. 1B). The CH2 domain of a human IgG Fc region (also referred to as "Cγ2" domain) is unique in that it is not closely paired with another domain. Rather, two N-linked branched carbohydrate chains are interposed between the two CH2 domains of an intact native IgG.

As used herein the terms "FcγR binding protein," "FcγR antibody," and "anti-FcγR antibody", are used interchangeably and refer to a variety of immunoglobulin-like or immunoglobulin-derived proteins. "FcγR binding proteins" bind FcγR via an interaction with $V_L$ and/or $V_H$ domains (as distinct from Fey-mediated binding). Examples of FcγR binding proteins include fully human, polyclonal, chimeric and humanized antibodies (e.g., comprising 2 heavy and 2 light chains), fragments thereof (e.g., Fab, Fab', $F(ab')_2$, and Fv fragments), bifunctional or multifunctional antibodies (see, e.g., Lanzavecchia et al. (1987) "*The Use Of Hybrid Hybridomas To Target Human Cytotoxic T Lymphocytes*," Eur. J. Immunol. 17:105-111), single chain antibodies (see, e.g., Bird et al. (1988) "*Single-Chain Antigen-Binding Proteins*," Science 242:423-26), fusion proteins (e.g., phage display fusion proteins), "minibodies" (see, e.g., U.S. Pat. No. 5,837,821) and other antigen binding proteins comprising a $V_L$ and/or $V_H$ domain or fragment thereof. In one aspect, the FcγRIIIA binding protein is a "tetrameric antibody" i.e., having generally the structure of a naturally occurring IgG and comprising variable and constant domains, i.e., two light chains comprising a $V_L$ domain and a light chain constant domain and two heavy chains comprising a $V_H$ domain and a heavy chain hinge and constant domains.

As used herein the term "FcγR antagonists" and analogous terms refer to protein and non-proteinacious substances, including small molecules which antagonize at least one biological activity of an FcγR, e.g., block signaling. For example, the molecules of the invention block signaling by blocking the binding of IgGs to an FcγR.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular an antigen or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, the term "diabody molecule" refers to a complex of two or more polypeptide chains or proteins, each comprising at least one VL and one VH domain or fragment thereof, wherein both domains are comprised within a single polypeptide chain. In certain embodiments "diabody molecule" includes molecules comprising an Fc or a hinge-Fc domain. Said polypeptide chains in the complex may be the same or different, i.e., the diabody molecule may be a homo-multimer or a hetero-multimer. In specific aspects, "diabody molecule" includes dimers or tetramers or said polypeptide chains containing both a VL and VH domain. The individual polypeptide chains comprising the multimeric proteins may be covalently joined to at least one other peptide of the multimer by interchain disulfide bonds.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

"Identical polypeptide chains" as used herein also refers to polypeptide chains having almost identical amino acid sequence, for example, including chains having one or more amino acid differences, preferably conservative amino acid substitutions, such that the activity of the two polypeptide chains is not significantly different As used herein, the term "cancer" refers to a neoplasm or tumor resulting from abnormal uncontrolled growth of cells. As used herein, cancer explicitly includes, leukemias and lymphomas. In some embodiments, cancer refers to a benign tumor, which has remained localized. In other embodiments, cancer refers to a malignant tumor, which has invaded and destroyed neighboring body structures and spread to distant sites. In some embodiments, the cancer is associated with a specific cancer antigen.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

"Effector function" as used herein is meant a biochemical event that results from the interaction of an antibody Fc region with an Fc receptor or an antigen. Effector functions include but are not limited to antibody dependent cell mediated cytotoxicity (ADCC), antibody dependent cell mediated phagocytosis (ADCP), and complement dependent cytotoxicity (CDC). Effector functions include both those that operate after the binding of an antigen and those that operate independent of antigen binding.

"Effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and may be from any organism including but not limited to humans, mice, rats, rabbits, and monkeys.

As used herein, the term "specifically binds an immune complex" and analogous terms refer to molecules that specifically bind to an immune complex and do not specifically bind to another molecule. A molecule that specifically binds to an immune complex may bind to other peptides or polypeptides with lower affinity as determined by, e.g., immunoassays, BIAcore, or other assays known in the art. Preferably, molecules that specifically bind an immune complex do not cross-react with other proteins. Molecules that specifically bind an immune complex can be identified, for example, by immunoassays, BIAcore, or other techniques known to those of skill in the art.

A "stable fusion protein" as used herein refers to a fusion protein that undergoes minimal to no detectable level of degradation during production and/or storage as assessed using common biochemical and functional assays known to one skilled in the art, and can be stored for an extended period of time with no loss in biological activity, e.g., binding to FcγR.

4. BRIEF DESCRIPTION OF THE DRAWINGS

FIGS. 1A-B AMINO ACID SEQUENCE OF HUMAN IgG CH1, HINGE and Fc REGIONS

FIGS. 1(A) and (B) provide the amino acid sequences of human IgG1, IgG2, IgG3 and IgG4 hinge (A) and Fc (B) domains. (IgG1 hinge domain (SEQ ID NO: 1); IgG2 hinge domain (SEQ ID NO: 2); IgG3 hinge domain (SEQ ID NO: 3); IgG4 hinge domain (SEQ ID NO: 4); IgG1 Fc domain (SEQ ID NO: 5); IgG2 Fc domain (SEQ ID NO: 6); IgG3 Fc domain (SEQ ID NO: 7); IgG1 Fc domain (SEQ ID NO: 8)). The amino acid residues shown in FIGS. 1A and 1B are numbered according to the numbering system of Kabat EU. Isotype sequences are aligned with the IgG1 sequence by placing the first and last cysteine residues of the respective hinge regions, which form the inter-heavy chain S—S bonds, in the same positions. For FIG. 1B, residues in the CH2 domain are indicated by +, while residues in the CH3 domain are indicated by ~.

FIG. 2 SCHEMATIC REPRESENTATION OF POLYPEPTIDE CHAINS OF COVALENT BIFUNCTIONAL DIABODIES

Polypeptides of a covalent, bifunctional diabody consist of an antibody VL and an antibody VH domain separated by a short peptide linker. The 8 amino acid residue linker prevents self-assembly of a single polypeptide chain into scFv constructs, and, instead, interactions between the VL and VH domains of differing polypeptide chains predominate. 4 constructs were created (each construct is described from the amino terminus ("n"), left side of the construct, to the carboxy terminus ("c"), right side of figure): construct (1) (SEQ ID NO: 9) comprised, n—the VL domain Hu2B6—linker (GGGSGGGG (SEQ ID NO: 10))—the VH domain of Hu3G8—and a C-terminal sequence (LGGC; SEQ ID NO:330)-c; construct (2) (SEQ ID NO: 11) comprised n—the VL domain Hu3G8—linker (GGGSGGGG (SEQ ID NO: 10))—the VH domain of Hu2B6—and a C-terminal sequence (LGGC; SEQ ID NO:330)-c; construct (3) (SEQ ID NO: 12) comprised n—the VL domain Hu3G8—linker (GGGSGGGG (SEQ ID NO: 10))—the VH domain of Hu3G8—and a C-terminal sequence (LGGC; SEQ ID NO:330)-c; construct (4) (SEQ ID NO: 13) comprised n—the VL domain Hu2B6—linker (GGGSGGGG (SEQ ID NO: 10))—the VH domain of Hu2B6—and a C-terminal sequence (LGGC; SEQ ID NO:330)-c.

FIG. 3 SDS-PAGE ANALYSIS OF AFFINITY PURIFIED DIABODIES

Affinity purified diabodies were subjected to SDS-PAGE analysis under reducing (lanes 1-3) or non-reducing (lanes 4-6) conditions. Approximate molecular weights of the standard (in between lanes 3 and 4) are indicated. Lanes 1 and 4, h3G8 CMD; Lanes 2 and 5, h2B6 CMD; and Lanes 3 and 6, h2B6-h3G8 CBD.

FIGS. 4 A-B SEC ANALYSIS OF AFFINITY PURIFIED DIABODIES

Affinity purified diabodies were subjected to SEC analysis. (A) Elution profile of known standards: full-length IgG (~150 kDa), Fab fragment of IgG (~50 kDa), and scFv (~30 kDa); (B) Elution profile of h2b6 CMD, h3G8 CMD, and h2B6-h3G8 CBD.

Figure 5:
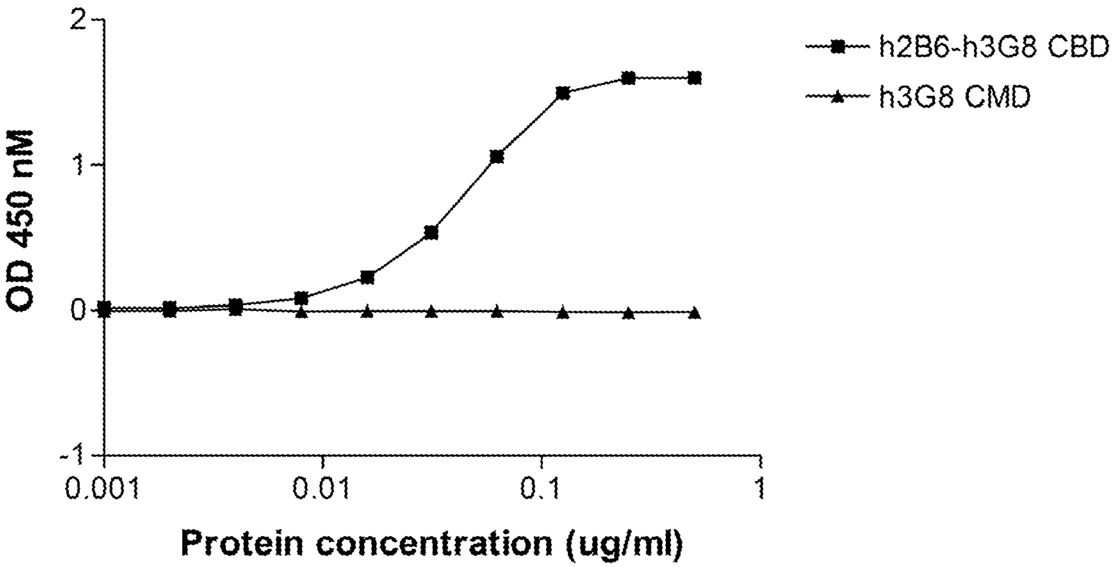

FIG. 5 BINDING OF h2B6-h3G8 CBD TO sCD32B AND sCD16A

The binding of h2B6-h3G8 CBD to sCD32B and sCD16A was assayed in a sandwich ELISA. sCD32B was used as the target protein. The secondary probe was HRP conjugated sCD16A. h3G8 CMD, which binds CD16A, was used as control.

FIGS. 6 A-C BIACORE ANALYSIS OF DIABODY BINDING TO sCD16A, sCD32B AND sCD32B

The binding of h2B6-h3G8 CBD, h2B6 CMD and h3G8 CMD to sCD16A, sCD32B, and sCD32A (negative control) was assayed by SPR analysis. h3G8 scFv was also tested as a control. (A) Binding to sCD16; (B) Binding to sCD32B and (C) Binding to sCD32A. Diabodies were injected at a concentration of 100 NM, and scFv at a concentration of 200 nM, over receptor surfaces at a flow rate of 50 ml/min for 60 sec.

FIGS. 7 A-C BIACORE ANALYSIS OF DIABODY BINDING TO sCD16A and sCD32B

The binding of h2B6-h3G8 CBD, h2B6 CMD and h3G8 CMD to sCD16A, and sCD32B was assayed by SPR analysis. h3G8 scFv was also tested as a control. (A) Binding of to h3G8 CMD sCD16A; (B) Binding of h2B6-h3G8 CBD to sCD16A; (C) Binding of h3G8 scFv to sCD16A; (D) Binding of h2B6 CMD to sCD32B; and (E) Binding of h2B6-h3G8 CBD to sCD32B. Diabodies were injected at concentrations of 6.25-200 nM over receptor surfaces at a flow rate of 70 ml/min for 180 sec.

Figure 8:
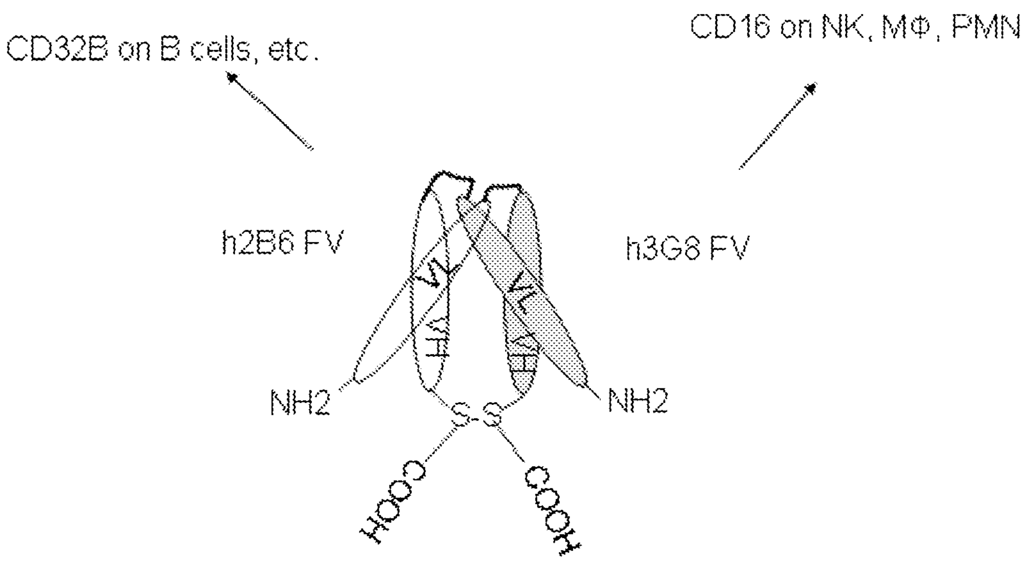

FIG. 8 SCHEMATIC DEPICTING THE INTERACTION OF POLYPEPTIDE CHAINS COMPRISING VL AND VH DOMAINS TO FORM A COVALENT BISPECIFIC DIABODY MOLECULE $NH_2$ and COOH represent the amino-terminus and carboxy terminus, respectively of each polypeptide chain. S represents the C-terminal cysteine residue on each polypeptide chain. VL and VH indicate the variable light domain and variable heavy domain, respectively. Dotted and dashed lines are to distinguish between the two polypeptide chains and, in particular, represent the linker portions of said chains. h2B6 Fv and h3G8 Fv indicate an epitope binding site specific for CD32B and CD16, respectively.

Figure 9:
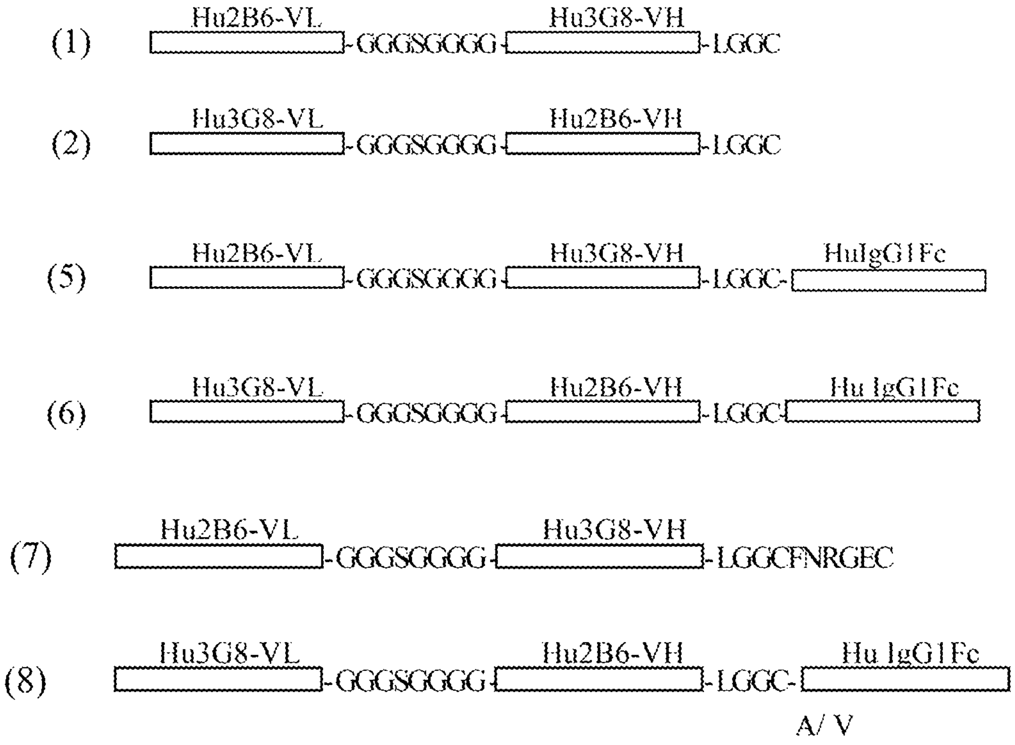

FIG. 9 SCHEMATIC REPRESENTATION OF POLYPEPTIDE CHAINS CONTAINING Fc DOMAINS OF COVALENT BISPECIFIC DIABODIES

Representation of polypeptide constructs of the diabody molecules of the invention (each construct is described from the amino terminus ("n"), left side of the construct, to the carboxy terminus ("c"), right side of figure). Construct (5) (SEQ ID NO: 14) comprised, n-VL domain Hu2B6—a first linker (GGGSGGGG (SEQ ID NO: 10))—the VH domain of Hu3G8—a second linker (LGGC; SEQ ID NO:330)—and a C-terminal Fc domain of human IgG1-c; construct (6) (SEQ ID NO: 15) comprised n—the VL domain Hu3G8—linker (GGGSGGGG (SEQ ID NO: 10))—the VH domain of Hu2B6—and second linker (LGGC; SEQ ID NO:330)—and a C-terminal Fc domain of human IgG1-c; construct (7) (SEQ ID NO: 16) comprised n—the VL domain Hu2B6—a first linker (GGGSGGGG (SEQ ID NO: 10))—the VH domain of Hu3G8- and a C-terminal sequence (LGGCFNRGEC) (SEQ ID NO: 17)-c; construct (8) (SEQ ID NO: 18) comprised n—the VL domain Hu3G8—linker (GGGSGGGG (SEQ ID NO: 10))—the VH domain of Hu2B6—and second linker (LGGC; SEQ ID NO:330)—and a C-terminal hinge/Fc domain of human IgG1 (with amino acid substitution A215V)-c.

Figure 10:
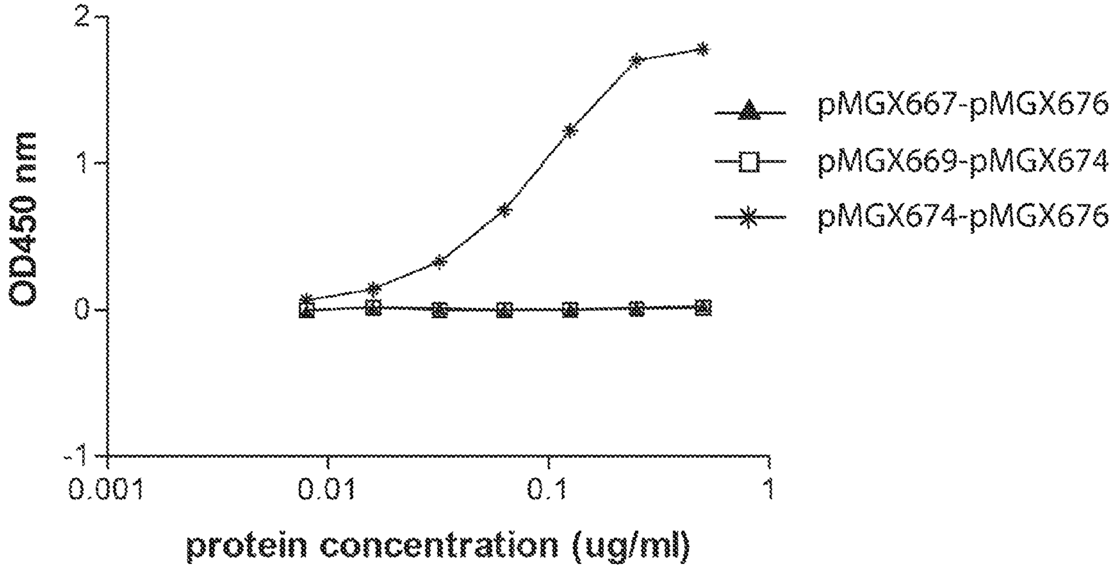

FIG. 10 BINDING OF DIABODY MOLECULES COMPRISING Fc DOMAINS TO sCD32B AND sCD16A

The binding of diabody molecules comprising Fc domains to sCD32B and sCD16A was assayed in a sandwich ELISA. Diabodies assayed were produced by 3 recombinant expression systems: cotransfection of pMGX669 and pMGX674, expressing constructs 1 and 6, respectively; cotransfection of pMGX667 and pMGX676, expressing constructs 2 and 5, respectively; and cotransfection of pMGX674 and pMGX676, expressing constructs 5 and 6, respectively. sCD32B was used as the target protein. The secondary probe was HRP conjugated sCD16A.

Figure 11:
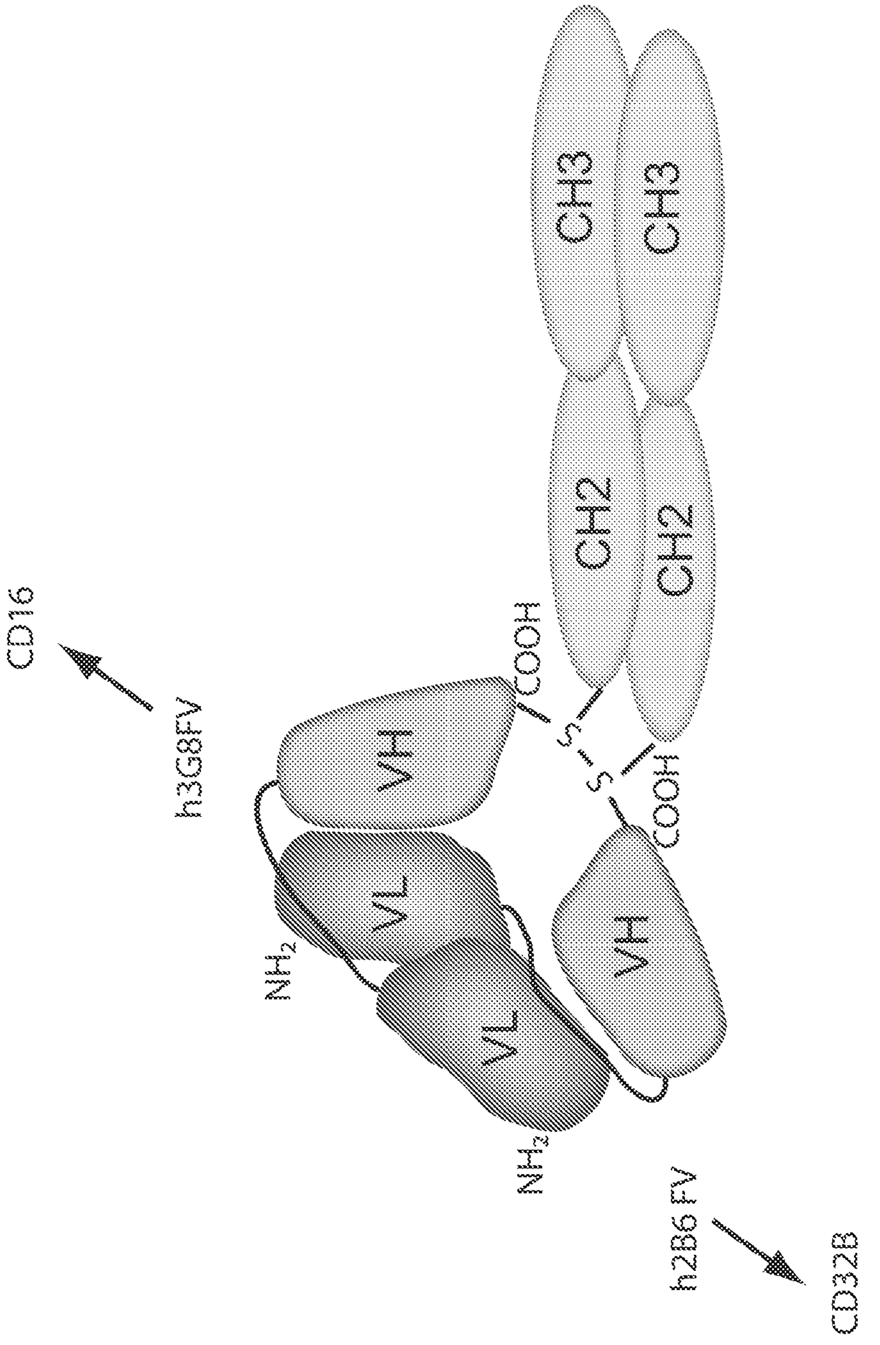

FIG. 11 SCHEMATIC DEPICTING THE INTERACTION OF TWO POLYPEPTIDE CHAINS EACH COMPRISING AN Fc DOMAIN TO FORM A BIVALENT, COVALENT DIABODY $NH_2$ and COOH represent the amino-terminus and carboxy terminus, respectively of each polypeptide chain. S represents the at least one disulfide bond between a cysteine residue in the second linker sequence of each polypeptide chain. VL and VH indicate the variable light domain and variable heavy domain, respectively. Dotted and dashed lines are to distinguish between the two polypeptide chains and, in particular, represent the first linker portions of said chains. CH2 and CH3 represent the CH2 and CH3 constant domains of an Fc domain. h2B6 Fv and h3G8 Fv indicate an epitope binding site specific for CD32B and CD16, respectively.

Figure 12:
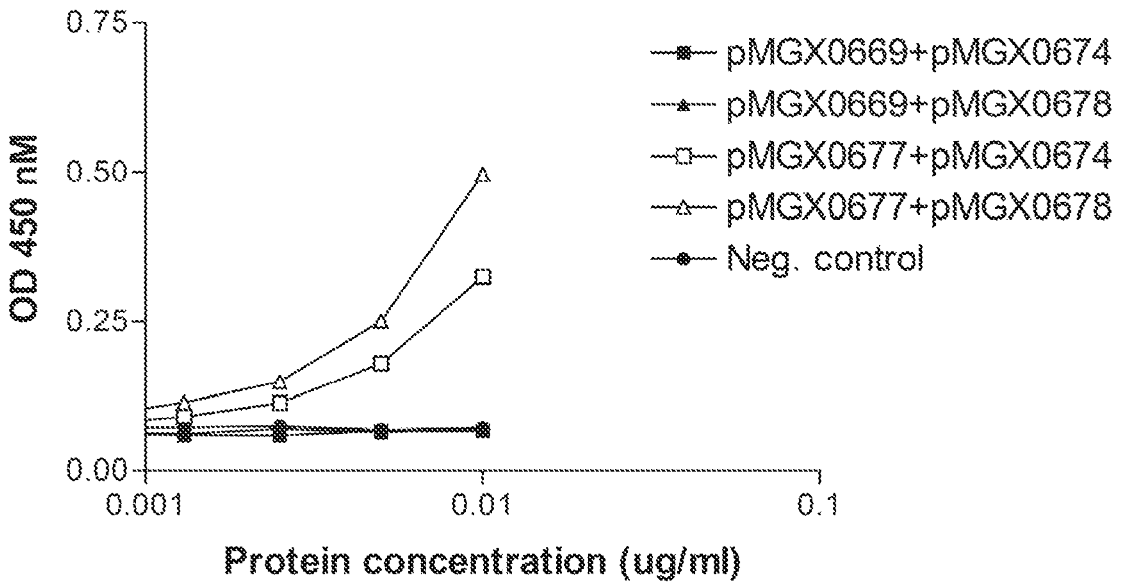

FIG. 12 BINDING OF DIABODY MOLECULES COMPRISING HINGE/Fc DOMAINS TO sCD32B AND sCD16A

The binding of diabody molecules comprising Fc domains to sCD32B and sCD16A was assayed in a sandwich ELISA. Diabodies assayed were produced by 4 recombinant expression systems: cotransfection of pMGX669+pMGX674, expressing constructs 1 and 6, respectively; cotransfection of pMGX669+pMGX678, expressing constructs 2 and 8, respectively; cotransfection of pMGX677+pMGX674, expressing constructs 7 and 6, respectively; and cotransfection of pMGX677+pMGX678, expressing constructs 7 and 8, respectively. sCD32B was used as the target protein. The secondary probe was HRP conjugated sCD16A.

Figure 13:
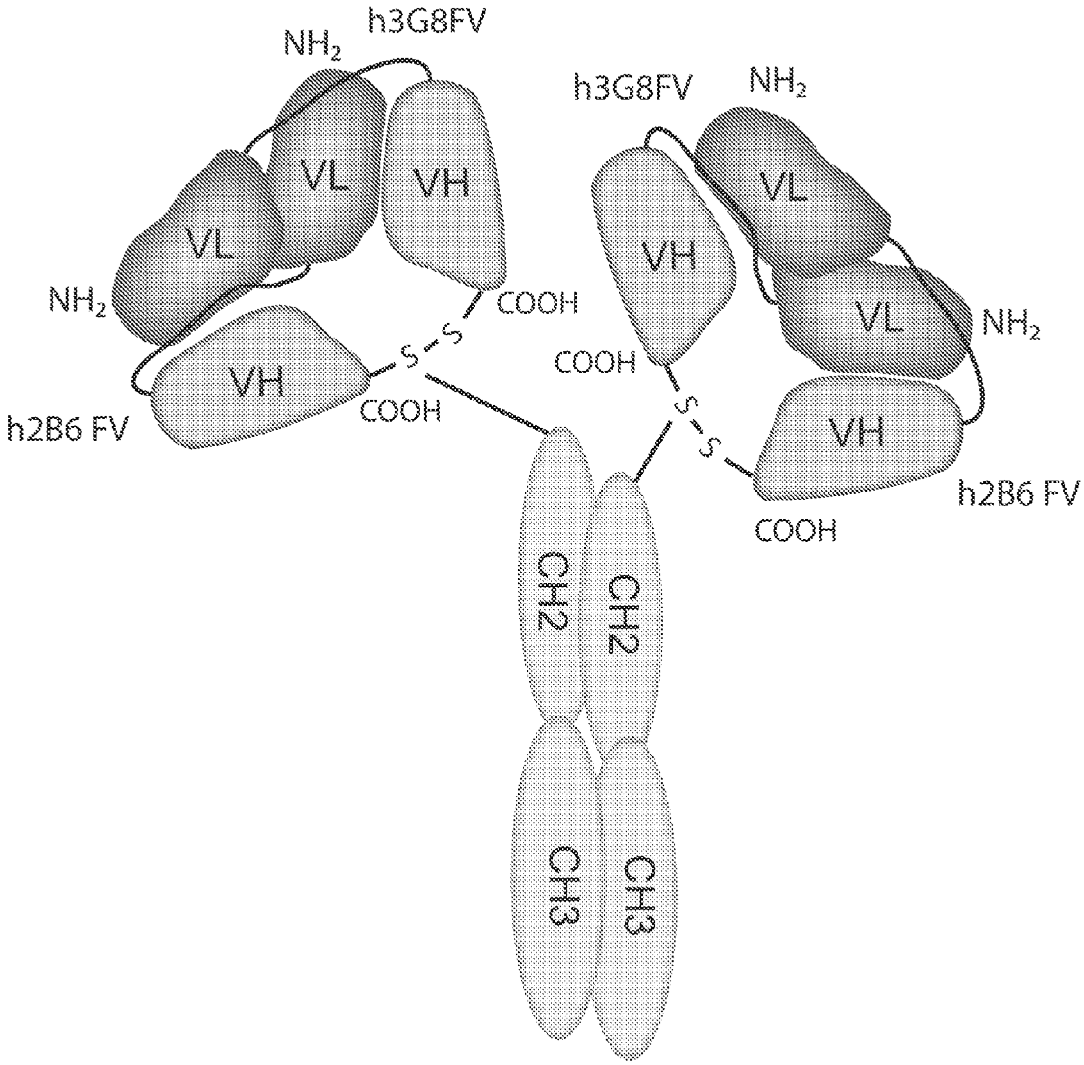

FIG. 13 SCHEMATIC DEPICTING THE INTERACTION OF POLYPEPTIDE CHAINS TO FORM A TETRAMERIC DIABODY MOLECULE $NH_2$ and COOH represent the amino-terminus and carboxy terminus, respectively of each polypeptide chain. S represents the at least one disulfide bond between a cysteine residue in the second linker sequence the Fc bearing, 'heavier,' polypeptide chain and a cysteine residue in the C-terminal sequence of the non-Fc bearing, 'lighter,' polypeptide chain. VL and VH indicate the variable light domain and variable heavy domain, respectively. Dotted and dashed lines are to distinguish between polypeptide chains and, in particular, represent the first linker portions of said heavier chains or the linker of said lighter chains. CH2 and CH3 represent the CH2 and CH3 constant domains of an Fc domain. h2B6 Fv and h3G8 Fv indicate an epitope binding site specific for CD32B and CD16, respectively.

Figure 14:
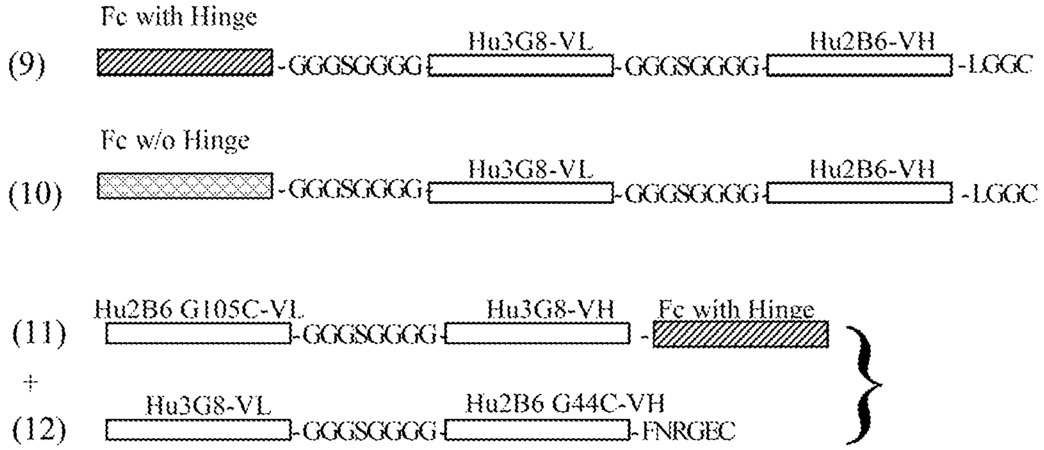

FIG. 14 SCHEMATIC REPRESENTATION OF POLYPEPTIDES CHAINS CONTAINING Fc DOMAINS WHICH Form COVALENT BISPECIFIC DIABODIES Representation of polypeptide constructs which form the diabody molecules of the invention (each construct is described from the amino terminus ("n"), left side of the construct, to the carboxy terminus ("c"), right side of figure). Construct (9) (SEQ ID NO: 19) comprised n-a Hinge/Fc domain of human IgG1—the VL domain Hu3G8—linker (GGGSGGGG (SEQ ID NO: 10))—the VH domain of Hu2B6—linker (GGGSGGGG (SEQ ID NO: 10))—and a C-terminal LGGC (SEQ ID NO:330) sequence-c; construct (10) (SEQ ID NO: 20) comprised n—an Fc domain of human IgG1—the VL domain Hu3G8—linker (GGGSGGGG (SEQ ID NO: 10)) —the VH domain of Hu2B6—linker (GGGSGGGG (SEQ ID NO: 10))—and a C -terminal LGGC (SEQ ID NO:330) sequence-c; construct (11) (SEQ ID NO: 21) comprised n—the VL domain Hu2B6 (G105C)—linker (GGGSGGGG (SEQ ID NO: 10))—the VH domain of Hu3G8—and a C-terminal hinge/Fc domain of human IgG1 with amino acid substitution A215V-c; construct (12) (SEQ ID NO: 22) comprised n—the VL domain Hu3G8—linker (GGGSGGGG (SEQ ID NO: 10))—the VH domain of Hu2B6 (G44C)—and a C-terminal FNRGEC (SEQ ID NO: 23) sequence-c.

FIG. 15 A-B SDS-PAGE AND WESTERN BLOT ANALYSIS OF AFFINITY TETRAMERIC DIABODIES

Diabodies produced by recombinant expression systems cotransfected with vectors expressing constructs 10 and 1, constructs 9 and 1, and constructs 11 and 12 were subjected to SDS-PAGE analysis non-reducing conditions (A) and Western Blot analysis using goat anti-human IgG1 H+L as the probe (B). Proteins in the SDS-PAGE gel were visualized with Simply Blue Safestain (Invitrogen). For both panels A and B, diabody molecules comprising constructs 10 and 1, constructs 9 and 1, and constructs 11 and 12A are in lanes 1, 2 and 3, respectively.

Figure 16:
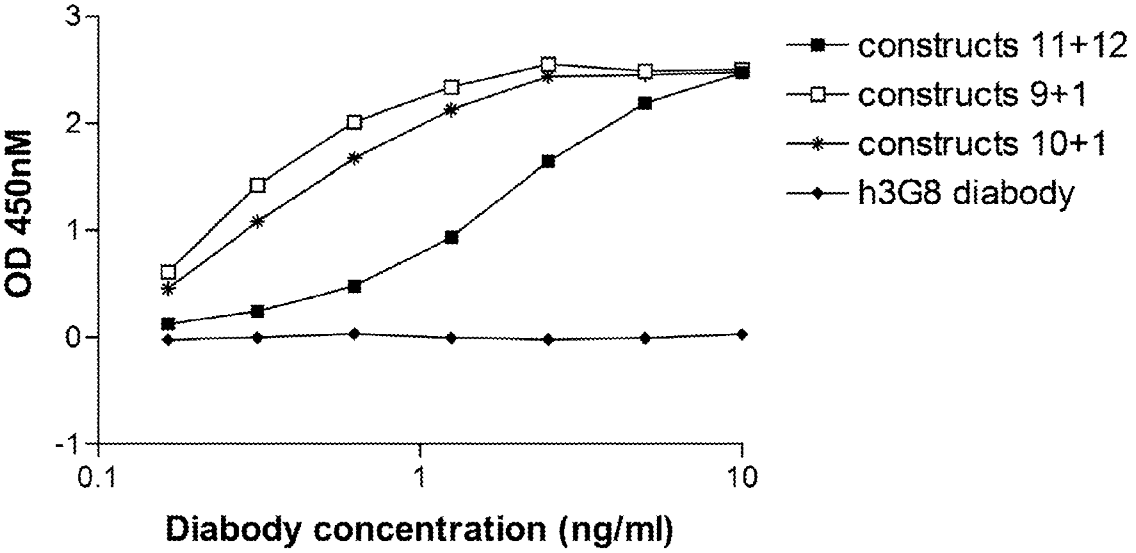

FIG. 16 BINDING OF DIABODY MOLECULES COMPRISING Fc DOMAINS AND ENGINEERED INTERCHAIN DISULFIDE BONDS TO sCD32B AND sCD16A

The binding of diabody molecules comprising Fc domains and engineered disulfide bonds between the 'lighter' and 'heavier' polypeptide chains to sCD32B and sCD16A was assayed in a sandwich ELISA. Diabodies assayed were produced by 3 recombinant expression systems: expressing constructs 1 and 10, expressing constructs 1 and 9, and expressing constructs 11 and 12, respectively. sCD32B was used as the target protein. The secondary probe was HRP conjugated sCD16A. Binding of h3G8 was used as control.

Figure 17:
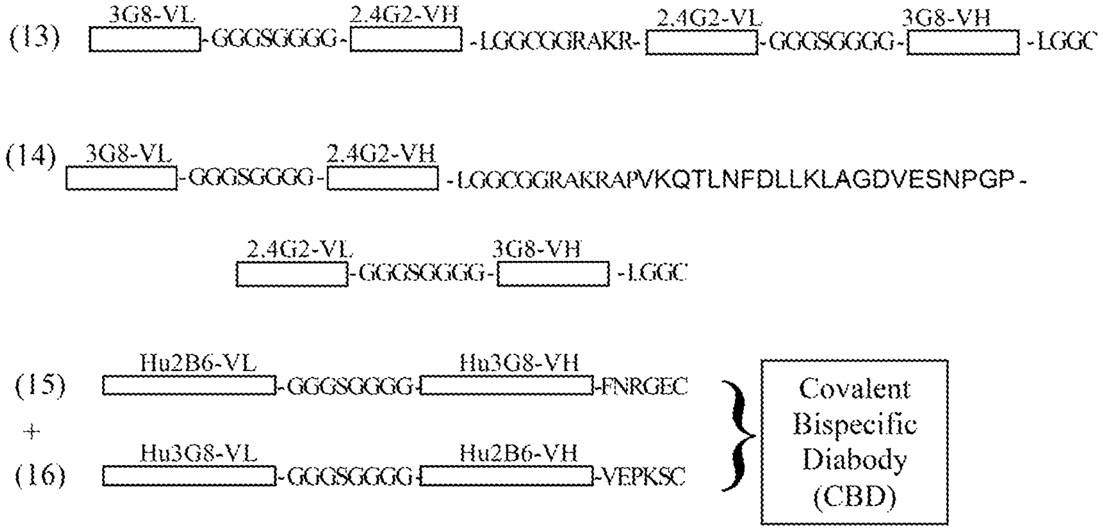

FIG. 17 SCHEMATIC REPRESENTATION OF POLYPROTEIN PRECURSOR OF DIABODY MOLECULE AND SCHEMATIC REPRESENTATION OF POLYPEPTIDE CHAINS CONTAINING LAMBDA LIGHT CHAIN AND/OR HINGE DOMAINS

Representation of polypeptide constructs which comprise the diabody molecules of the invention (each construct is described from the amino terminus ("n"), left side of the construct, to the carboxy terminus ("c"), right side of figure). Construct (13) (SEQ ID NO: 95) comprised, n-VL domain 3G8—a first linker (GGGSGGGG (SEQ ID NO: 10))—the VH domain of 2.4G2VH—a second linker (LGGC; SEQ ID NO:330)—furin recognition site (RAKR (SEQ ID NO: 93))—VL domain of 2.4G2—a third linker (GGGSGGG (SEQ ID NO: 10)—VH domain of 3G8—and a C-terminal LGGC (SEQ ID NO:330) domain; (nucleotide sequence encoding SEQ ID NO: 95 is provided in SEQ ID NO: 96). Construct (14) (SEQ ID NO: 97) comprised, n-VL domain 3G8—a first linker (GGGSGGGG (SEQ ID NO: 10))—the VH domain of 2.4G2VH—a second linker (LGGC; SEQ ID NO:330)—furin recognition site (RAKR (SEQ ID NO: 93))—FMD (Foot and Mouth Disease Virus Protease C3) site—VL domain of 2.4G2—a third linker (GGGSGGG (SEQ ID NO: 10)—VH domain of 3G8—and a C-terminal LGGC (SEQ ID NO:330)domain; (nucleotide sequence encoding SEQ ID NO: 97 is provided in SEQ ID NO: 98). Construct (15) (SEQ ID NO: 99) comprised, n-VL domain Hu2B6—a linker (GGGSGGGG (SEQ ID NO: 10))—the VH domain of Hu3G8- and a C-terminal FNRGEC (SEQ ID NO: 23) domain; (nucleotide sequence encoding SEQ ID NO: 99 is provided in SEQ ID NO: 100). Construct (16) (SEQ ID NO: 101) comprised, n-VL domain Hu3G8—a linker (GGGSGGGG (SEQ ID NO: 10))—the VH domain of Hu2B6- and a C-terminal VEPKSC (SEQ ID NO: 77) domain; (nucleotide sequence encoding SEQ ID NO: 101 is provided in SEQ ID NO: 102).

Figure 18:
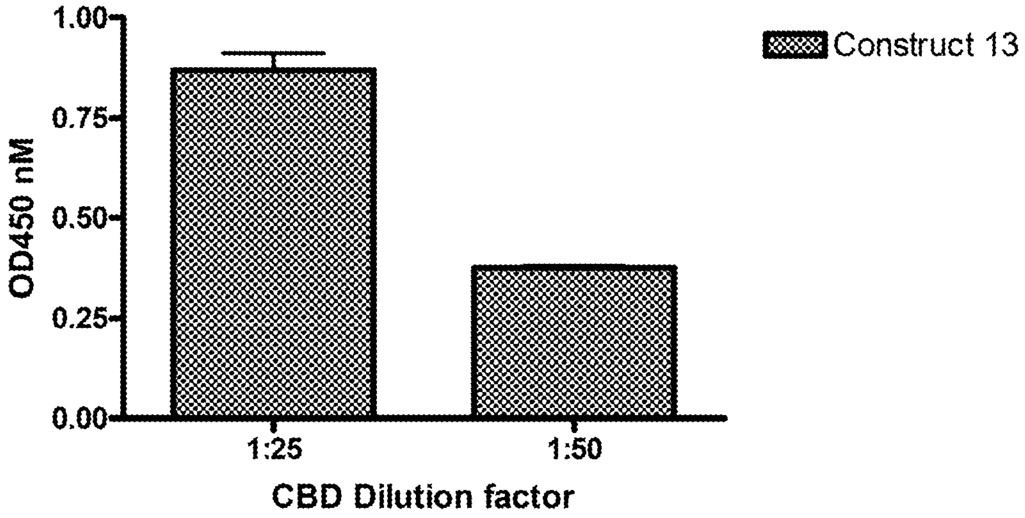

FIG. 18 BINDING OF DIABODY MOLECULES DERIVED FROM A POLYPROTEIN PRECURSOR MOLECULE TO mCD32B AND sCD16A

The binding of diabody molecules derived from the polyprotein precursor molecule construct 13 (SEQ ID NO: 95) to murine CD32B (mCD32B) and soluble CD16A (sCD16A) was assayed in a sandwich ELISA. mCD32B was used as the target protein. The secondary probe was biotin conjugated sCD16A.

Figure 19:
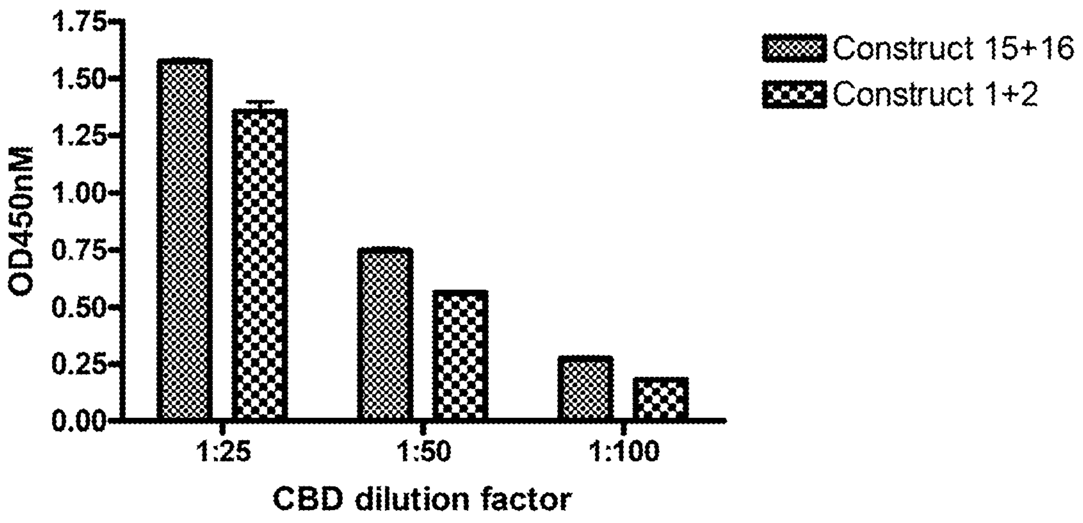

FIG. 19 BINDING OF DIABODY MOLECULES COMPRISING LAMBDA CHAIN AND/OR HINGE DOMAINS TO sCD32B AND sCD16A

The binding of diabody molecules comprising domains derived from the C-terminus of the human lambda light chain and/or the hinge domain of IgG to sCD32B and sCD16A was assayed and compared to the diabody comprising constructs 1 and 2 (FIG. 5) in a sandwich ELISA. Diabodies assayed were produced by the recombinant expression system expressing constructs 15 and 16 (SEQ ID NO: 99 and SEQ ID NO: 101, respectively). sCD32B was used as the target protein. The secondary probe was HRP conjugated sCD16A. Bars with small boxes represent the construct 15/16 combination while bars with large boxes represent construct ½ combination.

Figure 20:
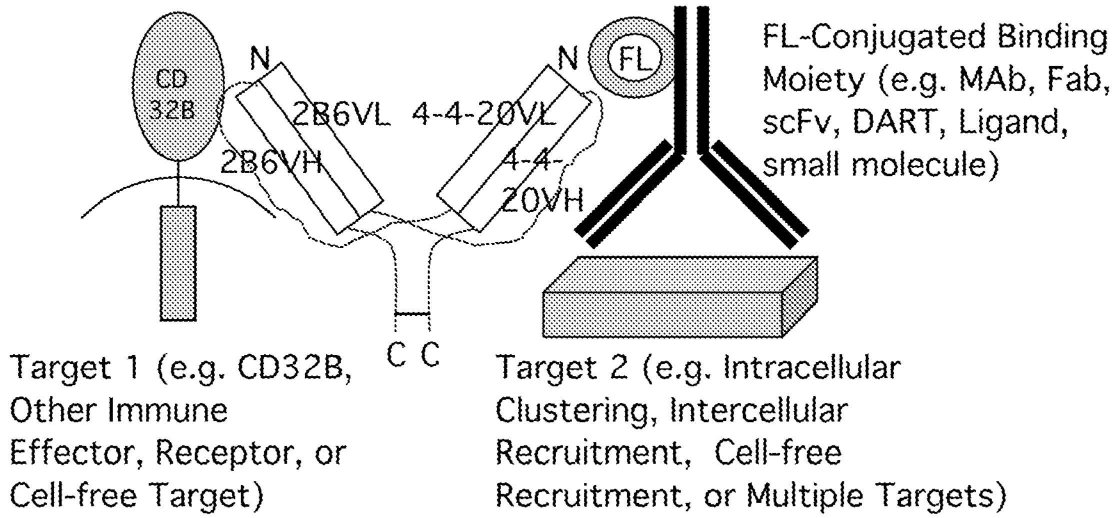

FIG. 20 SCHEMATIC REPRESENTATION OF 2B614420 DART BOUND TO CD32B LOCATED AT THE SURFACE OF A CELL AND A FLUORESCEIN-CONJUGATED MOLECULE

The diagram shows the flexibility of the "universal adaptor" anti-fluorescein arm of the DART as well as the possibility of substituting other specificities for the 2B6 arm. V-regions are shown as boxes, GGGSGGGG (SEQ ID NO: 10) linkers are shown as lines, the disulfide bond is shown connecting the two chains. The constituents of one chain are shown in blue while the other is colored pink. N, amino terminus; C, carboxy terminus; FL, fluorescein, VL, light chain variabile region; VH, heavy chain variable region.

Figure 21:
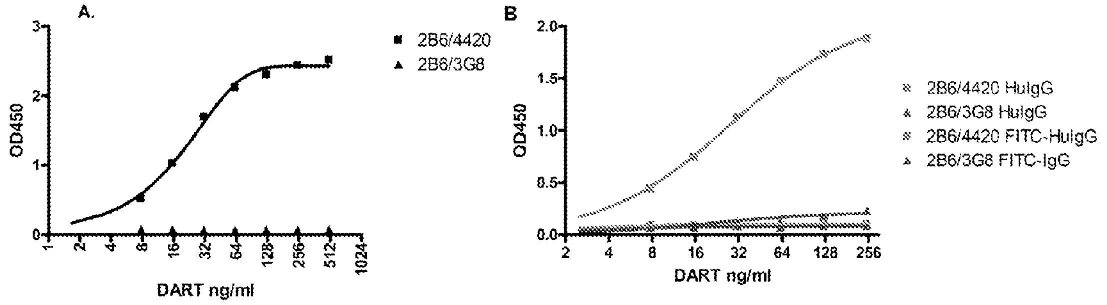

FIG. 21 (PANELS A AND B) THE 2B6/4420 DART BINDS SPECIFICALLY TO FLUORESCEIN-CONJUGATED MOLECULES AND CAN SIMULTANEOUSLY BIND CD32B.

(A) 2B6/4420 or 2B6/3G8 were bound to ELISA plates coated with FITC-S Protein. Binding and function of the 2B6 arm were detected by engagement of soluble CD32B, followed by an antibody specific for CD32B and a secondary detecting antibody conjugated to HRP. (B) 2B6/4420 or 2B6/3G8 were bound to ELISA plates coated with HuIgG or FITC-HuIgG (fluorescein-conjugated). Binding was detected by engagement with a polyclonal serum specific for 2B6 Fv followed by an HRP-conjugated secondary antibody.

Figure 22:
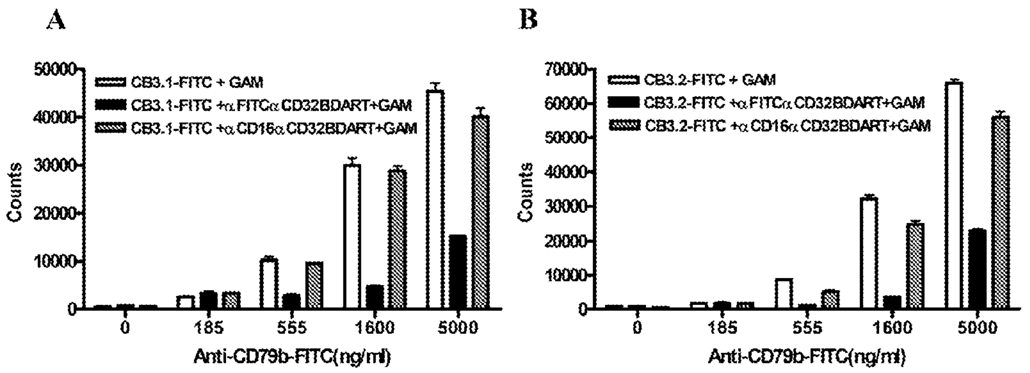

FIG. 22 (PANELS A AND B) ACTIVATION OF PURIFIED B CELLS USING ANTI-HUMAN CD79B ANTIBODIES.

Purified B cells were activated using increasing concentrations of anti-human CD79b antibodies FITC-conjugated, CB3.1-FITC (A) or CB3.2-FITC (B) and 50 µg/ml of $F(ab')_2$ fragment of GAM IgG Fc specific(x-axis). B cells were activate in the presence of PBS (white bars) or 5 µg/ml of either αFITCαCD32BDART (black bars) or αCD16αCD32BDART (grey bars). The reactions were performed in triplicate and standard deviations were calculated.

FIG. 23 (PANELS A AND B) ACTIVATION OF PURIFIED B CELLS

Purified B cells from a second healthy donor were activated as described in FIG. 22, Panel B. The proliferation index was measured in cells activated in the presence of the anti CD79b antibody FITC-conjugated CB3.2-FITC (A) and compared to the proliferation index of cells activated in the presence of the unlabeled CB3.2 antibody (B).

Figure 24:
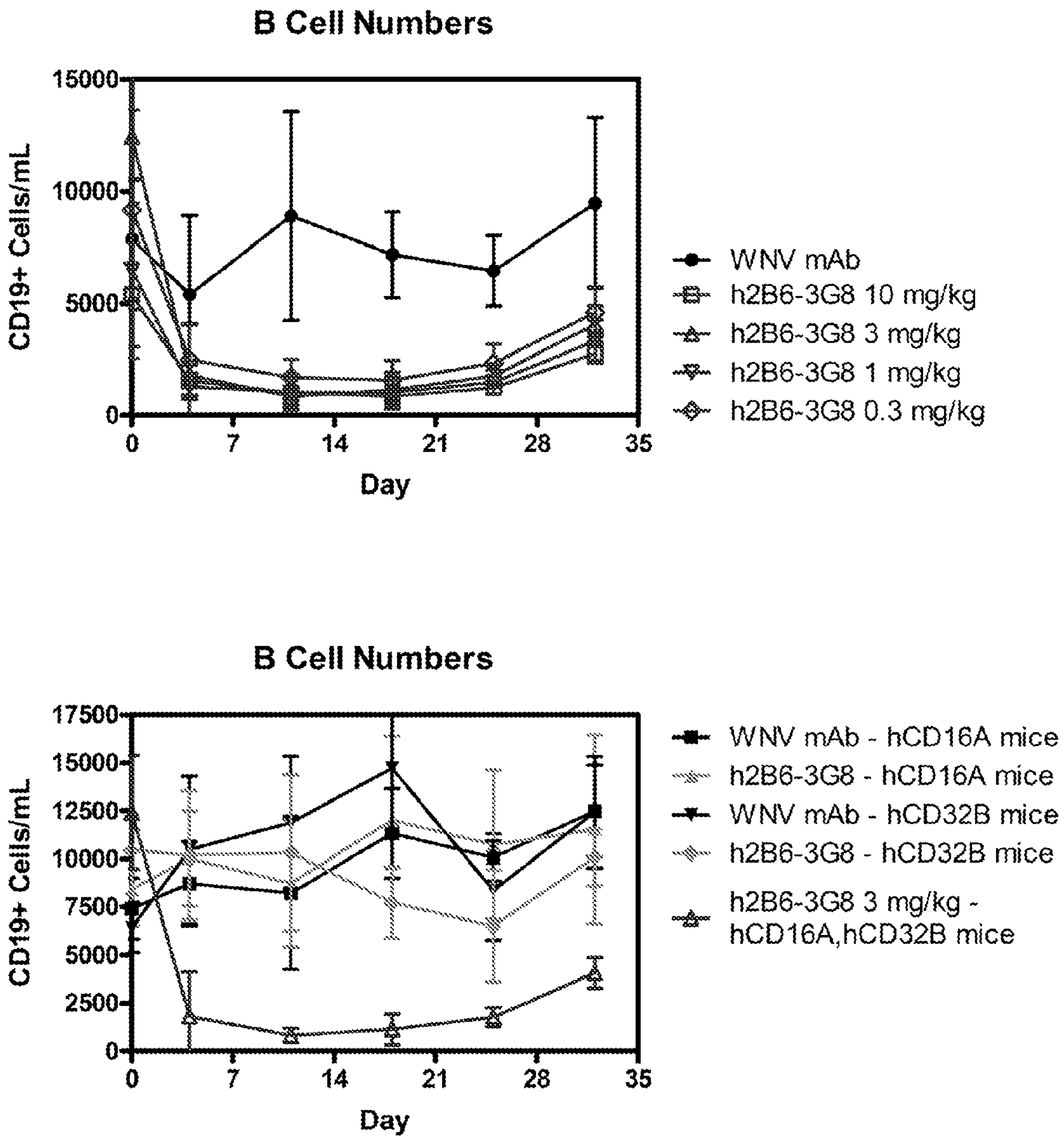

FIG. 24 (Upper and Lower Panels) IN VIVO MOUSE B CELL DEPLETION IN HCD16A/B TRANSGENIC MICE USING MGD261 mCD32−/− hCD16A+ C57B1/6, mCD32−/− hCD32B+ C57B1/6 and mCD32−/− hCD16A+hCD32B+ C57B1/6 mice from MacroGenics breeding colony were injected IV at days 0, 3, 7, 10, 14 and 17 with MGD261 (10, 3, 1 or 0.3 mg/kg), or an irrelevant antibody (hE16 10 mg/kg). Blood was collected at days −19 (pre-bleed), 4, 11, 18, 25 and 32 for FACS analysis. Animal health and activity was recorded three times a week. Upper Panel: h2B6-3G8 and WNV mAb; Lower Panel: h2B6-3G8-hCD16A or -hCD32B mice and WNV mAb-hCD16A or -hCD32B mice.

Figure 25:
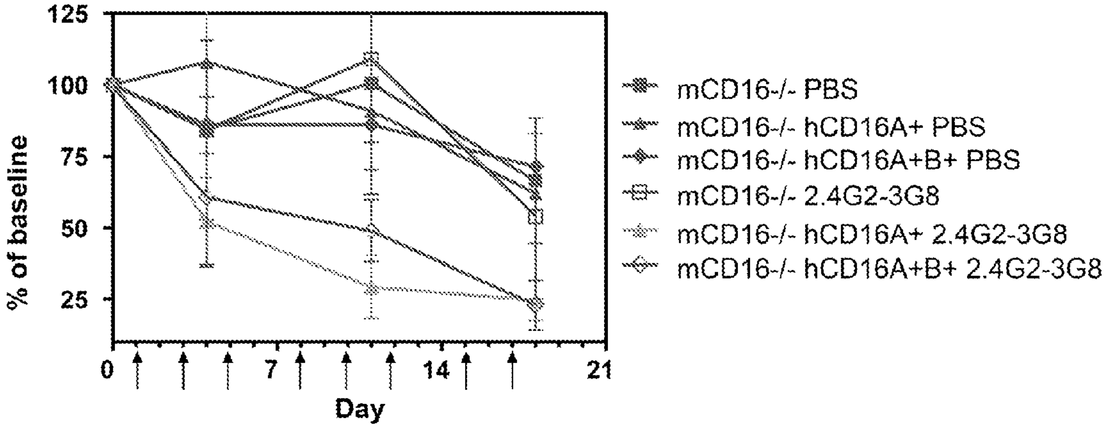

FIG. 25 IN VIVO MOUSE B CELL DEPLETION IN HCD16A/B TRANSGENIC MICE USING 2.4G2-3G8 DB mCD16−/−, mCD16−/− hCD16A+ C57B1/6, mCD16−/− hCD16B+ and mCD16−/− hCD16A+ hCD16B+ mice from MacroGenics breeding colony were injected IP at days 0, 2, 4, 7, 9, 11, 14, 16 and 18 with 2.4G2-3G8 DB (75 ug/mouse), or PBS. Blood was collected at days −10 (pre-bleed), 4, 11 and 18 for FACS analysis. Animal health and activity was recorded three times a week.

Figure 26:
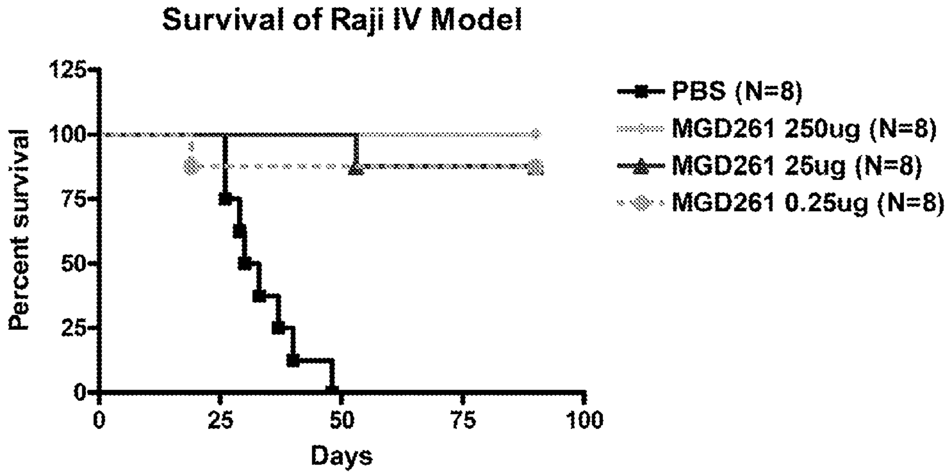

FIG. 26 DEMONSTRATION OF ANTI-TUMOR ACTIVITY OF MGD261 USING AN INTRAVENOUS (IV) MODEL OF THE HUMAN TUMOR CELL LINE RAJI.

Twelve-twenty week old mCD16−/−, hCD16A+, RAG1−/− C57B1/6 mice from MacroGenics breeding colony were injected IV at day 0 with $5\times10^6$ Raji cells. At Days 6, 9, 13, 16, 20, 23, 27 and 30 mice were also treated intraperitoneously (IP) with 250, 25 or 2.5 ug MGD261 or with PBS (negative control). Mice were then observed daily and body weight was recorded twice a week. Mice developing hind leg paralysis were sacrificed.

FIG. 27 DART EXPRESSION IN A NON-MAMMALIAN HOST

BL21DE3 cells (Novagen) were transformed with the pET25b(+) T7-lac+3G8/3G8 plasmid and an amp-resistant colony was used to seed broth culture. When the culture reached 0.5 OD600 units, 0.5 mM IPTG was added to induce expression. The culture was grown at 30° C. for 2 hours and the cell-free medium was collected.

Figure 28:
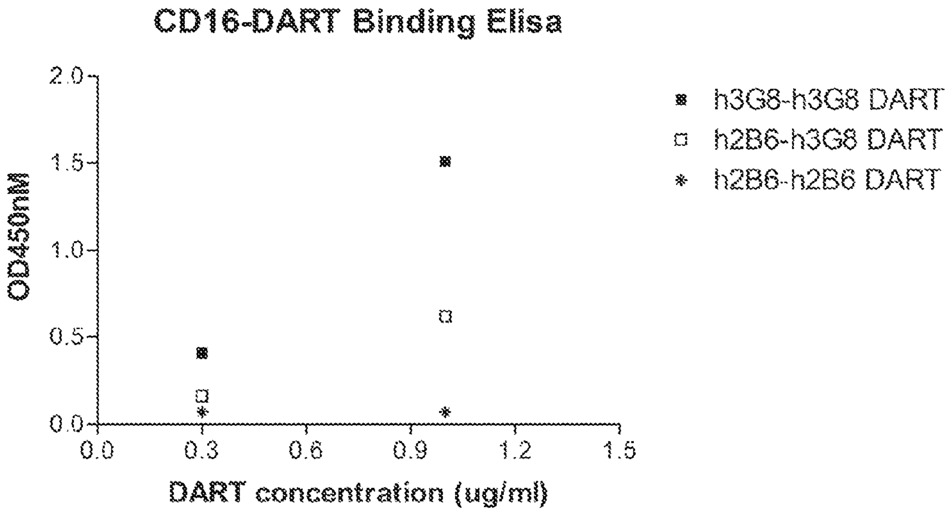

FIG. 28 DART ELISA h3G8-h3G8 DART binding ELISA were conducted using 96-well Maxisorp plates. After reaction, the plate was washed with PBS-T three times and developed with 80 µl/well of TMB substrate. After 5 minutes incubation, the reaction was stopped by 40 µl/well of 1% $H_2SO_4$. The OD450 nm was read using a 96-well plate reader and SOFTmax software. The read out was plotted using GraphPadPrism 3.03 software.

FIG. 29 DART-INDUCED HUMAN B-CELL DEATH

Human PBMC were incubated overnight with the indicated molecules. Apoptosis was assayed by FACS analysis as the percentage of $PI^+$Annexin-$V^+$ population of B cells (CD20+ cells) on the total FSC/SSC ungated population.

FIG. 30 8B5-CB3.1 DART CONSTRUCTS

Multiple 8B5-CB3.1 DART constructs were produced to illustrate the present invention. The construct 5 and 6, or 6 and 7, or 8 and 9, or 9 and 10, encoded expression plasmids were co-transfected into HEK-293 cells to express 8B5-CB3.1 DART with or without anti flag tag using Lipofectamine 2000 (Invitrogen). The conditioned medium was harvested in every three days for three times. The conditioned medium was then purified using CD32B affinity column.

FIG. 31 8B5-CB3.1 DART ELISA

8B5-CB3.1 DART/ch8B5 competition ELISA were conducted using 96-well Maxisorp plates. After reaction, the plate was washed with PBS-T three times and developed with 80 µl/well of TMB substrate. After 5 minutes incubation, the reaction was stopped by 40 µl/well of 1% $H_2SO_4$. The OD450 nm was read using a 96-well plate reader and SOFTmax software. The read out was plotted using GraphPadPrism 3.03 software.

FIG. 32 SCHEMATIC ILLUSTRATION OF TETRAVALENT DART STRUCTURE

Illustrates the general structure of a DART species produced through the assembly of four polypeptide chains. The four antigen-binding domains of the Ig-like DART are shown as striped and dark grey ellipses.

Figure 33:
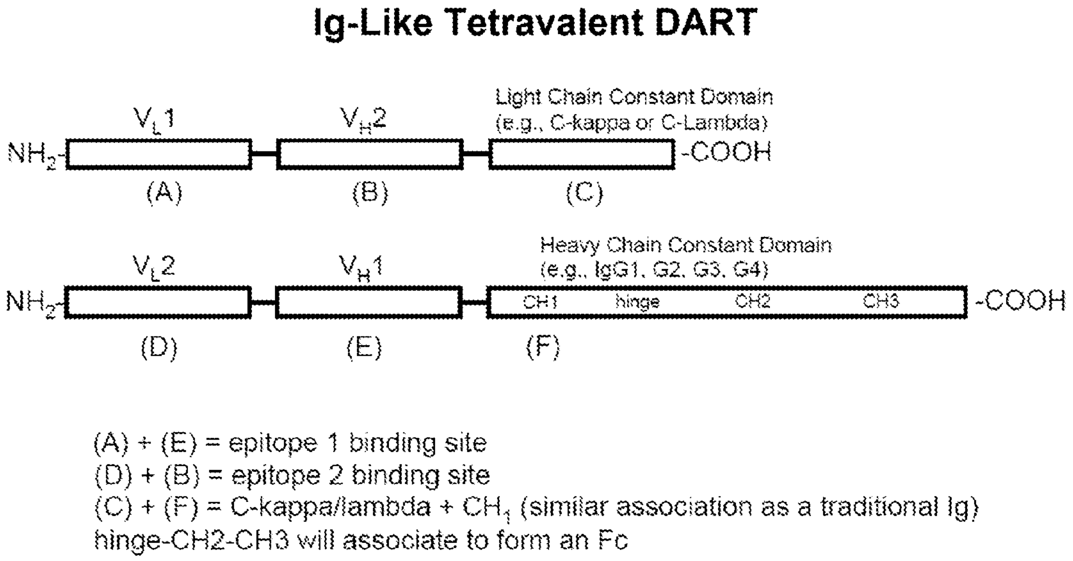

FIG. 33 Ig-LIKE TETRAVALENT DART

Provides a schematic of the epitope binding sites of an Ig-like tetravalent DART.

Figure 34:
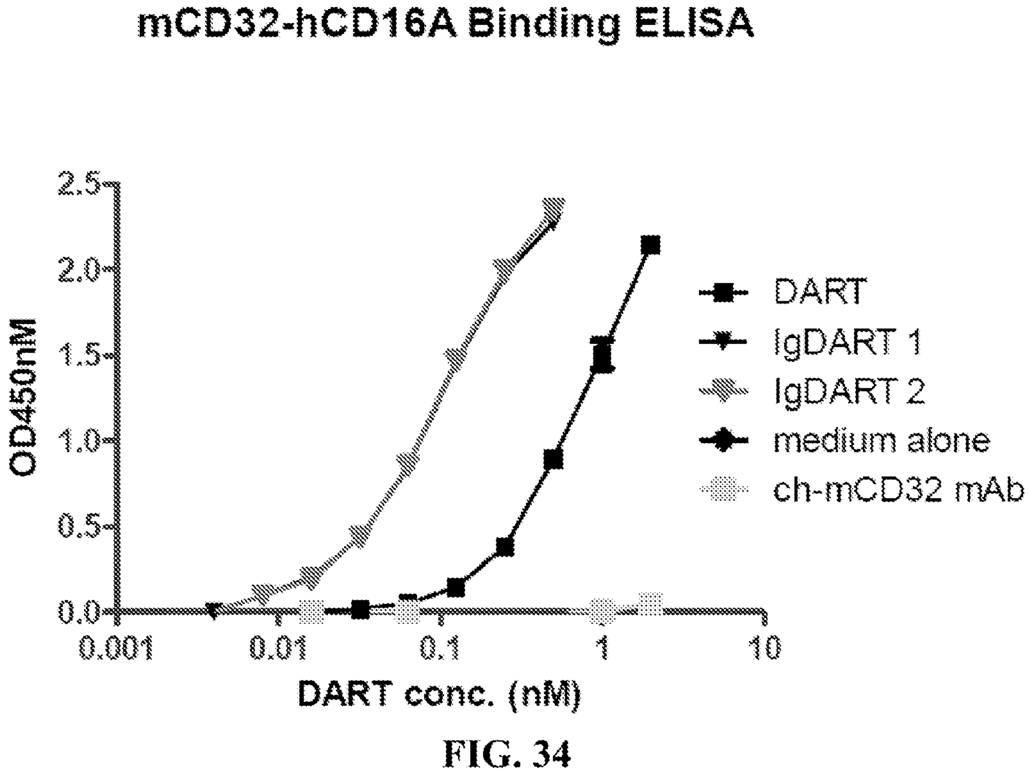

FIG. 34 mCD32-hCD16A BINDING ELISA

Provides the results of ELISAs that demonstrate that the Ig-like tetravalent DART species of Example 6.10 binds antigen with greater affinity than control (ch-mCD32 mAb) antibody or other DART species.

Figure 35:
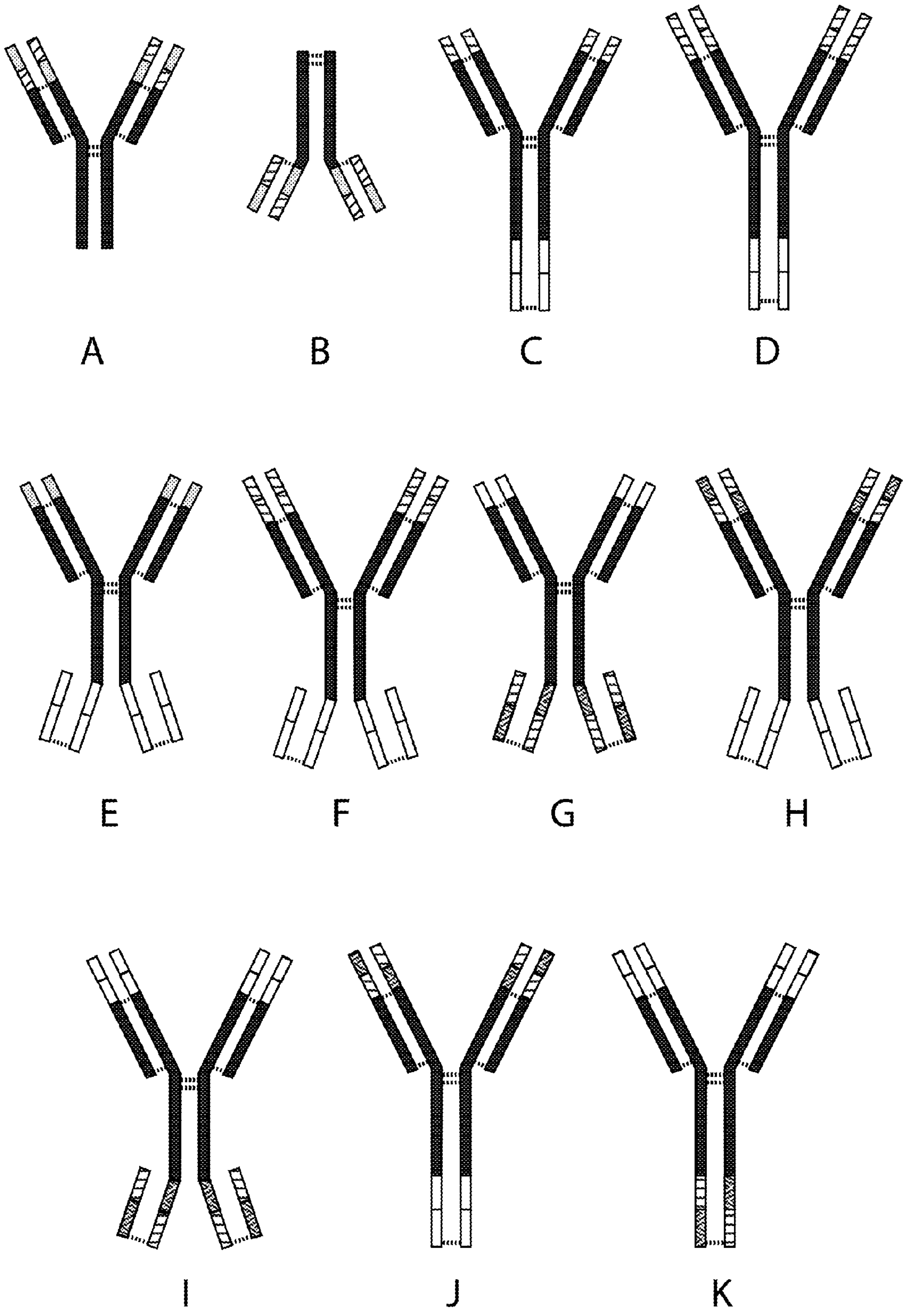

FIG. 35 SCHEMATIC ILLUSTRATION OF Ig DART MOLECULES

Provides a schematic of Ig DART molecules. Specificity is indicated by shading, pattern or white colored regions, constant regions are shown in black, and disulfide bonds are indicated by dotted black lines. The N-termini of all protein chains are oriented toward the top of the figure, while the C-termini of all protein chains are oriented toward the bottom of the Figure. Illustations A-E are bispecific and Illustations F-J are trispecific. Illustations A and E are tetravalent. Illustations B, C, F, I, and J are hexavalent. Illustations D, G, and H are octavalent. Refer to FIGS. 1, 2, 9, 14 and 17 and to Section 3.1 for detailed descriptions of the individual domains.

FIG. 36 BINDING ABILITY OF HU2B6 4.5-HU3G8 5.1 BIOSPECIFIC DIABODY

Figure 36:
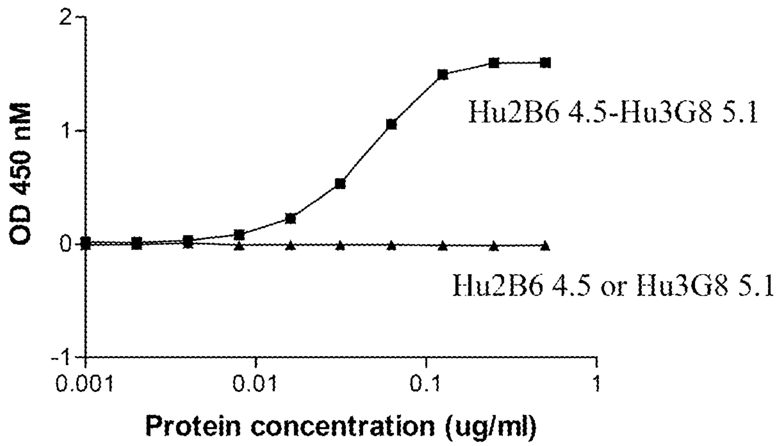

FIG. 36 shows the ability of the Hu2B6 4.5-Hu3G8 5.1 biospecific diabody (squares) to bind CD32b and CD16a relative to Hu2B6 4.5 or Hu3G8 5.1 diabodies (triangles).

FIG. 37 SCHEMATIC OF E-COIL AND K-COIL DART DERIVATIVES

Figure 37:
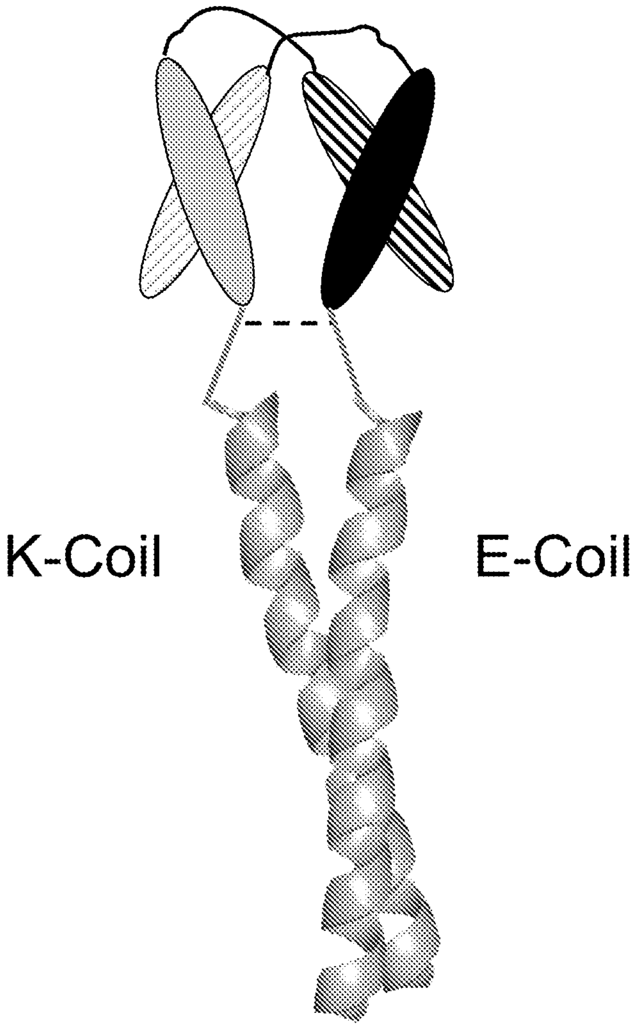

FIG. 37 illustrates the general conformation of E-coil and K-coil DART derivatives.

FIG. 38 HELIX ARRANGEMENT OF PREFERRED E-COIL AND K-COIL SEPARATORS

Figure 38:
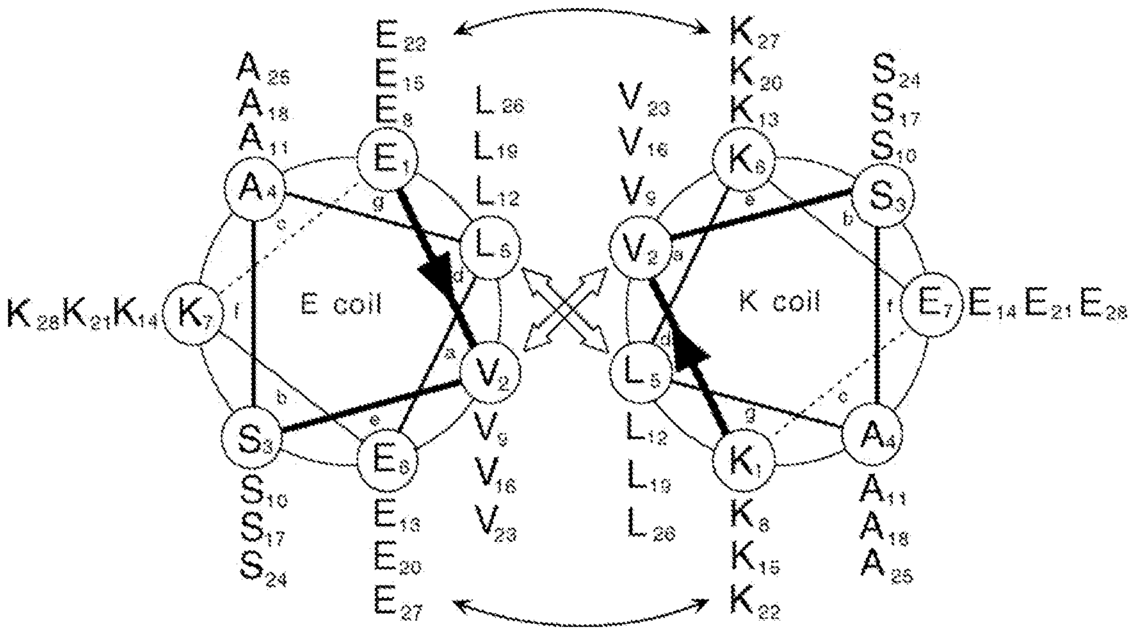

FIG. 38 shows the helix arrangement of preferred "E-coil" sequence $(EVAALEK)_4$ (SEQ ID NO: 299) and preferred "K-coil" sequence $(KVAALKE)_4$ (SEQ ID NO: 300).

Figure 39:
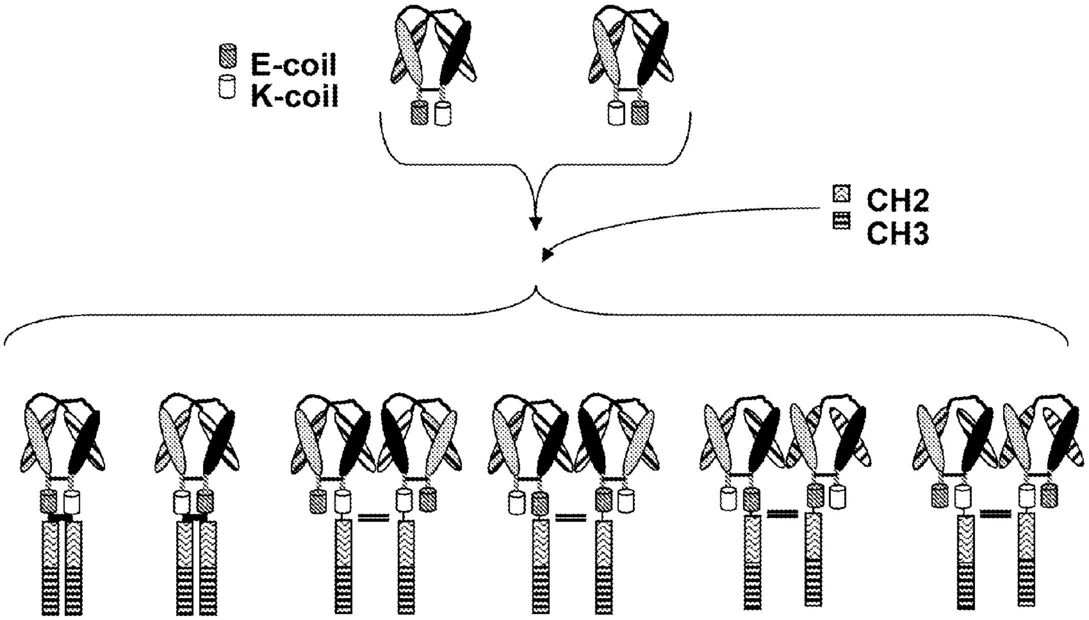

FIG. 39 E-COIL AND K-COIL Fc-CONTAINING DART DERIVATIVES

FIG. 39 illustrates the different species of E-coil and K-coil Fc-containing DART derivatives that can be formed via chain swapping.

Figure 40:
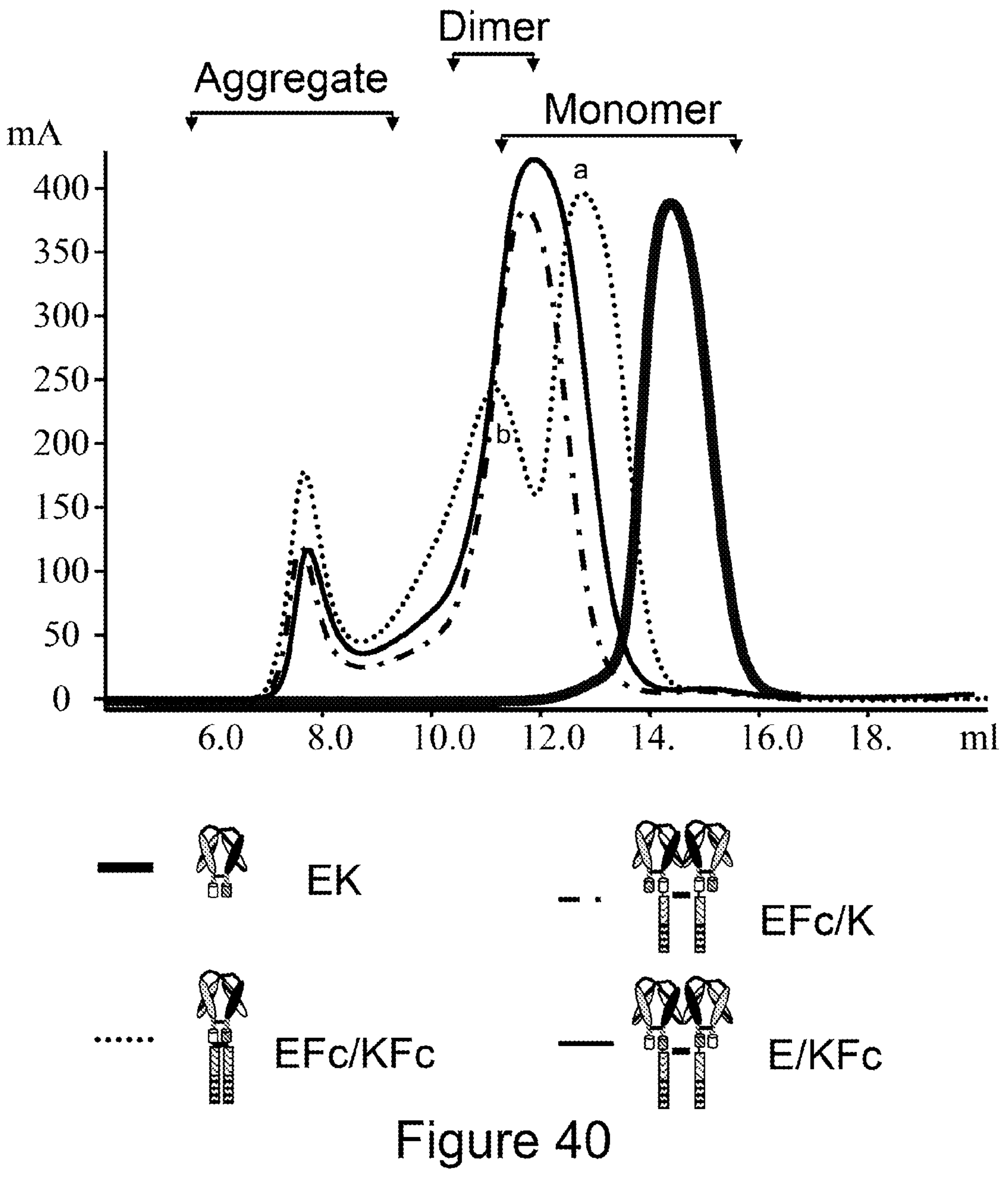

FIG. 40 SIZE EXCLUSION CHROMATOGRAPHY ON E-COIL AND/OR K-COIL DERIVATIVES AND E-COIL AND/OR K-COIL FC-CONTAINING DERIVATIVES OF h2B6YAhCB3 DARTS

FIG. 40 shows the results of size exclusion chromatography on E-coil and/or K-coil derivatives and E-coil and/or K-coil Fc-containing derivatives of h2B6YAhCB3 DARTS. Four species of such molecules were analyzed; all had an E-coli and a K-coil: EK (no Fc region), 2.1 mg; EFc/K (Fc linked to E-coil), 2.7 mgs; E/KFc (Fc linked to K-coil), 1.8 mgs; EFc/KFc (Fc linked to the K-coil and the E-coil of the same DART), 2.0 mg

FIG. 41 STRUCTURE OF PRODUCED DIMER MOLECULES

Figure 41:
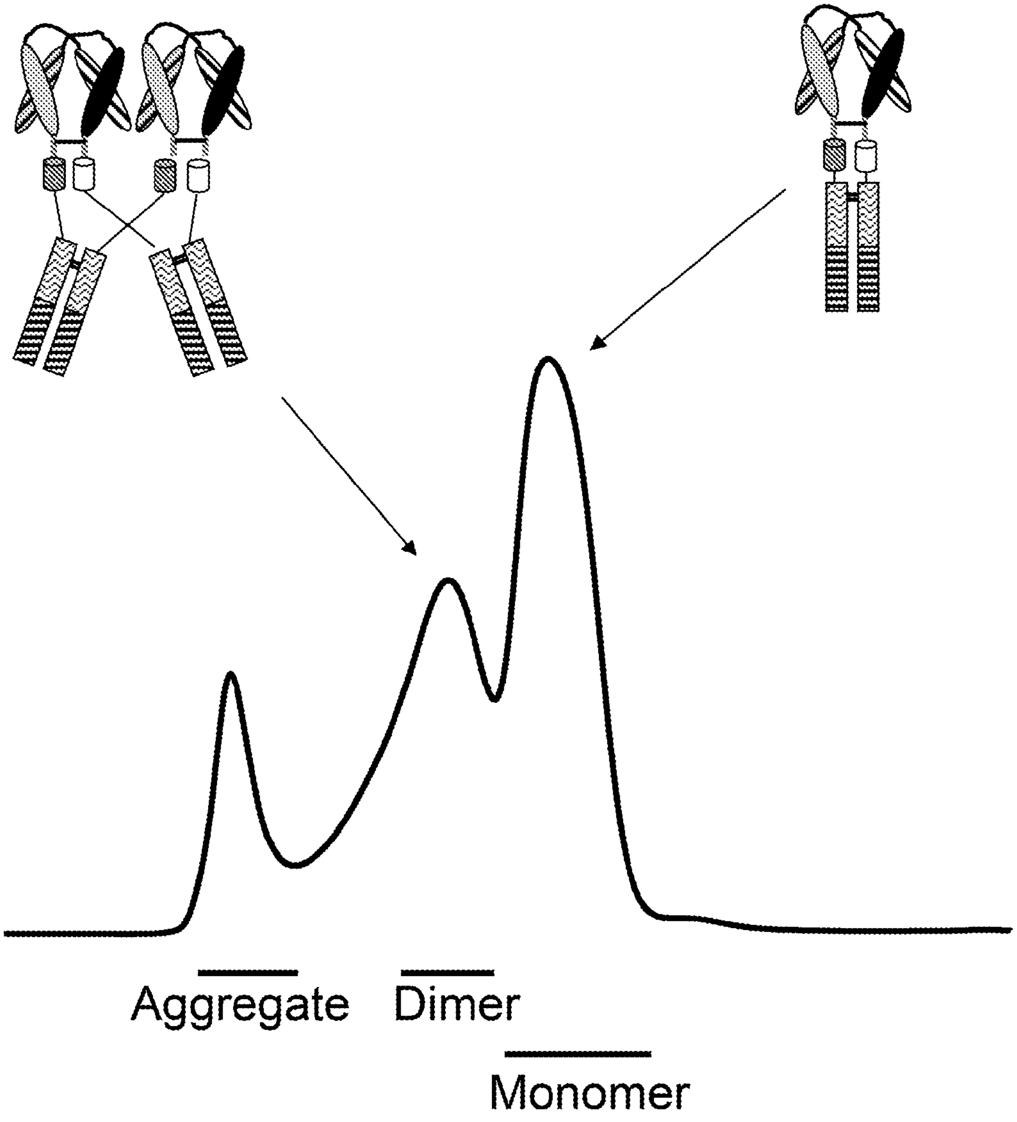

FIG. 41 shows the possible structure of the produced dimer molecule identified in the size exclusion chromatograph of FIG. 40.

Figure 42:
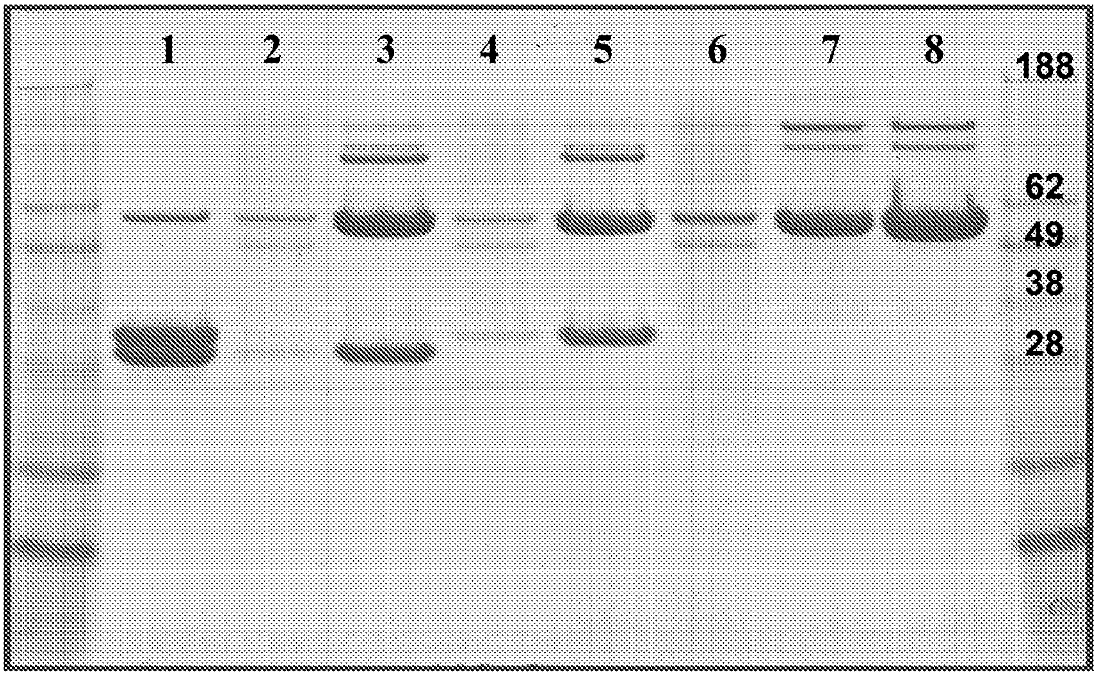

FIG. 42 SDS-POLYACRYLAMIDE GEL ELECTROPHORETIC ANALYSIS OF THE E-COIL AND/OR K-COIL DERIVATIVES AND E-COIL AND/OR K-COIL FC-CONTAINING DERIVATIVES OF h2B6YAhCB3 DARTS

FIG. 42 shows the results of an SDS polyacrylamide gel electrophoretic analysis of the fractions obtained from size exclusion chromatography (FIG. 40) of E-coil and/or K-coil derivatives and E-coil and/or K-coil Fc-containing derivatives of h2B6YAhCB3 DARTs. Flanking lanes: molecular marker controls; Lane 1: EK (no Fc region); Lane 2: EFc/K, aggregate fraction; Lane 3: EFc/K, monomer fraction; Lane 4: E/KFc, aggregate fraction; Lane 5: E/KFc, monomer fraction; Lane 6: EFc/KFc, aggregate fraction; Lane 7: EFc/KFc, dimer fraction; Lane 8: EFc/KFc, monomer fraction.

FIG. 43 BISPECIFIC BINDING ELISA ANALYSIS OF

Figure 43:
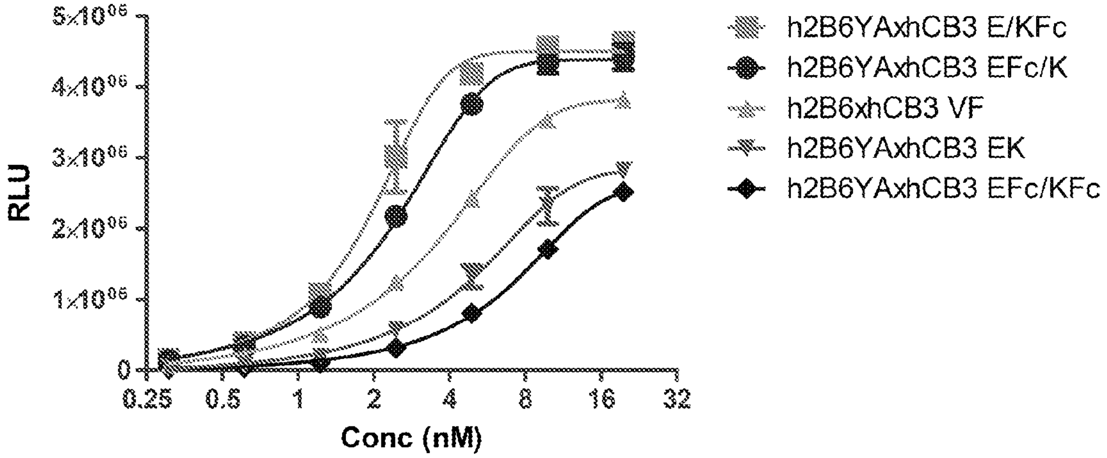

FIG. 43 shows the result of a bispecific binding ELISA comparing E-coil/K-coil Fc-containing h2B6YAhCB3 DART derivatives (EFc/K or E/KFc), h2B6YAhCB3 DART, control and an EFc/KFc h2B6YAhCB3 DART derivative.

Figure 44:
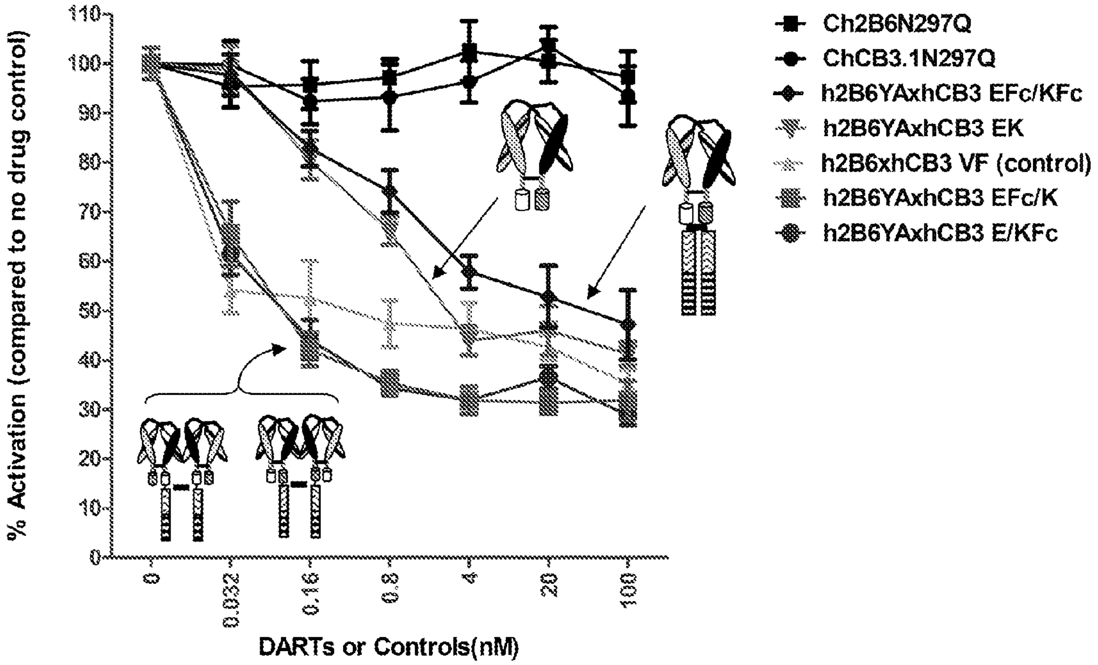

FIG. 44 ABILITY OF THE E-COIL AND/OR K-COIL DERIVATIVES AND E-COIL AND/OR K-COIL FC-CON-

TAINING DERIVATIVES OF h2B6YAhCB3 DARTS TO INHIBIT T-CELL PROLIFERATION

FIG. 44 shows the ability of the E-coil and/or K-coil derivatives and E-coil and/or K-coil Fc-containing derivatives of h2B6YAhCB3 DARTs to inhibit T-cell proliferation.

Figure 45:
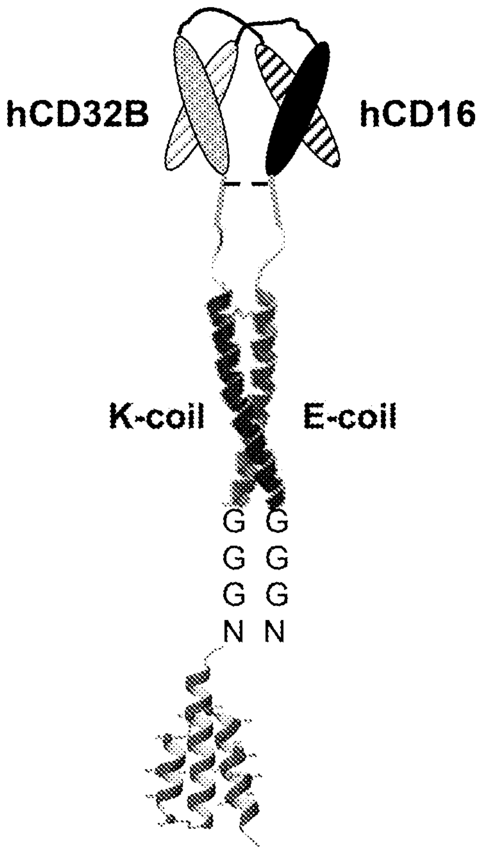

FIG. 45 hCD16-hCD32B ABD-DART

FIG. 45 shows a schematic of a recombinant antibody molecule, hCD16-hCD32B ABD-DART composed of the ABD3 domain of streptococcal protein G fused to a recombinant bispecific DART that is immunoreactive with hCD16 and hCD32B antigens.

FIG. 46A-46J BINDING AFFINITY OF hCD16-hCD32B ABD-DART

Figure 46A:
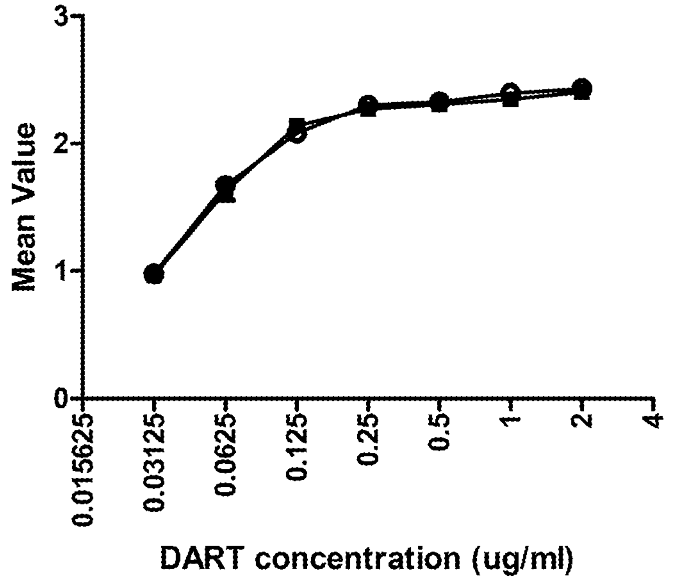
Figure 46B:
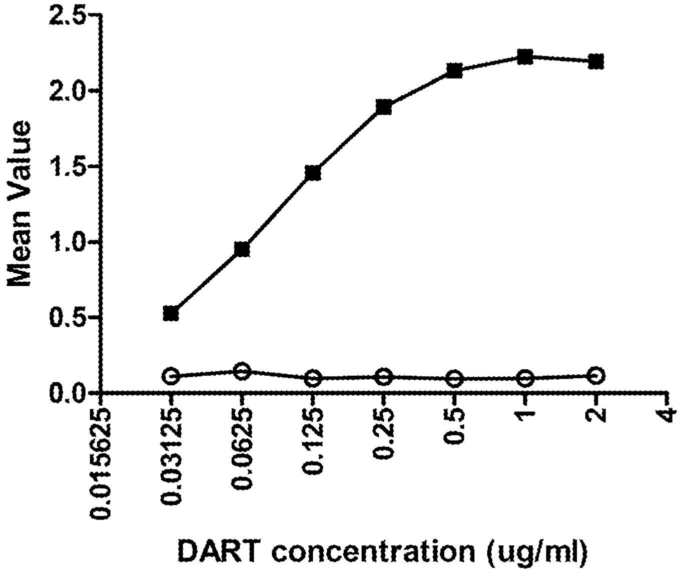
Figure 46C:
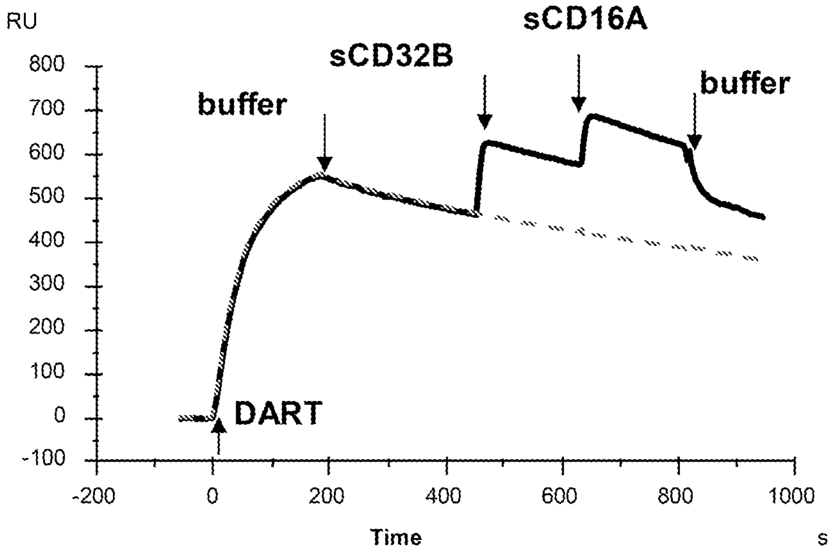
Figure 46D:
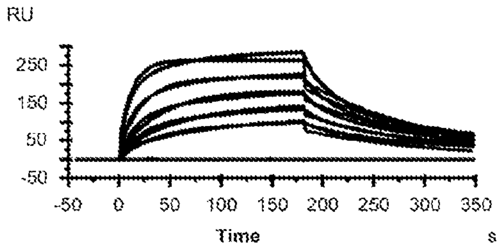
Figure 46E:
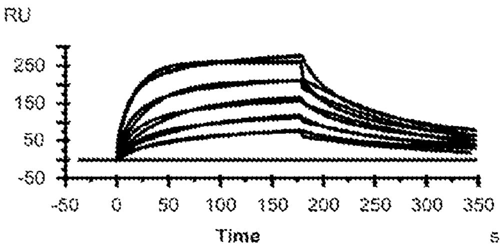
Figure 46F:
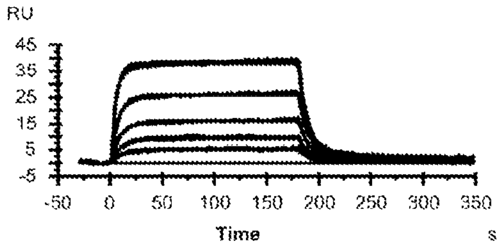
Figure 46G:
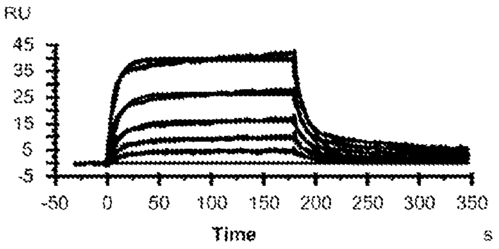
Figure 46H:
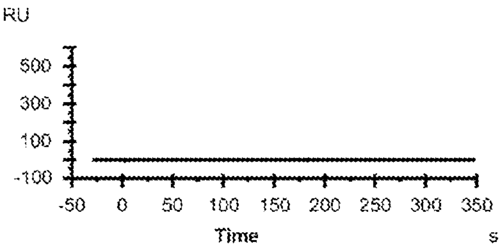
Figure 46I:
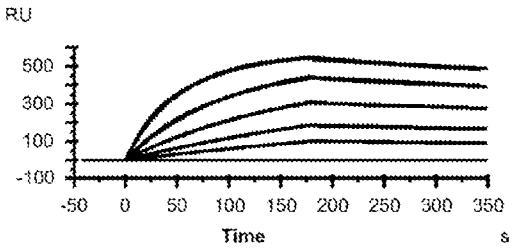
Figure 46J:
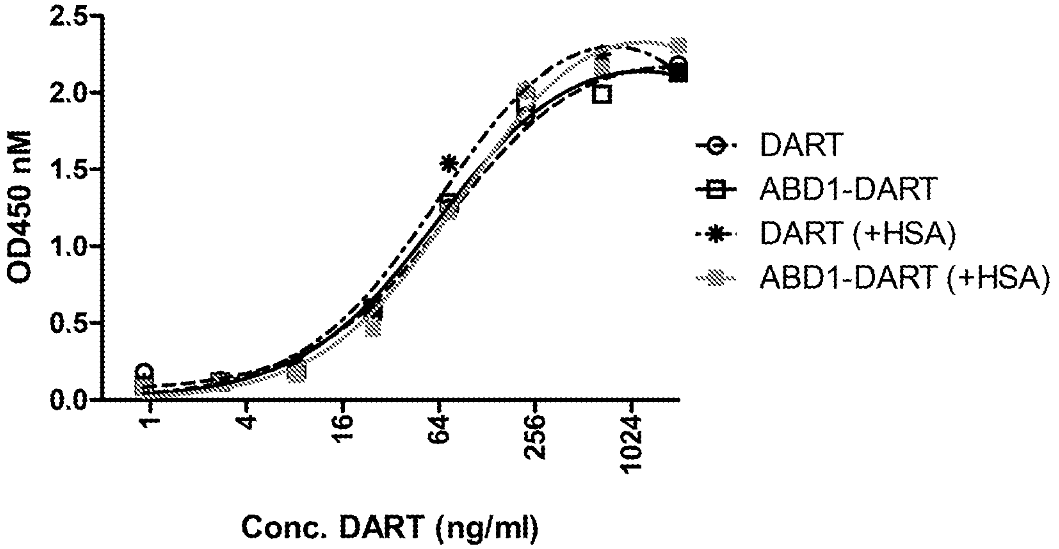

ELISA plates were coated with either CD16 antigen (FIG. 46A) or human serum albumin (FIG. 46B) at a concentration of 2 μg/mL. Varying concentrations of hCD16-hCD32B ABD-DART (■) and control hCD16-hCD32B DART (○) starting with 2 μg/mL were bound. Biotinylated sCD32B antigen was added to the plate followed by HRP conjugated Streptavidin for detection. FIG. 46C shows that the ABD-DART molecule was capable of simultaneous binding to CD32B, CD16A and HSA. FIGS. 46D-46I demonstrate that the hCD16-hCD32B ABD-DART and its ABD fusion derivative were found to exhibit equivalent binding soluble CD32B (sCD32B) and to soluble CD16A(158F) (sCD16A). FIG. 46J demonstrates that the DART ABD fusion retained the bi-specific binding of its parental DART, and exhibited binding to sCD16A and CD32B that was unaffected by the presence of human serum albumin.

FIG. 47A/47B CYTOTOXICITY OF DART PROTEINS

Figure 47A:
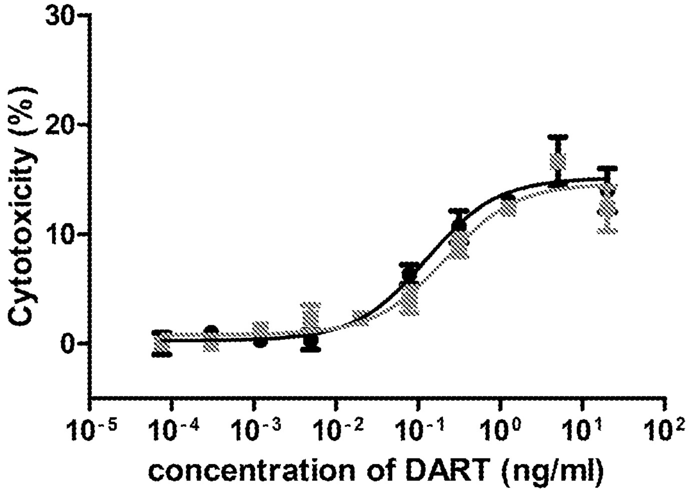
Figure 47B:
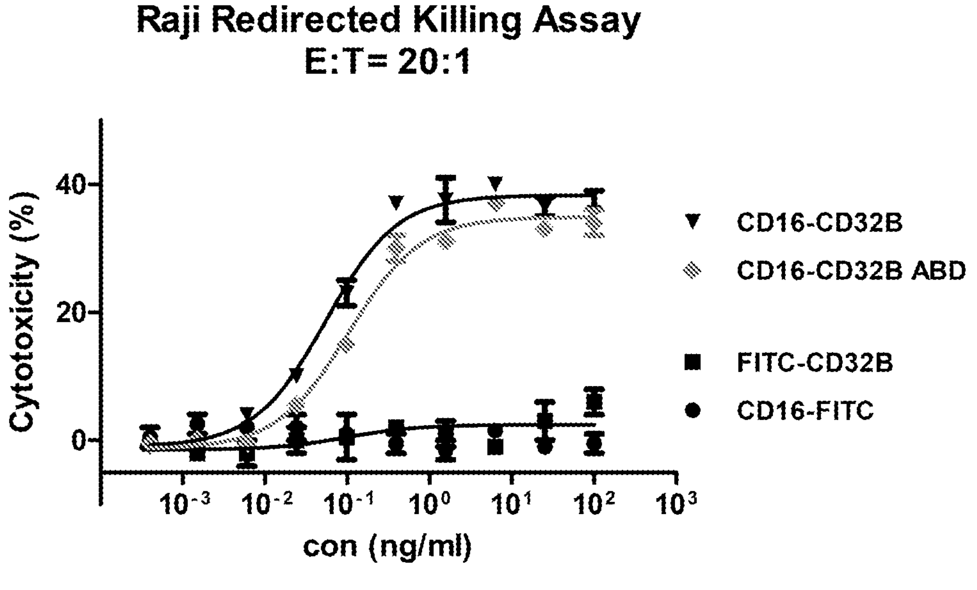

FIG. 47A demonstrates PBMC mediated cytotoxicity of DART proteins. ADCC assays were performed using human B-cell lines, Daudi as target cells incubated with PBMC as effector cells. Individual assays were done in triplicate at an effector-to-target ratio of 20:1 and a titration of antibodies: hCD16A-hCD32B DART (●) and hCD16A-hCD32B ABD DART (■). Cell mediated cytotoxicity was measured by LDH release assay. The lower curve at $10^0$ is hCD16A-hCD32B ABD DART (■). FIG. 47B demonstrates that the CD16×CD32B DART binds to CD16B-expressing effector cells and thereby recruits such cells to kill (via redirected killing) cells that that express CD32B.

Figure 48:
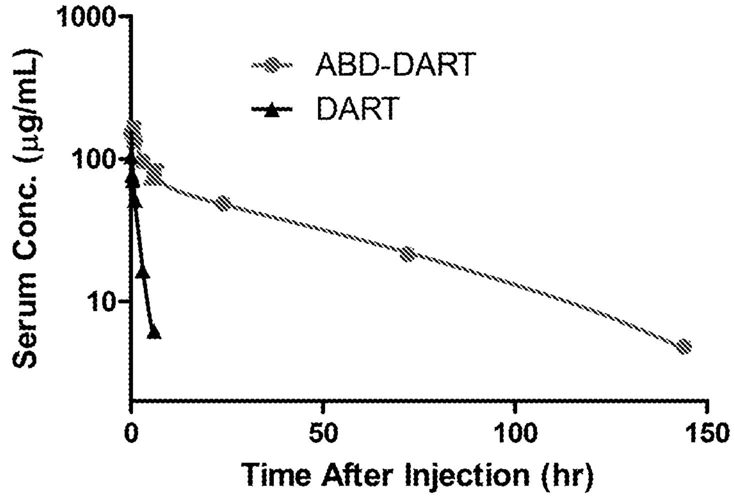

FIG. 48 IMPROVED PHARMACOKINETIC PROPERTIES OF hCD16-hCD32B ABD-DART IN C57B1/6 MICE

Mice (n=3) were injected with a single intravenous injection of (A) hCD16-hCD32B ABD-DART (●) and (B) hCD16-hCD32B DART (▲) at 5 mg/kg. Mouse serum was collected at various time points and concentrations of protein in serum were quantified by ELISA. Pharmacokinetic calculations were performed using WinNonlin Professional 5.1.

FIG. 49A-49C IN VIVO BIOLOGICAL ACTIVITY OF THE ABD-DART

Figure 49A:
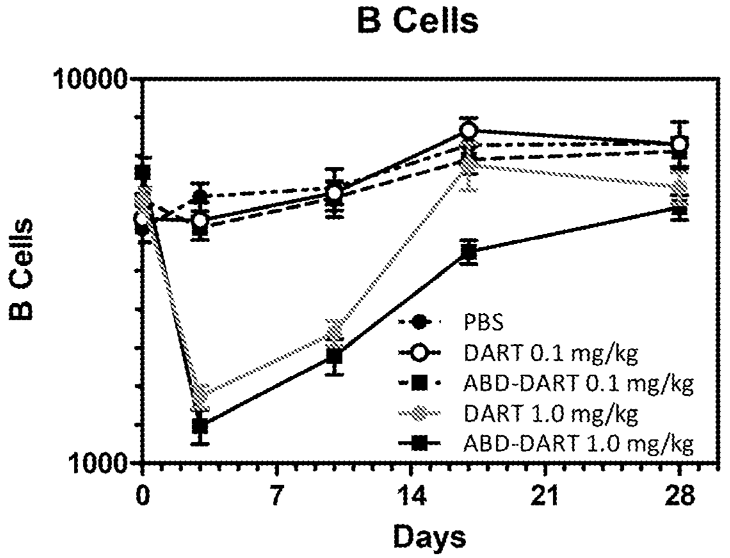
Figure 49B:
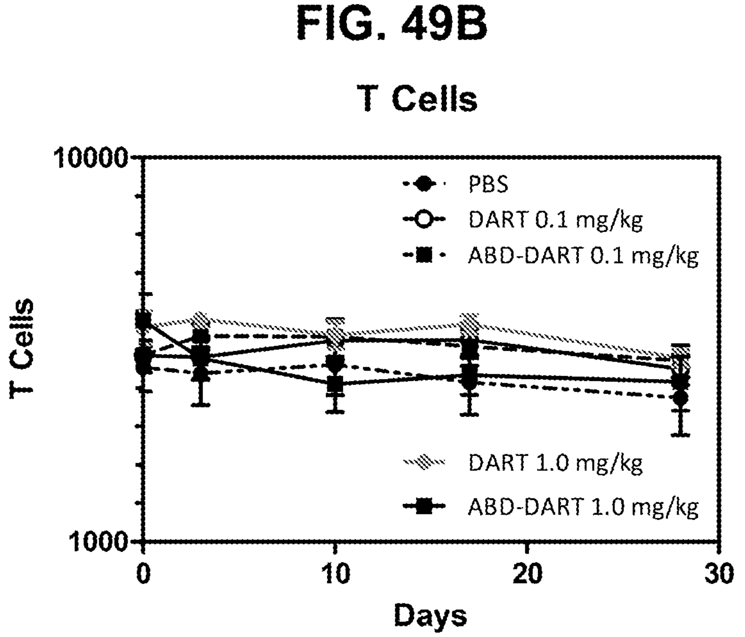
Figure 49C:
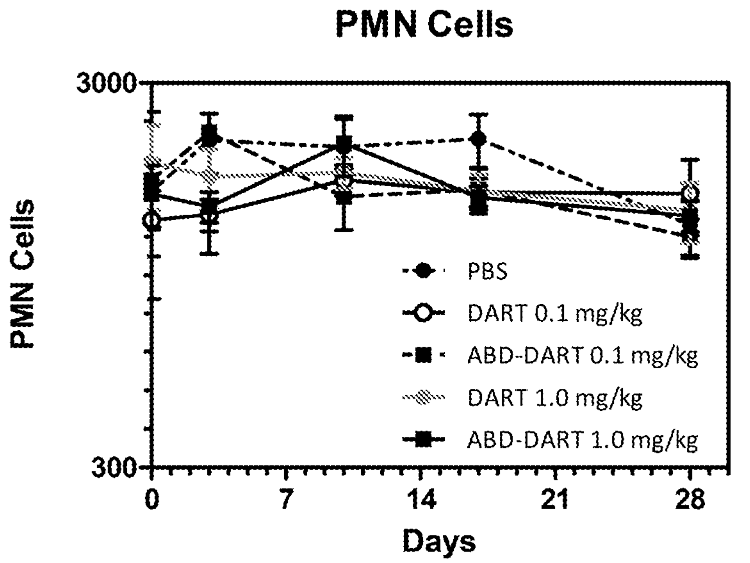

FIG. 49A-49C demonstrate that the hCD16-hCD32B ABD-DART retained and exhibited biological activity, in vivo, after administration to mice. A single dose of the ABD-DART or its parental DART into Tg (mCD16−/−hCD16A+ 32B+) mice was found to be capable of selectively depressing the concentrations of B cells (FIG. 49A) without affecting the concentrations of T cells (FIG. 49B) or PM cells (FIG. 49C).

FIG. 50A-50E HER2×TCRb DART ACTIVITY ON PANEL OF HER2 LOW EXPRESSING CELL LINES

Figure 50A:
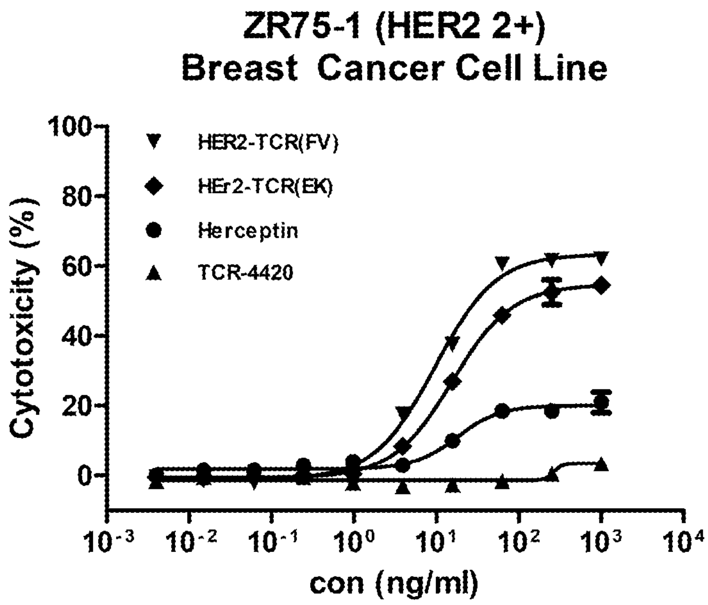
Figure 50B:
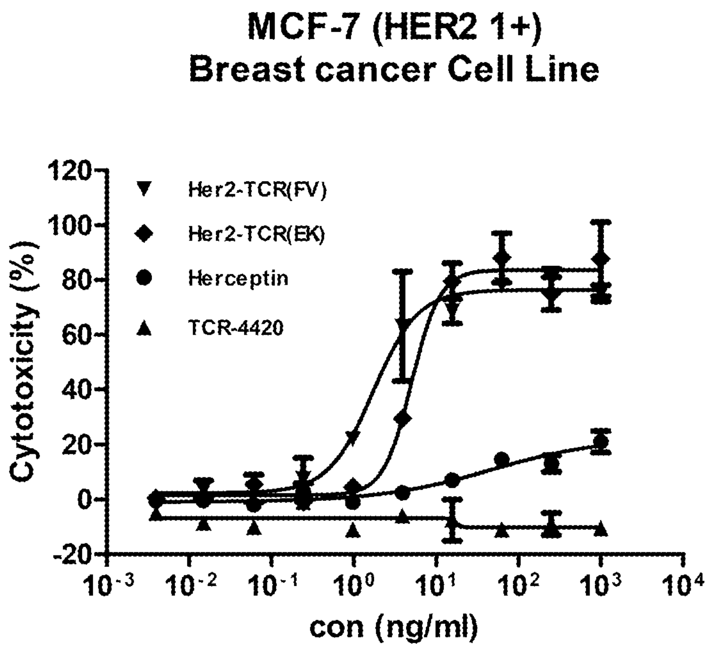
Figure 50C:
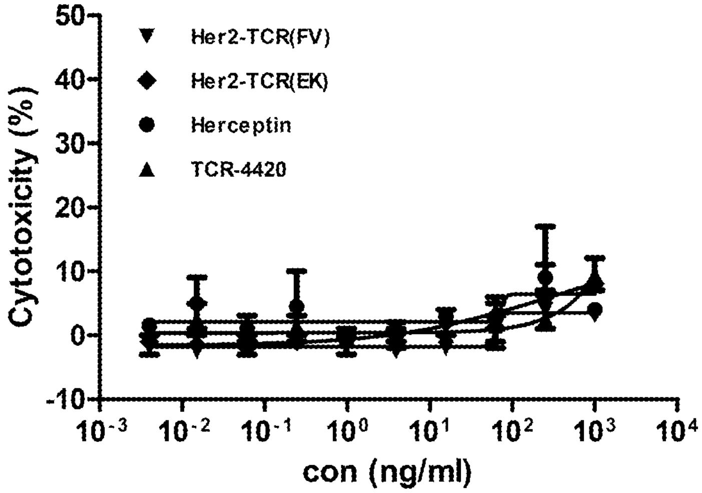
Figure 50D:
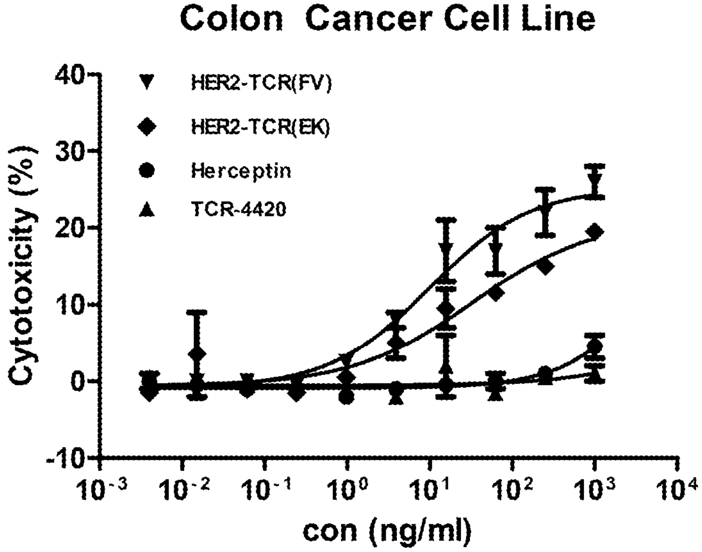
Figure 50E:
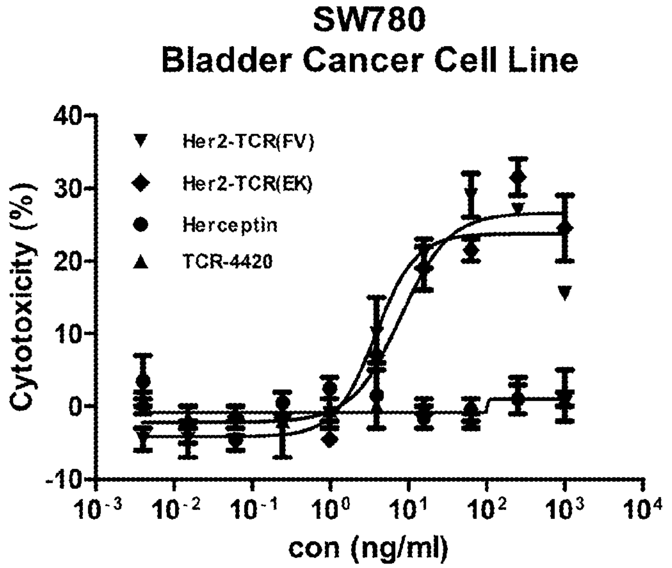

DART molecules having Her2 and T-cell receptor (TCR) binding domains were tested for their ability to mediate cytotoxicity in multiple breast cancer, colon cancer and bladder cancer cell lines that had been previously characterized as exhibiting low levels of HER2 expression (and thus being refractory to treatment with the anti-Her2/neu antibody, Herceptin®. The tested breast cancer cell lines are ZR75-1 (HER22+) (FIG. 50A), MCF-7 (HER21+) (FIG. 50B) and MDA-MB468 (HER2-ve) (FIG. 50C). The non-breast cancer cell lines tested are HT-29 (colon cancer cell line) (FIG. 50D) and SW780 (bladder cancer cell line) (FIG. 50E).

Figure 51A:
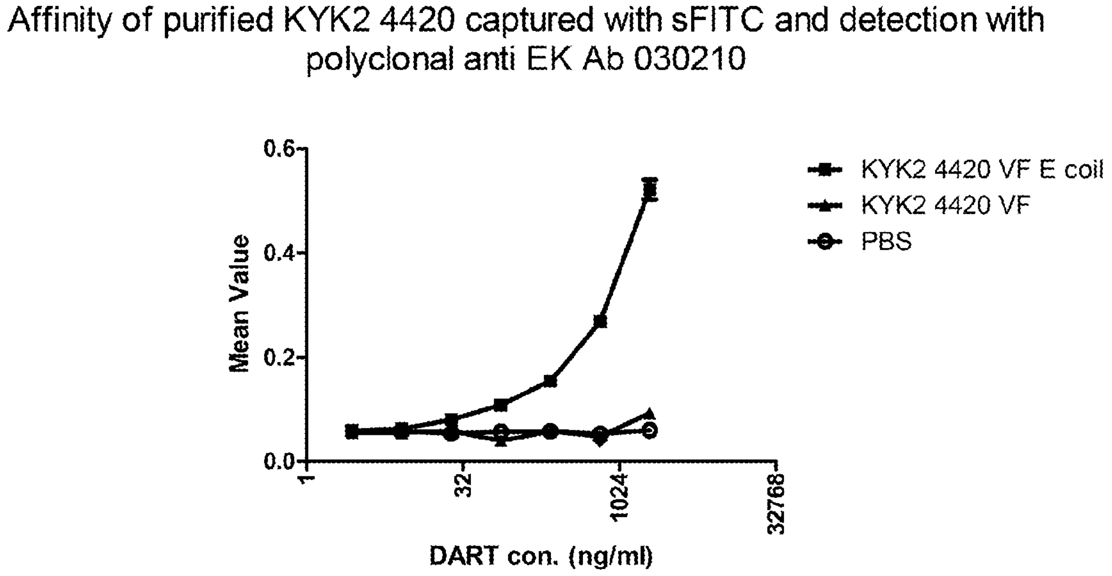
Figure 51B:
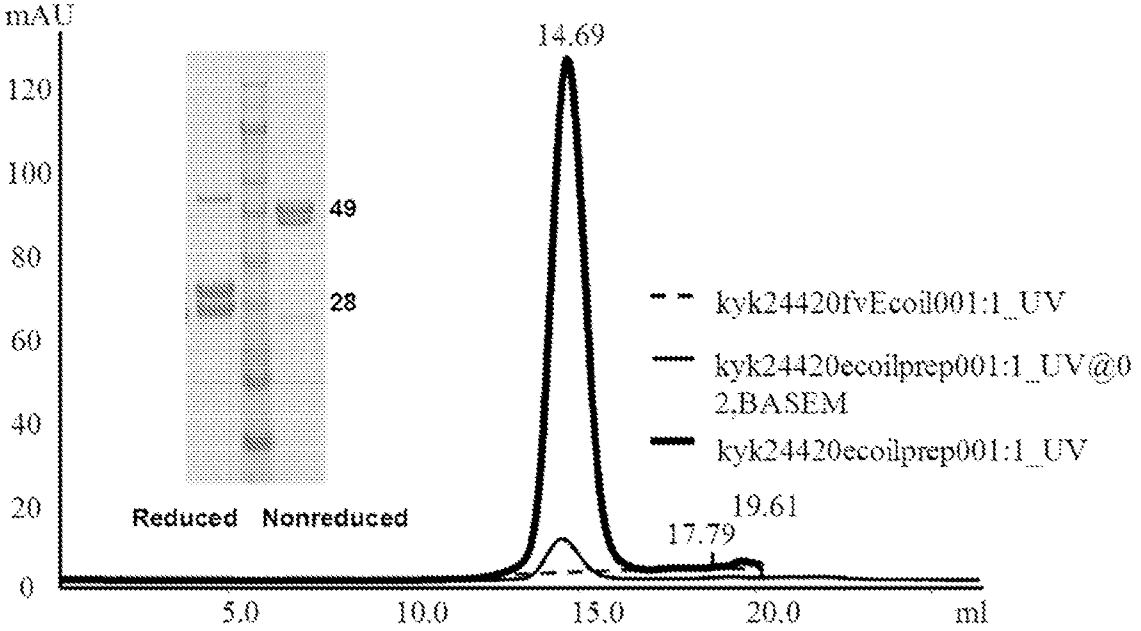

FIG. 51A-51B PURIFICATION OF KYK2VL-4420VH-GFNRGEC (SEQ ID NO: 313)—E COIL AND 4420VL-KYK2VH-GVEPKSC (SEQ ID NO: 314) POLYPEPTIDES

FIG. 51A-51B show the purification of KYK2VL-4420VH-GFNRGEC (SEQ ID NO: 313)—E Coil And 4420VL-KYK2VH-GVEPKSC (Seq Id No: 314) polypeptides.

FIG. 52 BINDING SPECIFICITY OF KYK2-4420 VF DART

Figure 52:
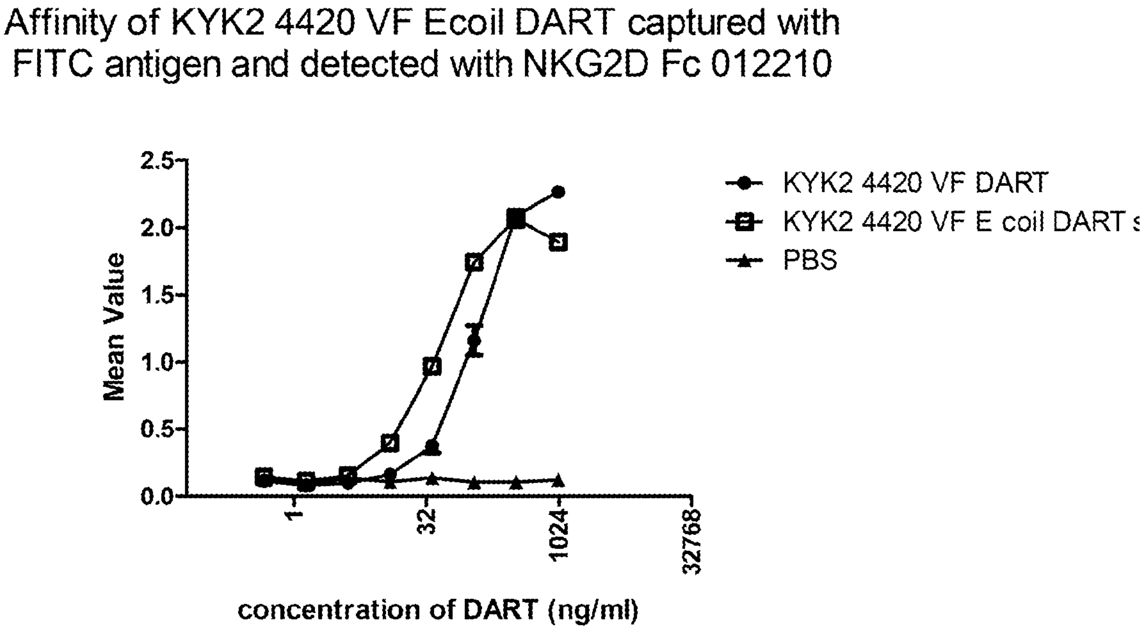

FIG. 52 shows the binding specificity of KYK2-4420 VF DART.

Figure 53:
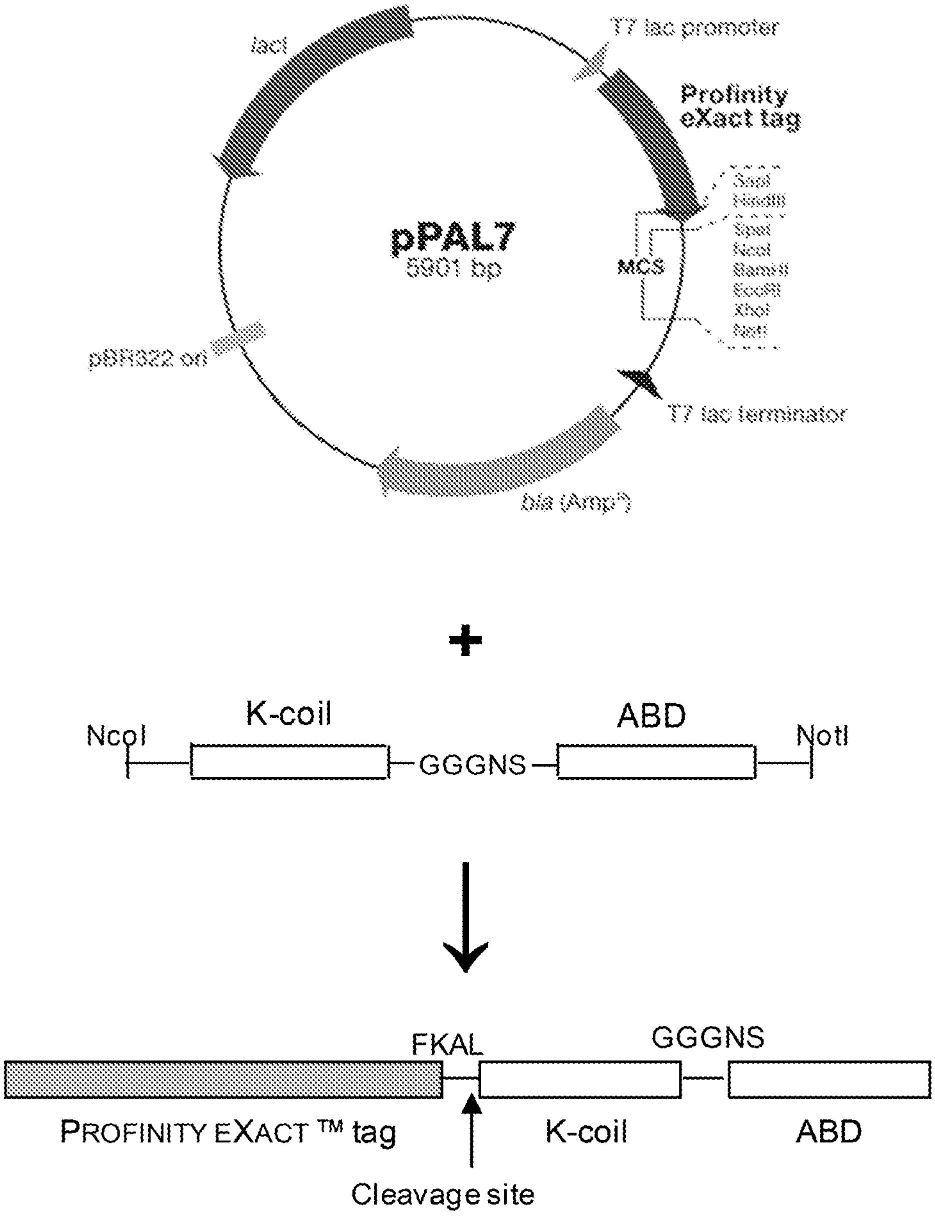

FIG. 53 CONSTRUCTION OF PLASMID pPAL7 KCOIL-ABD

FIG. 53 shows a schematic description of the construction of plasmid pPAL7 Kcoil-ABD.

Figure 54:
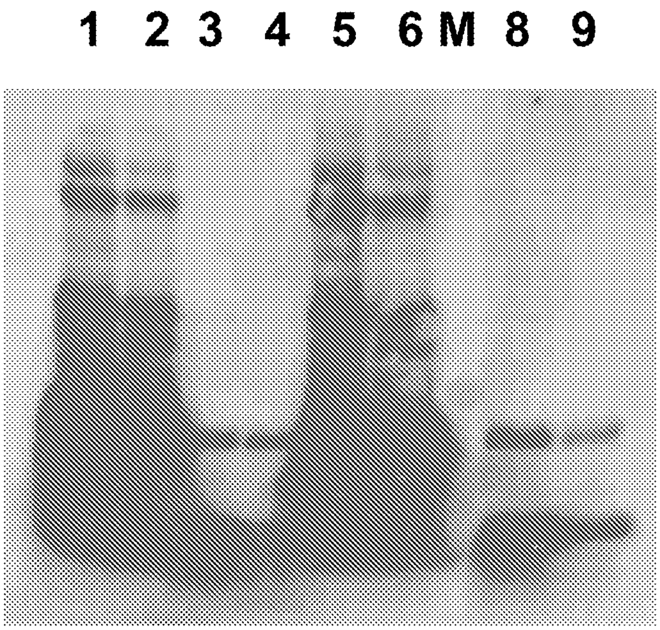

FIG. 54 WESTERN BLOT ANALYSIS OF KCOIL ABD PROTEIN PURIFIED BY THE PROFINITY EXACT™ PURIFICATION RESIN

FIG. 54 shows a Western blot analysis of Kcoil ABD protein purified by the Profinity eXact™ purification resin (small scale from 10 ml culture). Lanes 1 and 5: crude lysates; lanes 2 and 6: flow through, lanes 3, 4, 8, and 9: purified protein; lane 7: Marker. Primary antibody: Rabbit polyclonal anti-EK antibody; Secondary Antibody: anti-rabbit HRP.

Figure 55:
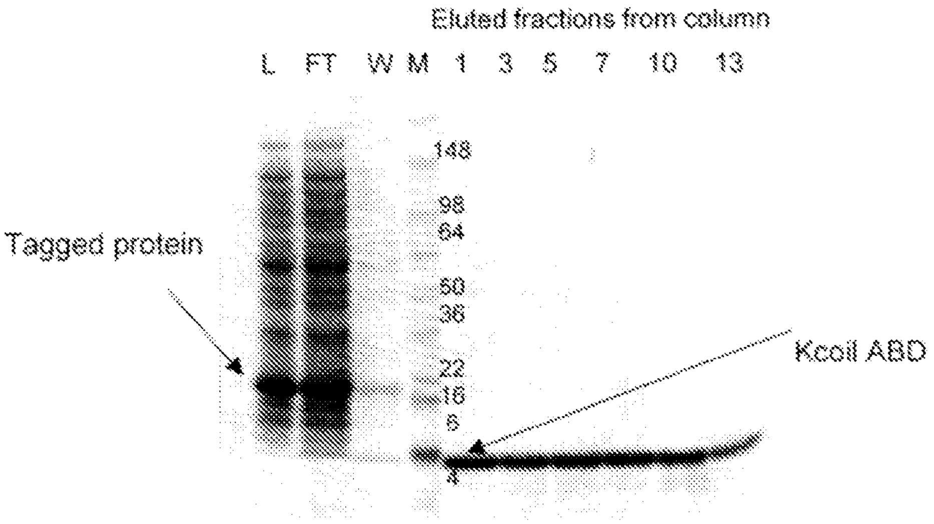

FIG. 55 SDS-PAGE ANALYSIS OF KCOIL ABD PROTEIN PURIFIED BY THE PROFINITY EXACT™ PURIFICATION RESIN

FIG. 55 shows the results of SDS-PAGE analysis on the fractions eluted from the Profinity eXact™ purification resin. L: Crude *E. coli* lysate; FT: Flow through; W: Washing; M: Marker.

FIG. 56A-56C KYK2 4420 EK ABD DART BINDING BY DUAL AFFINITY ELISA

Figure 56A:
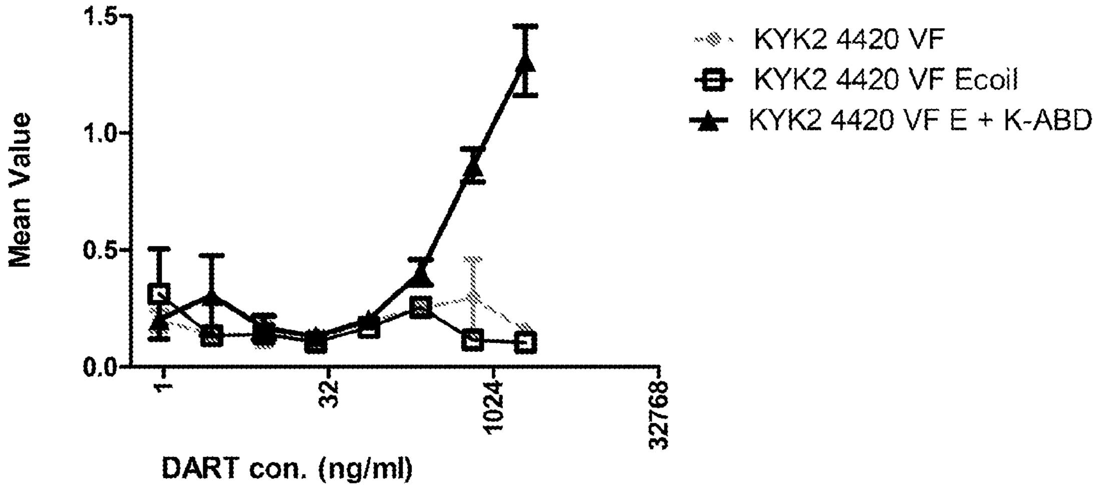
Figure 56B:
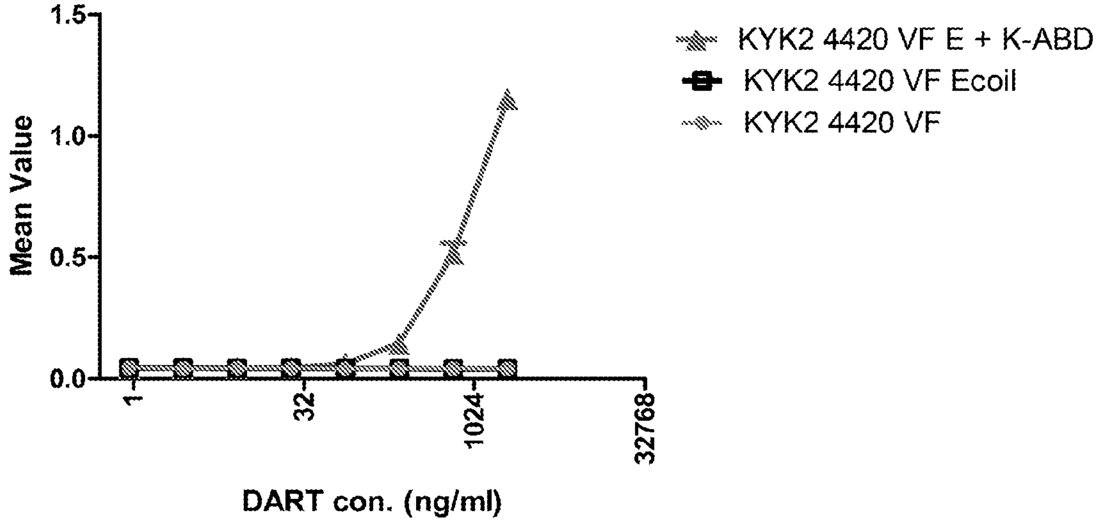
Figure 56C:
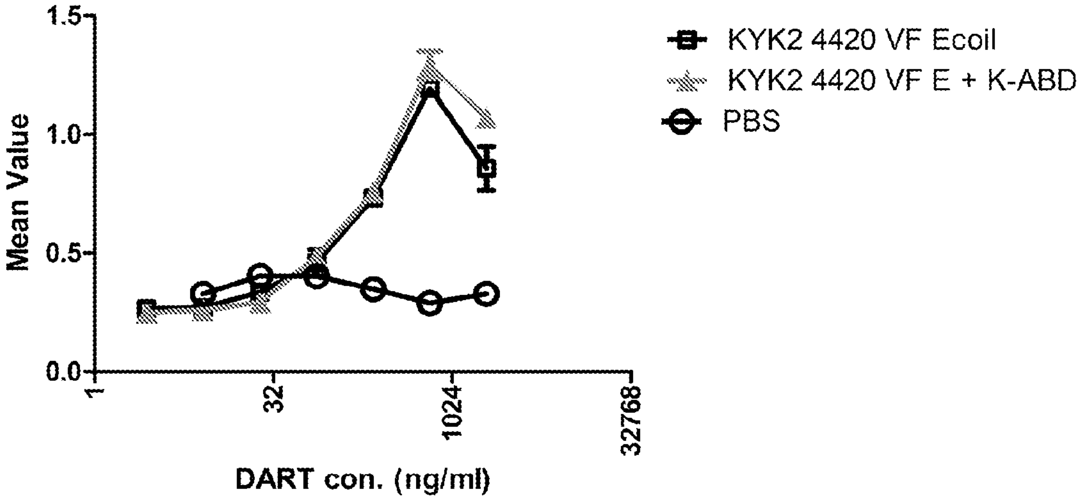

FIGS. 56A-56C show ELISA results that demonstrate the KYK2-4420 VF DART complexes with the K Coil-ABD molecule to form an E Coil-K Coil ABD DART having improved properties. FIG. 56A: DARTs captured with NKG2D Fc and detected with biotinylated monoclonal anti-EK antibody. FIG. 56B: DARTs captured with monoclonal anti-EK antibody and detected with HRP-human albumin. FIG. 56C: DARTs captured with NKG2D Fc and detected with biotinylated anti-FITC antibody. The ELISA results show that all of the domains in the complex can bind to their respective ligands.

FIG. 57 DEIMMUNIZED ABD ELISA

Figure 57:
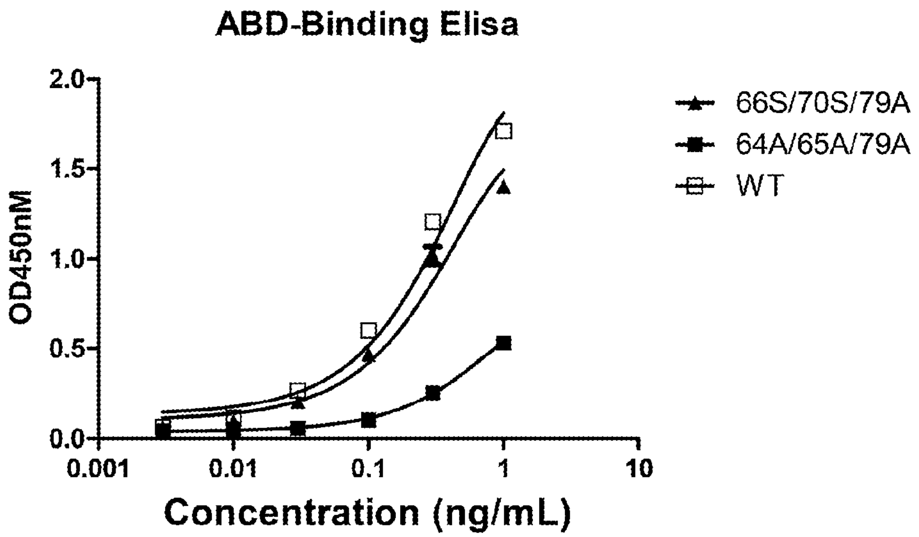

FIG. 57 shows ELISA results that demonstrate the binding changes caused by modifications in the sequence of albumin bindin fomains.

FIG. 58 ALBUMIN BINDING ASSAY

Figure 58:
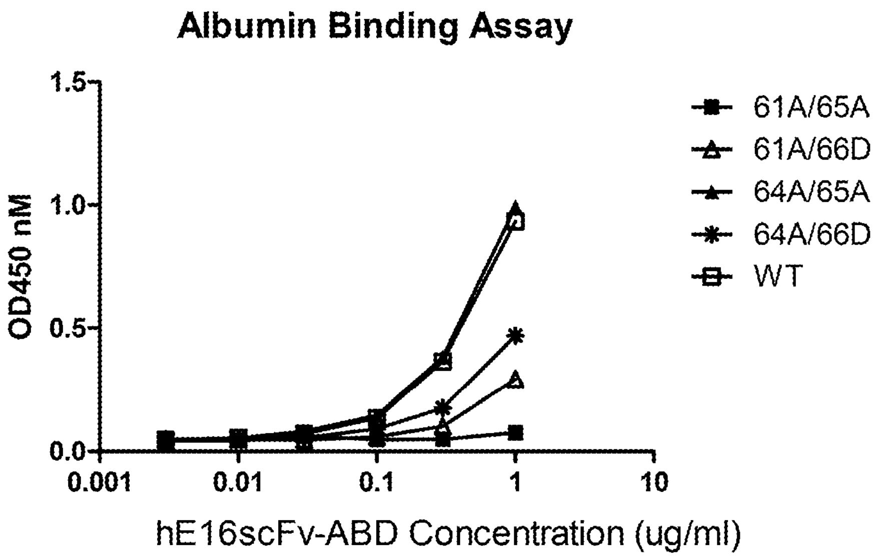

FIG. 58 shows the result of albumin binding assays for the ABD variants Y61A/165A, Y61A/N66D, L64A/I65A* and L64A/N66D and for wild-type.

FIG. 59 ALBUMIN BINDING ASSAY

Figure 59:
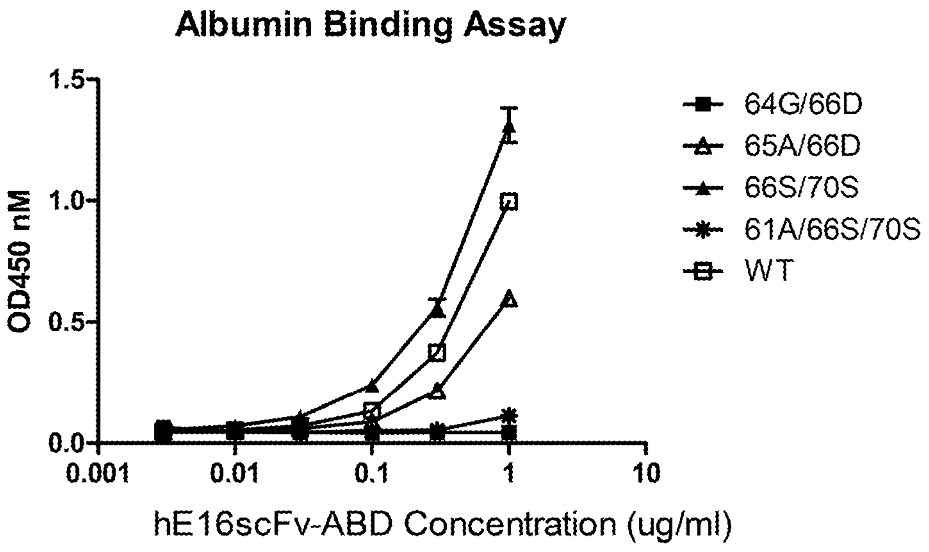

FIG. 59 shows the result of albumin binding assays for the ABD variants L64G/N66D, 165A/N66D, N66S/T70S* and Y61A/N66S/T70S and for wild-type.

FIG. 60 ALBUMIN BINDING ASSAY

Figure 60:
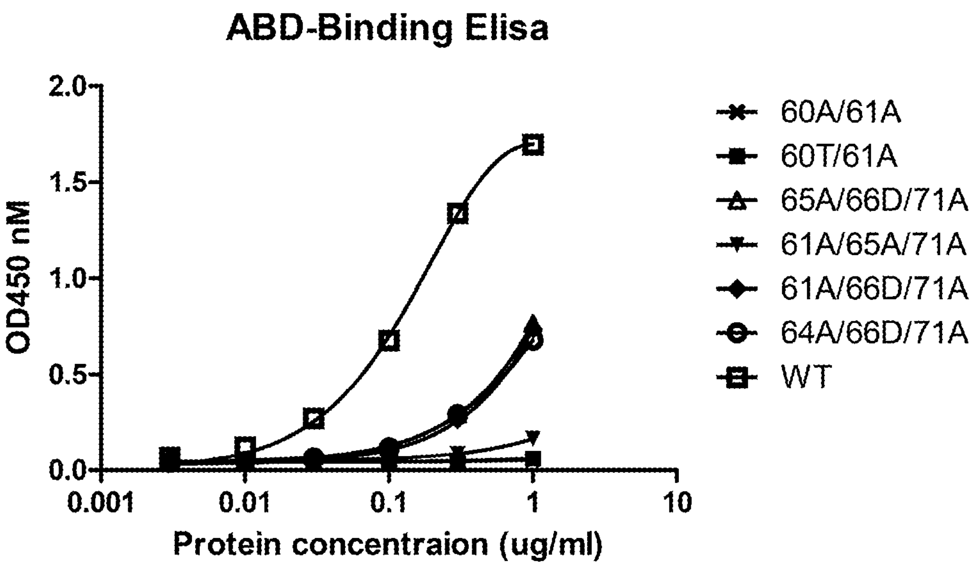

FIG. 60 shows the result of albumin binding assays for the ABD variants Y60A/Y61A, Y60T/Y61A, I65A/N66D/V71A, Y61A/165A/V71A, L64A/N66D/V71A and for wild-type.

FIG. 61 ALBUMIN BINDING ASSAY

Figure 61:
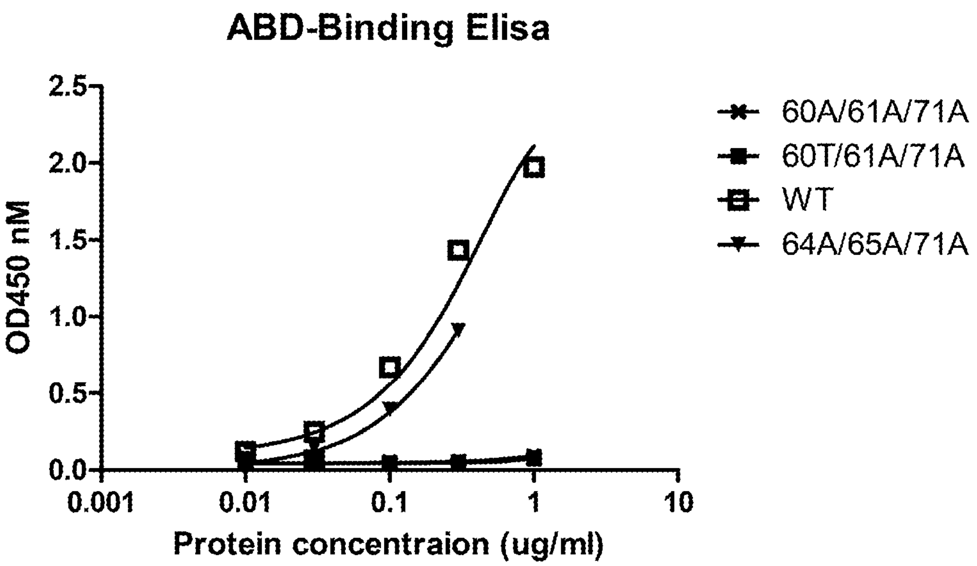

FIG. 61 shows the result of albumin binding assays for the ABD variants Y60A/Y61A/V71A, Y60T/Y61A/V71A, L64A/165A/V71A and for wild-type.

FIG. 62 ALBUMIN BINDING ASSAY

Figure 62:
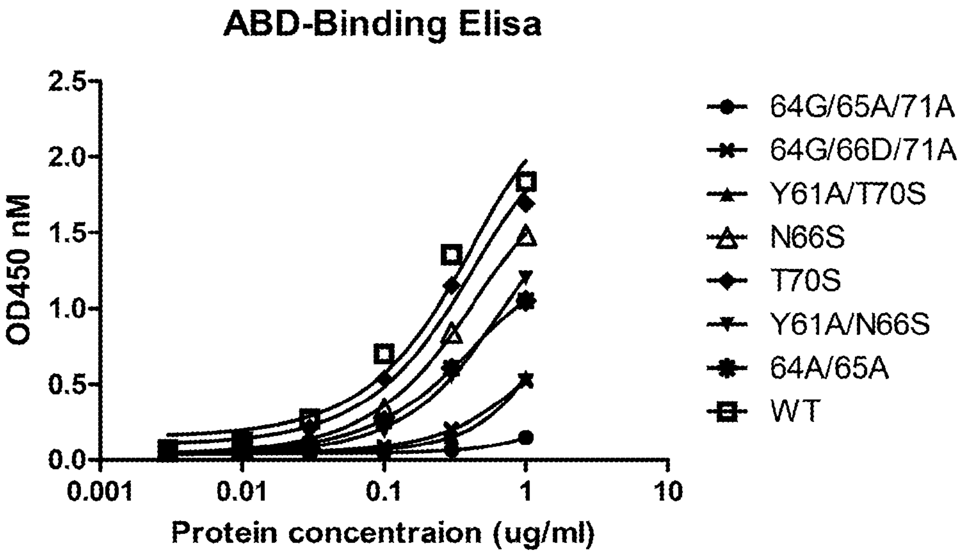

FIG. 62 shows the result of albumin binding assays for the ABD variants L64G/165A/V71A, L64G/N66D/V71A, Y61A/T70S, N66S, T70S, Y61A/N66S, L64A/165A and for wild-type.

Figure 63:
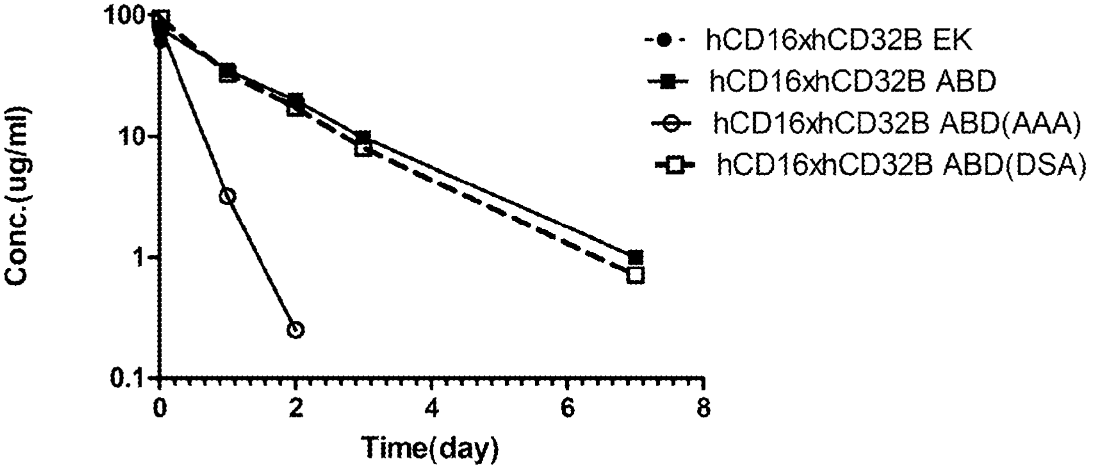

FIG. 63 IMPROVED PHARMACOKINETIC PROPERTIES OF CD16×CD32B ABD-DART AND ABD-DART VARIANTS IN C57BL/6 MICE

FIG. 63 shows the improved pharmacokinetic properties of CD16×CD32B ABD-DARTS and ABD-DART variants in C57Bl/6 mice. Mice (n=3) were injected with a single intravenous injection of ABD-DART proteins at 5 mg/kg. Mouse serum was collected at various time points and concentrations of protein in serum were quantified by ELISA. Pharmacokinetic calculations were performed using WinNonlin Professional 5.1

Figure 64A:
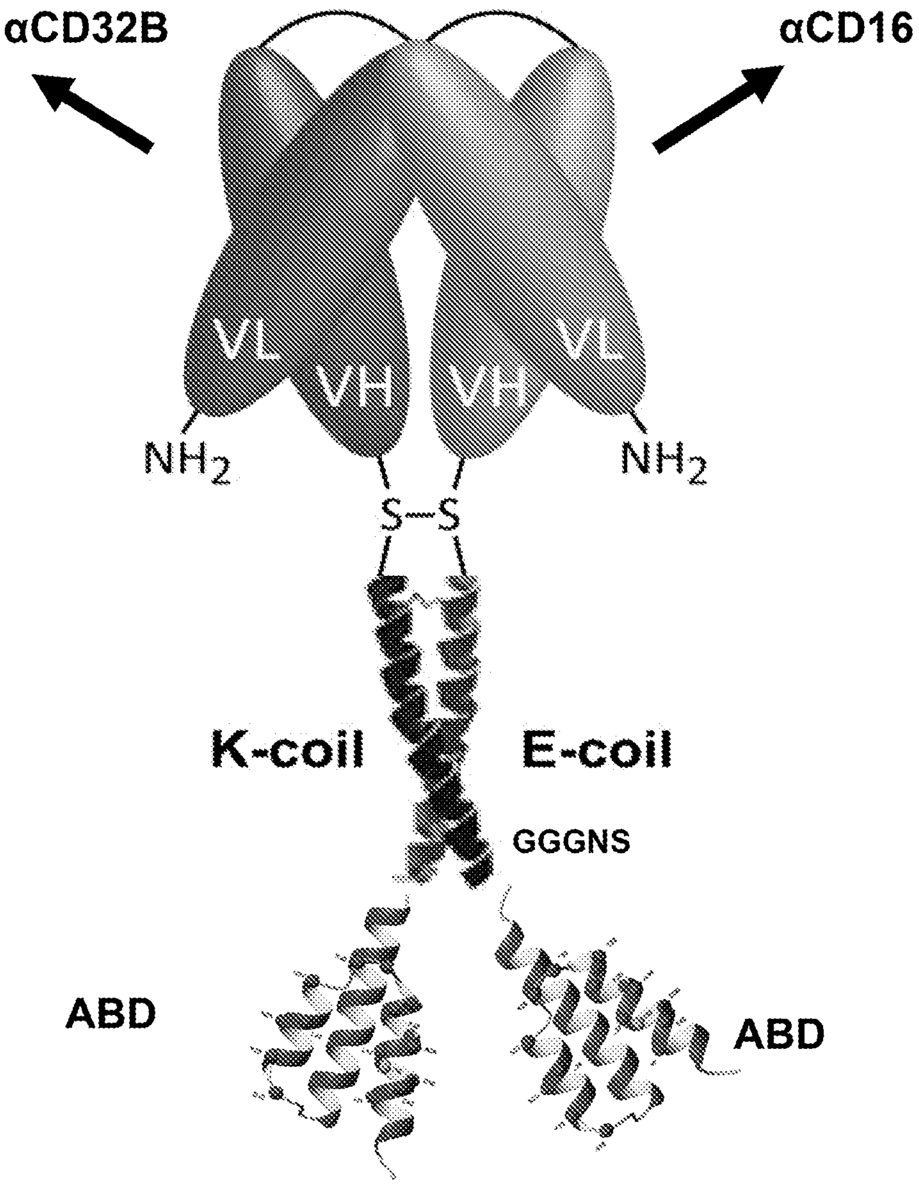
Figure 64B:
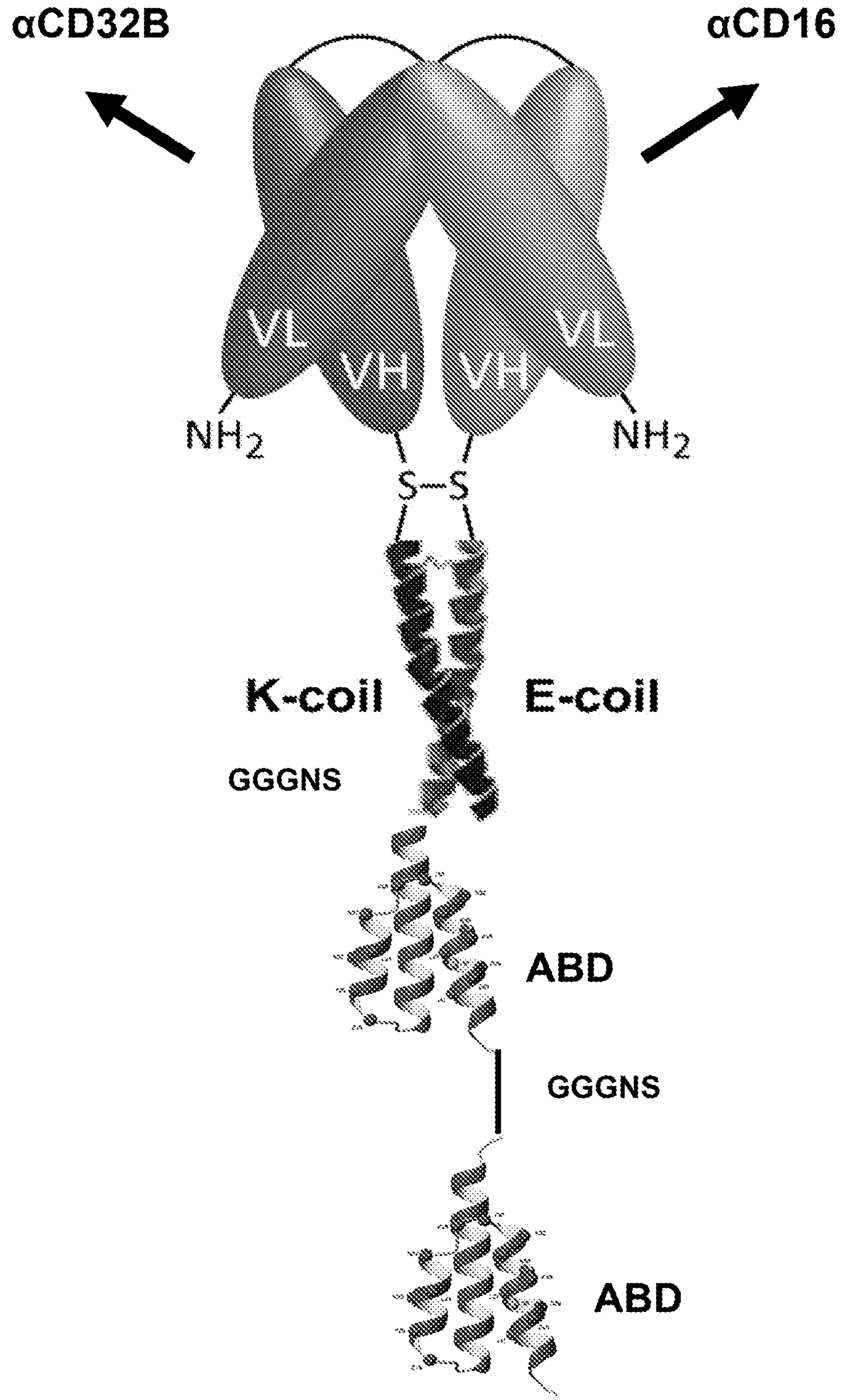

FIGS. 64A and 64B MULTI-VALENT ABD DART PROTEINS

FIGS. 64A and 64B illustrate the structures of DARTs containing multi-valent ABDs, constructed by fusing ABDs at the end of both chains (hCD16×hCD32B E ABD/K ABD DART) (FIG. 64A) or by fusing tandem ABDs at the end of one chain (hCD16×hCD32B E ABD ABD/K DART) (FIG. 64B).

FIG. 65(A-C) BISPECIFIC ACTIVITY OF hCD16×hCD32B ABD DARTs

Figure 65A:
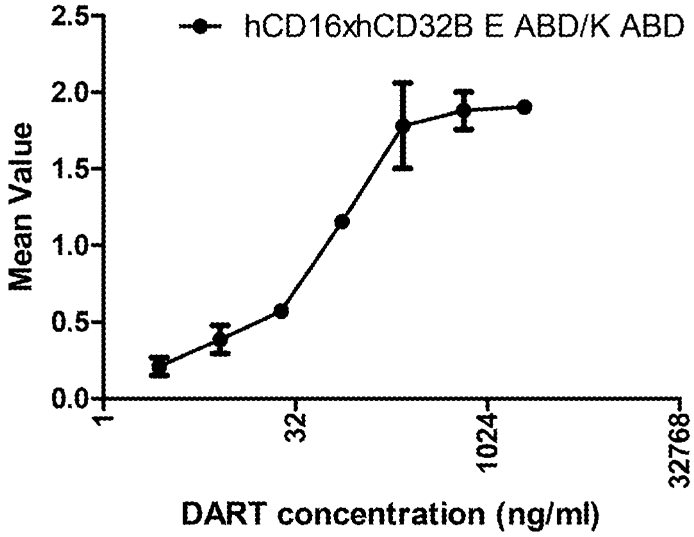
Figure 65B:
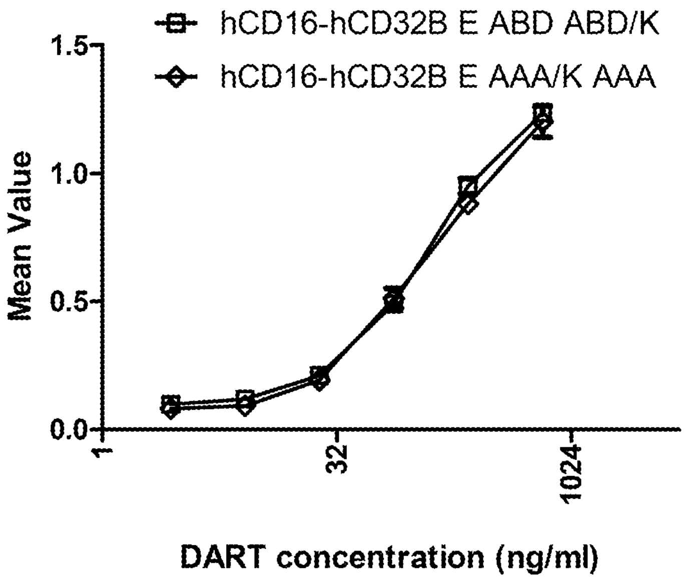
Figure 65C:
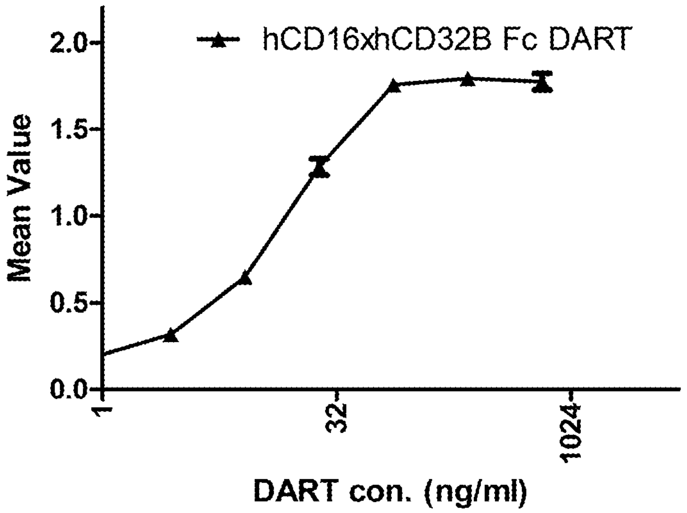

FIGS. 65A-65C illustrate the bispecific activity of hCD16×hCD32B ABD DARTs using dual specific ELISA. ELISA plates were coated with 2 μg/ml of CD16 antigen. Varying concentrations of ABD DARTs and Fc DART were bound to the plate. Finally biotinylated sCD32B antigen was added to the plate followed by HRP conjugated Streptavidin for detection.

FIG. 66 SERUM HALF-LIFE OF ABD DARTS AND FC DARTS

Figure 66:
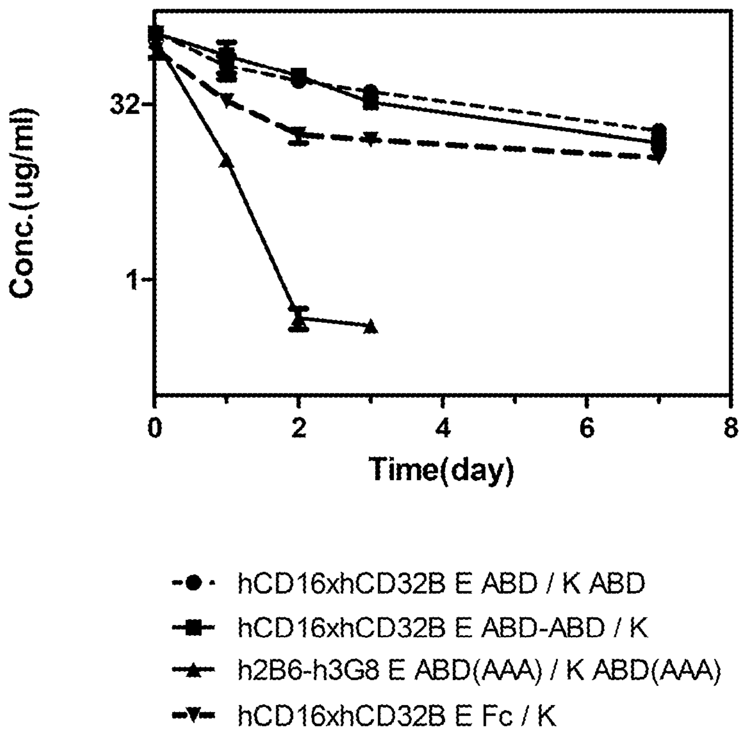

FIG. 66 shows the results of an in vivo PK study in which C57Bl/6 mice received a single IV injection of ABD DARTs or Fc DARTs (5 mg/kg) in order to assess serum half-life.

5. DESCRIPTION OF THE PREFERRED EMBODIMENTS

Each polypeptide chain of the diabody molecule comprises a VL domain and a VH domain, which are covalently linked such that the domains are constrained from self assembly. Interaction of two of the polypeptide chains will produce two VL-VH pairings, forming two eptipoe binding sites, i.e., a bivalent molecule. Neither the VH or VL domain is constrained to any position within the polypeptide chain, i.e., restricted to the amino (N) or carboxy (C) terminus, nor are the domains restricted in their relative positions to one another, i.e., the VL domain may be N-terminal to the VH domain and vice-versa. The only restriction is that a complimentary polypeptide chain be available in order to form functional diabody. Where the VL and VH domains are derived from the same antibody, the two complimentary polypeptide chains may be identical. For example, where the binding domains are derived from an antibody specific for epitope A (i.e., the binding domain is formed from a $VL_A$-$VH_A$ interaction), each polypeptide will comprise a $VH_A$ and a $VL_A$. Homodimerization of two polypeptide chains of the antibody will result in the formation two $VL_A$-$VH_A$ binding sites, resulting in a bivalent monospecific antibody. Where the VL and VH domains are derived from antibodies specific for different antigens, formation of a functional bispecific diabody requires the interaction of two different polypeptide chains, i.e., formation of a heterodimer. For example, for a bispecific diabody, one polypeptide chain will comprise a $VL_A$ and a $VL_B$; homodimerization of said chain will result in the formation of two $VL_A$-$VH_B$ binding sites, either of no binding or of unpredictable binding. In contrast, where two differing polypeptide chains are free to interact, e.g., in a recombinant expression system, one comprising a $VL_A$ and a $VH_B$ and the other comprising a $VL_B$ and a $VH_A$, two differing binding sites will form: $VL_A$-$VH_A$ and $VL_B$-$VH_B$. For all diabody polypeptide chain pairs, the possibly of misalignment or mis-binding of the two chains is a possibility, i.e., interaction of VL-VL or VH-VH domains; however, purification of functional diabodies is easily managed based on the immunospecificity of the properly dimerized binding site using any affinity based method known in the are or exemplified herein, e.g., affinity chromatography.

In other embodiments, one or more of the polypeptide chains of the diabody comprises an Fc domain. Fc domains in the polypeptide chains of the diabody molecules preferentially dimerize, resulting in the formation of a diabody molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent diabody comprising an Fc domain, albeit with a structure distinct from that of an unmodified bivalent antibody (FIG. 11). Such diabody molecules will exhibit altered phenotypes relative to a wild-type immunoglobulin, e.g., altered serum half-life, binding properties, etc. In other embodiments, diabody molecules comprising Fc domains may be tetramers. Such tertramers comprise two 'heavier' polypeptide chains, i.e. a polypeptide chain comprising a VL, aVH and an Fc domain, and two 'lighter' polypeptide chains, i.e., polypeptide chain comprising a VL and a VH. Said lighter and heavier chains interact to form a monomer, and said monomers interact via their unpaired Fc domains to form an Ig-like molecule. Such an Ig-like diabody is tetravalent and may be monospecific, bispecific or tetraspecific.

The at least two binding sites of the diabody molecule can recognize the same or different epitopes. Different epitopes can be from the same antigen or epitopes from different antigens. In one embodiment, the epitopes are from different cells. In another embodiment, the epitopes are cell surface antigens on the same cell or virus. The epitopes binding sites can recognize any antigen to which an antibody can be generated. For example, proteins, nucleic acids, bacterial toxins, cell surface markers, autoimmune markers, viral proteins, drugs, etc. In particular aspects, at least one epitope binding site of the diabody is specific for an antigen on a particular cell, such as a B-cell or T-cell, a phagocytotic cell, a natural killer (NK) cell or a dendritic cell.

Each domain of the polypeptide chain of the diabody, i.e., the VL, VH and FC domain may be separated by a peptide linker. The peptide linker may be 0, 1, 2, 3, 4, 5, 6, 7, 8, or 9. amino acids. In certain embodiments the amino acid linker sequence is GGGSGGGG (SEQ ID NO: 10) encoded by the nucleic acid sequence (SEQ ID NO: 74).

In certain embodiments, each polypeptide chain of the diabody molecule is engineered to comprise at least one cysteine residue that will interact with a counterpart at least one cysteine residue on a second polypeptide chain of the invention to form an inter-chain disulfide bond. Said interchain disulfide bonds serve to stabilize the diabody molecule, improving expression and recovery in recombinant systems, resulting in a stable and consistent formulation as well as improving the stability of the isolated and/or purified product in vivo. Said at least one cysteine residue may be introduced as a single amino acid or as part of larger amino-acid sequence, e.g. hinge domain, in any portion of the polypeptide chain. In a specific embodiment, said at least one cysteine residue is engineered to occur at the C-terminus of the polypeptide chain. In some embodiments, said at least one cysteine residue in introduced into the polypeptide chain within the amino acid sequence LGGC (SE ID NO:330). In a specific embodiment, the C-terminus of the polypeptide chain comprising the diabody molecule of the invention comprises the amino acid sequence LGGC (SEQ ID NO:330). In another embodiment, said at least one cysteine residue is introduced into the polypeptide within an amino acid sequence comprising a hinge domain, e.g. SEQ ID NO: 1 or SEQ ID NO: 4. In a specific embodiment, the C-terminus of a polypeptide chain of the diabody molecule of the invention comprises the amino acid sequence of an IgG hinge domain, e.g. SEQ ID NO: 1. In another embodiment, the C-terminus of a polypeptide chain of a diabody molecule of the invention comprises the amino acid sequence VEPKSC (SEQ ID NO: 77), which can be encoded by nucleotide sequence (SEQ ID NO: 78). In other embodiments, said at least one cysteine residue in introduced into the polypeptide chain within the amino acid sequence LGGCFNRGEC (SEQ ID NO: 17), which can be encoded by the nucleotide sequence (SEQ ID NO: 76). In a specific embodiment, the C-terminus of a polypeptide chain comprising the diabody of the invention comprises the amino acid sequence LGGCFNRGEC (SEQ ID NO: 17), which can be encoded by the nucleotide sequence (SEQ ID NO: 76). In yet other embodiments, said at least one cysteine residue in introduced into the polypeptide chain within the amino acid sequence FNRGEC (SEQ ID NO: 23), which can be encoded by the nucleotide sequence (SEQ ID NO: 75). In a specific embodiment, the C-terminus of a polypeptide chain comprising the diabody of the invention comprises the amino acid sequence FNRGEC (SEQ ID NO: 23), which can be encoded by the nucleotide sequence (SEQ ID NO: 75).

In certain embodiments, the diabody molecule comprises at least two polypeptide chains, each of which comprise the amino acid sequence LGGC (SEQ ID NO: 330) and are covalently linked by a disulfide bond between the cysteine residues in said LGGC (SEQ ID NO: 330) sequences. In another specific embodiment, the diabody molecule comprises at least two polypeptide chains, one of which comprises the sequence FNRGEC (SEQ ID NO: 23) while the other comprises a hinge domain (containing at least one cysteine residue), wherein said at least two polypeptide chains are covalently linked by a disulfide bond between the cysteine residue in FNRGEC (SEQ ID NO: 23) and a cysteine residue in the hinge domain. In particular aspects, the cysteine residue responsible for the disulfide bond located in the hinge domain is Cys-128 (as numbered according to Kabat EU; located in the hinge domain of an unmodified, intact IgG heavy chain) and the counterpart cysteine residue in SEQ ID NO: 23 is Cys-214 (as numbered according to Kabat EU; located at the C-terminus of an unmodified, intact IgG light chain) (Elkabetz et al. (2005) "*Cysteines In CH1 Underlie Retention Of Unassembled Ig Heavy Chains*," J. Biol. Chem. 280:14402-14412; hereby incorporated by reference herein in its entirety). In yet other embodiments, the at least one cysteine residue is engineered to occur at the N-terminus of the amino acid chain. In still other embodiments, the at least one cysteine residue is engineered to occur in the linker portion of the polypeptide chain of the diabody molecule. In further embodiments, the VH or VL domain is engineered to comprise at least one amino acid modification relative to the parental VH or VL domain such that said amino acid modification comprises a substitution of a parental amino acid with cysteine.

The invention encompasses diabody molecules comprising an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e. an Fc domain comprising the CH2 domain derived from IgG and the CH3 domain derived form IgE, or the CH2 domain derived from IgG1 and the CH3 domain derived from IgG2, etc.). Said Fc domain may be engineered into a polypeptide chain comprising the diabody molecule of the invention in any position relative to other domains or portions of said polypeptide chain (e.g., the Fc domain, or portion thereof, may be c-terminal to both the VL and VH domains of the polypeptide of the chain; may be n-terminal to both the VL and VH domains; or may be N-terminal to one domain and c-terminal to another (i.e., between two domains of the polypeptide chain)).

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG 1, IgG2, IgG3 or IgG4, or an allotype thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of said polypeptide chain. In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

As discussed above, the invention encompasses multimers of polypeptide chains, each of which polypeptide chains comprise a VH and VL domain. In certain aspects, the polypeptide chains in said multimers further comprise an Fc domain. Dimerization of the Fc domains leads to formation of a diabody molecule that exhibits immunoglobulin-like functionality, i.e., Fc mediated function (e.g., Fc-FcγR interaction, complement binding, etc.). In certain embodiments, the VL and VH domains comprising each polypeptide chain have the same specificity, and said diabody molecule is bivalent and monospecific. In other embodiments, the VL and VH domains comprising each polypeptide chain have differing specificity and the diabody is bivalent and bispecific.

In yet other embodiments, diabody molecules of the invention encompass tetramers of polypeptide chains, each of which polypeptide chain comprises a VH and VL domain. In certain embodiments, two polypeptide chains of the tetramer further comprise an Fc domain. The tetramer is therefore comprised of two 'heavier' polypeptide chains, each comprising a VL, VH and Fc domain, and two 'lighter' polypeptide chains, comprising a VL and VH domain. Interaction of a heavier and lighter chain into a bivalent monomer coupled with dimerization of said monomers via the Fc domains of the heavier chains will lead to formation of a tetravalent immunoglobulin-like molecule (exemplified in Example 6.2 and Example 6.3). In certain aspects the monomers are the same, and the tetravalent diabody molecule is monospecific or bispecific. In other aspects the monomers are different, and the tetra valent molecule is bispecific or tetraspecific.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to increase the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "*'Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety).

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain variants identified as altering effector function are disclosed in International Application WO04/063351, U.S. Patent Application Publications 2005/0037000 and 2005/0064514, U.S. Provisional Applications 60/626,510, filed Nov. 10, 2004, 60/636,663, filed Dec. 15, 2004, and 60/781,564, filed Mar. 10, 2006, and U.S. patent application Ser. No. 11/271,140, filed Nov. 10, 2005, and Ser. No. 11/305,787, filed Dec. 15, 2005, concurrent applications of the Inventors, each of which is incorporated by reference in its entirety.

The bispecific diabodies of the invention can simultaneously bind two separate and distinct epitopes. In certain embodiments the epitopes are from the same antigen. In other embodiments, the epitopes are from different antigens. In preferred embodiments, at least one epitope binding site is specific for a determinant expressed on an immune effector cell (e.g. CD3, CD16, CD32, CD64, etc.) which are expressed on T lymphocytes, natural killer (NK) cells or other mononuclear cells. In one embodiment, the diabody molecule binds to the effector cell determinant and also activates said effector cell. In this regard, diabody molecules of the invention may exhibit Ig-like functionality independent of whether they further comprise an Fc domain (e.g., as assayed in any effector function assay known in the art or exemplified herein (e.g., ADCC assay). In certain embodiments the bispecific diabody of the invention binds both a cancer antigen on a tumor cell and an effector cell determinant while activating said cell. In alternative embodiments, the bispecific diabody or diabody molecule of the invention may inhibit activation of a target, e.g., effector, cell by simultaneously binding, and thus linking, an activating and inhibitory receptor on the same cell (e.g., bind both CD32A and CD32B, BCR and CD32B, or IgERI and CD32B) as described supra (see, Background Section). In a further aspect of this embodiment, the bispecific diabody may exhibit anti-viral properties by simultaneously binding two neutralizing epitopes on a virus (e.g., RSV epitopes; WNV epitopes such as E16 and E53).

In certain embodiments, bispecific diabody molecules of the invention offer unique opportunities to target specific cell types. For example, the bispecific diabody or diabody molecule can be engineered to comprise a combination of epitope binding sites that recognize a set of antigens unique to a target cell or tissue type. Additionally, where either or both of the individual antigens is/are fairly common separately in other tissue and/or cell types, low affinity biding domains can be used to construct the diabody or diabody molecule. Such low affinity binding domains will be unable to bind to the individual epitope or antigen with sufficient avidity for therapeutic purposes. However, where both epitopes or antigens are present on a single target cell or tissue, the avidity of the diabody or diabody molecule for the cell or tissue, relative to a cell or tissue expressing only one of the antigens, will be increased such that said cell or tissue can be effectively targeted by the invention. Such a bispecific molecule can exhibit enhanced binding to one or both of its target antigens on cells expressing both of said antigens relative to a monospecific diabody or an antibody with a specificity to only one of the antigens.

Preferably, the binding properties of the diabodies of the invention are characterized by in vitro functional assays for determining binding activity and/or one or more FcγR mediator effector cell functions (mediated via Fc-FcγR interactions or by the immunospecific binding of a diabody molecule to an FcγR) (See Section 5.4.2 and 5.4.3). The affinities and binding properties of the molecules, e.g., diabodies, of the invention for an FcγR can be determined using in vitro assays (biochemical or immunological based assays) known in the art for determining binding domain-antigen or Fc-FcγR interactions, i.e., specific binding of an antigen to a binding domain or specific binding of an Fc region to an FcγR, respectively, including but not limited to ELISA assay, surface plasmon resonance assay, immunoprecipitation assays (See Section 5.4.2). In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, molecules of the invention are engineered to comprise an altered glycosylation pattern or an altered glycoform relative to the comparable portion of the template molecule. Engineered glycoforms may be useful for a variety of purposes, including, but not limited to, enhancing effector function. Engineered glycoforms may be generated by any method known to one skilled in the art, for example by using engineered or variant expression strains, by co-expression with one or more enzymes, for example, DI N-acetylglucosaminyltransferase III (GnTI11), by expressing a diabody of the invention in various organisms or cell lines from various organisms, or by modifying carbohydrate(s) after the diabody has been expressed and purified. Methods for generating engineered glycoforms are known in the art, and include but are not limited to those described in Umana et al. (1999) "*Engineered Glycoforms Of An Antineuroblastoma IgG*1 *With Optimized Antibody-Dependent Cellular Cytotoxic Activity*," Nat. Biotechnol 17:176-180; Davies et al. (2001) "*Expression Of GnTIII In A Recombinant Anti-CD*20 *CHO Production Cell Line: Expression Of Antibodies With Altered Glycoforms Leads To An Increase In Adcc Through Higher Affinity For Fc Gamma RIII*," Biotechnol Bioeng 74:288-294; Shields et al. (2002) "*Lack Of Fucose On Human IgG*1 *N-Linked Oligosaccharide Improves Binding To Human Fcgamma RIII And Antibody-Dependent Cellular Toxicity*," J Biol Chem 277:26733-26740; Shinkawa et al. (2003) "*The Absence Of Fucose But Not The Presence Of Galactose Or Bisecting N-Acetylglucosamine Of Human IgG*1 *Complex-Type Oligosaccharides Shows The Critical Role Of Enhancing Antibody-Dependent Cellular Cytotoxicity*," J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al. (2004) "*Fucose Depletion From Human IgG*1 *Oligosaccharide Enhances Binding Enthalpy And Association Rate Between IgG*1 *And FcGammaRIIIA*," JMB, 336: 1239-49 each of which is incorporated herein by reference in its entirety.

The invention further encompasses incorporation of unnatural amino acids to generate the diabodies of the invention. Such methods are known to those skilled in the art such as those using the natural biosynthetic machinery to allow incorporation of unnatural amino acids into proteins, see, e.g., Wang et al. (2002) "*Expanding The Genetic Code*," Chem. Comm. 1:1-11; Wang et al. (2001) "*Expanding The Genetic Code Of Escherichia coli*," Science, 292: 498-500; van Hest et al. (2001) "*Protein-Based Materials, Toward A New Level Of Structural Control*," Chem. Comm. 19: 1897-1904, each of which is incorporated herein by reference in its entirety. Alternative strategies focus on the enzymes responsible for the biosynthesis of amino acyl-tRNA, see, e.g., Tang et al. (2001) "*Biosynthesis Of A Highly Stable Coiled-Coil Protein Containing Hexafluoroleucine In An Engineered Bacterial Host*," J. Am. Chem. Soc. 123(44): 11089-11090; Kiick et al. (2001) "*Identification Of An Expanded Set Of Translationally Active Methionine Analogues In Escherichia coli*," FEBS Lett. 502(1-2):25-30; each of which is incorporated herein by reference in its entirety.

In some embodiments, the invention encompasses methods of modifying a VL, VH or Fc domain of a molecule of the invention by adding or deleting a glycosylation site. Methods for modifying the carbohydrate of proteins are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety.

The diabody molecules of the present invention may be constructed to comprise a domain that is a binding ligand for the Natural Killer Group 2D (NKG2D) receptor. Such binding ligands, and particularly those which are not expressed on normal cells, include the histocompatibility 60 (H60) molecule, the product of the retinoic acid early inducible gene-1 (RAE-1), and the murine UL16-binding proteinlike transcript 1 (MULT1) (Raulet D. H. (2003) "*Roles Of The NKG2D Immunoreceptor And Its Ligands*," Nature Rev. Immunol. 3:781-790; Coudert, J. D. et al. (2005) "*Altered NKG2D Function In NK Cells Induced By Chronic Exposure To Altered NKG2D Ligand-Expressing Tumor Cells*," Blood 106:1711-1717). Additional ligands reactive with human NKG2D include the polymorphic MHC class I chain-related molecules MICA and MICB (Diefenbach, A. et al. (1999) "*Natural Killer Cells: Stress Out, Turn On, Tune In*," Curr. Biol. 9(22):R851-R8533; Bauer, S. et al. (1999) "*Activation Of NK Cells And T Cells By NKG2D, A Receptor For Stress-Inducible MICA*," Science 285(5428):727-729; Stephens, H. A. (2001) "MICA and MICB genes: can the enigma of their polymorphism be resolved?," Trends Immunol. 22:378-385.

The sequence of MICA is SEQ ID NO: 311:

```
MGLGPVFLLL AGIFPFAPPG AAAEPHSLRY NLTVLSWDGS
VQSGFLTEVH LDGQPFLRCD RQKCRAKPQG QWAEDVLGNK
TWDRETRDLT GNGKDLRMTL AHIKDQKEGL HSLQEIRVCE
IHEDNSTRSS QHFYYDGELF LSQNLETKEW TMPQSSRAQT
LAMNVRNFLK EDAMKTKTHY HAMHADCLQE LRRYLKSGVV
LRRTVPPMVN VTRSEASEGN ITVTCRASGF YPWNITLSWR
QDGVSLSHDT QQWGDVLPDG NGTYQTWVAT RICQGEEQRF
TCYMEHSGNH STHPVPSGKV LVLQSHWQTF HVSAVAAAAI
FVIIIFYVRC CKKKTSAAEG PELVSLQVLD QHPVGTSDHR
DATQLGFQPL MSDLGSTGST EGA
```

The sequence of MICB is SEQ ID NO: 312:

```
PHSLRYNLMV LSQDGSVQSG FLAEGHLDGQ PFLRYDRQKR
RAKPQGQWAE DVLGAKTWDT ETEDLTENGQ DLRRTLTHIK
DQKGGLHSLQ EIRVCEIHED SSTRGSRHFY YDGELFLSQN
LETQESTVPQ SSRAQTLAMN VTNFWKEDAM KTKTHYRAMQ
ADCLQKLQLP PMVNVICSEV SEGNITVTCR ASSFYPRNIT
LTWRQDGVSL SHNTQQWGDV LPDGNGTYQT WVATRIRQGE
```

-continued

```
EQRFTCYMEH SGNHGTHPVP SGKALVLQSQ RTDFPYVSAA

MPCFVIIIIL CVPCCKKKTS AAEGP
```

Antibodies that specifically bind to the T-cell Receptor include the anti-TCR antibody BMA 031 (Kurrle, R. et al. (1989) "*BMA 031—A TCR-Specific Monoclonal Antibody For Clinical Application*," Transplant Proc. 21(1 Pt 1):1017-1019; Nashan, B. et al. (1987) "Fine Specificity Of A Panel Of Antibodies Against The TCR/CD3 Complex," Transplant Proc. 19(5):4270-4272; Shearman, C. W. et al. (1991) "Construction, Expression, And Biologic Activity Of Murine/Human Chimeric Antibodies With Specificity For The Human $\alpha/\beta$ T Cell," J. Immunol. 146(3):928-935; Shearman, C. W. et al. (1991) "*Construction, Expression And Characterization of Humanized Antibodies Directed Against The Human $\alpha/\beta$ T Cell Receptor*," J. Immunol. 147(12):4366-4373). Antibodies that specifically bind to the NKG2D Receptor include KYK-2.0 (Kwong, K Y et al. (2008) "*Generation, Affinity Maturation, And Characterization Of A Human Anti-Human NKG2D Monoclonal Antibody With Dual Antagonistic And Agonistic Activity*," J. Mol. Biol. 384:1143-1156; and PCT/US09/54911).

Through the use of such a diabody, the target cell is now redirected to be a cell that can be bound by cells that array the (NKG2D) receptor. The NKG2D receptor is expressed on all human (and other mammalian) Natural Killer cells (Bauer, S. et al. (1999) "*Activation Of NK Cells And T Cells By NKG2D, A Receptor For Stress-Inducible MICA*," Science 285(5428): 727-729; Jamieson, A. M. et al. (2002) "*The Role Of The NKG2D Immunoreceptor In Immune Cell Activation And Natural Killing*," Immunity 17(1):19-29) as well as on all $CD8^+$ T cells (Groh, V. et al. (2001) "*Costimulation Of CD8$\alpha\beta$ T Cells By NKG2D Via Engagement By MIC Induced On Virus-Infected Cells*," Nat. Immunol. 2(3):255-260; Jamieson, A. M. et al. (2002) "*The Role Of The NKG2D Immunoreceptor In Immune Cell Activation And Natural Killing*," Immunity 17(1):19-29).

Alternatively, the diabody molecules of the present invention may be constructed to comprise a domain that is a binding ligand for the T-cell receptor ("TCR"). The TCR is natively expressed by CD4+ or CD8+ T-cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the antigen-presenting cell (see, e.g., Armstrong, K. M. et al. (2008) "*Conformational Changes And Flexibility In T-Cell Receptor Recognition Of Peptide-MHC Complexes*," Biochem. J. 415(Pt 2):183-196; Willemsen, R. (2008) "*Selection Of Human Antibody Fragments Directed Against Tumor T-Cell Epitopes For Adoptive T-Cell Therapy*," Cytometry A. 73(11):1093-1099; Beier, K. C. et al. (2007) "*Master Switches Of T-Cell Activation And Differentiation*," Eur. Respir. J. 29:804-812; Mallone, R. et al. (2005) "*Targeting T Lymphocytes For Immune Monitoring And Intervention In Autoimmune Diabetes*," Am. J. Ther. 12(6): 534-550).

By constructing such diabody molecules to additionally comprise at least one epitope-binding domain capable of binding to, for example, a receptor present on the surface of a target cell, such diabody molecules will be DART molecules and thus be capable of binding to the target cells and thereby cause the target cells to display the binding ligand for the Natural Killer Group 2D (NKG2D) receptor or to the TCR (whichever is present on the target cell-bound diabody) (see, e.g., Germain, C. et al. (2008) "*Redirecting NK Cells Mediated Tumor Cell Lysis By A New Recombinant Bifunctional Protein*," Prot. Engineer. Design Selection 21(11):665-672).

Such diabodies can be used to redirect any desired target cell into a cell that is a target of NK cell-mediated cell lysis or T-cell mediated cytotoxicity. In one embodiment, the epitope-binding domain of the diabody capable of binding to a receptor present on the surface of a target cell is an epitope that binds to a tumor-associated antigen so as to redirect such cancer cells into substrates for NK cell-mediated cell lysis or T-cell mediated cytotoxicity. Of particular interest is a tumor-associated antigens that is a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkins lymphoma, or an antigen associated with chronic lymphocytic leukemia.

Suitable tumor-associated antigens for such use include A33 (a colorectal carcinoma antigen; Almqvist, Y. 2006, *Nucl Med. Biol.* November; 33(8):991-998); B1 (Egloff, A. M. et al. 2006, *Cancer Res.* 66(1):6-9); BAGE (Bodey, B. 2002 *Expert Opin Biol Ther.* 2(6):577-84); beta-catenin (Prange W. et al. 2003 *J Pathol.* 201(2):250-9); CA125 (Bast, R. C. Jr. et al. 2005 *Int J Gynecol Cancer* 15 Suppl 3:274-81); CD5 (Calin, G. A. et al. 2006 *Semin Oncol.* 33(2):167-73; CD19 (Troussard, X. et al. 1998 *Hematol Cell Ther.* 40(4):139-48); CD20 (Thomas, D. A. et al. 2006 *Hematol Oncol Clin North Am.* 20(5):1125-36); CD22 (Kreitman, R. J. 2006 AAPS J. 18; 8(3):E532-51); CD23 (Rosati, S. et al. 2005 *Curr Top Microbiol Immunol.* 5; 294:91-107); CD25 (Troussard, X. et al. 1998 *Hematol Cell Ther.* 40(4):139-48); CD27 (Bataille, R. 2006 *Haematologica* 91(9):1234-40); CD28 (Bataille, R. 2006 *Haematologica* 91(9):1234-40); CD36 (Ge, Y. 2005 *Lab Hematol.* 11(1):31-7); CD40/CD154 (Messmer, D. et al. 2005 *Ann N Y Acad. Sci.* 1062:51-60); CD45 (Jurcic, J. G. 2005 *Curr Oncol Rep.* 7(5):339-46); CD56 (Bataille, R. 2006 *Haematologica* 91(9):1234-40); CD79a/CD79b (Troussard, X. et al. 1998 *Hematol Cell Ther.* 40(4):139-48; Chu, P. G. et al. 2001 *Appl Immunohistochem Mol. Morphol.* 9(2):97-106); CD103 (Troussard, X. et al. 1998 *Hematol Cell Ther.* 40(4):139-48); CDK4 (Lee, Y. M. et al. 2006 *Cell Cycle* 5(18):2110-4); CEA (carcinoembryonic antigen; Mathelin, C. 2006 *Gynecol Obstet. Fertil.* 34(7-8):638-46; Tellez-Avila, F. I. et al. 2005 *Rev Invest Clin.* 57(6):814-9); CTLA4 (Peggs, K. S. et al. 2006 *Curr Opin Immunol.* 18(2):206-13); EGF-R (epidermal growth factor receptor; Adenis, A. et al. 2003 *Bull Cancer.* 90 Spec No:S228-32); Erb (ErbB1; ErbB3; ErbB4; Zhou, H. et al. 2002 *Oncogene* 21(57):8732-40; Rimon, E. et al. 2004 *Int J Oncol.* 24(5):1325-38); GAGE (GAGE-1; GAGE-2; Akcakanat, A. et al. 2006 *Int J Cancer.* 118(1):123-8); GD2/GD3/GM2 (Livingston, P. O. et al. 2005 *Cancer Immunol Immunother.* 54(10):1018-25); gp100 (Lotem, M. et al. 2006 *J Immunother.* 29(6):616-27); HER-2/neu (Kumar, Pal S et al. 2006 Semin Oncol. 33(4):386-91); human papillomavirus-E6/human papillomavirus-E7 (DiMaio, D. et al. 2006 *Adv Virus Res.* 66:125-59; KSA (17-1A) (Ragupathi, G. 2005 *Cancer Treat Res.* 123:157-80); MAGE (MAGE-1; MAGE-3; (Bodey, B. 2002 *Expert Opin Biol Ther.* 2(6):577-84); MART (Kounalakis, N. et al. 2005 *Curr Oncol Rep.* 7(5):377-82; MUC-1 (Mathelin, C. 2006 *Gynecol Obstet. Fertil.* 34(7-8):638-46); MUM-1 (Castelli, C. et al. 2000 *J Cell Physiol.* 182(3):323-31); N-acetylglucosaminyltransferase (Dennis, J. W. 1999 *Biochim Biophys Acta.* 6; 1473(1):

21-34); p15 (Gil, J. et al. 2006 *Nat Rev Mol Cell Biol.* 7(9): 667-77); PSA (prostate specific antigen; Cracco, C. M. et al. 2005 *Minerva Urol Nefrol.* 57(4):301-11); PSMA (Ragupathi, G. 2005 *Cancer Treat Res.* 123:157-80); sTn (Holmberg, L. A. 2001 Expert Opin Biol Ther. 1(5):881-91); TNF-receptor (TNF-α receptor, TNF-β receptor; or TNF-γ receptor; van Horssen, R. et al. 2006 *Oncologist.* 11(4):397-408; Gardnerova, M. et al. 2000 *Curr Drug Targets.* 1(4):327-64); or VEGF receptor (O'Dwyer. P. J. 2006 *Oncologist.* 11(9):992-8).

Additional tumor-associated antigens for such use (and publications disclosing specifically reactive antibodies for such antigens) include ADAM-9 (United States Patent Publication No. 2006/0172350; PCT Publication No. WO 06/084075); ALCAM (PCT Publication No. WO 03/093443); Carboxypeptidase M (United States Patent Publication No. 2006/0166291); CD46 (U.S. Pat. No. 7,148,038; PCT Publication No. WO 03/032814); Cytokeratin 8 (PCT Publication No. WO 03/024191); Ephrin receptors (and in particular EphA2 (U.S. Pat. No. 7,569,672; PCT Publication No. WO 06/084226); Integrin Alpha-V-Beta-6 (PCT Publication No. WO 03/087340); JAM-3 (PCT Publication No. WO 06/084078); KID3 (PCT Publication No. WO 05/028498); KID31 (PCT Publication No. WO 06/076584); LUCA-2 (United States Patent Publication No. 2006/0172349; PCT Publication No. WO 06/083852); Oncostatin M (Oncostatin Receptor Beta) (U.S. Pat. No. 7,572,896; PCT Publication No. WO 06/084092); PIPA (U.S. Pat. No. 7,405,061; PCT Publication No. WO 04/043239); RAAG10 (U.S. Pat. No. 7,527,969; PCT Publication No. WO 04/001381); ROR1 (U.S. Pat. No. 5,843,749); TEST (PCT Publication No. WO 08/066,691); and the Transferrin Receptor (U.S. Pat. No. 7,572,895; PCT Publication No. WO 05/121179).

Also of interest are antigens specific to particular infectious agents, e.g., viral agents including, but not limited to human immunodeficiency virus (HIV), hepatitis B virus (HBV), influenza, human papilloma virus (HPV), foot and mouth (coxsackieviruses), the rabies virus, herpes simplex virus (HSV), and the causative agents of gastroenteritis, including rotaviruses, adenoviruses, caliciviruses, astroviruses and Norwalk virus; bacterial agents including, but not limited to *E. coli, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis* and *Streptococcus pneumoniae*, fungal agents and parasites such as Giardi.

Alternatively, such epitope may bind to an Fc receptor (e.g., FcγRI or FcγRII), so as to, for example redirect acute monocytic leukemic cells into substrates for NK cell-mediated cell lysis.

5.1 Diabody Binding Domains

The diabodies of the present invention comprise antigen binding domains generally derived from immunoglobulins or antibodies. The antibodies from which the binding domains used in the methods of the invention are derived may be from any animal origin including birds and mammals (e.g., human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The invention contemplates the use of any antibodies known in the art for the treatment and/or prevention of cancer, autoimmune disease, inflammatory disease or infectious disease as source of binding domains for the diabodies of the invention. Non-limiting examples of known cancer antibodies are provided in section 5.7.1 as well as other antibodies specific for the listed target antigens and antibodies against the cancer antigens listed in section 5.6.1; nonlimiting examples of known antibodies for the treatment and/or prevention of autoimmune disease and inflammatory disease are provided in section 5.7.2. as well as antibodies against the listed target antigens and antibodies against the antigens listed in section 5.6.2; in other embodiments antibodies against epitopes associated with infectious diseases as listed in Section 5.6.3 can be used. In certain embodiments, the antibodies comprise a variant Fc region comprising one or more amino acid modifications, which have been identified by the methods of the invention to have a conferred effector function and/or enhanced affinity for FcγRIIB and a decreased affinity for FcγRIIIA relative to a comparable molecule comprising a wild type Fc region. A non-limiting example of the antibodies that are used for the treatment or prevention of inflammatory disorders which can be engineered according to the invention is presented in Table 9, and a non-limiting example of the antibodies that are used for the treatment or prevention of autoimmune disorder is presented in Table 10.

For some uses, including in vivo use of antibodies in humans and in vitro detection assays, it may be preferable to use diabodies with variable domains derived from human, chimeric or humanized antibodies. Variable domains from completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

A humanized antibody is an antibody, a variant or a fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan (1991) "*A Possible Procedure For Reducing The Immunogenicity Of Antibody Variable Domains While Preserving Their Ligand-Binding Properties*," Molecular Immunology 28(4/5): 489-498; Studnicka et al. (1994) "*Human-Engineered Monoclonal Antibodies Retain Full Specific Binding Activity By Preserving Non-CDR Complementarity-Modulating Residues*," Protein Engineering 7(6): 805-814; and Roguska et al. (1994) "*Humanization Of Murine Monoclonal Antibodies Through Variable Domain Resurfacing*," Proc Natl Acad Sci USA 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al. (2002) "'*Superhumanized' Antibodies: Reduction Of Immunogenic Potential By Complementarity-Determining Region Grafting With Human Germline Sequences: Application To An Anti-CD*28," J. Immunol. 169:1119-25, Caldas et al. (2000) "*Design And Synthesis Of Germline-Based Hemi-Humanized Single-Chain Fv Against The CD*18 *Surface Antigen*," Protein Eng. 13:353-60, Morea et al. (2000) "*Antibody Modeling: Implications For Engineering And Design*," Methods 20:267-79, Baca et al. (1997) "*Antibody Humanization Using Monovalent Phage Display*," J. Biol. Chem. 272:10678-84, Roguska et al. (1996) "*A Comparison Of Two Murine Monoclonal Antibodies Humanized By CDR-Grafting And Variable Domain Resurfacing*," Protein Eng. 9:895-904, Couto et al. (1995) "*Designing Human Consensus Antibodies With Minimal Positional Templates*," Cancer Res. 55 (23 Supp):5973s-5977s, Couto et al. (1995) "*Anti-BA*46 *Monoclonal Antibody Mc*3*: Humanization Using A Novel Positional Consensus And In Vivo And In Vitro Characterization*," Cancer Res. 55:1717-22, Sandhu (1994) "*A Rapid Procedure For The Humanization Of Monoclonal Antibodies*," Gene 150:409-10, Pedersen et al. (1994) "*Comparison Of Surface Accessible Residues In Human And Murine Immunoglobulin Fv Domains. Implication For Humanization Of Murine Antibodies*," J. Mol. Biol. 235:959-973, Jones et al. (1986) "*Replacing The Complementarity-Determining Regions In A Human Antibody With Those From A Mouse*," Nature 321:522-525, Riechmann et al. (1988) "*Reshaping Human Antibodies For Therapy*," Nature 332:323-327, and Presta (1992) "*Antibody Engineering*," Curr. Op. Biotech. 3(4):394-398. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al. (1988) "*Reshaping Human Antibodies For Therapy*," Nature 332:323-327, all of which are incorporated herein by reference in their entireties.).

In a most preferred embodiment, the humanized binding domain specifically binds to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically the donor antibody is a non-human antibody, such as a rodent mAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses a humanized FcγRIIB antibody comprising at least one CDR grafted heavy chain and at least one CDR-grafted light chain.

The diabodies used in the methods of the invention include derivatives that are modified, i.e., by the covalent attachment of any type of molecule to the diabody. For example, but not by way of limitation, the diabody derivatives include diabodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison (1985) "*Transfectomas Provide Novel Chimeric Antibodies*," Science 229:1202-1207; Oi et al. (1986) "*Chimeric Antibodies*," BioTechniques 4:214-221; Gillies et al. (1989) "*High-Level Expression Of Chimeric Antibodies Using Adapted cDNA Variable Region Cassettes*," J. Immunol. Methods 125:191-202; and U.S. Pat. Nos. 6,311,415, 5,807,715, 4,816,567, and 4,816,397, which are incorporated herein by reference in their entirety.

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al. (1988) "*Reshaping Human Antibodies For Therapy*," Nature 332:323-327, which are incorporated herein by reference in their entireties.)

Monoclonal antibodies from which binding domains of the diabodies of the invention can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones. Antigens of interest include, but are not limited to, antigens associated with the cancers provided in section 5.8.1, antigens associated with the autoimmune diseases and inflammatory diseases provided in section 5.8.2, antigens associated with the infectious diseases provided in section 5.8.3, and the toxins provided in section 5.8.4.

Antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkmann et al. (1995) "*Phage Display Of Disulfide-Stabilized Fv Fragments*," J. Immunol. Methods, 182:41-50; Ames et al. (1995) "*Conversion Of Murine Fabs Isolated From A Combinatorial Phage Display Library To Full Length Immunoglobulins*," J. Immunol. Methods, 184:177-186; Kettleborough et al. (1994) "*Isolation Of Tumor Cell-Specific Single-Chain Fv From Immunized Mice Using Phage-Antibody Libraries And The Re-Construction Of Whole Antibodies From These Antibody Fragments*," Eur. J. Immunol., 24:952-958; Persic et al. (1997) "*An Integrated Vector System For The Eukaryotic Expression Of Antibodies Or Their Fragments After Selection From Phage Display Libraries*," Gene, 187:9-18; Burton et al. (1994) "*Human Antibodies From Combinatorial Libraries*," Advances in Immunology, 57:191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Phage display technology can be used to increase the affinity of an antibody for its antigen. This technique would be useful in obtaining high affinity antibodies. The technology, referred to as affinity maturation, employs mutagenesis or CDR walking and re-selection using the cognate antigen to identify antibodies that bind with higher affinity to the antigen when compared with the initial or parental antibody (See, e.g., Glaser et al. (1992) "*Dissection Of The Combining Site In A Humanized Anti-Tac Antibody*," J. Immunology 149: 2607-2614). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al. (1998) "*Stepwise In Vitro Affinity Maturation Of Vitaxin, An Alphav Beta*3-*Specific Humanized mAb*," Proc Natl. Acad. Sci. USA 95:6037-6042; Yelton et al. (1995) "*Affinity Maturation Of The Br*96 *Anti-Carcinoma Antibody By Codon-Based Mutagenesis*," J. Immunology 155:1994-2004). CDR walking which randomizes the light chain is also possible (See Schier et al. (1996) "*Isolation Of Picomolar Affinity Anti-C-ErbB*-2 *Single-Chain Fv By Molecular Evolution Of The Complementarily Determining Regions In The Center Of The Antibody Binding Site*," J. Mol. Bio. 263:551-567).

The present invention also encompasses the use of binding domains comprising the amino acid sequence of any of the binding domains described herein or known in the art with mutations (e.g., one or more amino acid substitutions) in the framework or CDR regions. Preferably, mutations in these binding domains maintain or enhance the avidity and/or affinity of the binding domains for FcγRIIB to which they immunospecifically bind. Standard techniques known to those skilled in the art (e.g., immunoassays) can be used to assay the affinity of an antibody for a particular antigen.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

5.1.1 Diabodies Comprising Eptiope Binding Sites which Immunospecifically Bind FcγRIIB In a particular embodiment, at least one of the binding domains of the diabodies of the invention agonizes at least one activity of FcγRIIB. In one embodiment of the invention, said activity is inhibition of B cell receptor-mediated signaling. In another embodiment, the binding domain inhibits activation of B cells, B cell proliferation, antibody production, intracellular calcium influx of B cells, cell cycle progression, or activity of one or more downstream signaling molecules in the FcγRIIB signal transduction pathway. In yet another embodiment, the binding domain enhances phosphorylation of FcγRIIB or SHIP recruitment. In a further embodiment of the invention, the binding domain inhibits MAP kinase activity or Akt recruitment in the B cell receptor-mediated signaling pathway. In another embodiment, the binding domain agonizes FcγRIIB-mediated inhibition of FcεRI signaling. In a particular embodiment, said binding domain inhibits FcεRI-induced mast cell activation, calcium mobilization, degranulation, cytokine production, or serotonin release. In another embodiment, the binding domains of the invention stimulate phosphorylation of FcγRIIB, stimulate recruitment of SHIP, stimulate SHIP phosphorylation and its association with Shc, or inhibit activation of MAP kinase family members (e.g., Erk1, Erk2, JNK, p38, etc.). In yet another embodiment, the binding domains of the invention enhance tyrosine phosphorylation of p62dok and its association with SHIP and rasGAP. In another embodiment, the binding domains of the invention inhibit FcγR-mediated phagocytosis in monocytes or macrophages.

In another embodiment, the binding domains antagonize at least one activity of FcγRIIB. In one embodiment, said activity is activation of B cell receptor-mediated signaling. In a particular embodiment, the binding domains enhance B cell activity, B cell proliferation, antibody production, intracellular calcium influx, or activity of one or more downstream signaling molecules in the FcγRIIB signal transduction pathway. In yet another particular embodiment, the binding domains decrease phosphorylation of FcγRIIB or SHIP recruitment. In a further embodiment of the invention, the binding domains enhance MAP kinase activity or Akt recruitment in the B cell receptor mediated signaling pathway. In another embodiment, the binding domains antagonize FcγRIIB-mediated inhibition of FcεRI signaling. In a particular embodiment, the binding domains enhance FcεRI-induced mast cell activation, calcium mobilization, degranulation, cytokine production, or serotonin release. In another embodiment, the binding domains inhibit phosphorylation of FcγRIIB, inhibit recruitment of SHIP, inhibit SHIP phosphorylation and its association with Shc, enhance activation of MAP kinase family members (e.g., Erk1, Erk2, JNK, p38, etc.). In yet another embodiment, the binding domains inhibit tyrosine phosphorylation of p62dok and its association with SHIP and rasGAP. In another embodiment, the binding domains enhance FcγR-mediated phagocytosis in monocytes or macrophages. In another embodiment, the binding domains prevent phagocytosis, clearance of opsonized particles by splenic macrophages.

In other embodiments, at least one of the binding domains can be used to target the diabodies of the invention to cells that express FcγRIIB.

In one particular embodiment, one of the binding domains is derived from a mouse monoclonal antibody produced by clone 2B6 or 3H7, having ATCC accession numbers PTA-4591 and PTA-4592, respectively. Hybridomas producing antibodies 2B6 and 3H7 have been deposited with the American Type Culture Collection (10801 University Blvd., Manassas, Va. 20110-2209) on Aug. 13, 2002 under the provisions of the Budapest Treaty on the International Recognition of the Deposit of Microorganisms for the Purposes of Patent Procedures, and assigned accession numbers PTA-4591 (for hybridoma producing 2B6) and PTA-4592 (for hybridoma producing 3H7), respectively, and are incorporated herein by reference. In a preferred embodiment, the binding domains are human or have been humanized, preferably are derived from a humanized version of the antibody produced by clone 3H7 or 2B6.

The invention also encompasses diabodies with binding domains from other antibodies, that specifically bind FcγRIIB, preferably human FcγRIIB, more preferably native human FcγRIIB, that are derived from clones including but not limited to 1D5, 2E1, 2H9, 2D11, and 1F2 having ATCC Accession numbers, PTA-5958, PTA-5961, PTA-5962, PTA-5960, and PTA-5959, respectively. Hybridomas producing the above-identified clones were deposited under the provisions of the Budapest Treaty with the American Type Culture Collection (10801 University Blvd., Manassas, Va. 20110-2209) on May 7, 2004, and are incorporated herein by reference. In preferred embodiments, the binding domains from the antibodies described above are humanized.

In a specific embodiment, the binding domains used in the diabodies of the present invention are from an antibody or an antigen-binding fragment thereof (e.g., comprising one or more complementarily determining regions (CDRs), preferably all 6 CDRs) of the antibody produced by clone 2B6, 3H7, 1D5, 2E1, 2H9, 2D11, or 1F2. In another embodiment, the binding domain binds to the same epitope as the mouse monoclonal antibody produced from clone 2B6, 3H7, 1D5, 2E1, 2H9, 2D11, or 1F2, respectively and/or competes with the mouse monoclonal antibody produced from clone 2B6, 3H7, 1D5, 2E1, 2H9, 2D11, or 1F2 as determined, e.g., in an ELISA assay or other appropriate competitive immunoassay, and also binds FcγRIIB with a greater affinity than the binding domain binds FcγRIIA.

The present invention also encompasses diabodies with binding domains comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone 2B6, 3H7, 1D5, 2E1, 2H9, 2D11, or 1F2. The present invention further encompasses diabodies with binding domains that specifically bind FcγRIIB with greater affinity than said antibody or fragment thereof binds FcγRIIA, and that comprise an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6, 3H7, 1D5, 2E1, 2H9, 2D11, or 1F2. The determination of percent identity of two amino acid sequences can be determined by any method known to one skilled in the art, including BLAST protein searches.

The present invention also encompasses the use of diabodies containing binding domains that specifically bind FcγRIIB with greater affinity than binding domain binds FcγRIIA, which are encoded by a nucleotide sequence that hybridizes to the nucleotide sequence of the mouse monoclonal antibody produced by clone 2B6, 3H7, 1D5, 2E1, 2H9, 2D11, or 1F2 under stringent conditions. In a preferred embodiment, the binding domain specifically binds FcγRIIB with greater affinity than FcγRIIA, and comprises a variable light chain and/or variable heavy chain encoded by a nucleotide sequence that hybridizes under stringent conditions to the nucleotide sequence of the variable light chain and/or variable heavy chain of the mouse monoclonal antibody produced by clone 2B6, 3H7, 1D5, 2E1, 2H9, 2D11, or 1F2 under stringent conditions. In another preferred embodiment, the binding domains specifically bind FcγRIIB with greater affinity than FcγRIIA, and comprise one or more CDRs encoded by a nucleotide sequence that hybridizes under stringent conditions to the nucleotide sequence of one or more CDRs of the mouse monoclonal antibody produced by clone 2B6, 3H7, 1D5, 2E1, 2H9, 2D11, or 1F2. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 *Current Protocols in Molecular Biology*, vol. 1, Green Publishing Associates, Inc. and John Wiley and Sons, Inc., NY at pages 6.3.1 to 6.3.6 and 2.10.3, incorporated herein by reference).

The present invention also encompasses the use of binding domains comprising the amino acid sequence of any of the binding domains described above with mutations (e.g., one or more amino acid substitutions) in the framework or CDR regions. Preferably, mutations in these binding domains maintain or enhance the avidity and/or affinity of the binding domains for FcγRIIB to which they immunospecifically bind. Standard techniques known to those skilled in the art (e.g., immunoassays) can be used to assay the affinity of an antibody for a particular antigen.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

In preferred embodiments, the binding domains are derived from humanized antibodies. A humanized FcγRIIB specific antibody may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence.

The diabodies of present invention comprise humanized variable domains specific for FcγRIIB in which one or more regions of one or more CDRs of the heavy and/or light chain variable regions of a human antibody (the recipient antibody) have been substituted by analogous parts of one or more CDRs of a donor monoclonal antibody which specifically binds FcγRIIB, with a greater affinity than FcγRIIA, e.g., a monoclonal antibody produced by clone 2B6, 3H7, 1D5, 2E1, 2H9, 2D11, or 1F2. In other embodiments, the humanized antibodies bind to the same epitope as 2B6, 3H7, 1D5, 2E1, 2H9, 2D11, or 1F2, respectively.

In a preferred embodiment, the CDR regions of the humanized FcγRIIB binding domain are derived from a murine antibody specific for FcγRIIB. In some embodiments, the humanized antibodies described herein comprise alterations, including but not limited to amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein does not necessarily consist of the precise amino acid sequence of the framework region of a natural occurring human antibody variable region, but contains various alterations, including but not limited to amino acid deletions, insertions, modifications that alter the property of the humanized antibody, for example, improve the binding properties of a humanized antibody region that is specific for the same target as the murine FcγRIIB specific antibody. In most preferred embodiments, a minimal number of alterations are made to the framework region in order to avoid large-scale introductions of non-human framework residues and to ensure minimal immunogenicity of the humanized antibody in humans. The donor monoclonal antibody is preferably a monoclonal antibody produced by clones 2B6, 3H7, 1D5, 2E1, 2H9, 2D11, or 1F2.

In a specific embodiment, the binding domain encompasses variable domains of a CDR-grafted antibody which specifically binds FcγRIIB with a greater affinity than said antibody binds FcγRIIA, wherein the CDR-grafted antibody comprises a heavy chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6, 3H7, 1D5, 2E1, 2H9, 2D11, or 1F2. In another specific embodiment, the diabodies of the invention comprise variable domains from a CDR-grafted antibody which specifically binds FcγRIIB with a greater affinity than said antibody binds FcγRIIA, wherein the CDR-grafted antibody comprises a light chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6, 3H7, 1D5, 2E1, 2H9, 2D11, or 1F2.

The humanized anti-FcγRIIB variable domains used in the invention may have a heavy chain variable region comprising the amino acid sequence of CDR1 (SEQ ID NO: 24 or SEQ ID NO: 25) and/or CDR2 (SEQ ID NO: 26 or SEQ ID NO: 27) and/or CDR3 (SEQ ID NO: 28 or SEQ ID NO: 29) and/or a light chain variable region comprising the amino acid sequence of CDR1 (SEQ ID NO: 30 or SEQ ID NO: 31) and/or a CDR2 (SEQ ID NO: 32, SEQ ID NO: 33, SEQ ID NO: 34, or SEQ ID NO: 35) and/or CDR3 (SEQ ID NO: 36 or SEQ ID NO: 37).

In one specific embodiment, the diabody comprises variable domains from a humanized 2B6 antibody, wherein the VH region consists of the FR segments from the human germline VH segment VH1-18 (Matsuda et al. (1998) "*The Complete Nucleotide Sequence Of The Human Immunoglobulin Heavy Chain Variable Region Locus*," J. Exp. Med. 188:2151-2162) and JH6 (Ravetch et al. (1981) "*Structure Of The Human Immunoglobulin Mu Locus: Characterization Of Embryonic And Rearranged J And D Genes*," Cell 27(3 Pt. 2): 583-91), and one or more CDR regions of the 2B6 VH, having the amino acid sequence of SEQ ID NO:24, SEQ ID NO: 26, or SEQ ID NO: 28. In one embodiment, the 2B6 VH has the amino acid sequence of SEQ ID NO: 38. In another embodiment the 2B6 VH domain has the amino acid sequence of Hu2B6VH, SEQ ID NO: 85, and can be encoded by the nucleotide sequence of SEQ ID NO: 86. In another specific embodiment, the diabody further comprises a VL region, which consists of the FR segments of the human germline VL segment VK-A26 (Lautner-Rieske et al. (1992) "*The Human Immunoglobulin Kappa Locus. Characterization Of The Duplicated A Regions*," Eur. J. Immunol. 22:1023-1029) and JK4 (Hieter et al. (1982) "*Evolution Of Human Immunoglobulin Kappa J Region Genes*," J. Biol. Chem. 257:1516-22), and one or more CDR regions of 2B6VL, having the amino acid sequence of SEQ ID NO: 30, SEQ ID NO: 32, SEQ ID NO: 33, SEQ ID NO: 34, and SEQ ID NO: 36. In one embodiment, the 2B6 VL has the amino acid sequence of SEQ ID NO: 39; SEQ ID NO: 40, or SEQ ID NO: 41. In a specific embodiment, the 2B6 VL has the amino acid sequence of Hu2B6VL, SEQ ID NO: 87, and can be encoded by the nucleotide sequence provided in SEQ ID NO: 88.

In another specific embodiment, the diabody has variable domains from a humanized 3H7 antibody, wherein the VH region consists of the FR segments from a human germline VH segment and the CDR regions of the 3H7 VH, having the amino acid sequence of SEQ ID NO. 35. In another specific embodiment, the humanized 3H7 antibody further comprises a VL regions, which consists of the FR segments of a human germline VL segment and the CDR regions of 3H7VL, having the amino acid sequence of SEQ ID NO: 42.

In particular, binding domains immunospecifically bind to extracellular domains of native human FcγRIIB, and comprise (or alternatively, consist of) CDR sequences of 2B6, 3H7, 1D5, 2E1, 2H9, 2D11, or 1F2, in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

Antibodies for deriving binding domains to be included in the diabodies of the invention may be further characterized by epitope mapping, so that antibodies may be selected that have the greatest specificity for FcγRIIB compared to FcγRIIA. Epitope mapping methods of antibodies are well known in the art and encompassed within the methods of the invention. In certain embodiments fusion proteins comprising one or more regions of FcγRIIB may be used in mapping the epitope of an antibody of the invention. In a specific embodiment, the fusion protein contains the amino acid sequence of a region of an FcγRIIB fused to the Fc portion of human IgG2. Each fusion protein may further comprise amino acid substitutions and/or replacements of certain regions of the receptor with the corresponding region from a homolog receptor, e.g., FcγRIIA, as shown in Table 2 below. pMGX125 and pMGX132 contain the IgG binding site of the FcγRIIB receptor, the former with the C-terminus of FcγRIIB and the latter with the C-terminus of FcγRIIA and can be used to differentiate C-terminus binding. The others have FcγRIIA substitutions in the IgG binding site and either the FcγIIA or FcγIIB N-terminus. These molecules can help determine the part of the receptor molecule where the antibodies bind.

TABLE 2

List of the fusion proteins that may be used to investigate the epitope of the monoclonal anti-FcγRIIB antibodies. Residues 172 to 180 belong to the IgG binding site of FcγRIIA and B. The specific amino acids from FcγRIIA sequence are in bold.

| Plasmid | Receptor | N-terminus | 172-180 | SEQ ID NO: | C-terminus |
|---|---|---|---|---|---|
| pMGX125 | RIIb | IIb | KKFSRSDPN | 43 | APS------SS (IIb) |
| pMGX126 | RIIa/b | IIa | **Q**KFSR**L**DPN | 44 | APS------SS (IIb) |
| pMGX127 | | IIa | **Q**KFSR**L**DP**T** | 45 | APS------SS (IIb) |
| pMGX128 | | IIb | KKFSR**L**DP**T** | 46 | APS------SS (IIb) |
| pMGX129 | | IIa | **Q**KFS**HL**DP**T** | 47 | APS------SS (IIb) |
| pMGX130 | | IIb | KKFS**HL**DP**T** | 48 | APS------SS (IIb) |
| pMGX131 | | IIa | **Q**KFSR**L**DPN | 49 | VPSMGSSS(IIa) |
| pMGX132 | | IIb | KKFSRSDPN | 50 | VPSMGSSS(IIa) |
| pMGX133 | RIIa-131R | IIa | **Q**KFSR**L**DP**T** | 51 | VPSMGSSS(IIa) |
| pMGX134 | RIIa-131H | IIa | **Q**KFS**HL**DP**T** | 52 | VPSMGSSS(IIa) |
| pMGX135 | | IIb | KKFSR**L**DP**T** | 53 | VPSMGSSS(IIa) |
| pMGX136 | | IIb | KKFS**HL**DP**T** | 54 | VPSMGSSS(IIa) |

Note: APSSS is SEQ ID NO: 309; VPSMGSSS is SEQ ID NO: 310

The fusion proteins may be used in any biochemical assay for determination of binding to an anti-FcγRIIB antibody of the invention, e.g., an ELISA. In other embodiments, further confirmation of the epitope specificity may be done by using peptides with specific residues replaced with those from the FcγRIIA sequence.

The antibodies can be characterized using assays for identifying the function of the antibodies of the invention, particularly the activity to modulate FcγRIIB signaling. For example, characterization assays of the invention can measure phosphorylation of tyrosine residues in the ITIM motif of FcγRIIB, or measure the inhibition of B cell receptor-generated calcium mobilization. The characterization assays of the invention can be cell-based or cell-free assays.

It has been well established in the art that in mast cells coaggregation of FcγRIIB with the high affinity IgE receptor, FcεRI, leads to inhibition of antigen-induced degranulation, calcium mobilization, and cytokine production (Metcalfe D. D. et al. (1997) "Mast Cells," Physiol. Rev. 77:1033-1079; Long E. O. (1999) "*Regulation Of Immune Responses Through Inhibitory Receptors*," Annu Rev. Immunol. 17: 875-904). The molecular details of this signaling pathway have been recently elucidated (Ott V. L. (2002) "*Downstream Of Kinase, p62(dok), Is A Mediator Of FcgammaIIB Inhibition Of Fc Epsilon RI Signaling*," J. Immunol. 162(9):4430-4439). Once coaggregated with FcεRI, FcγRIIB is rapidly phosphorylated on tyrosine in its ITIM motif, and then recruits Src Homology-2 containing inositol-5-phosphatase (SHIP), an SH2 domain-containing inosital polyphosphate 5-phosphatase, which is in turn phosphorylated and associates with Shc and $p62^{dok}$ ($p62^{dok}$ is the prototype of a family of adaptor molecules, which includes signaling domains such as an aminoterminal pleckstrin homology domain (PH domain), a PTB domain, and a carboxy terminal region containing PXXP motifs and numerous phosphorylation sites (Carpino et al. (1997) "p62(dok): A Constitutively Tyrosine-Phosphorylated, GAP-Associated Protein In Chronic Myelogenous Leukemia Progenitor Cells," Cell, 88: 197-204; Yamanshi et al. (1997) "*Identification Of The Abl-And ras-GAP-Associated* 62 *kDa Protein As A Docking Protein, Dok*," Cell, 88:205-211).

The anti-FcγRIIB antibodies for use in the invention may likewise be characterized for ability to modulate one or more IgE mediated responses. Preferably, cells lines co-expressing the high affinity receptor for IgE and the low affinity receptor for FcγRIIB will be used in characterizing the anti-FcγRIIB antibodies in modulating IgE mediated responses. In a specific embodiment, cells from a rat basophilic leukemia cell line (RBL-H23; Barsumian E. L. et al. (1981) "*IgE-Induced Histamine Release From Rat Basophilic Leukemia Cell Lines: Isolation Of Releasing And Nonreleasing Clones*," Eur. J. Immunol. 11:317-323, which is incorporated herein by reference in its entirety) transfected with full length human FcγRIIB will be used. RBL-2H3 is a well characterized rat cell line that has been used extensively to study the signaling mechanisms following IgE-mediated cell activation. When expressed in RBL-2H3 cells and coaggregated with FcεRI, FcγRIIB inhibits FcεRI-induced calcium mobilization, degranulation, and cytokine production (Malbec et al. (1998) "*Fc Epsilon Receptor I-Associated Lyn-Dependent Phosphorylation Of Fc Gamma Receptor IIB During Negative Regulation Of Mast Cell Activation*," J. Immunol. 160:1647-1658; Daeron et al. (1995) "*Regulation Of High-Affinity IgE Receptor-Mediated Mast Cell Activation By Murine Low-Affinity IgG Receptors*," J. Clin. Invest. 95:577; Ott V. L. (2002) "*Downstream Of Kinase, p62(dok), Is A Mediator Of FcgammaIIB Inhibition Of Fc Epsilon RI Signaling*," J. Immunol. 162(9):4430-4439).

Antibodies for use in the invention may also be characterized for inhibition of FcεRI induced mast cell activation. For example, cells from a rat basophilic leukemia cell line (RBL-H23; Barsumian E. L. et al. (1981) "*IgE-Induced Histamine Release From Rat Basophilic Leukemia Cell Lines: Isolation Of Releasing And Nonreleasing Clones*," Eur. J. Immunol. 11:317-323) that have been transfected with FcγRIIB are sensitized with IgE and stimulated either with $F(ab')_2$ fragments of rabbit anti-mouse IgG, to aggregate FcεRI alone, or with whole rabbit anti-mouse IgG to coaggregate FcγRIIB and FcεRI. In this system, indirect modulation of down stream signaling molecules can be assayed upon addition of antibodies of the invention to the sensitized and stimulated cells. For example, tyrosine phosphorylation of FcγRIIB and recruitment and phosphorylation of SHIP, activation of MAP kinase family members, including but not limited to Erk1, Erk2, JNK, or p38; and tyrosine phosphorylation of $p62^{dok}$ and its association with SHIP and RasGAP can be assayed.

One exemplary assay for determining the inhibition of FcεRI induced mast cell activation by the antibodies of the invention can comprise of the following: transfecting RBL-H23 cells with human FcγRIIB; sensitizing the RBL-H23 cells with IgE; stimulating RBL-H23 cells with either $F(ab')_2$ of rabbit anti-mouse IgG (to aggregate FcεRI alone and elicit FcεRI-mediated signaling, as a control), or stimulating RBL-H23 cells with whole rabbit anti-mouse IgG to (to coaggregate FcγRIIB and FcεRI, resulting in inhibition of FcεRI-mediated signaling). Cells that have been stimulated with whole rabbit anti-mouse IgG antibodies can be further pre-incubated with the antibodies of the invention. Measuring FcεRI-dependent activity of cells that have been pre-incubated with the antibodies of the invention and cells that have not been pre-incubated with the antibodies of the invention, and comparing levels of FcεRI-dependent activity in these cells, would indicate a modulation of FcεRI-dependent activity by the antibodies of the invention.

The exemplary assay described above can be for example, used to identify antibodies that block ligand (IgG) binding to FcγRIIB receptor and antagonize FcγRIIB-mediated inhibition of FcεRI signaling by preventing coaggregating of FcγRIIB and FcεRI. This assay likewise identifies antibodies that enhance coaggregation of FcγRIIB and FcεRI and agonize FcγRIIB-mediated inhibition of FcεRI signaling by promoting coaggregating of FcγRIIB and FcεRI.

In some embodiments, the anti-FcγRIIB diabodies, comprising the epitope binding domains of anti-FcγRIIB antibodies identified described herein or known in the art, of the invention are characterized for their ability to modulate an IgE mediated response by monitoring and/or measuring degranulation of mast cells or basophils, preferably in a cell-based assay. Preferably, mast cells or basophils for use in such assays have been engineered to contain human FcγRIIB using standard recombinant methods known to one skilled in the art. In a specific embodiment the anti-FcγRIIB antibodies of the invention are characterized for their ability to modulate an IgE mediated response in a cell-based β-hexosaminidase (enzyme contained in the granules) release assay. β-hexosaminidase release from mast cells and basophils is a primary event in acute allergic and inflammatory condition (Aketani et al. (2001) "*Correlation Between Cytosolic Calcium Concentration And Degranulation In RBL-*2*H*3 *Cells In The Presence Of Various Concentrations Of Antigen-Specific IgEs*," Immunol. Lett. 75: 185-189; Aketani et al. (2000) "*A Screening Method For Antigen-Specific IgE Using Mast Cells Based On Intracellular Calcium Signaling*," Anal. Chem. 72: 2653-2658). Release of other inflammatory mediators including but not limited to serotonin and histamine may be assayed to measure an IgE mediated response in accordance with the methods of the invention. Although not intending to be bound by a particular mechanism of action, release of granules such as those containing β-hexosaminidase from mast cells and basophils is an intracellular calcium concentration dependent process that is initiated by the cross-linking of FcγRIs with multivalent antigen.

The ability to study human mast cells has been limited by the absence of suitable long term human mast cell cultures. Recently two novel stem cell factor dependent human mast cell lines, designated LAD 1 and LAD2, were established from bone marrow aspirates from a patient with mast cell sarcoma/leukemia (Kirshenbaum et al. (2003) "*Characterization Of Novel Stem Cell Factor Responsive Human Mast Cell Lines LAD* 1 *And* 2 *Established From A Patient With Mast Cell Sarcoma/Leukemia; Activation Following Aggregation Of FcRI Or FcγRI*," Leukemia research, 27:677-82, which is incorporated herein by reference in its entirety.). Both cell lines have been described to express FcεRI and several human mast cell markers. LAD 1 and 2 cells can be used for assessing the effect of the antibodies of the invention on IgE mediated responses. In a specific embodiment, cell-based β-hexosaminidase release assays such as those described supra may be used in LAD cells to determine any modulation of the IgE-mediated response by the anti-FcγRIIB antibodies of the invention. In an exemplary assay, human mast cells, e.g., LAD 1, are primed with chimeric human IgE anti-nitrophenol (NP) and challenged with BSA-NP, the polyvalent antigen, and cell degranulation is monitored by measuring the β-hexosaminidase released in the supernatant (Kirshenbaum et al. (2003) "*Characterization Of Novel Stem Cell Factor Responsive Human Mast Cell Lines LAD* 1 *And* 2 *Established From A Patient With Mast Cell Sarcoma/Leukemia; Activation Following Aggregation Of FcRI Or FcγRI*," Leukemia research, 27:677-82, which is incorporated herein by reference in its entirety.).

In some embodiments, if human mast cells have a low expression of endogenous FcγRIIB, as determined using standard methods known in the art, e.g., FACS staining, it may be difficult to monitor and/or detect differences in the activation of the inhibitory pathway mediated by the anti-FcγRIIB diabodies of the invention. The invention thus encompasses alternative methods, whereby the FcγRIIB expression may be upregulated using cytokines and particular growth conditions. FcγRIIB has been described to be highly up-regulated in human monocyte cell lines, e.g., THP1 and U937, (Tridandapani et al. (2002) "*Regulated Expression And Inhibitory Function Of Fcgamma RIIB In Human Monocytic Cells*," J. Biol. Chem., 277(7): 5082-5089) and in primary human monocytes (Pricop et al. (2001) "*Differential Modulation Of Stimulatory And Inhibitory Fc Gamma Receptors On Human Monocytes By Th*1 *And Th*2 *Cytokines*," J. of Immunol., 166: 531-537) by IL4. Differentiation of U937 cells with dibutyryl cyclic AMP has been described to increase expression of FcγRII (Cameron et al. (2002) "*Differentiation Of The Human Monocyte Cell Line, U*937, *With Dibutyryl CyclicAMP Induces The Expression Of The Inhibitory Fc Receptor, FcgammaRIIB*," Immunology Letters 83, 171-179). Thus the endogenous FcγRIIB expression in human mast cells for use in the methods of the invention may be up-regulated using cytokines, e.g., IL-4, IL-13, in order to enhance sensitivity of detection.

The anti-FcγRIIB diabodies can also be assayed for inhibition of B-cell receptor (BCR)-mediated signaling. BCR-mediated signaling can include at least one or more down stream biological responses, such as activation and proliferation of B cells, antibody production, etc. Coaggregation of FcγRIIB and BCR leads to inhibition of cell cycle progression and cellular survival. Further, coaggregation of FcγRIIB and BCR leads to inhibition of BCR-mediated signaling.

Specifically, BCR-mediated signaling comprises at least one or more of the following: modulation of down stream signaling molecules (e.g., phosphorylation state of FcγRIIB, SHIP recruitment, localization of Btk and/or PLCγ, MAP kinase activity, recruitment of Akt (anti-apoptotic signal), calcium mobilization, cell cycle progression, and cell proliferation.

Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, Ins(1,4,5)$P_3$ production, and Erk and Akt phosphorylation (Brauweiler et al. (2001) "*Partially Distinct Molecular Mechanisms Mediate Inhibitory FcgammaRIIB Signaling In Resting And Activated B Cells*," Journal of Immunology, 167 (1): 204-211). Accordingly, ex vivo B cells from SHIP deficient mice can be used to characterize the antibodies of the invention. One exemplary assay for determining FcγRIIB-mediated inhibition of BCR signaling by the antibodies of the invention can comprise the following: isolating splenic B cells from SHIP deficient mice, activating said cells with lipopolysachharide, and stimulating said cells with either F(ab')$_2$ anti-IgM to aggregate BCR or with anti-IgM to coaagregate BCR with FcγRIIB. Cells that have been stimulated with intact anti-IgM to coaggregate BCR with FcγRIIB can be further pre-incubated with the antibodies of the invention. FcγRIIB-dependent activity of cells can be measured by standard techniques known in the art. Comparing the level of FcγRIIB-dependent activity in cells that have been pre-incubated with the antibodies and cells that have not been pre-incubated, and comparing the levels would indicate a modulation of FcγRIIB-dependent activity by the antibodies.

Measuring FcγRIIB-dependent activity can include, for example, measuring intracellular calcium mobilization by flow cytometry, measuring phosphorylation of Akt and/or Erk, measuring BCR-mediated accumulation of PI(3,4,5)$P_3$, or measuring FcγRIIB-mediated proliferation B cells.

The assays can be used, for example, to identify diabodies or anti-FcγRIIB antibodies for use in the invention that modulate FcγRIIB-mediated inhibition of BCR signaling by blocking the ligand (IgG) binding site to FcγRIIB receptor and antagonizing FcγRIIB-mediated inhibition of BCR signaling by preventing coaggregation of FcγRIIB and BCR. The assays can also be used to identify antibodies that enhance coaggregation of FcγRIIB and BCR and agonize FcγRIIB-mediated inhibition of BCR signaling.

The anti-FcγRIIB antibodies can also be assayed for FcγRII-mediated signaling in human monocytes/macrophages. Coaggregation of FcγRIIB with a receptor bearing the immunoreceptor tyrosine-based activation motif (ITAM) acts to down-regulate FcγR-mediated phagocytosis using SHIP as its effector (Tridandapani et al. (2002) "*Regulated Expression And Inhibitory Function Of Fcgamma RIIB In Human Monocytic Cells*," J. Biol. Chem., 277(7): 5082-5089). Coaggregation of FcγRIIA with FcγRIIB results in rapid phosphorylation of the tyrosine residue on FcγRIIB's ITIM motif, leading to an enhancement in phosphorylation of SHIP, association of SHIP with Shc, and phosphorylation of proteins having the molecular weight of 120 and 60-65 kDa. In addition, coaggregation of FcγRIIA with FcγRIIB results in down-regulation of phosphorylation of Akt, which is a serine-threonine kinase that is involved in cellular regulation and serves to suppress apoptosis.

The anti-FcγRIIB diabodies can also be assayed for inhibition of FcγR-mediated phagocytosis in human monocytes/macrophages. For example, cells from a human monocytic cell line, THP-1 can be stimulated either with Fab fragments of mouse monoclonal antibody IV.3 against FcγRII and goat anti-mouse antibody (to aggregate FcγRIIA alone), or with whole IV.3 mouse monoclonal antibody and goat anti-mouse antibody (to coaggregate FcγRIIA and FcγRIIB). In this system, modulation of down stream signaling molecules, such as tyrosine phosphorylation of FcγRIIB, phosphorylation of SHIP, association of SHIP with Shc, phosphorylation of Akt, and phosphorylation of proteins having the molecular weight of 120 and 60-65 kDa can be assayed upon addition of molecules of the invention to the stimulated cells. In addition, FcγRIIB-dependent phagocytic efficiency of the monocyte cell line can be directly measured in the presence and absence of the antibodies of the invention.

Another exemplary assay for determining inhibition of FcγR-mediated phagocytosis in human monocytes/macrophages by the antibodies of the invention can comprise the following: stimulating THP-1 cells with either Fab of IV.3 mouse anti-FcγRII antibody and goat anti-mouse antibody (to aggregate FcγRIIA alone and elicit FcγRIIA-mediated signaling); or with mouse anti-FcγRII antibody and goat anti-mouse antibody (to coaggregate FcγRIIA and FcγRIIB and inhibiting FcγRIIA-mediated signaling. Cells that have been stimulated with mouse anti-FcγRII antibody and goat anti-mouse antibody can be further pre-incubated with the molecules of the invention. Measuring FcγRIIA-dependent activity of stimulated cells that have been pre-incubated with molecules of the invention and cells that have not been pre-incubated with the antibodies of the invention and comparing levels of FcγRIIA-dependent activity in these cells would indicate a modulation of FcγRIIA-dependent activity by the antibodies of the invention.

The exemplary assay described can be used for example, to identify binding domains that block ligand binding of FcγRIIB receptor and antagonize FcγRIIB-mediated inhibition of FcγRIIA signaling by preventing coaggregation of FcγRIIB and FcγRIIA. This assay likewise identifies binding domains that enhance coaggregation of FcγRIIB and FcγRIIA and agonize FcγRIIB-mediated inhibition of FcγRIIA signaling.

The FcγRIIB binding domains of interest can be assayed while comprised I antibodies by measuring the ability of THP-1 cells to phagocytose fluoresceinated IgG-opsonized sheep red blood cells (SRBC) by methods previously described (Tridandapani et al. (2000) "*The Adapter Protein LAT Enhances Fcgamma Receptor-Mediated Signal Transduction In Myeloid Cells*," J. Biol. Chem. 275: 20480-7). For example, an exemplary assay for measuring phagocytosis comprises of: treating THP-1 cells with the antibodies of the invention or with a control antibody that does not bind to FcγRII, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate a modulation of FcγRIIA-dependent activity by the antibodies of the invention. This assay can be used to identify, for example, antibodies that block ligand binding of FcγRIIB receptor and antagonize FcγRIIB-mediated inhibition of phagocytosis. This assay can also identify antibodies that enhance FcγRIIB-mediated inhibition of FcγRIIA signaling.

In a preferred embodiment, the binding domains modulate FcγRIIB-dependent activity in human monocytes/macrophages in at least one or more of the following ways: modulation of downstream signaling molecules (e.g., modulation of phosphorylation state of FcγRIIB, modulation of SHIP phosphorylation, modulation of SHIP and Shc association, modulation of phosphorylation of Akt, modulation of phosphorylation of additional proteins around 120 and 60-65 kDa) and modulation of phagocytosis.

5.1.2 CD16A Binding Domains

The following section discusses CD16A binding proteins which can be used as sources for light and heavy chain variable regions for covalent diabody production. In the present invention CD16A binding proteins includes molecules comprising VL and VH domains of anti-CD16A antibodies, which VH and VL domains are used in the production of the diabodies of the present invention.

A variety of CD16A binding proteins may be used in connection with the present invention. Suitable CD16A binding proteins include human or humanized monoclonal antibodies as well as CD16A binding antibody fragments (e.g., scFv or single chain antibodies, Fab fragments, minibodies) and another antibody-like proteins that bind to CD16A via an interaction with a light chain variable region domain, a heavy chain variable region domain, or both.

In some embodiments, the CD16A binding protein for use according to the invention comprises a VL and/or VH domain that has one or more CDRs with sequences derived from a non-human anti-CD16A antibody, such as a mouse anti-CD16A antibody, and one or more framework regions with derived from framework sequences of one or more human immunoglobulins. A number of non-human anti-CD16A monoclonal antibodies, from which CDR and other sequences may be obtained, are known (see, e.g., Tamm et al. (1996) "*The Binding Epitopes Of Human CD*16 (*Fc gamma RIII*) *Monoclonal Antibodies. Implications For Ligand Binding*," J. Imm. 157:1576-81; Fleit et al. (1989) p. 159; LEUKOCYTE TYPING II: HUMAN MYELOID AND HEMATOPOIETIC CELLS, Reinherz et al., eds. New York: Springer-Verlag; (1986); LEUCOCYTE TYPING III: WHITE CELL DIFFERENTIATION ANTIGENS McMichael A J, ed., Oxford: Oxford University Press, 1986); LEUKOCYTE TYPING IV: WHITE CELL DIFFERENTIATION ANTIGENS, Kapp et al., eds. Oxford Univ. Press, Oxford; LEUKOCYTE TYPING V: WHITE CELL DIFFERENTIATION ANTIGENS, Schlossman et al., eds. Oxford Univ. Press, Oxford; LEUKOCYTE TYPING VI: WHITE CELL DIFFERENTIATION ANTIGENS, Kishimoto, ed. Taylor & Francis. In addition, as shown in the Examples, new CD16A binding proteins that recognize human CD16A expressed on cells can be obtained using well known methods for production and selection of monoclonal antibodies or related binding proteins (e.g., hybridoma technology, phage display, and the like). See, for example, O'Connell et al. (2002) "*Phage Versus Phagemid Libraries For Generation Of Human Monoclonal Antibodies*," J. Mol. Biol. 321:49-56; Hoogenboom et al. (2000) "*Natural And Designer Binding Sites Made By Phage Display Technology,*" 1 mm. Today 21:371078; Krebs et al. (2001) "*High-Throughput Generation And Engineering Of Recombinant Human Antibodies*," J. Imm. Methods 254:67-84; and other references cited herein. Monoclonal antibodies from a non-human species can be chimerized or humanized using techniques using techniques of antibody humanization known in the art.

Alternatively, fully human antibodies against CD16A can be produced using transgenic animals having elements of a human immune system (see, e.g., U.S. Pat. Nos. 5,569,825 and 5,545,806), using human peripheral blood cells (Casali et al. (1986) "*Human Monoclonals From Antigen-Specific Selection Of B Lymphocytes And Transformation By EBV*," Science 234:476-479), by screening a DNA library from human B cells according to the general protocol outlined by Huse et al. (1989) "*Generation Of A Large Combinatorial Library Of The Immunoglobulin Repertoire In Phage Lambda*," Science 246:1275-1281, and by other methods.

In a preferred embodiment, the binding donor is from the 3G8 antibody or a humanized version thereof, e.g., such as those disclosed in U.S. patent application publication 2004/0010124, which is incorporated by reference herein in its entirety. It is contemplated that, for some purposes, it may be advantageous to use CD16A binding proteins that bind the CD16A receptor at the same epitope bound by 3G8, or at least sufficiently close to this epitope to block binding by 3G8. Methods for epitope mapping and competitive binding experiments to identify binding proteins with the desired binding properties are well known to those skilled in the art of experimental immunology. See, for example, Harlow and Lane, cited supra; Stähli et al. (1983) "*Distinction Of Epitopes By Monoclonal Antibodies*," Methods in Enzymology 92:242-253; Kirkland et al. (1986) "*Analysis Of The Fine Specificity And Cross-Reactivity Of Monoclonal Anti-Lipid A Antibodies*," J. Immunol. 137:3614-3619; Morel et al. (1988) "*Monoclonal Antibodies To Bovine Serum Albumin: Affinity And Specificity Determinations*," Molec. Immunol. 25:7-15; Cheung et al. (1990) "*Epitope-Specific Antibody Response To The Surface Antigen Of Duck Hepatitis B Virus In Infected Ducks*," Virology 176:546-552; and Moldenhauer et al. (1990) "*Identity Of HML-*1 *Antigen On Intestinal Intraepithelial T Cells And Of B-ly*7 *Antigen On Hairy Cell Leu-*

*kaemia*," Scand. J. Immunol. 32:77-82. For instance, it is possible to determine if two antibodies bind to the same site by using one of the antibodies to capture the antigen on an ELISA plate and then measuring the ability of the second antibody to bind to the captured antigen. Epitope comparison can also be achieved by labeling a first antibody, directly or indirectly, with an enzyme, radionuclide or fluorophore, and measuring the ability of an unlabeled second antibody to inhibit the binding of the first antibody to the antigen on cells, in solution, or on a solid phase.

It is also possible to measure the ability of antibodies to block the binding of the CD16A receptor to immune complexes formed on ELISA plates. Such immune complexes are formed by first coating the plate with an antigen such as fluorescein, then applying a specific anti-fluorescein antibody to the plate. This immune complex then serves as the ligand for soluble Fc receptors such as sFcRIIIa. Alternatively a soluble immune complex may be formed and labeled, directly or indirectly, with an enzyme radionuclide or fluorophore. The ability of antibodies to inhibit the binding of these labeled immune complexes to Fc receptors on cells, in solution or on a solid phase can then be measured.

CD16A binding proteins of the invention may or may not comprise a human immunoglobulin Fc region. Fc regions are not present, for example, in scFv binding proteins. Fc regions are present, for example, in human or humanized tetrameric monoclonal IgG antibodies. As described supra, in some embodiments of the present invention, the CD16A binding protein includes an Fc region that has an altered effector function, e.g., reduced affinity for an effector ligand such as an Fc receptor or Cl component of complement compared to the unaltered Fc region (e.g., Fc of naturally occurring IgG1, proteins). In one embodiment the Fc region is not glycosylated at the Fc region amino acid corresponding to position 297. Such antibodies lack Fc effector function.

Thus, the CD16A binding protein may not exhibit Fc-mediated binding to an effector ligand such as an Fc receptor or the C1 component of complement due to the absence of the Fc domain in the binding protein while, in other cases, the lack of binding or effector function is due to an alteration in the constant region of the antibody.

5.1.2.1 CD16A Binding Proteins Comprising CDR Sequences Similar to a mAb 3G8 CDR Sequences.

CD16A binding proteins that can be used in the practice of the invention include proteins comprising a CDR sequence derived from (i.e., having a sequence the same as or similar to) the CDRs of the mouse monoclonal antibody 3G8. Complementary cDNAs encoding the heavy chain and light chain variable regions of the mouse 3G8 monoclonal antibody, including the CDR encoding sequences, were cloned and sequenced as described. The nucleic acid and protein sequences of 3G8 are provided below. Using the mouse variable region and CDR sequences, a large number of chimeric and humanized monoclonal antibodies, comprising complementary determining regions derived from 3G8 CDRs were produced and their properties analyzed. To identify humanized antibodies that bind CD16A with high affinity and have other desirable properties, antibody heavy chains comprising a VH region with CDRs derived from 3G8 were produced and combined (by coexpression) with antibody light chains comprising a VL region with CDRs derived from 3G8 to produce a tetrameric antibody for analysis. Properties of the resulting tetrameric antibodies were determined as described below. As described below, CD16A binding proteins comprising 3G8 CDRs, such as the humanized antibody proteins described herein, may be used according to the invention.

5.1.2.1.1 VH Region

In one aspect, the CD16A binding protein of the invention may comprise a heavy chain variable domain in which at least one CDR (and usually three CDRS) have the sequence of a CDR (and more typically all three CDRS) of the mouse monoclonal antibody 3G8 heavy chain and for which the remaining portions of the binding protein are substantially human (derived from and substantially similar to, the heavy chain variable region of a human antibody or antibodies).

In an aspect, the invention provides a humanized 3G8 antibody or antibody fragment containing CDRs derived from the 3G8 antibody in a substantially human framework, but in which at least one of the CDRs of the heavy chain variable domain differs in sequence from the corresponding mouse antibody 3G8 heavy chain CDR. For example, in one embodiment, the CDR(S) differs from the 3G8 CDR sequence at least by having one or more CDR substitutions shown known in the art to affect binding of 3G8 to CD16A, as known in the art or as disclosed in Tables 3 and 4A-H. Suitable CD16 binding proteins may comprise 0, 1, 2, 3, or 4, or more of these substitutions (and often have from 1 to 4 of these substitutions) and optionally can have additional substitutions as well.

TABLE 3

$V_H$ Domain Substitutions

| No. | Kabat Position | Region | Substitutions |
|---|---|---|---|
| 1 | 2 | FR1 | Ile |
| 2 | 5 | FR1 | Lys |
| 3 | 10 | FR1 | Thr |
| 4 | 30 | FR1 | Arg |
| 5 | 34 | CDR1 | Val |
| 6 | 50 | CDR2 | Leu |
| 7 | 52 | CDR2 | Phe or Tyr or Asp |
| 8 | 54 | CDR2 | Asn |
| 9 | 60 | CDR2 | Ser |
| 10 | 62 | CDR2 | Ser |
| 11 | 70 | FR3 | Thr |
| 12 | 94 | FR3 | Gln or Lys or Ala or His |
| 13 | 99 | CDR3 | Tyr |
| 14 | 101 | CDR3 | Asp |

TABLE 4A $V_H$ Sequences Derived from 3G8 $V_H$*

| | FR1 | CDR1 | FR2 | CDR2 | FR3 | CDR3 | FR4 |
|---|---|---|---|---|---|---|---|
| 3G8VH | A | A | A | A | A | A | A |
| Ch3G8VH | A | A | A | A | A | A | B |
| HxC | B | A | B | A | A | A | B |
| CxH | A | A | A | A | B | A | B |
| Hu3G8VH-1 | B | A | B | A | B | A | B |
| Hu3G8VH-2 | C | A | B | A | B | A | B |
| Hu3G8VH-3 | D | A | B | A | B | A | B |
| Hu3G8VH-4 | B | A | B | A | C | B | B |
| Hu3G8VH-5 | B | A | B | A | C | A | B |
| Hu3G8VH-6 | B | B | B | A | B | B | B |
| Hu3G8VH-7 | B | B | B | A | B | A | B |
| Hu3G8VH-8 | B | A | B | A | B | C | B |

TABLE 4A-continued

| $V_H$ Sequences Derived from 3G8 $V_H$* | | | | | | | |
|---|---|---|---|---|---|---|---|
| | FR1 | CDR1 | FR2 | CDR2 | FR3 | CDR3 | FR4 |
| Hu3G8VH-9 | B | A | B | B | B | B | B |
| Hu3G8VH-10 | B | A | B | A | B | B | B |
| Hu3G8VH-11 | B | A | B | B | B | A | B |
| Hu3G8VH-12 | B | A | B | C | B | A | B |
| Hu3G8VH-13 | B | A | B | D | B | A | B |
| Hu3G8VH-14 | B | A | B | E | B | A | B |
| Hu3G8VH-15 | B | A | B | A | D | A | B |
| Hu3G8VH-16 | B | A | B | A | E | A | B |
| Hu3G8VH-17 | B | A | B | A | F | A | B |
| Hu3G8VH-18 | B | A | B | A | G | A | B |
| Hu3G8VH-19 | B | A | B | A | C | C | B |
| Hu3G8VH-20 | B | B | B | C | B | A | B |
| Hu3G8VH-21 | B | A | B | A | D | B | B |
| Hu3G8VH-22 | B | B | B | C | B | C | B |
| Hu3G8VH-23 | B | B | B | C | E | C | B |
| Hu3G8VH-24 | B | B | B | C | F | C | B |
| Hu3G8VH-25 | B | B | B | C | G | C | B |
| Hu3G8VH-26 | B | B | B | C | C | C | B |
| Hu3G8VH-27 | B | B | B | C | E | D | B |
| Hu3G8VH-28 | B | B | B | C | F | D | B |
| Hu3G8VH-29 | B | B | B | C | G | D | B |
| Hu3G8VH-30 | B | B | B | C | C | D | B |
| Hu3G8VH-31 | E | B | B | C | B | A | B |
| Hu3G8VH-32 | E | B | B | H | B | A | B |
| Hu3G8VH-33 | E | B | B | H | B | A | B |
| Hu3G8VH-34 | E | B | B | C | B | C | B |
| Hu3G8VH-35 | E | B | B | C | C | C | B |
| Hu3G8VH-36 | E | B | B | H | C | D | B |
| Hu3G8VH-37 | E | B | B | H | E | C | B |
| Hu3G8VH-38 | E | B | B | F | B | A | B |
| Hu3G8VH-39 | E | B | B | I | B | A | B |
| Hu3G8VH-40 | E | B | B | G | B | A | B |
| Hu3G8VH-41 | E | B | B | J | B | A | B |
| Hu3G8VH-42 | E | B | B | C | H | A | B |
| Hu3G8VH-43 | E | B | B | C | H | C | B |
| Hu3G8VH-44 | E | B | B | C | I | D | B |
| Hu3G8VH-45 | E | B | B | C | J | D | B |

* Letters in Table 4A refer to sequences in Tables 4 B-H.

TABLE 4B

| FR1 | | | | | |
|---|---|---|---|---|---|
| A | B | C | D | E | RESIDUE |
| Q | Q | Q | Q | Q | 1 |
| V | V | V | V | I | 2 |
| T | T | T | T | T | 3 |
| L | L | L | L | L | 4 |
| K | R | K | R | K | 5 |
| E | E | E | E | E | 6 |
| S | S | S | S | S | 7 |
| G | G | G | G | G | 8 |
| P | P | P | P | P | 9 |
| G | A | A | A | T | 10 |
| I | L | L | L | L | 11 |
| L | V | V | V | V | 12 |
| Q | K | K | K | K | 13 |
| P | P | P | P | P | 14 |
| S | T | T | T | T | 15 |
| Q | Q | Q | Q | Q | 16 |
| T | T | T | T | T | 17 |
| L | L | L | L | L | 18 |
| S | T | T | T | T | 19 |
| L | L | L | L | L | 20 |
| T | T | T | T | T | 21 |
| C | C | C | C | C | 22 |
| S | T | T | T | T | 23 |
| F | F | F | F | F | 24 |
| S | S | S | S | S | 25 |
| G | G | G | G | G | 26 |
| F | F | F | F | F | 27 |
| S | S | S | S | S | 28 |

TABLE 4B-continued

| FR1 | | | | | |
|---|---|---|---|---|---|
| L | L | L | L | L | 29 |
| R | S | S | R | S | 30 |
| 103 | 104 | 105 | 106 | 107 | SEQ ID NO. |

| SEQ ID NO. | Sequence |
|---|---|
| 103 | QVTLKESGPGILQPSQTLSLTCSFSGFSLR |
| 104 | QVTLRESGPALVKPTQTLTLTCTFSGFSLS |
| 105 | QVTLKESGPALVKPTQTLTLTCTFSGFSLS |
| 106 | QVTLRESGPALVKPTQTLTLTCTFSGFSLR |
| 107 | QITLKESGPTLVKPTQTLTLTCTFSGFSLS |

TABLE 4C

| CDR1 | | |
|---|---|---|
| A | B | RESIDUE |
| T | T | 31 |
| S | S | 32 |
| G | G | 33 |
| M | V | 34 |
| G | G | 35 |
| V | V | 35A |
| G | G | 35B |
| 108 | 109 | SEQ ID NO. |

| SEQ ID NO. | Sequence |
|---|---|
| 108 | TSGMGVG |
| 109 | TSGVGVG |

TABLE 4D

| FR2 | | |
|---|---|---|
| A | B | RESIDUE |
| W | W | 36 |
| I | I | 37 |
| R | R | 38 |
| Q | Q | 39 |
| P | P | 40 |
| S | P | 41 |
| G | G | 42 |
| K | K | 43 |
| G | A | 44 |
| L | L | 45 |
| E | E | 46 |
| W | W | 47 |
| L | L | 48 |
| A | A | 49 |
| 110 | 111 | SEQ ID NO. |

| SEQ ID NO. | Sequence |
|---|---|
| 110 | WIRQPSGKGLEWLA |
| 111 | WIRQPPGKALEWLA |

TABLE 4E

| CDR2 | | | | | | | | | | |
|---|---|---|---|---|---|---|---|---|---|---|
| A | B | C | D | E | F | G | H | I | J | RESIDUE |
| H | H | H | H | H | L | H | L | H | L | 50 |
| I | I | I | I | I | I | I | I | I | I | 51 |
| W | Y | W | Y | W | D | F | W | D | W | 52 |
| W | W | W | W | W | W | W | W | W | W | 53 |
| D | N | D | D | N | D | D | D | D | N | 54 |
| D | D | D | D | D | D | D | D | D | D | 55 |

TABLE 4E-continued

| CDR2 | | | | | | | | | | |
|---|---|---|---|---|---|---|---|---|---|---|
| D | D | D | D | D | D | D | D | D | D | 56 |
| K | K | K | K | K | K | K | K | K | K | 57 |
| R | R | R | R | R | R | R | R | R | R | 58 |
| Y | Y | Y | Y | Y | Y | Y | Y | Y | Y | 59 |
| N | N | S | N | N | S | S | S | S | S | 60 |
| P | P | P | P | P | P | P | P | P | P | 61 |
| A | A | S | A | A | S | S | S | S | S | 62 |
| L | L | L | L | L | L | L | L | L | L | 63 |
| K | K | K | K | K | K | K | K | K | K | 64 |
| S | S | S | S | S | S | S | S | S | S | 65 |
| 112 | 113 | 114 | 115 | 116 | 117 | 118 | 119 | 120 | 121 | SEQ ID NO |

| SEQ ID NO. | Sequence |
|---|---|
| 112 | HIWWDDDKRYNPALKS |
| 113 | HIYWNDDKRYNPALKS |
| 114 | HIWWDDDKRYSPSLKS |
| 115 | HIYWDDDKRYNPALKS |
| 116 | HIWWNDDKRYNPALKS |
| 117 | LIDWDDDKRYSPSLKS |
| 118 | HIFWDDDKRYSPSLKS |
| 119 | LIWWDDDKRYSPSLKS |
| 120 | HIDWDDDKRYSPSLKS |
| 121 | LIWWNDDKRYSPSLKS |

TABLE 4F

| FR3 | | | | | | | | | | |
|---|---|---|---|---|---|---|---|---|---|---|
| A | B | C | D | E | F | G | H | I | J | RESIDUE |
| R | R | R | R | R | R | R | R | R | R | 66 |
| L | L | L | L | L | L | L | L | L | L | 67 |
| T | T | T | T | T | T | T | T | T | T | 68 |
| I | I | I | I | I | I | I | I | I | I | 69 |
| S | S | S | S | S | S | S | T | T | T | 70 |
| K | K | K | K | K | K | K | K | K | K | 71 |
| D | D | D | D | D | D | D | D | D | D | 72 |
| T | T | T | T | T | T | T | T | T | T | 73 |
| S | S | S | S | S | S | S | S | S | S | 74 |
| S | K | K | K | K | K | K | K | K | K | 75 |
| N | N | N | N | N | N | N | N | N | N | 76 |
| Q | Q | Q | Q | Q | Q | Q | Q | Q | Q | 77 |
| V | V | V | V | V | V | V | V | V | V | 78 |
| F | V | V | V | V | V | V | V | V | V | 79 |
| L | L | L | L | L | L | L | L | L | L | 80 |
| K | T | T | T | T | T | T | T | T | T | 81 |
| I | M | M | M | M | M | M | M | M | M | 82 |
| A | T | T | T | T | T | T | T | T | T | 82A |
| S | N | N | N | N | N | N | N | N | N | 82B |
| V | M | M | M | M | M | M | M | M | M | 82C |
| D | D | D | D | D | D | D | D | D | D | 83 |
| T | P | P | P | P | P | P | P | P | P | 84 |
| A | V | V | V | V | V | V | V | V | V | 85 |
| D | D | D | D | D | D | D | D | D | D | 86 |
| T | T | T | T | T | T | T | T | T | T | 87 |
| A | A | A | A | A | A | A | A | A | A | 88 |
| T | T | T | T | T | T | T | T | T | T | 89 |
| Y | Y | Y | Y | Y | Y | Y | Y | Y | Y | 90 |
| Y | Y | Y | Y | Y | Y | Y | Y | Y | Y | 91 |
| C | C | C | C | C | C | C | C | C | C | 92 |
| A | A | A | A | A | A | A | A | A | A | 93 |
| Q | R | Q | T | K | A | H | R | H | Q | 94 |
| 122 | 123 | 124 | 125 | 126 | 127 | 128 | 129 | 130 | 131 | 82 SEQ ID NO. |
| 132 | 133 | 134 | 135 | 136 | 137 | 138 | 139 | 140 | 141 | 82A SEQ ID NO. |
| 142 | 143 | 144 | 145 | 146 | 147 | 148 | 149 | 150 | 151 | 82B SEQ ID NO. |
| 152 | 153 | 154 | 155 | 156 | 157 | 158 | 159 | 160 | 161 | 82C SEQ ID NO. |

TABLE 4F-continued

| FR3 | |
|---|---|
| SEQ ID NO. | Sequence |
| 122 | RLTISKDTSSNQVFLKIDTADTATYYCAQ |
| 123 | RLTISKDTSKNQVVLTMDPVDTATYYCAR |
| 124 | RLTISKDTSKNQVVLTMDPVDTATYYCAQ |
| 125 | RLTISKDTSKNQVVLTMDPVDTATYYCAT |
| 126 | RLTISKDTSKNQVVLTMDPVDTATYYCAK |
| 127 | RLTISKDTSKNQVVLTMDPVDTATYYCAA |
| 128 | RLTISKDTSKNQVVLTMDPVDTATYYCAH |
| 129 | RLTITKDTSKNQVVLTMDPVDTATYYCAR |
| 130 | RLTITKDTSKNQVVLTMDPVDTATYYCAH |
| 131 | RLTITKDTSKNQVVLTMDPVDTATYYCAQ |
| 132 | RLTISKDTSSNQVFLKADTADTATYYCAQ |
| 133 | RLTISKDTSKNQVVLTTDPVDTATYYCAR |
| 134 | RLTISKDTSKNQVVLTTDPVDTATYYCAQ |
| 135 | RLTISKDTSKNQVVLTTDPVDTATYYCAT |
| 136 | RLTISKDTSKNQVVLTTDPVDTATYYCAK |
| 137 | RLTISKDTSKNQVVLTTDPVDTATYYCAA |
| 138 | RLTISKDTSKNQVVLTTDPVDTATYYCAH |
| 139 | RLTITKDTSKNQVVLTTDPVDTATYYCAR |
| 140 | RLTITKDTSKNQVVLTTDPVDTATYYCAH |
| 141 | RLTITKDTSKNQVVLTTDPVDTATYYCAQ |
| 142 | RLTISKDTSSNQVFLKSDTADTATYYCAQ |
| 143 | RLTISKDTSKNQVVLTNDPVDTATYYCAR |
| 144 | RLTISKDTSKNQVVLTNDPVDTATYYCAQ |
| 145 | RLTISKDTSKNQVVLTNDPVDTATYYCAT |
| 146 | RLTISKDTSKNQVVLTNDPVDTATYYCAK |
| 147 | RLTISKDTSKNQVVLTNDPVDTATYYCAA |
| 148 | RLTISKDTSKNQVVLTNDPVDTATYYCAH |
| 149 | RLTITKDTSKNQVVLTNDPVDTATYYCAR |
| 150 | RLTITKDTSKNQVVLTNDPVDTATYYCAH |
| 151 | RLTITKDTSKNQVVLTNDPVDTATYYCAQ |
| 152 | RLTISKDTSSNQVFLKVDTADTATYYCAQ |
| 153 | RLTISKDTSKNQVVLTMDPVDTATYYCAR |
| 154 | RLTISKDTSKNQVVLTMDPVDTATYYCAQ |
| 155 | RLTISKDTSKNQVVLTMDPVDTATYYCAT |
| 156 | RLTISKDTSKNQVVLTMDPVDTATYYCAK |
| 157 | RLTISKDTSKNQVVLTMDPVDTATYYCAA |
| 158 | RLTISKDTSKNQVVLTMDPVDTATYYCAH |
| 159 | RLTITKDTSKNQVVLTMDPVDTATYYCAR |
| 160 | RLTITKDTSKNQVVLTMDPVDTATYYCAH |
| 161 | RLTITKDTSKNQVVLTMDPVDTATYYCAQ |

TABLE 4G

| CDR3 | | | | |
|---|---|---|---|---|
| A | B | C | D | RESIDUE |
| I | I | I | I | 95 |
| N | N | N | N | 96 |
| P | P | P | P | 97 |
| A | A | A | A | 98 |
| W | W | Y | Y | 99 |
| F | F | F | F | 100 |
| A | D | A | D | 101 |
| Y | Y | Y | Y | 102 |
| 162 | 163 | 164 | 165 | SEQ ID NO |

| SEQ ID NO. | Sequence |
|---|---|
| 162 | INPAWFAY |
| 163 | INPAWFDY |
| 164 | INPAYFAY |
| 165 | INPAYFDY |

TABLE 4H

| FR4 | | |
|---|---|---|
| A | B | RESIDUE |
| W | W | 103 |
| G | G | 104 |
| Q | Q | 105 |
| G | G | 106 |
| T | T | 107 |
| L | L | 108 |
| V | V | 109 |
| T | T | 110 |
| V | V | 111 |
| S | S | 112 |
| A | S | 113 |
| 166 | 167 | SEQ ID NO |

| SEQ ID NO. | Sequence |
|---|---|
| 166 | WGQGTLVTVSA |
| 167 | WGQGTLVTVSS |

In one embodiment, a CD16A binding protein may comprise a heavy chain variable domain sequence that is the same as, or similar to, the VH domain of the Hu3G8VH-1 construct, the sequence of which is provided in SEQ ID NO: 68. For example, the invention provides a CD16A binding protein comprising a VH domain with a sequence that (1) differs from the VH domain of Hu3G8VH-1 (SEQ ID NO: 68) by zero, one, or more than one of the CDR substitutions set forth in Table 1; (2) differs from the VH domain of Hu3G8VH-1 by zero, one or more than one of the framework substitutions set forth in Table 1; and (3) is at least about 80% identical, often at least about 90%, and sometimes at least about 95% identical, or even at least about 98% identical to the Hu3G8VH-1 VH sequence at the remaining positions.

Exemplary VH domains of CD16 binding proteins of the invention have the sequence of 3G8VH, Hu3G8VH-5 and Hu3G8VH-22 (SEQ ID NO: 79, SEQ ID NO: 69 and SEQ ID NO: 70, respectively). Exemplary nucleotide sequences encoding the sequences of 3G8VH and Hu3G8VH-5 (SEQ ID NO: 79 and SEQ ID NO: 69, respectively) are provided by SEQ ID NO: 80 and SEQ ID NO: 81, respectively.

The VH domain may have a sequence that differs from that of Hu3G8VH-1 (SEQ ID NO: 68) by at least one, at least two, at least three, at least four 4, at least five, or at least six of the substitutions shown in Table 3. These substitutions are believed to result in increased affinity for CD16A and/or reduce the immunogenicity of a CD16A binding protein when administered to humans. In certain embodiments, the degree of sequence identity with the Hu3G8VH-1 VH domain at the remaining positions is at least about 80%, at least about 90%, at least about 95% or at least about 98%.

For illustration and not limitation, the sequences of a number of CD16A building protein VH domains is shown in Table 4. Heavy chains comprising these sequences fused to a human Cγ1 constant region were coexpressed with the hu3G8VL-1 light chain (described below) to form tetrameric antibodies, and binding of the antibodies to CD16A was measured to assess the effect of amino acid substitutions compared to the hu3G8VH-1 VH domain. Constructs in which the VH domain has a sequence of hu3G8VH-1, 2, 3, 4, 5, 8, 12, 14, 16, 17, 18, 19, 20, 22, 23, 24, 25, 26, 27, 28, 29, 30, 31, 32, 33, 34, 35, 36, 37, 42, 43, 44 and 45 showed high affinity binding, with hu3G8VH-6 and −40 VH domains showing intermediate binding. CD16A binding proteins comprising the VH domains of hu3G8VH-5 and hu3G8VH-22 (SEQ ID NO: 69 and SEQ ID NO: 70, respectively) are considered to have particularly favorable binding properties.

5.1.2.2 VL Region

Similar studies were conducted to identify light chain variable domain sequences with favorable binding properties. In one aspect, the invention provides a CD16A binding protein containing a light chain variable domain in which at least one CDR (and usually three CDRs) has the sequence of a CDR (and more typically all three CDRs) of the mouse monoclonal antibody 3G8 light chain and for which the remaining portions of the binding protein are substantially human (derived from and substantially similar to, the heavy chain variable region of a human antibody or antibodies).

In one aspect, the invention provides a fragment of a humanized 3G8 antibody containing CDRs derived from the 3G8 antibody in a substantially human framework, but in which at least one of the CDRs of the light chain variable domain differs in sequence from the mouse monoclonal antibody 3G8 light chain CDR. In one embodiment, the CDR(s) differs from the 3G8 sequence at least by having one or more amino acid substitutions in a CDR, such as, one or more substitutions shown in Table 2 (e.g., arginine at position 24 in CDR1; serine at position 25 in CDR1; tyrosine at position 32 in CDR1; leucine at position 33 in CDR1; aspartic acid, tryptophan or serine at position 50 in CDR2; serine at position 53 in CDR2; alanine or glutamine at position 55 in CDR2; threonine at position 56 in CDR2; serine at position 93 in CDR3; and/or threonine at position 94 in CDR3). In various embodiments, the variable domain can have 0, 1, 2, 3, 4, 5, or more of these substitutions (and often have from 1 to 4 of these substitutions) and optionally, can have additional substitutions as well.

In one embodiment, a suitable CD16A binding protein may comprise a light chain variable domain sequence that is the same as, or similar to, the VL domain of the Hu3G8VL-1 (SEQ ID NO: 71) construct, the sequence of which is provided in Table 6. For example, the invention provides a CD16A binding protein comprising a VL domain with a sequence that (1) differs from the VL domain of Hu3G8VL-1 (SEQ ID NO: 71) by zero, one, or more of the CDR substitutions set forth in Table 5; (2) differs from the VL domain of Hu3G8VL-1 by zero, one or more of the framework substitutions set forth in Table 5; and (3) is at least about 80% identical, often at least about 90%, and sometimes at least about 95% identical, or even at least about 98% identical to the Hu3G8VL-1 VL sequence (SEQ ID NO: 71) at the remaining positions.

TABLE 5

3G8 $V_L$ Domain Substitutions

| No. | Kabat Position | Region | Substitutions |
|---|---|---|---|
| 1 | 24 | CDR1 | Arg |
| 2 | 25 | CDR1 | Ser |
| 3 | 32 | CDR1 | Tyr |
| 4 | 33 | CDR1 | Leu |
| 5 | 50 | CDR2 | Asp or Trp or Ser |
| 6 | 51 | CDR2 | Ala |
| 7 | 53 | CDR2 | Ser |
| 8 | 55 | CDR2 | Ala or Gln |
| 9 | 56 | CDR2 | Thr |
| 10 | 93 | CDR3 | Ser |
| 11 | 94 | CDR3 | Thr |

TABLE 6

| $V_L$ Sequences Derived from 3G8 $V_L$* | | | | | | | |
|---|---|---|---|---|---|---|---|
| | FR1 | CDR1 | FR2 | CDR2 | FR3 | CDR3 | FR4 |
| 3G8VL | A | A | A | A | A | A | A |
| Ch3G8VL | A | A | A | A | A | A | A |
| Hu3G8VL-1 | B | A | A | A | B | A | B |
| Hu3G8VL-2 | B | B | A | A | B | A | B |
| Hu3G8VL-3 | B | C | A | A | B | A | B |
| Hu3G8VL-4 | B | D | A | A | B | A | B |
| Hu3G8VL-5 | B | E | A | A | B | A | B |
| Hu3G8VL-6 | B | F | A | A | B | A | B |
| Hu3G8VL-7 | B | G | A | A | B | A | B |
| Hu3G8VL-8 | B | A | A | B | B | A | B |
| Hu3G8VL-9 | B | A | A | C | B | A | B |
| Hu3G8VL-10 | B | A | A | D | B | A | B |
| Hu3G8VL-11 | B | A | A | E | B | A | B |
| Hu3G8VL-12 | B | A | A | F | B | A | B |
| Hu3G8VL-13 | B | A | A | G | B | A | B |
| Hu3G8VL-14 | B | A | A | A | B | B | B |
| Hu3G8VL-15 | B | A | A | A | B | C | B |
| Hu3G8VL-16 | B | A | A | A | B | D | B |
| Hu3G8VL-17 | B | A | A | A | B | E | B |
| Hu3G8VL-18 | B | B | A | D | B | A | B |
| Hu3G8VL-19 | B | B | A | D | B | D | B |
| Hu3G8VL-20 | B | B | A | D | B | E | B |
| Hu3G8VL-21 | B | C | A | D | B | A | B |
| Hu3G8VL-22 | B | C | A | D | B | D | B |
| Hu3G8VL-23 | B | C | A | D | B | E | B |
| Hu3G8VL-24 | B | D | A | D | B | A | B |
| Hu3G8VL-25 | B | D | A | D | B | D | B |
| Hu3G8VL-26 | B | D | A | D | B | E | B |
| Hu3G8VL-27 | B | E | A | D | B | A | B |
| Hu3G8VL-28 | B | E | A | D | B | D | B |
| Hu3G8VL-29 | B | E | A | D | B | E | B |
| Hu3G8VL-30 | B | A | A | D | B | D | B |
| Hu3G8VL-31 | B | A | A | D | B | E | B |
| Hu3G8VL-32 | B | A | A | H | B | A | B |
| Hu3G8VL-33 | B | A | A | I | B | A | B |
| Hu3G8VL-34 | B | A | A | J | B | A | B |
| Hu3G8VL-35 | B | B | A | H | B | D | B |
| Hu3G8VL-36 | B | C | A | H | B | D | B |
| Hu3G8VL-37 | B | E | A | H | B | D | B |
| Hu3G8VL-38 | B | B | A | I | B | D | B |
| Hu3G8VL-39 | B | C | A | I | B | D | B |
| Hu3G8VL-40 | B | E | A | I | B | D | B |
| Hu3G8VL-41 | B | B | A | J | B | D | B |
| Hu3G8VL-42 | B | C | A | J | B | D | B |
| Hu3G8VL-43 | B | E | A | J | B | D | B |
| Hu3G8VL-44 | B | A | A | K | B | A | B |

*Letters in Table 6A refer to sequences in Tables 6B-H.

TABLE 6B

| FR1 | | |
|---|---|---|
| A | B | RESIDUE |
| D | D | 1 |
| T | I | 2 |
| V | V | 3 |
| L | M | 4 |
| T | T | 5 |
| Q | Q | 6 |
| S | S | 7 |
| P | P | 8 |
| A | D | 9 |
| S | S | 10 |
| L | L | 11 |
| A | A | 12 |
| V | V | 13 |
| S | S | 14 |
| L | L | 15 |
| G | G | 16 |
| Q | E | 17 |
| R | R | 18 |
| A | A | 19 |

TABLE 6B-continued

| FR1 | | |
|---|---|---|
| T | T | 20 |
| I | I | 21 |
| S | N | 22 |
| C | C | 23 |
| 168 | 169 | SEQ ID NO |

| SEQ ID NO. | Sequence |
|---|---|
| 168 | DTVLTQSPASLAVSL |
| 169 | DIVMTQSPDSLAVSL |

TABLE 6C

| CDR1 | | | | | | | |
|---|---|---|---|---|---|---|---|
| A | B | C | D | E | F | G | RESIDUE |
| K | R | K | K | K | K | K | 24 |
| A | A | S | A | A | A | A | 25 |
| S | S | S | S | S | S | S | 26 |
| Q | Q | Q | Q | Q | Q | Q | 27 |
| S | S | S | S | S | S | S | 27A |
| V | V | V | V | V | V | V | 27B |
| D | D | D | D | D | D | D | 27C |
| F | F | F | F | F | F | F | 27D |
| D | D | D | D | D | D | D | 28 |
| G | G | G | G | G | G | G | 29 |
| D | D | D | D | D | D | D | 30 |
| S | S | S | S | S | S | S | 31 |
| F | F | F | Y | F | F | Y | 32 |
| M | M | M | M | L | M | L | 33 |
| N | N | N | N | N | A | A | 34 |
| 170 | 171 | 172 | 173 | 174 | 175 | 176 | 27 SEQ ID NO |
| 177 | 178 | 179 | 180 | 181 | 182 | 183 | 27A SEQ ID NO |
| 184 | 185 | 186 | 187 | 188 | 189 | 190 | 27B SEQ ID NO |
| 191 | 192 | 193 | 194 | 195 | 196 | 197 | 27C SEQ ID NO |
| 198 | 199 | 200 | 201 | 202 | 203 | 204 | 27D SEQ ID NO |

| SEQ ID NO. | Sequence |
|---|---|
| 170 | KASQDGDSFMN |
| 171 | RASQDGDSFMN |
| 172 | KSSQDGDSFMN |
| 173 | KASQDGDSYMN |
| 174 | KASQDGDSFLN |
| 175 | KASQDGDSFMA |
| 176 | KASQDGDSYLA |
| 177 | KASSDGDSFMN |
| 178 | RASSDGDSFMN |
| 179 | KSSSDGDSFMN |
| 180 | KASSDGDSYMN |
| 181 | KASSDGDSFLN |
| 182 | KASSDGDSFMA |
| 183 | KASSDGDSYLA |
| 184 | KASVDGDSFMN |
| 185 | RASVDGDSFMN |
| 186 | KSSVDGDSFMN |
| 187 | KASVDGDSYMN |
| 188 | KASVDGDSFLN |
| 189 | KASVDGDSFMA |
| 190 | KASVDGDSYLA |
| 191 | KASDDGDSFMN |
| 192 | RASDDGDSFMN |
| 193 | KSSDDGDSFMN |
| 194 | KASDDGDSYMN |
| 195 | KASDDGDSFLN |
| 196 | KASDDGDSFMA |
| 197 | KASDDGDSYLA |

TABLE 6C-continued

| CDR1 | |
|---|---|
| 198 | KASFDGDSFMN |
| 199 | RASFDGDSFMN |
| 200 | KSSFDGDSFMN |
| 201 | KASFDGDSYMN |
| 202 | KASFDGDSFLN |
| 203 | KASFDGDSFMA |
| 204 | KASFDGDSYLA |

TABLE 6D

| FR2 | |
|---|---|
| A | RESIDUE |
| W | 35 |
| Y | 36 |
| Q | 37 |
| Q | 38 |
| K | 39 |
| P | 40 |
| G | 41 |
| Q | 42 |
| P | 43 |
| P | 44 |
| K | 45 |
| L | 46 |
| L | 47 |
| I | 48 |
| Y | 49 |
| 205 | SEQ ID NO |

| SEQ ID NO. | Sequence |
|---|---|
| 205 | WYQQKAPGQPPKLLIY |

TABLE 6E

| CDR2 | | | | | | | | | | | |
|---|---|---|---|---|---|---|---|---|---|---|---|
| A | B | C | D | E | F | G | H | I | J | K | RESIDUE |
| T | D | W | T | D | D | S | S | S | T | T | 50 |
| T | A | A | T | A | A | A | T | T | T | T | 51 |
| S | S | S | S | S | S | S | S | S | S | S | 52 |
| N | N | N | N | N | N | N | N | N | N | S | 53 |
| L | L | L | L | L | L | L | L | L | L | L | 54 |
| E | E | E | E | E | A | Q | E | Q | Q | Q | 55 |
| S | S | S | T | T | T | S | S | S | S | S | 56 |
| 206 | 207 | 208 | 209 | 210 | 211 | 212 | 213 | 214 | 215 | 216 | SEQ ID NO |

| SEQ ID NO. | Sequence |
|---|---|
| 206 | TTSNLQS |
| 207 | DASNLES |
| 208 | WASNLES |
| 209 | TTSNLET |
| 210 | DASNLET |
| 211 | DASNLAT |
| 212 | SASNLQS |
| 213 | STSNLES |
| 214 | SASNLQS |
| 215 | TTSNLQS |
| 216 | TTSSLQS |

TABLE 6F

| FR3 | | |
|---|---|---|
| A | B | RESIDUE |
| G | G | 57 |
| I | V | 58 |
| P | P | 59 |
| A | D | 60 |
| R | R | 61 |
| F | F | 62 |
| S | S | 63 |
| A | G | 64 |
| S | S | 65 |
| G | G | 66 |
| S | S | 67 |
| G | G | 68 |
| T | T | 69 |
| D | D | 70 |
| F | F | 71 |
| T | T | 72 |
| L | L | 73 |
| N | T | 74 |
| I | I | 75 |
| H | S | 76 |
| P | S | 77 |
| V | L | 78 |
| E | Q | 79 |
| E | A | 80 |
| E | E | 81 |
| D | D | 82 |
| T | V | 83 |
| A | A | 84 |
| T | V | 85 |
| Y | Y | 86 |
| Y | Y | 87 |
| C | C | 88 |
| 217 | 218 | SEQ ID NO |

| SEQ ID NO. | Sequence |
|---|---|
| 217 | GIPARFSASGSGTDFTLNIHPVEEEDTATYYC |
| 218 | GVPDRFSGSGSGTDFTLTISSLQAEDVAVYYC |

TABLE 6G

| CDR3 | | | | | |
|---|---|---|---|---|---|
| A | B | C | D | E | RESIDUE |
| Q | Q | Q | Q | Q | 89 |
| Q | Q | Q | Q | Q | 90 |
| S | S | S | S | S | 91 |
| N | Y | Y | N | N | 92 |
| E | S | E | S | E | 93 |
| D | T | D | D | T | 94 |
| P | P | P | P | P | 95 |
| Y | Y | Y | Y | Y | 96 |
| T | T | T | T | T | 97 |
| 219 | 220 | 221 | 222 | 223 | SEQ ID NO |

| SEQ ID NO. | Sequence |
|---|---|
| 219 | QQSNEDPYT |
| 220 | QQSYSTPYT |
| 221 | QQSYEDPYT |
| 222 | QQSNSDPYT |
| 223 | QQSNETPYT |

TABLE 6H

| FR4 | | |
|---|---|---|
| A | B | RESIDUE |
| F | F | 98 |
| G | G | 99 |
| G | Q | 100 |
| G | G | 101 |
| T | T | 102 |
| K | K | 103 |
| L | L | 104 |
| E | E | 105 |
| I | I | 106 |
| K | K | 107 |
| 224 | 225 | SEQ ID NO |

| SEQ ID NO. | Sequence |
|---|---|
| 224 | FGGGTKLEIK |
| 225 | FGQGTKLEIK |

Exemplary VL domains of CD16 binding proteins of the invention have the sequence of 3G8VL, Hu3G8VL-1 or Hu3G8VL-43, (SEQ ID NO: 82, SEQ ID NO: 71 and SEQ ID NO: 72, respectively) as shown in Tables 5 and 6. Exemplary nucleotide sequences encoding 3G8VL (SEQ ID NO: 82) and Hu3G8VL-1 (SEQ ID NO: 71) are provided in SEQ ID NO: 83 and SEQ ID NO: 84, respectively.

The VL domain may have a sequence that differs from that of Hu3G8VL-1 (SEQ ID NO: 71) by zero, one, at least two, at least 3, at least 4, at least 5, at least 6, at least 7, at least 8, or at least 9 of the substitutions shown in Table 2. These substitutions are believed to result in increased affinity for CD16A and/or reduce the immunogenicity of a CD16A binding protein when administered to humans. In certain embodiments, the degree of sequence identity at the remaining positions is at least about 80%, at least about 90% at least about 95% or at least about 98%.

For illustration and not limitation, the sequences of a number of CD16A binding proteins VL domains is shown in Table 6. Light chains comprising these sequences fused to a human Cκ. constant domain were coexpressed with a Hu3G8VH heavy chain (described above) to form tetrameric antibodies, and the binding of the antibodies to CD16A was measured to assess the effect of amino acid substitutions compared to the Hu3G8VL-1 VL domain (SEQ ID NO: 71). Constructs in which the VL domain has a sequence of hu3G8VL-1, 2, 3, 4, 5, 10, 16, 18, 19, 21, 22, 24, 27, 28, 32, 33, 34, 35, 36, 37, and 42 showed high affinity binding and hu3G8VL-15, 17, 20, 23, 25, 26, 29, 30, 31, 38, 39, 40 and 41 showed intermediate binding. CD16A binding proteins comprising the VL domains of hu3G8VL-1, hu3G8VL-22, and hu3G8VL-43 are considered to have particularly favorable binding properties (SEQ ID NO: 71, SEQ ID NO: 73 and SEQ ID NO: 72, respectively).

5.1.2.2.1. Combinations of VL and/or VH Domains

As is known in the art and described elsewhere herein, immunoglobulin light and heavy chains can be recombinantly expressed under conditions in which they associate to produce a diabody, or can be so combined in vitro. It will thus be appreciated that a 3G8-derived VL-domain described herein can be combined a 3G8-derived VH-domain described herein to produce a CD16A binding diabody, and all such combinations are contemplated.

For illustration and not for limitation, examples of useful CD16A diabodies are those comprising at least one VH domain and at least one VL domain, where the VH domain is from hu3G8VH-1, hu3G8VH-22 or hu3G8VH-5 (SEQ ID NO: 68, SEQ ID NO: 70 and SEQ ID NO: 69, respectively) and the VL domain is from hu3G8VL-1, hu3G8VL-22 or hu3G8VL-43 (SEQ ID NO: 71, SEQ ID NO: 73 and SEQ ID NO: 41, respectively). In particular, humanized antibodies that comprise hu3G8VH-22 (SEQ ID NO: 22) and either, hu3G8VL-1, hu3G8VL-22 or hu3G8VL-43 (SEQ ID NO: 71, SEQ ID NO: 70 and SEQ ID NO: 72, respectively), or hu3G8VH-5 (SEQ ID NO: 69) and hu3G8VL-1 (SEQ ID NO: 71) have favorable properties.

It will be appreciated by those of skill that the sequences of VL and VH domains described here can be further modified by art-known methods such as affinity maturation (see Schier et al. (1996) "*Isolation Of Picomolar Affinity Anti-C-ErbB-2 Single-Chain Fv By Molecular Evolution Of The Complementarity Determining Regions In The Center Of The Antibody Binding Site*," J. Mol. Biol. 263:551-567; Daugherty et al. (1998) "*Antibody Affinity Maturation Using Bacterial Surface Display*," Protein Eng. 11:825-832; Boder et al. (1997) "*Yeast Surface Display For Screening Combinatorial Polypeptide Libraries*," Nat. Biotechnol. 15:553-557; Boder et al. (2000) "*Directed Evolution Of Antibody Fragments With Monovalent Femtomolar Antigen-Binding Affinity*," Proc. Natl. Acad. Sci. U.S.A 97:10701-10705; Hudson et al. (2003) "*Engineered Antibodies*," Nature Medicine 9:129-39). For example, the CD16A binding proteins can be modified using affinity maturation techniques to identify proteins with increased affinity for CD16A and/or decreased affinity for CD16B.

One exemplary CD16 binding protein is the mouse 3G8 antibody. Amino acid sequence comprising the VH and VL domains of humanized 3G8 are described in FIGS. 2, 9, 14 and set forth in SEQ ID NO: 9, SEQ ID NO: 11, SEQ ID NO: 12, SEQ ID NO: 14, SEQ ID NO: 15, SEQ ID NO: 16, SEQ ID NO: 18, SEQ ID NO: 19, SEQ ID NO: 20, SEQ ID NO: 21, SEQ ID NO: 22, SEQ ID NO: 68, SEQ ID NO: 69, SEQ ID NO: 70, SEQ ID NO: 71 and SEQ ID NO: 72.

5.2. Diabodies Comprising Fc Regions or Portions Thereof

The invention encompasses diabody molecules comprising Fc domains or portions thereof (e.g., a CH2 or CH3 domain). In certain embodiments, the Fc domain, or portion(s) thereof, comprises one or more constant domain(s) of the Fc region of IgG2, IgG3 or IgG4 (e.g., CH2 or CH3). In other embodiments, the invention encompasses molecules comprising and Fc domain or portion thereof, wherein said Fc domain or portion thereof comprises at least one amino acid modification (e.g. substitution) relative to a comparable wild-type Fc domain or portion thereof. Variant Fc domains are well known in the art, and are primarily used to alter the phenotype of the antibody comprising said variant Fc domain as assayed in any of the binding activity or effector function assays well known in the art, e.g. ELISA, SPR analysis, or ADCC. Such variant Fc domains, or portions thereof, have use in the present invention by conferring or modifying the effector function exhibited by a diabody molecule of the invention comprising an Fc domain (or portion thereof) as functionally assayed, e.g., in an NK dependent or macrophage dependent assay. Fc domain variants identified as altering effector function are disclosed in International Application WO04/063351, U.S. Patent Application Publications 2005/0037000 and 2005/0064514, U.S. Provisional Applications 60/626,510, filed Nov. 10, 2004, 60/636,663, filed Dec. 15, 2004, and 60/781,564, filed Mar. 10, 2006, and U.S. patent application Ser. No. 11/271,140, filed Nov. 10, 2005, and Ser. No. 11/305,787, filed Dec. 15, 2005, concurrent applications of the Inventors, each of which is incorporated by reference in its entirety.

In other embodiments, the invention encompasses the use of any Fc variant known in the art, such as those disclosed in Duncan et al. (1988) "*Localization Of The Binding Site For The Human High-Affinity Fc Receptor On IgG*," Nature 332: 563-564; Lund et al. (1991) "*Human Fc Gamma RI And Fc Gamma RII Interact With Distinct But Overlapping Sites On Human IgG*," J. Immunol. 147:2657-2662; Lund et al. (1992) "*Multiple Binding Sites On The CH2 Domain Of IgG For Mouse Fc Gamma RII*," Mol. Immunol. 29:53-59; Alegre et al. (1994) "*A Non-Activating "Humanized" Anti-CD3 Monoclonal Antibody Retains Immunosuppressive Properties In Vivo*," Transplantation 57:1537-1543; Hutchins et al. (1995) "*Improved Biodistribution, Tumor Targeting, And Reduced Immunogenicity In Mice With A Gamma 4 Variant Of Campath-1H*," Proc. Natl. Acad. Sci. USA 92:11980-11984; Jefferis et al. (1995) "*Recognition Sites On Human IgG For Fc Gamma Receptors: The Role Of Glycosylation*," Immunol. Lett. 44:111-117; Lund et al. (1995) "*Oligosaccharide-Protein Interactions In IgG Can Modulate Recognition By Fc Gamma Receptors*," FASEB J. 9:115-119; Jefferis et al. (1996) "*Modulation Of Fc(Gamma)R And Human Complement Activation By IgG3-Core Oligosaccharide Interactions*," Immunol. Lett. 54:101-104; Lund et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969; Armour et al. (1999) "*Recombinant Human IgG Molecules Lacking Fcgamma Receptor I Binding And Monocyte Triggering Activities*," Eur. J. Immunol. 29:2613-2624; Idusogie et al. (2000) "*Mapping Of The ClQ Binding Site On Rituxan, A Chimeric Antibody With A Human IgG1 Fc*," J. Immunol. 164:4178-4184; Reddy et al. (2000) "*Elimination Of Fc Receptor-Dependent Effector Functions Of A Modified IgG4 Monoclonal Antibody To Human CD4*," J. Immunol. 164: 1925-1933; Xu et al. (2000) "*In Vitro Characterization Of Five Humanized OKT3 Effector Function Variant Antibodies*," Cell. Immunol. 200:16-26; Idusogie et al. (2001) "*Engineered Antibodies With Increased Activity To Recruit Complement*," J. Immunol. 166:2571-2575; Shields et al. (2001) "*High Resolution Mapping Of The Binding Site On Human IgG1 For Fc gamma RI, Fc gamma RII, Fc gamma RIII, And FcRn And Design Of IgG1 Variants With Improved Binding To The Fc gamma R*," J. Biol. Chem. 276:6591-6604; Jefferis et al. (2002) "*Interaction Sites On Human IgG-Fc For FcgammaR: Current Models*," Immunol. Lett. 82:57-65; Presta et al. (2002) "*Engineering Therapeutic Antibodies For Improved Function*," Biochem. Soc. Trans. 30:487-490); U.S. Pat. Nos. 5,624,821; 5,885,573; 6,194,551; PCT WO 00/42072; PCT WO 99/58572; each of which is incorporated herein by reference in its entirety.

In certain embodiments, said one or more modifications to the amino acids of the Fc region reduce the affinity and avidity of the Fc region and, thus, the diabody molecule of the invention, for one or more FcγR receptors. In a specific embodiment, the invention encompasses diabodies comprising a variant Fc region, or portion thereof, wherein said variant Fc region comprises at least one amino acid modification relative to a wild type Fc region, which variant Fc region only binds one FcγR, wherein said FcγR is FcγRIIIA. In another specific embodiment, the invention encompasses diabodies comprising a variant Fc region, or portion thereof, wherein said variant Fc region comprises at least one amino acid modification relative to a wild type Fc region, which variant Fc region only binds one FcγR, wherein said FcγR is FcγRIIA. In another specific embodiment, the invention encompasses diabodies comprising a variant Fc region, or portion thereof, wherein said variant Fc region comprises at least one amino acid modification relative to a wild type Fc region, which variant Fc region only binds one FcγR, wherein said FcγR is FcγRIIB. In certain embodiments, the invention encompasses molecules comprising a variant Fc domain wherein said variant confers or mediates increased ADCC activity and/or an increased binding to FcγRIIA (CD32A), relative to a molecule comprising no Fc domain or comprising a wild-type Fc domain, as measured using methods known to one skilled in the art and described herein. In alternate embodiments, the invention encompasses molecules comprising a variant Fc domain wherein said variant confers or mediates decreased ADCC activity (or other effector function) and/or an increased binding to FcγRIIB (CD32B), relative to a molecule comprising no Fc domain or comprising a wild-type Fc domain, as measured using methods known to one skilled in the art and described herein.

The invention also encompasses the use of an Fc domain comprising domains or regions from two or more IgG isotypes. As known in the art, amino acid modification of the Fc region can profoundly affect Fc-mediated effector function and/or binding activity. However, these alterations in functional characteristics can be further refined and/or manipulated when implemented in the context of selected IgG isotypes. Similarly, the native characteristics of the isotype Fc may be manipulated by the one or more amino acid modifications. The multiple IgG isotypes (i.e., IgG1, IgG2, IgG3 and IgG4) exhibit differing physical and functional properties including serum half-life, complement fixation, FcγR binding affinities and effector function activities (e.g. ADCC, CDC) due to differences in the amino acid sequences of their hinge and/or Fc domains. In certain embodiments, the amino acid modification and IgG Fc region are independently selected based on their respective, separate binding and/or effector function activities in order to engineer a diabody with desired characteristics. In most embodiments, said amino acid modifications and IgG hinge/Fc regions have been separately assayed for binding and/or effector function activity as described herein or known in the art in an the context of an IgG1. In certain embodiments, said amino acid modification and IgG hinge/Fc region display similar functionality, e.g., increased affinity for FcγRIIA, when separately assayed for FcγR binding or effector function in the context of the diabody molecule or other Fc-containing molecule (e.g. and immunoglobulin). The combination of said amino acid modification and selected IgG Fc region then act additively or, more preferably, synergistically to modify said functionality in the diabody molecule of the invention, relative to a diabody molecule of the invention comprising a wild-type Fc region. In other embodiments, said amino acid modification and IgG Fc region display opposite functionalities, e.g., increased and decreased, respectively, affinity for FcγRIIA, when separately assayed for FcγR binding and/or effector function in the context of the diabody molecule or other Fc containing molecule (e.g., an immunoglobulin) comprising a wild-type Fc region as described herein or known in the art; the combination of said "opposite" amino acid modification and selected IgG region then act to selectively temper or reduce a specific functionality in the diabody of the invention relative to a diabody of the invention not comprising an Fc region or comprising a wild-type Fc region of the same isotype. Alternatively, the invention encompasses variant Fc regions comprising combinations of amino acid modifications known in the art and selected IgG regions that exhibit novel properties, which properties were not detectable when said modifications and/or regions were independently assayed as described herein.

The functional characteristics of the multiple IgG isotypes, and domains thereof, are well known in the art. The amino acid sequences of IgG1, IgG2, IgG3 and IgG4 are presented in FIGS. 1A-1B. Selection and/or combinations of two or more domains from specific IgG isotypes for use in the methods of the invention may be based on any known parameter of the parent istoypes including affinity to FcγR (Table 7; Flesch et al. (2000) "*Functions Of The Fc Receptors For Immunoglobulin G*," J. Clin. Lab. Anal. 14:141-156; Chappel et al. (1993) "*Identification Of A Secondary Fc Gamma RI Binding Site Within A Genetically Engineered Human IgG Antibody*," J. Biol. Chem. 33:25124-25131; Chappel et al. (1991) "*Identification Of The Fc Gamma Receptor Class I Binding Site In Human IgG Through The Use Of Recombinant IgG1/IgG2 Hybrid And Point-Mutated Antibodies*," Proc. Natl. Acad. Sci. USA 88:9036-9040, each of which is hereby incorporated by reference in its entirety). For example, use of regions or domains from IgG isotypes that exhibit limited or no binding to FcγRIIB, e.g., IgG2 or IgG4, may find particular use where a diabody is desired to be engineered to maximize binding to an activating receptor and minimize binding to an inhibitory receptor. Similarly, use of Fc regions or domains from IgG isotypes known to preferentially bind Clq or FcγRIIIA, e.g., IgG3 (Brüggemann et al. (1987) "*Comparison Of The Effector Functions Of Human Immunoglobulins Using A Matched Set Of Chimeric Antibodies*," J. Exp. Med. 166:1351-1361), may be combined with Fc amino acid modifications of known in the art to enhance ADCC, to engineer a diabody molecule such that effector function activity, e.g., complement activation or ADCC, is maximized.

TABLE 7

General characteristics of IgG binding to FcγR, adapted from Flesch and Neppert, 1999, J. Clin. Lab. Anal. 14: 141-156

| Receptor | Estimated Affinity for IgG ($M^{-1}$) | Relative Affinity |
|---|---|---|
| FcγRI | $10^8$-$10^9$ | IgG3 > IgG1 >> IgG4<br>no-binding: IgG2 |
| FcγRIIA $R^{131\,A}$ | <$10^7$ | IgG3 > IgG1<br>no-binding: IgG2, IgG4 |
| FcγRIIA $H^{131\,A}$ | <$10^7$ | IgG3 > IgG1 > IgG2<br>no-binding: IgG4 |
| FcγRIIB $^A$ | <$10^7$ | IgG3 > IgG1 > IgG4<br>no-binding: IgG2 |
| FcγRIII | <$10^7$ | IgG3 = IgG1<br>no-binding: IgG2, IgG4 |

$^A$ binds only complexed IgG 5.3 Molecular Conjugates

The diabody molecules of the invention may be recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide to generate fusion proteins. The fusion does not necessarily need to be direct, but may occur through linker sequences.

Further, the diabody molecules of the invention (i.e., polypeptides) may be conjugated to a therapeutic agent or a drug moiety that modifies a given biological response. As an alternative to direct conjugation, owing to the multiple epitope binding sites on the multivalent, e.g., tetravalent, diabody molecules of the invention, at least one binding region of the diabody may be designed to bind the therapeutic agent or desired drug moiety without affecting diabody binding.

Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas ligand, and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF"), macrophage colony stimulating factor, ("M-CSF"), or a growth factor (e.g., growth hormone ("GH"); proteases, or ribonucleases.

The diabody molecules of the invention (i.e., polypeptides) can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al. (1989) "*Bioassay For Trans-Activation Using Purified Human Immunodeficiency Virus TAT-Encoded Protein: Trans-Activation Requires mRNA Synthesis*," Proc. Natl. Acad. Sci. USA, 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al. (1984) "*The Structure Of An Antigenic Determinant In A Protein*," Cell, 37:767-778) and the "flag" tag (Knappik et al. (1994) "*An Improved Affinity Tag Based On The FLAG Peptide For The Detection And Purification Of Recombinant Antibody Fragments*," Biotechniques, 17(4):754-761).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the invention (e.g., epitope binding sites with higher affinities and lower dissociation rates). See, generally, U.S. Pat. Nos. 5,605,793; 5,811,238; 5,830,721; 5,834,252; and 5,837,458, and Patten et al. (1997) "*Applications Of DNA Shuffling To Pharmaceuticals And Vaccines*," Curr. Opinion Biotechnol. 8:724-733; Harayama (1998) "*Artificial Evolution By DNA Shuffling*," Trends Biotechnol. 16:76-82; Hansson et al. (1999) "*Evolution Of Differential Substrate Specificities In Mu Class Glutathione Transferases Probed By DNA Shuffling*," J. Mol. Biol. 287: 265-276; and Lorenzo et al. (1998) "*PCR-Based Method For The Introduction Of Mutations In Genes Cloned And Expressed In Vaccinia Virus*," BioTechniques 24:308-313 (each of these patents and publications are hereby incorporated by reference in its entirety). The diabody molecules of the invention, or the nucleic acids encoding the molecules of the invention, may be further altered by being subjected to random mutagenesis by error-prone PCR, random nucleotide insertion or other methods prior to recombination. One or more portions of a polynucleotide encoding a molecule of the invention, may be recombined with one or more components, motifs, sections, parts, domains, fragments, etc. of one or more heterologous molecules.

The present invention also encompasses diabody molecules of the invention conjugated to or immunospecifically recognizing a diagnostic or therapeutic agent or any other molecule for which serum half-life is desired to be increased/decreased and/or targeted to a particular subset of cells. The molecules of the invention can be used diagnostically to, for example, monitor the development or progression of a disease, disorder or infection as part of a clinical testing procedure to, e.g., determine the efficacy of a given treatment regimen. Detection can be facilitated by coupling the molecules of the invention to a detectable substance or by the molecules immunospecifically recognizing the detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the molecules of the invention or indirectly, through an intermediate (such as, for example, a linker known in the art) using techniques known in the art, or the molecule may immunospecifically recognize the detectable substance: immunospecifically binding said substance. See, for example, U.S. Pat. No. 4,741,900 for metal ions which can be conjugated to antibodies for use as diagnostics according to the present invention. Such diagnosis and detection can be accomplished designing the molecules to immunospecifically recognize the detectable substance or by coupling the molecules of the invention to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The diabody molecules of the invention may immunospecifically recognize or be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, a diabody molecule of the invention can be conjugated to or be designed to immunospecifically recognize therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the polypeptide via a linker molecule. Such linker molecules are commonly known in the art and described in Denardo et al. (1998) "*Comparison Of* 1,4,7,10-*Tetraazacyclododecane-N,N',N'',N'''-Tetraacetic Acid* (*DOTA*)-*Peptide-ChL*6, *A Novel Immunoconjugate With Catabolizable Linker, To* 2-*Iminothiolane*-2-[*p*-(*bromoacetamido*)*benzyl*]-*DOTA-ChL*6 *In Breast Cancer Xenografts*," Clin. Cancer Res. 4:2483-2490; Peterson et al. (1999) "*Enzymatic Cleavage Of Peptide-Linked Radiolabels From Immunoconjugates*," Bioconjug. Chem. 10:553-; and Zimmerman et al, (1999) "*A Triglycine Linker Improves Tumor Uptake And Biodistributions Of* 67-*Cu-Labeled Anti-Neuroblastoma mAb chCE*7 *F*(*ab*')2 *Fragments*," Nucl. Med. Biol. 26:943-950 each of which is incorporated herein by reference in their entireties.

Techniques for conjugating such therapeutic moieties to polypeptides, including e.g., Fc domains, are well known; see, e.g., Amon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al. (1982) "*The Preparation And Cytotoxic Properties Of Antibody-Toxin Conjugates*," Immunol. Rev., 62:119-158.

The diabody molecule of the invention may be administered with or without a therapeutic moiety conjugated to it, administered alone, or in combination with cytotoxic factor(s) and/or cytokine(s) for use as a therapeutic treatment. Where administered alone, at least one epitope of a multivalent, e.g., tetravalent, diabody molecule may be designed to immunospecifically recognize a therapeutic agent, e.g., cytotoxic factor(s) and/or cytokine(s), which may be administered concurrently or subsequent to the molecule of the invention. In this manner, the diabody molecule may specifically target the therapeutic agent in a manner similar to direct conjugation. Alternatively, a molecule of the invention can be conjugated to an antibody to form an antibody heteroconjugate as described by Segal in U.S. Pat. No. 4,676,980, which is incorporated herein by reference in its entirety. Diabody molecules of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Characterization of Binding of Diabody Molecules

The diabody molecules of the present invention may be characterized in a variety of ways. In particular, molecules of the invention may be assayed for the ability to immunospecifically bind to an antigen, e.g., FcRIIIA or FcRIIB, or, where the molecule comprises an Fc domain (or portion thereof) for the ability to exhibit Fc-FcγR interactions, i.e. specific binding of an Fc domain (or portion thereof) to an FcγR. Such an assay may be performed in solution (e.g., Houghten (1992) "*The Use Of Synthetic Peptide Combinatorial Libraries For The Identification Of Bioactive Peptides*," BioTechniques, 13:412-421), on beads (Lam (1991) "*A New Type Of Synthetic Peptide Library For Identifying Ligand-Binding Activity*," Nature, 354:82-84, on chips (Fodor (1993) "*Multiplexed Biochemical Assays With Biological Chips*," Nature, 364:555-556), on bacteria (U.S. Pat. No. 5,223,409), on spores (U.S. Pat. Nos. 5,571,698; 5,403,484; and 5,223,409), on plasmids (Cull et al. (1992) "*Screening For Receptor Ligands Using Large Libraries Of Peptides Linked To The C Terminus Of The Lac Repressor*," Proc. Natl. Acad. Sci. USA, 89:1865-1869) or on phage (Scott et al. (1990) "*Searching For Peptide Ligands With An Epitope Library*," Science, 249: 386-390; Devlin (1990) "*Random Peptide Libraries: A Source Of Specific Protein Binding Molecules*," Science, 249: 404-406; Cwirla et al. (1990) "*Peptides On Phage: A Vast Library Of Peptides For Identifying Ligands*," Proc. Natl. Acad. Sci. USA, 87:6378-6382; and Felici (1991) "*Selection Of Antibody Ligands From A Large Library Of Oligopeptides Expressed On A Multivalent Exposition Vector*," J. Mol. Biol., 222:301-310) (each of these references is incorporated by reference herein in its entirety). Molecules that have been identified to immunospecifically bind to an antigen, e.g., FcγRIIIA, can then be assayed for their specificity and affinity for the antigen.

Molecules of the invention that have been engineered to comprise multiple epitope binding domains may be assayed for immunospecific binding to one or more antigens (e.g., cancer antigen and cross-reactivity with other antigens (e.g., FcγR)) or, where the molecules comprise am Fc domain (or portion thereof) for Fc-FcγR interactions by any method known in the art. Immunoassays which can be used to analyze immunospecific binding, cross-reactivity, and Fc-FcγR interactions include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, *Current Protocols in Molecular Biology*, Vol. 1, John Wiley & Sons, Inc., New York, which is incorporated by reference herein in its entirety).

The binding affinity and the off-rate of antigen-binding domain interaction or Fc-FcγR interaction can be determined by competitive binding assays. One example of a competitive binding assay is a radioimmunoassay comprising the incubation of labeled antigen, such as tetrameric FcγR (e.g., $^{3}H$ or $^{125}I$, see Section 5.4.1) with a molecule of interest (e.g., molecules of the present invention comprising multiple epitope binding domains in the presence of increasing amounts of unlabeled epitope, such as tetrameric FcγR (see Section 5.4.1), and the detection of the molecule bound to the labeled antigen. The affinity of the molecule of the present invention for an antigen and the binding off-rates can be determined from the saturation data by Scatchard analysis.

The affinities and binding properties of the molecules of the invention for an antigen or FcγR may be initially determined using in vitro assays (biochemical or immunological based assays) known in the art for antigen-binding domain or Fc-FcγR, interactions, including but not limited to ELISA assay, surface plasmon resonance assay, immunoprecipitation assays. Preferably, the binding properties of the molecules of the invention are also characterized by in vitro functional assays for determining one or more FcγR mediator effector cell functions, as described in section 5.4.2. In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, screening and identifying molecules comprising multiple epitope binding domains and, optionally, Fc domains (or portions thereof) are done functional based assays, preferably in a high throughput manner. The functional based assays can be any assay known in the art for characterizing one or more FcγR mediated effector cell functions such as those described herein in Sections 5.4.2 and 5.4.3. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1 q binding, and complement dependent cell mediated cytotoxicity.

In a preferred embodiment, BIAcore kinetic analysis is used to determine the binding on and off rates of molecules of the present invention to an antigen or and FcγR. BIAcore kinetic analysis comprises analyzing the binding and dissociation of an antigen or FcγR from chips with immobilized molecules (e.g., molecules comprising epitope binding domains or Fc domains (or portions thereof), respectively) on their surface. BIAcore analysis is described in Section 5.4.3.

Preferably, fluorescence activated cell sorting (FACS), using any of the techniques known to those skilled in the art, is used for immunological or functional based assay to characterize molecules of the invention. Flow sorters are capable of rapidly examining a large number of individual cells that have been bound, e.g., opsonized, by molecules of the invention (e.g., 10-100 million cells per hour) (Shapiro et al. (1995) *Practical Flow Cytometry*). Additionally, specific parameters used for optimization of diabody behavior, include but are not limited to, antigen concentration (i.e., FcγR tetrameric complex, see Section 5.4.1), kinetic competition time, or FACS stringency, each of which may be varied in order to select for the diabody molecules comprising molecules of the invention which exhibit specific binding properties, e.g., concurrent binding to multiple epitopes. Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477; the entire contents of which are incorporated by reference herein. Other known flow cytometers are the FACS Vantage™ system manufactured by Becton Dickinson and Company, and the COPAS™ system manufactured by Union Biometrica.

Characterization of target antigen binding affinity or Fc-FcγR binding affinity, and assessment of target antigen or FcγR density on a cell surface may be made by methods well known in the art such as Scatchard analysis or by the use of kits as per manufacturer's instructions, such as Quantum™ Simply Cellular® (Bangs Laboratories, Inc., Fishers, Ind.). The one or more functional assays can be any assay known in the art for characterizing one or more FcγR mediated effector cell function as known to one skilled in the art or described herein. In specific embodiments, the molecules of the invention comprising multiple epitope binding domains and, optionally, and Fc domain (or portion thereof) are assayed in an ELISA assay for binding to one or more target antigens or one or more FcγRs, e.g., FcγRIIIA, FcγRIIA, FcγRIIA; followed by one or more ADCC assays. In some embodiments, the molecules of the invention are assayed further using a surface plasmon resonance-based assay, e.g., BIAcore. Surface plasmon resonance-based assays are well known in the art, and are further discussed in Section 5.4.3, and exemplified herein, e.g., in Example 6.1.

In most preferred embodiments, the molecules of the invention comprising multiple epitope binding domains and, optionally, and Fc domain (or portion thereof) is further characterized in an animal model for interaction with a target antigen (e.g., an FcγR) or for Fc-FcγR interaction. Where Fc-FcγR interactions are to be assessed, preferred animal models for use in the methods of the invention are, for example, transgenic mice expressing human FcγRs, e.g., any mouse model described in U.S. Pat. Nos. 5,877,397, and 6,676,927 which are incorporated herein by reference in their entirety. Further transgenic mice for use in such methods include, but are not limited to, nude knockout FcγRIIIA mice carrying human FcγRIIIA; nude knockout FcγRIIIA mice carrying human FcγRIIA; nude knockout FcγRIIIA mice carrying human FcγRIIB and human FcγRIIIA; nude knockout FcγRIIIA mice carrying human FcγRIIB and human FcγRIIA; nude knockout FcγRIIIA and FcγRIIA mice carrying human FcγRIIIA and FcγRIIA and nude knockout FcγRIIIA, FcγRIIA and FcγRIIB mice carrying human FcγRIIIA, FcγRIIA and FcγRIIB.

5.3.1. Binding Assays Comprising FcγR

Characterization of binding to FcγR by molecules comprising an Fc domain (or portion thereof) and/or comprising epitope binding domain specific for an FcγR may be done using any FcγR, including but not limited to polymorphic variants of FcγR. In some embodiments, a polymorphic variant of FcγRIIIA is used, which contains a phenylalanine at position 158. In other embodiments, characterization is done using a polymorphic variant of FcγRIIIA which contains a valine at position 158. FcγRIIIA 158V displays a higher affinity for IgG1 than 158F and an increased ADCC activity (see, e.g., Koene et al. (1997) "*Fc gammaRIIIa-158V/F Polymorphism Influences The Binding Of IgG By Natural Killer Cell Fc gammaRIIIa, Independently Of The Fc gammaRIIIa-48L/R/H Phenotype*," Blood, 90:1109-14; Wu et al. (1997) "*A Novel Polymorphism Of FcgammaRIIIa (CD16) Alters Receptor Function And Predisposes To Autoimmune Disease*," J. Clin. Invest. 100: 1059-70, both of which are incorporated herein by reference in their entireties); this residue in fact directly interacts with the lower hinge region of IgG1 as recently shown by IgG1-FcγRIIIA co-crystallization studies, see, e.g., Sondermann et al. (2000) "*The 3.2-A Crystal Structure Of The Human IgG1 Fc Fragment-Fc gammaRIII complex*," Nature, 406(6793):267-273, which is incorporated herein by reference in its entirety. Studies have shown that in some cases, therapeutic antibodies have improved efficacy in FcγRIIIA-158V homozygous patients. For example, humanized anti-CD20 monoclonal antibody Rituximab was therapeutically more effective in FcγRIIIA158V homozygous patients compared to FcγRIIIA 158F homozygous patients (See, e.g., Cartron et al. (2002) "*Therapeutic Activity Of Humanized Anti-CD20 Monoclonal Antibody And Polymorphism In IgG Fc Receptor FcgammaRIIIA Gene*," Blood, 99(3): 754-758). In other embodiments, therapeutic molecules comprising this region may also be more effective on patients heterozygous for FcγRIIIA-158V and FcγRIIIA-158F, and in patients with FcγRIIA-131H. Although not intending to be bound by a particular mechanism of action, selection of molecules of the invention with alternate allotypes may provide for variants that once engineered into therapeutic diabodies will be clinically more efficacious for patients homozygous for said allotype.

An FcγR binding assay was developed for determining the binding of the molecules of the invention to FcγR, and, in particular, for determining binding of Fc domains to FcγR. The assay allowed detection and quantitation of Fc-FcγR interactions, despite the inherently weak affinity of the receptor for its ligand, e.g., in the micromolar range for FcγRIIB and FcγRIIIA. The method is described in detail in International Application WO04/063351 and U.S. Patent Application Publications 2005/0037000 and 2005/0064514, each of which is hereby incorporated by reference in its entirety. Briefly, the method involves the formation of an FcγR complex that may be sued in any standard immunoassay known in the art, e.g., FACS, ELISA, surface plasmon resonance, etc. Additionally, the FcγR complex has an improved avidity for an Fc region, relative to an uncomplexed FcγR. According to the invention, the preferred molecular complex is a tetrameric immune complex, comprising: (a) the soluble region of FcγR (e.g., the soluble region of FcγRIIIA, FcγRIIA or FcγRIIB); (b) a biotinylated 15 amino acid AVITAG sequence (AVITAG) operably linked to the C-terminus of the soluble region of FcγR (e.g., the soluble region of FcγRIIIA, FcγRIIA or FcγRIIB); and (c) streptavidin-phycoerythrin (SA-PE); in a molar ratio to form a tetrameric FcγR complex (preferably in a 5:1 molar ratio). The fusion protein is biotinylated enzymatically, using for example, the *E. coli* Bir A enzyme, a biotin ligase which specifically biotinylates a lysine residue in the 15 amino acid AVITAG sequence. The biotinylated soluble FcγR proteins are then mixed with SA-PE in a 1×SA-PE:5×biotinylated soluble FcγR molar ratio to form a tetrameric FcγR complex.

Polypeptides comprising Fc regions have been shown to bind the tetrameric FcγR complexes with at least an 8-fold higher affinity than the monomeric uncomplexed FcγR. The binding of polypeptides comprising Fc regions to the tetrameric FcγR complexes may be determined using standard techniques known to those skilled in the art, such as for example, fluorescence activated cell sorting (FACS), radioimmunoassays, ELISA assays, etc.

The invention encompasses the use of the immune complexes comprising molecules of the invention, and formed according to the methods described above, for determining the functionality of molecules comprising an Fc region in cell-based or cell-free assays.

As a matter of convenience, the reagents may be provided in an assay kit, i.e., a packaged combination of reagents for assaying the ability of molecules comprising Fc regions to bind FcγR tetrameric complexes. Other forms of molecular complexes for use in determining Fc-FcγR interactions are also contemplated for use in the methods of the invention, e.g., fusion proteins formed as described in U.S. Provisional Application 60/439,709, filed on Jan. 13, 2003; which is incorporated herein by reference in its entirety.

5.3.2. Functional Assays of Molecules with Variant Heavy Chains

The invention encompasses characterization of the molecules of the invention comprising multiple epitope binding domains and, optionally, Fc domains (or portions thereof) using assays known to those skilled in the art for identifying the effector cell function of the molecules. In particular, the invention encompasses characterizing the molecules of the invention for FcγR-mediated effector cell function. Additionally, where at least one of the target antigens of the diabody molecule of the invention is an FcγR, binding of the FcγR by the diabody molecule may serve to activate FcγR-mediated pathways similar to those activated by FcγR-Fc binding. Thus, where at least one eptiope binding domain of the diabody molecule recognizes an FcγR, the diabody molecule may elicit FcγR-mediated effector cell function without containing an Fc domain (or portion thereof), or without concomitant Fc-FcγR binding. Examples of effector cell functions that can be assayed in accordance with the invention, include but are not limited to, antibody-dependent cell mediated cytotoxicity, phagocytosis, opsonization, opsonophagocytosis, C1 q binding, and complement dependent cell mediated cytotoxicity. Any cell-based or cell free assay known to those skilled in the art for determining effector cell function activity can be used (For effector cell assays, see Perussia et al. (2000) "*Assays For Antibody-Dependent Cell-Mediated Cytotoxicity (ADCC) And Reverse ADCC (Redirected Cytotoxicity) In Human Natural Killer Cells*," Methods Mol. Biol. 121: 179-92; Baggiolini et al. (1988) "*Cellular Models For The Detection And Evaluation Of Drugs That Modulate Human Phagocyte Activity*," Experientia, 44(10): 841-848; Lehmann et al. (2000) "*Phagocytosis: Measurement By Flow Cytometry*," J. Immunol. Methods, 243(1-2): 229-42; Brown (1994) "*In Vitro Assays Of Phagocytic Function Of Human Peripheral Blood Leukocytes: Receptor Modulation And Signal Transduction*," Methods Cell Biol., 45: 147-64; Munn et al. (1990) "*Phagocytosis Of Tumor Cells By Human Monocytes Cultured In Recombinant Macrophage Colony-Stimulating Factor*," J. Exp. Med., 172: 231-237, Abdul-Majid et al. (2002) "*Fc Receptors Are Critical For Autoimmune Inflammatory Damage To The Central Nervous System In Experimental Autoimmune Encephalomyelitis*," Scand. J. Immunol. 55: 70-81; Ding et al. (1998) "*Two Human T Cell Receptors Bind In A Similar Diagonal Mode To The HLA-A2/Tax Peptide Complex Using Different TCR Amino Acids*," Immunity 8:403-411, each of which is incorporated by reference herein in its entirety).

In one embodiment, the molecules of the invention can be assayed for FcγR-mediated phagocytosis in human monocytes. Alternatively, the FcγR-mediated phagocytosis of the molecules of the invention may be assayed in other phagocytes, e.g., neutrophils (polymorphonuclear leuckocytes; PMN); human peripheral blood monocytes, monocyte-derived macrophages, which can be obtained using standard procedures known to those skilled in the art (e.g., see Brown (1994) "*In Vitro Assays Of Phagocytic Function Of Human Peripheral Blood Leukocytes: Receptor Modulation And Signal Transduction*," Methods Cell Biol., 45: 147-164). In one embodiment, the function of the molecules of the invention is characterized by measuring the ability of THP-1 cells to phagocytose fluoresceinated IgG-opsonized sheep red blood cells (SRBC) by methods previously described (Tridandapani et al. (2000) "*The Adapter Protein LAT Enhances Fcgamma Receptor-Mediated Signal Transduction In Myeloid Cells*," J. Biol. Chem. 275: 20480-20487).

Another exemplary assay for determining the phagocytosis of the molecules of the invention is an antibody-dependent opsonophagocytosis assay (ADCP) which can comprise the following: coating a target bioparticle such as *Escherichia coli*-labeled FITC (Molecular Probes) or *Staphylococcus aureus*-FITC with (i) wild-type 4-4-20 antibody, an antibody to fluorescein (See Bedzyk et al. (1989) "*Comparison Of Variable Region Primary Structures Within An Anti-Fluorescein Idiotype Family*," J. Biol. Chem., 264(3): 1565-1569, which is incorporated herein by reference in its entirety), as the control antibody for FcγR-dependent ADCP; or (ii) 4-4-20 antibody harboring the D265A mutation that knocks out binding to FcγRIII, as a background control for FcγR-dependent ADCP (iii) a diabody comprising the epitope binding domain of 4-4-20 and an Fc domain and/or an epitope binding domain specific for FcγRIII; and forming the opsonized particle; adding any of the opsonized particles described (1-11i) to THP-1 effector cells (a monocytic cell line available from ATCC) at a 1:1, 10:1, 30:1, 60:1, 75:1 or a 100:1 ratio to allow FcγR-mediated phagocytosis to occur; preferably incubating the cells and *E. coli*-FITC/antibody at 37° C. for 1.5 hour; adding trypan blue after incubation (preferably at room temperature for 2-3 min.) to the cells to quench the fluoroscence of the bacteria that are adhered to the outside of the cell surface without being internalized; transferring cells into a FACS buffer (e.g., 0.1%, BSA in PBS, 0.1%, sodium azide), analyzing the fluorescence of the THP1 cells using FACS (e.g., BD FACS Calibur). Preferably, the THP-1 cells used in the assay are analyzed by FACS for expression of FcγR on the cell surface. THP-1 cells express both CD32A and CD64. CD64 is a high affinity FcγR that is blocked in conducting the ADCP assay in accordance with the methods of the invention. The THP-1 cells are preferably blocked with 100 μg/mL soluble IgG1 or 10% human serum. To analyze the extent of ADCP, the gate is preferably set on THP-1 cells and median fluorescence intensity is measured. The ADCP activity for individual mutants is calculated and reported as a normalized value to the wild type chMab 4-4-20 obtained. The opsonized particles are added to THP-1 cells such that the ratio of the opsonized particles to THP-1 cells is 30:1 or 60:1. In most preferred embodiments, the ADCP assay is conducted with controls, such as *E. coli*-FITC in medium, *E. coli*-FITC and THP-1 cells (to serve as FcγR-independent ADCP activity), *E. coli*-FITC, THP-1 cells and wild-type 4-4-20 antibody (to serve as FcγR-dependent ADCP activity), *E. coli*-FITC, THP-1 cells, 4-4-20 D265A (to serve as the background control for FcγR-dependent ADCP activity).

In another embodiment, the molecules of the invention can be assayed for FcγR-mediated ADCC activity in effector cells, e.g., natural killer cells, using any of the standard methods known to those skilled in the art (See e.g., Perussia et al. (2000) "*Assays For Antibody-Dependent Cell-Mediated Cytotoxicity (ADCC) And Reverse ADCC (Redirected Cytotoxicity) In Human Natural Killer Cells*," Methods Mol. Biol. 121: 179-92; Weng et al. (2003) "*Two Immunoglobulin G Fragment C Receptor Polymorphisms Independently Predict Response To Rituximab In Patients With Follicular Lymphoma*," J. Clin. Oncol. 21:3940-3947; Ding et al. (1998) "*Two Human T Cell Receptors Bind In A Similar Diagonal Mode To The HLA-A2/Tax Peptide Complex Using Different TCR Amino Acids*," Immunity 8:403-411). An exemplary assay for determining ADCC activity of the molecules of the invention is based on a $^{51}Cr$ release assay comprising of: labeling target cells with $[^{51}Cr]Na_2CrO_4$ (this cell-membrane permeable molecule is commonly used for labeling since it binds cytoplasmic proteins and although spontaneously released from the cells with slow kinetics, it is released massively following target cell necrosis); opsonizing the target cells with the molecules of the invention comprising variant heavy chains; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the invention can then be determined, for example using the following formula: % lysis=(experimental cpm−target leak cpm)/(detergent lysis cpm−target leak cpm)×100%. Alternatively, % lysis =(ADCC−AICC)/(maximum release−spontaneous release). Specific lysis can be calculated using the formula: specific lysis=% lysis with the molecules of the invention−% lysis in the absence of the molecules of the invention. A graph can be generated by varying either the target: effector cell ratio or antibody concentration.

Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. Preferred effector cells for use in the methods of the invention express different FcγR activating receptors. The invention encompasses, effector cells, THP-1, expressing FcγRI, FcγRIIA and FcγRIIB, and monocyte derived primary macrophages derived from whole human blood expressing both FcγRIIIA and FcγRIIB, to determine if heavy chain antibody mutants show increased ADCC activity and phagocytosis relative to wild type IgG1 antibodies.

The human monocyte cell line, THP-1, activates phagocytosis through expression of the high affinity receptor FcγRI and the low affinity receptor FcγRIIA (Fleit et al. (1991) "*The Human Monocyte-Like Cell Line THP-*1 *Expresses Fc Gamma RI And Fc Gamma RII*," J. Leuk. Biol. 49: 556-565). THP-1 cells do not constitutively express FcγRIIA or FcγRIIB. Stimulation of these cells with cytokines affects the FcR expression pattern (Pricop et al. (2001) "*Differential Modulation Of Stimulatory And Inhibitory Fc Gamma Receptors On Human Monocytes By Th*1 *And Th*2 *Cytokines*," J. of Immunol., 166: 531-537). Growth of THP-1 cells in the presence of the cytokine IL4 induces FcγRIIB expression and causes a reduction in FcγRIIA and FcγRI expression. FcγRIIB expression can also be enhanced by increased cell density (Tridandapani et al. (2002) "*Regulated Expression And Inhibitory Function Of Fcgamma RIIB In Human Monocytic Cells*," J. Biol. Chem., 277(7): 5082-5089). In contrast, it has been reported that IFNγ can lead to expression of FcγRIIIA (Pearse et al. (1993) "*Interferon Gamma-Induced Transcription Of The High-Affinity Fc Receptor For IgG Requires Assembly Of A Complex That Includes The* 91-*kDa Subunit Of Transcription Factor ISGF*3," Proc. Nat. Acad. Sci. USA 90: 4314-4318). The presence or absence of receptors on the cell surface can be determined by FACS using common methods known to one skilled in the art. Cytokine induced expression of FcγR on the cell surface provides a system to test both activation and inhibition in the presence of FcγRIIB. If THP-1 cells are unable to express the FcγRIIB the invention also encompasses another human monocyte cell line, U937. These cells have been shown to terminally differentiate into macrophages in the presence of IFNγ and TNF (Koren et al. (1979) "*In Vitro Activation Of A Human Macrophage-Like Cell Line*," Nature 279: 328-331).

FcγR dependent tumor cell killing is mediated by macrophage and NK cells in mouse tumor models (Clynes et al. (1998) "*Fc Receptors Are Required In Passive And Active Immunity To Melanoma*," Proc. Nat. Acad. Sci. USA 95: 652-656). The invention encompasses the use of elutriated monocytes from donors as effector cells to analyze the efficiency Fc mutants to trigger cell cytotoxicity of target cells in both phagocytosis and ADCC assays. Expression patterns of FcγRI, FcγRIIIA, and FcγRIIB are affected by different growth conditions. FcγR expression from frozen elutriated monocytes, fresh elutriated monocytes, monocytes maintained in 10% FBS, and monocytes cultured in FBS +GM-CSF and or in human serum may be determined using common methods known to those skilled in the art. For example, cells can be stained with FcγR specific antibodies and analyzed by FACS to determine FcR profiles. Conditions that best mimic macrophage in vivo FcγR expression is then used for the methods of the invention.

In some embodiments, the invention encompasses the use of mouse cells especially when human cells with the right FcγR profiles are unable to be obtained. In some embodiments, the invention encompasses the mouse macrophage cell line RAW264.7(ATCC) which can be transfected with human FcγRIIIA and stable transfectants isolated using methods known in the art, see, e.g., Ralph et al. (1977) "*Antibody-Dependent Killing Of Erythrocyte And Tumor Targets By Macrophage-Related Cell Lines Enhancement By PPD And LPS*," J. Immunol. 119: 950-4). Transfectants can be quantitated for FcγRIIIA expression by FACS analysis using routine experimentation and high expressors can be used in the ADCC assays of the invention. In other embodiments, the invention encompasses isolation of spleen peritoneal macrophage expressing human FcγR from knockout transgenic mice such as those disclosed herein.

Lymphocytes may be harvested from peripheral blood of donors (PBM) using a Ficoll-Paque gradient (Pharmacia). Within the isolated mononuclear population of cells the majority of the ADCC activity occurs via the natural killer cells (NK) containing FcγRIIIA but not FcγRIIB on their surface. Results with these cells indicate the efficacy of the mutants on triggering NK cell ADCC and establish the reagents to test with elutriated monocytes.

Target cells used in the ADCC assays of the invention include, but are not limited to, breast cancer cell lines, e.g., SK-BR-3 with ATCC accession number HTB-30 (see, e.g., Tremp et al. (1976) "*Human Breast Cancer In Culture*," Recent Results Cancer Res. 33-41); B-lymphocytes; cells derived from Burkitts lymphoma, e.g., Raji cells with ATCC accession number CCL-86 (see, e.g., Epstein et al. (1965) "*Characteristics And Mode Of Growth Of Tissue Culture Strain* (*EBI*) *Of Human Lymphoblasts From Burkitt's Lymphoma*," J. Natl. Cancer Inst. 34: 231-240), and Daudi cells with ATCC accession number CCL-213 (see, e.g., Klein et al. (1968) "*Surface IgM-Kappa Specificity On A Burkitt Lymphoma Cell In Vivo And In Derived Culture Lines*," Cancer Res. 28: 1300-1310). The target cells must be recognized by the antigen binding site of the diabody molecule to be assayed.

The ADCC assay is based on the ability of NK cells to mediate cell death via an apoptotic pathway. NK cells mediate cell death in part by FcγRIIIA's recognition of an IgG Fc domain bound to an antigen on a cell surface. The ADCC assays used in accordance with the methods of the invention may be radioactive based assays or fluorescence based assays. The ADCC assay used to characterize the molecules of the invention comprising variant Fc regions comprises labeling target cells, e.g., SK-BR-3, MCF-7, OVCAR3, Raji, Daudi cells, opsonizing target cells with an antibody that recognizes a cell surface receptor on the target cell via its antigen binding site; combining the labeled opsonized target cells and the effector cells at an appropriate ratio, which can be determined by routine experimentation; harvesting the cells; detecting the label in the supernatant of the lysed target cells, using an appropriate detection scheme based on the label used. The target cells may be labeled either with a radioactive label or a fluorescent label, using standard methods known in the art. For example the labels include, but are not limited to, $[^{51}Cr]Na_2CrO_4$; and the acetoxymethyl ester of the fluorescence enhancing ligand, 2,2':6',2"-terpyridine-6-6"-dicarboxylate (TDA).

In a specific preferred embodiment, a time resolved fluorimetric assay is used for measuring ADCC activity against target cells that have been labeled with the acetoxymethyl ester of the fluorescence enhancing ligand, 2,2':6',2"-terpyridine-6-6"-dicarboxylate (TDA). Such fluorimetric assays are known in the art, e.g., see, Blomberg et al. (1996) "*Time-Resolved Fluorometric Assay For Natural Killer Activity Using Target Cells Labelled With A Fluorescence Enhancing Ligand*," Journal of Immunological Methods, 193: 199-206; which is incorporated herein by reference in its entirety. Briefly, target cells are labeled with the membrane permeable acetoxymethyl diester of TDA (bis(acetoxymethyl) 2,2':6',2"-terpyridine-6-6"-dicarboxylate, (BATDA), which rapidly diffuses across the cell membrane of viable cells. Intracellular esterases split off the ester groups and the regenerated membrane impermeable TDA molecule is trapped inside the cell. After incubation of effector and target cells, e.g., for at least two hours, up to 3.5 hours, at 37° C., under 5% $CO_2$, the TDA released from the lysed target cells is chelated with Eu3+ and the fluorescence of the Europium-TDA chelates formed is quantitated in a time-resolved fluorometer (e.g., Victor 1420, Perkin Elmer/Wallace).

In another specific embodiment, the ADCC assay used to characterize the molecules of the invention comprising multiple epitope binding sites and, optionally, an Fc domain (or portion thereof) comprises the following steps: Preferably $4\text{-}5\times10^6$ target cells (e.g., SK-BR-3, MCF-7, OVCAR3, Raji cells) are labeled with bis(acetoxymethyl) 2,2':6',2"-terpyridine-t-6"-dicarboxylate (DELFIA BATDA Reagent, Perkin Elmer/Wallac). For optimal labeling efficiency, the number of target cells used in the ADCC assay should preferably not exceed $5\times10^6$. BATDA reagent is added to the cells and the mixture is incubated at 37° C. preferably under 5% $CO_2$, for at least 30 minutes. The cells are then washed with a physiological buffer, e.g., PBS with 0.125 mM sulfinpyrazole, and media containing 0.125 mM sulfinpyrazole. The labeled target cells are then opsonized (coated) with a molecule of the invention comprising an epitope binding domain specific for FcγRIIA and, optionally, an Fc domain (or portion thereof). In preferred embodiments, the molecule used in the ADCC assay is also specific for a cell surface receptor, a tumor antigen, or a cancer antigen. The diabody molecule of the invention may specifically bind any cancer or tumor antigen, such as those listed in section 5.6.1. The target cells in the ADCC assay are chosen according to the epitope binding sites engineered into the diabody of the invention, such that the diabody binds a cell surface receptor of the target cell specifically.

Target cells are added to effector cells, e.g., PBMC, to produce effector:target ratios of approximately 1:1, 10:1, 30:1, 50:1, 75:1, or 100:1. The effector and target cells are incubated for at least two hours, up to 3.5 hours, at 37° C., under 5% $CO_2$. Cell supernatants are harvested and added to an acidic europium solution (e.g., DELFIA Europium Solution, Perkin Elmer/Wallac). The fluorescence of the Europium-TDA chelates formed is quantitated in a time-resolved fluorometer (e.g., Victor 1420, Perkin Elmer/Wallac). Maximal release (MR) and spontaneous release (SR) are determined by incubation of target cells with 1% TX-100 and media alone, respectively. Antibody independent cellular cytotoxicity (AICC) is measured by incubation of target and effector cells in the absence of a test molecule, e.g., diabody of the invention. Each assay is preferably performed in triplicate. The mean percentage specific lysis is calculated as: Experimental release (ADCC)−AICC)/(MR−SR)×100.

The invention encompasses assays known in the art, and exemplified herein, to characterize the binding of C1q and mediation of complement dependent cytotoxicity (CDC) by molecules of the invention comprising Fc domains (or portions thereof). To determine C1q binding, a Clq binding ELISA may be performed. An exemplary assay may comprise the following: assay plates may be coated overnight at 4 C with polypeptide comprising a molecule of the invention or starting polypeptide (control) in coating buffer. The plates may then be washed and blocked. Following washing, an aliquot of human Clq may be added to each well and incubated for 2 hrs at room temperature. Following a further wash, 100 uL of a sheep anti-complement C1q peroxidase conjugated antibody may be added to each well and incubated for 1 hour at room temperature. The plate may again be washed with wash buffer and 100 ul of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 ul of 4.5 NH2 SO4. The absorbance may then read at (492-405) nm.

To assess complement activation, a complement dependent cytotoxicity (CDC) assay may be performed, e.g. as described in Gazzano-Santoro et al. (1997) "*A Non-Radioactive Complement-Dependent Cytotoxicity Assay For Anti-CD*20 *Monoclonal Antibody*," J. Immunol. Methods 202:163-171, which is incorporated herein by reference in its entirety. Briefly, various concentrations of the molecule comprising a (variant) Fc domain (or portion thereof) and human complement may be diluted with buffer. Cells which express the antigen to which the diabody molecule binds may be diluted to a density of about $1\times10^6$ cells/ml. Mixtures of the diabody molecules comprising a (variant) Fc domain (or portion thereof), diluted human complement and cells expressing the antigen may be added to a flat bottom tissue culture 96 well plate and allowed to incubate for 2 hrs at 37° C. and 5% CO2 to facilitate complement mediated cell lysis. 50 uL of alamar blue (Accumed International) may then be added to each well and incubated overnight at 37° C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant molecule, i.e., a molecule not comprising an Fc domain or comprising a non-variant Fc domain, is reported for the variant of interest.

5.3.3. Other Assays

The molecules of the invention comprising multiple epitope binding domain and, optionally, an Fc domain may be assayed using any surface plasmon resonance based assays known in the art for characterizing the kinetic parameters of an antigen-binding domain or Fc-FcγR binding. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al. (2000) "*Surface Plasmon Resonance-Based Immunoassays*," Methods 22: 77-91; Dong et al. (2002) "*Some new aspects in biosensors*," Reviews in Mol. Biotech. 82: 303-23; Fivash et al. (1998) "*BIAcore For Macromolecular Interaction*," Current Opinion in Biotechnology 9: 97-101; Rich et al. (2000) "*Advances In Surface Plasmon Resonance Biosensor Analysis*," Current Opinion in Biotechnology 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125, all of which are incorporated herein by reference in their entirety, are contemplated in the methods of the invention.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occurs is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

In some embodiments, the kinetic parameters of the binding of molecules of the invention comprising multiple epitope binding sites and, optionally, and Fc domain, to an antigen or an FcγR may be determined using a BIAcore instrument (e.g., BIAcore instrument 1000, BIAcore Inc., Piscataway, N.J.). As discussed supra, see section 5.4.1, any FcγR can be used to assess the binding of the molecules of the invention either where at least one epitope binding site of the diabody molecule immunospecifically recognizes an FcγR, and/or where the diabody molecule comprises an Fc domain (or portion thereof). In a specific embodiment the FcγR is FcγRIIIA, preferably a soluble monomeric FcγRIIIA. For example, in one embodiment, the soluble monomeric FcγRIIIA is the extracellular region of FcγRIIIA joined to the linker-AVITAG sequence (see, U.S. Provisional Application No. 60/439,498, filed on Jan. 9, 2003 and U.S. Provisional Application No. 60/456,041 filed on Mar. 19, 2003, which are incorporated herein by reference in their entireties). In another specific embodiment, the FcγR is FcγRIIB, preferably a soluble dimeric FcγRIIB. For example in one embodiment, the soluble dimeric FcγRIIB protein is prepared in accordance with the methodology described in U.S. Provisional application No. 60/439,709 filed on Jan. 13, 2003, which is incorporated herein by reference in its entirety.

For all immunological assays, FcγR recognition/binding by a molecule of the invention may be effected by multiple domains: in certain embodiments, molecules of the invention immunospecifically recognize an FcγR via one of the multiple epitope binding domains; in yet other embodiments, where the molecule of the invention comprises an Fc domain (or portion thereof), the diabody molecule may immunospecifically recognize an FcγR via Fc-FcγR interactions; in yet further embodiments, where a molecule of the invention comprises both an Fc domain (or portion thereof) and an epitope binding site that immunospecifically recognizes an FcγR, the diabody molecule may recognize an FcγR via one or both of an epitope binding domain and the Fc domain (or portion thereof). An exemplary assay for determining the kinetic parameters of a molecule comprising multiple epitope binding domains and, optionally, and Fc domain (or portion thereof) to an antigen and/or an FcγR using a BIAcore instrument comprises the following: a first antigen is immobilized on one of the four flow cells of a sensor chip surface, preferably through amine coupling chemistry such that about 5000 response units (RU) of said first antigen is immobilized on the surface. Once a suitable surface is prepared, molecules of the invention that immunospecifically recognize said first antigen are passed over the surface, preferably by one minute injections of a 20 μg/mL solution at a 5 μL/mL flow rate. Levels of molecules of the invention bound to the surface at this stage typically ranges between 400 and 700 RU. Next, dilution series of a second antigen (e.g., FcγR) or FcγR receptor in HBS-P buffer (20 mM HEPES, 150 mM NaCl, 3 mM EDTA, pH 7.5) are injected onto the surface at 100 μL/min Regeneration of molecules between different second antigen or receptor dilutions is carried out preferably by single 5 second injections of 100 mM $NaHCO_3$ pH 9.4; 3M NaCl. Any regeneration technique known in the art is contemplated in the method of the invention.

Once an entire data set is collected, the resulting binding curves are globally fitted using computer algorithms supplied by the SPR instrument manufacturer, e.g., BIAcore, Inc. (Piscataway, N.J.). These algorithms calculate both the $K_{on}$ and $K_{off}$, from which the apparent equilibrium binding constant, $K_d$ is deduced as the ratio of the two rate constants (i.e., $K_{off}/K_{on}$). More detailed treatments of how the individual rate constants are derived can be found in the BIAevaluaion Software Handbook (BIAcore, Inc., Piscataway, N.J.). The analysis of the generated data may be done using any method known in the art. For a review of the various methods of interpretation of the kinetic data generated see Myszka (1997) "*Kinetic Analysis Of Macromolecular Interactions Using Surface Plasmon Resonance Biosensors*," Current Opinion in Biotechnology 8: 50-7; Fisher et al. (1994) "*Surface Plasmon Resonance Based Methods For Measuring The Kinetics And Binding Affinities Of Biomolecular Interactions*," Current Opinion in Biotechnology 5: 389-95; O'Shannessy (1994) "*Determination Of Kinetic Rate And Equilibrium Binding Constants For Macromolecular Interactions: A Critique Of The Surface Plasmon Resonance Literature*," Current Opinion in Biotechnology, 5:65-71; Chaiken et al. (1992) "*Analysis Of Macromolecular Interactions Using Immobilized Ligands*," Analytical Biochemistry, 201: 197-210; Morton et al. (1995) "*Interpreting Complex Binding Kinetics From Optical Biosensors: A Comparison Of Analysis By Linearization, The Integrated Rate Equation, And Numerical Integration*," Analytical Biochemistry 227: 176-85; O'Shannessy et al., 1996, *Analytical Biochemistry* 236: 275-83; all of which are incorporated herein by reference in their entirety.

In preferred embodiments, the kinetic parameters determined using an SPR analysis, e.g., BIAcore, may be used as a predictive measure of how a molecule of the invention will function in a functional assay, e.g., ADCC. An exemplary method for predicting the efficacy of a molecule of the invention based on kinetic parameters obtained from an SPR analysis may comprise the following: determining the $K_{off}$ values for binding of a molecule of the invention to FcγRIIIA and FcγRIIB (via an epitope binding domain and/or an Fc domain (or portion thereof)); plotting (1) $K_{off}$ (wt)/$K_{off}$ (mut) for FcγRIIIA; (2) $K_{off}$ (mut)/$K_{off}$ (wt) for FcγRIIB against the ADCC data. Numbers higher than one show a decreased dissociation rate for FcγRIIIA and an increased dissociation rate for FcγRIIB relative to wild type; and possess and enhanced ADCC function.

5.4 Methods of Producing Diabody Molecules of the Invention

The diabody molecules of the present invention can be produced using a variety of methods well known in the art, including de novo protein synthesis and recombinant expression of nucleic acids encoding the binding proteins. The desired nucleic acid sequences can be produced by recombinant methods (e.g., PCR mutagenesis of an earlier prepared variant of the desired polynucleotide) or by solid-phase DNA synthesis. Usually recombinant expression methods are used. In one aspect, the invention provides a polynucleotide that comprises a sequence encoding a CD16A VH and/or VL; in another aspect, the invention provides a polynucleotide that comprises a sequence encoding a CD32B VH and/or VL. Because of the degeneracy of the genetic code, a variety of nucleic acid sequences encode each immunoglobulin amino acid sequence, and the present invention includes all nucleic acids encoding the binding proteins described herein.

5.4.1. Polynucleotides Encoding Molecules of the Invention

The present invention also includes polynucleotides that encode the molecules of the invention, including the polypeptides and antibodies. The polynucleotides encoding the molecules of the invention may be obtained, and the nucleotide sequence of the polynucleotides determined, by any method known in the art.

Once the nucleotide sequence of the molecules that are identified by the methods of the invention is determined, the nucleotide sequence may be manipulated using methods well known in the art, e.g., recombinant DNA techniques, site directed mutagenesis, PCR, etc. (see, for example, the techniques described in Sambrook et al., 2001, *Molecular Cloning, A Laboratory Manual,* 3rd Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate, for example, antibodies having a different amino acid sequence, for example by generating amino acid substitutions, deletions, and/or insertions.

In one embodiment, human libraries or any other libraries available in the art, can be screened by standard techniques known in the art, to clone the nucleic acids encoding the molecules of the invention.

5.4.2. Recombinant Expression of Molecules of the Invention

Once a nucleic acid sequence encoding molecules of the invention (i.e., antibodies) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, *Molecular Cloning, A Laboratory Manual,* 2d Ed., Cold Spring Harbor Laboratory, Cold Spring Harbor, N.Y. and Ausubel et al. eds., 1998, *Current Protocols in Molecular Biology*, John Wiley & Sons, NY).

An expression vector comprising the nucleotide sequence of a molecule identified by the methods of the invention can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter.

The host cells used to express the molecules identified by the methods of the invention may be either bacterial cells such as *Escherichia coli*, or, preferably, eukaryotic cells, especially for the expression of whole recombinant immunoglobulin molecule. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "*Powerful And Versatile Enhancer-Promoter Unit For Mammalian Expression Vectors*," Gene 45:101-106; Cockett et al. (1990) "*High Level Expression Of Tissue Inhibitor Of Metalloproteinases In Chinese Hamster Ovary Cells Using Glutamine Synthetase Gene Amplification*," Biotechnology 8:662-667).

A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the molecules identified by the methods of the invention; yeast (e.g., *Saccharomyces pichia*) transformed with recombinant yeast expression vectors containing sequences encoding the molecules identified by the methods of the invention; insect cell systems infected with recombinant virus expression vectors (e.g., baclovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Rüther et al. (1983) "*Easy Identification Of cDNA Clones*," EMBO J. 2:1791-1794), in which the antibody coding sequence may be ligated individually into the vector in frame with the lac Z coding region so that a fusion protein is produced; pIN vectors (Inouye et al. (1985) "*Up-Promoter Mutations In The* 1*pp Gene Of Escherichia Coli*," Nucleic Acids Res. 13:3101-3110; Van Heeke et al. (1989) "*Expression Of Human Asparagine Synthetase In Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "*Adenovirus Tripartite Leader Sequence Enhances Translation Of mRNAs Late After Infection*," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "*Expression And Secretion Vectors For Yeast*," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides comprising a diabody molecule of the invention may be expressed as a single gene product (e.g., as a single polypeptide chain, i.e., as a polyprotein precursor), requiring proteolytic cleavage by native or recombinant cellular mechanisms to form the separate polypeptides of the diabody molecules of the invention. The invention thus encompasses engineering a nucleic acid sequence to encode a polyprotein precursor molecule comprising the polypeptides of the invention, which includes coding sequences capable of directing post translational cleavage of said polyprotein precursor. Post-translational cleavage of the polyprotein precursor results in the polypeptides of the invention. The post translational cleavage of the precursor molecule comprising the polypeptides of the invention may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action). Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin (which recognizes the amino acid sequence LVPR^GS (SEQ ID NO: 89)), or factor Xa (which recognizes the amino acid sequence I(E/D)GR^ (SEQ ID NO: 90) (Nagai et al. (1985) "*Oxygen Binding Properties Of Human Mutant Hemoglobins Synthesized In Escherichia Coli*," Proc. Nat. Acad. Sci. USA 82:7252-7255, and reviewed in Jenny et al. (2003) "*A Critical Review Of The Methods For Cleavage Of Fusion Proteins With Thrombin And Factor Xa*," Protein Expr. Purif. 31:1-11, each of which is incorporated by reference herein in its entirety)), enterokinase (which recognizes the amino acid sequence DDDDK^ (SEQ ID NO: 91) (Collins-Racie et al. (1995) "*Production Of Recombinant Bovine Enterokinase Catalytic Subunit In Escherichia Coli Using The Novel Secretory Fusion Partner DsbA*," Biotechnology 13:982-987 hereby incorporated by reference herein in its entirety)), furin (which recognizes the amino acid sequence RXXR^, with a preference for RX(K/R)R^ (SEQ ID NO: 92 and SEQ ID NO: 93, respectively) (additional R at P6 position appears to enhance cleavage)), and AcTEV (which recognizes the amino acid sequence ENLYFQ^G (SEQ ID NO: 94) (Parks et al. (1994) "*Release Of Proteins And Peptides From Fusion Proteins Using A Recombinant Plant Virus Proteinase*," Anal. Biochem. 216:413-417 hereby incorporated by reference herein in its entirety)) and the Foot and Mouth Disease Virus Protease C3. See for example, section 6.4, supra.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the molecules of the invention.

A number of selection systems may be used, including but not limited to the herpes simplex virus thymidine kinase (Wigler et al. (1977) "*Transfer Of Purified Herpes Virus Thymidine Kinase Gene To Cultured Mouse Cells*," Cell 11: 223-232), hypoxanthine-guanine phosphoribosyltransferase (Szybalska et al. (1992) "*Use Of The HPRT Gene And The HAT Selection Technique In DNA-Mediated Transformation Of Mammalian Cells First Steps Toward Developing Hybridoma Techniques And Gene Therapy*," Bioessays 14: 495-500), and adenine phosphoribosyltransferase (Lowy et al. (1980) "*Isolation Of Transforming DNA: Cloning The Hamster aprt Gene*," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "*Transformation Of Mammalian Cells With An Amplifiable Dominant-Acting Gene*," Proc. Natl. Acad. Sci. USA 77:3567-3570; O'Hare et al. (1981) "*Transformation Of Mouse Fibroblasts To Methotrexate Resistance By A Recombinant Plasmid Expressing A Prokaryotic Dihydrofolate Reductase*," Proc. Natl. Acad. Sci. USA 78: 1527-1531); gpt, which confers resistance to mycophenolic acid (Mulligan et al. (1981) "*Selection For Animal Cells That Express The Escherichia coli Gene Coding For Xanthine-Guanine Phosphoribosyltransferase*," Proc. Natl. Acad. Sci. USA 78: 2072-2076); neo, which confers resistance to the aminoglycoside G-418 (Tolstoshev (1993) "*Gene Therapy, Concepts, Current Trials And Future Directions*," Ann. Rev. Pharmacol. Toxicol. 32:573-596; Mulligan (1993) "*The Basic Science Of Gene Therapy*," Science 260:926-932; and Morgan et al. (1993) "*Human Gene Therapy*," Ann. Rev. Biochem. 62:191-217) and hygro, which confers resistance to hygromycin (Santerre et al. (1984) "*Expression Of Prokaryotic Genes For Hygromycin B And G418 Resistance As Dominant-Selection Markers In Mouse L Cells*," Gene 30:147-156). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al. (1981) "*A New Dominant Hybrid Selective Marker For Higher Eukaryotic Cells*," J. Mol. Biol. 150: 1-14.

The expression levels of a molecule of the invention can be increased by vector amplification (for a review, see Bebbington and Hentschel, *The use of vectors based on gene amplification for the expression of cloned genes in mammalian cells in DNA cloning*, Vol. 3 (Academic Press, New York, 1987). When a marker in the vector system expressing an antibody is amplifiable, increase in the level of inhibitor present in culture of host cell will increase the number of copies of the marker gene. Since the amplified region is associated with the nucleotide sequence of a polypeptide of the diabody molecule, production of the polypeptide will also increase (Crouse et al. (1983) "*Expression And Amplification Of Engineered Mouse Dihydrofolate Reductase Minigenes*," Mol. Cell. Biol. 3:257-266).

The host cell may be co-transfected with two expression vectors of the invention, the first vector encoding the first polypeptide of the diabody molecule and the second vector encoding the second polypeptide of the diabody molecule. The two vectors may contain identical selectable markers which enable equal expression of both polypeptides. Alternatively, a single vector may be used which encodes both polypeptides. The coding sequences for the polypeptides of the molecules of the invention may comprise cDNA or genomic DNA.

Once a molecule of the invention (i.e., diabodies) has been recombinantly expressed, it may be purified by any method known in the art for purification of polypeptides, polyproteins or diabodies (e.g., analogous to antibody purification schemes based on antigen selectivity) for example, by chromatography (e.g., ion exchange, affinity, particularly by affinity for the specific antigen (optionally after Protein A selection where the diabody molecule comprises an Fc domain (or portion thereof)), and sizing column chromatography), centrifugation, differential solubility, or by any other standard technique for the purification of polypeptides, polyproteins or diabodies.

5.5 Prophylactic and Therapeutic Methods

The molecules of the invention are particularly useful for the treatment and/or prevention of a disease, disorder or infection where an effector cell function (e.g., ADCC) mediated by FcγR is desired (e.g., cancer, infectious disease). As discussed supra, the diabodies of the invention may exhibit antibody-like functionality in eliciting effector function although the diabody molecule does not comprise and Fc domain. By comprising at least one epitope binding domain that immunospecifically recognizes an FcγR, the diabody molecule may exhibit FcγR binding and activity analogous to Fc-FcγR interactions. For example, molecules of the invention may bind a cell surface antigen and an FcγR (e.g., FcγRIIIA) on an immune effector cell (e.g., NK cell), stimulating an effector function (e.g., ADCC, CDC, phagocytosis, opsonization, etc.) against said cell.

In other embodiments, the diabody molecule of the invention comprises an Fc domain (or portion thereof). In such embodiments, the Fc domain may further comprise at least one amino acid modification relative to a wild-type Fc domain (or portion thereof) and/or may comprise domains from one or more IgG isotypes (e.g., IgG1, IgG2, IgG3 or IgG4). Molecules of the invention comprising variant Fc domains may exhibit conferred or altered phenotypes relative to molecules comprising the wild type Fc domain such as an altered or conferred effector function activity (e.g., as assayed in an NK dependent or macrophage dependent assay). In said embodiments, molecules of the invention with conferred or altered effector function activity are useful for the treatment and/or prevention of a disease, disorder or infection where an enhanced efficacy of effector function activity is desired. In certain embodiments, the diabody molecules of the invention comprising an Fc domain (or portion thereof) mediate complement dependent cascade. Fc domain variants identified as altering effector function are disclosed in International Application WO04/063351, U.S. Patent Application Publications 2005/0037000 and 2005/0064514, U.S. Provisional Applications 60/626,510, filed Nov. 10, 2004, 60/636,663, filed Dec. 15, 2004, and 60/781,564, filed Mar. 10, 2006, and U.S. patent application Ser. No. 11/271,140, filed Nov. 10, 2005, and Ser. No. 11/305,787, filed Dec. 15, 2005, concurrent applications of the Inventors, each of which is incorporated by reference in its entirety.

The invention encompasses methods and compositions for treatment, prevention or management of a cancer in a subject, comprising administering to the subject a therapeutically effective amount of one or more molecules comprising one or more epitope binding sites, and optionally, an Fc domain (or portion thereof) engineered in accordance with the invention, which molecule further binds a cancer antigen. Molecules of the invention are particularly useful for the prevention, inhibition, reduction of growth or regression of primary tumors, metastasis of cancer cells, and infectious diseases. Although not intending to be bound by a particular mechanism of action, molecules of the invention mediate effector function resulting in tumor clearance, tumor reduction or a combination thereof. In alternate embodiments, the diabodies of the invention mediate therapeutic activity by cross-linking of cell surface antigens and/or receptors and enhanced apoptosis or negative growth regulatory signaling.

Although not intending to be bound by a particular mechanism of action, the diabody molecules of the invention exhibit enhanced therapeutic efficacy relative to therapeutic antibodies known in the art, in part, due to the ability of diabody to immunospecifically bind a target cell which expresses a particular antigen (e.g., FcγR) at reduced levels, for example, by virtue of the ability of the diabody to remain on the target cell longer due to an improved avidity of the diabody-epitope interaction.

The diabodies of the invention with enhanced affinity and avidity for antigens (e.g., FcγRs) are particularly useful for the treatment, prevention or management of a cancer, or another disease or disorder, in a subject, wherein the FcγRs are expressed at low levels in the target cell populations. As used herein, FcγR expression in cells is defined in terms of the density of such molecules per cell as measured using common methods known to those skilled in the art. The molecules of the invention comprising multiple epitope binding sites and, optionally, and FcγR (or portion thereof) preferably also have a conferred or an enhanced avidity and affinity and/or effector function in cells which express a target antigen, e.g., a cancer antigen, at a density of 30,000 to 20,000 molecules/cell, at a density of 20,000 to 10,000 molecules/cell, at a density of 10,000 molecules/cell or less, at a density of 5000 molecules/cell or less, or at a density of 1000 molecules/cell or less. The molecules of the invention have particular utility in treatment, prevention or management of a disease or disorder, such as cancer, in a sub-population, wherein the target antigen is expressed at low levels in the target cell population.

The molecules of the invention may also be advantageously utilized in combination with other therapeutic agents known in the art for the treatment or prevention of diseases, such as cancer, autoimmune disease, inflammatory disorders, and infectious diseases. In a specific embodiment, molecules of the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The molecules of the invention may also be advantageously utilized in combination with one or more drugs used to treat a disease, disorder, or infection such as, for example anti-cancer agents, anti-inflammatory agents or anti-viral agents, e.g., as detailed in Section 5.7.

5.5.1 Cancers

The invention encompasses methods and compositions for treatment or prevention of cancer in a subject comprising administering to the subject a therapeutically effective amount of one or more molecules comprising multiple epitope binding domains. In some embodiments, the invention encompasses methods and compositions for the treatment or prevention of cancer in a subject with FcγR polymorphisms such as those homozygous for the FγRIIIA-158V or FcγRIIIA-158F alleles. In some embodiments, the invention encompasses engineering at least one epitope binding domain of the diabody molecule to immunospecifically bind FcγRIIIA (158F). In other embodiments, the invention encompasses engineering at least one epitope binding domain of the diabody molecule to immunospecifically bind FcγRIIIA (158V).

The efficacy of standard monoclonal antibody therapy depends on the FcγR polymorphism of the subject (Cartron et al. (2002) "*Therapeutic Activity Of Humanized Anti-CD20 Monoclonal Antibody And Polymorphism In IgG Fc Receptor FcRIIIa Gene*," Blood 99: 754-758; Weng et al. (2003) "*Two Immunoglobulin G Fragment C Receptor Polymorphisms Independently Predict Response To Rituximab In Patients With Follicular Lymphoma*," J Clin Oncol. 21(21):3940-3947, both of which are incorporated herein by reference in their entireties). These receptors are expressed on the surface of the effector cells and mediate ADCC. High affinity alleles, of the low affinity activating receptors, improve the effector cells' ability to mediate ADCC. In contrast to relying on Fc-FcγR interactions to effect effector function, the methods of the invention encompass engineering molecules to immunospecifically recognize the low affinity activating receptors, allowing the molecules to be designed for a specific polymorphism. Alternately or additionally, the molecule of the invention may be engineered to comprise a variant Fc domain that exhibits enhanced affinity to FcγR (relative to a wild type Fc domain) on effector cells. The engineered molecules of the invention provide better immunotherapy reagents for patients regardless of their FcγR polymorphism.

Diabody molecules engineered in accordance with the invention are tested by ADCC using either a cultured cell line or patient derived PMBC cells to determine the ability of the Fc mutations to enhance ADCC. Standard ADCC is performed using methods disclosed herein. Lymphocytes are harvested from peripheral blood using a Ficoll-Paque gradient (Pharmacia). Target cells, i.e., cultured cell lines or patient derived cells, are loaded with Europium (PerkinElmer) and incubated with effectors for 4 hrs at 37° C. Released Europium is detected using a fluorescent plate reader (Wallac). The resulting ADCC data indicates the efficacy of the molecules of the invention to trigger NK cell mediated cytotoxicity and establish which molecules can be tested with both patient samples and elutriated monocytes. Diabody molecules showing the greatest potential for eliciting ADCC activity are then tested in an ADCC assay using PBMCs from patients. PBMC from healthy donors are used as effector cells.

Accordingly, the invention provides methods of preventing or treating cancer characterized by a cancer antigen by engineering the diabody molecule to immunospecifically recognize said cancer antigen such that the diabody molecule is itself cytotoxic (e.g., via crosslinking of surface receptors leading to increased apoptosis or downregulation of proliferative signals) and/or comprises an Fc domain, according to the invention, and/or mediates one or more effector function (e.g., ADCC, phagocytosis). The diabodies that have been engineered according to the invention are useful for prevention or treatment of cancer, since they have an cytotoxic activity (e.g., enhanced tumor cell killing and/or enhanced for example, ADCC activity or CDC activity).

Cancers associated with a cancer antigen may be treated or prevented by administration of a diabody that binds a cancer antigen and is cytotoxic, and/or has been engineered according to the methods of the invention to exhibit effector function. For example, but not by way of limitation, cancers associated with the following cancer antigens may be treated or prevented by the methods and compositions of the invention: KS 1/4 pan-carcinoma antigen (Perez et al. (1989) "*Isolation And Characterization Of A Cdna Encoding The Ks1/4 Epithelial Carcinoma Marker*," J. Immunol. 142:3662-3667;

Möller et al. (1991) "*Bispecific-Monoclonal-Antibody-Directed Lysis Of Ovarian Carcinoma Cells By Activated Human T Lymphocytes*," Cancer Immunol. Immunother. 33(4):210-216), ovarian carcinoma antigen (CA125) (Yu et al. (1991) "*Coexpression Of Different Antigenic Markers On Moieties That Bear CA* 125 *Determinants*," Cancer Res. 51(2):468-475), prostatic acid phosphate (Tailor et al. (1990) "*Nucleotide Sequence Of Human Prostatic Acid Phosphatase Determined From A Full-Length cDNA Clone*," Nucl. Acids Res. 18(16):4928), prostate specific antigen (Henttu et al. (1989) "*cDNA Coding For The Entire Human Prostate Specific Antigen Shows High Homologies To The Human Tissue Kallikrein Genes*," Biochem. Biophys. Res. Comm. 10(2): 903-910; Israeli et al. (1993) "*Molecular Cloning Of A Complementary DNA Encoding A Prostate-Specific Membrane Antigen*," Cancer Res. 53:227-230), melanoma-associated antigen p97 (Estin et al. (1989) "*Transfected Mouse Melanoma Lines That Express Various Levels Of Human Melanoma-Associated Antigen p*97," J. Natl. Cancer Instit. 81(6):445-454), melanoma antigen gp75 (Vijayasardahl et al. (1990) "*The Melanoma Antigen Gp*75 *Is The Human Homologue Of The Mouse B* (*Brown*) *Locus Gene Product*," J. Exp. Med. 171(4):1375-1380), high molecular weight melanoma antigen (HMW-MAA) (Natali et al. (1987) "*Immunohistochemical Detection Of Antigen In Human Primary And Metastatic Melanomas By The Monoclonal Antibody* 140.240 *And Its Possible Prognostic Significance*," Cancer 59:55-63; Mittelman et al. (1990) "*Active Specific Immunotherapy In Patients With Melanoma. A Clinical Trial With Mouse Antiidiotypic Monoclonal Antibodies Elicited With Syngeneic Anti-High-Molecular-Weight-Melanoma-Associated Antigen Monoclonal Antibodies*," J. Clin. Invest. 86:2136-2144)), prostate specific membrane antigen, carcinoembryonic antigen (CEA) (Foon et al. (1995) "*Immune Response To The Carcinoembryonic Antigen In Patients Treated With An Anti-Idiotype Antibody Vaccine*," J. Clin. Invest. 96(1):334-42), polymorphic epithelial mucin antigen, human milk fat globule antigen, Colorectal tumor-associated antigens such as: CEA, TAG-72 (Yokota et al. (1992) "*Rapid Tumor Penetration Of A Single-Chain Fv And Comparison With Other Immunoglobulin Forms*," Cancer Res. 52:3402-3408), CO17-1A (Ragnhammar et al. (1993) "*Effect Of Monoclonal Antibody* 17-1*A And GM-CSF In Patients With Advanced Colorectal Carcinoma—Long-Lasting, Complete Remissions Can Be Induced*," Int. J. Cancer 53:751-758); GICA 19-9 (Herlyn et al. (1982) "*Monoclonal Antibody Detection Of A Circulating Tumor-Associated Antigen. I. Presence Of Antigen In Sera Of Patients With Colorectal, Gastric, And Pancreatic Carcinoma*," J. Clin. Immunol. 2:135-140), CTA-1 and LEA, Burkitt's lymphoma antigen-38.13, CD19 (Ghetie et al. (1994) "*Anti-CD*19 *Inhibits The Growth Of Human B-Cell Tumor Lines In Vitro And Of Daudi Cells In SCID Mice By Inducing Cell Cycle Arrest*," Blood 83:1329-1336), human B-lymphoma antigen-CD20 (Reff et al. (1994) "*Depletion Of B Cells In Vivo By A Chimeric Mouse Human Monoclonal Antibody To CD*20," Blood 83:435-445), CD33 (Sgouros et al. (1993) "*Modeling And Dosimetry Of Monoclonal Antibody M*195 (*Anti-CD*33) *In Acute Myelogenous Leukemia*," J. Nucl. Med. 34:422-430), melanoma specific antigens such as ganglioside GD2 (Saleh et al. (1993) "*Generation Of A Human Anti-Idiotypic Antibody That Mimics The GD*2 *Antigen*," J. Immunol., 151, 3390-3398), ganglioside GD3 (Shitara et al. (1993) "*A Mouse/Human Chimeric Anti-*(*Ganglioside GD*3) *Antibody With Enhanced Antitumor Activities*," Cancer Immunol. Immunother. 36:373-380), ganglioside GM2 (Livingston et al. (1994) "*Improved Survival In Stage III Melanoma Patients With GM*2 *Antibodies: A Randomized Trial Of Adjuvant Vaccination With GM*2 *Ganglioside*," J. Clin. Oncol. 12:1036-1044), ganglioside GM3 (Hoon et al. (1993) "*Molecular Cloning Of A Human Monoclonal Antibody Reactive To Ganglioside GM*3 *Antigen On Human Cancers*," Cancer Res. 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellström et al. (1985) "*Monoclonal Antibodies To Cell Surface Antigens Shared By Chemically Induced Mouse Bladder Carcinomas*," Cancer. Res. 45:2210-2188), differentiation antigen such as human lung carcinoma antigen L6, L20 (Hellström et al. (1986) "*Monoclonal Mouse Antibodies Raised Against Human Lung Carcinoma*," Cancer Res. 46:3917-3923), antigens of fibrosarcoma, human leukemia T cell antigen-Gp37 (Bhattacharya-Chatterjee et al. (1988) "*Idiotype Vaccines Against Human T Cell Leukemia. II. Generation And Characterization Of A Monoclonal Idiotype Cascade* (*Ab*1, *Ab*2, *and Ab*3)," J. Immunol. 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al. (1992) "*Cell Membrane-Associated Mucins And Their Adhesion-Modulating Property*," Trends in Biochem. Sci. 17:359-363), malignant human lymphocyte antigen-APO-1 (Trauth et al. (1989) "*Monoclonal Antibody-Mediated Tumor Regression By Induction Of Apoptosis*," Science 245:301-304), differentiation antigen (Feizi (1985) "*Demonstration By Monoclonal Antibodies That Carbohydrate Structures Of Glycoproteins And Glycolipids Are Onco-Developmental Antigens*," Nature 314:53-57) such as I antigen found in fetal erthrocytes and primary endoderm, I(Ma) found in gastric adenocarcinomas, M18 and M39 found in breast epithelium, SSEA-1 found in myeloid cells, VEP8, VEP9, Myl, VIM-D5, and $D_1$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma, CO-514 (blood group $Le^a$) found in adenocarcinoma, NS-10 found in adenocarcinomas, CO-43 (blood group $Le^b$), G49, EGF receptor, (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson (1998) "*Cutaneous T-Cell Lymphoma: A Model For Selective Immunotherapy*," Cancer J Sci Am. 4:62-71).

Cancers and related disorders that can be treated or prevented by methods and compositions of the present invention include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma, gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, superficial spreading melanoma, nodular melanoma, lentigo malignant melanoma, acral lentiginous melanoma; kidney cancers including but not limited to, renal cell cancer, adenocarcinoma, hypernephroma, fibrosarcoma, transitional cell cancer (renal pelvis and/or uterer); Wilms' tumor; bladder cancers including but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al. (1985) *Medicine,* 2d Ed., J.B. Lippincott Co., Philadelphia; and Murphy et al. (1997) *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, prostate, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

In a specific embodiment, a molecule of the invention (e.g., a diabody comprising multiple epitope binding domains and, optionally, and Fc domain (or portion thereof)) inhibits or reduces the growth of cancer cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of cancer cells in the absence of said molecule of the invention.

In a specific embodiment, a molecule of the invention (e.g., a diabody comprising multiple epitope binding domains and, optionally, and Fc domain (or portion thereof)) kills cells or inhibits or reduces the growth of cancer cells at least 5%, at least 10%, at least 20%, at least 25%, at least 30%, at least 35%, at least 40%, at least 45%, at least 50%, at least 60%, at least 70%, at least 75%, at least 80%, at least 85%, at least 90%, at least 95%, or at least 100% better than the parent molecule.

5.5.2 Autoimmune Disease and Inflammatory Diseases

In some embodiments, molecules of the invention comprise an epitope binding domain specific for FcγRIIB and or/a variant Fc domain (or portion thereof), engineered according to methods of the invention, which Fc domain exhibits greater affinity for FcγRIIB and decreased affinity for FcγRIIIA and/or FcγRIIA relative to a wild-type Fc domain. Molecules of the invention with such binding characteristics are useful in regulating the immune response, e.g., in inhibiting the immune response in connection with autoimmune diseases or inflammatory diseases. Although not intending to be bound by any mechanism of action, molecules of the invention with an affinity for FcγRIIB and/or comprising an Fc domain with increased affinity for FcγRIIB and a decreased affinity for FcγRIIIA and/or FcγRIIA may lead to dampening of the activating response to FcγR and inhibition of cellular responsiveness, and thus have therapeutic efficacy for treating and/or preventing an autoimmune disorder.

The invention also provides methods for preventing, treating, or managing one or more symptoms associated with an inflammatory disorder in a subject further comprising, administering to said subject a therapeutically or prophylactically effective amount of one or more anti-inflammatory agents. The invention also provides methods for preventing, treating, or managing one or more symptoms associated with an autoimmune disease further comprising, administering to said subject a therapeutically or prophylactically effective amount of one or more immunomodulatory agents. Section 5.7 provides non-limiting examples of anti-inflammatory agents and immunomodulatory agents.

Examples of autoimmune disorders that may be treated by administering the molecules of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. As described herein in Section 2.2.2, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections.

Molecules of the invention comprising at least one epitope binding domain specific for FcγRIIB and/or a variant Fc domain with an enhanced affinity for FcγRIIB and a decreased affinity for FcγRIIIA can also be used to reduce the inflammation experienced by animals, particularly mammals, with inflammatory disorders. In a specific embodiment, a molecule of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal, which is not administered the said molecule.

Molecules of the invention comprising at least one epitope binding domain specific for FcγRIIB and/or a variant Fc domain with an enhanced affinity for FcγRIIB and a decreased affinity for FcγRIIIA can also be used to prevent the rejection of transplants.

5.5.3 Infectious Disease

The invention also encompasses methods for treating or preventing an infectious disease in a subject comprising administering a therapeutically or prophylatically effective amount of one or more molecules of the invention comprising at least one epitope binding domain specific for an infectious agent associated with said infectious disease. In certain embodiments, the molecules of the invention are toxic to the infectious agent, enhance immune response against said agent or enhance effector function against said agent, relative to the immune response in the absence of said molecule. Infectious diseases that can be treated or prevented by the molecules of the invention are caused by infectious agents including but not limited to viruses, bacteria, fungi, protozae, and viruses.

Viral diseases that can be treated or prevented using the molecules of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox.

Bacterial diseases that can be treated or prevented using the molecules of the invention in conjunction with the methods of the present invention, that are caused by bacteria include, but are not limited to, mycobacteria *rickettsia*, mycoplasma, *neisseria, S. pneumonia, Borrelia burgdorferi* (Lyme disease), *Bacillus antracis* (anthrax), tetanus, *streptococcus, staphylococcus, mycobacterium*, tetanus, pertissus, cholera, plague, diptheria, chlamydia, *S. aureus* and *legionella.*

Protozoal diseases that can be treated or prevented using the molecules of the invention in conjunction with the methods of the present invention, that are caused by protozoa include, but are not limited to, *leishmania*, kokzidioa, *trypanosoma* or malaria.

Parasitic diseases that can be treated or prevented using the molecules of the invention in conjunction with the methods of the present invention, that are caused by parasites include, but are not limited to, chlamydia and *rickettsia.*

According to one aspect of the invention, molecules of the invention comprising at least one epitope binding domain specific for an infectious agent exhibit an antibody effector function towards said agent, e.g., a pathogenic protein. Examples of infectious agents include but are not limited to bacteria (e.g., *Escherichia coli, Klebsiella pneumoniae, Staphylococcus aureus, Enterococcus faecials, Candida albicans, Proteus vulgaris, Staphylococcus viridans*, and *Pseudomonas aeruginosa*), a pathogen (e.g., B-lymphotropic papovavirus (LPV); Bordatella pertussis; Borna Disease virus (BDV); Bovine coronavirus; Choriomeningitis virus; Dengue virus; a virus, *E. coli*; Ebola; Echovirus 1; Echovirus-11 (EV); Endotoxin (LPS); Enteric bacteria; Enteric Orphan virus; Enteroviruses; Feline leukemia virus; Foot and mouth disease virus; Gibbon ape leukemia virus (GALV); Gram-negative bacteria; *Heliobacter pylori*; Hepatitis B virus (HBV); Herpes Simplex Virus; HIV-1; Human cytomegalovirus; Human coronovirus; Influenza A, B & C; *Legionella; Leishmania mexicana; Listeria monocytogenes*; Measles virus; Meningococcus; Morbilliviruses; Mouse hepatitis virus; Murine leukemia virus; Murine gamma herpes virus; Murine retrovirus; Murine coronavirus mouse hepatitis virus; *Mycobacterium avium*-M; *Neisseria gonorrhoeae*; Newcastle disease virus; Parvovirus B19; *Plasmodium falciparum*; Pox Virus; *Pseudomonas*; Rotavirus; *Salmonella typhiurium; Shigella*; Streptococci; T-cell lymphotropic virus 1; Vaccinia virus).

5.5.4 Detoxification

The invention also encompasses methods of detoxification in a subject exposed to a toxin (e.g., a toxic drug molecule) comprising administering a therapeutically or prophylatically effective amount of one or more molecules of the invention comprising at least one epitope binding domain specific for the toxic drug molecule. In certain embodiments, binding of a molecule of the invention to the toxin reduces or eliminates the adverse physiological effect of said toxin. In yet other embodiments, binding of a diabody of the invention to the toxin increases or enhances elimination, degradation or neutralization of the toxin relative to elimination, degradation or neutralization in the absence of said diabody. Immunotoxicotherapy in accordance with the methods of the invention can be used to treat overdoses or exposure to drugs including, but not limited to, digixin, PCP, cocaine, colchicine, and tricyclic antidepressants.

Combination Therapy

The invention further encompasses administering the molecules of the invention in combination with other therapies known to those skilled in the art for the treatment or prevention of cancer, autoimmune disease, infectious disease or intoxication, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more agents, therapeutic antibodies or other agents known to those skilled in the art for the treatment and/or prevention of cancer, autoimmune disease, infectious disease or intoxication.

In certain embodiments, one or more molecule of the invention is administered to a mammal, preferably a human, concurrently with one or more other therapeutic agents useful for the treatment of cancer. The term "concurrently" is not limited to the administration of prophylactic or therapeutic agents at exactly the same time, but rather it is meant that a molecule of the invention and the other agent are administered to a mammal in a sequence and within a time interval such that the molecule of the invention can act together with the other agent to provide an increased benefit than if they were administered otherwise. For example, each prophylactic or therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active. One skilled in the art would be able to determine such a time frame by determining the half life of the administered agents.

In certain embodiments, the prophylactic or therapeutic agents of the invention are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

In other embodiments, courses of treatment are administered concurrently to a mammal, i.e., individual doses of the therapeutics are administered separately yet within a time interval such that molecules of the invention can work together with the other agent or agents. For example, one component may be administered one time per week in combination with the other components that may be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the molecules of the invention and the prophylactic and/or therapeutic agent can act additively or, more preferably, synergistically. In one embodiment, a molecule of the invention is administered concurrently with one or more therapeutic agents in the same pharmaceutical composition. In another embodiment, a molecule of the invention is administered concurrently with one or more other therapeutic agents in separate pharmaceutical compositions. In still another embodiment, a molecule of the invention is administered prior to or subsequent to administration of another prophylactic or therapeutic agent. The invention contemplates administration of a molecule of the invention in combination with other prophylactic or therapeutic agents by the same or different routes of administration, e.g., oral and parenteral. In certain embodiments, when a molecule of the invention is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* ($56^{th}$ ed., 2002).

5.5.5 Anti-cancer Agents

In a specific embodiment, the methods of the invention encompass the administration of one or more molecules of the invention with one or more therapeutic agents used for the treatment and/or prevention of cancer. In one embodiment, angiogenesis inhibitors may be administered in combination with the molecules of the invention. Angiogenesis inhibitors that can be used in the methods and compositions of the invention include but are not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kDa fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Anti-cancer agents that can be used in combination with the molecules of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin;

temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include but are not limited to ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Smart M195 which is a humanized anti-CD33 IgG antibody (Protein Design Lab/Kanebo); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-$\beta_2$ antibody (Cambridge Ab Tech). Other examples of therapeutic antibodies that can be used in accordance with the invention are presented in Table 8.

TABLE 8

Anti-cancer therapeutic antibodies

| Company | Product | Disease | Target |
|---|---|---|---|
| Abgenix | ABX-EGF | Cancer | EGF receptor |
| AltaRex | OvaRex | ovarian cancer | tumor antigen CA125 |
| | BravaRex | metastatic cancers | tumor antigen MUC1 |
| Antisoma | Theragyn (pemtumomabytrrium-90) | ovarian cancer | PEM antigen |
| | Therex | breast cancer | PEM antigen |

TABLE 8-continued

Anti-cancer therapeutic antibodies

| Company | Product | Disease | Target |
|---|---|---|---|
| Boehringer Ingelheim | Blvatuzumab | head & neck cancer | CD44 |
| Centocor/J&J | Panorex | Colorectal cancer | 17-1A |
| | ReoPro | PTCA | gp IIIb/IIIa |
| | ReoPro | Acute MI | gp IIIb/IIIa |
| | ReoPro | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | Herceptin | metastatic breast cancer | HER-2 |
| | Herceptin | early stage breast cancer | HER-2 |
| | Rituxan | Relapsed/refractory low-grade or follicular NHL | CD20 |
| | Rituxan | intermediate & high-grade NHL | CD20 |
| | MAb-VEGF | NSCLC, metastatic | VEGF |
| | MAb-VEGF | Colorectal cancer, metastatic | VEGF |
| | AMD Fab | age-related macular degeneration | CD18 |
| | E-26 (2$^{nd}$ gen. IgE) | allergic asthma & rhinitis | IgE |
| IDEC | Zevalin (Rituxan + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
| | Cetuximab + cisplatin & radiation | newly diagnosed or recurrent head & neck cancer | EGF receptor |
| | Cetuximab + gemcitabine | newly diagnosed metastatic pancreatic carcinoma | EGF receptor |
| | Cetuximab + cisplatin + 5FU or Taxol | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IM-1C11 | colorectal cancer with liver metasteses | VEGF-receptor |

TABLE 8-continued

| Anti-cancer therapeutic antibodies | | | |
|---|---|---|---|
| Company | Product | Disease | Target |
| ImmonoGen | nuC242-DM1 | Colorectal, gastric, and pancreatic cancer | nuC242 |
| ImmunoMedics | LymphoCide | Non-Hodgkins lymphoma | CD22 |
| | LymphoCide Y-90 | Non-Hodgkins lymphoma | CD22 |
| | CEA-Cide | metastatic solid tumors | CEA |
| | CEA-Cide Y-90 | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radio imaging) | CEA |
| | LeukoScan (Tc-99m-labeled sulesomab) | soft tissue infection (radioimaging) | CEA |
| | LymphoScan (Tc-99m-labeled) | lymphomas (radioimaging) | CD22 |
| | AFP-Scan (Tc-99m-labeled) | liver 7 gem-cell cancers (radioimaging) | AFP |
| Intracel | HumaRAD-HN (+ yttrium-90) | head & neck cancer | NA |
| | HumaSPECT | colorectal imaging | NA |
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v\beta_3$ |
| Merck KGaA | MAb 425 | Various cancers | EGF receptor |
| | IS-IL-2 | Various cancers | Ep-CAM |
| Millennium | Campath (alemtuzumab) | chronic lymphocytic leukemia | CD52 |
| NeoRx | CD20-streptavidin (+biotin-yttrium 90) | Non-Hodgkins lymphoma | CD20 |
| | Avidicin (albumin + NRLU13) | metastatic cancer | NA |
| Peregrine | Oncolym (+iodine-131) | Non-Hodgkins lymphoma | HLA-DR 10 beta |
| | Cotara (+iodine-131) | unresectable malignant glioma | DNA-associated proteins |
| Pharmacia Corporation | C215 (+staphylococcal enterotoxin) | pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | Nuvion | T cell malignancies | CD3 |
| | SMART M195 | AML | CD33 |
| | SMART 1D10 | NHL | HLA-DR antigen |
| Titan | CEAVac | colorectal cancer, advanced | CEA |
| | TriGem | metastatic melanoma & small cell lung cancer | GD2-ganglioside |
| | TriAb | metastatic breast cancer | MUC-1 |
| Trilex | CEAVac | colorectal cancer, advanced | CEA |
| | TriGem | metastatic melanoma & small cell lung cancer | GD2-ganglioside |
| | TriAb | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+gelonin toxin) | gliorna, melanoma & neuroblastoma | NA |
| Xoma | Rituxan | Relapsed/refractory low-grade or follicular NHL | CD20 |
| | Rituxan | intermediate & high-grade NHL | CD20 |
| | ING-1 | adenomcarcinoma | Ep-CAM |

5.5.6 Immunomodulatory Agents and Anti-inflammatory Agents

The present invention provides methods of treatment for autoimmune diseases and inflammatory diseases comprising administration of the molecules of the invention in conjunction with other treatment agents. Examples of immunomodulatory agents include, but are not limited to, methothrexate, ENBREL, REMICADE™, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCINT™), ketoralac (TORADOL™), oxaprozin (DAYPRO™), nabumentone (RELAFEN™), sulindac (CLINORILT™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

A non-limiting example of the antibodies that can be used for the treatment or prevention of inflammatory disorders in conjunction with the molecules of the invention is presented in Table 9, and a non-limiting example of the antibodies that can used for the treatment or prevention of autoimmune disorder is presented in Table 10.

TABLE 9

| Antibody Name | Target Antigen | Product Type | Isotype | Sponsors | Indication |
|---|---|---|---|---|---|
| Therapeutic antibodies for the treatment of inflammatory diseases | | | | | |
| 5G1.1 | Complement (C5) | Humanized | IgG | Alexion Pharm Inc | Rheumatoid Arthritis |
| 5G1.1 | Complement (C5) | Humanized | IgG | Alexion Pharm Inc | SLE |
| 5G1.1 | Complement (C5) | Humanized | IgG | Alexion Pharm Inc | Nephritis |
| 5G1.1-SC | Complement (C5) | Humanized | ScFv | Alexion Pharm Inc | Cardiopulmonary Bypass |
| 5G1.1-SC | Complement (C5) | Humanized | ScFv | Alexion Pharm Inc | Myocardial Infarction |
| 5G1.1-SC | Complement (C5) | Humanized | ScFv | Alexion Pharm Inc | Angioplasty |
| ABX-CBL | CBL | Human | | Abgenix Inc | GvHD |
| ABX-CBL | CD147 | Murine | IgG | Abgenix Inc | Allograft rejection |
| ABX-IL8 | IL-8 | Human | IgG2 | Abgenix Inc | Psoriasis |
| Antegren | VLA-4 | Humanized | IgG | Athena/Elan | Multiple Sclerosis |
| Anti-CD11a | CD11a | Humanized | IgG1 | Genentech Inc/Xoma | Psoriasis |
| Anti-CD18 | CD18 | Humanized | Fab'2 | Genentech Inc | Myocardial infarction |
| Anti-LFA1 | CD18 | Murine | Fab'2 | Pasteur-Merieux/ Immunotech | Allograft rejection |
| Antova | CD40L | Humanized | IgG | Biogen | Allograft rejection |
| Antova | CD40L | Humanized | IgG | Biogen | SLE |
| BTI-322 | CD2 | Rat | IgG | Medimmune Inc | GvHD, Psoriasis |
| CDP571 | TNF-alpha | Humanized | IgG4 | Celltech | Crohn's |
| CDP571 | TNF-alpha | Humanized | IgG4 | Celltech | Rheumatoid Arthritis |
| CDP850 | E-selectin | Humanized | | Celltech | Psoriasis |
| Corsevin M | Fact VII | Chimeric | | Centocor | Anticoagulant |
| D2E7 | TNF-alpha | Human | | CAT/BASF | Rheumatoid Arthritis |
| Hu23F2G | CD11/18 | Humanized | | ICOS Pharm Inc | Multiple Sclerosis |
| Hu23F2G | CD11/18 | Humanized | IgG | ICOS Pharm Inc | Stroke |
| IC14 | CD14 | | | ICOS Pharm Inc | Toxic shock |
| ICM3 | ICAM-3 | Humanized | | ICOS Pharm Inc | Psoriasis |
| IDEC-114 | CD80 | Primatised | | IDEC Pharm/ Mitsubishi | Psoriasis |
| IDEC-131 | CD40L | Humanized | | IDEC Pharm/Eisai | SLE |
| IDEC-131 | CD40L | Humanized | | IDEC Pharm/Eisai | Multiple Sclerosis |
| IDEC-151 | CD4 | Primatised | IgG1 | IDEC Pharm/ GlaxoSmithKline | Rheumatoid Arthritis |
| IDEC-152 | CD23 | Primatised | | IDEC Pharm | Asthma/ Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanized | IgG | Millennium Inc (LeukoSite Inc.) | Stroke |
| LDP-01 | beta2-integrin | Humanized | IgG | Millennium Inc (LeukoSite Inc.) | Allograft rejection |
| LDP-02 | alpha4beta7 | Humanized | | Millennium Inc (LeukoSite Inc.) | Ulcerative Colitis |
| MAK-195F | TNF alpha | Murine | Fab'2 | Knoll Pharm, BASF | Toxic shock |

TABLE 9-continued

Therapeutic antibodies for the treatment of inflammatory diseases

| Antibody Name | Target Antigen | Product Type | Isotype | Sponsors | Indication |
|---|---|---|---|---|---|
| MDX-33 | CD64 (FcR) | Human | | Medarex/Centeon | Autoimmune haematogical disorders |
| MDX-CD4 | CD4 | Human | IgG | Medarex/Eisai/Genmab | Rheumatoid Arthritis |
| MEDI-507 | CD2 | Humanized | | Medimmune Inc | Psoriasis |
| MEDI-507 | CD2 | Humanized | | Medimmune Inc | GvHD |
| OKT4A | CD4 | Humanized | IgG | Ortho Biotech | Allograft rejection |
| OrthoClone OKT4A | CD4 | Humanized | IgG | Ortho Biotech | Autoimmune disease |
| Orthoclone/anti-CD3 OKT3 | CD3 | Murine | mIgG2a | Ortho Biotech | Allograft rejection |
| RepPro/Abciximab | gpIIbIIIa | Chimeric | Fab | Centocor/Lilly | Complications of coronary angioplasty |
| rhuMab-E25 | IgE | Humanized | IgG1 | Genentech/Novartis/Tanox Biosystems | Asthma/Allergy |
| SB-240563 | IL5 | Humanized | | GlaxoSmithKline | Asthma/Allergy |
| SB-240683 | IL-4 | Humanized | | GlaxoSmithKline | Asthma/Allergy |
| SCH55700 | IL-5 | Humanized | | Celltech/Schering | Asthma/Allergy |
| Simulect | CD25 | Chimeric | IgG1 | Novartis Pharm | Allograft rejection |
| SMART a-CD3 | CD3 | Humanized | | Protein Design Lab | Autoimmune disease |
| SMART a-CD3 | CD3 | Humanized | | Protein Design Lab | Allograft rejection |
| SMART a-CD3 | CD3 | Humanized | IgG | Protein Design Lab | Psoriasis |
| Zenapax | CD25 | Humanized | IgG1 | Protein Design Lab/Hoffman-La Roche | Allograft rejection |

TABLE 10

Therapeutic antibodies for the treatment of autoimmune disorders

| Antibody | Indication | Target Antigen |
|---|---|---|
| ABX-RB2 | | antibody to CBL antigen on T cells, B cells and NK cells fully human antibody from the Xenomouse |
| 5c8 (Anti CD-40 an antigen antibody) | Phase II trials were halted in Oct. 99 examine “adverse events” | CD-40 |
| IDEC 131 | systemic lupus erythyematous (SLE) | anti CD40 humanized |
| IDEC 151 | rheumatoid arthritis | primatized; anti-CD4 |
| IDEC 152 | Asthma | primatized; anti-CD23 |
| IDEC 114 | Psoriasis | primatized anti-CD80 |
| MEDI-507 | rheumatoid arthritis; multiple sclerosis Crohn’s disease Psoriasis | anti-CD2 |
| LDP-02 (anti-b7 mAb) | inflammatory bowel disease Chron’s disease ulcerative colitis | a4b7 integrin receptor on white blood cells (leukocytes) |
| SMART Anti-Gamma Interferon antibody | autoimmune disorders | Anti-Gamma Interferon |

TABLE 10-continued

Therapeutic antibodies for the treatment of autoimmune disorders

| Antibody | Indication | Target Antigen |
|---|---|---|
| Verteportin | rheumatoid arthritis | |
| MDX-33 | blood disorders caused by autoimmune reactions Idiopathic Thrombocytopenia Purpurea (ITP) autoimmune hemolytic anemia | monoclonal antibody against FcRI receptors |
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response) |
| VX-745 | specific to inflammation involved in chemical signalling of immune | inhibitor of P38MAP kinase mitogen activated protein kinase |

TABLE 10-continued

| Therapeutic antibodies for the treatment of autoimmune disorders | | |
|---|---|---|
| Antibody | Indication | Target Antigen |
| | response<br>onset and progression of inflammation | |
| Enbrel (etanercept) | | targets TNF (tumor necrosis factor) |
| IL-8 | | fully human monoclonal antibody against IL-8 (interleukin 8) |
| Apogen MP4 | | recombinant antigen<br>selectively destroys disease associated T-cells<br>induces apoptosis<br>T-cells eliminated by programmed cell death<br>no longer attack body's own cells specific apogens target specific T-cells |

5.5.7 Agents for Use in the Treatment of Infectious Disease

In some embodiments, the molecules of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with antibiotics known to those skilled in the art for the treatment and or prevention of an infectious disease. Antibiotics that can be used in combination with the molecules of the invention include, but are not limited to, macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In certain embodiments, the molecules of the invention can be administered in combination with a therapeutically or prophylactically effective amount of one or more antifungal agents. Antifungal agents that can be used in combination with the molecules of the invention include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

In some embodiments, the molecules of the invention can be administered in combination with a therapeutically or prophylactically effective amount of one or more anti-viral agent. Useful anti-viral agents that can be used in combination with the molecules of the invention include, but are not limited to, protease inhibitors, nucleoside reverse transcriptase inhibitors, non-nucleoside reverse transcriptase inhibitors and nucleoside analogs. Examples of antiviral agents include but are not limited to zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, the alpha-interferons; adefovir, clevadine, entecavir, pleconaril.

5.6 Vaccine Therapy

The invention further encompasses using a composition of the invention to induce an immune response against an antigenic or immunogenic agent, including but not limited to cancer antigens and infectious disease antigens (examples of which are disclosed infra). The vaccine compositions of the invention comprise one or more antigenic or immunogenic agents to which an immune response is desired, wherein the one or more antigenic or immunogenic agents is coated with a variant antibody of the invention that has an enhanced affinity to FcγRIIIA. The vaccine compositions of the invention are particularly effective in eliciting an immune response, preferably a protective immune response against the antigenic or immunogenic agent.

In some embodiments, the antigenic or immunogenic agent in the vaccine compositions of the invention comprises a virus against which an immune response is desired. The viruses may be recombinant or chimeric, and are preferably attenuated. Production of recombinant, chimeric, and attenuated viruses may be performed using standard methods known to one skilled in the art. The invention encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaptation can be made into deletion mutations. These mutations should be more stable than the point mutations associated with cold or temperature sensitive mutants and reversion frequencies should be extremely low. Recombinant DNA technologies for engineering recombinant viruses are known in the art and encompassed in the invention. For example, techniques for modifying negative strand RNA viruses are known in the art, see, e.g., U.S. Pat. No. 5,166,057, which is incorporated herein by reference in its entirety.

Alternatively, chimeric viruses with "suicide" characteristics may be constructed for use in the intradermal vaccine formulations of the invention. Such viruses would go through only one or a few rounds of replication within the host. When used as a vaccine, the recombinant virus would go through limited replication cycle(s) and induce a sufficient level of immune response but it would not go further in the human host and cause disease. Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

In certain embodiments, completely foreign epitopes, including antigens derived from other viral or non-viral pathogens can be engineered into the virus for use in the intradermal vaccine formulations of the invention. For example, antigens of non-related viruses such as HIV (gp160, gp120, gp41) parasite antigens (e.g., malaria), bacterial or fungal antigens or tumor antigens can be engineered into the attenuated strain.

Virtually any heterologous gene sequence may be constructed into the chimeric viruses of the invention for use in the intradermal vaccine formulations. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to, influenza and parainfluenza hemagglutinin neuraminidase and fusion glycoproteins such as the FIN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

In yet other embodiments, the invention encompasses pathogenic cells or viruses, preferably attenuated viruses, which express the variant antibody on their surface.

In alternative embodiments, the vaccine compositions of the invention comprise a fusion polypeptide wherein an antigenic or immunogenic agent is operatively linked to a variant antibody of the invention that has an enhanced affinity for FcγRIIIA. Engineering fusion polypeptides for use in the vaccine compositions of the invention is performed using routine recombinant DNA technology methods and is within the level of ordinary skill.

The invention further encompasses methods to induce tolerance in a subject by administering a composition of the invention. Preferably a composition suitable for inducing tolerance in a subject comprises an antigenic or immunogenic agent coated with a variant antibody of the invention, wherein the variant antibody has a higher affinity to FcγRIIB. Although not intending to be bound by a particular mechanism of action, such compositions are effective in inducing tolerance by activating the FcγRIIB mediatated inhibitory pathway.

5.7 Compositions and Methods of Administering

The invention provides methods and pharmaceutical compositions comprising molecules of the invention (i.e., diabodies) comprising multiple epitope binding domains and, optionally, an Fc domain (or portion thereof). The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, an antibody, a fusion protein, or a conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human. In yet another preferred embodiment, the antibody of the invention is from the same species as the subject.

Various delivery systems are known and can be used to administer a composition comprising molecules of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262:4429-4432), construction of a nucleic acid as part of a retroviral or other vector, etc. Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the molecules of the invention are packaged in a hermetically sealed container such as an ampoule or sachette indicating the quantity of antibody. In one embodiment, the molecules of the invention are supplied as a dry sterilized lyophilized powder or water free concentrate in a hermetically sealed container and can be reconstituted, e.g., with water or saline to the appropriate concentration for administration to a subject. Preferably, the molecules of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized molecules of the invention should be stored at between 2 and 8° C. in their original container and the molecules should be administered within 12 hours, preferably within 6 hours, within 5 hours, within 3 hours, or within 1 hour after being reconstituted. In an alternative embodiment, molecules of the invention are supplied in liquid form in a hermetically sealed container indicating the quantity and concentration of the molecule, fusion protein, or conjugated molecule. Preferably, the liquid form of the molecules of the invention are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the molecules.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For diabodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage and frequency of administration of diabodies of the invention may be reduced or altered by enhancing uptake and tissue penetration of the diabodies by modifications such as, for example, lipidation.

In one embodiment, the dosage of the molecules of the invention administered to a patient may be from 0.01 mg to 1000 mg/day when used as single agent therapy. In another embodiment the molecules of the invention are used in combination with other therapeutic compositions and the dosage administered to a patient are lower than when said molecules are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "*New Methods Of Drug Delivery*," Science 249:1527-1533); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled release of antibodies (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in *Medical Applications of Controlled Release*, supra, vol. 2, pp. 115-138 (1984)). In another embodiment, polymeric compositions useful as controlled release implants are used according to Dunn et al. (See U.S. Pat. No. 5,945, 155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888, 533).

Controlled release systems are discussed in the review by Langer (1990, "*New Methods Of Drug Delivery*," Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

In a specific embodiment where the composition of the invention is a nucleic acid encoding a diabody of the invention, the nucleic acid can be administered in vivo to promote expression of its encoded diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis*," Proc. Natl. Acad. Sci. USA 88:1864-1868), etc. Alternatively, a nucleic acid can be introduced intracellularly and incorporated within host cell DNA for expression by homologous recombination.

Treatment of a subject with a therapeutically or prophylactically effective amount of molecules of the invention can include a single treatment or, preferably, can include a series of treatments. In a preferred example, a subject is treated with molecules of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

5.7.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more molecules of the invention and a pharmaceutically acceptable carrier.

The invention also encompasses pharmaceutical compositions comprising a diabody molecule of the invention and a therapeutic antibody (e.g., tumor specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

5.7.2 Gene Therapy

In a specific embodiment, nucleic acids comprising sequences encoding molecules of the invention are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al. (1993) "*Human Gene Therapy*," Clinical Pharmacy 12:488-505; Wu et al. (1991) "*Delivery Systems For Gene Therapy*," Biotherapy 3:87-95; Tolstoshev (1993) "*Gene Therapy, Concepts, Current Trials And Future Directions*," Ann. Rev. Pharmacol. Toxicol. 32:573-596; Mulligan (1993) "*The Basic Science Of Gene Therapy*," Science 260: 926-932; and Morgan et al. (1993) "*Human Gene Therapy*," Ann. Rev. Biochem. 62:191-217. Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect, a composition of the invention comprises nucleic acids encoding a diabody of the invention, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller et al. (1989) "*Inactivating The Beta 2-Microglobulin Locus In Mouse Embryonic Stem Cells By Homologous Recombination*," Proc. Natl. Acad. Sci. USA 86:8932-8935; and Zijlstra et al. (1989) "*Germ-Line Transmission Of A Disrupted Beta 2-Microglobulin Gene Produced By Homologous Recombination In Embryonic Stem Cells*," Nature 342:435-438).

In another preferred aspect, a composition of the invention comprises nucleic acids encoding a fusion protein, said nucleic acids being a part of an expression vector that expresses the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a an antigen subject to receptor-mediated endocytosis (See, e.g., Wu et al. (1987) "*Receptor-Mediated In Vitro Gene Transformation By A Soluble DNA Carrier System*," J. Biol. Chem. 262:4429-4432) (which can be used to target cell types specifically expressing the receptors), etc. In another embodiment, nucleic acid-antigen complexes can be formed in which the antigen comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (See, e.g., PCT Publications WO 92/06180; WO 92/22635; WO92/20316; WO93/14188; WO 93/20221). Alternatively, the nucleic acid can be introduced intracellularly and incorporated within host cell DNA for expression, by homologous recombination (Koller et al. (1989) "*Inactivating The Beta 2-Microglobulin Locus In Mouse Embryonic Stem Cells By Homologous Recombination*," Proc. Natl. Acad. Sci. USA 86:8932-8935; and Zijlstra et al. (1989) "*Germ-Line Transmission Of A Disrupted Beta 2-Microglobulin Gene Produced By Homologous Recombination In Embryonic Stem Cells*," Nature 342:435-438).

In a specific embodiment, viral vectors that contain nucleic acid sequences encoding a molecule of the invention (e.g., a diabody or a fusion protein) are used. For example, a retroviral vector can be used (See Miller et al. (1993) "*Use Of Retroviral Vectors For Gene Transfer And Expression*," Meth. Enzymol. 217:581-599). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitate delivery of the nucleotide sequence into a subject. More detail about retroviral vectors can be found in Boesen et al. (1993) "*Circumvention Of Chemotherapy-Induced Myelosuppression By Transfer Of The Mdr1 Gene*," Biotherapy 6:291-302), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al. (1994) "*Long-Term Biological Response Of Injured Rat Carotid Artery Seeded With Smooth Muscle Cells Expressing Retrovirally Introduced Human Genes*," J. Clin. Invest. 93:644-651; Keim et al. (1994) "*Retrovirus-Mediated Gene Transduction Into Canine Peripheral Blood Repopulating Cells*," Blood 83:1467-1473; Salmons et al. (1993) "*Targeting Of Retroviral Vectors For Gene Therapy*," Human Gene Therapy 4:129-141; and Grossman et al. (1993) "*Retroviruses: Delivery Vehicle To The Liver*," Curr. Opin. Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky et al. (1993, "*Gene Therapy: Adenovirus Vectors*," Current Opinion in Genetics and Development 3:499-503) present a review of adenovirus-based gene therapy. Bout et al. (1994, "*Lung Gene Therapy: In Vivo Adenovirus-Mediated Gene Transfer To Rhesus Monkey Airway Epithelium*," Human Gene Therapy, 5:3-10) demonstrated the use of adenovirus vectors to transfer genes to the respiratory epithelia of rhesus monkeys. Other instances of the use of adenoviruses in gene therapy can be found in Rosenfeld et al. (1991) "*Adenovirus-Mediated Transfer Of A Recombinant Alpha 1-Antitrypsin Gene To The Lung Epithe-*

*lium In Vivo*," Science 252:431-434; Rosenfeld et al. (1992) "*In Vivo Transfer Of The Human Cystic Fibrosis Transmembrane Conductance Regulator Gene To The Airway Epithelium*," Cell 68:143-155; Mastrangeli et al. (1993) "*Diversity Of Airway Epithelial Cell Targets For In Vivo Recombinant Adenovirus-Mediated Gene Transfer*," J. Clin. Invest. 91:225-234; PCT Publication WO94/12649; and Wang et al. (1995) "*A Packaging Cell Line For Propagation Of Recombinant Adenovirus Vectors Containing Two Lethal Gene-Region Deletions*," Gene Therapy 2:775-783. In a preferred embodiment, adenovirus vectors are used.

Adeno-associated virus (AAV) has also been proposed for use in gene therapy (see, e.g., Walsh et al. (1993) "*Gene Therapy For Human Hemoglobinopathies*," Proc. Soc. Exp. Biol. Med. 204:289-300 and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to, transfection, electroporation, microinjection, infection with a viral or bacteriophage vector, containing the nucleic acid sequences, cell fusion, chromosome-mediated gene transfer, microcellmediated gene transfer, spheroplast fusion, etc. Numerous techniques are known in the art for the introduction of foreign genes into cells (See, e.g., Loeffler et al. (1993) "*Gene Transfer Into Primary And Established Mammalian Cell Lines With Lipopolyamine-Coated DNA*," Meth. Enzymol. 217:599-618, Cotten et al. (1993) "*Receptor-Mediated Transport Of DNA Into Eukaryotic Cells*," Meth. Enzymol. 217:618-644) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (See e.g., PCT Publication WO 94/08598; Stemple et al. (1992) "*Isolation Of A Stem Cell For Neurons And Glia From The Mammalian Neural Crest*," Cell 7 1:973-985; Rheinwald (1980) "*Serial Cultivation Of Normal Human Epidermal Keratinocytes*," Meth. Cell Bio. 21A:229-254; and Pittelkow et al. (1986) "*New Techniques For The In Vitro Culture Of Human Skin Keratinocytes And Perspectives On Their Use For Grafting Of Patients With Extensive Burns*," Mayo Clinic Proc. 61:771-777).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.7.3 Kits

The invention provides a pharmaceutical pack or kit comprising one or more containers filled with the molecules of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

5.8 Characterization and Demonstration of Therapeutic Utility

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary. Said aspects include the temporal regime of administering the prophylactic and/or therapeutic agents, and whether such agents are administered separately or as an admixture.

Preferred animal models for use in the methods of the invention are, for example, transgenic mice expressing human FcγRs on mouse effector cells, e.g., any mouse model described in U.S. Pat. No. 5,877,396 (which is incorporated herein by reference in its entirety) can be used in the present invention. Transgenic mice for use in the methods of the invention include, but are not limited to, mice carrying human FcγRIIIA; mice carrying human FcγRIIA; mice carrying human FcγRIIB and human FcγRIIIA; mice carrying human FcγRIIB and human FcγRIIA. Preferably, mutations showing the highest levels of activity in the functional assays described above will be tested for use in animal model studies prior to use in humans. Sufficient quantities of antibodies may be prepared for use in animal models using methods described supra, for example using mammalian expression systems and purification methods disclosed and exemplified herein.

Mouse xenograft models may be used for examining efficacy of mouse antibodies generated against a tumor specific target based on the affinity and specificity of the epitope bing domains of the diabody molecule of the invention and the ability of the diabody to elicit an immune response (Wu et al. (2001) "*Mouse Models For Multistep Tumorigenesis*," Trends Cell Biol. 11: S2-9). Transgenic mice expressing human FcγRs on mouse effector cells are unique and are tailor-made animal models to test the efficacy of human Fc-FcγR interactions. Pairs of FcγRIIIA, FcγRIIIB and FcγRIIA transgenic mouse lines generated in the lab of Dr. Jeffrey Ravetch (Through a licensing agreement with Rockefeller University and Sloan Kettering Cancer Center) can be used such as those listed in the Table 11 below.

TABLE 11

Mice Strains

| Strain Background | Human FcR |
|---|---|
| Nude/CD16A KO | None |
| Nude/CD16A KO | FcγRIIIA |
| Nude/CD16A KO | FcγR IIA |
| Nude/CD16A KO | FcγR IIA and IIIA |
| Nude/CD32B KO | None |
| Nude/CD32B KO | FcγR IIB |

The anti-inflammatory activity of the combination therapies of invention can be determined by using various experimental animal models of inflammatory arthritis known in the art and described in Crofford L. J. and Wilder R. L., "*Arthritis and Autoimmunity in Animals*", in *Arthritis and Allied Conditions: A Textbook of Rheumatology*, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "*Arthritis and Autoimmunity in Animals*", in *Arthritis and Allied Conditions: A Textbook of Rheumatology*, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model are described in Hansra P. et al. (2000) "*Carrageenan-Induced Arthritis In The Rat*," Inflammation, 24(2): 141-155. Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al. (1962) "*Carrageenan-Induced Edema In Hind Paw Of The Rat As An Assay For Anti-Inflammatory Drugs*" Proc. Soc. Exp. Biol Med. 111, 544-547. This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al. (1992) "*Experimental Colitis In Animal Models*," Scand. J. Gastroentrol. 27:529-537; Strober (1985) "*Animal Models Of Inflammatory Bowel Disease—An Overview*," Dig. Dis. Sci. 30(12 Suppl):3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed (Flanders et al. (1999) "*Prevention Of Type 1 Diabetes From Laboratory To Public Health*," Autoimmunity 29:235-246; Rasmussen et al. (1999) "*Models To Study The Pathogenesis Of Thyroid Autoimmunity*," Biochimie 81:511-515; Foster (1999) "*Relevance Of Systemic Lupus Erythematosus Nephritis Animal Models To Human Disease*," Semin. Nephrol. 19:12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in *Relevance of Tumor Models for Anticancer Drug Development* (1999, eds. Fiebig and Burger); Contributions to Oncology (1999, Karger); The Nude Mouse in Oncology Research (1991, eds. Boven and Winograd); and *Anticancer Drug Development Guide* (1997 ed. Teicher), herein incorporated by reference in their entireties.

Preferred animal models for determining the therapeutic efficacy of the molecules of the invention are mouse xenograft models. Tumor cell lines that can be used as a source for xenograft tumors include but are not limited to, SKBR3 and MCF7 cells, which can be derived from patients with breast adenocarcinoma. These cells have both erbB2 and prolactin receptors. SKBR3 cells have been used routinely in the art as ADCC and xenograft tumor models. Alternatively, OVCAR3 cells derived from a human ovarian adenocarcinoma can be used as a source for xenograft tumors.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^{3}H$-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

EXAMPLES 6

6.1 Design and Characterization of Covalent Bispecific Diabodies

A monospecific covalent diabody and a bispecific covalent diabody were constructed to assess the recombinant production, purification and binding characteristics of each. The affinity purified diabody molecules that were produced by the recombinant expression systems described herein were found by SDS-PAGE and SEC analysis to consist of a single dimerc species. ELISA and SPR analysis further revealed that the covalent bispecific diabody exhibited affinity for both target antigens and could bind both antigens simultaneously.

Materials and Methods:

Construction and Design of Polypeptide Molecules: Nucleic acid expression vectors were designed to produce four polypeptide constructs, schematically represented in FIG. 2. Construct 1 (SEQ ID NO: 9) comprised the VL domain of humanized 2B6 antibody, which recognizes FcγRIIB, and the VH domain of humained 3G8 antibody, which recognizes FcγRIIIA. Construct 2 (SEQ ID NO: 11) comprised the VL domain of Hu3G8 and the VH domain of Hu2B6. Construct 3 (SEQ ID NO: 12) comprised the VL domain of Hu3G8 and the VH domain of Hu3G8. Construct 4 (SEQ ID NO: 13) comprised the VL domain of Hu2B6 and the VH domain of Hu2B6.

PCR and Expression Vector Construction: The coding sequences of the VL or VH domains were amplified from template DNA using forward and reverse primers designed such that the initial PCR products would contain overlapping sequences, allowing overlapping PCR to generate the coding sequences of the desired polypeptide constructs.

Initial PCR amplification of template DNA: Approximately 35 ng of template DNA, e.g. light chain and heavy chain of antibody of interest; 1 ul of 10 uM forward and reverse primers; 2.5 ul of 10×pfuUltra buffer (Stratagene, Inc.); 1 ul of 10 mM dNTP; 1 ul of 2.5 units/ul of pfuUltra DNA polymerase (Stratagene, Inc.); and distilled water to 25 ul total volume were gently mixed in a microfuge tube and briefly spun in a microcentrifuge to collect the reaction mixture at the bottom of the tube. PCR reactions were performed using GeneAmp PCR System 9700 (PE Applied Biosystem) and the following settings: 94° C., 2 minutes; 25 cycles of 94° C., each 15 seconds; 58° C., 30 seconds; and 72° C., 1 minute.

The VL of Hu2B6 was amplified from the light chain of Hu2B6 using forward and reverse primers SEQ ID NO: 55 and SEQ ID NO: 56, respectively. The VH of Hu2B6 was amplified from the heavy chain of Hu2B6 using forward and reverse primers SEQ ID NO: 57 and SEQ ID NO: 58, respectively. The VL of Hu3G8 was amplified from the light chain of Hu3G8 using forward and reverse primers SEQ ID NO: 55 and SEQ ID NO: 59, respectively. The VH of Hu3G8 was amplified from the heavy chain of Hu3G8 using forward and reverse primers SEQ ID NO: 60 and SEQ ID NO: 61, respectively.

PCR products were electrophoresed on a 1% agarose gel for 30 minutes at 120 volts. PCR products were cut from the gel and purified using MinElute GE1 Extraction Kit (Qiagen, Inc.).

Overlapping PCR: Intitial PCR products were combined as described below and amplified using the same PCR conditions described for initial amplification of template DNA. Products of overlapping PCR were also purified as described supra.

The nucleic acid sequence encoding construct 1, SEQ ID NO: 9 (shown schematically in FIG. 2), was amplified by combining the PCR products of the amplifications of VL Hu2B6 and VH Hu3G8, and forward and reverse primers SEQ ID NO: 55 and SEQ ID NO: 61, respectively. The nucleic acid sequence encoding construct 2, SEQ ID NO: 11 (shown schematically in FIG. 2), was amplified by combining the PCR products of the amplifications of VL Hu3G8 and VH Hu2B6, and forward and reverse primers SEQ ID NO: 55 and SEQ ID NO: 58, respectively. The nucleic acid sequence encoding construct 3, SEQ ID NO: 12 (shown schematically in FIG. 2), was amplified by combining the PCR products of the amplifications of VL Hu3G8 and VH Hu3G8, and forward and reverse primers SEQ ID NO: 55 and SEQ ID NO: 61, respectively. The nucleic acid sequence encoding construct 4, SEQ ID NO: 13 (shown schematically in FIG. 2), was amplified by combining the PCR products of the amplifications of VL Hu2B6 and VH Hu2B6, and forward and reverse primers SEQ ID NO: 55 and SEQ ID NO: 58, respectively.

The forward primers of the VL domains (i.e., SEQ ID NO: 55) and reverse primers of the VH domains (i.e., SEQ ID NO: 58 and SEQ ID NO: 61) contained unique restriction sites to allow cloning of the final product into an expression vector. Purified overlapping PCR products were digested with restriction endonucleases Nhe I and EcoR I, and cloned into the pCIneo mammalian expression vector (Promega, Inc.). The plasmids encoding constructs were designated as identified in Table 12:

TABLE 12

PLASMID CONSTRUCTS

| Encoding Construct | Plasmid Designation | Insert |
|---|---|---|
| 1 | pMGX0669 | hu2B6VL-hu3G8VH |
| 2 | pMGX0667 | hu3G8VL-hu2B6VH |
| 3 | pMGX0666 | hu3G8VL-hu3G8VH |
| 4 | pMGX0668 | hu2B6VL-hu2B6VH |

Polypeptide/diabody Expression: pMGX0669, encoding construct 1, was cotransfected with pMGX0667, encoding construct 2, in HEK-293 cells using Lipofectamine 2000 according to the manufacturer's directions (Invitrogen). Co-transfection of these two plasmids was designed to lead to the expression of a covalent bispecific diabody (CBD) immunospecific for both FcγRIIB and FcγRIIIA (the h2B6-h3G8 diabody). pMGX0666 and pMGX0668, encoding constructs 3 and 4, respectively, were separately transfected into HEK-293 cells for expression of a covalent monospecific diabody (CMD), immunospecific for FcγRIIIA (h3G8 diabody) and FcγRIIB (h2B6 diabody), respectively. Following three days in culture, secreted products were purified from the conditioned media.

Purification: Diabodies were captured from the conditioned medium using the relevant antigens coupled to CNBr activated Sepharose 4B. The affinity Sepharose resin was equilibrated in 20 mM Tris/HCl, pH 8.0 prior to loading. After loading, the resin was washed with equilibration buffer prior to elution. Diabodies were eluted from the washed resin using 50 mM Glycine pH 3.0. Eluted diabodies were immediately neutralized with 1M Tris/HCl pH 8.0 and concentrated using a centrifugation type concentrator. The concentrated diabodies were further purified by size exclusion chromatography using a Superdex 200 column equilibrated in PBS.

SEC: Size exclusion chromatography was used to analyze the approximate size and heterogeneity of the diabodies eluted from the column. SEC analysis was performed on a GE healthcare Superdex 200HR 10/30 column equilibrated with PBS. Comparison with the elution profiles of a full length IgG (~150 kDa), an Fab fragment (~50 kDa) and a single chain Fv (~30 kDa) were used as controls).

ELISA: The binding of eluted and purified diabodies was characterized by ELISA assay, as described in 5.4.2. 50 ul/well of a 2 ug/ml solution of sCD32B-Ig was coated on 96-well Maxisorp plate in Carbonate buffer at 4° C. over night. The plate was washed three times with PBS-T (PBS, 0.1% Tween 20) and blocked by 0.5% BSA in PBS-T for 30 minutes at room temperature. Subsequently, h2B6-h3G8 CBD, h2B6 CMD, or h3G8 CMD were diluted into the blocking buffer in a serial of two-fold dilutions to generate a range of diabody concentrations, from 0.5 μg/ml to 0.001 μg/ml. The plate was then incubated at room temperature for 1 hour. After washing with PBS-T three times, 50 ul/well of 0.2 ug/ml sCD16A-Biotin was added to each well. The plate was again incubated at room temperature for 1 hour. After washing with PBS-T three times, 50 ul/well of a 1:5000 dilution of HRP conjugated streptavidin (Amersham Pharmacia Biotech) was used for detection. The HRP-streptavidin was allowed to incubate for 45 minutes at room temperature. The plate was washed with PBS-T three times and developed using 80 ul/well of TMB substrate. After a 10 minute incubation, the HRP-TMB reaction was stopped by adding 40 ul/well of 1% $H_2SO_4$. The OD450 nm was read by using a 96-well plate reader and SOFTmax software, and results plotted using GraphPadPrism 3.03 software.

BIAcore Assay: The kinetic parameters of the binding of eluted and purified diabodies were analyzed using a BIAcore assay (BIAcore instrument 1000, BIAcore Inc., Piscataway, N.J.) and associated software as described in section 5.4.3.

sCD16A, sCD32B or sCD32A (negative control) were immobilized on one of the four flow cells (flow cell 2) of a sensor chip surface through amine coupling chemistry (by modification of carboxymethyl groups with mixture of NHS/EDC) such that about 1000 response units (RU) of either receptor was immobilized on the surface. Following this, the unreacted active esters were "capped off" with an injection of 1M Et-NH2. Once a suitable surface was prepared, covalent bispecific diabodies (h2B6-h3G8 CBD) or covalent monospecific diabodies (h2B6 CMD or h3G8 CMB) were passed over the surface by 180 second injections of a 6.25-200 nM solution at a 70 mL/min flow rate. h3G8 scFV was also tested for comparison.

Once an entire data set was collected, the resulting binding curves were globally fitted using computer algorithms supplied by the manufacturer, BIAcore, Inc. (Piscataway, N.J.). These algorithms calculate both the $K_{on}$, and $K_{off}$, from which the apparent equilibrium binding constant, $K_D$ is deduced as the ratio of the two rate constants (i.e., $K_{off}/K_{on}$). More detailed treatments of how the individual rate constants are derived can be found in the BIAevaluaion Software Handbook (BIAcore, Inc., Piscataway, N.J.).

Association and dissociation phases were fitted separately. Dissociation rate constant was obtained for interval 32-34 sec of the 180 sec dissociation phase; association phase fit was obtained by a 1:1 Langmuir model and base fit was selected on the basis $R_{max}$ and $chi^2$ criteria for the bispecific diabodies and scFv; Bivalent analyte fit was used for CMD binding.

Results

Figure 3:
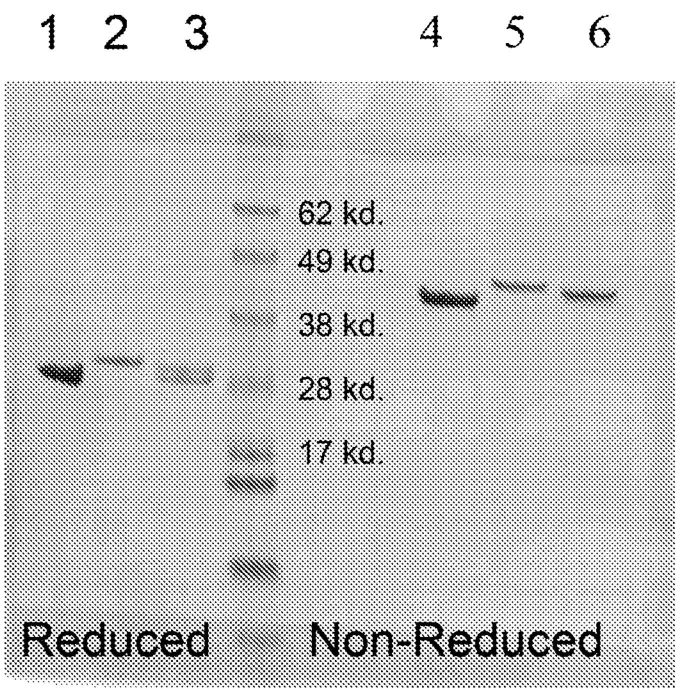

SDS-PAGE analysis under non-reducing conditions revealed that the purified product of the h3G8 CMD, h2B6 CMD and h2B6-h3G8 CBD expression systems were each a single species with an estimated molecular weight of approximately 50 kDa (FIG. 3, lanes 4, 5 and 6, respectively). Under reducing conditions, the product purified from either of the CMD expression systems ran as a single band (lanes 1 and 2), while the product purified from the h2B6-h3G8 CBD system was revealed to be 2 separate proteins (FIG. 3, lane 3). All polypeptides purified from the expression system and visualized by SDS-PAGE under reducing conditions migrated at approximately 28 kDa.

Figure 4A:
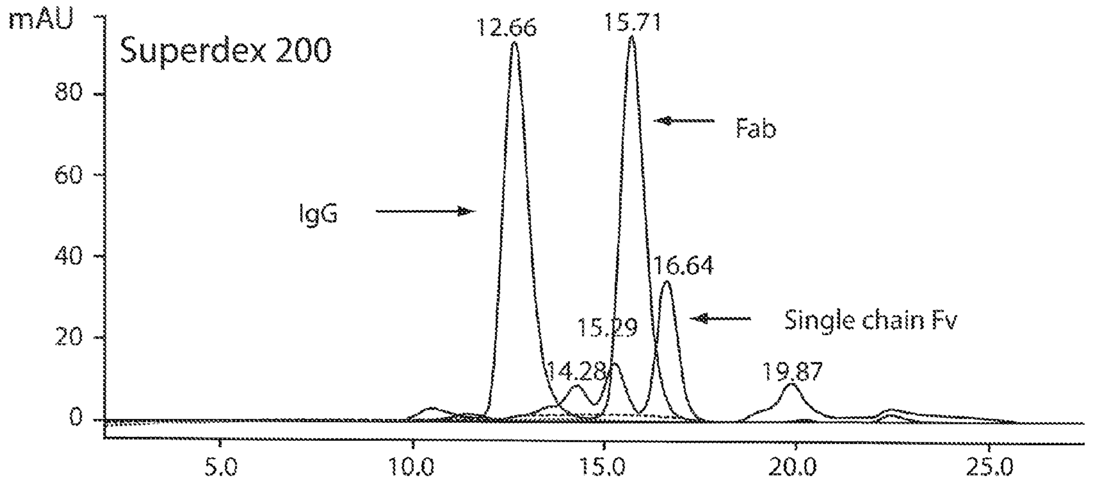
Figure 4B:
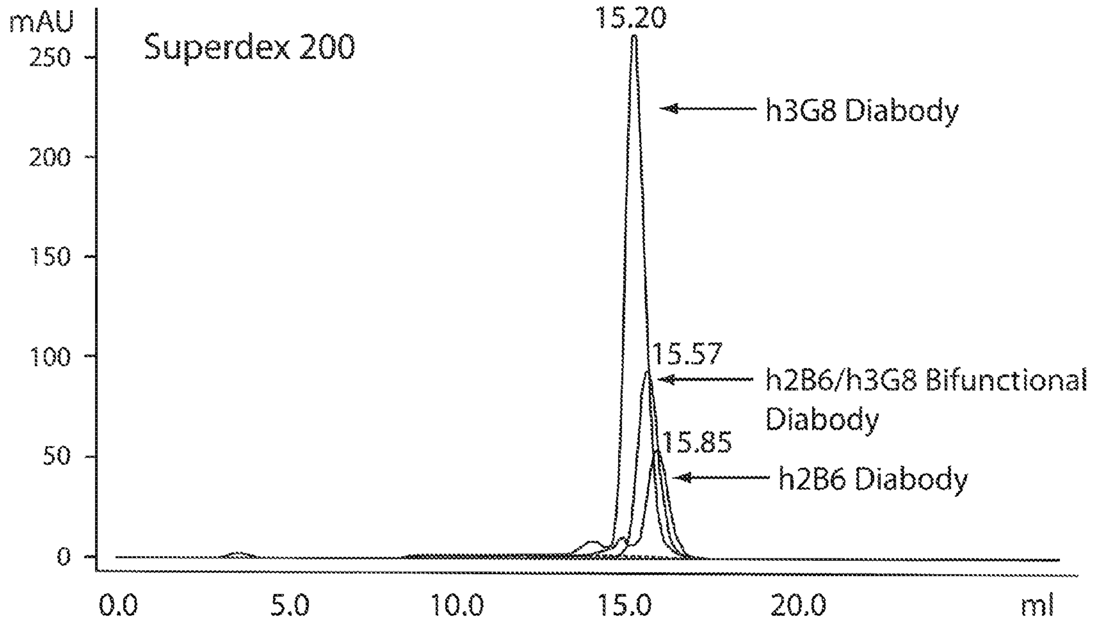

SEC analysis of each of the expression system products also revealed a single molecular species (FIG. 4B), each of which eluted at the same approximate time as an Fab fragment of IgG (~50 kDa) (FIG. 4A). The results indicate that affinity purified product was a homogenous covalent homodimer for the case of CMD expression system and a homogenous covalent heterodimer for the case of the h2B6-h3G8 CBD.

An ELISA sandwich assay was used to test binding of the h2B6-h3G8 CBD for specificity to either or both of CD32B and/or CD16A (FIG. 5). CD32B served as the target antigen and CD16A was used as the secondary probe. The positive signal in the ELIZA revealed that the heterodimeric h2B6-h3G8 CBD had specificity for both antigens. Similar testing of the h3G8 CMD (which should not bind CD32B) showed no signal.

Figure 6A:
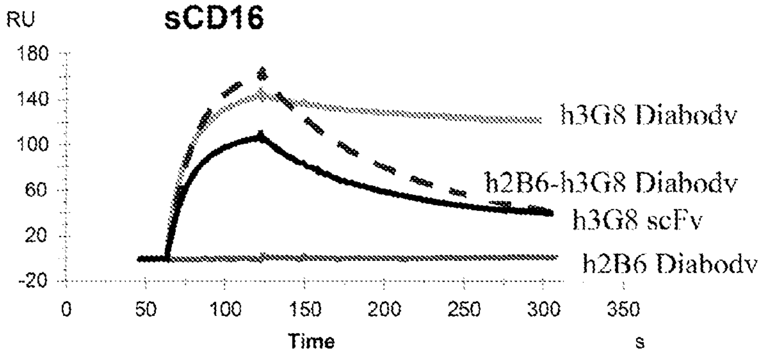
Figure 6B:
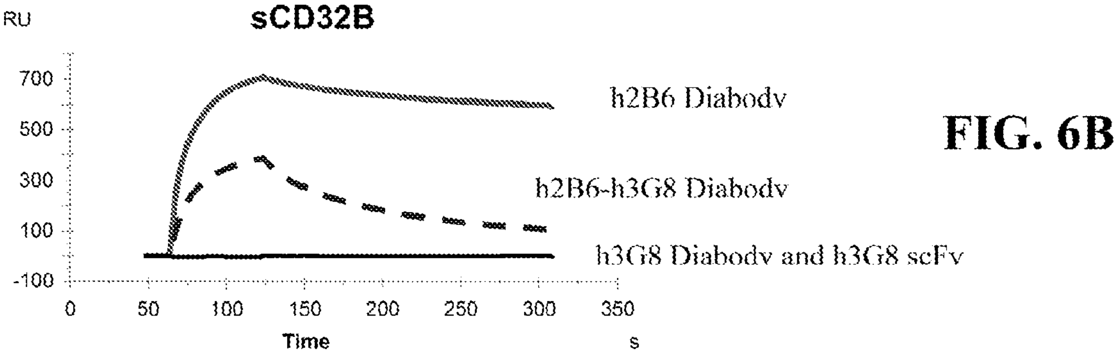
Figure 6C:
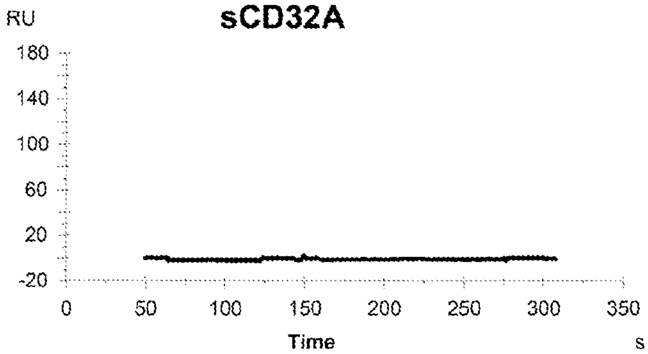
Figure 7A:
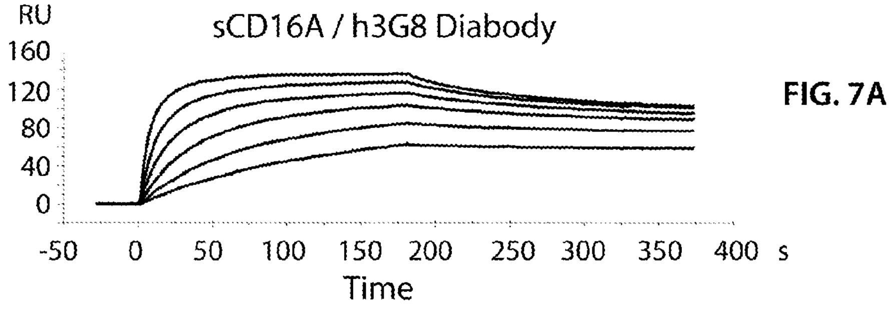
Figure 7B:
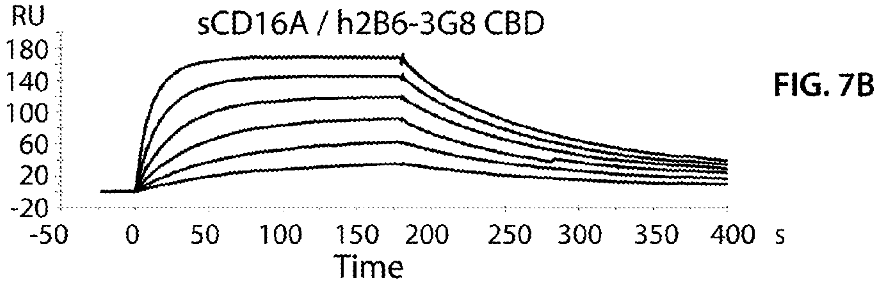
Figure 7C:
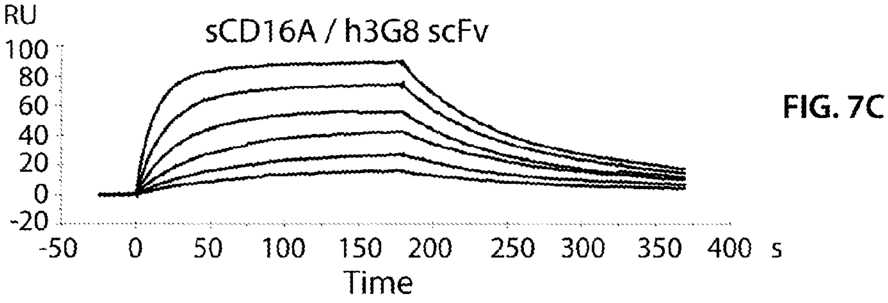
Figure 7D:
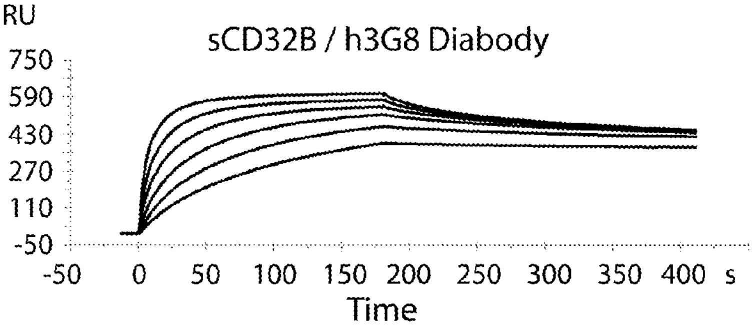
Figure 7E:
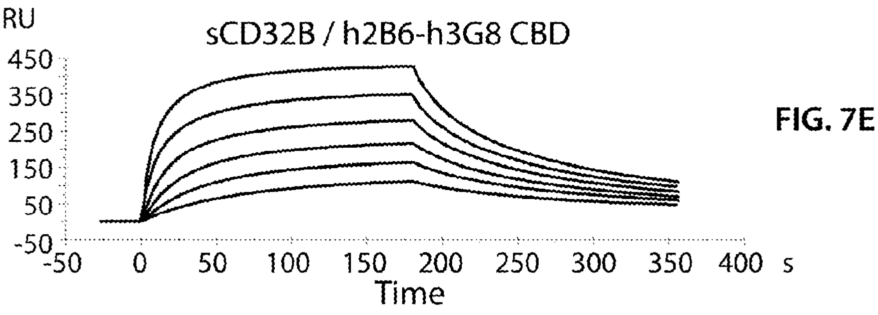

SPR analysis indicated that h3G8 CMD immunospecifically recognized sCD16 but not sCD32B, that h2B6 CMD immunospecifically recognized sCD32B but not sCD16, and that h2B6-h3G8 CBD immunospecifically recognized both sCD16 and sCD32B (FIGS. 6A-B). None of the diabodies tested bound the control receptor, sCD32A (FIG. 6C).

SPR analysis was also used to estimate the kinetic and equilibrium constants of the CMDs and h2B6-h3G8 CBD to sCD16 and/or sCD32B. Results were compared to the same constants calculated for an h3G8 scFV. FIGS. 7A-E show the graphical results of the SPR analysis. The kinetic on and off rates, as well as the equilibrium constant, calculated from the results depicted in FIG. 7 are provided in Table 13.

TABLE 13

Kinetic and Equilibrium Constants Calculated from BIAcore Data.

| Receptor/Analyte | k-on | k-off | Kd |
|---|---|---|---|
| sCD16/h3G8 diabody | $2.3 \times 10^5$ | 0.004 | 18.0 |
| sCD16/h2B6-h3G8 CBD | $4.6 \times 10^5$ | 0.010 | 22.7 |
| sCD16/h3G8 scFv | $3.2 \times 10^5$ | 0.013 | 38.7 |
| sCD32B/h2B6-h3G8 CBD | $3.6 \times 10^5$ | 0.005 | 15.0 |
| sCD32B/h2B6 diabody | $6.2 \times 10^5$ | 0.013 | 21.0 |

Coupled with the results of the ELISA analysis, the studies confirm that the h2B6-h3G8 covalent heterodimer retained specificity for both CD32B and CD16, and was capable of binding both antigens simultaneously. The molecule is schematically represented in FIG. 8.

6.2 Design and Characterization of Covalent Bispecific Diabodies Comprising Fc Domains In an effort to create an IgG like molecule, i.e., comprising an Fc domain, one of the polypeptides comprising the heterodimeric CBD molecule presented in Example 6.1 was modified to further comprise an Fc domain (creating a 'heavier' and 'lighter' chain, analogous to an antibody heavy and light chain). The heterodimeric bispecific molecule would then contain an Fc domain that will dimerize with a homologous molecule, forming a tetrameric IgG-like molecule with tetravalency (i.e, formed by dimerization via the Fc domains of the heterodimeric bispecific molecules). Interestingly, such tetrameric molecules were not detected in the conditioned media of recombinant expression systems using functional assays, e.g., testing the conditioned media for immunospecific binding to target antigens. Instead, only a dimeric molecule, comprising monomers consisting of a VL, VH and Fc domain, were detected in such functional assays. To test whether stability of the theoretical tetrameric structure was at issue, polypeptides comprising the Fc domain were engineered to further comprise a hinge region while the polypeptides comprising the 'lighter' chain were engineered to further comprise the 6 C-terminal amino acids of the constant domain of the human kappa light chain. When such reengineered 'heavier' and 'lighter; chains were co-expressed in the recombinant expression systems, functional assays detected diabody molecules that were able to immunospecifically bind both of the target antigens and anti-Fc antibodies.

Materials and Methods

Construction and Design of Polypeptide Molecules: Nucleic acid expression vectors were designed to produce modified versions of constructs 1 and 2 presented in Example 6.1. Construct 5 (SEQ ID NO: 14) and 6 (SEQ ID NO: 15), were created by engineering construct 1 and 2, respectively to further comprise an Fc domain. Construct 7 (SEQ ID NO: 16) was created by engineering construct 1 was to further comprise the sequence FNRGEC (SEQ ID NO: 23) at its C-terminus. Construct 8 (SEQ ID NO: 18) was created by engineering construct 2 to further comprise a hinge region and Fc domain (comprising V215A mutation). Schematic representation of constructs 5-8 is shown in FIG. 9.

PCR and Expression Vector Construction: All PCR and PCR product purification protocols were as described in Example 6.1 Plasmids pMGX0669 and pMGX0667 served as templates for the coding sequences of constructs 1 and 2, respectively. The coding sequences for the of HuIgG Fc domain and/or hinge domain were SEQ ID NO: 5 or SEQ ID NO: 1 and SEQ ID NO: 5, respectively. The coding sequences of the template DNAs were amplified using forward and reverse primers such that the PCR products would contain overlapping sequences, allowing overlapping PCR to generate the coding sequences of the desired products.

The coding sequence of construct 1 was amplified from pMGX0669 using forward and reverse primers SEQ ID NO: 55 and SEQ ID NO: 62, respectively. The coding sequence of construct 2 was amplified from pMGX0667 using forward and reverse primers SEQ ID NO: 55 and SEQ ID NO: 63, respectively. HuIgG hinge-Fc was amplified using forward and reverse primers SEQ ID NO: 65 and SEQ ID NO: 66, respectively. Construct 7 (SEQ ID NO: 16) was amplified from pMGX0669 using forward and reverse primers SEQ ID NO: 55 and SEQ ID NO: 67.

Overlapping PCR: Initial PCR products were combined as described below, amplified and purified as described in example 6.1.

The nucleic acid sequence encoding construct 5, SEQ ID NO: 14 (shown schematically in FIG. 9), was amplified by combining the PCR products of the amplifications of construct 1 and HuIgG Fc, and forward and reverse primers SEQ ID NO: 55 and SEQ ID NO: 64, respectively. The nucleic acid sequence encoding construct 6, SEQ ID NO: 15 (shown schematically in FIG. 9), was amplified by combining the PCR products of the amplifications of construct 2 and HuIgG Fc, and forward and reverse primers SEQ ID NO: 55 and SEQ ID NO: 66, respectively. The nucleic acid sequence encoding construct 8, SEQ ID NO: 18 (shown schematically in FIG. 9), was amplified by combining the PCR products of the amplifications of construct 2 and HuIgG hinge-Fc, and forward and reverse primers SEQ ID NO: 55 and SEQ ID NO: 66, respectively.

Final products were cloned into pCIneo mammalian expression vector (Promega, Inc.) as previously described. The plasmid encoding constructs were designated as identified in Table 14:

TABLE 14

| PLASMID CONSTRUCTS | | |
|---|---|---|
| Encoding Construct | Plasmid Designation | Insert |
| 5 | pMGX0676 | hu2B6VL-hu3G8VH-huFc |
| 6 | pMGX0674 | hu3G8VL-hu2B6VH-huFc |
| 7 | pMGX0677 | Hu2B6VL-hu3G8VH-FNRGEC |
| 8 | pMGX0678 | Hu3G8VL-hu2B6VH-huhinge-Fc (A215V) |

Polypeptide/diabody Expression: Four separate cotransfections into in HEK-293 cells using Lipofectamine 2000, as described in section 6.1, were performed: pMGX0669 and pMGX0674, encoding constructs 1 and 6, respectively; pMGX0667 and pMGX0676, encoding constructs 2 and 5, respectively; and pMGX0677 and pMGX0678, encoding constructs 7 and 8, respectively.

Co-transfection of these plasmids was designed to lead to the expression of a bispecific diabody (CBD) of tetravalency with IgG-like structure, immunospecific for both FcγRIIB and FcγRIIIA. An additional cotransfection was also performed: pMGX0674 and pMGX0676, encoding constructs 6 and 5, respectively. Following three days in culture, conditioned media was harvested. The amount of secreted product in the conditioned media was quantitiated by anti IgG Fc ELISA using purified Fc as a standard. The concentrations of product in the samples was then normalized based on the quantitation, and the normalized samples used for the remaining assays.

ELISA: The binding of diabody molecules secreted into the medium was assayed by sandwich ELISA as described, supra. Unless indicated, CD32B was used to coat the plate, i.e., as the target protein, and HRP-conjugated CD16 was used as the probe.

Results

An ELISA assay was used to test the normalized samples from the recombinant expression systems comprising constructs 1 and 6 (pMGX669-pMGX674), constructs 2 and 5 (pMGX667-pNGX676) and constructs 5 and 6 (pMGX674-pMGX676) for expression of diabody molecules capable of simultaneous binding to CD32B and CD16A (FIG. 10). The ELISA data indicated that co-transfection with constructs 1 and 6 or co-transfection with constructs 2 and 5 failed to produce a product that could bind either or both antigens (FIG. 10, □ and ▲, respectively). However, co-transfection of constructs 5 and 6 lead to secretion of a product capable of binding to both CD32B and CD16 antigens. The latter product was a dimer of constructs 5 and 6, containing one binding site for each antigen with a structure schematically depicted in FIG. 11.

In order to drive formation of an IgG like heterotetrameric structure, the coding sequence for six additional amino acids was appended to the C-terminal of construct 1, generating construct 7 (SEQ ID NO: 16 and shown schematically in FIG. 9). The six additional amino acids, FNRGEC (SEQ ID NO: 23), were derived from the C-terminal end of the Kappa light chain and normally interact with the upper hinge domain of the heavy chain in an IgG molecule. A hinge domain was then engineered into construct 6, generating construct 8 (SEQ ID NO: 18 and FIG. 9). Construct 8 additionally comprised an amino-acid mutation in the upper hinge region, A215V. Expression plasmids encoding construct 7 and construct 8, pMGX677 and pMGX678, respectively, were then cotransfected into HEK-293 cells and expressed as described.

Diabody molecules produced from the recombinant expression system comprising constructs 7 and 8 (pMGX0677+pMGX0678), were compared in an ELISA assay for binding to CD32B and CD16A to diabody molecules produced from expression systems comprising constructs 1 and 6 (pMGX669+pMGX674), constructs 2 and 8 (pMGX669+pMGX678), and constructs 6 and 7 (pMGX677+pMGX674) (FIG. 12).

As before, the molecule produced by the expression system comprising constructs 1 and 6 (pMGX669+pMGX674) proved unable to bind both CD32A and CD16A (FIG. 10 and FIG. 12). In contrast, the product from the co-expression of either constructs 7 and 6 (pMGX0677+pMGX0674) or from the co-expression of constructs 7 and 8 (pMGX0677-pMGX0678) were able to bind both CD32B and CD16 (FIG. 12). It is noted that construct 7 is analogous to construct 1, with the exception that construct 7 comprises the C-terminal sequence FNRGEC (SEC ID NO:23); and that construct 8 is analogous to construct 6, except that construct 8 comprises a hinge domain and the mutation A215V. The data indicate that the addition of the 6 extra amino-acids from the C-terminus of the C-kappa light chain (FNRGEC; SEQ ID NO: 23) to the non-Fc bearing, 'lighter,' chain helped stabilize the formation of the tetrameric IgG-like diabody molecules, regardless of whether the corresponding heavier chain comprised a hinge domain (i.e., pMGX0677+pMGX0674 and pMGX0677-pMGX0678, FIG. 12). The addition of the hinge domain to the Fc bearing 'heavier' polypeptide, without the addition of the FNRGEC (SEQ ID NO: 23) C-terminal sequence to the corresponding 'lighter' chain, was apparently unable to effect similar stabilization (i.e., lack of binding by product of co-transfection of constructs 2 and 8 (pMGX669+pMGX678)). The structure of the tetrameric diabody molecule is schematically represented in FIG. 13.

6.3 Effect of Domain Order and Additional Disulfide Bonds on Formation of Tetrameric Igg-like Diabody The effect of additional stabilization between the 'lighter' and 'heavier' polypeptide chains of the tetrameric IgG-like diabody molecule was investigated by substitution of selected residues on the polypeptide chains with cysteines. The additional cysteine residues provide for additional disulfide bonds between the 'heavier' and 'lighter' chains. Additionally, domain order on binding activity was investigated by moving the Fc domain or the hinge-Fc domain from the C-terminal end of the polypeptide chain to the N-terminus. Although the binding activity of the molecule comprising the additional disulfide bonds was not altered relative to earlier constructed diabody molecules with such bonds, transferring the Fc or hinge-Fc domain to the N-terminus of the 'heavier' polypeptide chain comprising the diabody surprisingly improved binding affinity and/or avidity of the bispecific molecule to one or both of its target antigens.

Materials and Methods

Construction and Design of Polypeptide Molecules: Nucleic acid expression vectors were designed to produce modified versions of constructs 5, 6 and 8 presented in Example 6.2. Construct 9 (SEQ ID NO: 19) and construct 10 (SEQ ID NO: 20) (both shown schematically in FIG. 13) were analogous to constructs 8 and 6, with the exception that Fc domain or hinge-Fc domain, respectively, was shifted from the C-terminus of the polypeptide to the N-terminus. Additionally all Fc domains used were wild-type IgG1 Fc domains. Construct 11, SEQ ID NO: 21, (shown schematically in FIG. 14) was analogous to construct 2 from Example 6.1 except that the C-terminus was designed to further comprise the sequence FNRGEC (SEQ ID NO: 23). Construct 12, SEQ ID NO: 22 (shown schematically in FIG. 14) was analogous to construct 5 from Example 6.2 except that the Fc domain further comprised a hinge region. Also, for constructs 11 and 12, the 2B6 VL domain and 2B6 VH domain comprised a single amino acid modification (G105C and G44C, respectively) such that a glycine in each domain was replaced by cysteine.

PCR and Expression Vector Construction: All PCR and PCR product purification protocols were as described in Example 6.1 and 6.2

Overlapping PCR: Final products were constructed, amplified and purified using methods described in example 6.1 and example 6.2.

Final products were cloned into pCIneo mammalian expression vector (Promega, Inc.) as previously described. The plasmid encoding constructs were designated as identified in Table 15:

TABLE 15

PLASMID CONSTRUCTS

| Encoding Construct | Plasmid Designation | Insert |
|---|---|---|
| 9 | pMGX0719 | Huhinge/Fc-hu3G8VL-hu2B6VH |
| 10 | pMGX0718 | HuFc-hu2B6VL-hu3G8VH |
| 11 | pMGX0716 | Hu2B6VL(G/C)-hu3G8VH-huhingeFC |
| 12 | pMGX0717 | Hu3G8VL-hu2B6VH (G/C)-FNRGEC |

Polypeptide/diabody Expression: Three separate cotransfections in to in HEK-293 cells using Lipofectamine 2000, as described in section 6.1, were performed: pMGX0669 and pMGX0719, encoding constructs 1 and 9, respectively; pMGX0669 and pMGX0718, encoding constructs 1 and 10, respectively; and pMGX0617 and pMGX0717, encoding constructs 11 and 12, respectively. Co-transfection of these plasmids was designed to lead to the expression of a bispecific diabody (CBD) of tetravalency with IgG-like structure, immunospecific for both FcγRIIB and FcγRIIIA. Following three days in culture, conditioned media was harvested. The amount of secreted product in the conditioned media was quantitiated by anti IgG Fc ELISA using purified Fc as a standard. The concentrations of product in the samples were then normalized based on the quantitation, and the normalized samples used for the remaining assays.

ELISA: The binding of diabody molecules secreted into the medium was assayed by sandwich ELISA as described, supra. Unless indicated, CD32B was used to coat the plate, i.e., as the target protein, and HRP-conjugated CD16 was used as the probe.

Western Blot: Approximately 15 ml of conditioned medium form the three above-described cotransfections were analyzed by SDS-PAGE under non-reducing conditions. One gel was stained with Simply Blue Safestain (Invitrogen) and an identical gel was transferred to PVDF membrane (Invitrogen) using standard transfer methods. After transfer, the membrane was blocked with 5% dry skim milk in 1×PBS. The membrane was then incubated in 10 ml of 1:8,000 diluted HRP conjugated Goat anti human IgG1 H+L in 2% dry skim milk 1×PBS/0.1% Tween 20 at room temperature for 1 hr with gentle agitation. Following a wash with 1×PBS/0.3% Tween 20, 2×5 min each, then 20 min at room temperature, the membrane was developed with ECL Western blotting detection system (Amersham Biosciences) according to the manufacturer's instructions. The film was developed in X-ray processor.

Results

Conditioned media from the recombinant expression systems comprising constructs 1 and 9; constructs 1 and 10; and constructs 11 and 12 were analyzed by SDS-PAGE (under non reducing conditions) analysis and Western-blotting (using an anti-IgG as the probe). Western blot revealed that the product from the systems comprising constructs 11 and 12 or comprising constructs 9 and 1 predominately formed a single species of molecule of approximately 150 kDa (FIG. 14, lanes 3 and 2, respectively). Both of these products have engineered internal disulfide bonds between the 'lighter' and 'heavier' chains comprising the diabody. In contrast, the molecule without engineered internal disulfide bonds between the 'lighter' and 'heavier' chains, formed of constructs 10 and 1, formed at least two molecular species of molecular weights ~75 and ~100 kDa (FIG. 14, lane 1).

Figure 15A:
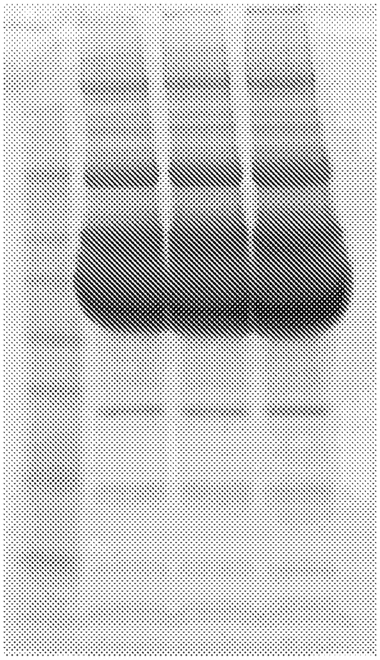
Figure 15B:
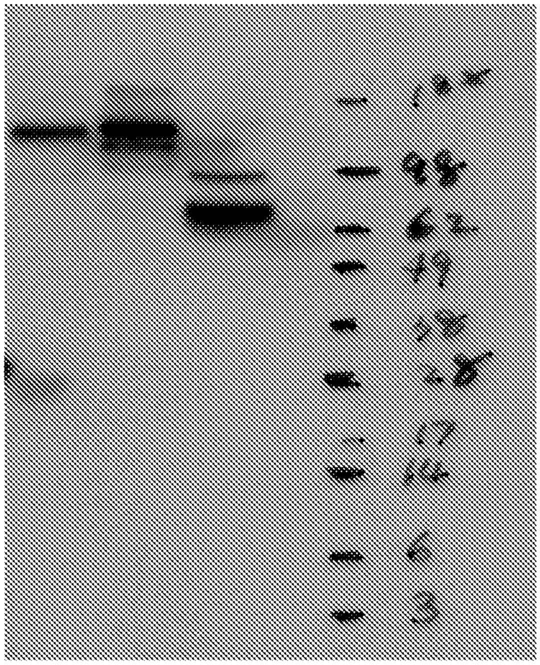

Despite the results of the Western Blot, each of the three products was found capable of binding both CD32A and CD16 (FIG. 15). Surprisingly, relative to the product comprising a C-terminal hinge-Fc domain (formed of constructs 11 and 12), the product from both systems wherein the Fc (or Fc-hinge) domain was at the amino terminus of the Fc containing polypeptide chain (i.e., the 'heavier' chain) (constructs 9+1 and constructs 10+1) demonstrated enhanced affinity and/or avidity to one or both of its target peptides (i.e. CD32B and/or CD16).

6.4 Effect of Internal/External Cleavage Site on Processing of Polyprotein Precursor and Expression of Covalent Bispecific Diabody; Design and Characterization of Bispecific Diabody Comprising Portions of Human IgG LAMBDA Chain and Hinge Domain As described herein, the individual polypeptide chains of the diabody or diabody molecule of the invention may be expressed as a single polyprotein precursor molecule. The ability of the recombinant systems described in Examples 6.1-6.3 to properly process and express a functional CBD from such a polyprotein precursor was tested by engineering a nucleic acid to encode, both the first and second polypeptide chains of a CBD separated by an internal cleavage site, in particular, a furin cleavage site. Functional, CBD was isolated from the recombinant system comprising the polyprotein precursor molecule.

As discussed in Example 6.3, addition of the 6 C-terminal amino acids from the human kappa light chain, FNRGEC (SEQ ID NO: 23), was found to stabilize diabody formation—presumably through enhanced inter-chain interaction between the domains comprising SEQ ID NO: 23 and those domains comprising an Fc domain or a hinge-Fc domain. The stabilizing effect of this lambda chain/Fc like interaction was tested in CBD wherein neither polypeptide chain comprised an Fc domain. One polypeptide chain of the diabody was engineered to comprise SEQ ID NO: 23 at its C-terminus; the partner polypeptide chain was engineered to comprise the amino acid sequence VEPKSC (SEQ ID NO: 77), which was derived from the hinge domain of an IgG. Comparison of this CBD to that comprised of constructs 1 and 2 (from example 6.1) revealed that the CBD comprising the domains derived from hinge domain and lambda chain exhibited slightly greater affinity to one or both of its target epitopes.

Materials and Methods

Construction and Design of Polypeptide Molecules: Polyprotein precursor: Nucleic acid expression vectors were designed to produce 2 polyprotein precursor molecules, both represented chematically in FIG. 17. Construct 13 (SEQ ID NO: 95) comprised from the N-terminus of the polypeptide chain, the VL domain of 3G8, the VH domain of 2.4G2 (which binds mCD32B), a furin cleavage site, the VL domain of 2.4G2 and the VH domain of 3G8. The nucleotide sequence encoding construct 13 is provided in SEQ ID NO: 96. Construct 14 (SEQ ID NO: 97) (FIG. 17), comprised from the N-terminus of the polypeptide chain, the VL domain of 3G8, the VH domain of 2.4G2 (which binds mCD32B), a furin cleavage site, a FMD (Foot and Mouth Disease Virus Protease C3) site, the VL domain of 2.4G2 and the VH domain of 3G8. The nucleotide sequence encoding construct 14 is provided in SEQ ID NO: 98.

Nucleic acid expression vectors were designed to produce modified versions of constructs 1 and 2 presented in Example 6.1. Construct 15 (SEQ ID NO: 99) (FIG. 17) was analagous to construct 1 (SEQ ID NO: 9), presented in example 6.1, with the exception that the C-terminus of contruct 15 comprised the amino acid sequence FNRGEC (SEQ ID NO: 23). The nucleic acid sequence encoding construct 15 is provided in SEQ ID NO: 100. Construct 16 (SEQ ID NO: 101) (FIG. 17) was analogous to construct 2, presented in Example 6.1, with the exception that the C-terminus of construct 16 comprised the amino acid sequence VEPKSC (SEQ ID NO: 77). The nucleic acid sequence encoding construct 16 is provided in SEQ ID NO: 102.

PCR and Expression Vector Construction: All PCR and PCR product purification protocols were as described in Example 6.1 and 6.2

Overlapping PCR: Final products were constructed, amplified and purified using methods described in example 6.1 and example 6.2 with appropriate primers Final products were cloned into pCIneo mammalian expression vector (Promega, Inc.) as previously described. The plasmid encoding constructs were designated as identified in Table 16:

TABLE 16

| PLASMID CONSTRUCTS | | |
|---|---|---|
| Encoding Construct | Plasmid Designation | Insert |
| 13 | pMGX0750 | 3G8VL-2.4G2VH-Furin-2.4G2VL-3G8VH |
| 15 | pMGX0752 | Hu2B6VL-Hu3G8VH-FNRGEC |
| 16 | pMGX0753 | Hu3G8VL-Hu2B6VH-VEPKSC |

Polypeptide/diabody Expression: One transfection and one cotransfection into in HEK-293 cells using Lipofectamine 2000, as described in section 6.1, were performed: single: pMGX0750, encoding construct 13; and cotranfection: pMGX0752 and pMGX0753, encoding constructs 15 and 16, respectively. Following three days in culture, conditioned media was harvested, and secreted product affinity purified as described.

ELISA: The binding of diabody molecules secreted into the medium was assayed by sandwich ELISA as described, supra. Murine CD32B was used to coat the plate, i.e., as the target protein, and HRP-conjugated CD16A was used as the probe for the product of the co-transfection of constructs 15 and 16. mCD32B was used as the target protein and biotin-conjugated CD16A was used as the probe for the recombinant system comprising construct 13.

Results

Conditioned media from the recombinant expression systems comprising constructs 13 was analysed by sandwich ELISA. The ELISA assay tested the binding of the CBD for specificity to either or both of mCD32B and/or CD16 (FIG. 18). CD32B served as the target antigen and CD16A was used as the secondary probe. The positive signal in the ELISA revealed that the heterodimeric h2.4G2-h3G8 CBD produced from the polyprotein precursor had specificity for both antigens.

Similarly, the purified product generated by cotransfection of the vectors encoding constructs 15 and 16 was tested in an ELISA assay and compared to the product comprised of constructs 1 and 2 (Example 6.1). CD32B served as the target antigen and CD16A was used as the secondary probe. As with the product comprised of constructs 1 and 2, the product of constructs 15 and 16 was found to be capable of simultaneously binding CD32B and CD16A. In fact, the product of constructs 15 and 16 showed slightly enhanced affinity for one or both of the target antigens, i.e. CD32B or CD16A. This is perhaps due to increased stability and or fidelity (relative to a wild type VH-VL domain interaction) of the interchain association afforded by the interaction of the lambda chain region, FNRGEC (SEQ ID NO: 23) and hinge region VEPKSC (SEQ ID NO: 77), which is absent in the product comprised of constructs 1 and 2.

6.5 Use of Dual Affinity Retargeting Reagents ("DARTs") to Link Multiple Affinities Together One aspect of the present invention relates to new dual affinity retargeting reagents ("DARTs") as well as new ways of linking multiple affinities together. "DARTS" may be monospecific, bispecific, trispecific, etc., thus being able to simultaneously bind one, two, three or more different epitopes (which may be of the same or of different antigens). "DARTS" may additionally be monovalent, bivalent, trivalent, tetravalent, pentavalent, hexavelent, etc., thus being able to simultaneously bind one, two, three, four, five, six or more molecules. As shown in FIG. 35, these two attributes of DARTS may be combined, for example to produce bispecific antibodies that are tetravalent, etc.

One advance is the development of a DART that has affinity for a prototypic immune receptor, huCD32B, as well as affinity for a hapten, fluorescein. This DART, termed "2B6/4420," serves as a universal adaptor, able to co-ligate huCD32B with molecules that interact with fluorescein-conjugated binding partners. CD32B is an Fc receptor that has the ability to quench activating signals by virtue of clustering with activation signaling immune complexes. In its initial implementation, this technology allows rapid screening of several biological targets for clustering with huCD32B without the need to generate new DART constructs. The 2B6/4420 can simply be mixed with a fluoresceinated antibody against a cell surface receptor and thereby mimic the action of a DART with affinity for that receptor (FIG. 20). Further, this reagent allows efficient linkage of affinity reagents that are not easily expressed or produced, allowing one to overcome technical limitations. 2B6/4420-containing DARTs are clearly useful as research tools and also as clinical candidates. 2B6/4420 produced from HEK293 cells can simultaneously bind CD32B and fluorescein in an ELISA assay. Additionally, it can inhibit cell proliferation by recruiting CD32B to the BCR complex via colligation with CD79. The 2B6 arm of the DART may be replaced with a different antibody sequence or a binding sequence having other relevant specificity.

Materials and Methods:

Plasmid Constructs: 2B6/4420 is derived from sequences of humanized 2B6 MAb (hu2B6, MGA321) and a chimeric mouse Fv/human Fc version of the anti-fluorescein MAb, 4420. The fully assembled DART consists of two polypeptides, resulting in covalent linkage of two Fv regions. The first polypeptide consists of a secretion signal sequence followed by the hu2B6VL produced as a fusion protein with 4420VH separated by a linker consisting of the amino acid residues GGGSGGGG. The sequence FNRGEC, derived from the C-terminus of the kappa light chain, is appended to the C-terminus of this polypeptide. The other polypeptide consists of signal sequence-4420VL-GGGSGGGG-hu2B6VH, with the sequence VEPKSC, derived from the C-terminus of the human IgG1 Fd fragment, appended to the C-terminus. The cysteines in the two chains form a disulfide bond, covalently linking the two polypeptides together (FIG. 20). The DNA sequences encoding the described polypeptides were PCR amplified from existing plasmids, combined by overlap PCR and cloned into pCIneo (Promega) between the Nhe I and EcoR I sites. Finally, a DART with affinity for huCD32B and huCD16 (2B6/3G8) that has been previously constructed using methods similar to those described above was used as a control.

Antibodies: The murine monoclonal antibodies anti-human CD79b, CB3.1 and CB3.2 (hybridomas) were obtained from Dr. Cooper MD, University of Alabama at Birmingham, Birmingham Ala. CB3.1 and CB3.2 were labeled with fluorescein isothiocyanate (FITC) following the manufacturer instructions (Pierce, Rockford Ill.). The F(ab')2 fragment of an Fc-fragment-specific, goat anti-mouse (GAM) IgG was obtained from Jackson Laboratories (West Grove, Pa.). Anti-huCD32B mouse MAb, 3H7, was produced and purified in house. Goat anti-2B6Fv was produced by immunizing goats with hu2B6 whole antibody and affinity purifying against the Fv region of hu2B6. HuIgG, FITC-huIgG, and HRP-anti-mouse IgG were obtained from Jackson Immunoresearch. HRP-anti-goat was obtained from Southern Biotech.

DART expression: Plasmids encoding each chain were cotransfected into 293H cells (Invitrogen) using Lipofectamine 2000 (Invitrogen) according to the manufacturer's instructions. Secreted protein was harvested 3-4 times at three day intervals and purified by liquid chromatography against an immobilized soluble form of CD32B.

ELISA: 2B6/4420 or 2B6/3G8 DARTs were captured on MaxiSorp plates (Nalge Nunc) coated with FITC-labeled Protein S (Novagen), human IgG, or FITC-huIgG. Detection proceeded by binding soluble CD32B ectodomain, followed by 3H7 (a mouse monoclonal antibody specific for CD32B), and finally anti-mouse-HRP. Alternatively, detection was performed by binding goat anti-2B6 Fv polyclonal affinity purified antiserum, followed by anti-goat-HRP. HRP activity was detected using a colorimetric TMB substrate (BioFX) and read on a VersaMax ELISA plate reader.

B Cell Purification and Proliferation Assay: Peripheral blood mononuclear cells were separated by a Ficoll/Paque Plus (Amersham Pharmacia Biotech, UK) gradient method using blood from healthy donors. B lymphocytes were isolated using Dynal B Cell Negative Isolation Kit (Dynal Biotechnology Inc., NY) following the manufacture's instructions. The purity of the isolated B cells ($CD20^+$) was greater than 90% as estimated by FACS analysis. For the proliferation assay, purified B cells were seeded in complete RPMI 1640 medium in flat-bottomed 96-well microtiter plates at a cell density of $1\times10^5$ cells per well in a final volume of 200 μl and incubated for 48 hrs in the presence or absence of antibodies and diabodies at 37° C. in 5% $CO_2$. 1 μCi/well of [$^3$H]thymidine (Perkin Elmer, Wellesley, Mass.) was then added and the incubation continued for an additional 16-18 h prior to harvesting. [$^3$H]thymidine incorporation was measured by liquid scintillation counting.

Results

In order to demonstrate that 2B6/4420 DART was active and specific, two ELISA experiments were conducted. First, 2B6/4420 or 2B6/3G8 (as a negative control) was bound to a fluorescein-conjugated protein (S-protein) that had been coated onto ELISA plates. Next, the 2B6 arm of the DART was engaged by soluble CD32B. Binding was detected by another antibody to CD32B with an epitope that does not overlap that of 2B6 followed an HRP-conjugated secondary antibody. While 2B6/4420 DART is capable of simultaneously binding fluorescein and CD32B, 2B6/3G8 is not (FIG. 21, Panel A). When the DARTs are captured on plates coated with soluble CD32B and binding is detected by an antibody specific for hu2B6 Fv, both DARTS show good binding. To demonstrate that 2B6/4420 DART was capable of binding fluorescein conjugated to human IgG (given that this is the context of the initial implementation of this reagent), HuIgG, unlabeled or labeled with fluorescein, was bound to ELISA plates and used to capture 2B6/4420. Again, 2B6/3G8 was used as a negative control. Binding was detected using an antibody specific for Hu2B6 Fv. 2B6/4420 DART clearly binds to FITC-HuIgG, but does not bind to unlabeled HuIgG, demonstrating that this DART is capable of binding fluorescein conjugated to an antibody and that there is no significant binding to antibody alone. As expected, no binding was detected by 2B6/3G8 DART in either of these contexts.

Experiments were conducted to demonstrate that the 2B6/4420 DART was capable of functioning as a dual affinity reagent that could have an effect upon signaling in the context of a cell-based assay. Co-aggregation of CD32B with the BCR has been shown to inhibit B cell activation. The ability of the 2B6/4420 DART to co-engage CD32B with the BCR coated with αCD79b antibodies labeled with fluorescein and trigger inhibition of cell proliferation was explored. B cells were negatively selected from human blood and activated through treatment with increasing concentrations of mouse anti-human-CD79b FITC-labeled, clones CB3.1 and CB3.2, and by the addition of a F(ab')$_2$ fragment of an Fc-specific GAM as a secondary reagent to cross-link the BCR, together with a fixed concentration (5 μg/mL) of 2B6/4420 DART or an equivalent amount of 2B6/3G8 DART, a molecule which does not target fluorescein, thus used as control. Cell proliferation, measured as [$^3$H]-thymidine incorporation, increased with increasing concentrations of the monoclonal anti-CD79b-FITC activator in the absence of DARTS or in the presence of the control 2B6/3G8 DART. The presence of 2B6/4420 DART led to a profound reduction in B-cell proliferation at all concentrations of anti-human CD79b-FITC (FIG. 22, Panels A and B and FIG. 23, Panel A).

Figure 23:
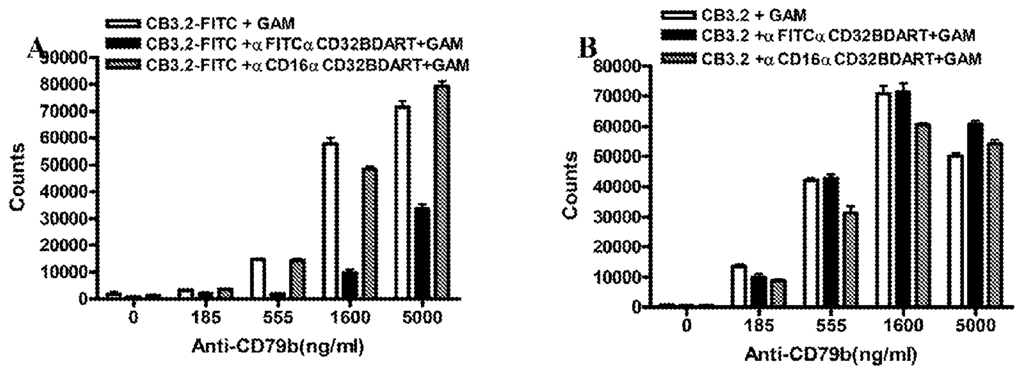

Inhibition of proliferation was not observed when B cells coated with unlabeled CB3.2 and activated using the same experimental conditions were treated with 2B6/4420 DART proving its target-specificity (FIG. 23, Panel B). These data demonstrate that 2B6/4420 DART is able to cross-link CD32B and the BCR and deliver an inhibitory signal capable of blocking antigen-receptor-induced cell activation.

6.6 DART Immunotherapeutic Against CD32B Expressing B Cell Malignancies

Currently, B cell malignancies are treated using Rituxan® anti-CD20 antibody. Some B cell malignancies, however do not express CD20 or become resistant to Rituxan. The DARTs of the present invention provide an alternative immunotherapeutic capable of overcoming the problems associated with Rituxan® anti-CD20 antibody.

MGD261 is a dual-affinity re-targeting (DART) molecule binding to hCD32B (via h2B6 antibody) and hCD16A and hCD16B (via h3G8 antibody).

The efficacy (B cell depletion) and safety of MGD261 was tested in mCD32−/− hCD16A+ C57B1/6, mCD32−/− hCD32B+ C57B1/6 and mCD32−/− hCD16A+ hCD32B+ C57B1/6. In this repeat dose experiment, mice received 6 IV injections (twice a week for 3 weeks). B cell depletion was monitored by FACS. Safety was monitored by cage side observation.

Data indicate that MGD261 is capable of depleting B cells in double transgenic mice without inducing any significant side effects.

Data: mCD32−/− hCD16A+ C57B1/6, mCD32−/− hCD32B+ C57B1/6 and mCD32−/− hCD16A+hCD32B+ C57B1/6 mice from MacroGenics breeding colony were injected IV at days 0, 3, 7, 10, 14 and 17 with MGD261 (10, 3, 1 or 0.3 mg/kg), or an irrelevant antibody (hE16 10 mg/kg). Blood was collected at days −19 (pre-bleed), 4, 11, 18, 25 and 32 for FACS analysis. Animal health and activity was recorded three times a week.

Design:

| | Animals | | Test | Dose |
|---|---|---|---|---|
| Group | # | Mice | Article | (mg/kg) |
| A | 4 | mCD32 −/− hCD16A + | hE16 | 10 |
| B | 5 | mCD32 −/− hCD16A + | MGD261 | 10 |
| C | 3 | mCD32 −/− hCD32B + | hE16 | 10 |
| D | 3 | mCD32 −/− hCD32B + | MGD261 | 10 |
| E | 5 | mCD32 −/− hCD16A + hCD32B + | hE16 | 10 |
| F | 5 | mCD32 −/− hCD16A + hCD32B + | MGD261 | 10 |
| G | 5 | mCD32 −/− hCD16A + hCD32B + | MGD261 | 3 |
| H | 5 | mCD32 −/− hCD16A + hCD32B + | MGD261 | 1 |
| I | 5 | mCD32 −/− hCD16A + hCD32B + | MGD261 | 0.3 |

FACS analysis Method: Whole blood samples were collected at 18 days prior to h2B6-h3G8 administration and 4, 11, 18, 25 and 32 days after the treatment. The blood samples were analyzed to determine the effect of h2B6-h3G8 on the B cell counts by a FACS based assay. A non-wash protocol was used for B cell, T cell and PMN count by using FlowCount beads, obtained from Beckman Coulter. The panel of antibodies used in the analysis was 1A8-FITC for PMN, CD3-PE for T cell, CD19-APC for B cell and CD45-PerCP for total leukocytes.

Results

Mice treated with hE16 or MGD261 (at any concentration) did not show any sign of discomfort at anytime during the duration of the experimentation.

B cell depletion was observed in hCD16A and hCD32B double transgenic mice. Diabody h2B6-3G8 engages hCD16A expressing effector cells and hCD32B expressing B cells; the engagements were required for the B cell killing. B cell depletion was not observed in singly transgenic mice (FIG. 24). There were no significant changes for T cells and PMN level during the study.

As a further demonstration of the alternative immunotherapeutics of the present invention, a surrogate of MGD261, termed "2.4G2-3G8 DB," was constructed. 2.4G2-3G8 DB is a dual-affinity re-targeting (DART) molecule binding to mCD32B (via 2.4G2 antibody) and hCD16A and hCD16B (via h3G8 antibody).

The efficacy (B cell depletion) and safety of 2.4G2-3G8 DB was tested in mCD16−/−, mCD16−/− hCD16A+ C57B1/6, mCD16−/− hCD16B+ and mCD16−/− hCD16A+ hCD16B+ mice. In this repeat dose experiment, mice received 9 IP injections (Three times a week for 3 weeks). B cell depletion was monitored by FACS. Safety was monitored by cage side observation.

Data indicate that 2.4G2-3G8 DB is capable of depleting B cells in hCD16 transgenic mice without inducing any significant side effects.

Data: mCD16−/−, mCD16−/− hCD16A+ C57B1/6, mCD16−/− hCD16B+ and mCD16−/− hCD16A+ hCD16B+ mice from MacroGenics breeding colony were injected IP at days 0, 2, 4, 7, 9, 11, 14, 16 and 18 with 2.4G2-3G8 DB (75 ug/mouse), or PBS. Blood was collected at days −10 (pre-bleed), 4, 11 and 18 for FACS analysis. Animal health and activity was recorded three times a week.

| Group | # of Animals | Dose μg/ms | Test Article | Route | Blood Collection Timepoints |
|---|---|---|---|---|---|
| A | 2 mCD16 −/− | — | PBS | IP | Days - 10, 4, 11, 18 |
| B | 2 mCD16 −/− 16A + B6 | — | PBS | IP | Days - 10, 4, 11, 18 |
| C | 2 mCD16 −/− 16B + | — | PBS | IP | Days - 10, 4, 11, 18 |
| D | 2 mCD16 −/− 16A + 16B + | — | PBS | IP | Days - 10, 4, 11, 18 |
| E | 6 mCD16 −/− | 75 | 2.4G2 - 3G8 DB | IP | Days - 10, 4, 11, 18 |
| F | 6 mCD16 −/− 16A + B6 | 75 | 2.4G2 - 3G8 DB | IP | Days - 10, 4, 11, 18 |
| G | 6 mCD16 −/− 16B + | 75 | 2.4G2 - 3G8 DB | IP | Days - 10, 4, 11, 18 |
| H | 6 mCD16 −/− 16A + 16B + | 75 | 2.4G2 - 3G8 DB | IP | Days - 10, 4, 11, 18 |

FACS analysis Method: Whole blood samples were collected 10 days prior to 2.4G2-3G8 administration and 4, 11 and 18 days after the initiation of the treatment. The blood samples were analyzed to determine the effect of 2.4G2-3G8 on the B cell counts by a FACS based assay. A non-wash protocol was used for B cell, T cell and PMN count by using TruCOUNT tubes, obtained from BD Immunocytometry System. The panel of antibodies used in the analysis was 1A8-FITC for PMN, CD3-PE for T cell, CD19-APC for B cell and CD45-PerCP for total leukocytes.

Results

Mice treated with hE16 or 2.4G2-3G8 DB did not show any sign of discomfort at anytime during the duration of the experimentation.

B cell depletion was observed in mCD16−/− hCD16A+ or mCD16−/− hCD16A+hCD16B+ mice but not in mCD16−/− mice. These data indicate that hCD16A carrying effector cells were required for the B cell killing (FIG. 25). There were no significant changes for T cells and PMN level during the study.

Intravenous (IV) Model: The anti-tumor activity of MGD261 was tested using an intravenous (IV) model of the human tumor cell line Raji. Raji is a human Burkitt's lymphoma cell line expressing hCD32B. When injected intravenously in mCD16−/−, hCD16A+, RAG1−/− mice, tumor cells locate to the spine and results in hind leg paralysis.

Data indicate that MGD261 is capable of blocking Raji tumor cell growth in vivo in mCD16−/−, hCD16A+, RAG1−/− mice. Data indicate that MGD261 can be used in the treatment of CD32B expressing B cell malignancies in the human.

Data: Twelve-twenty week old mCD16−/−, hCD16A+, RAG1−/− C57B1/6 mice from MacroGenics breeding colony were injected IV at day 0 with $5\times10^6$ Raji cells. At Days 6, 9, 13, 16, 20, 23, 27 and 30 mice were also treated intraperitoneously (IP) with 250, 25 or 2.5 ug MGD261 or with PBS (negative control). Mice were then observed daily and body weight was recorded twice a week. Mice developing hind leg paralysis were sacrificed.

Results: Mice treated with PBS died between day 25 and day 50. Mice treated with MGD261 survived at least until day 90 (FIG. 26). The increased survival is statistically significant. A comparison of survival curves using a Logrank Test gave a $\chi^2$ of 96.46 (df 9; P value <0.0001).

6.7 DART Expression in Prokaryotes

Experiments were conducted to demonstrate the ability to produce DARTs in non-mammalian hosts. Accordingly, *Escherichia coli* was transformed with a DART-expressing plasmid, and DART expression was monitored.

Materials and Methods:

Plasmid construction: 3G8 is a humanized monoclonal antibody against HuCD16. The DART described here consists of two covalently linked chains, each of which has a VL followed by a spacer, then a VH followed by a Cys in a good context to form a disulfide bond to the opposite chain. The DART sequence encoding 3G8VL-GlyGlyGlySerGlyGlyGlyGly (SEQ ID NO: 10)-3G8VH-LeuGlyGlyCys was PCR amplified from an existing eukaryotic expression construct and digested with Nco I and EcoR I. The target vector was pET25b (+) (Novagen), which contains a pelB leader sequence for secretion in *E. coli*. Prior to insertion of the 3G8/3G8 DART sequences, the vector was modified as follows: First, the T7 promoter was replaced by the lower activity lac promoter in order to favor soluble, albeit lower level, expression of proteins under its control. Additionally, two point mutations were introduced to eliminate two internal Met codons present at the beginning of the multiple cloning site (MCS) in order to favor initiation at the Met present at the beginning of the pelB leader. The DART that is produced by this construct consists of two V-region arms that have the same specificity, namely HuCD16.

Expression: BL21DE3 cells (Novagen) were transformed with the pET25b(+) T7-lac+ 3G8/3G8 plasmid and an amp-resistant colony was used to seed broth culture. When the culture reached 0.5 OD600 units, 0.5 mM IPTG was added to induce expression. The culture was grown at 30° C. for 2 hours and the cell-free medium was collected.

Purification: The 3G8/3G8 DART was purified in a two step process utilizing affinity and size exclusion chromatography. The DART was captured from the conditioned medium using affinity chromatography. Specifically, CD16A coupled to CNBr activated Sepharose 4B (GE Healthcare). The CD16A-Sepharose resin was equilibrated in 20 mM Tris/HCl, pH 8.0 prior to loading. Upon completion of loading, the resin was washed with equilibration buffer prior to elution of the bound DART with 50 mM Glycine pH 3.0. The eluted DART was immediately neutralized with 1M Tris/HCl pH 8.0 and concentrated using a centrifugation type concentrator (Vivaspin 20, 10k MWCO PES, VivaScience Inc.). The concentrated DART was further purified by size exclusion chromatography using a Superdex 200 column (GE Healthcare) equilibrated in PBS.

Figure 27:
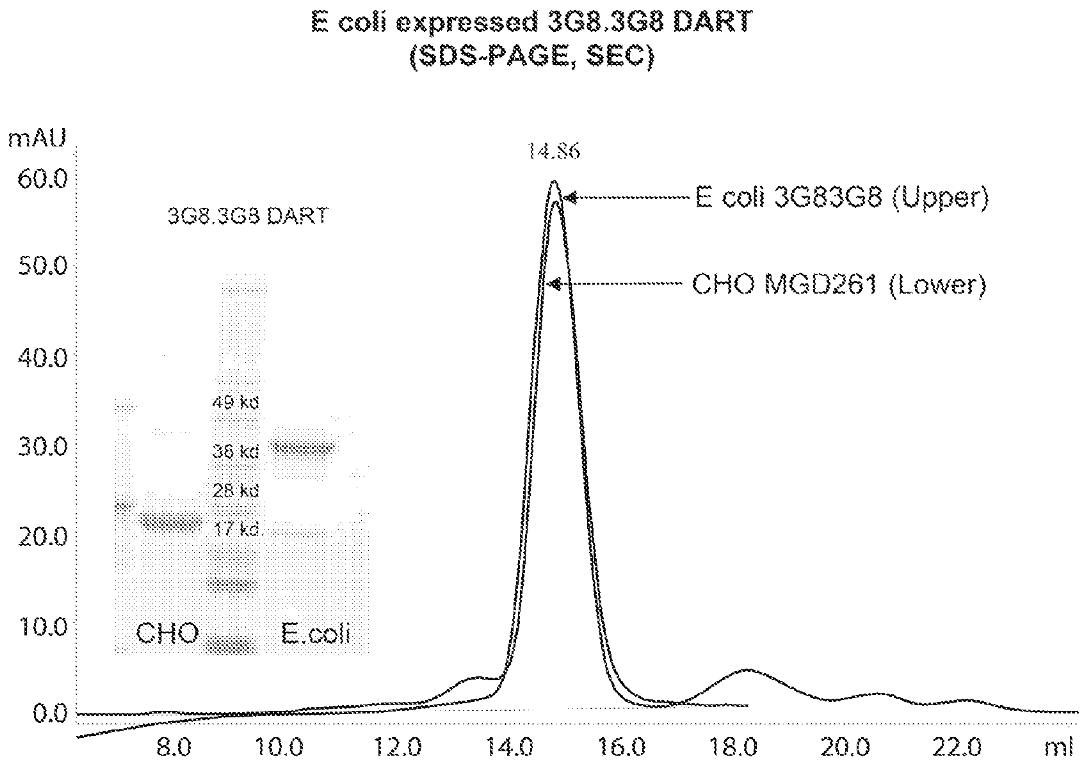

Results 1.7 liters of *E. coli* cultured conditioned medium was processed through the CD16A Sepharose column. The yield of DART was 0.12 mg. Analysis of the purified DART by SDS-PAGE and SEC demonstrated comparability to the mammalian cell (CHO) expressed control DART (FIG. 27).

*E. coli* Expressed h3G8-h3G8 DART Binding ELISA: Expression of h3G8-h3G8 DART in *E. coli* was measured using an ELISA. 50 µl/well of 2 µg/ml of anti-h3G8 Fv specific antibody 2C11 was coated on 96-well Maxisorp plate in Carbonate buffer at 4° C. over night. The plate was washed three times with PBS-T (PBS, 0.1% Tween 20) and then blocked by 0.5% BSA in PBS-T for 30 minutes at room temperature before adding testing DART. During blocking, *E. coli* expressed h3G8-h3G8 DART, h2B6-h3G8 DART, and h2B6-h2B6 DART (negative control) were diluted in 1 µg/ml, and 0.3 µg/ml in PBST/BSA. 50 µl/well of diluted DARTs were added to the each well. The plate was incubated at room temperature for 1 hour. After washing with PBS-T three times, 50 µl/well of 0.1 µg/ml of Biotinlated sCD16-Fc fusion was added to the plate. The plate was incubated at room temperature for 1 hour. After washing with PBS-T three times, 50 µl/well of a 1:5000 dilution of HRP conjugated streptavidin (Amersham Pharmacia Biotech) was used for detection and incubated at room temperature for 1 hour. The plate was washed with PBS-T three times and developed using 80 ul/well of TMB substrate. After 5 minutes incubation, the reaction was stopped by 40 µl/well of 1% $H_2SO_4$. The OD450 nm was read by using a 96-well plate reader and SOFTmax software. The read out was plotted using GraphPadPrism 3.03 software (FIG. 28).

6.8 DART-induced Human B-cell Death

Human PBMC were incubated overnight with: CD16-CD32B-hu3G8-hu2b6 (described above); ch2B6-aglyc-aglycosylated chimeric 2B6 antibody (described in co-pending U.S. patent application Ser. No. 11/108,135, published as US2005/0260213, herein incorporated by reference) and CD16-CD79. The DNA and encoded protein sequences of CD16-CD79 are as follows:

H3G8VL-CB3.1VH
Nucleotide Sequence(SEQ ID NO: 226):
gacatcgtga tgacccaatc tccagactct ttggctgtgt ctctagggga 50
gagggccacc atcaactgca aggccagcca aagtgttgat tttgatggtg 100
atagttttat gaactggtac caacagaaac caggacagcc acccaaactc 150
ctcatctata ctacatccaa tctagaatct ggggtcccag acaggtttag 200
tggcagtggg tctgggacag acttcaccct caccatcagc agcctgcagg 250
ctgaggatgt ggcagtttat tactgtcagc aaagtaatga ggatccgtac 300
acgttcggac aggggaccaa gcttgagatc aaaggaggcg gatccggagg 350
cggaggccag gtccaactgc agcagcctgg ggctgagctg gtgaggcctg 400
gggcttcagt gaagctgtcc tgcaaggctt ctggctacac cttcaccagc 450
tactggatga actgggtgaa gcagaggcct ggacaaggcc ttgaatggat 500
tggtatggtt gatccttcag acagtgaaac tcactacaat caaatgttca 550
aggacaaggc cacattgact gttgacaaat cctccagcac agcctacatg 600
cagctcagca gcctgacatc tgaggactct gcggtctatt actgtgcaag 650
agctatgggc tactggggtc aaggaacctc agtcaccgtc tcctcagttg 700
agcccaaatc ttgt 714

Amino Acid Sequence (SEQ ID NO: 227):
DIVMTQSPDS LAVSLGERAT INCKASQSVD FDGDSFMNWY QQKPGQPPKL 50

LIYTTSNLES GVPDRFSGSG SGTDFTLTIS SLQAEDVAVY YCQQSNEDPY 100

TFGQGTKLEI KGGGSGGGGQ VQLQQPGAEL VRPGASVKLS CKASGYTFTS 150

YWMNWVKQRP GQGLEWIGMV DPSDSETHYN QMFKDKATLT VDKSSSTAYM 200

QLSSLTSEDS AVYYCARAMG YWGQGTSVTV SSVEPKSC 238

CB3.1VL-h3G8VH
Nucleotide Sequence(SEQ ID NO: 228):
gatgttgtga tgacccagac tccactcact ttgtcggtta acattggaca 50
accagcctcc atctcttgta agtcaagtca gagcctctta gatactgatg 100
gaaagacata tttgaattgg ttgttacaga ggccaggcca gtctccaaac 150
cgcctaatct atctggtgtc taaactggac tctggagtcc ctgacaggtt 200
cactggcagt ggatcaggga cagatttcac actgaaaatc agcagagtgg 250
aggctgagga tttgggaatt tattattgct ggcaaggtac acattttccg 300
ctcacgttcg gtgctgggac caagctggag ctgaaaggag gcggatccgg 350
aggcggaggc caggttaccc tgagagagtc tggccctgcg ctggtgaagc 400
ccacacagac cctcacactg acttgtacct tctctgggtt ttcactgagc 450
acttctggta tgggtgtagg ctggattcgt cagcctcccg ggaaggctct 500
agagtggctg gcacacattt ggtgggatga tgacaagcgc tataatccag 550
ccctgaagag ccgactgaca atctccaagg atacctccaa aaaccaggta 600
gtcctcacaa tgaccaacat ggaccctgtg gatactgcca catactactg 650
tgctcaaata aaccccgcct ggtttgctta ctggggccaa gggactctgg 700
tcactgtgag ctcattcaac aggggagagt gt 732

Amino Acid Sequence (SEQ ID NO: 229):
DVVMTQTPLT LSVNIGQPAS ISCKSSQSLL DTDGKTYLNW LLQRPGQSPN 50

RLIYLVSKLD SGVPDRFTGS GSGTDFTLKI SRVEAEDLGI YYCWQGTHFP 100

LTFGAGTKLE LKGGGSGGGG QVTLRESGPA LVKPTQTLTL TCTFSGFSLS 150

-continued

```
TSGMGVGWIR QPPGKALEWL AHIWWDDDKR YNPALKSRLT ISKDTSKNQV     200

VLTMTNMDPV DTATYYCAQI NPAWFAYWGQ GTLVTVSSFN RGEC          244
```

Figure 29:
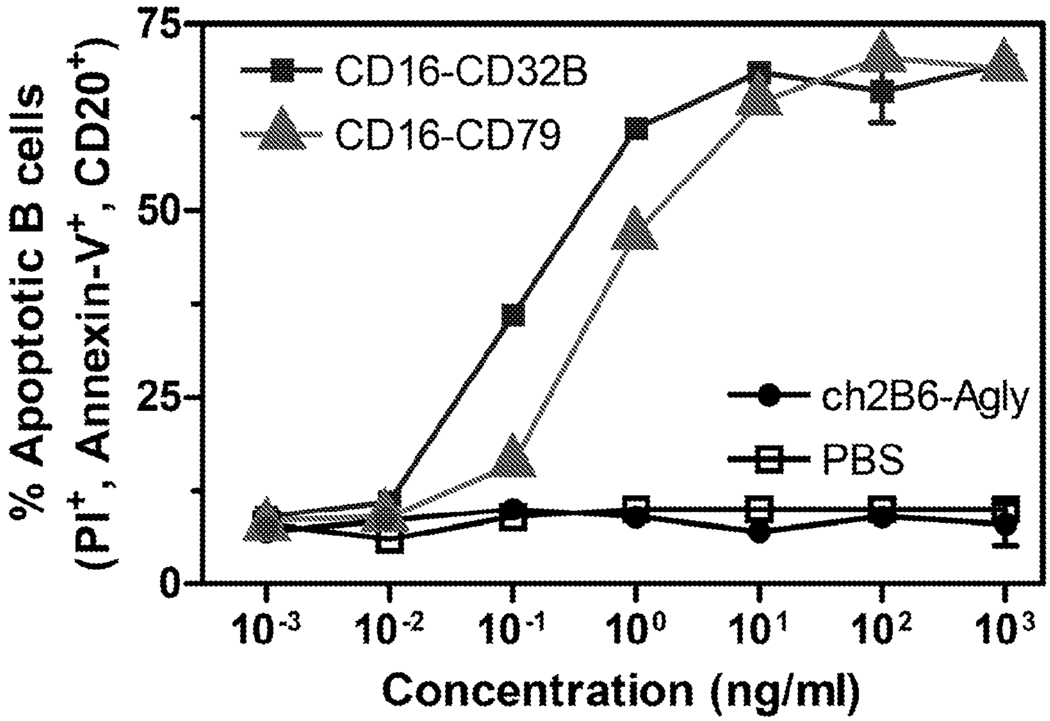

Apoptosis was assayed by FACS analysis as the percentage of PI+Annexin-V+ population of B cells (CD20+ cells) on the total FSC/SSC ungated population (FIG. 29).

6.9 8B5-CB3.1 DART

8B5VL-CB3.1VH-VEPKSC

8B5VL was amplified by using H9 and lgh630R as primers, ch8B5Lc as template. CB3.1VH was amplified by using lgh628F and lgh629R as primers, ch8B5Hc as template. The linker sequence was incorporated in the primers lgh630R and lgh628F. The c-terminal linker and stop codon was incorporated in lgh629R primer. The PCR products were gel purified and mixed together in equal molar ratio, then amplified by using H9 and lgh629R as primers. The overlapped PCR product was then digested with NheI/EcoRI restriction endonucleases, and cloned into pCIneo vector.

CB3.1VL-8B5VH-FNRGEC

CB3.1VL was amplified by using H9 and lgh630R, which shared the same sequence as 8B5VL at FR4, as primers, and chCB3.1Lc as template. 8B5VH was amplified by using lgh631F and lgh640R as primers, and ch8B5Hc as template. The linker sequence was incorporated in the primers lgh630R and lgh631F. The c-terminal linker and stop codon was incorporated in lgh640R primer. The PCR products were gel purified and mixed together in equal molar ratio, then amplified by using H9 and lgh640R as primers. The overlapped PCR product was then digested with NheI/EcoRI restriction endonucleases, and cloned into pCIneo vector.

Anti-Flag tag-8B5VL-CB3.1VH-VEPKSC

Anti-Flag tag was inserted between signal sequence and 8B5VL by overlapping PCR. The signal sequence and Flag tag was amplified by using H9 and lgh647R as primers and ch8B5Lc as temperate. 8B5VL-CB3.1VH-VEPKSC was re-amplified by using lgh647F and lgh629R as primers and 8B5VL-CB3.1VH-VEPKSC as temperate. The PCR products were gel purified and mixed together in equal molar ratio, then amplified by using H9 and lgh629R as primers. The overlapped PCR product was then digested with NheI/EcoRI restriction endonucleases, and cloned into pCIneo vector.

8B5VL-CB3.1VH-LGGC

To generate a different C-terminal linker in 8B5VL-CB3.1VH-VEPKSC construct, the construct was re-amplified by using H9 and lgh646R as primers. The C-terminal LGGC (SEQ ID NO:330) linker was integrated in lgh646R primer. The PCR product was then digested with NheI/EcoRI restriction endonucleases, and cloned into pCIneo vector.

CB3.1VL-8B5VH-LGGC

The same strategy was used to create CB3.1VL-8B5VH-LGGC. The C-terminal LGGC ( SEQ ID NO:330) linker was integrated in lgh648R primer and CB3.1VL-8B5VH-FNRGEC was used as temperate. The PCR product was then digested with NheI/EcoRI restriction endonucleases, and cloned into pCIneo vector.

Anti-Flag tag-8B5VL-CB3.1VH-LGGC

The same strategy was also used to create Anti-Flag tag-8B5VL-CB3.1VH-LGGC. The C-terminal LGGC (SEQ ID NO:330) linker was integrated in lgh648R primer and Anti-Flag tag-8B5VL-CB3.1VH-VEPKSC was used as temperate. The PCR product was then digested with NheI/EcoRI restriction endonucleases, and cloned into pCIneo vector.

```
8B5-CB3.1-VEPKSC Nucleotide sequence (SEQ ID NO: 230):
gacattcaga tgacacagtc tccatcctcc ctacttgcgg cgctgggaga     50

aagagtcagt ctcacttgtc gggcaagtca ggaaattagt ggttacttaa    100

gctggcttca gcagaaacca gatggaacta ttaaacgcct gatctacgcc    150

gcatccactt tagattctgg tgtcccaaaa aggttcagtg gcagtgagtc    200

tgggtcagat tattctctca ccatcagcag tcttgagtct gaagattttg    250

cagactatta ctgtctacaa tattttagtt atccgctcac gttcggtgct    300

gggaccaagc tggagctgaa aggaggcgga tccggaggcg gaggccaggt    350

ccaactgcag cagcctgggg ctgagctggt gaggcctggg gcttcagtga    400

agctgtcctg caaggcttct ggctacacct tcaccagcta ctggatgaac    450

tgggtgaagc agaggcctgg acaaggcctt gaatggattg gtatggttga    500

tccttcagac agtgaaactc actacaatca aatgttcaag gacaaggcca    550

cattgactgt tgacaaatcc tccagcacag cctacatgca gctcagcagc    600

ctgacatctg aggactctgc ggtctattac tgtgcaagag ctatgggcta    650

ctggggtcaa ggaacctcag tcaccgtctc ctcagttgag cccaaatctt    700

gt                                                        702

8B5-CB3.1-VEPKSC Amino acid sequence (SEQ ID NO: 231):
DIQMTQSPSS LLAALGERVS LTCRASQEIS GYLSWLQQKP DGTIKRLIYA     50

ASTLDSGVPK RFSGSESGSD YSLTISSLES EDFADYYCLQ YFSYPLTFGA    100
```

-continued

```
GTKLELKGGG SGGGGQVQLQ QPGAELVRPG ASVKLSCKAS GYTFTSYWMN    150

WVKQRPGQGL EWIGMVDPSD SETHYNQMFK DKATLTVDKS SSTAYMQLSS    200

LTSEDSAVYY CARAMGYWGQ GTSVTVSSVE PKSC                     234
```

CB3.1-8B5-FNRGEC Nucleotide sequence (SEQ ID NO: 232):

```
gatgttgtga tgacccagac tccactcact ttgtcggtta acattggaca     50

accagcctcc atctcttgta agtcaagtca gagcctctta gatactgatg    100

gaaagacata tttgaattgg ttgttacaga ggccaggcca gtctccaaac    150

cgcctaatct atctggtgtc taaactggac tctggagtcc ctgacaggtt    200

cactggcagt ggatcaggga cagatttcac actgaaaatc agcagagtgg    250

aggctgagga tttgggaatt tattattgct ggcaaggtac acattttccg    300

ctcacgttcg gtgctgggac caagctggag ctgaaaggag gcggatccgg    350

aggcggaggc gaagtgaagc ttgaggagtc tggaggaggc ttggtgcaac    400

ctggaggatc catgaaactc tcttgtgaag cctctggatt cacttttagt    450

gacgcctgga tggactgggt ccgtcagtct ccagagaagg ggcttgagtg    500

ggttgctgaa attagaaaca aagctaaaaa tcatgcaaca tactatgctg    550

agtctgtgat agggaggttc accatctcaa gagatgattc caaaagtagt    600

gtctacctgc aaatgaacag cttaagagct gaagacactg gcatttatta    650

ctgtggggct ctgggccttg actactgggg ccaaggcacc actctcacag    700

tctcctcgtt caacagggga gagtgt                              726
```

CB3.1-8B5-FNRGEC Amino acid sequence (SEQ ID NO: 233):

```
DVVMTQTPLT LSVNIGQPAS ISCKSSQSLL DTDGKTYLNW LLQRPGQSPN     50

RLIYLVSKLD SGVPDRFTGS GSGTDFTLKI SRVEAEDLGI YYCWQGTHFP    100

LTFGAGTKLE LKGGGSGGGG EVKLEESGGG LVQPGGSMKL SCEASGFTFS    150

DAWMDWVRQS PEKGLEWVAE IRNKAKNHAT YYAESVIGRF TISRDDSKSS    200

VYLQMNSLRA EDTGIYYCGA LGLDYWGQGT TLTVSSFNRG EC            242
```

8B5VL-CB3.1VH-LGGC

8B5VL was amplified by using H9 and lgh694R as primers, ch8B5Lc as template. 8B5VH was amplified by using lgh695F and lgh696R as primers, ch8B5Hc as template. The linker sequence was incorporated in the primers lgh694R and lgh695F. HuIgG1Fc was amplified by using lgh355F and lgh366R as primers, ch8B5Hc as template. The PCR products were gel purified and mixed together in equal molar ratio, then amplified by using H9 and lgh366R as primers. The overlapped PCR product was then digested with NheI/EcoRI restriction endonucleases, and cloned into pCI-neo vector.

8B5VL-CB3.1VH-LGGC Nucleotide sequence (SEQ ID NO: 234):

```
gacattcaga tgacacagtc tccatcctcc ctacttgcgg cgctgggaga     50

aagagtcagt ctcacttgtc gggcaagtca ggaaattagt ggttacttaa    100

gctggcttca gcagaaacca gatggaacta ttaaacgcct gatctacgcc    150

gcatccactt tagattctgg tgtcccaaaa aggttcagtg gcagtgagtc    200

tgggtcagat tattctctca ccatcagcag tcttgagtct gaagattttg    250

cagactatta ctgtctacaa tattttagtt atccgctcac gttcggtgct    300

gggaccaagc tggagctgaa aggaggcgga tccggaggcg gaggccaggt    350

ccaactgcag cagcctgggg ctgagctggt gaggcctggg gcttcagtga    400

agctgtcctg caaggcttct ggctacacct tcaccagcta ctggatgaac    450

tgggtgaagc agaggcctgg acaaggcctt gaatggattg gtatggttga    500

tccttcagac agtgaaactc actacaatca aatgttcaag gacaaggcca    550
```

-continued

```
cattgactgt tgacaaatcc tccagcacag cctacatgca gctcagcagc     600

ctgacatctg aggactctgc ggtctattac tgtgcaagag ctatgggcta     650

ctggggtcaa ggaacctcag tcaccgtctc ctcactggga ggctgc         696
```

8B5VL-CB3.1VH-LGGC Amino acid sequence (SEQ ID NO: 235):

```
DIQMTQSPSS LLAALGERVS LTCRASQEIS GYLSWLQQKP DGTIKRLIYA      50

ASTLDSGVPK RFSGSESGSD YSLTISSLES EDFADYYCLQ YFSYPLTFGA     100

GTKLELKGGG SGGGGQVQLQ QPGAELVRPG ASVKLSCKAS GYTFTSYWMN     150

WVKQRPGQGL EWIGMVDPSD SETHYNQMFK DKATLTVDKS SSTAYMQLSS     200

LTSEDSAVYY CARAMGYWGQ GTSVTVSSLG GC                        232
```

CB3.1-8B5-LGGC Nucleotide sequence (SEQ ID NO: 236):

```
gatgttgtga tgacccagac tccactcact ttgtcggtta acattggaca      50

accagcctcc atctcttgta agtcaagtca gagcctctta gatactgatg     100

gaaagacata tttgaattgg ttgttacaga ggccaggcca gtctccaaac     150

cgcctaatct atctggtgtc taaactggac tctggagtcc ctgacaggtt     200

cactggcagt ggatcaggga cagatttcac actgaaaatc agcagagtgg     250

aggctgagga tttgggaatt tattattgct ggcaaggtac acattttccg     300

ctcacgttcg gtgctgggac caagctggag ctgaaaggag gcggatccgg     350

aggcggaggc gaagtgaagc ttgaggagtc tggaggaggc ttggtgcaac     400

ctggaggatc catgaaactc tcttgtgaag cctctggatt cacttttagt     450

gacgcctgga tggactgggt ccgtcagtct ccagagaagg ggcttgagtg     500

ggttgctgaa attagaaaca aagctaaaaa tcatgcaaca tactatgctg     550

agtctgtgat agggaggttc accatctcaa gagatgattc caaaagtagt     600

gtctacctgc aaatgaacag cttaagagct gaagacactg gcatttatta     650

ctgtggggct ctgggccttg actactgggg ccaaggcacc actctcacag     700

tctcctcgct gggaggctgc                                      720
```

CB3.1-8B5-LGGC Amino acid sequence (SEQ ID NO: 237):

```
DVVMTQTPLT LSVNIGQPAS ISCKSSQSLL DTDGKTYLNW LLQRPGQSPN      50

RLIYLVSKLD SGVPDRFTGS GSGTDFTLKI SRVEAEDLGI YYCWQGTHFP     100

LTFGAGTKLE LKGGGSGGGG EVKLEESGGG LVQPGGSMKL SCEASGFTFS     150

DAWMDWVRQS PEKGLEWVAE IRNKAKNHAT YYAESVIGRF TISRDDSKSS     200

VYLQMNSLRA EDTGIYYCGA LGLDYWGQGT TLTVSSLGGC                240
```

Primers:

Lgh628F (SEQ ID NO: 238):

```
ggaggcggat ccggaggcggaggccaggtc caactgcagc agcctgg          47
```

Lgh629R (SEQ ID NO: 239):

```
tttgaattct aacaagatttgggctcaact gaggagacgg tgactgagg        49
```

Lgh630R (SEQ ID NO: 240):

```
gcctccgcct ccggatccgcctcctttcag ctccagcttg gtccc            45
```

Lgh631F (SEQ ID NO: 241):

```
ggaggcggat ccggaggcggaggcgaagtg aagcttgagg agtctgg          47
```

Lgh640R (SEQ ID NO: 242):

```
tttgaattct aacactctcccctgttgaac gaggagactg tgagagtgg        49
```

Lgh644R (SEQ ID NO: 243):

```
tttgtcgtca tcatcgtctttgtagtcgga gtggacacct gtggagag         48
```

Lgh646R (SEQ ID NO: 244):

```
tttgaattct agcagcctcccagtgaggag acggtgactg ag               42
```

-continued

```
Lgh647F (SEQ ID NO: 245):
caaagacgat gatgacgacaaagacattca gatgacacag tctcc          45

Lgh648R (SEQ ID NO: 246):
tttgaattct agcagcctcccagcgaggag actgtgagag tgg            43
```

Figure 30:
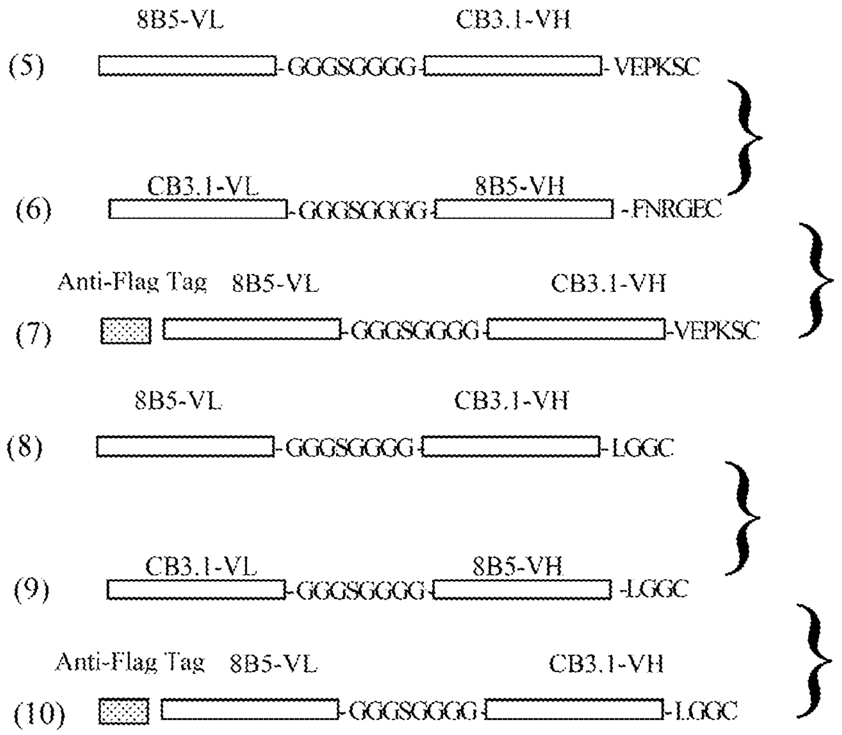

Expression: The construct 5 and 6, or 6 and 7, or 8 and 9, or 9 and 10, encoded expression plasmids (FIG. 30) were co-transfected into HEK-293 cells to express 8B5-CB3.1 DART with or without anti flag tag using Lipofectamine 2000 (Invitrogen). The conditioned medium was harvested in every three days for three times. The conditioned medium was then purified using CD32B affinity column.

Figure 31:
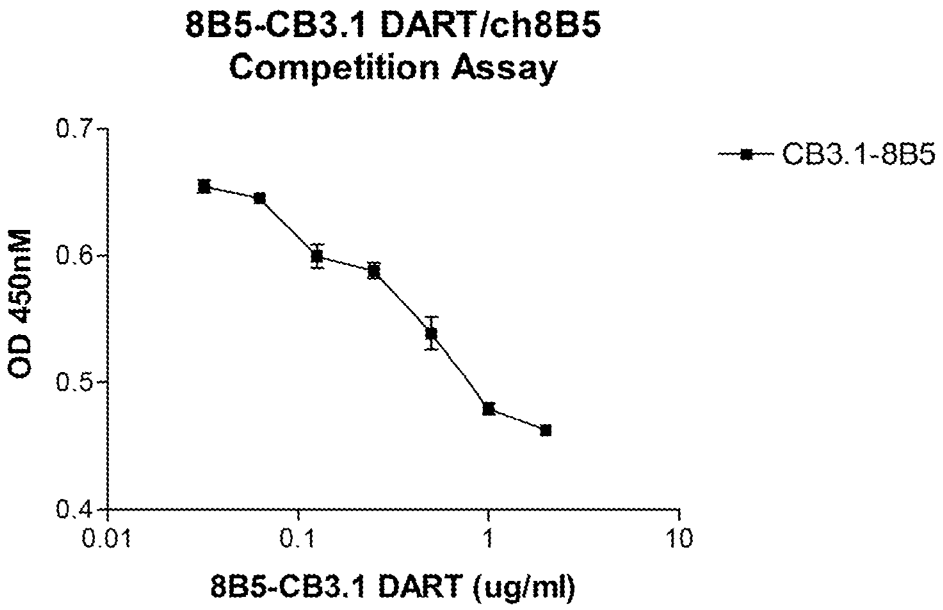

ELISA: ELISA were conducted as follows: 50 µl/well of 2 ug/ml of CD32B-Fc was coated on 96-well Maxisorp plate in Carbonate buffer at 4° C. over night. The plate was washed three times with PBS-T (PBS, 0.1% Tween 20) and then blocked by 0.5% BSA in PBS-T for 30 minutes at room temperature before adding testing single chain Fc fusion protein. During blocking, 8B5-CB3.1 DART was diluted in a serial of two-fold dilution starting at 2 µg/ml. 25 µl/well of diluted DART mixed with 25 µl/well of 50 ng/ml ch8B5 was transferred from dilution plate to the ELISA plate. The plate was incubated at room temperature for 1 hour. After washing with PBS-T three times, 50 µl/well of 1:10,000 diluted HRP conjugated $F(ab')_2$ goat anti human IgG $F(ab')_2$ (Jackson ImmunoResearch) was added to the plate. The plate was incubated at room temperature for 1 hour. The plate was washed with PBS-T three times and developed with 80 µl/well of TMB substrate. After 5 minutes incubation, the reaction was stopped by 40 µl/well of 1% $H_2SO_4$. The OD450 nm was read using a 96-well plate reader and SOFTmax software. The read out was plotted using GraphPadPrism 3.03 software (FIG. 31).

6.10 Design and Characterization of Ig-like Tetravalent DART

Figure 32:
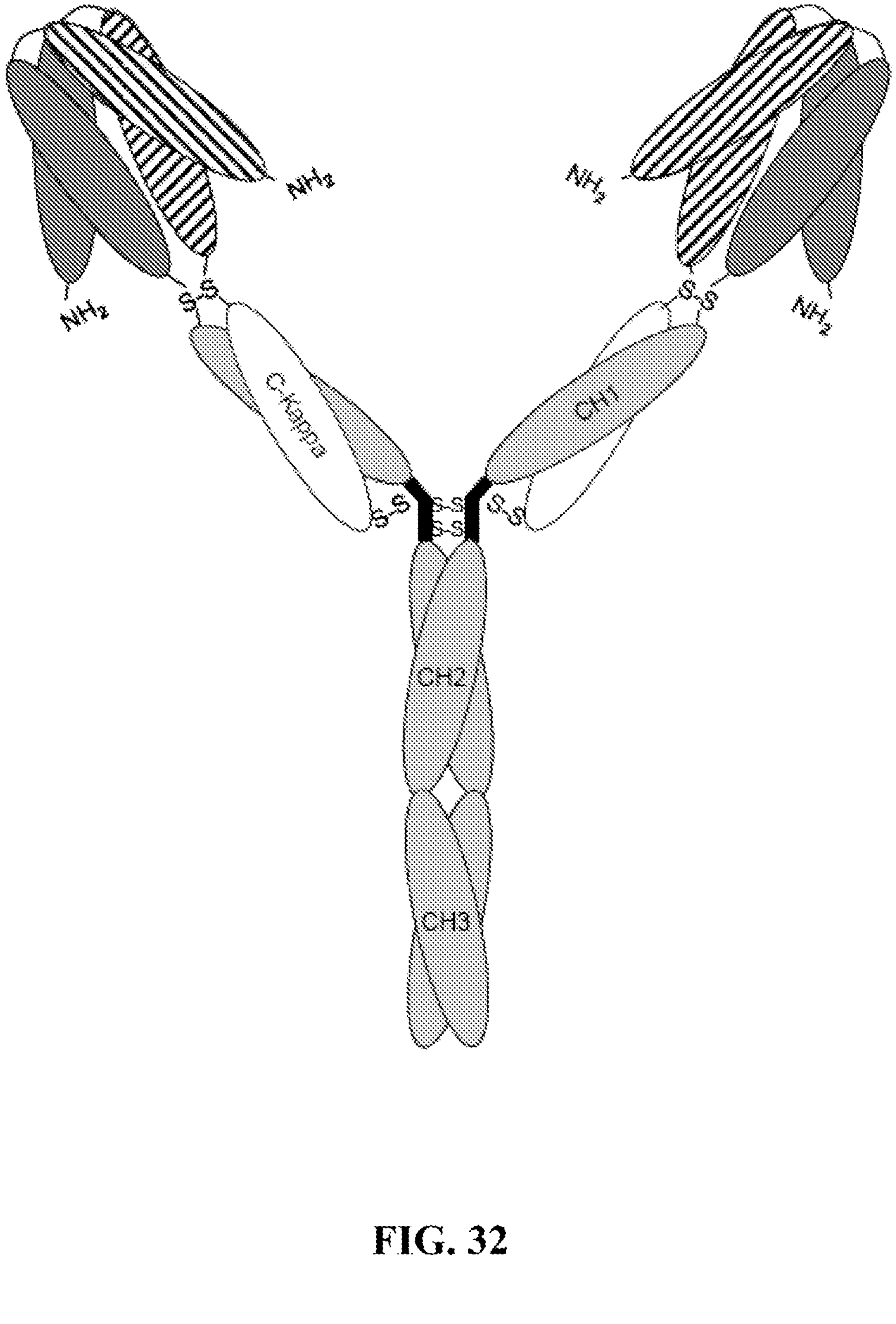

Four polypeptide chains were employed to produce an Ig-like DART species having tetravalent antigen binding sites (FIG. 32; FIG. 33). The Ig-like DART species has unique properties, since its domains may be designed to bind to the same epitope (so as to form a tetravalent, mono-epitope specific Ig-like DART capable of binding four identical antigen molecules), or to different epitopes or antigens For example, its domains may be designed to bind to two epitopes of the same antigen (so as to form a tetravalent, mono-antigen specific, bi-epitope specific Ig-like DART), or to epitopes of different antigen molecules so as to form a tetravalent Ig-like DART having a pair of binding sites specific for a first antigen and a second pair of binding sites specific for a second antigen). Hybrid molecules having combinations of such attributes can be readily produced.

To illustrate the characteristics of such Ig-like DART species, an exemplary tetravalent Ig-like DART species was produced having a pair of binding sites specific for CD32 and a second pair of binding sites specific CD16A. This Ig-like DART species was produced using the following four polypeptide chains:

```
2.4G2-3G8-hKappa Nucleotide Sequence
(SEQ ID NO: 247):
gatgtccaga tgacccagtc tccatctaat cttgctgcct ctcctggaga     50

aagtgtttcc atcaattgca aggcaagtga gagcattagc aagtatttag    100

cctggtatct acagaaacct gggaaagcaa ataagcttct tatgtacgat    150

gggtcaactt tgcaatctgg aattccatcg aggttcagtg gcagtggatc    200

tggtacagat ttcactctca ccatcagaag cctggagcct gaagattttg    250

gactctatta ctgtcaacag cattatgaat atccagccac gttcggttct    300

gggaccaagc tggagatcaa aggaggcgga tccggaggcg gaggccaggt    350

taccctgaaa gagtctggcc ctgggatatt gcagccctcc cagaccctca    400

gtctgacttg ttctttctct gggttttcac tgaggacttc tggtatgggt    450

gtaggctgga ttcgtcagcc ttcagggaag ggtctagagt ggctggcaca    500

catttggtgg gatgatgaca agcgctataa tccagccctg aagagccgac    550

tgacaatctc caaggatacc tccagcaacc aggtattcct caaaatcgcc    600

agtgtggaca ctgcagatac tgccacatac tactgtgctc aaataaaccc    650

cgcctggttt gcttactggg gccaagggac tctggtcact gtgagctcac    700

tgggaggctg cggcggaggg agccgtacgg tggctgcacc atcggtcttc    750

atcttcccgc catctgatga gcagttgaaa tctggaactg cctctgttgt    800

gtgcctgctg aataacttct atcccagaga ggccaaagta cagtggaagg    850

tggataacgc cctccaatcg ggtaactccc aggagagtgt cacagagcag    900

gacagcaagg acagcaccta cagcctcagc agcaccctga cgctgagcaa    950
```

-continued

```
agcagactac gagaaacaca aagtctacgc ctgcgaagtc acccatcagg   1000

gcctgagctc gcccgtcaca aagagcttca acaggggaga gtgt         1044
```

2.4G2-3G8-hKappa Encoded Amino Acid Sequence
(SEQ ID NO: 248):

```
DVQMTQSPSN LAASPGESVS INCKASESIS KYLAWYLQKP GKANKLLMYD     50

GSTLQSGIPS RFSGSGSGTD FTLTIRSLEP EDFGLYYCQQ HYEYPATFGS    100

GTKLEIKGGG SGGGGQVTLK ESGPGILQPS QTLSLTCSFS GFSLRTSGMG    150

VGWIRQPSGK GLEWLAHIWW DDDKRYNPAL KSRLTISKDT SSNQVFLKIA    200

SVDTADTATY YCAQINPAWF AYWGQGTLVT VSSLGGCGGG SRTVAAPSVF    250

IFPPSDEQLK SGTASVVCLL NNFYPREAKV QWKVDNALQS GNSQESVTEQ    300

DSKDSTYSLS STLTLSKADY EKHKVYACEV THQGLSSPVT KSFNRGEC      350
```

3G8-2.4G2-hG1 Nucleotide Sequence
(SEQ ID NO: 249):

```
gacactgtgc tgacccaatc tccagcttct ttggctgtgt ctctagggca     50

gagggccacc atctcctgca aggccagcca aagtgttgat tttgatggtg    100

atagttttat gaactggtac caacagaaac caggacagcc acccaaactc    150

ctcatctata ctacatccaa tctagaatct gggatcccag ccaggtttag    200

tgccagtggg tctgggacag acttcaccct caacatccat cctgtggagg    250

aggaggatac tgcaacctat tactgtcagc aaagtaatga ggatccgtac    300

acgttcggag gggggaccaa gctggaaata aaaggaggcg gatccggagg    350

cggaggcgag gtggagctag tggagtctgg gggaggctta gtgcagcctg    400

gaaggtccct gaaactctcg tgtgcagcct caggattcac tttcagtgac    450

tattacatgg cctgggtccg gcaggctcca acgacgggtc tggagtgggt    500

cgcatccatt agttatgatg gtggtgacac tcactatcga gactccgtga    550

agggccgatt tactatttcc agagataatg caaaaagcag cctatacctg    600

caaatggaca gtctgaggtc tgaggacacg gccacttatt actgtgcaac    650

agagactacg ggaataccta caggtgttat ggatgcctgg ggtcaaggag    700

tttcagtcac tgtctcctca ctgggaggct gcggcggagg gagcgcctcc    750

accaagggcc catcggtctt cccoctggca ccctcctcca agagcacctc    800

tgggggcaca gcggccctgg gctgcctggt caaggactac ttccccgaac    850

cggtgacggt gtcgtggaac tcaggcgccc tgaccagcgg cgtgcacacc    900

ttcccggctg tcctacagtc ctcaggactc tactccctca gcagcgtggt    950

gaccgtgccc tccagcagct tgggcaccca gacctacatc tgcaacgtga   1000

atcacaagcc cagcaacacc aaggtggaca agagagttga gcccaaatct   1050

tgtgacaaaa ctcacacatg cccaccgtgc ccagcacctg aactcctggg   1100

gggaccgtca gtcttcctct tccccccaaa acccaaggac accctcatga   1150

tctcccggac ccctgaggtc acatgcgtgg tggtggacgt gagccacgaa   1200

gaccctgagg tcaagttcaa ctggtacgtg gacggcgtgg aggtgcataa   1250

tgccaagaca aagccgcggg aggagcagta caacagcacg taccgtgtgg   1300

tcagcgtcct caccgtcctg caccaggact ggctgaatgg caaggagtac   1350

aagtgcaagg tctccaacaa agccctccca gcccccatcg agaaaaccat   1400

ctccaaagcc aaagggcagc cccgagaacc acaggtgtac accctgcccc   1450
```

-continued

```
catcccggga tgagctgacc aagaaccagg tcagcctgac ctgcctggtc   1500

aaaggcttct atcccagcga catcgccgtg gagtgggaga gcaatgggca   1550

gccggagaac aactacaaga ccacgcctcc cgtgctggac tccgacggct   1600

ccttcttcct ctacagcaag ctcaccgtgg acaagagcag gtggcagcag   1650

gggaacgtct tctcatgctc cgtgatgcat gaggctctgc acaaccacta   1700

cacgcagaag agcctctccc tgtctccggg taaa                    1734
```

3G8-2.4G2-hG1 Encoded Amino Acid Sequence
(SEQ ID NO: 250):

```
DTVLTQSPAS LAVSLGQRAT ISCKASQSVD FDGDSFMNWY QQKPGQPPKL     50

LIYTTSNLES GIPARFSASG SGTDFTLNIH PVEEEDTATY YCQQSNEDPY    100

TFGGGTKLEI KGGGSGGGGE VELVESGGGL VQPGRSLKLS CAASGFTFSD    150

YYMAWVRQAP TTGLEWVASI SYDGGDTHYR DSVKGRFTIS RDNAKSSLYL    200

QMDSLRSEDT ATYYCATETT GIPTGVMDAW GQGVSVTVSS LGGCGGGSAS    250

TKGPSVFPLA PSSKSTSGGT AALGCLVKDY FPEPVTVSWN SGALTSGVHT    300

FPAVLQSSGL YSLSSVVTVP SSSLGTQTYI CNVNHKPSNT KVDKRVEPKS    350

CDKTHTCPPC PAPELLGGPS VFLFPPKPKD TLMISRTPEV TCVVVDVSHE    400

DPEVKFNWYV DGVEVHNAKT KPREEQYNST YRVVSVLTVL HQDWLNGKEY    450

KCKVSNKALP APIEKTISKA KGQPREPQVY TLPPSRDELT KNQVSLTCLV    500

KGFYPSDIAV EWESNGQPEN NYKTTPPVLD SDGSFFLYSK LTVDKSRWQQ    550

GNVFSCSVMH EALHNHYTQK SLSLSPGK                            578
```

Preparations of Ig-like DART molecules having the above sequences were obtained from different plasmid isolates and were denominated "Ig DART 1" and "Ig DART 2." The ability of these Ig-like DART species to bind mCD32-hCD16A in an ELISA was compared with that of medium alone, a DART having a single CD32 and a single CD16A binding site ("DART"), and control anti-ch-mCD32 mAb (FIG. 34). The Ig-like DART of the present invention was found to have much greater antigen binding affinity than either DART or the control antibody.

6.11 Design and Characterization of CD32B-CD79-1 and CD32B-CD79-2 Bispecific Diabodies Genes encoding CD79VL-CD32BVH (Sequence 1), CD32BVL-CD79VH-1 (Sequence 2), and CD32BVL-CD79VH-2 (Sequence 3) were cloned into expression vector pEE13 resulting in expression constructs 1, 2, and 3 respectively. The construct 1 expression plasmid was co-transfected together with either expression plasmid 2 or 3 into HEK-293 cells to make CD32B-CD79-1 and CD32B-CD79-2 bispecific diabodies, respectively. The conditioned medium was harvested in every three days for three times. The conditioned medium was then purified using CD32B affinity column.

ELISA were conducted as follows: 50 μl/well of 2 μg/ml of CD32B-Fc was coated on 96-well Maxisorp plate in Carbonate buffer at 4° C. over night. The plate was washed three times with PBS-T (PBS, 0.1% Tween 20) and then blocked by 0.5% BSA in PBS-T for 30 minutes at room temperature before adding testing single chain Fc fusion protein. During blocking, the CD32B-CD79-1 or CD32B-CD79-2 bispecific diabody was diluted in a serial of two-fold dilution starting at 2 μg/ml. 25 μl/well of diluted bispecific diabody was mixed with 25 μl/well of 50 ng/ml anti-CD32B antibody and added to an ELISA plate. The plate was incubated at room temperature for 1 hour. After washing with PBS-T three times, 50 μl/well of 1:10,000 diluted HRP conjugated $F(ab')_2$ goat anti human IgG $F(ab')_2$ (Jackson ImmunoResearch) was added to the plate. The plate was incubated at room temperature for 1 hour. The plate was washed with PBS-T three times and developed with 80 μl/well of TMB substrate. After 5 minutes incubation, the reaction was stopped by 40 μl/well of 1% $H_2SO_4$. The OD450 nm was read using a 96-well plate reader and SOFTmax software. The read out was plotted using GraphPadPrism 3.03 software. The experiment revealed that the CD32B-CD79-1 and CD32B-CD79-2 bispecific Diabodies were capable of immunospecific binding to CD32-Fc with an affinity equivalent to that of the anti-CD32B control antibody. The nucleotide and encoded amino acid sequences of the above-described constructs are provided below:

Sequence 1 - CD79VL-CD32BVH nucleotide sequence
(SEQ ID NO: 251):

```
gatgttgtga tgactcagtc tccactctcc ctgcccgtca cccttggaca     50

gccggcctcc atctcctgca agtcaagtca gagcctctta gatagtgatg    100

gaaagacata tttgaattgg tttcagcaga ggccaggcca atctccaaac    150

cgcctaattt atctggtgtc taaactggac tctggggtcc cagacagatt    200
```

-continued

```
cagcggcagt gggtcaggca ctgatttcac actgaaaatc agcagggtgg   250

aggctgagga tgttggggtt tattactgct ggcaaggtac acattttccg   300

ctcacgttcg gcggagggac caagcttgag atcaaaggag gcggatccgg   350

aggcggaggc gaagtgaagc ttgaggagtc tggaggaggc ttggtgcaac   400

ctggaggatc catgaaactc tcttgtgaag cctctggatt cacttttagt   450

gacgcctgga tggactgggt ccgtcagtct ccagagaagg ggcttgagtg   500

ggttgctgaa attagaaaca aagctaaaaa tcatgcaaca tactatgctg   550

agtctgtgat agggaggttc accatctcaa gagatgattc caaaagtagt   600

gtctacctgc aaatgaacag cttaagagct gaagacactg gcatttatta   650

ctgtggggct ctgggccttg actactgggg ccaaggcacc actctcacag   700

tctcctcgct gggaggctgc                                    720
```

Sequence 2 - CD79VL-CD32BVH amino acide sequence
(SEQ ID NO: 252):

```
DVVMTQSPLS LPVTLGQPAS ISCKSSQSLL DSDGKTYLNW FQQRPGQSPN    50

RLIYLVSKLD SGVPDRFSGS GSGTDFTLKI SRVEAEDVGV YYCWQGTHFP   100

LTFGGGTKLE IKGGGSGGGG EVQLVESGGG LVQPGGSLRL SCAASGFTFS   150

DAWMDWVRQA PGKGLEWVAE IRNKAKNHAT YYAESVIGRF TISRDDAKNS   200

LYLQMNSLRA EDTAVYYCGA LGLDYWGQGT LVTVSSLGGC              240
```

Sequence 3 - CD32BVL-CD79VH-1 nucleotide sequence
(SEQ ID NO: 253):

```
gacatccaga tgacccagtc tccatcctcc ttatctgcct ctgtgggaga    50

tagagtcacc atcacttgtc gggcaagtca ggaaattagt ggttacttaa   100

gctggctgca gcagaaacca ggcaaggccc ctagacgcct gatctacgcc   150

gcatccactt tagattctgg tgtcccatcc aggttcagtg gcagtgagtc   200

tgggaccgag ttcaccctca ccatcagcag ccttcagcct gaagattttg   250

caacctatta ctgtctacaa tattttagtt atccgctcac gttcggaggg   300

gggaccaagg tggaaataaa aggaggcgga tccggaggcg gaggccaggt   350

tcagctggtg cagtctggag ctgaggtgaa gaagcctggc gcctcagtga   400

aggtctcctg caaggcttct ggttacacct ttaccagcta ctggatgaac   450

tgggtgcgac aggcccctgg acaagggctt gagtggatcg gaatgattga   500

tccttcagac agtgaaactc actacaatca aatgttcaag gacagagtca   550

ccatgaccac agacacatcc acgagcacag cctacatgga gctgaggagc   600

ctgagatctg acgacacggc cgtgtattac tgtgcgagag ctatgggcta   650

ctgggggcaa gggaccacgg tcaccgtctc ctcactggga ggctgc       696
```

Sequence 4 - CD32BVL-CD79VH-1 amino acid sequence
(SEQ ID NO: 254):

```
DIQMTQSPSS LSASVGDRVT ITCRASQEIS GYLSWLQQKP GKAPRRLIYA    50

ASTLDSGVPS RFSGSESGTE FTLTISSLQP EDFATYYCLQ YFSYPLTFGG   100

GTKVEIKGGG SGGGGQVQLV QSGAEVKKPG ASVKVSCKAS GYTFTSYWMN   150

WVRQAPGQGL EWIGMIDPSD SETHYNQMFK DRVTMTTDTS TSTAYMELRS   200

LRSDDTAVYY CARAMGYWGQ GTTVTVSSLG GC                      232
```

Sequence 5 - CD32BVL-CD79VH-2 nucleotide sequence
(SEQ ID NO: 255):

```
gacatccaga tgacccagtc tccatcctcc ttatctgcct ctgtgggaga    50

tagagtcacc atcacttgtc gggcaagtca ggaaattagt ggttacttaa   100
```

-continued

```
gctggctgca gcagaaacca ggcaaggccc ctagacgcct gatctacgcc   150

gcatccactt tagattctgg tgtcccatcc aggttcagtg gcagtgagtc   200

tgggaccgag ttcaccctca ccatcagcag ccttcagcct gaagattttg   250

caacctatta ctgtctacaa tattttagtt atccgctcac gttcggaggg   300

gggaccaagg tggaaataaa aggaggcgga tccggaggcg gaggccaggt   350

tcagctggtg cagtctggag ctgaggtgaa gaagcctggc gcctcagtga   400

aggtctcctg caaggcttct ggttacacct ttaccagcta ctggatgaac   450

tgggtgcgac aggcccctgg acaagggctt gagtggatcg gaatgattga   500

tccttcagac agtgaaactc actacaatca aaagttcaag gacagagtca   550

ccatgaccac agacacatcc acgagcacag cctacatgga gctgaggagc   600

ctgagatctg acgacacggc cgtgtattac tgtgcgagag ctatgggcta   650

ctgggggcaa gggaccacgg tcaccgtctc ctcactggga ggctgc        696
```

Sequence 6 - CD32BVL-CD79VH-2 amino acid sequence
(SEQ ID NO: 256):

```
DIQMTQSPSS LSASVGDRVT ITCRASQEIS GYLSWLQQKP GKAPRRLIYA    50

ASTLDSGVPS RFSGSESGTE FTLTISSLQP EDFATYYCLQ YFSYPLTFGG   100

GTKVEIKGGG SGGGGQVQLV QSGAEVKKPG ASVKVSCKAS GYTFTSYWMN   150

WVRQAPGQGL EWIGMIDPSD SETHYNQKFK DRVTMTTDTS TSTAYMELRS   200

LRSDDTAVYY CARAMGYWGQ GTTVTVSSLG GC                      232
```

6.12 Construction and Optimization of H8B5-HBCRC Bio-Functional Diabodies

A diabody was constructed that contains variable regions capable of binding to CD32 and B-cell receptor complex ("BCRC").

Cloning. The constructs were constructed using standard PCR/overlapping PCR:

h8B5VL-G3SG4-hBCRCVH M48I-LGGC:

A fully humanized 8B5 VL (recognizing CD32) was amplified by using lgh321F and lgh788R as primers. hBCRCVH M48I was amplified by using lgh784F and lgh386R as primers. The PCR products were gel purified and mix together and amplified by using lgh321F and lgh386R. The overlapping PCR fragment was then cloned into pEE6 at XbaI-EcoRI site. "G3SG4" is a linker having the sequence: GGGSGGGG (SEQ ID NO: 10).

hBCRCVL R45N-G3SG4-h8B5VH-LGGC

The hBCRCVL R45N was amplified by using lgh321F and lgh785R as primers. The h8B5VH was amplified by using lgh787F and lgh786R as primers. The PCR products were gel purified and mix together and amplified by using lgh321F and lgh786R. The overlapping PCR fragment was then cloned into pEE13 at XbaI-EcoRI site.

Single Vector Construction. The pEE6hHBCRCVL R45N-h8B5VH was digested at Bgl II-Sal I sites and a 3.3 kb fragment was purified and inseted into pEE13 hHBCRCVL 45N-h8B5VH at BamHI-SalI sites. The Bgl II and BamH I shares compatible cohesive ends. The sequence of the DART and primers used for constructing the DART are depicted below:

hHBCRCVL. R45N-h8B5VH-LGGC nucleotide sequence
(SEQ ID NO: 257):

```
gatgttgtga tgactcagtc tccactctcc ctgcccgtca cccttggaca    50

gccggcctcc atctcctgca agtcaagtca gagcctctta gatagtgatg   100

gaaagacata tttgaattgg tttcagcaga ggccaggcca atctccaaac   150

cgcctaattt atctggtgtc taaactggac tctggggtcc cagacagatt   200

cagcggcagt gggtcaggca ctgatttcac actgaaaatc agcagggtgg   250

aggctgagga tgttggggtt tattactgct ggcaaggtac acattttccg   300

ctcacgttcg gcggagggac caagcttgag atcaaaggag gcggatccgg   350

aggcggaggc gaagtgaagc ttgaggagtc tggaggaggc ttggtgcaac   400

ctggaggatc catgaaactc tcttgtgaag cctctggatt cacttttagt   450

gacgcctgga tggactgggt ccgtcagtct ccagagaagg ggcttgagtg   500
```

-continued

```
ggttgctgaa attagaaaca aagctaaaaa tcatgcaaca tactatgctg   550

agtctgtgat agggaggttc accatctcaa gagatgattc caaaagtagt   600

gtctacctgc aaatgaacag cttaagagct gaagacactg gcatttatta   650

ctgtggggct ctgggccttg actactgggg ccaaggcacc actctcacag   700

tctcctcgct gggaggctgc                                    720
```

hHBCRCVL. R45N-h8B5VH-LGGC amino acide sequence
(SEQ ID NO: 258):

```
DVVMTQSPLS LPVTLGQPAS ISCKSSQSLL DSDGKTYLNW FQQRPGQSPN    50

RLIYLVSKLD SGVPDRFSGS GSGTDFTLKI SRVEAEDVGV YYCWQGTHFP   100

LTFGGGTKLE IKGGGSGGGG EVQLVESGGG LVQPGGSLRL SCAASGFTFS   150

DAWMDWVRQA PGKGLEWVAE IRNKAKNHAT YYAESVIGRF TISRDDAKNS   200

LYLQMNSLRA EDTAVYYCGA LGLDYWGQGT LVTVSSLGGC              240
```

H8B5VL-hHBCRCVH M48I-LGGC nucleotide sequence
(SEQ ID NO: 259):

```
gacatccaga tgacccagtc tccatcctcc ttatctgcct ctgtgggaga    50

tagagtcacc atcacttgtc gggcaagtca ggaaattagt ggttacttaa   100

gctggctgca gcagaaacca ggcaaggccc ctagacgcct gatctacgcc   150

gcatccactt tagattctgg tgtcccatcc aggttcagtg gcagtgagtc   200

tgggaccgag ttcaccctca ccatcagcag ccttcagcct gaagattttg   250

caacctatta ctgtctacaa tattttagtt atccgctcac gttcggaggg   300

gggaccaagg tggaaataaa aggaggcgga tccggaggcg gaggccaggt   350

tcagctggtg cagtctggag ctgaggtgaa gaagcctggc gcctcagtga   400

aggtctcctg caaggcttct ggttacacct ttaccagcta ctggatgaac   450

tgggtgcgac aggcccctgg acaagggctt gagtggatcg gaatgattga   500

tccttcagac agtgaaactc actacaatca aatgttcaag gacagagtca   550

ccatgaccac agacacatcc acgagcacag cctacatgga gctgaggagc   600

ctgagatctg acgacacggc cgtgtattac tgtgcgagag ctatgggcta   650

ctgggggcaa gggaccacgg tcaccgtctc ctcactggga ggctgc       696
```

H8B5VL-HBCRCVH M48I-LGGC amino acid sequence
(SEQ ID NO: 260):

```
DIQMTQSPSS LSASVGDRVT ITCRASQEIS GYLSWLQQKP GKAPRRLIYA    50

ASTLDSGVPS RFSGSESGTE FTLTISSLQP EDFATYYCLQ YFSYPLTFGG   100

GTKVEIKGGG SGGGGQVQLV QSGAEVKKPG ASVKVSCKAS GYTFTSYWMN   150

WVRQAPGQGL EWIGMIDPSD SETHYNQMFK DRVTMTTDTS TSTAYMELRS   200

LRSDDTAVYY CARAMGYWGQ GTTVTVSSLG GC                      232
```

Primers:

Lgh321F Primer (SEQ ID NO: 261):

```
cgagctagct ctagatgaga tcacagttct ctctac                   36
```

Lgh386R Primer (SEQ ID NO: 262):

```
tttgaattct agcagcctcc cagtgaggag acggtgaccg tggtc         45
```

Lgh784F Primer (SEQ ID NO: 263):

```
ggcggatccg gaggcggagg ccaggttcag ctggtgcag                39
```

Lgh785R Primer (SEQ ID NO: 264):

```
cctccggatc cgcctccttt gatctcaagc ttggtccc                 38
```

-continued

```
Lgh786R Primer (SEQ ID NO: 265):
tttgaattct agcagcctcc caggctggag acggtcacca gg          42

Lgh787F Primer (SEQ ID NO: 266):
ggaggcggat ccggaggcgg aggcgaagtg cagcttgtgg agtc        44
```

The Hu3G8VL 1-G3SG4-Hu2B6VH 4-LGGC expression plasmid was co-transfected together with Hu2B6VL 5-G3SG4-Hu3G8VH 5-LGGC into HEK-293 cells to make Hu2B6 4.5-Hu3G8 5.1 biospecific diabody recognizing CD32 and CD79. At the same time, Hu2B6VL 5-G3SG4-Hu2B6VH 4-LGGC and Hu3G8VL 1-G3SG4-Hu3G8VH 5-LGGC were transfected individually into HEK-293 cells to make Hu2B6 4.5 and Hu3G8 5.1 diabody. After three days in culture, the conditioned medium were harvested and characterized by binding ELISA. The result of this experiment is depicted in FIG. 36.

Experimental Design: 100 ng/well of soluble FcRIIb-G2-Agly was coated on 96-well Maxisorp plate in Carbonate buffer at 40° C. overnight. Plate was washed three times with PBS/0.1% Tween20 and then blocked by 0.5% BSA in PBS/0.1% Tween 20 for 30 mins at room temperature before adding diabodies. A serial of two-fold dilution of conditioned medium of Hu2B6 4.5-Hu3G8 5.1 biospecific diabody, Hu2B6 4.5 diabody, and hu3G8 5.1 diabody starting from 25 ng/well was added to the each well. The plate was incubated at room temperature for 1 hour. After washed with PBS/0.1% Tween20 three times, 10 ng/well of FcRIIIa-G2-Biotin was added to the plate. The plate was incubated at room temperature for 1 hour. After washed with PBS/0.1% Tween20 three times, 50 ul of 1:5000 dilution of HRP conjugated Streptavidin (Amersham Pharmacia Biotech) was used for detection. After 45 minutes incubation at room temperature, the plate was washed with PBS/0.1% Tween20 three times and developed using TMB substrate. After 10 minutes incubation, the reaction was stopped by 1% H2SO4. The OD450 nm was read by SOFTmax program. The read out was plotted using GraphPadPrism 3.03 software.

6.13 Construction of IgDART Diabodies

IgDART Diabodies were constructed that contain variable regions capable of binding to CD32 and B-cell receptor complex ("BCRC"). The first diabody employed an LGGCGGGS (SEQ ID NO: 267) linker between the VH sequences and the Fc sequences of the molecule. The second diabody employed either a LEIK linker having the sequence: LEIK (SEQ ID NO: 268) or a TVSS linker having the sequence TVSS (SEQ ID NO: 269). The sequences of the chains of these diabodies and encoding polynucleotides are shown below:

```
H8B5VL-hBCRCVH M48I, M62K_LGGCG3S_hKappa
(SEQ ID NO: 270):
DIQMTQSPSS LSASVGDRVT ITCRASQEIS GYLSWLQQKP GKAPRRLIYA     50

ASTLDSGVPS RFSGSESGTE FTLTISSLQP EDFATYYCLQ YFSYPLTFGG    100

GTKVEIKGGG SGGGGQVQLV QSGAEVKKPG ASVKVSCKAS GYTFTSYWMN    150

WVRQAPGQGL EWIGMIDPSD SETHYNQKFK DRVTMTTDTS TSTAYMELRS    200

LRSDDTAVYY CARAMGYWGQ GTTVTVSSLG GCGGGSRTVA APSVFIFPPS    250

DEQLKSGTAS VVCLLNNFYP REAKVQWKVD NALQSGNSQE SVTEQDSKDS    300

TYSLSSTLTL SKADYEKHKV YACEVTHQGL SSPVTKSFNR GEC           343
```

The H8B5VL sequences are fused to the hBCRCVH sequences by the linker GGGSGGGG (SEQ ID NO: 10) located at position 108-115. The hBCRCVH sequences are fused to the Fc sequences by the linker LGGCGGGS (SEQ ID NO: 267) located at position 229-236 (both shown underlined above). The polynucleotide encoding the H8B5VL-hBCRCVH M48I, M62K_LGGCG3S_hKappa sequence is:

```
(SEQ ID NO: 271):
gacatccaga tgacccagtc tccatcctcc ttatctgcct ctgtgggaga     50

tagagtcacc atcacttgtc gggcaagtca ggaaattagt ggttacttaa    100

gctggctgca gcagaaacca ggcaaggccc ctagacgcct gatctacgcc    150

gcatccactt tagattctgg tgtcccatcc aggttcagtg gcagtgagtc    200

tgggaccgag ttcaccctca ccatcagcag ccttcagcct gaagattttg    250

caacctatta ctgtctacaa tattttagtt atccgctcac gttcggaggg    300

gggaccaagg tggaaataaa aggaggcgga tccggaggcg gaggccaggt    350

tcagctggtg cagtctggag ctgaggtgaa gaagcctggc gcctcagtga    400
```

-continued

```
aggtctcctg caaggcttct ggttacacct ttaccagcta ctggatgaac     450

tgggtgcgac aggcccctgg acaagggctt gagtggatcg gaatgattga     500

tccttcagac agtgaaactc actacaatca aaagttcaag gacagagtca     550

ccatgaccac agacacatcc acgagcacag cctacatgga gctgaggagc     600

ctgagatctg acgacacggc cgtgtattac tgtgcgagag ctatgggcta     650

ctgggggcaa gggaccacgg tcaccgtctc ctcactggga ggctgcggcg     700

gagggagccg aactgtggct gcaccatcgg tcttcatctt cccgccatct     750

gatgagcagt tgaaatctgg aactgcctct gttgtgtgcc tgctgaataa     800

cttctatccc agagaggcca aagtacagtg gaaggtggat aacgccctcc     850

aatcgggtaa ctcccaggag agtgtcacag agcaggacag caaggacagc     900

acctacagcc tcagcagcac cctgacgctg agcaaagcag actacgagaa    1000

acacaaagtc tacgcctgcg aagtcaccca tcagggcctg agctcgcccg    1050

tcacaaagag cttcaacagg ggagagtgtt ag                       1082
```

where the sequences encoding the linkers: GGGSGGGG (SEQ ID NO: 10) and LGGCGGGS (SEQ ID NO: 267) are located at position 322-345 and 685-708, respectively (both shown underlined above).

```
HBCRCVL R45N-h8B5VH LGGCGGGS-hG1
(SEQ ID NO: 272):
DVVMTQSPLS LPVTLGQPAS ISCKSSQSLL DSDGKTYLNW FQQRPGQSPN      50

RLIYLVSKLD SGVPDRFSGS GSGTDFTLKI SRVEAEDVGV YYCWQGTHFP     100

LTFGGGTKLE IKGGGSGGGG EVQLVESGGG LVQPGGSLRL SCAASGFTFS     150

DAWMDWVRQA PGKGLEWVAE IRNKAKNHAT YYAESVIGRF TISRDDAKNS     200

LYLQMNSLRA EDTAVYYCGA LGLDYWGQGT LVTVSSLGGC GGGSASTKGP     250

SVFPLAPSSK STSGGTAALG CLVKDYFPEP VTVSWNSGAL TSGVHTFPAV     300

LQSSGLYSLS SVVTVPSSSL GTQTYICNVN HKPSNTKVDK RVEPKSCDKT     350

HTCPPCPAPE LLGGPSVFLF PPKPKDTLMI SRTPEVTCVV VDVSHEDPEV     400

KFNWYVDGVE VHNAKTKPRE EQYNSTYRVV SVLTVLHQDW LNGKEYKCKV     450

SNKALPAPIE KTISKAKGQP REPQVYTLPP SRDELTKNQV SLTCLVKGFY     500

PSDIAVEWES NGQPENNYKT TPPVLDSDGS FFLYSKLTVD KSRWQQGNVF     550

SCSVMHEALH NHYTQKSLSL SPGK                                 574
```

The hBCRCVL sequences are fused to the H8B5VH sequences by the linker GGGSGGGG (SEQ ID NO: 10) located at position 113-120. The H8B5VH sequences are fused to the Fc sequences by the linker LGGCGGGS (SEQ ID NO: 267) located at position 237-244 (both shown underlined above). The polynucleotide encoding the HBCRCVL R45N-h8B5VH_LGGCGGGS-hG1 sequence is:

```
(SEQ ID NO: 273):
gatgttgtga tgactcagtc tccactctcc ctgcccgtca cccttggaca      50

gccggcctcc atctcctgca agtcaagtca gagcctctta gatagtgatg     100

gaaagacata tttgaattgg tttcagcaga ggccaggcca atctccaaac     150

cgcctaattt atctggtgtc taaactggac tctggggtcc cagacagatt     200

cagcggcagt gggtcaggca ctgatttcac actgaaaatc agcagggtgg     250
```

-continued

```
aggctgagga tgttggggtt tattactgct ggcaaggtac acattttccg     300
ctcacgttcg gcggagggac caagcttgag atcaaaggag gcggatccgg     350
aggcggaggc gaagtgcagc ttgtggagtc tggaggaggc ttggtgcaac     400
ctggaggatc cctgagactc tcttgtgccg cctctggatt cacttttagt     450
gacgcctgga tggactgggt ccgtcaggcc ccaggcaagg ggcttgagtg     500
ggttgctgaa attagaaaca aagctaaaaa tcatgcaaca tactatgctg     550
agtctgtgat agggaggttc accatctcaa gagatgacgc caaaaacagt     600
ctgtacctgc aaatgaacag cttaagagct gaagacactg ccgtgtatta     650
ctgtggggct ctgggccttg actactgggg ccaaggcacc ctggtgaccg     700
tctccagcct gggaggctgc ggcggaggga gcgcctccac caagggccca     750
tcggtcttcc ccctggcacc ctcctccaag agcacctctg ggggcacagc     800
ggccctgggc tgcctggtca aggactactt ccccgaaccg gtgacggtgt     850
cgtggaactc aggcgccctg accagcggcg tgcacacctt cccggctgtc     900
ctacagtcct caggactcta ctccctcagc agcgtggtga ccgtgccctc     950
cagcagcttg ggcacccaga cctacatctg caacgtgaat cacaagccca    1000
gcaacaccaa ggtggacaag agagttgagc ccaaatcttg tgacaaaact    1050
cacacatgcc caccgtgccc agcacctgaa ctcctggggg gaccgtcagt    1100
cttcctcttc cccccaaaac ccaaggacac cctcatgatc tcccggaccc    1150
ctgaggtcac atgcgtggtg gtggacgtga gccacgaaga ccctgaggtc    1200
aagttcaact ggtacgtgga cggcgtggag gtgcataatg ccaagacaaa    1250
gccgcgggag gagcagtaca acagcacgta ccgtgtggtc agcgtcctca    1300
ccgtcctgca ccaggactgg ctgaatggca aggagtacaa gtgcaaggtc    1350
tccaacaaag ccctcccagc ccccatcgag aaaaccatct ccaaagccaa    1400
agggcagccc cgagaaccac aggtgtacac cctgccccca tcccgggatg    1450
agctgaccaa gaaccaggtc agcctgacct gcctggtcaa aggcttctat    1500
cccagcgaca tcgccgtgga gtgggagagc aatgggcagc cggagaacaa    1550
ctacaagacc acgcctcccg tgctggactc cgacggctcc ttcttcctct    1600
acagcaagct caccgtggac aagagcaggt ggcagcaggg gaacgtcttc    1650
tcatgctccg tgatgcatga ggctctgcac aaccactaca cgcagaagag    1700
cctctccctg tctccgggta aa                                  1722
```

where the sequences encoding the linkers: GGGSGGGG (SEQ ID NO: 10) and LGGCGGGS (SEQ ID NO: 267) are located at position 337-360 and 709-732, respectively (both shown underlined above).

```
H8B5VL-HBCRCVH M48I, M62K_(-4)LEIK_hKappa
(SEQ ID NO: 274):
DIQMTQSPSS LSASVGDRVT ITCRASQEIS GYLSWLQQKP GKAPRRLIYA      50
ASTLDSGVPS RFSGSESGTE FTLTISSLQP EDFATYYCLQ YFSYPLTFGG     100
GTKVEIKGGG SGGGGQVQLV QSGAEVKKPG ASVKVSCKAS GYTFTSYWMN     150
WVRQAPGQGL EWIGMIDPSD SETHYNQKFK DRVTMTTDTS TSTAYMELRS     200
LRSDDTAVYY CARAMGYWGQ GTTVLEIKRT VAAPSVFIFP PSDEQLKSGT     250
```

-continued

```
ASVVCLLNNF YPREAKVQWK VDNALQSGNS QESVTEQDSK DSTYSLSSTL    300

TLSKADYEKH KVYACEVTHQ GLSSPVTKSF NRGEC                    335
```

The $H_8$B5VL sequences are fused to the HBCRCVH sequences by the linker GGGSGGGG (SEQ ID NO: 10) located at position 108-115. The HBCRCVH sequences are fused to the Fc sequences by the linker LE IK (SEQ ID NO: 268) located at position 225-228 (both shown underlined above). The polynucleotide encoding the H8B5VL-HBCRCVH M48I, M62K_(−4)LEIK_hKappa sequence is:

```
(SEQ ID NO: 275):
gacatccaga tgacccagtc tccatcctcc ttatctgcct ctgtgggaga      50

tagagtcacc atcacttgtc gggcaagtca ggaaattagt ggttacttaa     100

gctggctgca gcagaaacca ggcaaggccc ctagacgcct gatctacgcc     150

gcatccactt tagattctgg tgtcccatcc aggttcagtg gcagtgagtc     200

tgggaccgag ttcaccctca ccatcagcag ccttcagcct gaagattttg     250

caacctatta ctgtctacaa tattttagtt atccgctcac gttcggaggg     300

gggaccaagg tggaaataaa aggaggcgga tccggaggcg gaggccaggt     350

tcagctggtg cagtctggag ctgaggtgaa gaagcctggc gcctcagtga     400

aggtctcctg caaggcttct ggttacacct ttaccagcta ctggatgaac     450

tgggtgcgac aggcccctgg acaagggctt gagtggatcg gaatgattga     500

tccttcagac agtgaaactc actacaatca aaagttcaag gacagagtca     550

ccatgaccac agacacatcc acgagcacag cctacatgga gctgaggagc     600

ctgagatctg acgacacggc cgtgtattac tgtgcgagag ctatgggcta     650

ctgggggcaa gggaccacgg tcctggagat caagcgaact gtggctgcac     700

catcggtctt catcttcccg ccatctgatg agcagttgaa atctggaact     750

gcctctgttg tgtgcctgct gaataacttc tatcccagag aggccaaagt     800

acagtggaag gtggataacg ccctccaatc gggtaactcc caggagagtg     850

tcacagagca ggacagcaag gacagcacct acagcctcag cagcaccctg     900

acgctgagca aagcagacta cgagaaacac aaagtctacg cctgcgaagt     950

cacccatcag ggcctgagct cgcccgtcac aaagagcttc aacaggggag    1000

agtgt                                                     1005
```

where the sequences encoding the linkers: GGGSGGGG (SEQ ID NO: 10) and LEIK (SEQ ID NO: 268) are located at position 322-345 and 673-684, respectively (both shown underlined above).

```
HBCRCVL R45N-h8B5VH_(-4)TVSS-hG1 = HBCRCVL R45N-h8B5VH_-hG1
(SEQ ID NO: 276):
DVVMTQSPLS LPVTLGQPAS ISCKSSQSLL DSDGKTYLNW FQQRPGQSPN      50

RLIYLVSKLD SGVPDRFSGS GSGTDFTLKI SRVEAEDVGV YYCWQGTHFP     100

LTFGGGTKLE IKGGGSGGGG EVQLVESGGG LVQPGGSLRL SCAASGFTFS     150

DAWMDWVRQA PGKGLEWVAE IRNKAKNHAT YYAESVIGRF TISRDDAKNS     200

LYLQMNSLRA EDTAVYYCGA LGLDYWGQGT LVTVSSASTK GPSVFPLAPS     250

SKSTSGGTAA LGCLVKDYFP EPVTVSWNSG ALTSGVHTFP AVLQSSGLYS     300

LSSVVTVPSS SLGTQTYICN VNHKPSNTKV DKRVEPKSCD KTHTCPPCPA     350

PELLGGPSVF LFPPKPKDTL MISRTPEVTC VVVDVSHEDP EVKFNWYVDG     400
```

-continued

```
VEVHNAKTKP REEQYNSTYR VVSVLTVLHQ DWLNGKEYKC KVSNKALPAP    450

IEKTISKAKG QPREPQVYTL PPSRDELTKN QVSLTCLVKG FYPSDIAVEW    500

ESNGQPENNY KTTPPVLDSD GSFFLYSKLT VDKSRWQQGN VFSCSVMHEA    550

LHNHYTQKSL SLSPGK                                         566
```

The HBCRCVL sequences are fused to the h8B5VH sequences by the linker GGGSGGGG (SEQ ID NO: 10) located at position 113-120. The h8B5VH sequences are fused to the Fc sequences by the linker TVSS (SEQ ID NO: 269) located at position 233-236 (both shown underlined above). The polynucleotide encoding the HBCRCVL R45N-h8B5VH_(−4)TVSS-hG1 is:

(SEQ ID NO: 277):

```
gatgttgtga tgactcagtc tccactctcc ctgcccgtca cccttggaca      50

gccggcctcc atctcctgca agtcaagtca gagcctctta gatagtgatg     100

gaaagacata tttgaattgg tttcagcaga ggccaggcca atctccaaac     150

cgcctaattt atctggtgtc taaactggac tctggggtcc cagacagatt     200

cagcggcagt gggtcaggca ctgatttcac actgaaaatc agcagggtgg     250

aggctgagga tgttggggtt tattactgct ggcaaggtac acattttccg     300

ctcacgttcg gcggagggac caagcttgag atcaaaggag gcggatccgg     350

aggcggaggc gaagtgcagc ttgtggagtc tggaggaggc ttggtgcaac     400

ctggaggatc cctgagactc tcttgtgccg cctctggatt cacttttagt     450

gacgcctgga tggactgggt ccgtcaggcc ccaggcaagg ggcttgagtg     500

ggttgctgaa attagaaaca aagctaaaaa tcatgcaaca tactatgctg     550

agtctgtgat agggaggttc accatctcaa gagatgacgc caaaaacagt     600

ctgtacctgc aaatgaacag cttaagagct gaagacactg ccgtgtatta     650

ctgtggggct ctgggccttg actactgggg ccaaggcacc ctggtgaccg     700

tctccagcgc ctccaccaag ggcccatcgg tcttccccct ggcaccctcc     750

tccaagagca cctctggggg cacagcggcc ctgggctgcc tggtcaagga     800

ctacttcccc gaaccggtga cggtgtcgtg gaactcaggc gccctgacca     850

gcggcgtgca caccttcccg gctgtcctac agtcctcagg actctactcc     900

ctcagcagcg tggtgaccgt gccctccagc agcttgggca cccagaccta     950

catctgcaac gtgaatcaca agcccagcaa caccaaggtg gacaagagag    1000

ttgagcccaa atcttgtgac aaaactcaca catgcccacc gtgcccagca    1050

cctgaactcc tggggggacc gtcagtcttc ctcttccccc caaaacccaa    1100

ggacaccctc atgatctccc ggacccctga ggtcacatgc gtggtggtgg    1150

acgtgagcca cgaagaccct gaggtcaagt tcaactggta cgtggacggc    1200

gtggaggtgc ataatgccaa gacaaagccg cgggaggagc agtacaacag    1250

cacgtaccgt gtggtcagcg tcctcaccgt cctgcaccag gactggctga    1300

atggcaagga gtacaagtgc aaggtctcca acaaagccct cccagccccc    1350

atcgagaaaa ccatctccaa agccaaaggg cagccccgag aaccacaggt    1400

gtacaccctg cccccatccc gggatgagct gaccaagaac caggtcagcc    1450
```

-continued

```
tgacctgcct ggtcaaaggc ttctatccca gcgacatcgc cgtggagtgg   1500

gagagcaatg ggcagccgga gaacaactac aagaccacgc ctcccgtgct   1550

ggactccgac ggctccttct tcctctacag caagctcacc gtggacaaga   1600

gcaggtggca gcaggggaac gtcttctcat gctccgtgat gcatgaggct   1650

ctgcacaacc actacacgca gaagagcctc tccctgtctc cgggtaaa     1698
```

where the sequences encoding the linkers: GGGSGGGG (SEQ ID NO: 10) and TVSS (SEQ ID NO: 269) are located at position 337-360 and 697-708, respectively (both shown underlined above).

6.14 Optimization of Linkers

As discussed above, the IgDART diabodies of the present invention preferably contain linkers between the VH sequences and the Fc sequences of the molecule. Experiments were conducted to optimize the linkers in order to maximize yield and activity. The following linkers were employed.

| SEQ ID NO | Linker |
|---|---|
| 278 | FNRGECGGGS |
| 279 | FNRGECLQVYYRM |
| 280 | LEGEEG |
| 281 | LEGEEGC |
| 282 | LEIK |
| 283 | LGEEG |
| 284 | LGEEGC |
| 285 | LGGCGGGS |
| 286 | LGKKG |
| 287 | LGKKGC |
| 288 | LKGKKG |
| 289 | LKGKKGC |
| 290 | LQVYYRM |
| 291 | LQVYYRMC |
| 292 | TVSS |
| 293 | VEPKSCGGGS |
| 294 | VEPKSCYLYLRARV |
| 295 | VQVHYRM |
| 296 | VQVHYRMC |
| 297 | YLYLRARV |
| 298 | YLYLRARVC |

The above linkers were introduced into plasmids in order to make a set of IgDART Diabodies having different combinations of linkers:

| Plasmid pMGX | Chain A Linker SEQ ID NO | pEE13.4 | Chain B Linker SEQ ID NO | pEE6.4 | ELISA (μg/ml) | Purified protein (After SEC) (1 liter) |
|---|---|---|---|---|---|---|
| 900 | 285 | ✓ | 285 | ✓ | 0.799 | 0.3 mg |
| 901 | 283 | ✓ | 286 | ✓ | 0.628 | 0.4 mg |
| 902 | 284 | ✓ | 287 | ✓ | 0.896 | 0.47 mg |
| 903 | 280 | ✓ | 288 | ✓ | 0.557 | |
| 904 | 281 | ✓ | 289 | ✓ | 0.450 | 0.4 mg |
| 905 | 293 | ✓ | 278 | ✓ | 0.360 | |
| 906 | 294 | ✓ | 279 | ✓ | N/A | |
| 907 | 282 | ✓ | 292 | ✓ | N/A | |
| 908 | 297 | ✓ | 295 | ✓ | 0.428 | 0.2 mg |
| 909 | 297 | ✓ | 290 | ✓ | 0.305 | 0.3 mg |
| 910 | 298 | ✓ | 296 | ✓ | N/A | |
| 911 | 298 | ✓ | 291 | ✓ | 0.218 | |

The aggregation properties of the produced IgDARTS was determined.

| IgDART Linkers | Total Protein (mg) | Oligomer % | Monomer % | Fragment % | SB Rank |
|---|---|---|---|---|---|
| 900 A/900 B | 0.51 | 12 | 45 | 43 | 4 |
| 901 A/901 B | 0.72 | 5 | 83 | 12 | 1 |
| 902 A/902 B | 0.78 | 21 | 48 | 31 | 4 |
| 903 A/903 B | 0.5 | 3 | 84 | 13 | 1 |
| 904 A/904 B | 0.66 | 16 | 65 | 26 | 4 |
| 905 A/905 B | 0.5 | 20 | 60 | 20 | 3 |
| 908 A/908 B | 0.5 | 13 | 65 | 17 | 2 |
| 908 A/909 B | 0.38 | 22 | 50 | 28 | 3 |
| 910 A/911 B | 0.2 | 45 | 10 | 45 | 5 |

The data unexpectedly showed that constructs having linkers, such as those employed in 901A/901B; 903A/903B; and 908A/908B gave dramatically superior results (less oligomerization and/or less fragment production) than constructs having linkers, such as 910A/911B.

6.15 E-coil/K-coil DARTS

As will be appreciated in view of the foregoing, the individual polypeptides of a bispecific DART can form two species of homodimers and one species of heterodimer. In one embodiment of the present invention, a charged polypeptide can be added to the C-terminus of one, or more preferably, both DART polypeptides. By selecting charged polypeptides of opposite charge for the individual polypeptides of the bispecific DART, the inclusion of such charged polypeptides favors formation of heterodimers and lessens formation of homodimers. Preferably, a positively charged polypeptide will contain a substantial content of arginine, glutamine, histidine and/or lysine (or mixtures of such amino acids) and a negatively charged polypeptide will contain a substantial content of aspartate or glutamate (or a mixture of such amino acids). Positively charged polypeptides containing a substantial content of lysine and negatively charged polypeptides containing a substantial content of glutamate are particularly preferred. In order to maximize the electrostatic attraction between such opposingly charged polypeptides, it is preferred to employ polypeptides capable of spontaneously assuming a helical conformation.

Thus, in a preferred embodiment, a positively charged, "E-coil" will be appended to one of the polypeptides being used to form a bispecific DART and a negatively charged "K-coil" will be appended to the second of the DART's polypeptides (FIG. 37).

A particularly preferred E-coil will have the sequence: (EVAALEK)$_4$:

SEQ ID NO: 299
EVAALEKEVAALEKEVAALEKEVAALEK

A particularly preferred K-coil will have the sequence: (KVAALKE)$_4$:

SEQ ID NO: 300
KVAALKEKVAALKEKVAALKEKVAALKE

A preferred DART polypeptide possessing such an E-coil will have the general sequence: [VL Domain]-[GGGSGGGG]-[VH Domain]-[(EVAALEK)$_4$]-GGGNS, where VL is the DART's variable light Ig domain, GGGSGGGG is SEQ ID NO: 10, VH is the DART's variable heavy Ig domain, (EVAALEK)$_4$ is SEQ ID NO: 299, and GGGNS is SEQ ID NO: 301. A preferred DART polypeptide possessing such a K-coil will have the general sequence: [VL Domain]-[GGGSGGGG]-[VH Domain]-[(KVAALKE)$_4$]-GGGNS, where VL is the DART's variable light Ig domain, GGGSGGGG is SEQ ID NO: 10, VH is the DART's variable heavy Ig domain, (KVAALKE)$_4$ is SEQ ID NO: 300, and GGGNS is SEQ ID NO: 301.

6.16 E-coil/K-coil FC-containing DARTS

In a further embodiment, Fc-regions can be linked to the E and/or K coils of E-coil or K-coil DARTs.

Furthering the separation between the Fc regions and the DART VH domain of an Fc-containing DART is desirable in cases in which a less separated arrangement of such domains results in diminished interaction between such domains and their binding ligands or otherwise interferes with DART assembly. Although separators of any amino acid sequence may be employed, it is preferable to employ separators that form an a helix coils, so as to maximally extend and project the Fc domain away from the variable domains (FIG. 37). Because the above-described coiled polypeptides of opposing charge additionally function to promote heterodimer formation, such molecules are particularly preferred separators. Such coil-containing Fc-DART molecules provide benefits similar to those of Fc-DARTS, including improved serum half-life and effector function recruitment. The above-described E-coil and K-coil polypeptides are particularly preferred for this purpose.

Thus, in a preferred embodiment, the E-coil Fc-containing DART will have the general sequence: [VL Domain]-[GGGSGGGG]-[VH Domain]-[(EVAALEK)$_4$]-GGG-Fc domain starting with D234 (Kabat numbering), where VL is the DART's variable light Ig domain, GGGSGGGG is SEQ ID NO: 10, VH is the DART's variable heavy Ig domain and (EVAALEK)$_4$ is SEQ ID NO: 299.

Similarly, in a preferred embodiment, the K-coil Fc-containing DART will have the general sequence: [VL Domain]-[GGGSGGGG]-[VH Domain]-[(KVAALKE)$_4$]-GGG-Fc domain starting with D234 (Kabat numbering), where VL is the DART's variable light Ig domain, GGGSGGGG is SEQ ID NO: 10, VH is the DART's variable heavy Ig domain and (KVAALKE)$_4$ is SEQ ID NO: 300.

As indicated above, a coil-containing DART molecule or a coil-containing Fc-containing DART molecule may contain only a single such coil separator, or it may contain more than one such separators (e.g., two separators, preferably of opposite charge, of which one is linked to each of the VH domain of the DART's polypeptides). By linking the Fc region to such separator molecule(s), the ability to make bivalent, tetravalent, etc. versions of the Fc-DART molecules by chain swapping is enhanced (FIG. 39). As shown in FIG. 39, Fc-DART molecules can be produced that form monomers or dimers depending upon whether the Fc domain is linked to one or both of the DART VH domains.

6.17 Functional Activity of E-coil/K-coil FC-containing DARTS

E-coil and/or K-coil Fc-DART species were produced from bi-specific DART molecules having: (1) the variable light and heavy regions of the CD79b (BCR complex)-reactive antibody, CB3 and (2) the variable light and heavy regions of a low affinity variant (termed "YA" Variant) of the CD32B-reactive antibody, 2B6. This light chain variable region of this antibody differs from that of antibody 2B6 in containing mutations: N50Y and V51A. Thus, antibody YA2B6 has a light chain variable region sequence:

(SEQ ID NO: 302)
EIVLTQSPDFQSVTPKEKVTITCRTSQSIGTNIHWYQQKPDQSPKLLIKY

ASESISGVPSRFSGSGSGTDFTLTINSLEAEDAATYYCQQSNTWPFTFGG

GTKVEIK.

The sequence of the heavy chain variable region of this antibody is:

(SEQ ID NO: 303)
QVQLVQSGAEVKKPGASVKVSCKASGYTFTNYWIHWVRQAPGQGLEWMGV

IDPSDTYPNYNKKFKGRVTMTTDTSTSTAYMELRSLRSDDTAVYYCARNG

DSDYYSGMDYWGQGTTVTVSS;
or

The low affinity antibody was selected since it will preferentially bind CD32B in cis on cells expressing CD79b (B cells). As such, the configuration will diminish interaction with other CD32B-expressing cells (monocytes, endothelial cells, liver) as well as the undesirable trans interaction E-coil and/or K-coil derivatives and E-coil and/or K-coil Fc-containing derivatives of such h2B6YAhCB3 DARTS were made. Size exclusion chromatography was used to analyze the approximate size and heterogeneity of the produced molecules. As shown in FIG. 40, dimers were formed from E-coil/K-coil DARTS having a single linked Fc region linked to an K-coil domain as well as to E-coil/K-coil DARTS having a single linked Fc region linked to an E-coil domain. Desired monomer, as well as dimer molecules were recovered from preparations in which Fc regions were linked to both the E and K coils of the same DART molecule, with the monomer being the majority product formed. FIG. 41 shows the possible structure of the produced dimer molecules.

The size exclusion chromatography fractions were analyzed using SDS-polyacrylamide gel electrophoresis to further analyze the structures of the produced molecules (FIG. 42). E-coil/K-coil DART derivatives (no Fc region) migrated as two predominant bands each of approximately 28 kD (corresponding to the KFc-containing polypeptide and slightly smaller EFc-containing polypeptide) and a less prominent band at approximately 49 kD (corresponding to the E-coil/K- coil DART). The monomer fractions of the E-coil/K-coil Fc-containing DART derivatives (EFc/K or E/KFc) from the size exclusion chromatography showed only either the larger or smaller molecular weight band at approximately 28 kD (corresponding to whether the DART was the KFc-containing DART (larger molecular weight band) or the EFc-containing DART (smaller molecular weight band). Material predominantly migrated at at approximately 49 kD (corresponding to the E-coil/K-coil DART). Significant higher molecular weight bands were also observed.

A bispecific binding ELISA was preformed to characterize the produced molecules. CD79 was put down on an ELISA plate. DARTs were then bound to the plate. DART binding was detected using sCD32B-biotin followed by incubation with streptavidin-HRP. As shown in FIG. 43, E-coil/K-coil Fc-containing h2B6YAhCB3 DART derivatives (EFc/K or E/KFc) showed significant enhancement of binding relative to a h2B6YAhCB3 DART, or to an EFc/KFc h2B6YAhCB3 DART derivative.

The cross-linking of antibodies that have bound to CD79b leads to B cell activation (Van Kooten, C. et al. (1997) "Cross-Linking Of Antigen Receptor Via Ig-B (B29, CD79b) Can Induce Both Positive And Negative Signals In CD40-Activated Human B Cells," Clin. Exp. Immunol. 110:509-515). Since the h2B6YAhCB3 DART molecules are capable of binding to both CD79b and the CD32B inhibitory receptor, they have the ability to "recruit" CD32B to sites of CD79b binding, and to thereby block B cell proliferation. To demonstrate this ability, DARTS were incubated with B cells that had been exposed to antibodies capable of crosslinking bound anti-CD79b antibodies. The results of this experiment are shown in FIG. 44. The results show that antibodies directed solely against CD79b or CD32B (Ch2B6N297Q and ChCB3.1N297Q, respectively) failed to inhibit B cell proliferation. EFc/KFc h2B6YA×hCB3 DART derivatives were substantially more effective in inhibiting B cell proliferation, as was h2B6YA×hCB3 DART itself and the h2B6YA×hCB3 VF control. E-coil/K-coil DARTS having only a single linked Fc region (E/KFc h2B6YA×hCB3 DART derivatives and EFc/K h2B6YA×hCB3 DART derivatives) were found to exert the greatest inhibition on B cell proliferation.

6.18 DART Modifications for Altering IN VIVO Serum Half-life

As discussed above, small recombinant antibody molecules such as bispecific single-chain molecules (e.g., possessing a molecular mass of approximately 55 kDa) are rapidly cleared from circulation. in vivo pharmacokinetic studies of DART molecules in mice showed the expected short terminal half life of approximately 2 hours.

In some embodiments, such as in the treatment of an acute inflammatory condition, such short half-life is desired, however, in other embodiments such as in the treatment of cancer and chronic diseases and conditions, it is preferred for the DART molecules of the present invention to exhibit longer half-lives.

In order to improve the in vivo pharmacokinetic properties of DART molecules for such uses, DART molecules may be modified to contain a polypeptide portion of a serum-binding protein at one or more of the termini of the DART molecule. Most preferably, such polypeptide portion of a serum-binding protein will be installed at the C-terminus of the DART molecule. A particularly preferred polypeptide portion of a serum-binding protein for this purpose is the albumin-binding domain (ABD) from streptococcal protein G. The albumin-binding domain 3 (ABD3) of protein G of *Streptococcus* strain G148 is particularly preferred.

The albumin-binding domain 3 (ABD3) of protein G of *Streptococcus* strain G148 consists of 46 amino acid residues forming a stable three-helix bundle and has broad albumin binding specificity (Johansson, M. U. et al. (2002) "*Structure, Specificity, And Mode Of Interaction For Bacterial Albumin-Binding Modules*," J. Biol. Chem. 277(10):8114-8120). Albumin is the most abundant protein in plasma and has a half-life of 19 days in humans. Albumin possesses several small molecule binding sites that permit it to non-covalently bind to other proteins and thereby extend their serum half-lives.

To demonstrate the ability of a polypeptide portion of a serum protein to extend the half-life of a DART, the ABD3 domain of streptococcal protein G was fused to a recombinant bispecific DART (immunoreactive with hCD16 and hCD32B antigens) to generate a recombinant antibody molecule, hCD16-hCD32B ABD-DART (FIG. 45). This ABD-DART showed specific binding to both antigens as well as with human serum albumin (HSA) and was able to retarget effector cells in vitro. Compared with the control DART, this ABD-DART showed strong increase of serum half-life in mice. This approach can be used as a viable route for increasing the half-life of potentially important pharmaceuticals like DART to greater than 90 minutes, greater than 2 hours, greater than 5 hours, greater than 10 hours, greater than 20 hours, and most preferably, greater than 30 hours.

Materials and Methods:

Design and Construction of ABD DART: hCD16-hCD32B ABD DART was made using as chain1:

hCD16VL-G3SG4-hCD32BVH-K coil [(KVAALKE)$_4$]

where CD16VL denotes the 3G8 CD16VL, G3SG4 denotes SEQ ID NO: 10, hCD32BVH denotes the 2B6 CD32BVH, and (KVAALKE)$_4$ denotes SEQ ID NO: 300;

and as chain 2:

hCD32BVL-G3SG4-hCD16VH-GGCGGG-E coil[(EVAALEK)$_4$]-GGGNS-ABD where CD32BVL denotes CD32BVL, G3SG4 denotes SEQ ID NO: 10, hCD16VH denotes CD16VH, GGCGGG is residues 2-7 of SEQ ID NO: 267, E coil [(EVAALEK)$_4$] is SEQ ID NO: 299, GGGNS is SEQ ID NO: 301, and ABD is:

(SEQ ID NO: 304)
LAEAKVLANR ELDKYGVSDY YKNLINNAKT VEGVKALIDE ILAALP

Accordingly, the sequence of chain 1 (h3G8VL1-G3SG4-h2B6VH4-Kcoil-GGGNS) is:

(SEQ ID NO: 305)
DIVMTQSPDS LAVSLGERAT INCKASQSVD FDGDSFMNWY
QQKPGQPPKL LIYTTSNLES GVPDRFSGSG SGTDFTLTIS
SLQAEDVAVY YCQQSNEDPY TPGQGTKLEI KGGGSGGGGQ
VQLVQSGAEV KKPGASVKVS CKASGYTFTN YWIHWVRQAP
GQGLEWIGVI DPSDTYPNYN KKFKGRVTMT VVVSTSTAYM
ELRSLRSDDT AVYYCARNGD SDYYSGMDYW GQGTTVTVSS
GGCGGGKVAA LKEKVAALKE KVAALKEKVA ALKEGGGNS

A preferred polynucleotide encoding chain 1 (h3G8VL1-G3SG4-h2B6VH4-Kcoil-GGGNS) is:

(SEQ ID NO: 306)

```
gacatcgtga tgacccaatc tccagactct ttggctgtgt
ctctagggga gagggccacc atcaactgca aggccagcca
aagtgttgat tttgatggtg atagttttat gaactggtac
caacagaaac caggacagcc acccaaactc ctcatctata
ctacatccaa tctagaatct ggggtcccag acaggtttag
tggcagtggg tctgggacag acttcaccct caccatcagc
agcctgcagg ctgaggatgt ggcagtttat tactgtcagc
aaagtaatga agatccgtac acgttcggac aggggaccaa
gcttgagatc aaaggaggcg gatccggcgg cggaggccag
gttcagctgg tgcagtctgg agctgaggtg aagaagcctg
gggcctcagt gaaggtctcc tgcaaggctt ctggttacac
ctttaccaac tactggatac actgggtgcg acaggcccct
ggacaagggc ttgagtggat tggagtgatt gatccttctg
atacttatcc aaattacaat aaaaagttca agggcagagt
caccatgacc gtagtcgtat ccacgagcac agcctacatg
gagctgagga gcctgagatc tgacgacacg gccgtgtatt
actgtgcgag aaacggtgat tccgattatt actctggtat
ggactactgg gggcaaggga ccacggtcac cgtctcctcc
ggaggatgtg gcggtggaaa agtggccgca ctgaaggaga
aagttgctgc tttgaaagag aaggtcgccg cacttaagga
aaaggtcgca gccctgaaag agggcggcgg gaattct
```

Accordingly, the sequence of chain 2 (h2B6VL5-G3SG4-h3G8VH5-Ecoil-GGGNS-ABD) is:

(SEQ ID NO: 307)

```
EIVLTQSPDF QSVTPKEKVT FTCRTSQSIG TNIHWYQQKP
DQSPKLLIKE VSESISGVPS RFSGSGSGTD FTLTINSLEA
EDAATYYCQQ SNTWPFTFGG GTKVEIKGGG SGGGGQVTLR
ESGPALVKPT QTLTLTCTFS GFSLSTSGMG VGWIRQPPGK
ALEWLAHIWW DDDKRYNPAL KSRLTISKDT SKNQVVLTMT
NMDPVDTATY YCAQINPAWF AYWGQGTLVT VSSGGCGGGE
VAALEKEVAA LEKEVAALEK EVAALEKGGG NSLAEAKVLA
NPELDKYGVS DYYKNLINNA KTVEGVKALI DEILAALP
```

A preferred polynucleotide encoding chain 2 (h2B6VL5-G3SG4-h3G8VH5-Ecoil-GGGNS-ABD) is:

(SEQ ID NO: 308)

```
gaaattgtgc tgactcagtc tccagacttt cagtctgtga
ctccaaagga gaaagtcacc ttcacctgca ggaccagtca
gagcattggc acaaacatac actggtacca gcagaaacca
gatcagtctc caaagctcct catcaaggag gtttctgagt
ctatctctgg agtcccatcg aggttcagtg gcagtggatc
```

-continued

```
tgggacagat ttcaccctca ccatcaatag cctggaagct
gaagatgctg caacgtatta ctgtcaacaa agtaatacct
ggccgttcac gttcggcgga gggaccaagg tggagatcaa
aggaggcgga tccggcggcg gaggccaggt taccctgaga
gagtctggcc ctgcgctggt gaagcccaca cagaccctca
cactgacttg taccttctct gggttttcac tgagcacttc
tggtatgggt gtaggctgga ttcgtcagcc tcccgggaag
gctctagagt ggctggcaca catttggtgg gatgatgaca
agcgctataa tccagccctg aagagccgac tgacaatctc
caaggatacc tccaaaaacc aggtagtcct cacaatgacc
aacatggacc ctgtggatac tgccacatac tactgtgctc
aaataaaccc cgcctggttt gcttactggg gccaagggac
tctggtcact gtgagctccg gaggatgtgg cggtggagaa
gtggccgcac tggagaaaga ggttgctgct ttggagaagg
aggtcgctgc acttgaaaag gaggtcgcag ccctggagaa
aggcggcggg aattctctgg ccgaagcaaa agtgctggcc
aaccgcgaac tggataaata tggcgtgagc gattattata
agaacctgat taacaacgca aagaccgtgg aaggcgtgaa
agcactgatt gatgaaattc tggccgccct gcct
```

Each VL and VH segment was amplified by PCR using hCD16-hCD32B DART as template. For chain 2, nucleotide sequences containing *E. coli* and ABD were formed by primer dimer and then subcloned at the C-terminal end of VH region of hCD16 using restriction digestion and ligation. Both chains were cloned into pCIneo vector (Promega, inc.) at NheI-NotII sites. The individual plasmids harboring the respective chain1 digested at NgoMIV-NheI and chain2 expression cassettes digested at BstBI-PmeI were then cloned into a single plasmid for transfection into CHO cells to generate stable cell lines.

Expression and Purification of Protein: For stable transfection, CHO-S cells were transfected with hCD16-hCD32B EK ABD-DART plasmid DNA. The ABD-DART protein was purified by affinity chromatography using the soluble version of FcRIIB antigen coupled to CNBr activated Sepharose 4B. The concentrated protein was further purified by size exclusion chromatography using Superdex 200HR 10/30.

Binding assay by ELISA: For CD-16 based capture, plates were coated with FcRIIB antigen at a concentration of 2 ug/mL at 4° C. for overnight. Plates were then blocked with 0.5% Peptone in PBS-T. Purified proteins diluted in a serial dilution of two fold were bound on plate for 1 h at room temperature. Finally, detection was performed using biotinylated CD32B (50 ng/mL) followed by HRP conjugated Streptavidin (1/1000, BD-Pharm). HRP activity was measured by addition of TMB and plate was read in a plate reader at OD 450 nm.

For human serum albumin (HSA) capture, plates were coated with HSA at a concentration of 2 ug/mL at 4° C. for overnight. After that the same procedures were followed to perform the dual affinity ELISA.

Peripheral-blood mononuclear cell-mediated ADCC assay: Cytotoxicity was measured by LDH release assay. Peripheral blood mononuclear cells (PBMC) were purified from whole human blood (Lonza Walkersville, Inc, Gaithersburg, Md.) by Ficoll-Hypaque (Amersham Biosciences, Piscataway, N.J.) density gradient centrifugation following manufacturer's instruction. $2\times10^4$ target cells are plated into each well of a round-bottom 96-well tissue culture plate. A one to four serial dilution of different DART or antibody molecules are added to the cells in the plate. After that, $6\times10^5$ PBMCs are added to the same wells. Plate is then incubated for overnight at 37° C. and 5% $CO_2$ incubator. The plate is then spun at 1200 rpm for 5 minutes, 50 μl of supernatant is transferred to a flat bottom ELISA plate. 50 μl of LDH substrate solution (Promega) is added to each well, and the plate is incubated for 30 min in dark at room temperature. Then 50 μl of stop solution is added to each well, and the plate is read at 490 nm within one hour. The percent cytotoxicity of each well is calculated with raw O.D. reading as $$(\text{Sample}-\text{AICC})/(\text{Target Max}-\text{Target Spontaneous})\times 100$$

where AICC is the antibody-independent cellular cytotoxicity. The dose response curve is generated using Prism software.

Pharmacokinetic Study: C57B1/6 mice were injected with a single intravenous injection of hCD16-hCD32B DART at 5 mg/kg. Mouse serum was collected at Pre-dose, 2, min; 1, 3, 6, 24 and 72 h. hCD16-hCD32B DART concentration in serum were quantified. Pharmacokinetic calculations of hCD16-hCD32B DART were performed by means of the pharmacokinetic software package WinNonlin Professional 5.1 (Pharsight Corporation, USA). Parameters were determined by non-compartmental analysis (NCA). The non-compartmental analysis was based on a model (Model 201) requiring an intravenous injection of the drug. The linear trapezoidal method was used for parameter calculation.

Results

Expression and binding study by ELISA: The hCD16-hCD32B ABD-DART was expressed efficiently at a concentration of 6.5 mg per liter in mammalian CHO-S cells. Binding activity of the purified ABD-DART protein to the respective antigens was assessed by ELISA. Results showed that hCD16-hCD32B ABD-DART binds simultaneously with both of the antigens, CD16 as well as with CD32B (FIG. 46A). The binding profile coincides with control hCD16-hCD32B DART protein binding. Affinity of the purified hCD16-hCD32B ABD-DART to human serum albumin (HSA) was also demonstrated by ELISA (FIG. 46B). The result showed strong binding of ABD fusion DART to HSA, whereas no binding was observed with control hCD16-hCD32B DART. To demonstrate that the ABD-DART molecule was capable of simultaneous binding to CD32B, CD16A and HSA, an injection of ABD-DART over the surface with immobilized HSA was followed by consequent injections of 200 nM CD32B and 200 nM CD16A(F158) (FIG. 46C, solid line). In control experiment (FIG. 46C, dashed line) antigens were replaced with buffer. The results show that the ABD-DART molecule was capable of simultaneous binding to CD32B, CD16A and HSA.

The hCD16-hCD32B ABD-DART and its ABD fusion derivative were found to exhibit equivalent binding soluble CD32B (sCD32B) and to soluble CD16A(158F) (sCD16A); the DARTS could be readily distinguished by the ability of the DART ABD fusion to bind human serum albumin (HSA); (FIGS. 46D-461). DARTs were incubated on CD16A-coated plates and binding was detected using biotinylated sCD32B in the presence or absence of 3 mg/ml HSA (blocking was done with 0.5% peptone in PBS-T). The DART ABD fusion was found to retain the bi-specific binding of the parental DART, and to exhibit binding to sCD16A and CD32B that was unaffected by the presence of human serum albumin (FIG. 46J).

In vitro cytotoxicity of ABD-DART: In order to demonstrate the simultaneous binding of this bispecific ABD-DART to two antigens, one on the effector cell and one on a target cell, the redirected cell killing assay was performed. Using human PBMC as effector cells, hCD16-hCD32B ABD-DART induced potent, dose-dependent, cytotoxicity against CD32B positive B cell lines, Daudi (FIG. 47A). The result showed that the potency of ABD-DART was equivalent to that of parental DART. The CD16×CD32B DART can bind to CD16B-expressing effector cells and thereby recruit such cells to kill (via redirected killing) cells that that express CD32B. The CD16×CD32B DART was thus found to display potent killing against Raji cells (FIG. 47B).

Pharmacokinetic Properties of ABD-DART: The pharmacokinetic properties of hCD16-hCD32B ABD-DART were analyzed by ELISA of serum samples after a single dose i.v. injection into C57B1/6 mice (FIG. 48). Both of the proteins, DART and ABD-DART showed biphasic elimination from circulation. The PK study of ABD-DART showed a prolonged circulation time, with an increased terminal half-life of 35.1 h compared to 1.2 h for regular DART (FIG. 48, Table 17). The improvement of pharmacokinetic properties was also demonstrated by comparison of the area under the curve (AUC). For the construct ABD-DART the AUC increased by a factor of almost 30 after fusion to ABD (Table 17).

TABLE 17

| | ABD-DART | DART |
|---|---|---|
| T ½ (hr) | 35.1 | 1.2 |
| Cmax (μg/mL) | 156.3 | 103.7 |
| Tmax (hr) | 0.5 | 0.033 |
| AUC | 4408.2 | 138.3 |

In vivo Biological Activity of the ABD-DART: In order to demonstrate that the hCD16-hCD32B ABD-DART retained biological activity in vivo, a single dose of the ABD-DART or its parental DART were administered to Tg (mCD16−/− hCD16A+32B+) mice and the concentrations of B cells, T cells and PM cells were monitored. The results indicate that the DARTs were capable of depressing the concentrations of B cells (FIG. 49A) and are interpreted as indicating that a targeted redirected killing of B cells was attained in vivo until the DARTS were removed from the mouse circulation. The concentrations of T cells (FIG. 49B) and PM cells (FIG. 49C) were not depressed by the DARTS, confirming their specificity.

In sum, an albumin binding domain fused DART protein (referred to as ABD-DART) was successfully designed and produced. The hCD16-hCD32B ABD-DART was found to retain the specificities to its two recognized antigenic determinants: CD16 and CD32B. ABD-DART was found to show high affinity with human serum albumin. The fusion of ABD did not reduce the biological activity (i.e., the potency of the DART for redirected tumor cell killing). The fusion of DART molecule to ABD led to a substantial improvement (increase) in its in vivo half-life, and accomplished this goal without a dramatic increase in size. The ability to retain a small size is significant and advantageous since it facilitats the ability of the DART to diffuse into tumor tissues.

6.19 Her2/B Cell Receptor DARTS

An IgDART Diabody was constructed that contained variable regions capable of binding to Her2/neu and to the T-cell receptor ("TCR").

As discussed above, the TCR is natively expressed by CD4+ or CD8+ T-cells, and permits such cells to recognize antigenic peptides that are bound and presented by class I or class II MHC proteins of antigen-presenting cells. Recognition of a pMHC (peptide-MHC) complex by a TCR initiates the propagation of a cellular immune response that leads to the production of cytokines and the lysis of the antigen-presenting cell. HER2/neu, an important member of the ErbB family, has been extensively investigated because of its role in several human carcinomas and in mammalian development. (Hynes and Stern (1994) Biochim. et Biophys. Acta 1198: 165-184; and Dougall et al. (1994) Oncogene 9:2109-2123; Lee et al. (1995) Nature 378:394-398). The human HER2/neu gene and HER2/neu protein are described in Semba et al. (1985) Proc. Natl. Acad. Sci. (U.S.A.) 82:6497-6501 and Yamamoto et al. (1986) Nature 319:230-234, and the sequence is available in GenBank as accession number X03363. HER2/neu comprises four domains: an extracellular domain to which ligand binds; a lipophilic transmembrane domain; a conserved intracellular tyrosine kinase domain; and a carboxyl-terminal signaling domain harboring several tyrosine residues that can be phosphorylated. (Plowman et al. (1993) Proc. Natl. Acad. Sci. (U.S.A.) 90:1746-1750). The sequence of the HER2/neu extracellular (ECD) domain was described by Franklin et al. (2004) Cancer Cell. 5(4):317-328, and is available in Protein DataBank Record 1S78 (2004).

HER2/neu functions as a growth factor receptor and is often expressed by tumors such as breast cancer, colon cancer, bladder cell cancer, ovarian cancer and lung cancer. HER2/neu is overexpressed in 25-30% of human breast and ovarian cancers, and is associated with aggressive clinical progression and poor prognosis in these patients. (Slamon et al. (1987) Science 235:177-182; Slamon et al. (1989) Science 244:707-712). Overexpression of HER2/neu has also been observed in other carcinomas including carcinomas of the stomach, endometrium, salivary gland, lung, kidney, colon, thyroid, pancreas and bladder. (See, e.g., King et al. (1985) Science 229:974; McCann et al. (1990) Cancer 65:88-92; Yonemura et al. (1991) Cancer Research 51:1034).

A number of monoclonal antibodies and small molecule tyrosine kinase inhibitors targeting HER-1 or HER2/neu have been developed, including, in particular, a humanized variant of a murine monoclonal antibody known as 4D5 (HERCEPTIN®, Genentech, Inc.) that recognizes an extracellular epitope (amino acids 529 to 627) in the cysteine-rich II domain of HER2/neu, which resides very close to the protein's transmembrane region. Studies have shown that in HER2/neu overexpressing breast cancer cells, treatment with antibodies specific to HER2/neu in combination with chemotherapeutic agents (e.g., cisplatin, doxoubicin, taxol) elicits a higher cytotoxic response than treatment with chemotherapy alone. (Hancock et al. (1991) Cancer Res. 51:4575-4580; Arteaga et al. (1994) Cancer 54:3758-3765; Pietras et al. (1994) Oncogene 9:1829-1838). One possible mechanism by which HER2/neu antibodies might enhance response to chemotherapeutic agents is through the modulation of HER2/neu protein expression or by interfering with DNA repair. (Stancovski et al. (1991) Proc. Natl. Acad. Sci. (U.S.A.) 88:8691-8695; Bacus et al. (1992) Cell Growth & Diff. 3:401-411; Bacus et al. (1993) Cancer Res. 53:5251-5261; Klapper et al. (1997) Oncogene 14:2099-2109; Klapper et al. (2000) Cancer Res. 60:3384-3388; Arteaga et al. (2001) J Clinical Oncology 19(18s):32s-40s. Although in certain cases, anti-HER2/neu antibodies such as HERCEPTIN® provide therapeutic benefit to patients, the majority of breast cancer and other patients exhibit refractory responses to such antibodies. These responses reflect, in part, differences in the extent of the overexpression of HER2/neu by the patient's cancer cells.

As a consequence of containing variable regions capable of binding to Her2/neu and to the T-cell receptor ("TCR"), the DART has the ability to bind to HER2-expressing cells and to thereby attach to such cells a domain capable of binding to the T-cell receptor. When such T cells bind to this domain, they activate to initiate an immune response that leads to the killing of the HER2-expressing cells.

The amino acid and nucleic acid sequences for such DART are provided below, with VL and VH sequences shown in plain text, the VL-VH linker shown in underlined text, and the sequence encoding the C-terminal heterodimerization motif (SEQ ID NO: 313: GFNRGEC or SEQ ID NO: 314: GVEPKSC) shown in bold and italics.

TCRVL-HER2VH amino acid sequence
(SEQ ID NO: 315)

EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIKGGGS GGGGQVQLQQ

SGPELVKPGA SLKLSCTASG FNIKDTYIHW VKQRPEQGLE

WIGRIYPTNG YTRYDPKFQD KATITADTSS NTAYLQVSRL

TSEDTAVYYC SRWGGDGFYA MDYWGQGASV TVSS*GFNRGE*

*C*

TCRVL-HER2VH-encoding nucleic acid sequence
(SEQ ID NO: 316)

gaaattgtgt tgacacagtc tccagccacc ctgtctttgt ctccagggga aagagccacc ctctcctgca gtgccacctc aagtgtaagt tacatgcact ggtatcagca gaaaccaggg aaagccccta agcgctggat ctatgacaca tccaaactgg cttctggggt cccatcaagg ttcagcggca gtggatctgg gacagaattt actctcacaa tcagcagcct gcagcctgaa gattttgcaa cttattactg tcagcagtgg agtagtaacc cgctcacgtt tggccagggg accaagcttg agatcaaagg aggcggatcc ggcggcggag gccaggttca gctgcagcag tctgggccag agcttgtgaa gccaggggcc tcactcaagt tgtcctgtac agcttctggc ttcaacatta aagacaccta tatacactgg gtgaaacaga ggcctgaaca gggcctggaa tggattggaa ggatttatcc tacgaatggt tatactagat atgacccgaa gttccaggac aaggccacta taacagcaga cacatcctcc aacacagcct acctgcaggt cagccgcctg acatctgagg acactgccgt ctattattgt tctagatggg gaggggacgg cttctatgct atggactact ggggtcaagg agcctcggtc accgtgagct cc*ggattcaa caggggagag*

*tgt*

HER2VL-TCRVH amino acid sequence
(SEQ ID NO: 317)

DIVMTQSHKF MSTSVGDRVS ITCKASQDVN TAVAWYQQKP

GHSPKLLIYS ASFRYTGVPD RFTGSRSGTD FTFTISSVQA

-continued

EDLAVYYCQQ HYTTPPTFGG GTKVEIKGGG SGGGGQVQLV

QSGAEVKKPG ASVKVSCKAS GYKFTSYVMH WVRQAPGQGL

EWIGYINPYN DVTKYNEKFK GRVTITADKS TSTAYMELSS

LRSEDTAVHY CARGSYYDYD GFVYWGQGTL VTVSS*GVEPK*

*SC*

HER2VL-TCRVH-encoding nucleic acid sequence (SEQ ID NO: 318)

gacatcgtga tgacccagtc ccacaagttc atgtccacct ctgtgggcga tagggtcagc atcacctgca aggccagcca ggatgtgaat actgctgtag cctggtatca gcagaaacca ggacattctc ccaaactgct gatttactcc gcatccttcc ggtacactgg agtccctgat cgcttcactg gcagcagatc tgggacagat ttcactttca ccatcagcag tgtgcaggct gaagacctgg cagtttatta ctgtcagcaa cattatacta cacctcccac cttcggaggg ggtaccaagg tggagatcaa aggaggcgga tccggcggcg gaggccaggt tcagctggtg cagtctggag ctgaggtgaa gaagcctggg gcctcagtga aggtctcctg caaggccagc ggttacaagt ttaccagcta cgtgatgcac tgggtgcgac aggcccctgg acaagggctt gagtggatcg gatatattaa tccttacaat gatgttacta agtacaatga gaagttcaaa ggcagagtca cgattaccgc ggacaaatcc acgagcacag cctacatgga gctgagcagc ctgagatccg aggacacggc cgtgcactac tgtgcgagag ggagctacta tgattacgac gggtttgttt actggggcca agggactctg gtcactgtga gctcc*ggagt tgagcccaaa*

*tcttgt*

In a preferred embodiment, such constructs are modified to contain an E coil or K coil domain that facilitates the formation of heterodimers (i.e., TCRVL-HER2VH×HER2VL-TCRVH dimers). The amino acid and nucleic acid sequences for such DART are provided below, with VL and VH sequences shown in plain text, the VL-VH linker shown in underlined text, and the sequence encoding Cys-containing linker for dimerization (GGCGGG; residues 2-7 of SEQ ID NO: 267) shown in italics. The E coil of K coil heterodimerization domain is double-underlined (the preferred "E-coil" sequence is 4 heptameric repeats of EVAALEK; SEQ ID NO: 299; the preferred "K-coil" sequence is 4 heptameric repeats of KVAALKE (SEQ ID NO: 300). The sequence following the E coil or the K coil has no ascribed function.

TCRVL-HER2VH-E coil amino acid sequence (SEQ ID NO: 319)

EIVLTQSPAT LSLSPGERAT LSCSATSSVS YMHWYQQKPG

KAPKRWIYDT SKLASGVPSR FSGSGSGTEF TLTISSLQPE

DFATYYCQQW SSNPLTFGQG TKLEIKGGGS GGGGQVQLQQ

SGPELVKPGA SLKLSCTASG FNIKDTYIHW VKQRPEQGLE

-continued

WIGRIYPTNG YTRYDPKFQD KATITADTSS NTAYLQVSRL

TSEDTAVYYC SRWGGDGFYA MDYWGQGASV TVSS*GGCGGG*

EVAALEKEVA ALEKEVAALE KEVAALEKGG GNS

TCRVL-HER2VH-E coil-encoding nucleic acid sequence (SEQ ID NO: 320)

gaaattgtgt tgacacagtc tccagccacc ctgtctttgt ctccagggga aagagccacc ctctcctgca gtgccacctc aagtgtaagt tacatgcact ggtatcagca gaaaccaggg aaagccccta agcgctggat ctatgacaca tccaaactgg cttctggggt cccatcaagg ttcagcggca gtggatctgg gacagaattt actctcacaa tcagcagcct gcagcctgaa gattttgcaa cttattactg tcagcagtgg agtagtaacc cgctcacgtt tggccagggg accaagcttg agatcaaagg aggcggatcc ggcggcggag gccaggttca gctgcagcag tctgggccag agcttgtgaa gccaggggcc tcactcaagt tgtcctgtac agcttctggc ttcaacatta aagacaccta tatacactgg gtgaaacaga ggcctgaaca gggcctggaa tggattggaa ggatttatcc tacgaatggt tatactagat atgacccgaa gttccaggac aaggccacta taacagcaga cacatcctcc aacacagcct acctgcaggt cagccgcctg acatctgagg acactgccgt ctattattgt tctagatggg gaggggacgg cttctatgct atggactact ggggtcaagg agcctcggtc accgtgagct *ccggaggatg tggcggtgga* gaagtggccg cactggagaa agaggttgct gctttggaga aggaggtcgc tgcacttgaa aaggaggtcg cagccctgga gaaaggcggc gggaattct HER2VL-TCRVH-K coil amino acid sequence (SEQ ID NO: 321)

DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIKGGG SGGGGQVQLV

QSGAEVKKPG ASVKVSCKAS GYKFTSYVMH WVRQAPGQGL

EWIGYINPYN DVTKYNEKFK GRVTITADKS TSTAYMELSS

LRSEDTAVHY CARGSYYDYD GFVYWGQGTL VTVS*SGGCGG*

*G*KVAALKEKV AALKEKVAAL KEKVAALKEG GGNS

HER2VL-TCRVH-K coil-encoding nucleic acid sequence (SEQ ID NO: 322)

gacatcgtga tgacccagtc ccacaagttc atgtccacct ctgtgggcga tagggtcagc atcacctgca aggccagcca ggatgtgaat actgctgtag cctggtatca gcagaaacca ggacattctc ccaaactgct gatttactcc gcatccttcc ggtacactgg agtccctgat cgcttcactg gcagcagatc tgggacagat ttcactttca ccatcagcag tgtgcaggct -continued

```
gaagacctgg cagtttatta ctgtcagcaa cattatacta

cacctcccac cttcggaggg ggtaccaagg tggagatcaa

aggaggcgga tccggcggcg gaggccaggt tcagctggtg

cagtctggag ctgaggtgaa gaagcctggg gcctcagtga

aggtctcctg caaggccagc ggttacaagt ttaccagcta

cgtgatgcac tgggtgcgac aggcccctgg acaagggctt

gagtggatcg gatatattaa tccttacaat gatgttacta

agtacaatga gaagttcaaa ggcagagtca cgattaccgc

ggacaaatcc acgagcacag cctacatgga gctgagcagc

ctgagatccg aggacacggc cgtgcactac tgtgcgagag

ggagctacta tgattacgac gggtttgttt actggggcca

agggactctg gtcactgtga gctccggagg atgtggcggt

ggaaaagtgg ccgcactgaa ggagaaagtt gctgctttga

aagagaaggt cgccgcactt aaggaaaagg tcgcagccct

gaaagagggc ggcgggaatt ct
```

DART molecules having Her2 and T-cell receptor (TCR) binding domains were tested for their ability to mediate cytotoxicity in multiple breast cancer, colon cancer and bladder cancer cell lines that had been previously characterized as exhibiting low levels of HER2 expression (and thus being refractory to treatment with the anti-Her2/neu antibody, Herceptin®. The tested breast cancer cell lines are ZR75-1 (HER2 2+) (FIG. 50A), MCF-7 (HER2 1+) (FIG. 50B) and MDA-MB468 (HER2-ve) (FIG. 50C). The non-breast cancer cell lines tested are HT-29 (colon cancer cell line) (FIG. 50D) and SW780 (bladder cancer cell line) (FIG. 50E). As shown in FIG. 49A-E, such DART molecules were substantially more effective than HERCEPTIN® in mediating cytotoxicity of tumor-derived cell lines, both in terms of the concentrations required to achieve equivalent cytotoxicity, and in terms of the maximum levels of cytotoxicity observed.

6.20 In vitro Fusion of DART with ABD Through E and K Coils

As discussed above, the DART molecules of the present invention can be designed to exhibit bispecific binding to the NKG2D Receptor as affinity for a hapten, fluorescein, so that they may serve as universal adaptors, able to co-ligate the NKG2D Receptor with molecules that interact with fluorescein-conjugated binding partners. To further demonstrate the use of ABDs, a DART were constructed using the polypeptide chains:

(1) KYK2VL-4420VH-GFNRGEC (SEQ ID NO: 313)-Ecoil: This polypeptide was constructed using the VL domain of the above-described KYK 2.0 antibody (Kwong, K Y et al. (2008) "*Generation, Affinity Maturation, And Characterization Of A Human Anti-Human NKG2D Monoclonal Antibody With Dual Antagonistic And Agonistic Activity*," J. Mol. Biol. 384:1143-1156; and PCT/US09/54911) and the VH domain of the above-described anti-fluorescein MAb, 4420.

(2) 4420VL-KYK2VH-GVEPKSC (SEQ ID NO: 314): This polypeptide was constructed using the VL domain of the above-described anti-fluorescein MAb, 4420 and the VH domain of the KYK 2.0 antibody. "Ecoil" denotes the E coil amino acid sequence of 4 heptameric repeats of EVAALEK; SEQ ID NO: 299.

The KYK2VL-4420VH-GFNRGEC (SEQ ID NO: 313)-E coil and 4420VL-KYK2VH-GVEPKSC (SEQ ID NO: 314) polypeptides were transfected into CHO cells to express a DART designated as "KYK2 4420 VF Ecoil." The purification of these molecules is shown in FIGS. 51A and 51B. The affinity of the KYK2 4420 VF Ecoil DART was determined by detecting with NKG2D Fc 012210 the binding of the DART to captured FITC antigen. The results of the experiment demonstrate that the DART was capable of binding to both molecules (FIG. 52).

Additionally, a Kcoil-GGGNS (SEQ ID NO: 301)-ABD fusion was made, where "Kcoil" denotes the K coil amino acid sequence of 4 heptameric repeats of KVAALKE (SEQ ID NO: 300). FIG. 53 provides a restriction map of plasmid pPAL7, and depicts the construction of plasmid pPAL7 Kcoil ABD, which expresses the Kcoil-ABD fusion using a PROFINITY EXACT™ (Bio-Rad, Hercules, Calif.) tag to facilitate purification. The pPAL7 Kcoil ABD vector was transformed into *E. coli* BL21DE3 cells. Expression of tagged Kcoil ABD was induced by addition of 2 mM IPTG for 4 hours. Expression of protein was verified either by SDS-PAGE or by Western Blot. In brief, the PROFINITY EXACT™ fusion tag system involves mediating the lysis of the cells, binding the released proteins to an immobilized subtilisin protease affinity column, washing the column to elute unbound proteins, applying a fluoride-containing elution buffer to trigger subtilisin to quickly and precisely cleave the tag from the fusion protein after the cleavage recognition sequence, washing the tag-free protein from the column after such cleavage, and dialyzing the eluted protein in PBS. FIG. 54 shows a Western blot analysis of Kcoil ABD protein purified by the PROFINITY EXACT™ purification resin (small scale from 10 ml culture).

The Kcoil-AFD protein obtained from the PROFINITY EXACT™ purification resin was further purified using SDS-PAGE (FIG. 55). The 250 ml *E. coli* culture yielded 6.523 mg of purified protein (Table 18).

TABLE 18

| Eluted Fractions | Buffer | Conc. (mg/ml) | Volume | Total Protein (mg) |
|---|---|---|---|---|
| 1-6 | PBS | 0.412 | 6 | 2.06 |
| 7-9 | PBS + 100 mM NaF | 0.924 | 1.8 | 1.663 |
| 10-13 | PBS + 100 mM NaF | 0.800 | 3.5 | 2.8 |
| | | | | 6.523 |

The KYK2 4420 VF E coil DART and the Kcoil ABD protein were incubated in PBS for 30 min at room temperature to form an E Coil-K Coil ABD DART having improved properties. ELISA results show that all the domains in the complex are able to bind to their respective ligands (FIGS. 56A-56C). If desired, further purification of the KYK2 4420 VF E coil and K-ABD complex can be achieved using an anti-EK column.

Since the formation of the complex is independent of the particular binding domains of the DART, the above method can be used to generate E Coil-K Coil ABD DARTs having other binding specificities (for example, by complexing a CD32B (e.g., antibody 2B6)/CD16A (e.g., antibody 3G8) VF E DART with a K Coil ABD).

Thus, as indicated above, in one embodiment of the invention, both of the antigen binding domain-containing polypeptides of the DART can comprise an additional sequence that serves to drive heterodimer formation (e.g., a K coil or an E coil) and optionally one of such polypeptides can contain a polypeptide portion of a serum-binding protein capable of binding to the serum protein (e.g., FIG. 45). In an alternative embodiment, one, and preferably only one, of the antigen binding domain-containing polypeptides of the DART can comprise such additional sequence for driving heterodimer formation (e.g., either a K coil or an E coil) and the DART can comprise a complex with a further (e.g., a third) polypeptide that does not contain an antigen binding site, but which comprises a polypeptide having a complementing sequence for driving heterodimer formation (e.g., a K coil where the antigen binding domain-containing polypeptide of the DART comprises an E coil; or an E coil where the antigen binding domain-containing polypeptide of the DART comprises an K coil) and optionally a polypeptide portion of a serum-binding protein capable of binding to the serum protein. The polypeptide portion of such serum-binding protein of such further (e.g. third) polypeptide can be located either N-terminal or C-terminal to the polypeptide having such complementing sequence.

6.21 Deimmunization of Albumin Binding Domain

As discussed above, the DART molecules of the present invention can be designed to comprise an albumin binding domain (ABD) such as the ABD from streptococcal protein G, and more preferably the albumin-binding domain 3 (ABD3) of protein G of *Streptococcus* strain G148.

In order to decrease the immunogenicity of the ABD, amino acid modifications were introduced into residues 60-79 of the amino acid sequence of ABD3: (SEQ ID NO: 304):

```
LAEAKVLANR ELDKYGVSDY YKNLINNAKT VEGVKALIDE
41        50          60          70          80

ILAALP
     86
```

and the effect of such variations on HSA binding was measured (Table 19).

TABLE 19

| Amino Acid | HSA Binding |
|---|---|
| WT | 1 |
| Y60F | 1 |
| Y60L | 1 |
| Y60I | 1 |
| Y60M | 1 |
| Y60V | 0.87 |
| Y60S | 0.26 |
| Y60P | 0.43 |
| Y60T | 0.74 |
| Y60A | 0.56 |
| Y60H | 0.22 |
| Y60Q | 0.47 |
| Y60N | 0.19 |
| Y60K | 0.56 |
| Y60D | N/B |
| Y60E | N/B |
| Y60C | N/B |
| Y60W | 1.7 |
| Y60R | 0.73 |
| Y60G | N/B (Low Exp) |
| Y61L | 0.48 |
| Y61I | 1.33 |
| Y61M | 1.2 |
| Y61V | 1.24 |
| Y61S | 0.47 |
| Y61P | 0.87 (Low Exp) |
| Y61T | 1 |
| Y61A | 1 |
| Y61H | 1 (Low Exp) |
| Y61Q | 0.35 |
| Y61N | 0.26 (Low Exp) |

TABLE 19-continued

| Amino Acid | HSA Binding |
|---|---|
| Y61K | N/B |
| Y61D | N/B |
| Y61E | N/B (Low Exp) |
| Y61C | N/B (Low Exp) |
| Y61W | 0.33 (Low Exp) |
| Y61R | 0.41 |
| Y61G | 0.45 |
| L64F | 0.6 (Low Exp) |
| L64I | 1 |
| L64M | 1 |
| L64V | 1 |
| L64S | 0.55 |
| L64P | 0.8 (Low Exp) |
| L64T | 0.8 |
| L64A | 0.6 |
| L64Y | 0.85 |
| L64H | 1 |
| L64Q | 0.4 (Low Exp) |
| L64N | 0.7 (Low Exp) |
| L64K | 0.5 |
| L64D | N/B |
| L64E | N/B |
| L64C | 0.6 (Low Exp) |
| L64W | 1.2 |
| L64R | 0.94 |
| L64G | 1 |
| I65F | 0.43 |
| I65L | 1 |
| I65M | 1.1 |
| I65V | 1 |
| I65S | 0.5 |
| I65P | N/A (Low Exp) |
| I65T | 0.6 |
| I65A | 1 |
| I65Y | N/A (Low Exp) |
| I65H | N/A (Low Exp) |
| I65Q | N/A (Low Exp) |
| I65N | N/B |
| I65K | 0.2 |
| I65D | N/B (Low Exp) |
| I65E | N/B (Low Exp) |
| 165C | N/B |
| 165W | N/B |
| I65R | N/B |
| I65G | 0.2 (Low Exp) |
| A68F | 0.1 |
| A68L | 0.06 |
| A68I | 0.1 |
| A68M | N/B |
| A68V | 0.05 |
| A68S | 0.9 |
| A68P | N/B (Low Exp) |
| A68T | 0.56 |
| A68Y | 0.09 |
| A68H | N/B |
| A68Q | N/B |
| A68N | N/B |
| A68K | N/B |
| A68D | N/B |
| A68E | N/B |
| A68C | 0.25 |
| A68W | 0.05 |
| A68R | N/B |
| A68G | 1 |
| K69F | 0.2 |
| K69L | 0.55 |
| K69I | 0.38 |
| K69M | 0.69 |
| K69V | 0.58 |
| K69S | 0.47 |
| K69P | N/B |
| K69T | 0.15 |
| K69A | 1 |
| K69Y | 0.48 |
| K69H | 0.67 |
| K69Q | 0.6 |
| K69N | 0.75 |
| K69D | 0.19 |

TABLE 19-continued

| Amino Acid | HSA Binding |
|---|---|
| K69E | 0.2 |
| K69C | 0.35 |
| K69W | 0.27 |
| K69R | 1 |
| K69G | 1 |
| V71F | 0.1 |
| V71L | 1 |
| V71I | 1 |
| V71M | 1 |
| V71S | 1 |
| V71P | 1 |
| V71T | 1 |
| V71A | 1 |
| V71Y | 0.8 |
| V71H | 1 |
| V71Q | 1 |
| V71N | 1 |
| V71K | 1 |
| V71D | 0.4 |
| V71E | 0.8 |
| V71C | 1 |
| V71W | 0.4 |
| V71R | 1 |
| V71G | 1 |
| E72F | 0.2 |
| E72L | 0.3 |
| E72I | 0.5 |
| E72M | 0.4 |
| E72V | 0.5 |
| E72S | 1 |
| E72P | 0.4 |
| E72T | 0.4 |
| E72A | 1 |
| E72Y | 0.6 |
| E72H | 1 |
| E72Q | 0.34 |
| E72N | 1 |
| E72K | 1 |
| E72D | 1 |
| E72C | 0.1 |
| E72W | 0.34 |
| E72R | 1 |
| E72G | 1 |
| G73F | 0.1 |
| G73L | 0.15 |
| G73I | 0.1 |
| G73M | 0.1 |
| G73V | 0.15 |
| G73S | 0.3 |
| G73P | 0.1 |
| G73T | 0.15 |
| G73A | 1 |
| G73Y | 0.15 |
| G73H | 0.15 |
| G73Q | 0.1 |
| G73N | 0.1 |
| G73K | 0.1 |
| G73D | 0.1 |
| G73E | 0.1 |
| G73C | 0.1 |
| G73W | 0.1 |
| G73R | 0.1 |
| D79F | 1 |
| D79L | 1 |
| D79I | 1.2 |
| D79M | 0.6 |
| D79V | 1.1 |
| D79S | 1.2 |
| D79P | 1 |
| D79T | 1 |
| D79A | 1 |
| D79Y | 1 |
| D79H | 1 |
| D79Q | 1 |
| D79N | 1 |
| D79K | 1 |
| D79E | 1 |
| D79C | 0.4 |

TABLE 19-continued

| Amino Acid | HSA Binding |
|---|---|
| D79W | 0.2 |
| D79R | 1 |
| D79G | 1 |

To further improve the ABDs, it was desirable to attenuate or eliminate MHC class II binding. Peptides from Y60 and Y61 share a common pocket residue at N66 (P6/P7) and also L64 and 165 share a P6/P7 pocket residue at T70. Mutation of N66 to D or E in combination with T70D was therefore postulated to have the ability to effectively remove MHC class II binding. Alternatively, it was postualted that MHC class II binding could be removed by targeting the four pl anchors Y60, Y61, L64 and 165. Accordingly a two round process of mutational analysis was conducted. Table 20 shows the result of the first round of mutational analysis.

TABLE 20

| pl Anchor | Suggested Mutations | High Affinity MHC II Ligands | Average Score | HSA Binding* |
|---|---|---|---|---|
| Y60 | — | 10 | 0.6176 | |
| | P1 Y60A | 0 | 0 | ++ |
| | P1 Y60H | 0 | 0 | + |
| | P1 Y60T | | | +++ |
| | P1 Y60S | | | + |
| | P1 Y60G | | | (–) |
| | P7 N66D | 2 | 0.5891 | +++ |
| | P7 N66E | 3 | 0.5967 | +++ |
| | P7 N66S | 4 | | |
| Y61 | — | 12 | 0.6577 | |
| | P1 Y61A | 0 | 0 | +++ |
| | P1 Y61H | 0 | 0 | +++ |
| | P1 Y61T | | | +++ |
| | P1 Y61S | | | ++ |
| | P1 Y61G | | | ++ |
| | P6 N66D | 4 | 0.6120 | +++ |
| | P6 N66E | 3 | 0.5940 | +++ |
| | P6 N66S | 0 | | |
| L64 | — | 11 | 0.6067 | |
| | P1 L64A | 0 | 0 | + |
| | P1 L64T | | | +++ |
| | P1 L64S | | | ++ |
| | P1 L64G | | | +++ |
| | P7 T70D | 5 | 0.5998 | (–) |
| | P7 T70S | 4 | | |
| I65 | — | 20 | 0.6235 | |
| | P1 I65A | 0 | 0 | +++ |
| | P1 I65T | | | ++ |
| | P1 I65S | | | ++ |
| | P1 I65G | | | + |
| | P7 T70D | 0 | 0 | (–) |
| | P7 T70S | 3 | | |
| V71 | — | 8 | 0.61430 | |
| | P1 V71A | 0 | 0 | +++ |

*The four classes used were: +++ (0.7-1.0), ++ (0.4-0.7), + (0.1-0.4), (–) (<0.1) of HSA binding The results show that the mutation of pl anchor V71 to A was the most effective option, and suggest a (1+3) combination or a (2+3) combination. All of the tested combinations worked except T70D and Y60G.

The results of the second round of mutational analysis are shown in Table 21 and Table 22.

TABLE 21

| Y61A/N66S/T70S | |
|---|---|
| p1 Anchor | High Affinity Binders |
| Y60 | 4 |
| Y61 | 0 |
| L64 | 4 |
| I65 | 3 |
| | Additional V71A |

TABLE 22

| Result | |
|---|---|
| Amino Acid Mutations | HSA Binding |
| 66S/70S | +++ |
| 61A/66S 70S | (-) |

Table 23 provides a summary of the results obtained from the two rounds of mutational analysis.

TABLE 23

| Amino Acid Mutations | HSA Binding | Amino Acid Mutations | HSA Binding* |
|---|---|---|---|
| 60A/61A | (-) | 70S | +++ |
| 60T/61A | (-) | 60A/61A/65A | (-) |
| 61A/65A | (-) | 60T/61A/65A | (-) |
| 61A/66D | + | 60A/61A/71A | (-) |
| 61A/66S | ++ | 60T/61A/71A | (-) |
| 64A/70S | + | 61A/65A/71A | (-) |
| 64A/65A | ++ | 61A/66D/71A | + |
| 64A/66D | + | 64A/65A/71A | ++ |
| 64G/65A | N/A | 64A/66D/71A | + |
| 64G/66D | (-) | 64G/65A/71A | - |
| 65A/66D | ++ | 64G/66D/71A | + |
| 66S/70S | +++ | 65A/66D/71A | + |
| 66S | +++ | Y61A/N66S/T70S | (-) |

*The four classes used were: +++ (0.7-1.0), ++ (0.4-0.7), + (0.1-0.4), (–) (<0.1) of HSA binding Based on combinational mutation results, the following combinations of substitutions are considered to be preferred substitutions for forming a deimmunized albumin binding domain: 66S/70S +71A; 66S/70S +79A; 64A/65A/71A+66S; 64A/65A/71A+66D; 64A/65A/71A+66E; 64A/65A/79A+66S; 64A/65A/79A+66D; 64A/65A/79A+66E. The asterisk ("*") denotes position 71→P1 and position 79→P9.

As shown in FIG. 57, variant ABDs having the modifications L64A, 165A and D79A or the modifications N66S, T70S and D79A:

(SEQ ID NO: 323)

LAEAKVLANR ELDKYGVSDY YKN$\underline{A}_{64}\underline{A}_{65}$NNAKT VEGVKALI$\underline{A}_{79}$E

ILAALP, (SEQ ID NO: 324)

LAEAKVLANR ELDKYGVSDY YKNLI$\underline{S}_{66}$NAK$\underline{S}_{70}$ VEGVKALI$\underline{A}_{79}$E

ILAALP, exhibited substantially wild-type binding.

The ABD variants 61A/65A, 61A/66D, 64A/65A* and 64A/66D were evaluated along with wild-type for their ability to bind albumin. The results of such assays are shown in FIG. 58. The ABD variants 64G/66D, 65A/66D, 66S/70S* and 61A/66S/70S were evaluated along with wild-type for their ability to bind albumin. The results of such assays are shown in FIG. 59. FIG. 60 shows the results of albumin binding assays for the ABD variants Y60A/Y61A, Y60T/Y61A, 165A/N66DN71A, Y61A/165A/V71A, L64A/N66DN71A and for wild-type (SEQ ID NO: 304). FIG. 61 shows the results of albumin binding assays for the ABD variants Y60A/Y61A/V71A, Y60T/Y61A/V71A, L64A/165A/V71A and for wild-type. FIG. 62 shows the results of albumin binding assays for the ABD variants L64G/165A/V71A, L64G/N66D/V71A, Y61A/T70S, N66S, T70S, Y61A/N66S, L64A/165A and for wild-type.

6.22 Evidence of Deimmunization of Albumin Binding Domain

ABD variants, including particularly variants at position V71 (e.g., V71A) exhibit decreased immunogenicity. To demonstrate such deimmunization, three peptide samples were assessed for immunogenic potential using EpiScreen™ time course T cell assays. The assesed samples were 21-mer fragments (Y60-E80)) of the wild-type ABD peptide (SEQ ID NO: 304):

LAEAKVLANR ELDKYGVSDY YKNLINNAKT VEGVKALIDE 41 50 60 70 80

ABD Y60-E80 wt ("Sample 1") (SEQ ID NO: 325):

Y YKNLINNAKT VEGVKALIDE

ABD Y60-E80 Variant N66D/T70S/V71A ("Sample 2") (SEQ ID NO: 326):

Y YKNLI$\underline{D}_{66}$NAK$\underline{S}_{70}$ $\underline{A}_{71}$EGVKALIDE and ABD Y60-E80 Variant L64A/165A/V71A ("Sample 3") (SEQ ID NO: 327):

Y YKN$\underline{A}_{64}\underline{A}_{65}$NNAKT $\underline{A}_{71}$EGVKALIDE

Peripheral blood mononuclear cells (PBMC) were isolated from healthy community donor buffy coats (from blood drawn within 24 hours). PBMC were isolated from buffy coats by Lymphoprep™ (Axis-shield, Dundee, UK) density centrifugation and CD8' T cells were depleted using CD8' RosetteSep™ (StemCell Technologies Inc, London, UK). Donors were characterized by identifying HLA-DR haplotypes using an HLA SSP-PCR based tissue-typing kit (Biotest, Solihull, UK). T cell responses to control antigens (Keyhole Limpet Haemocyanin (KLH), [Pierce (Perbio), Cramlington, UK)] as well as peptides derived from Influenza A and Epstein Barr viruses were also determined. PBMC were then frozen and stored in liquid nitrogen until required. A cohort of 50 donors was employed, whose allotypes indicated that coverage of >80% of world allotypes had been achieved and that all major HLA-DR allotypes (individual allotypes with a frequency >5% expressed in the world population) were well represented.

PBMCs from each donor were thawed, counted and viability assessed. Cells were revived in room temperature AIM-V® culture medium, washed and resuspended in AIM-V® to 4–6×$10^6$ PBMC/ml. For each donor, bulk cultures were established in which 1 ml proliferation cell stock was added to the appropriate wells of a 24 well plate. Culture medium (0.5 ml) and test peptide (0.5 ml) were added to the PBMC to give a final concentration of 5 μM. For each donor, a reproducibility control (cells incubated with 100 μg/ml KLH), and a "culture medium only" well were also included. Cultures were incubated for a total of 8 days at 37° C. with 5% $CO_2$. On days 5, 6, 7 and 8, the cells in each well were gently resuspended and 3×100 μl aliquots transferred to each well of a round bottomed 96 well plate. The cultures were pulsed with 0.75 μCi [$^3$H]-Thymidine (Perkin Elmer®, Beaconsfield, UK) in 100 μl AIM-V® culture medium and incubated for a further 18 hours before harvesting onto filter mats (Perkin Elmer) using a TomTec Mach III™ cell harvester. Counts per minute (cpm) for each well were determined by Meltilex™ (Perkin Elmer®) scintillation counting on a 1450 Microbeta Wallac Trilux Liquid Scintillation Counter (Perkin Elmer®) in paralux, low background counting.

In order to assess the effect of such treatment on cell viability, on day 7, bulk cultures may be gently resuspended and 20 μl of each sample removed from all donors and mixed with 20 μl trypan blue. These samples may then be assessed for viability using trypan blue dye exclusion with a Countess® Automated Cell Counter (Invitrogen). Viability is preferably expressed as a percentage of trypan blue excluded/total cell count. In experiments conducted with sample 1 (wt), and with various test peptides other than sample 2 or sample 3, the cultured cells were found to remain on average greater than 87% viability for all the donors tested. The mean viability of cells incubated with media alone was calculated to be 90% whilst the mean viabilities of cells incubated with the test peptides were 88, 88 and 87% respectively. The viability of KLH treated cells was 83% which is not significantly different to the viability of peptide treated cells. It was therefore concluded that the incubation of the cells (PBMC) with the peptides did not result in any obvious toxicity during the cell culture period.

Identical donors to those used in the proliferation assay were also used for the IL-2 ELISpot™ assay. Cells were thawed and revived as described above. ELISpot plates (Millipore, Watford, UK) were pre-wetted and coated overnight with 100 μl/well IL-2 capture antibody (R&D Systems, Abingdon, UK) in PBS. Plates were then washed 3 times in PBS, incubated overnight in blocking buffer (1% BSA (Bovine Serum Albumin, Sigma) in PBS) and washed in AIM-V® medium. The cell density for each donor was adjusted to 4–6×$10^6$ PBMC/ml in AIM V® culture medium and 100 μl of cells were added to each well. 50 μl of test peptide and controls were added to the appropriate wells.

Peptides (ABD Y60-E80 ("Sample 1"), ABD Y60-E80 Variant N66D/T70S/V71A ("Sample 2") (SEQ ID NO: 326) or ABD Y60-E80 Variant L64A/165A/V71A ("Sample 3") (SEQ ID NO: 327) were added to the bulk cultures of CD8' depleted PBMC. After incubation with the samples, CD4' T cell proliferation was measured by incorporation of [$^3$H]-thymidine at various time points with additional parallel measurement of IL-2 secretion using ELISpot™ (the IL-2 ELISpot™ assay comprises a membrane pre-coated with capture antibody which binds secreted cytokine) The peptides were diluted in AIM-V® culture medium (Invitrogen, Paisley, UK) just before use and the final assay concentration was 504. KLH was used as a reproducibility control and stored at −20° C. as a 10 mg/ml stock solution in water. For the studies, an aliquot of KLH was thawed before immediately diluting to 400 μg/ml in AIM-V® (final concentration 100 μg/ml). Phytohaemagglutanin (PHA, Sigma, Poole, UK) was used as a positive control in the ELISpot™ and a 1 mg/ml stock was stored at −20° C. before diluting to a final concentration of 2.5 μg/ml in cell cultures.

The test peptides were tested in sextuplicate cultures and, for each donor, a negative control (AIM-V® medium alone), no cells control and a mitogen positive control (PHA at 2.5 m/ml—used as an internal test for ELISpot™ function and cell viability, Sigma) were also included on each plate. After an 8 day incubation period, ELISpot™ plates were developed by sequential washing in dH2O and PBS (×3) prior to the addition of 100 μl filtered, biotinylated detection antibody (R&D Systems) in PBS/1% BSA. Following incubation at 37° C. for 1.5 hours, plates were further washed in PBS (×3) and 100 μl filtered streptavidin-AP(R&D Systems) in PBS/1% BSA was added for 1.5 hours at room temperature. Streptavidin-AP was discarded and plates were washed in PBS (×4). BCIP/NBT substrate (R&D Systems) (100 μl) was added to each well and incubated for 30 minutes at room temperature. Spot development was stopped by washing the wells and the backs of the wells three times with dH2O. Dried plates were scanned on an Immunoscan® Analyser and spots per well (spw) were determined using Immunoscan® Version 4 software.

For proliferation and IL-2 ELISpot™ assays, samples inducing responses equal to or greater than twice an empirical threshold of a stimulation index (SI) (SI≥2.00) were deemed to be positive. For both proliferation (n=3) and IL-2 ELISpot data (n=6) sets, positive responses were defined by statistical and empirical thresholds: Significance ($p<0.05$) of the response by comparing cpm or spw of test wells against medium control wells using unpaired two sample student's t-test; Stimulation index greater than or equal to 2 (SI≥2.00), where SI=mean of test wells (cpm or spw)/baseline (cpm or spw). Data presented in this way is indicated as SI≥2.00, $p<0.05$. In addition, intra-assay variation was assessed by calculating the coefficient of variance and standard deviation (SD) of the raw data from replicate cultures.

The wild-type peptide was found to induce positive proliferation responses in the EpiScreen™ time course T cell proliferation assay of CD4' T cell responses with an SI≥2.00 ($p<0.05$) in seven donors including one borderline response (SI≥1.90 ($p<0.05$)) giving a positive response frequency of 14%. The mean magnitude (SI) of positive (S I≥2.00 $p<0.05$) T cell proliferation responses against the wt peptide was S12.55, which was slightly higher than the two deimmunized peptides (Table 24). Table 24 provides a summary of the magnitude (±SD) of positive T cell proliferation responses against the test peptides and KLH. The mean SI was calculated from the average of all positive donor responses observed during the entire time course (days 5-8). The data includes borderline proliferation responses (SI≥1.90), $p<0.05$).

TABLE 24

| Sample | Mean SI | SD | % Response |
|---|---|---|---|
| WT | 2.55 | 0.73 | 14 |
| N66D/T70S/V71A | 2.63 | 0.56 | 4 |
| L64A/I65A/V71A | 2.17 | 0.24 | 6 |
| KLH Control | 5.38 | 5.22 | 92 |

Thus, from the proliferation assay, the magnitude (SI) of the T cell response along with the frequency (%) of responding donors in the study cohort indicates that the overall immunogenic potential of the wt peptide was considered to be moderate, whereas the immunogenic potential of the deimmunized peptides was considered to be low. These data support the fact that removal of wt specific T cell epitopes was successful by the mutations in N66D/T70S/V71A and L64A/165A/V71A.

The overall timing of the proliferative responses can provide an indication as to the potential type of T cell response (naïve or recall). Maximal T cell proliferation detected on day 5 indicates that existing T cell precursor frequencies are high whereas maximal proliferation on day 8 indicates a low existing T cell precursor frequency. A high immunogenic potential would be concordant with stimulation of T cells during the early phase of the time course. Test peptide ABD Y60-E80 Variant N66D/T70S/V71A ("Sample 2") (SEQ ID NO: 326) gave 1, 0, 1, and 1 response on days 5, 6, 7, and 8, respectively. Test peptide ABD Y60-E80 Variant L64A/165A/V71A ("Sample 3") (SEQ ID NO: 327) gave 0, 1, 2, and 1 response on days 5, 6, 7, and 8, respectively. The low number of responding donors observed against N66D/T70S/V71A and L64A/165A/V71A makes this type of kinetic analysis of T cell proliferation response difficult to interpret although the few responses that were observed against these samples occurred late in the time course and support the notion that healthy individuals are not primed against T cell epitopes in these sequences.

Similar to the proliferation assay, positive responses were recorded in donors that produced an S I>2.00 with a significant ($p<0.05$) difference observed between test spw and background (untreated medium control). The N66D/T70S/V71A peptide induced 6% of donors to respond positively in the IL-2 ELISpot assay and the L64A/165A/V71A peptide induced 4% positive responses. This is in contrast with the results seen for the wt sequence in which positive IL-2 ELISpot responses in 20% of the donor cohort were detected. The mean magnitude of positive T cell responses for the both deimmunized peptides was low at 2.02 and 2.43 (Table 25) respectively, and this was similar to that seen for the wt peptide. Table 25 provides a summary of the magnitude (±SD) of positive T cell IL-2 secretion responses (SI≥2.00, $p<0.05$) against test peptides and KLH. The mean SI was calculated from the average of all positive donor responses observed. The data includes borderline proliferation responses (SI≥1.90, $p<0.05$).

TABLE 25

| Sample | Mean SI | SD | % Response |
|---|---|---|---|
| WT | 2.25 | 0.38 | 20 |
| N66D/T70S/V71A | 2.02 | 0.15 | 6 |
| L64A/I65A/V71A | 2.43 | 0.19 | 4 |
| KLH Control | 4.14 | 2.02 | 96 |

For the two test peptides, the overall correlation between the proliferation and IL-2 ELISpot™ assay data was high with 100% and 67% of the donors that responded positively in the proliferation assay also responded in the IL-2 ELISpot assay. This high correlation between the two assays was also observed in the reproducibility control KLH where 98% of the donors that responded in the proliferation assay also produced responses in the IL-2 ELISpot™ assay (typical range 85-100% for the EpiScreen™ time course T cell assay). Thus, for both proliferation and IL-2 ELISpot™ assays, the frequency and the magnitude of T cell responses against the N66D/T70S/V71A and L64A/165A/V71A peptides suggest that they both can be considered to have a low potential for clinical immunogenicity, compared to the high risk of clinical immunogenicity of the wt peptide.

The proliferation and IL-2 ELISpot assay data show that positive T cell responses were detected against the test peptides in a number of the donors. The overall correlation between proliferation and IL-2 ELISpot assays was 98% for KLH, 70% for the wt peptide, and 100% and 67% for N66D/T70S/V74A and L64A/165A/V74A respectively. Therefore, responding donors were defined as those that mounted a positive response to each sample in both IL-2 ELISpot and proliferation assays. All donors produced a positive T cell response against PHA indicating that cells in the ex vivo cultures were functional. Analysis of the combined datasets from these two assays indicated that the overall frequency and magnitude of responses in both proliferation and ELISpot assays was low for the two deimmunized peptides with 4% of donors responding against both N66D/T70S/V71A and L64A/165A/V71A. This is in contrast to study results obtained for the wt peptide (which had a significantly higher number of positive responses (14% of donors responding in both IL-2 ELISpot and proliferation assays)). No HLA analysis was carried out as the responses to the two test peptides were below the minimum threshold for this type of analysis.

In sum, the EpiScreen™ time course T cell assay was used to determine the potential for clinical immunogenicity of two test peptides. The ability of the peptides to induce CD4' T cell responses measured by proliferation and IL-2 ELISpot was tested against a panel of 50 HLA-typed donors. Data from the study of the wt peptide had indicated that the overall potential risk of immunogenicity for the wt peptide was moderate as the combined frequency of proliferation and IL-2 responses was 14% of the study cohort. However the combined frequency of proliferation and IL-2 responses to the two deimmunized peptides in this study was low with 4% of donors responding against N66D/T70S/V71A and 6% of donors responding against L64A/165A/V71A.

EpiScreen™ time course T cell assays of multiple commercial biologics have shown a clear correlation between the percentage of donor T cell responses in the EpiScreen™ assay and the level of immunogenicity (anti-protein therapeutic antibody responses) observed in the clinic. High frequency donor responses were observed in EpiScreen™ assays for immunogenic antibodies such as Campath, whereas relatively low frequency donor responses were observed for non-immunogenic antibodies such as Xolair and Herceptin. In general, protein therapeutics that induce >10% positive responses in the EpiScreen™ assay are associated with a significant risk of immunogenicity in the clinic. In comparison to protein therapeutics tested in EpiScreen™ assays, the data shows that the deimmunized peptides N66D/T70S/V71A and L64A/165A/V71A give CD4' T cell responses which fall into the same range as Xolair, Herceptin and Avastin, and would be considered as having a low potential risk of immunogenicity. Therefore, it is concluded that the deimmunized peptides exhibit a favourable immunogenicity profile in the EpiScreen™ immunogenicity assay.

6.23 Improved in vivo Pharmacokinetic Properties of ABD-DARTS

As discussed above, the albumin-binding domain (ABD) from streptococcal protein G was fused to the C-terminal end of a DART (away from antigen binding sites) ("ABD-DART") in order to improve the in vivo pharmacokinetic properties of the DART. The pharmacokinetics study of such ABD-DARTs showed a prolonged circulation time, with an increased terminal half-life of 35.1 h compared to 1.2 h for regular DARTs (lacking the ABD). In silico analysis revealed that there are five pl anchor positions with high MHC class II binding potential in the ABD sequence. In order to produce deimmunized version of ABD, site directed mutations were performed based on the prediction provided by the in silico analysis. After several rounds of single and combination mutations, two ABD variants, "ABD (AAA)" and "ABD (DSA)" were obtained with similar or lower affinity relative to that of wild type ABD with serum albumin.

L64A/165A/V71A ("ABD (AAA)") (SEQ ID NO: 328):

LAEAKVLANR ELDKYGVSDY YKN$\underline{A}_{64}\underline{A}_{65}$NNAKT $\underline{A}_{71}$EGVKALIDE

ILAALP

N66D/T70S/V71A ("ABD (DSA)") (SEQ ID NO: 329):

LAEAKVLANR ELDKYGVSDY YKNLI$\underline{D}_{66}$NAK$\underline{S}_{70}$ $\underline{A}_{71}$EGVKALIDE

ILAALP

These two variants showed greatest reduction in binding score with MHC class II peptides (Table 26).

TABLE 26

In silico Assessment of Mutation Combinations

| Mutation | AA60 | | AA61 | | AA64 | | AA65 | | AA71 | |
|---|---|---|---|---|---|---|---|---|---|---|
| Combination | Lig. | Score | Lig. | Score | Lig. | Score | Lig. | Score | Lig. | Score |
| Wild-Type | 10 | 0.6102 | 12 | 0.6577 | 11 | 0.6067 | 20 | 0.6235 | 8 | 0.6143 |
| ABD (AAA) | 10 | 0.6102 | 12 | 0.6577 | 0 | — | 0 | — | 0 | — |
| ABD (DSA) | 2 | 0.5891 | 4 | 0.6120 | 7 | 0.6086 | 2 | 0.5776 | 0 | — |

Lig. = Ligands

To observe the serum half-life of these two ABD variants, in vivo PK study was conducted in C57B1/6 mice with a single IV injection of the proteins at 5 mg/kg. The PK study showed similar prolonged circulation time of the mutant ABD (DSA) as that of wild type ABD (FIG. 63). The other mutant, hCD16×hCD32B ABD (AAA) DART stayed few hours longer in serum than the basic hCD16×hCD32B EK DART. The study thus demonstrates that despite a lower affinity with albumin; the fusion of deimmunized version of ABD, (i.e., ABD (DSA)) drastically increases the serum half-life of DART proteins. Such increased serum half-life makes it advantageous to use this less immunogenic ABD-DART as a potential therapeutic candidate, especially with less frequent and/or lower dosing. The PK profiles of hCD16×hCD32B ABD DARTs are shown in Table 27.

TABLE 27

PK profiles of hCD16xhCD32B ABD DARTs

| | EK DART | ABD | ABD (AAA) | ABD (DSA) |
|---|---|---|---|---|
| $T_{1/2}$ beta (day) | NA | 1.1693 | 0.2388 | 1.0883 |
| $C_{max}$ (μg/ml) | 60.7800 | 78.0000 | 78.3600 | 94.2100 |
| $T_{max}$ (day) | 0.0208 | 0.0208 | 0.0208 | 0.0208 |
| AUC (day*ug/ml) | 30.3900 | 119.8113 | 42.5868 | 118.1240 |

Legend: $T_{1/2}$ beta (terminal half-life); $C_{max}$ (peak serum concentration); $T_{max}$ (amount of time concentration is at $C_{max}$); AUC (Area under curve (value is proportional to the total amount in the patient's blood)

6.24 Effect of Increased Valency of ABD on IN VIVO Half-life of Recombinant ABD-DARTS Different ABD DART proteins were constructed, either by fusing ABD at the end of both chains (FIG. 64A) or by fusing tandem ABDs at the end of one chain (FIG. 64B). One construct was also made by fusing ABD(AAA) at the C-terminal end of both chains. In this study hCD16×hCD32B Fc DART was generated to compare the serum half-life. All of the ABD variants showed bispecific binding with both of the antigens (FIG. 65). To observe the serum half-life of all of these ABD DARTs and Fc DARTs, an in vivo PK study was conducted in C57B1/6 mice with a single IV injection of the proteins at 5 mg/kg. The result shows that half-life extending property of ABD is influenced by the valency of albumin binding (FIG. 66). The terminal half-life of DART fused with two ABDs is unexpectedly three times higher than that of DART with one ABD (Table 28).

TABLE 28

PK profiles of hCD16xhCD32B ABD and Fc DARTs

| | E ABD/K ABD | E ABD(AAA)/ K ABD(AAA) | E ABD-ABD/K | E Fc/K |
|---|---|---|---|---|
| $T_{1/2}$ beta (day) | 3.55 | 0.31 | 2.29 | 9.02 |
| $C_{max}$ (μg/ml) | 132.20 | 111.50 | 130.00 | 93.97 |
| $T_{max}$ (day) | 0.02 | 0.02 | 0.02 | 0.02 |
| AUC (day*ug/ml) | 30.3900 | 119.8113 | 42.5868 | 118.1240 |

Legend: $T_{1/2}$ beta (terminal half-life); $C_{max}$ (peak serum concentration); $T_{max}$ (amount of time concentration is at $C_{max}$); AUC (Area under curve (value is proportional to the total amount in the patient's blood)

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims. All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A polypeptide that comprises a portion of a deimmunized albumin-binding protein capable of binding to serum albumin; wherein said deimmunized albumin-binding protein portion is a variant of a wild-type albumin-binding domain (ABD) of a Streptococcal Protein G, said wild-type ABD having the amino acid sequence of SEQ ID NO: 304; wherein said variant ABD has an amino acid sequence that differs from that of SEQ ID NO: 304 in comprising:

(A) a valine to alanine variation at position 31 of SEQ ID NO:304; a valine to alanine variation at position 34 of SEQ ID NO:304; or an aspartate to alanine variation at position 39 of SEQ ID NO:304;

(B) a leucine to alanine variation at position 24 of SEQ ID NO:304; an isoleucine to alanine variation at, position 25 of SEQ ID NO:304; and a valine to alanine variation at position 25 of SEQ ID NO:304; or (C) an asparagine to aspartic acid variation at position 26 of SEQ ID NO:304; a threonine to serine substitution at position 30 of SEQ ID NO:304; and a valine to alanine variation at position 31 of SEQ ID NO:304;

wherein said deimmunized albumin-binding protein portion extends the serum half-life of said polypeptide, relative to the serum half-life of said polypeptide if lacking said portion of said deimmunized albumin-binding protein.

2. The polypeptide of claim 1, wherein said polypeptide comprises an additional portion of a deimmunized albumin-binding protein, wherein said portions of said deimmunized albumin-binding protein are both capable of binding to said serum albumin.

3. The polypeptide of claim 1, wherein said variant ABD comprises said valine to alanine variation at position 31 of SEQ ID NO:304; said valine to alanine variation at position 34 of SEQ ID NO:304; or said aspartate to alanine variation at position 39 of SEQ ID NO:304.

4. The polypeptide of claim 1, wherein said variant ABD comprises said leucine to alanine variation at position 24 of SEQ ID NO:304; said isoleucine to alanine variation at position 25 of SEQ ID NO:304; and said valine to alanine variation at position 31 of SEQ ID NO:304.

5. The polypeptide of claim 1, wherein said variant ABD comprises said asparagine to aspartic acid variation at position 26 of SEQ ID NO:304; said threonine to serine substitution at position 30 of SEQ ID NO:304; and said valine to alanine variation at position 31 of SEQ ID NO:304.

6. The polypeptide of claim 1, wherein said variant ABD has the sequence of SEQ ID NO: 323, SEQ ID NO: 324, SEQ ID NO: 326, SEQ ID NO: 327, SEQ ID NO: 328, or SEQ ID NO: 329.

7. The polypeptide of claim 1, wherein said polypeptide comprises an antigen-binding molecule.

8. The polypeptide of claim 7, wherein said antigen-binding molecule is a diabody composed of at least a first and a second polypeptide chain which interact with one another to form two antigen-binding sites, wherein at least one of said polypeptide chains comprises said portion of said deimmunized albumin-binding protein that is capable of binding to said serum albumin.

9. The polypeptide of claim 8, wherein both said first and said second polypeptide chains comprise said portion of said deimmunized albumin-binding protein capable of binding to said serum albumin.

10. The polypeptide of claim 8, wherein said first and said second polypeptide chains are covalently linked to one another.

11. The polypeptide of claim 8, wherein said diabody binds to:

(A) the Natural Killer Group 2D (NKG2D) receptor or the T-cell receptor (TCR); and (B) a tumor-associated antigen.

12. The polypeptide of claim 7, wherein said antigen is a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkin's lymphoma, or an antigen associated with chronic lymphocytic leukemia.

13. A method for extending the serum half-life of a polypeptide, which comprises covalently linking said polypeptide to a polypeptide portion of a deimmunized albumin-binding protein, said extension of serum half-life being relative to the serum half-life of said polypeptide if lacking said albumin-binding protein; wherein said deimmunized albumin-binding protein portion is a variant of a wild-type albumin-binding domain (ABD) of a Streptococcal Protein G, said wild-type ABD having the amino acid sequence of SEQ ID NO: 304; wherein said variant ABD has an amino acid sequence that differs from that of SEQ ID NO: 304 in comprising:

(A) a valine to alanine variation at position 31 of SEQ ID NO:304; a valine to alanine variation at position 34 of SEQ ID NO:304; or an aspartate to alanine variation at position 39 of SEQ ID NO:304;

(B) a leucine to alanine variation at position 24 of SEQ ID NO:304; an isoleucine to alanine variation at, position 25 of SEQ ID NO:304; and a valine to alanine variation at position 31 of SEQ ID NO:304; or (C) an asparagine to aspartic acid variation at position 26 of SEQ ID NO:304; a threonine to serine substitution at position 30 of SEQ ID NO:304; and a valine to alanine variation at position 31 of SEQ ID NO:304.

14. The method of claim 13, wherein said polypeptide comprises an additional portion of a deimmunized albumin-binding protein, wherein said portions of said deimmunized albumin-binding protein are both capable of binding to said serum albumin.

15. The method of claim 13, wherein said variant ABD comprises said valine to alanine variation at position 31 of SEQ ID NO:304; said valine to alanine variation at position 34 of SEQ ID NO:304; or said aspartate to alanine variation at position 39 of SEQ ID NO:304.

16. The method of claim 13, wherein said variant ABD comprises said leucine to alanine variation at position 24 of SEQ ID NO:304; said isoleucine to alanine variation at position 25 of SEQ ID NO:304; and said valine to alanine variation at position 31 of SEQ ID NO:304.

17. The method of claim 16, wherein said variant ABD comprises said asparagine to aspartic acid variation at position 26 of SEQ ID NO:304; said threonine to serine substitution at position 30 of SEQ ID NO:304; and said valine to alanine variation at position 31 of SEQ ID NO:304.

18. The method of claim 13, wherein said variant ABD has the sequence of SEQ ID NO: 323, SEQ ID NO: 324, SEQ ID NO: 326, SEQ ID NO: 327, SEQ ID NO: 328, or SEQ ID NO: 329.

19. The method of claim 13, wherein said polypeptide comprises an antigen-binding molecule.

20. The method of claim 19, wherein said antigen-binding molecule is a diabody composed of at least a first and a second polypeptide chain which interact with one another to form two antigen-binding sites, wherein at least one of said polypeptide chains comprises said portion of said deimmunized albumin-binding protein that is capable of binding to said serum albumin.

21. The method of claim 20, wherein both said first and said second polypeptide chains comprise said portion of said deimmunized albumin-binding protein capable of binding to said serum albumin.

22. The method of claim 20, wherein said first and said second polypeptide chains are covalently linked to one another.

23. The method of claim 20, wherein said diabody binds to:

(A) the Natural Killer Group 2D (NKG2D) receptor or the T-cell receptor (TCR); and (B) a tumor-associated antigen.

24. The method of claim 19, wherein said antigen is a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkin's lymphoma, or an antigen associated with chronic lymphocytic leukemia.

25. The polypeptide of claim 8, wherein said diabody has an antigen-binding site that binds to a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkin's lymphoma, or an antigen associated with chronic lymphocytic leukemia.

26. The method of claim 20, wherein said diabody has an antigen binding site that binds to a breast cancer antigen, an ovarian cancer antigen, a prostate cancer antigen, a cervical cancer antigen, a pancreatic carcinoma antigen, a lung cancer antigen, a bladder cancer antigen, a colon cancer antigen, a testicular cancer antigen, a glioblastoma cancer antigen, an antigen associated with a B cell malignancy, an antigen associated with multiple myeloma, an antigen associated with non-Hodgkin's lymphoma, or an antigen associated with chronic lymphocytic leukemia.

* * * * *